US007868205B2

(12) United States Patent
Moradei et al.

(10) Patent No.: US 7,868,205 B2
(45) Date of Patent: Jan. 11, 2011

(54) INHIBITORS OF HISTONE DEACETYLASE

(75) Inventors: Oscar Moradei, Kirkland (CA); Isabelle Paquin, LaSalle (CA); Silvana Leit, Kirkland (CA); Sylvie Frechette, Verdun (CA); Arkadii Vaisburg, Kirkland (CA); Jeffrey M. Besterman, Baie D'urfe (CA); Pierre Tessier, Hawkesbury (CA); Tammy C. Mallais, Kirkland (CA)

(73) Assignee: MethylGene Inc., Montreal (CA)

( * ) Notice: Subject to any disclaimer, the term of this patent is extended or adjusted under 35 U.S.C. 154(b) by 1009 days.

(21) Appl. No.: 10/574,088

(22) PCT Filed: Sep. 24, 2004

(86) PCT No.: PCT/US2004/031591

§ 371 (c)(1),
(2), (4) Date: Jan. 30, 2007

(87) PCT Pub. No.: WO2005/030705

PCT Pub. Date: Apr. 7, 2005

(65) Prior Publication Data

US 2008/0132459 A1 Jun. 5, 2008

Related U.S. Application Data

(60) Provisional application No. 60/505,884, filed on Sep. 24, 2003, provisional application No. 60/532,973, filed on Dec. 29, 2003, provisional application No. 60/561,082, filed on Apr. 9, 2004.

(51) Int. Cl.
C07C 233/65 (2006.01)
A61K 31/165 (2006.01)

(52) U.S. Cl. ........................ 564/175; 564/176; 514/395; 514/438; 514/613; 514/620; 544/379; 544/369; 544/359; 544/295; 546/213; 548/304.4; 549/77

(58) Field of Classification Search ................. 564/175, 564/176; 514/395, 438, 613, 620; 544/379, 544/369, 359, 295; 546/213; 548/304.4; 549/77
See application file for complete search history.

(56) References Cited

U.S. PATENT DOCUMENTS

| 3,576,869 A | 4/1971 | Schellenbaum et al. |
| 5,137,918 A | 8/1992 | Weisershausen et al. |
| 5,332,750 A | 7/1994 | Mederski et al. |
| 5,366,878 A | 11/1994 | Pederson et al. |
| 5,635,377 A | 6/1997 | Pederson et al. |
| 5,652,355 A | 7/1997 | Metelev et al. |
| 5,945,450 A | 8/1999 | Takenouchi et al. |
| 6,034,251 A | 3/2000 | Aslanian et al. |
| 6,174,905 B1 | 1/2001 | Suzuki et al. |
| 6,376,515 B2 | 4/2002 | Zhu et al. |
| 6,541,661 B1 | 4/2003 | Delorme et al. |
| 6,632,815 B2 | 10/2003 | Zhu et al. |
| 6,653,309 B1 | 11/2003 | Saunders et al. |
| 6,777,217 B1 | 8/2004 | Schreiber et al. |
| 6,897,220 B2 | 5/2005 | Delorme et al. |
| 7,253,204 B2 | 8/2007 | Delorme et al. |
| 7,282,608 B2 | 10/2007 | Raeppel et al. |
| 2002/0061860 A1 | 5/2002 | Li et al. |
| 2003/0096844 A1 | 5/2003 | Kozlowski et al. |
| 2003/0232859 A1 | 12/2003 | Kozlowski et al. |
| 2004/0010013 A1 | 1/2004 | Friary et al. |
| 2004/0044051 A1 | 3/2004 | Kozlowski et al. |
| 2004/0087798 A1 | 5/2004 | Yamada |
| 2004/0106599 A1 | 6/2004 | Delorme et al. |
| 2004/0132804 A1 | 7/2004 | Tong et al. |
| 2004/0147569 A1 | 7/2004 | Suzuki et al. |
| 2004/0186148 A1 | 9/2004 | Shankar et al. |
| 2005/0096222 A1 | 5/2005 | Hidaka et al. |
| 2005/0288282 A1 | 12/2005 | Delorme et al. |
| 2006/0058298 A1 | 3/2006 | Delorme et al. |
| 2007/0213330 A1 | 9/2007 | Delorme et al. |
| 2008/0132503 A1 | 6/2008 | Moradei et al. |

FOREIGN PATENT DOCUMENTS

| CA | 2136288 | 11/1994 |
| CA | 2480356 | 10/2003 |
| CA | 2484065 | 11/2003 |
| CA | 2490579 | 1/2004 |
| DE | 14 70 097 A1 | 6/1969 |
| EP | 0 657 454 | 11/1994 |
| EP | 0 847 992 | 9/1997 |
| EP | 0 847 992 A | 6/1998 |
| EP | 1 256 341 | 11/2002 |

(Continued)

OTHER PUBLICATIONS

Valentino J. Stella et al.: "Prodrugs: Challenges and Rewards Part 1," Biotechnology: Pharmaceutical Aspects (2007).

(Continued)

Primary Examiner—Shailendra Kumar
(74) Attorney, Agent, or Firm—McDonnell Boehnen Hulbert & Berghoff LLP

(57) ABSTRACT

The invention relates to the inhibition of histone deacetylase. The invention provides compounds and methods for inhibiting histone deacetylase enzymatic activity. The invention also provides compositions and methods for treating cell proliferative diseases and conditions.

32 Claims, 10 Drawing Sheets

FOREIGN PATENT DOCUMENTS

| | | |
|---|---|---|
| JP | 1996-258863 | 9/1996 |
| JP | 1999-269146 | 10/1999 |
| JP | 11269146 | 10/1999 |
| JP | 11269146 A | 10/1999 |
| JP | 1999-302173 | 11/1999 |
| JP | 2001131130 A | 5/2001 |
| JP | 2003-137866 | 5/2003 |
| JP | 2003221380 | 8/2003 |
| WO | 98/42672 A1 | 10/1998 |
| WO | WO 98/45252 | 10/1998 |
| WO | WO 00/03704 | 1/2000 |
| WO | WO 01/16106 | 3/2001 |
| WO | WO 01/16106 A | 3/2001 |
| WO | WO 01/38322 | 5/2001 |
| WO | WO 01/38322 A | 5/2001 |
| WO | WO 01/60354 | 8/2001 |
| WO | WO 01/64643 A2 | 9/2001 |
| WO | WO 01/68585 | 9/2001 |
| WO | WO 01/70675 A2 | 9/2001 |
| WO | WO 02/069947 | 9/2002 |
| WO | WO 03/024448 A | 3/2003 |
| WO | WO 03/024448 A2 | 3/2003 |
| WO | WO 03/075929 | 9/2003 |
| WO | WO 03/076395 | 9/2003 |
| WO | WO 03/076400 | 9/2003 |
| WO | WO 03/076401 | 9/2003 |
| WO | WO 03/076421 | 9/2003 |
| WO | WO 03/076422 | 9/2003 |
| WO | WO 03/076430 | 9/2003 |
| WO | WO 03/076438 | 9/2003 |
| WO | WO 03/087057 | 10/2003 |
| WO | WO 03/092686 | 11/2003 |
| WO | WO 2004/058234 | 7/2004 |
| WO | WO 2004/069133 | 8/2004 |
| WO | WO 2004/069823 | 8/2004 |
| WO | WO 2004/071400 | 8/2004 |
| WO | 2005/030705 A1 | 4/2005 |
| WO | 2005/092899 A2 | 10/2005 |
| WO | 2006/122319 A | 11/2006 |
| WO | 2007/118137 A1 | 10/2007 |

OTHER PUBLICATIONS

Sudha R. Vippagunta et al.: "Crystalline solids," Advanced Drug Delivery Reviews 48 (2001) pp. 3-26.

Charles et al, "Synthesis of substituted Benzamides, Benzimidazoles and Benzoxazines as potential Anthelmintic and Antimicrobial Agents", Archiv Der Pharmazie, 1982, 97-103, 315(2).

European Patent Office Additional Exemplary Search for Application No. EP 02 763 627.3 dated Apr. 26, 2007, 53 pages.

Ye et al., CNS Drug Rev., 2001 Summer, 7(2), 199-213.

STN International Search in U.S. Appl. No. 11/687,398, filed Feb. 10, 2008, 195 pages.

U.S. Appl. No. 12/043,450, filed Mar. 6, 2008.

Weidle et al., "XP-001098720—Inhibition of Histone Deacetylase: a New Strategy to Target Epigenetic Modification for Anticancer Treatment", Anticancer Research 20, 2000, pp. 1471-1486.

U.S. Appl. No. 11/620,917, filed Jan. 8, 2007.

Graneb et al., "A Novel Mitogenic Signaling Pathway of Bradykinin in the Human Colon Carcinoma Cell Line SW-480 Involves Sequential Activation of a Gq/11 Protein, Phosphatidylinositol 3-Kinase β, and Protein Kinase Cε*", The Journal of Biological Chemistry, 273(48), 1998, 32016-32022.

Cecil Textbook of Medicine, edited by Bennett, J.C., and Plum F., 20th Edition, vol. 1, 1004-1010, (1996).

Ragione, Fulvio Della et al., "Genes Modulated by Histone Acetylation as New Effectors of Butyrate Activity", FEBS Letters 499, 199-204, (2001).

Turner, W. W. et al., "Recent Advances in the Medicinal Chemistry of Antifungal Agents", Current Pharmaceutical Design, 2, 209-224 (1996).

Sugar, Alan M. et al., "Comparison of Three Methods of Antifunal Susceptibility Testing with the Proposed NCCLS Standard Broth Macrodilution Assay: Lack of Effect of Phenol Red", Diagn. Microbiol. Infect. Dis., 21, 129-133 (1995).

Snyder, JW et al., "Common Bacteria Whose Susceptibility to Antimicrobials is no Longer Predictable", J. Med. Liban, 48(4), 208-14 (2000).

Suzuki, et al., "Synthesis and Histone Deacetylase Inhibitory Activity of New Benzamide Derivatives," Journal of Medicinal Chemistry, American Chemical Society, Washington U.S., vol. 42, No. 15, 1999, pp. 3001-3003.

Database Crossfire Beilstein (Online) Beilstein Institut zur Föerderung der Chemischen Wissenschaftern, Frankfurt am Main, DE, N,N'-di (o-aminophenyl) terephthalamide, Database accession No. 5619310 XP-002229372, Third invention Abstract & Indian J. Chem. Sect. B., vol. 25, 1986, pp. 1146-1149.

Database Crossfire Beilstein (Online) Beilstein Institut zur Föerderung der Chemischen Wissenschaften, Frankfurt am Main, DE, Database accession No. 3016237 XP-002229373, 4, 6-diamino-N, N'-bis-(2-amino-phenyl)-isophthalamide. Third invention abstract & Chem. Heterocycl. Compd. vol. 13, 1977, pp. 1029-1032.

Database Crossfire Beilstein (Online) Beilstein Institut zur Föerderung der Chemischen Wissenschaftern, Frankfurt am Main, DE, Database accession No. 3458834 XP-002229374, N, N'-bis-(2-amino-phenyl)-phthalamide. Third invention abstract & Justus Liebigs Ann. Chem., vol. 347, 1906, p. 116.

Picard et al., "Desymmetrization Reactions: A Convenient Synthesis of Aromatic Diamide Diamines" Synthesis, vol. 10, 2001, pp. 1471-1478.

Rabilloud G et al., "Réactions de condensation de l'o-phénylenediamine avec les benzoxazin-3, 1-ones-4 substituées en position 2", Bull. Soc. Chim. Fr., 1975, pp. 2682-2686.

Csordas, Adam, "On the Biological Role of Histone Acetylation," Biochem. J., vol. 265 (1990) pp. 23-38.

Taunton, Jack, et al. "A Mammalian Histone Deacetylase Related to the Yeast Transcriptional Regulator Rpd3p," Science, vol. 272 (1996) pp. 408-411.

Grozinger, Christina M., et al., "Three Proteins Define a Class of Human Histone Deacetylases Related to Yeast Hda1p," PNAS, vol. 96 (1999) pp. 4868-4873.

Kao, Hung-Ying, et al., "Isolation of a Novel Histone Deacetylase Reveals that Class I and Class II Deacetylases Promote SMRT-Mediated Repression," Genes & Development, vol. 14 (2000) pp. 55-66.

Van den Wyngaert, Ilse, et al. "Cloning and Characterization of Human Histone Deacetylase 8," FEBS Letters, vol. 478 (2000) pp. 77-83.

Zhou, Xianbo, et al., "Cloning and Characterization of a Histone Deacetylase, HDAC9," PNAS, vol. 98, No. 19, (2001) pp. 10572-10577.

Kao, Hung-Ying, et al., "Isolation and Characterization of Mammalian HDAC10, a Novel Histone Deacetylase," J. Biol. Chem., vol. 277, No. 1 (2002) pp. 187-193.

Gao, Lin, et al. "Cloning and Functional Characterization of HDAC11, a Novel Member of the Human Histone Deacetylase Family," J. Biol. Chem., vol. 277, No. 28 (2002) pp. 25748-25755.

Richon, Victoria M., et al. "A Class of Hybrid Polar Inducers of Transformed Cell Differentiation Inhibits Histone Deacetylases," PNAS, vol. 95 (1998) pp. 3003-3007.

Yoshida, Minoru et al., "Reversible Arrest of Proliferation of Rat 3Y1 Fibroblasts in Both the G1 and G2 Phases by Trichostatin A," Experimental Cell Research, vol. 177 (1988) pp. 122-131.

Finnin, Michael S., et al., "Structures of a Histone Deacetylase Homologue Bound to the TSA and SAHA Inhibitors," Nature, vol. 401 (1999) pp. 188-193.

Yoshida, Minoru, et al., "Potent and Specific Inhibition of Mammalian Histone Deacetylase Both in Vivo and in Vitro by Trichostatin A," J. Biol. Chem., vol. 265, No. 28 (1990) pp. 17174-17179.

Ramchandani, Shyam, et al., "Inhibition of Tumorigenesis by a Cytosine-DNA, Methyltransferase, Antisense Oligodeoxynucleotide," PNAS, vol. 94 (1997) pp. 684-689.

Pon, Richard T., "Solid Phase Supports for Oligonucleotide Synthesis," Methods in Molecular Biology, vol. 20 (1993) pp. 465-496.

Alaimo, Robert J., "The Preparation and Characterization of 2-Amino-5,6-Dichloro and 2-Amino-6,7-Dichlorobenzothiazole," J. Het. Chem., vol. 8 (1971) pp. 309-310.

Zee-Cheng, Robert K. Y. et al., "Antileukemic Activity of Substituted Ureidothiazoles, Ureidothiadiazoles, and Related Compounds," J. Med. Chem., vol. 22, No. 1 (1979) pp. 28-32.

Taurins, Alfred et al., "Synthesis of Pyridyl- and Quinolyl-Substituted 2-Aminothiazoles," J. Het. Chem., vol. 7 (1970) pp. 1137-1141.

Rosowsky, Andre, et al., "5-Deaza-7-Desmethylene Analogues of 5,10-Methylene-5,6,7,8-Tetrahydrofolic Acid and Related Compounds: Synthesis and in Vitro Biological Activity," J. Het Chem., vol. 31 (1994) pp. 1241-1250.

Meyer, Thomas, et al., "A Derivative of Staurosporine (CGP 41 251) Shows Selectivity for Protein Kinase C Inhibition and in Vitro Anti-Proliferative as Well as in Vivo Anti-Tumor Activity," Int. J. Cancer, vol. 43 (1989) pp. 851-856.

Anderson, Malcolm, et al., "Imidazo[1,2-a]pyridines: A Potent and Selective Class of Cyclin-Dependent Kinase Inhibitors Identified Through Structure-Based Hybridisation," Bioorganic & Medical Chemistry Letters, vol. 13 (2003) pp. 3021-3026.

Zlatoidský, P. et al., "Synthesis of 4-(4-Guanidinobenzoyloxy)Benzamides and 1-(4-Guanidinobenzoyloxy)Benzoyloxy Acetamides as Trypsin Inhibitors," Eur. J. Med. Chem., vol. 31 (1996) pp. 895-899.

Zimmermann, Jürg, et al., "Phenylamino-Pyrimidine (PAP)—Derivates: A New Class of Potent and Highly Selective PDGF-Receptor Autophosphorylation Inhibitors," Bioorganic & Medicinal Chemistry Letters, vol. 6, No. 11 (1996) pp. 1221-1226.

Barvian, Mark, et al., "Pyrido[2,3-d]Pyrimidin-7-one Inhibitors of Cyclin-Dependent Kinases," J. Med. Chem., vol. 44 (2001), p. 1016.

Barvian, Mark, et al., "Pyrido[2,3-d]Pyrimidin-7-one Inhibitors of Cyclin-Dependent Kinases," J. Med. Chem., vol. 43, No. 24 (2000) pp. 4606-4616.

Piper, James R. et al., "Analogues of Methotrexate in Rheumatoid Arthritis. 2. Effects of 5-Deazaaminopterin, 5,10-Dideazaaminopterin, and Analogues on Type II Collagen-Induced Arthritis in Mice," J. Med. Chem., vol. 40, No. 3 (1997) pp. 377-381.

Grell, Wolfgang, et al., "Repaglinide and Related Hypoglycemic Benzoic Acid Derivatives," J. Med. Chem, vol. 41 (1998) pp. 5219-5246.

Geoffroy, Otto J. et al., "Chemoselective One-Pot Reductive Deamination of Aryl Amines," Tetrahedron Letters, vol. 42 (2001) pp. 5367-5369.

Boger, Dale L. et al., "Total Synthesis of Distamycin A and 2640 Analogues: A Solution-Phase Combinatorial Approach to the Discovery of New, Bioactive DNA Binding Agents and Development of a Rapid, High-Throughput Screen for Determining Relative DNA Binding Affinity or DNA Binding Sequence Selectivity," J. Am. Chem. Soc., vol. 122 (2000) pp. 6382-6394.

Matsuoka, Hiroharu, et al., "Antirheumatic Agents: Novel Methotrexate Derivatives Bearing a Benzoxazine or Benzothiazine Moiety," J. Med. Chem., vol. 40 (1997) pp. 105-111.

Hennequin, Laurent F., et al., "Novel 4-Anilinoquinazolines with C-7 Basic Side Chains: Design and Structure Activity Relationship of a Series of Potent, Orally Active, VEGF Receptor Tyrosine Kinase Inhibitors," J. Med. Chem., vol. 45 (2002) pp. 1300-1312.

Taylor, Edward C., "Novel 5-Desmethylene Analogues of 5,10-Dideaza-5,6,7,8-Tetrahydrofolic Acid as Potential Anticancer Agents," J. Org. Chem., vol. 57 (1992) pp. 3218-3225.

Zhu, Zhijian, et al., "Synthesis of 2,6,7-Trichloro-1-(β-D-Ribofuranosyl)Naphtho[2,3-d]Imidazole: A Linear Dimensional Analogue of the Antiviral Agent TCRB," J. Org. Chem., vol. 63 (1998) pp. 977-983.

International Search Report for PCT/CA2005/000454 dated Aug. 11, 2005.

Suzuki et al., "Benzamide Analogs As Nuclear Receptor Agonists and Reinforcement Agents for Treatment of Cell Proliferation-, Hormone-, and Vitamin-related Diseases", JP 2000256194, CA 133:247304, 2000.

Suzuki et al., Benzamide Derivatives As Histone Deacetylase Inhibitors For Treating Tumors and Other Diseases, JP 11302173, CA 131:319669, 1999.

Suzuki et al., "Preparation Of Cell Differentiation-Inducing N-Phenylbenzamides and Anticancers", JP 11269146, CA 131:257321, 1999.

INHIBITORS OF HISTONE DEACETYLASE

This application is a 371 of PCT/US04/31591, filed Sep. 24, 2004, and claims priority from U.S. Provisional Patent Application No. 60/505,884, filed on Sep. 24, 2003, U.S. Provisional Patent Application No. 60/532,973, filed on Dec. 29, 2003, and U.S. Provisional Patent Application No. 60/561,082, filed on Apr. 9, 2004

BACKGROUND OF THE INVENTION

1. Field of the Invention

This invention relates to the inhibition of histone deacetylase. More particularly, the invention relates to compounds and methods for inhibiting histone deacetylase enzymatic activity.

2. Summary of the Related Art

In eukaryotic cells, nuclear DNA associates with histones to form a compact complex called chromatin. The histones constitute a family of basic proteins which are generally highly conserved across eukaryotic species. The core histones, termed H2A, H2B, H3, and H4, associate to form a protein core. DNA winds around this protein core, with the basic amino acids of the histones interacting with the negatively charged phosphate groups of the DNA. Approximately 146 base pairs of DNA wrap around a histone core to make up a nucleosome particle, the repeating structural motif of chromatin.

Csordas, *Biochem. J.,* 286: 23-38 (1990) teaches that histones are subject to posttranslational acetylation of the α,ε-amino groups of N-terminal lysine residues, a reaction that is catalyzed by histone acetyl transferase (HAT1). Acetylation neutralizes the positive charge of the lysine side chain, and is thought to impact chromatin structure. Indeed, Taunton et al., *Science,* 272: 408-411 (1996), teaches that access of transcription factors to chromatin templates is enhanced by histone hyperacetylation. Taunton et al. further teaches that an enrichment in underacetylated histone H4 has been found in transcriptionally silent regions of the genome.

Histone acetylation is a reversible modification, with deacetylation being catalyzed by a family of enzymes termed histone deacetylases (HDACs). Grozinger et al., *Proc. Natl. Acad. Sci. USA,* 96: 4868-4873 (1999), teaches that HDACs are divided into two classes, the first represented by yeast Rpd3-like proteins, and the second represented by yeast Hda1-like proteins. Grozinger et al. also teaches that the human HDAC1, HDAC2, and HDAC3 proteins are members of the first class of HDACs, and discloses new proteins, named HDAC4, HDAC5, and HDAC6, which are members of the second class of HDACs. Kao et al., *Genes & Dev.,* 14: 55-66 (2000), discloses HDAC7, a new member of the second class of HDACs. More recently, Hu et al. *J. Bio. Chem.* 275:15254-13264 (2000) and Van den Wyngaert, *FEBS,* 478: 77-83 (2000) disclose HDAC8, a new member of the first class of HDACs.

Richon et al., *Proc. Natl. Acad. Sci. USA,* 95: 3003-3007 (1998), discloses that HDAC activity is inhibited by trichostatin A (TSA), a natural product isolated from *Streptomyces hygroscopicus,* and by a synthetic compound, suberoylanilide hydroxamic acid (SAHA). Yoshida and Beppu, *Exper. Cell Res.,* 177: 122-131 (1988), teaches that TSA causes arrest of rat fibroblasts at the $G_1$ and $G_2$ phases of the cell cycle, implicating HDAC in cell cycle regulation. Indeed, Finnin et al., *Nature,* 401: 188-193 (1999), teaches that TSA and SAHA inhibit cell growth, induce terminal differentiation, and prevent the formation of tumors in mice. Suzuki et al., U.S. Pat. No. 6,174,905, EP 0847992, JP 258863/96, and Japanese Application No. 10138957, disclose benzamide derivatives that induce cell differentiation and inhibit HDAC. Delorme et al., WO 01/38322 and PCT/IB01/00683, disclose additional compounds that serve as HDAC inhibitors.

The molecular cloning of gene sequences encoding proteins with HDAC activity has established the existence of a set of discrete HDAC enzyme isoforms. Some isoforms have been shown to possess specific functions, for example, it has been shown that HDAC-6 is involved in modulation of microtubule activity. However, the role of the other individual HDAC enzymes has remained unclear.

These findings suggest that inhibition of HDAC activity represents a novel approach for intervening in cell cycle regulation and that HDAC inhibitors have great therapeutic potential in the treatment of cell proliferative diseases or conditions. To date, few inhibitors of histone deacetylase are known in the art.

BRIEF SUMMARY OF THE INVENTION

Ortho-amino benzamides are known HDAC inhibitors. Substitutions at the ortho- and meta-positions relative to the amino group are detrimental to the potency of the inhibitors; however, some small substituents such as —$CH_3$, —F, or —$OCH_3$ can be tolerated to a certain extent. We have now found that o-amino benzamide HDAC inhibitors having a much bigger but flat aromatic and heteroaromatic substituents such as phenyl, furyl, thienyl and the like para to the amino moiety are not only well tolerated but cause significant increase in HDAC inhibition activity.

Accordingly, the present invention provides new compounds and methods for treating cell proliferative diseases. The invention provides new inhibitors of histone deacetylase enzymatic activity.

In a first aspect, the invention provides compounds that are useful as inhibitors of histone deacetylase.

In a second aspect, the invention provides a composition comprising an inhibitor of histone deacetylase according to the invention or a pharmaceutically acceptable salt thereof and a pharmaceutically acceptable carrier, excipient, or diluent.

In a third aspect, the invention provides a method of inhibiting histone deacetylase in a cell, comprising contacting a cell in which inhibition of histone deacetylase is desired with an inhibitor of histone deacetylase of the invention.

The foregoing merely summarizes certain aspects of the invention and is not intended to be limiting in nature. These aspects and other aspects and embodiments are described more fully below. All publications (patent or other) are hereby incorporated by reference in their entirety; in the event of any conflict between these materials and the present specification, the present specification shall control.

BRIEF DESCRIPTION OF THE DRAWING

The figures displays antineoplastic effects of a histone deacetylase inhibitor according to the invention on human tumor xenografts in vivo, as described in Assay Example 2, infra.

DETAILED DESCRIPTION OF THE PREFERRED EMBODIMENTS

Figure 1:
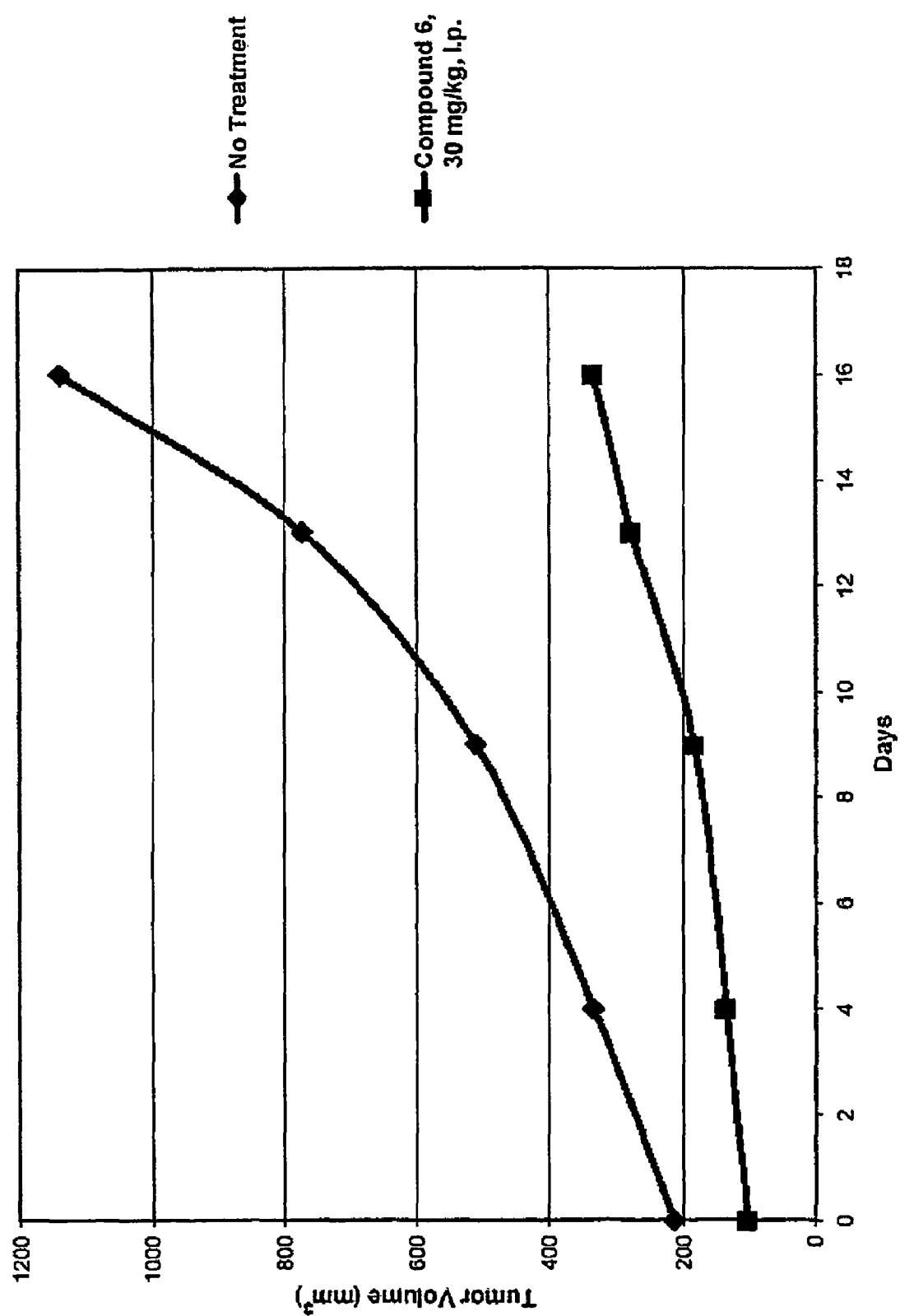
FIG. 1 displays antineoplastic effects of a histone deacetylase inhibitor in hct116 human colorectal carcinoma cells using compound 6.

The invention provides compounds and methods for inhibiting histone deacetylase enzymatic activity. The invention also provides compositions and methods for treating cell proliferative diseases and conditions. The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

For purposes of the present invention, the following definitions will be used (unless expressly stated otherwise):

As used herein, the terms "histone deacetylase" and "HDAC" are intended to refer to any one of a family of enzymes that remove acetyl groups from the ω-amino groups of lysine residues at the N-terminus of a histone. Unless otherwise indicated by context, the term "histone" is meant to refer to any histone protein, including H1, H2A, H$_2$B, H3, H4, and H5, from any species. Preferred histone deacetylases include class I and class II enzymes. Preferably the histone deacetylase is a human HDAC, including, but not limited to, HDAC-1, HDAC-2, HDAC-3, HDAC-4, HDAC-5, HDAC-6, HDAC-7, HDAC-8, HDAC-9, HDAC-10, and HDAC-11. In some other preferred embodiments, the histone deacetylase is derived from a protozoal or fungal source.

The terms "histone deacetylase inhibitor" and "inhibitor of histone deacetylase" are used to identify a compound having a structure as defined herein, which is capable of interacting with a histone deacetylase and inhibiting its enzymatic activity. "Inhibiting histone deacetylase enzymatic activity" means reducing the ability of a histone deacetylase to remove an acetyl group from a histone. In some preferred embodiments, such reduction of histone deacetylase activity is at least about 50%, more preferably at least about 75%, and still more preferably at least about 90%. In other preferred embodiments, histone deacetylase activity is reduced by at least 95% and more preferably by at least 99%.

Preferably, such inhibition is specific, i.e., the histone deacetylase inhibitor reduces the ability of a histone deacetylase to remove an acetyl group from a histone at a concentration that is lower than the concentration of the inhibitor that is required to produce another, unrelated biological effect. Preferably, the concentration of the inhibitor required for histone deacetylase inhibitory activity is at least 2-fold lower, more preferably at least 5-fold lower, even more preferably at least 10-fold lower, and most preferably at least 20-fold lower than the concentration required to produce an unrelated biological effect.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g. CH$_3$—CH$_2$—), in certain circumstances a bivalent linking moiety can be "alkyl," in which case those skilled in the art will understand the alkyl to be a divalent radical (e.g., —CH$_2$—CH$_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for O, and 2, 4, or 6 for S, depending on the oxidation state of the S). On occasion a moiety may be defined, for example, as (A)$_a$-B—, wherein a is 0 or 1. In such instances, when a is 0 the moiety is B- and when a is 1 the moiety is A-B—.

For simplicity, reference to a "C$_n$-C$_m$" heterocyclyl or "C$_n$-C$_m$" heteroaryl means a heterocyclyl or heteroaryl having from "n" to "m" annular atoms, where "n" and "m" are integers. Thus, for example, a C$_5$-C$_6$-heterocyclyl is a 5- or 6-membered ring having at least one heteroatom, and includes pyrrolidinyl (C$_5$) and piperidinyl (C$_6$); C$_6$-hetoaryl includes, for example, pyridyl and pyrimidyl.

The term "hydrocarbyl" refers to a straight, branched, or cyclic alkyl, alkenyl, or alkynyl, each as defined herein. A "C$_0$" hydrocarbyl is used to refer to a covalent bond. Thus, "C$_0$-C$_3$-hydrocarbyl" includes a covalent bond, methyl, ethyl, ethenyl, ethynyl, propyl, propenyl, propynyl, and cyclopropyl.

The term "alkyl" as employed herein refers to straight and branched chain aliphatic groups having from 1 to 12 carbon atoms, preferably 1-8 carbon atoms, and more preferably 1-6 carbon atoms, which is optionally substituted with one, two or three substituents. Preferred alkyl groups include, without limitation, methyl, ethyl, propyl, isopropyl, butyl, isobutyl, sec-butyl, tert-butyl, pentyl, and hexyl. A "C$_0$" alkyl (as in "C$_0$-C$_3$-alkyl") is a covalent bond (like "C$_0$" hydrocarbyl).

The term "alkenyl" as used herein means an unsaturated straight or branched chain aliphatic group with one or more carbon-carbon double bonds, having from 2 to 12 carbon atoms, preferably 2-8 carbon atoms, and more preferably 2-6 carbon atoms, which is optionally substituted with one, two or three substituents. Preferred alkenyl groups include, without limitation, ethenyl, propenyl, butenyl, pentenyl, and hexenyl.

The term "alkynyl" as used herein means an unsaturated straight or branched chain aliphatic group with one or more carbon-carbon triple bonds, having from 2 to 12 carbon atoms, preferably 2-8 carbon atoms, and more preferably 2-6 carbon atoms, which is optionally substituted with one, two or three substituents. Preferred alkynyl groups include, without limitation, ethynyl, propynyl, butynyl, pentynyl, and hexynyl.

An "alkylene," "alkenylene," or "alkynylene" group is an alkyl, alkenyl, or alkynyl group, as defined hereinabove, that is positioned between and serves to connect two other chemical groups. Preferred alkylene groups include, without limitation, methylene, ethylene, propylene, and butylene. Preferred alkenylene groups include, without limitation, ethenylene, propenylene, and butenylene. Preferred alkynylene groups include, without limitation, ethynylene, propynylene, and butenylene.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally is optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroalkyl" refers to an alkyl group, as defined hereinabove, wherein one or more carbon atoms in the chain are replaced by a heteroatom selected from the group consisting of O, S, and N.

An "aryl" group is a $C_6$-$C_{14}$ aromatic moiety comprising one to three aromatic rings, which is optionally substituted. Preferably, the aryl group is a $C_6$-$C_{10}$ aryl group. Preferred aryl groups include, without limitation, phenyl, naphthyl, anthracenyl, and fluorenyl. An "aralkyl" or "arylalkyl" group comprises an aryl group covalently linked to an alkyl group, either of which may independently be optionally substituted or unsubstituted. Preferably, the aralkyl group is $(C_1$-$C_6)$alk$(C_9$-$C_{10})$aryl, including, without limitation, benzyl, phenethyl, and naphthylmethyl.

A "heterocyclic" group (or "heterocyclyl") is an optionally substituted non-aromatic mono-, bi-, or tricyclic structure having from about 3 to about 14 atoms, wherein one or more atoms are selected from the group consisting of N, O, and S. One ring of a bicyclic heterocycle or two rings of a tricyclic heterocycle may be aromatic, as in indan and 9,10-dihydro anthracene. The heterocyclic group is optionally substituted on carbon with oxo or with one of the substituents listed above. The heterocyclic group may also independently be substituted on nitrogen with alkyl, aryl, aralkyl, alkylcarbonyl, alkylsulfonyl, arylcarbonyl, arylsulfonyl, alkoxycarbonyl, aralkoxycarbonyl, or on sulfur with oxo or lower alkyl. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain preferred embodiments, the heterocyclic group is fused to an aryl, heteroaryl, or cycloalkyl group. Examples of such fused heterocycles include, without limitation, tetrahydroquinoline and dihydrobenzofuran. Specifically excluded from the scope of this term are compounds where an annular O or S atom is adjacent to another O or S atom.

In certain preferred embodiments, the heterocyclic group is a heteroaryl group. As used herein, the term "heteroaryl" refers to optionally substituted groups having 5 to 14 ring atoms, preferably 5, 6, 9, or 10 ring atoms; having 6, 10, or 14 pi electrons shared in a cyclic array; and having, in addition to carbon atoms, between one or more heteroatoms selected from the group consisting of N, O, and S. For example, a heteroaryl group may be pyrimidinyl, pyridinyl, benzimidazolyl, thienyl, benzothiazolyl, benzofuranyl and indolinyl. Preferred heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, and isoxazolyl.

A "heteroaralkyl" or "heteroarylalkyl" group comprises a heteroaryl group covalently linked to an alkyl group, either of which is independently optionally substituted or unsubstituted. Preferred heteroalkyl groups comprise a $C_1$-$C_6$ alkyl group and a heteroaryl group having 5, 6, 9, or 10 ring atoms. Specifically excluded from the scope of this term are compounds having adjacent annular O and/or S atoms. Examples of preferred heteroaralkyl groups include pyridylmethyl, pyridylethyl, pyrrolylmethyl, pyrrolylethyl, imidazolylmethyl, imidazolylethyl, thiazolylmethyl, and thiazolylethyl.

An "arylene," "heteroarylene," or "heterocyclylene" group is an aryl, heteroaryl, or heterocyclyl group, as defined hereinabove, that is positioned between and serves to connect two other chemical groups.

Preferred heterocyclyls and heteroaryls include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl (hereinafter embodiment [0034]).

As employed herein, when a moiety (e.g., cycloalkyl, hydrocarbyl, aryl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH-substituted with oxo is —C(O)—) nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, (b) $C_1$-$C_5$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$ alkylsulfinyl, arylalkylsulfinyl, arylsulfinyl, $C_1$-$C_8$ alkylsulfonyl, arylalkylsulfonyl, arylsulfonyl, $C_0$-$C_6$ N-alkyl carbamoyl, $C_2$-$C_{15}$ N,N-dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, $C_5$-$C_{15}$ heteroaryl or any of these rings fused or spiro-fused to a cycloalkyl, heterocyclyl, or aryl, wherein each of the foregoing is further optionally substituted with one more moieties listed in (a), above; and (c) —$(CH_2)_s$—$NR^{30}R^{31}$, wherein s is from 0 (in which case the nitrogen is directly bonded to the moiety that is substituted) to 6, and $R^{30}$ and $R^{31}$ are each independently hydrogen, cyano, oxo, carboxamido, amidino, $C_1$-$C_8$ hydroxyalkyl, $C_1$-$C_3$ alkylaryl, aryl-$C_1$-$C_3$ alkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, aryl-$C_1$-$C_3$ alkoxycarbonyl, $C_2$-$C_8$ acyl, $C_1$-$C_8$ alkylsulfonyl, arylalkylsulfonyl, arylsulfonyl, aroyl, aryl, cycloalkyl, heterocyclyl, or heteroaryl, wherein each of the foregoing is further optionally substituted with one more moieties listed in (a), above; or $R^{30}$ and $R^{31}$ taken together with the N to which they are attached form a heterocyclyl or heteroaryl, each of which is optionally substituted with from 1 to 3 substituents from (a), above.

In addition, substituents on cyclic moieties (i.e., cycloalkyl, heterocyclyl, aryl, heteroaryl) include 5-6 membered mono- and 9-14 membered bi-cyclic moieties fused to the parent cyclic moiety to form a bi- or tri-cyclic fused ring system. For example, an optionally substituted phenyl includes, but not limited to, the following:

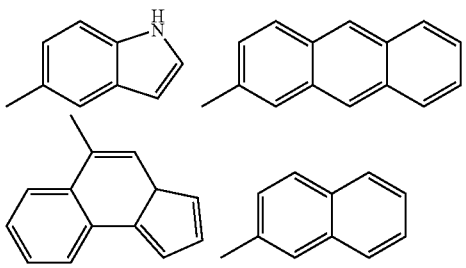

A "halohydrocarbyl" is a hydrocarbyl moiety in which from one to all hydrogens have been replaced with one or more halo.

The term "halogen" or "halo" as employed herein refers to chlorine, bromine, fluorine, or iodine. As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., $NH_2$—CO—). The nitrogen atom of an acylamino or carbamoyl substituent is additionally substituted. The term "sulfonamido" refers to a sulfonamide substituent attached by either the sulfur or the nitrogen atom. The term "amino" is meant to include $NH_2$, alkylamino, arylamino, and cyclic amino groups. The term "ureido" as employed herein refers to a substituted or unsubstituted urea moiety.

The term "radical" as used herein means a chemical moiety comprising one or more unpaired electrons.

A moiety that is substituted is one in which one or more hydrogens have been independently replaced with another chemical substituent. As a non-limiting example, substituted phenyls include 2-fluorophenyl, 3,4-dichlorophenyl, 3-chloro-4-fluoro-phenyl, 2-fluoro-3-propylphenyl. As another non-limiting example, substituted N-octyls include 2,4 dimethyl-5-ethyl-octyl and 3-cyclopentyl-octyl. Included within this definition are methylenes (—$CH_2$—) substituted with oxygen to form carbonyl —CO—).

An "unsubstituted" moiety as defined above (e.g., unsubstituted cycloalkyl, unsubstituted heteroaryl, etc.) means that moiety as defined above that does not have any of the optional substituents for which the definition of the moiety (above) otherwise provides. Thus, for example, while an "aryl" includes phenyl and phenyl substituted with a halo, "unsubstituted aryl" does not include phenyl substituted with a halo.

Throughout the specification preferred embodiments of one or more chemical substituents are identified. Also preferred are combinations of preferred embodiments. For example, embodiment [0055] describes preferred embodiments of $Cy^2$ in the compound of formula (1) and embodiment [0071] describes preferred embodiments of $R^2$ to $R^4$ of the compound of formula (1). Thus, also contemplated as within the scope of the invention are compounds of formula (1) in which $Cy^2$ is as described in embodiment [0055] and $Ay^2$ and $R^1$ to $R^4$ are as described in embodiment [0071].

Some compounds of the invention may have chiral centers and/or geometric isomeric centers (E- and Z-isomers), and it is to be understood that the invention encompasses all such optical, diastereoisomers and geometric isomers. The invention also comprises all tautomeric forms of the compounds disclosed herein.

The compounds of the invention may be administered in the form of an in vivo hydrolyzable ester or in vivo hydrolyzable amide. An in vivo hydrolyzable ester of a compound of the invention containing carboxy or hydroxy group is, for example, a pharmaceutically acceptable ester which is hydrolyzed in the human or animal body to produce the parent acid or alcohol. Suitable pharmaceutically acceptable esters for carboxy include $C_{1-6}$-alkoxymethyl esters (e.g., methoxymethyl), $C_{1-6}$-alkanoyloxymethyl esters (e.g., for example pivaloyloxymethyl), phthalidyl esters, $C_{3-8}$-cycloalkoxycarbonyloxy$C_{1-6}$-alkyl esters (e.g., 1-cyclohexylcarbonyloxyethyl); 1,3-dioxolen-2-onylmethyl esters (e.g., 5-methyl-1,3-dioxolen-2-onylmethyl; and $C_{1-6}$-alkoxycarbonyloxyethyl esters (e.g., 1-methoxycarbonyloxyethyl) and may be formed at any carboxy group in the compounds of this invention.

An in vivo hydrolyzable ester of a compound of the invention containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolyzable ester forming groups for hydroxy include alkanoyl, benzoyl, phenylacetyl and substituted benzoyl and phenylacetyl, alkoxycarbonyl (to give alkyl carbonate esters), dialkylcarbamoyl and N—(N,N-dialkylaminoethyl)-N-alkylcarbamoyl(to give carbamates), N,N-dialkylaminoacetyl and carboxyacetyl. Examples of substituents on benzoyl include morpholino and piperazino linked from a ring nitrogen atom via a methylene group to the 3- or 4-position of the benzoyl ring. A suitable value for an in vivo hydrolyzable amide of a compound of the invention containing a carboxy group is, for example, a N—$C_{1-6}$-alkyl or N,N-di-$C_{1-6}$-alkyl amide such as N-methyl, N-ethyl, N-propyl, N,N-dimethyl, N-ethyl-N-methyl or N,N-diethylamide.

Compounds

In the first aspect, the invention comprises the histone deacetylase inhibitors of formula (1) (hereinafter embodiment [0046]:

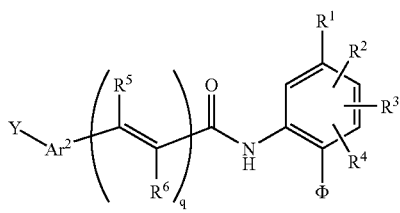

(1)

or a pharmaceutically acceptable salt thereof, wherein $Ar^2$ is a saturated or mono- or poly-unsaturated $C_5$-$C_{14}$-mono- or fused poly-cyclic hydrocarbyl, optionally containing one, two, three, or four annular heteroatoms per ring optionally substituted with one or more groups selected from $C_1$-$C_7$-alkyl, hydroxy, $C_1$-$C_7$-alkoxy, halo, and amino, provided that an annular O or S is not adjacent to another annular O or S;

$R^5$ and $R^6$ are independently selected from the group consisting of hydrogen, $C_1$-$C_7$-alkyl, aryl, and aralkyl;

$R^2$, $R^3$ and $R^4$ are independently selected from the group consisting of hydrogen, halogen, —$NH_2$, nitro, hydroxy, aryl, heterocyclyl, $C_3$-$C_8$-cycloalkyl, heteroaryl, $C_1$-$C_7$-alkyl, haloalkyl, $C_1$-$C_7$-alkenyl, $C_1$-$C_7$-alkynyl, $C_1$-$C_7$-acyl, $C_1$-$C_7$-alkyl-aryloxy, $C_1$-$C_7$-alkyl-arylsulfanyl, $C_1$-$C_7$-alkyl-arylsulfinyl, $C_1$-$C_7$-alkyl-arylsulfonyl, $C_1$-$C_7$-alkyl-arylaminosulfonyl, $C_1$-$C_7$-alkyl-arylamine, $C_1$-$C_7$-alkynyl-C(O)-amine, $C_1$-$C_7$-alkenyl-C(O)-amine, $C_1$-$C_7$-alkynyl-$R^9$, $C_1$-$C_7$-alkenyl-$R^9$ wherein $R^9$ is hydrogen, hydroxy, amino, $C_1$-$C_7$-alkyl or $C_1$-$C_7$-alkoxy;

q is 0 or 1;

$R^1$ is a mono-, bi-, or tri-cyclic aryl or heteroaryl, each of which is optionally substituted;

Φ is —$NH_2$ or —OH and

Y is any pharmaceutically acceptable chemical moiety consisting of 1 to 50 atoms;

provided that when $R^1$ is N-imidazolyl, $R^2$-$R^4$ are H, q is 0, and $Ar^2$ is pyridine, Y is not Cl; and when $R^1$ is p-aminophenyl, $R^2$-$R^4$ are H, q is 0, and $Ar^2$ is phenyl, Y is not H.

The atoms that comprise the Y moiety are preferably those found in pharmaceuticals, including, but not limited to, H, C, N, O, S, F, Cl, Br, I, and P (hereinafter embodiment [0047]). Numerous representative examples of Y are displayed in embodiments [0050]-[0088], [0098]-[0110], and [0115]-[0207]. Y moieties of the compounds of the present invention also can be found in the following publications (either per se or as part of a disclosed molecule): WO 03/024448, U.S. Pat. No. 6,174,905, JP 11-269146 (1999), JP 11-302173 (1999), JP 2001131130, EP 0847992, JP 10152462, JP 2002332267, JP 11302173, and JP 2003137866. For example, in these publications many different Y moieties are readily identified in molecules of structure Y—$Ar^2$—(CH=CH)$_a$—C(O)—NH—Z, wherein $Ar^2$ is defined herein, a is 0 or 1, Z is —OH or aryl, and the $Ar^2$, —CH=CH—, and aryl moieties may be optionally substituted as suggested in the publication.

In a preferred embodiment of the compounds according to embodiment [0046], $R^1$ is an aryl selected from phenyl, naphthyl, anthracenyl, and fluorenyl. In another preferred embodiment, $R^1$ is a heteroaryl selected from those recited in embodiment [0034]. Other preferred $R^1$ moieties include azolyls (e.g., thiazolyl, oxazolyl, oxadiazolyl, thiadiazolyl, etc.), pyridyl, and pyridinyl. More preferably, $R^1$ is furanyl or thienyl. Such preferred embodiments are hereinafter collectively referred to as embodiment [0048]).

In a preferred embodiment of all the compounds of the invention, $R^2$, $R^3$, and $R^1$ are all hydrogen. Also preferred are compounds in which Φ is —$NH_2$ or —OH. Such preferred embodiments are hereinafter collectively referred to as embodiment [0049]).

In a preferred embodiment of the compounds of embodiments [0046], [0048], and [0049] (hereinafter embodiment [0050], Y is $Cy^2$—$X^1$—, wherein $Cy^2$ is hydrogen, cycloalkyl, aryl, heteroaryl, or heterocyclyl, each of which is optionally substituted and each of which is optionally fused to one or two aryl or heteroaryl rings, or to one or two saturated or partially unsaturated cycloalkyl or heterocyclic rings, and wherein any of the aforementioned rings are optionally substituted; and $X^1$ is selected from the group consisting of a covalent bond, $M^1$-$L^2$-$M^1$, and $L^2$-$M^2$-$L^2$ wherein $L^2$, at each occurrence, is independently selected from the group consisting of a chemical bond, $C_0$-$C_4$-hydrocarbyl, $C_0$-$C_4$-hydrocarbyl-(NH)—$C_0$-$C_4$-hydrocarbyl, $C_0$-$C_4$-hydrocarbyl-(S)—$C_0$-$C_4$-hydrocarbyl, and $C_0$-$C_4$-hydrocarbyl-(O)—$C_0$-$C_4$-hydrocarbyl, provided that $L^2$ is not a chemical bond when $X^1$ is $M^1$-$L^2$-$M^1$;

$M^1$, at each occurrence, is independently selected from the group consisting of —O—, —N($R^7$)—, —S—, —S(O)—, S(O)$_2$—, —S(O)$_2$N($R^7$)—, —N($R^7$)—S(O)$_2$—, —C(O)—, —C(O)—NH—, —NH—C(O)—, —NH—C(O)—O— and —O—C(O)—NH—, —NH—C(O)—NH—, $R^7$ is selected from the group consisting of hydrogen, $C_1$-$C_6$-hydrocarbyl, aryl, aralkyl, acyl, $C_0$-$C_6$-hydrocarbyl-heterocyclyl, and $C_0$-$C_6$-hydrocarbyl-heteroaryl, wherein the hydrocarbyl moieties are optionally substituted with —OH, —$NH_2$, —N(H)$CH_3$, —N($CH_3$)$_2$, or halo; and $M^2$ is selected from the group consisting of $M^1$, heteroarylene, and heterocyclylene, either of which rings optionally is substituted.

In some preferred embodiments according to embodiment [0050] (hereinafter collectively referred to as embodiment [0051]), the optional substituents of $Cy^2$ are selected from $C_1$-$C_7$-alkyl, $C_1$-$C_7$-alkoxy, halo, di-$C_1$-$C_7$-alkylamino-$C_1$-$C_7$-alkoxy and heteroaryl.

In some preferred embodiments according to embodiment [0050] (hereinafter collectively referred to as embodiment [0052]), $X^1$ is selected from the group consisting of a —N(Z)-$C_0$-$C_7$-alkyl-, —O—$C_0$-$C_7$-alkyl-, —C(H)=CH—$C_0$-$C_7$-alkyl-, —S—$C_0$-$C_7$-alkyl-, or —$C_1$-$C_7$-alkyl-, wherein Z is —H or —$C_1$-$C_7$-alkyl-optionally substituted with —OH, —$NH_2$, or halo.

In some embodiments of the compounds according to embodiment [0050], $X^1$ is a chemical bond. In some embodiments, $X^1$ is $L^2$-$M^2$-$L^2$, and $M^2$ is selected from the group consisting of —NH—, —N($CH_3$)—, —S—, —C(O)—N(H)—, and —O—C(O)—N(H)—. In some embodiments, $X^1$ is $L^2$-$M^2$-$L^2$, where at least one occurrence of $L^2$ is a chemical bond. In other embodiments, $X^1$ is $L^2$-$M^2$-$L^2$, where at least one occurrence of $L^2$ is alkylene, preferably methylene. In still other embodiments, $X^1$ is $L^2$-$M^2$-$L^2$, where at least one occurrence of $L^2$ is alkenylene. In some embodiments, $X^1$ is $M^1$-$L^2$-$M^1$ and $M^1$ is selected from the group consisting of —NH—, —N($CH_3$)—, —S—, and —C(O)—N(H)—. Preferred $X^1$ are selected from methylene, aminomethyl, and thiomethyl. Such preferred embodiments are hereinafter collectively referred to as embodiment [0053].

In some embodiments of the compounds according to embodiment [0050], Cy² is aryl or heteroaryl, e.g., phenyl, pyridyl, imidazolyl, or quinolyl, each of which optionally is substituted. In some embodiments, Cy² is heterocyclyl, e.g.,

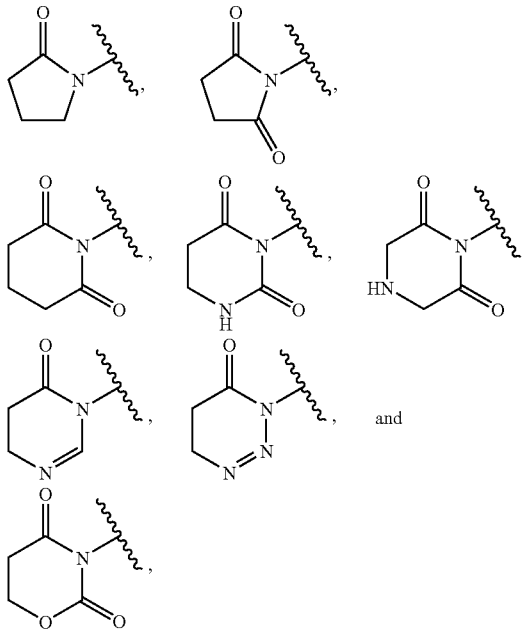

each of which optionally is substituted and optionally is fused to one or more aryl rings. In some embodiments, Cy² has from one and three substituents independently selected from the group consisting of alkyl, alkoxy, amino, nitro, halo, haloalkyl, and haloalkoxy. Examples of preferred substituents include methyl, methoxy, fluoro, trifluoromethyl, trifluoromethoxy, nitro, amino, aminomethyl, and hydroxymethyl. Such embodiments are hereinafter collectively referred to as embodiment [0054]).

In some preferred embodiments of the compounds according to embodiment [0050], Cy² is phenyl, pyrimidinyl, benzimidazolyl or benzothiazolyl, each optionally substituted with one to three CH₃O—, dimethylamino-ethoxy, chloro, fluoro and pyridinyl. In a more preferred embodiment, Cy² is phenyl substituted with one to three CH₃O—. Such preferred embodiments are hereinafter collectively referred to as embodiment [0055].

In some embodiments according to embodiment [0046] (hereinafter collectively referred to as embodiment [0056]), Y is (V'-L⁴)$_t$-V-L³-, wherein
  L³ is a direct bond, —C₁-C₆-hydrocarbyl, —(C₁-C₃-hydrocarbyl)$_{m1}$-X'—(C₁-C₃-hydrocarbyl)$_{m2}$, —NH—(C₀-C₃-hydrocarbyl), (C₁-C₃-hydrocarbyl)-NH—, or —NH—(C₁-C₃-hydrocarbyl)-NH—;
  m1 and m2 are independently 0 or 1;
  X' is —N(R²¹)—, —C(O)N(R²¹)—, N(R²¹)C(O)—, —O—, or —S—;
  R²¹ is —H, V'''-(C₁-C₆-hydrocarbyl)$_a$;
  L⁴ is (C₁-C₆-hydrocarbyl)$_a$-M-(C₁-C₆-hydrocarbyl)$_b$;
  a and b are independently 0 or 1;
  M is —NH—, —NH—, NHC(O)—, —C(O)NH—, —C(O)—, —SO₂—, —NHSO₂—, or —SO₂NH—
  V, V' and V''' are independently selected from cycloalkyl, heterocyclyl, aryl, and heteroaryl;
  t is 0 or 1.

In some embodiments according to embodiment [0056] (hereinafter collectively referred to as embodiment [0057]), Y is V-L³, wherein
  L³ is —NH—CH— or —CH—NH—;
  V is phenyl optionally substituted with from 1 to 3 moieties independently selected from halo, hydroxy, C₁-C₆-hydrocarbyl, C₁-C₆-hydrocarbyl-oxy or -thio (particularly methoxy or methylthio), wherein each of the hydrocarbyl moieties are optionally substituted with one or more moieties independently selected from halo, nitro, nitroso, formyl, acetyl, amino, sulfonamido, and cyano.

In some preferred embodiments of the compound according to embodiment [0056] (hereinafter collectively referred to as embodiment [0058]), V is an optionally substituted ring moiety selected from:

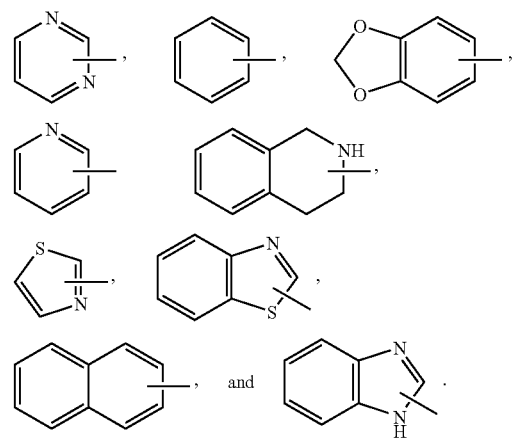

In another preferred embodiment of the compounds according to embodiment [0046] (hereinafter embodiment [0059]), Y is selected from:

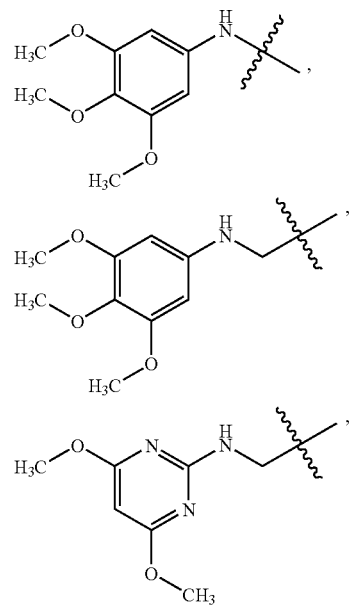

-continued
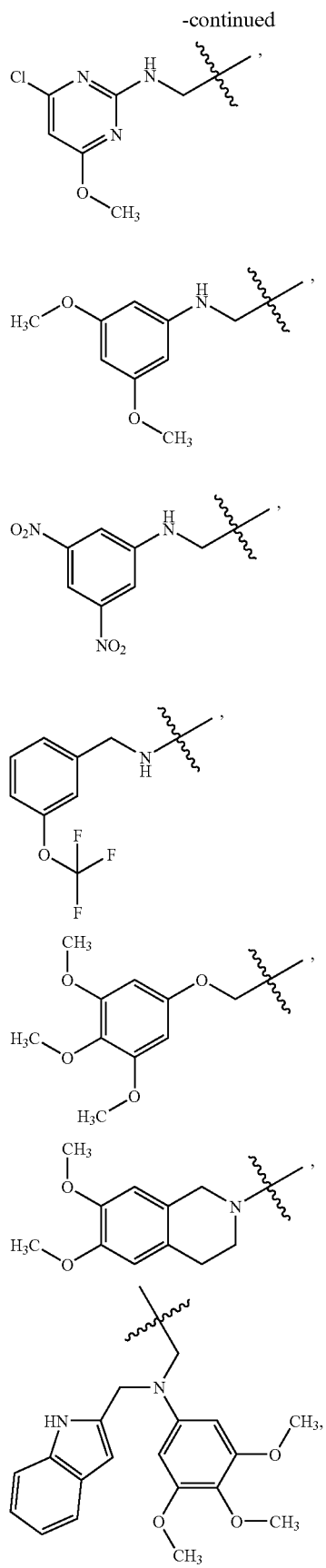
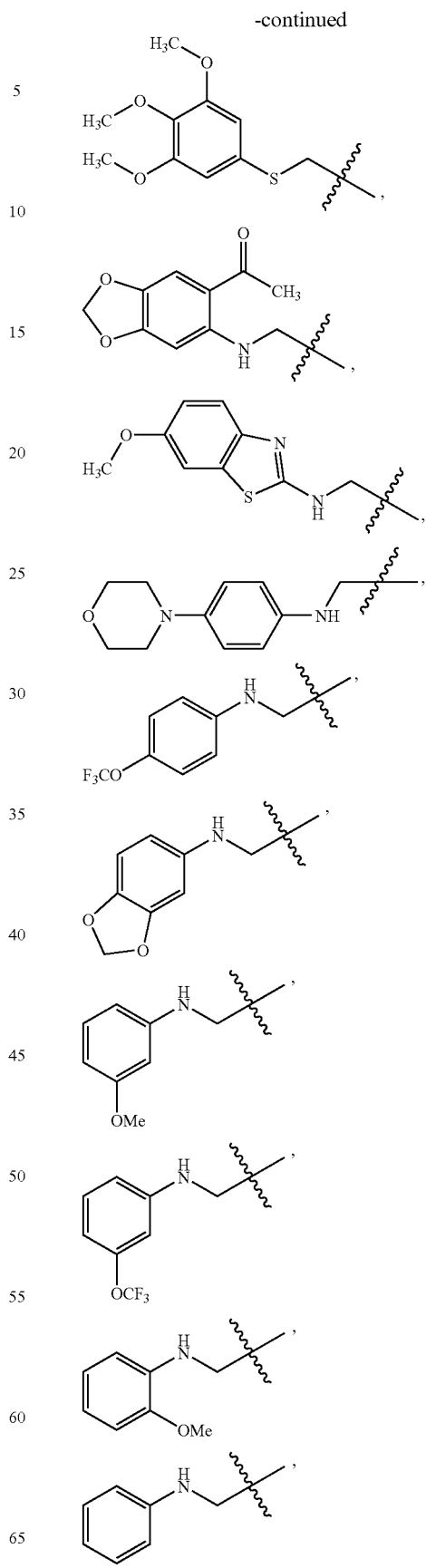

-continued
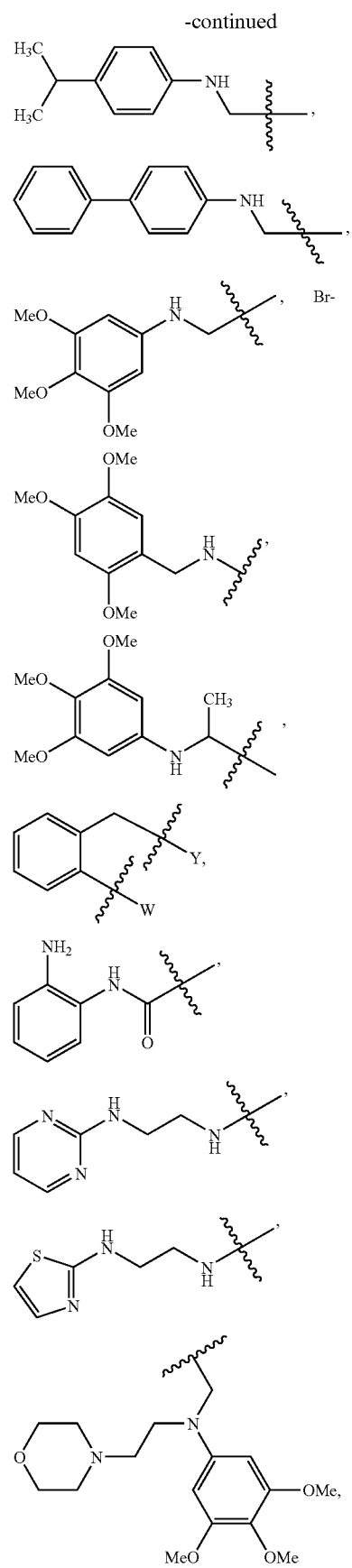
-continued
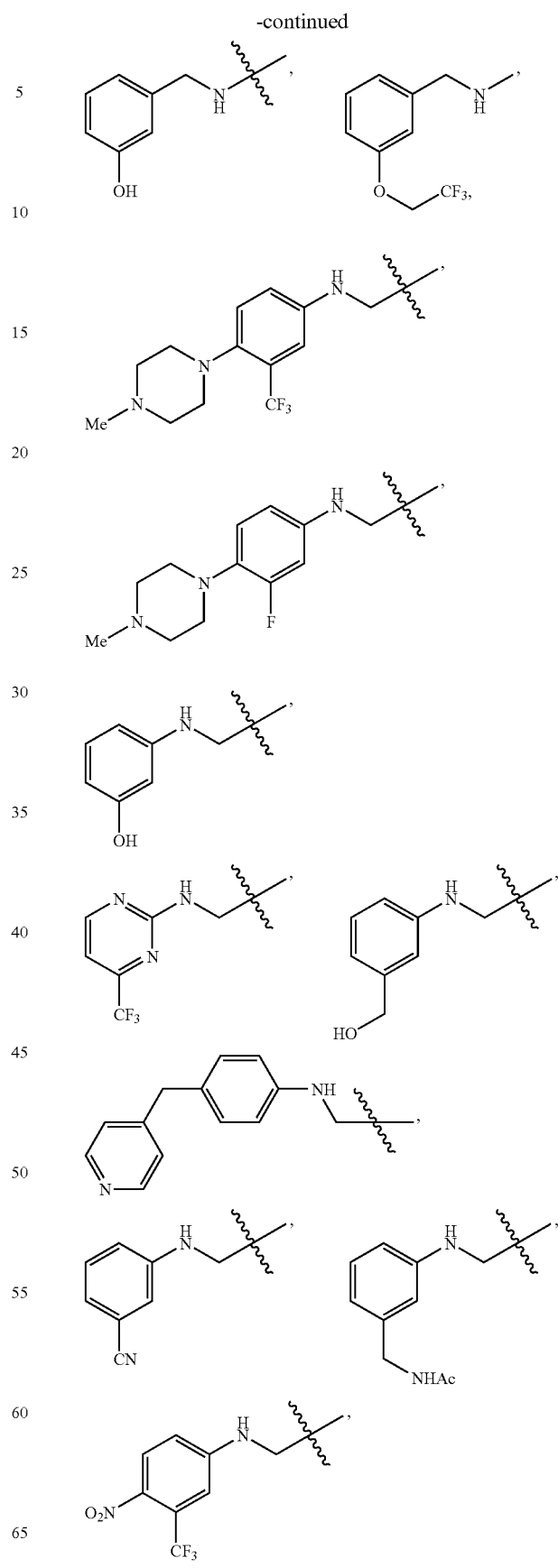

-continued
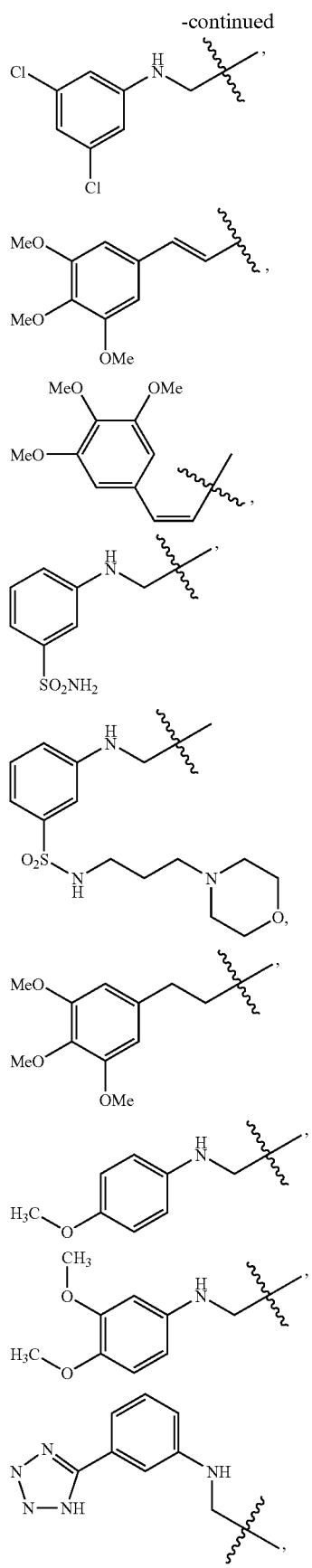
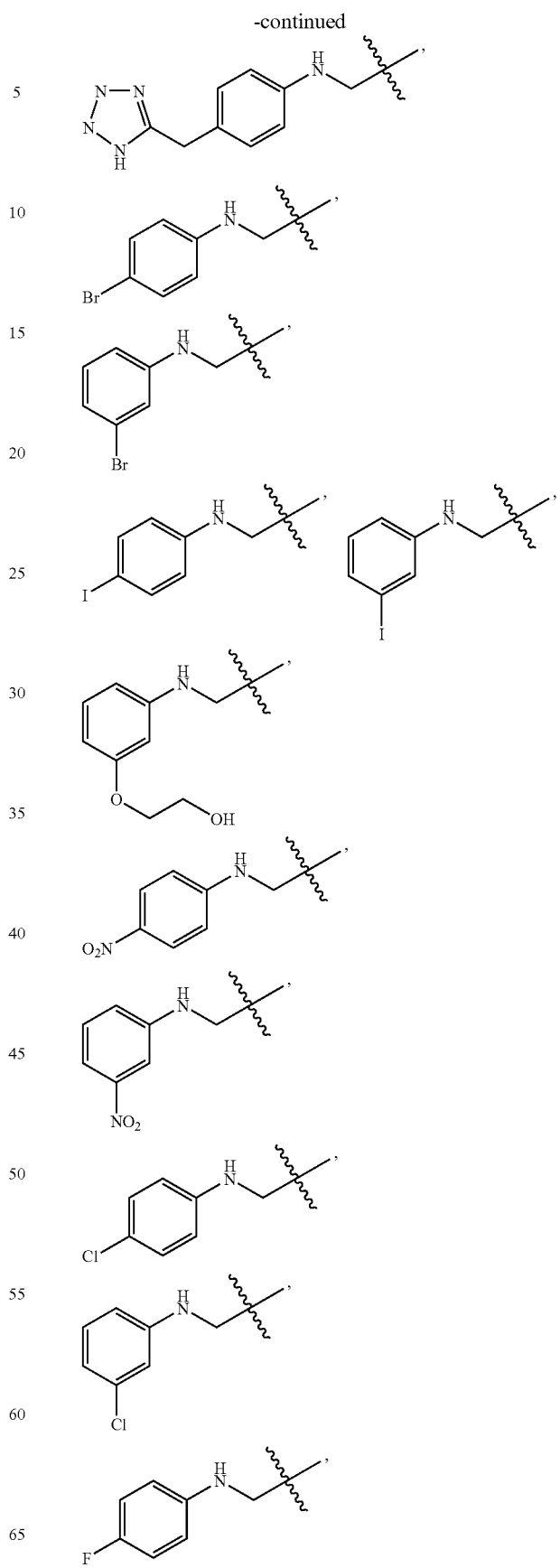

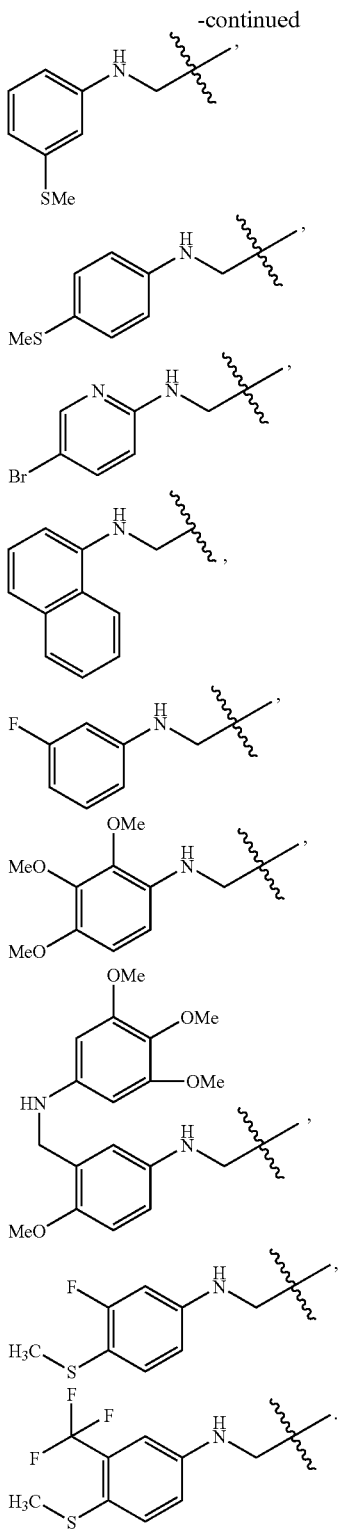

In other embodiments of the compounds according to embodiment [0046] (hereinafter collectively referred to as embodiment [0060]), $X^1$ is selected from —CH$_2$—, —NH—CH$_2$, and —S—CH$_2$—; and Cy$^2$ is monocyclic or fused bicyclic aryl or heteroaryl optionally substituted with one to three substituents selected from CH$_3$—, CH$_3$O—, phenyl optionally substituted with one to three CH$_3$O—, morphylinyl, morphylinyl-C$_1$-C$_3$-alkoxy, cyano, and CH$_3$C(O)NH—.

In other embodiments of the compounds according to embodiment [0046] (hereinafter collectively referred to as embodiment [0061]), $X^1$ is selected from —OCH$_2$, —CH$_2$O—, —CH$_2$—NH$_2$—, and —CH$_2$S—; and Cy$^2$ is monocyclic or fused bicyclic aryl or heteroaryl optionally substituted with one to three substituents selected from CH$_3$—, CH$_3$O—, phenyl optionally substituted with one to three CH$_3$O—, morphylinyl, morphylinyl-C$_1$-C$_3$-alkoxy, cyano, and CH$_3$C(O)NH—.

In one embodiment according to embodiment [0060] (hereinafter embodiment [0062]), Cy$^2$ is phenyl, pyridinyl, pyrimidinyl, benzimidazolyl, benzothiazolyl, thienyl, tetrahydroquinozolinyl, or 1,3-dihydroquinazoline-2,4-dione, each optionally substituted with one to three CH$_3$O—. More preferably, Cy$^2$ is phenyl substituted with one to three CH$_3$O—.

In yet other embodiments of the compound according to embodiment [0046] (hereinafter collectively referred to as embodiment [0063]), Cy$^2$ is cycloalkyl, aryl, heteroaryl, or heterocyclyl, each of which optionally is substituted, and each of which optionally is fused to one or more aryl or heteroaryl rings, or to one or more saturated or partially unsaturated cycloalkyl or heterocyclic rings, each of which rings optionally is substituted, provided that when Cy$^2$ is a cyclic moiety having —C(O)—, —C(S)—, —S(O)—, or —S(O)$_2$— in the ring, then Cy$^2$ is not additionally substituted with a group comprising an aryl or heteroaryl ring; and $X^1$ is selected from the group consisting of a chemical bond, L$^3$, W$^1$-L$^3$, L$^3$-W$^1$, W$^1$-L$^3$-W$^1$, and L$^3$-W$^1$-L$^3$, wherein W$^1$, at each occurrence, is S, O, or N(R$^9$), where R$^9$ is selected from the group consisting of hydrogen, alkyl, aryl, and aralkyl; and L$^3$ is C$_1$-C$_4$ alkylene, C$_2$-C$_4$ alkenylene, or C$_2$-C$_4$ alkynylene.

Preferably in the compounds according to embodiment [0063] (hereinafter embodiment [0064]), X$^2$ is selected from the group consisting of L$^3$, W$^1$-L$^3$, L$^3$-W$^1$, W$^1$-L$^3$-W$^1$, and L$^3$-W$^1$-L$^3$.

In some embodiments of the compounds according to embodiment [0063], X$^1$ is a chemical bond. In other embodiments, X$^1$ is a non-cyclic hydrocarbyl. In some such embodiments, X$^1$ is alkylene, preferably methylene or ethylene. In other such embodiments, X$^1$ is alkenylene. In still other such embodiments, one carbon in the hydrocarbyl chain is replaced with —NH— or —S—, and in others with a —O—. In some preferred embodiments, X$^1$ is W$^1$-L$^3$-W$^1$ and W$^1$ is —NH— or —N(CH$_3$)—. Such embodiments are hereinafter collectively referred to as embodiment [0065].

In some embodiments of the compounds according to embodiment [0063], Cy$^2$ is cycloalkyl, preferably cyclohexyl. In other embodiments, Cy$^2$ is aryl or heteroaryl, e.g., phenyl, pyridyl, pyrimidyl, imidazolyl, thiazolyl, oxadiazolyl, quinolyl, or fluorenyl, each of which optionally is substituted and optionally is fused to one or more aryl rings. In some embodiments, the cyclic moiety of Cy$^2$ is fused to a benzene ring. In some embodiments, Cy$^2$ has from one to three substituents independently selected from the group consisting of alkyl, alkoxy, aryl, aralkyl, amino, halo, haloalkyl, and hydroxyalkyl. Examples of preferred substituents include methyl, methoxy, fluoro, trifluoromethyl, amino, nitro, aminomethyl, hydroxymethyl, and phenyl. Some other preferred substituents have the formula —$K^1$—N(H)($R^{10}$), wherein $K^1$ is a chemical bond or $C_1$-$C_4$ alkylene;

$R^{10}$ is selected from the group consisting of Z' and -$Ak^2$-Z', wherein $Ak^2$ is $C_1$-$C_4$ alkylene; and Z' is cycloalkyl, aryl, heteroaryl, or heterocyclyl, each of which optionally is substituted, and each of which optionally is fused to one or more aryl or heteroaryl rings, or to one or more saturated or partially unsaturated cycloalkyl or heterocyclic rings.

Such embodiments are hereinafter collectively referred to as embodiment [0066].

Examples of such preferred substituents according to embodiment [0066] (hereinafter collectively referred to as embodiment [0067]) include

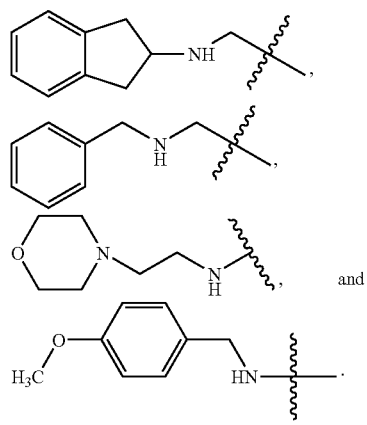

In some embodiments of the compounds according to embodiment [0063], $Cy^2$ is heterocyclyl, e.g.,

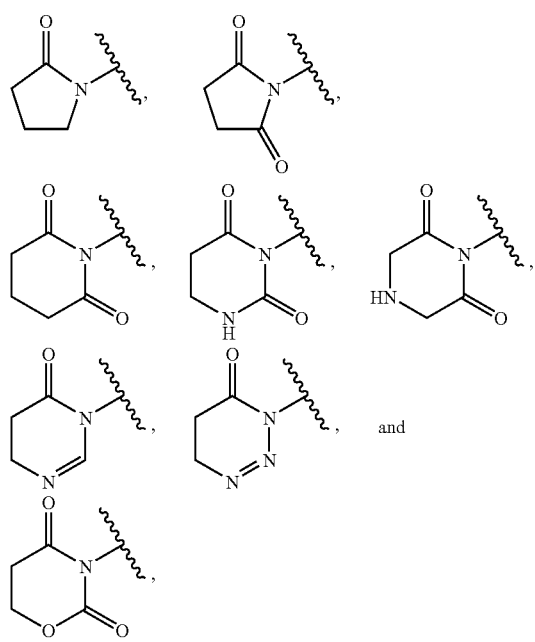

each of which optionally is substituted and optionally is fused to one or more aryl rings. In some embodiments, the heterocycle of $Cy^2$ is fused to a benzene ring. Such embodiments are hereinafter collectively referred to as embodiment [0068].

In certain preferred embodiments (hereinafter collectively referred to as embodiment [0069]) of the compound according to embodiment [0046], $Cy^2$-$X^1$— is collectively selected from the group consisting of a) $A_1$-$L_1$-$B_1$—, wherein $A_1$ is an optionally substituted aryl, optionally substituted heteroaryl or optionally substituted heterocyclyl; wherein $L_1$ is —$(CH_2)_{0-1}$NH$(CH_2)_{0-1}$—, —NHC(O)—, or —NHCH$_2$—; and wherein $B_1$ is phenyl or a covalent bond;

b) $A_2$-$L_2$-$B_2$—, wherein $A_2$ is $CH_3$(C≡$CH_2$)—, optionally substituted cycloalkyl, optionally substituted alkyl, or optionally substituted aryl; wherein $L_2$ is —C≡C—; and wherein $B_2$ is a covalent bond;

c) $A_3$-$L_3$-$B_3$—, wherein $A_3$ is an optionally substituted aryl, optionally substituted heteroaryl or optionally substituted heterocyclyl; wherein $L_3$ is a covalent bond; and wherein $B_3$ is —$CH_2$NH—;

d) $A_4$-$L_4$-$B_4$—, wherein $A_4$ is an optionally substituted aryl; wherein $L_4$ is —NHCH$_2$—; and wherein $B_4$ is a thienyl group;

e) $A_5$-$L_5$-$B_4$—, wherein $A_5$ is an optionally substituted heteroaryl or optionally substituted heterocyclyl; wherein $L_5$ is a covalent bond; and wherein $B_5$ is —SCH$_2$—;

f) morpholinyl-$CH_2$— g) optionally substituted aryl;

h) $A_6$-$L_6$-$B_6$—, wherein $A_6$ is an optionally substituted aryl, optionally substituted heteroaryl or optionally substituted heterocyclyl; wherein $L_6$ is a covalent bond; and wherein $B_6$ is —NHCH$_2$—;

i) $A_7$-$L_7$-$B_7$—, wherein $A_7$ is an optionally substituted heteroaryl or optionally substituted heterocyclyl; wherein $L_7$ is a covalent bond; and wherein $B_7$ is —$CH_2$—;

j) optionally substituted heteroaryl or optionally substituted heterocyl;

k) $A_8$-$L_8$-$B_8$—, wherein $A_8$ is optionally substituted phenyl; wherein $L_8$ is a covalent bond; and wherein $B_8$ is —O—;

l) $A_9$-$L_9$-$B_9$—, wherein $A_9$ is an optionally substituted aryl; wherein $L_9$ is a covalent bond; and wherein $B_9$ is a furan group;

m) $A_{10}$-$L_{10}$-$B_{10}$—, wherein $A_{10}$ is an optionally substituted heteroaryl or optionally substituted heterocyclyl; wherein $L_{10}$ is —CH(CH$_2$CH$_3$)—; and wherein $B_{10}$ is —NHCH$_2$—;

n) $A_{11}$-$L_{11}$-$B_{11}$—, wherein $A_{11}$ is an optionally substituted heteroaryl or optionally substituted heterocyclyl; wherein $L_{11}$ is a covalent bond; and wherein $B_{11}$ is —OCH$_2$—;

o) $A_{12}$-$L_{12}$-$B_{12}$—, wherein $A_{12}$ is an optionally substituted aryl, optionally substituted heteroaryl or optionally substituted heterocyclyl; wherein $L_{12}$ is —NHC(O)—; and wherein $B_{12}$ is —N(optionally substituted aryl)CH$_2$—;

p) $A_{13}$-$L_{13}$-$B_{13}$—, wherein $A_{13}$ is an optionally substituted aryl, optionally substituted heteroaryl or optionally substituted heterocyclyl; wherein $L_{13}$ is a covalent bond; and wherein $B_{13}$ is —NHC(O)—;

q) $A_{14}$-$L_{14}$-$B_{14}$—, wherein $A_{14}$ is an optionally substituted aryl, optionally substituted heteroaryl or optionally substituted heterocyclyl; wherein $L_{14}$ is —NHC(O) (optionally substituted heteroaryl); and wherein $B_{14}$ is —S—S—;

r) $F_3$CC(O)NH—;

s) $A_{15}$-$L_{15}$-$B_{15}$—, wherein $A_{15}$ is an optionally substituted aryl, optionally substituted heteroaryl or optionally substituted heterocyclyl; wherein $L_{15}$ is —$(CH_2)_{0-1}$NH(optionally substituted heteroaryl)-; and wherein $B_{15}$ is —NHCH$_2$—;

t) $A_{16}$-$L_{16}$-$B_{16}$—, wherein $A_{16}$ is an optionally substituted aryl, optionally substituted heteroaryl or optionally substituted heterocyclyl; wherein $L_{16}$ is a covalent bond; and wherein $B_{16}$ is —N(optionally substituted alkyl)CH$_2$—; and u) $A_{17}$-$L_{17}$-$B_{17}$—, wherein $A_{17}$ is an optionally substituted aryl, optionally substituted heteroaryl or optionally substituted heterocyclyl; wherein $L_{17}$ is a covalent bond; and wherein $B_{17}$ is -(optionally substituted aryl-CH$_2$)$_2$—N—.

In another preferred embodiment (hereinafter embodiment [0070]) of the compounds according to embodiment [0046], Cy$^2$—X$^1$— is collectively selected from the group consisting of a) $D_1$-$E_1$-$F_1$—, wherein $D_1$ is an optionally substituted aryl, optionally substituted heteroaryl or optionally substituted heterocyclyl; wherein $E_1$ is —CH$_2$— or a covalent bond; and wherein $F_1$ is a covalent bond;

b) $D_2$-$E_2$-$F_2$—, wherein $D_2$ is an optionally substituted aryl, optionally substituted heteroaryl or optionally substituted heterocyclyl; wherein $E_2$ is —NH(CH$_2$)$_{0-2}$—; and wherein $F_2$ is a covalent bond;

c) $D_3$-$E_3$-$F_3$—, wherein $D_3$ is an optionally substituted aryl, optionally substituted heteroaryl or optionally substituted heterocyclyl; wherein $E_3$ is —(CH$_2$)$_{0-2}$NH—; and wherein $F_3$ is a covalent bond;

d) $D_4$-$E_4$-$F_4$—, wherein $D_4$ is an optionally substituted aryl, optionally substituted heteroaryl or optionally substituted heterocyclyl; wherein $E_4$ is —S(CH$_2$)$_{0-2}$—; and wherein $F_4$ is a covalent bond;

e) $D_5$-$E_5$-$F_5$, wherein $D_5$ is an optionally substituted aryl, optionally substituted heteroaryl or optionally substituted heterocyclyl; wherein $E_5$ is —(CH$_2$)$_{0-2}$S—; and wherein $F_5$ is a covalent bond; and f) $D_6$-$E_6$-$F_6$—, wherein $D_6$ is an optionally substituted aryl, optionally substituted heteroaryl or optionally substituted heterocyclyl; wherein $E_6$ is —NH(CH$_2$)$_{0-2}$NH—; and wherein $F_6$ is a covalent bond.

In some embodiments (hereinafter collectively referred to as embodiment [0071]) according to embodiments [0046] and [0048]-[0063], R$^2$ to R$^4$ are independently hydrogen, —NH$_2$, nitro, furanyl, chloro, fluoro, butyl, trifluoromethyl, bromo, thienyl, phenyl, —CHCHC(O)—NH$_2$, —C≡CCH$_2$—R$^9$ wherein R$^9$ is hydrogen, C$_1$-C$_7$-alkyl, hydroxy, amino, or C$_1$-C$_7$-alkoxy.

In some preferred embodiments (hereinafter collectively referred to as embodiment [0072]) of the compound according to embodiments [0046] and [0048]-[0071], q is 0 and X$^1$ is independently selected from the group consisting of —NH—CH$_2$, —S—CH$_2$— and —CH$_2$—.

In some preferred embodiments (hereinafter collectively referred to as embodiment [0073]) of the compound according to embodiments [0046] and [0048]-[0071], q is 0 and X$^1$ is independently selected from the group consisting of —OCH$_2$, —CH$_2$O—, —CH$_2$—NH$_2$—, and —CH$_2$S—.

In some embodiments (hereinafter collectively referred to as embodiment [0071]) of the compound according to embodiments [0046] and [0048]-[0072], the compound has Ar$^2$ of formula

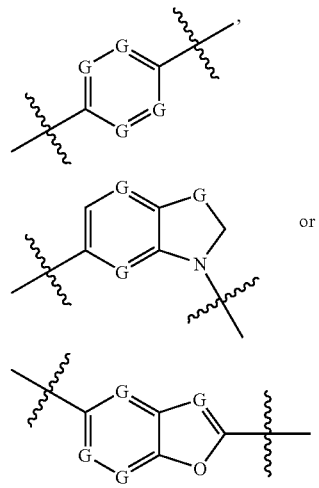

wherein G, at each occurrence, is independently N or C, and C is optionally substituted.

In some embodiments of the compounds according to embodiment [0074], G at each occurrence is C(R$^8$), wherein R$^8$ selected from the group consisting of hydrogen and C$_1$-C$_7$-alkyl. In some more preferred embodiments, G is —CH—. Such embodiments are hereinafter collectively referred to as embodiment [0075].

In some preferred embodiments (hereinafter collectively referred to as embodiment [0076]), the compounds according to embodiment [0074] are those wherein Ar$^2$ is selected from the group consisting of phenylene, benzofuranylene and indolinylene.

In some preferred embodiments, Cy$^2$ is aryl or heteroaryl, each of which is optionally substituted. More preferably, Cy$^2$ is phenyl, pyrimidinyl, benzimidazolyl or benzothiazolyl, each of which is optionally substituted. Preferred substituents of Cy$^2$ are from one to three substituents independently selected from the group consisting of C$_1$-C$_7$-alkyl, C$_1$-C$_7$-alkoxy, halo, di-C$_1$-C$_7$-alkylamino-C$_1$-C$_7$-alkoxy and heteroaryl. More preferably, the substituents of Cy$^2$ are selected from methyl, methoxy, fluoro, chloro, pyridinyl and dimethylamino-ethoxy. Such embodiments are hereinafter collectively referred to as embodiment [0077].

In some preferred embodiments (hereinafter collectively referred to as embodiment [0078]), the moiety formed by Cy$^2$-X$^1$ is selected from the following:

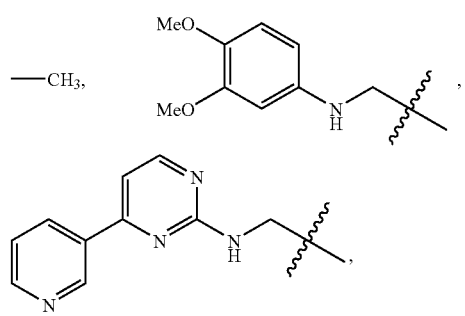

-continued

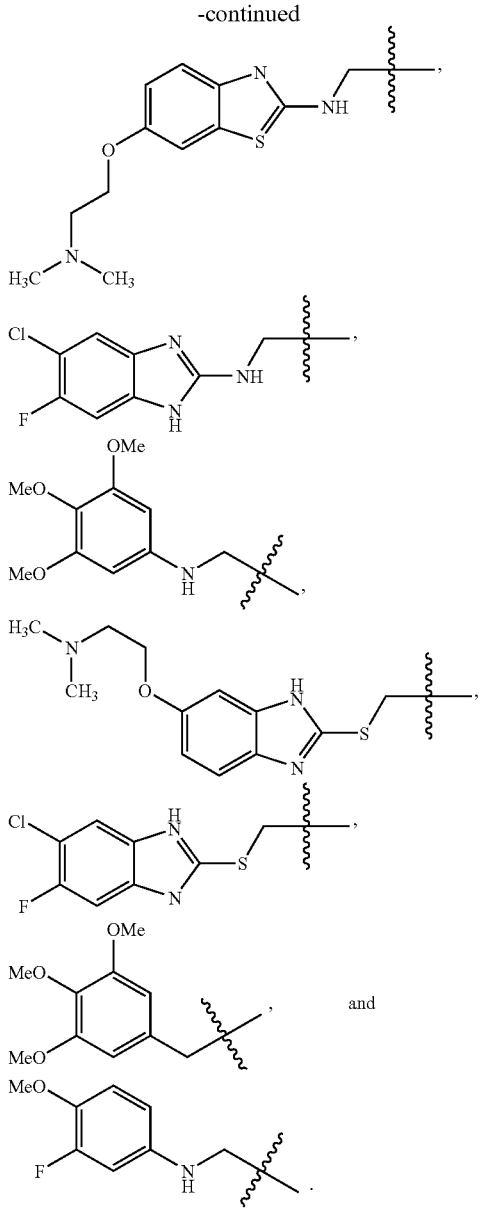

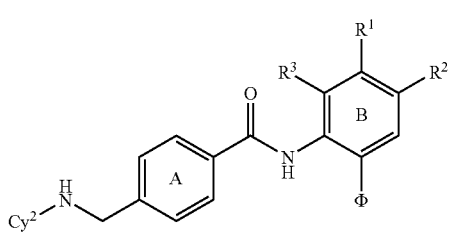

In a preferred embodiment, the compounds of embodiment [0050] are represented by the general formula (2) (hereinafter embodiment [0079]):

(2)

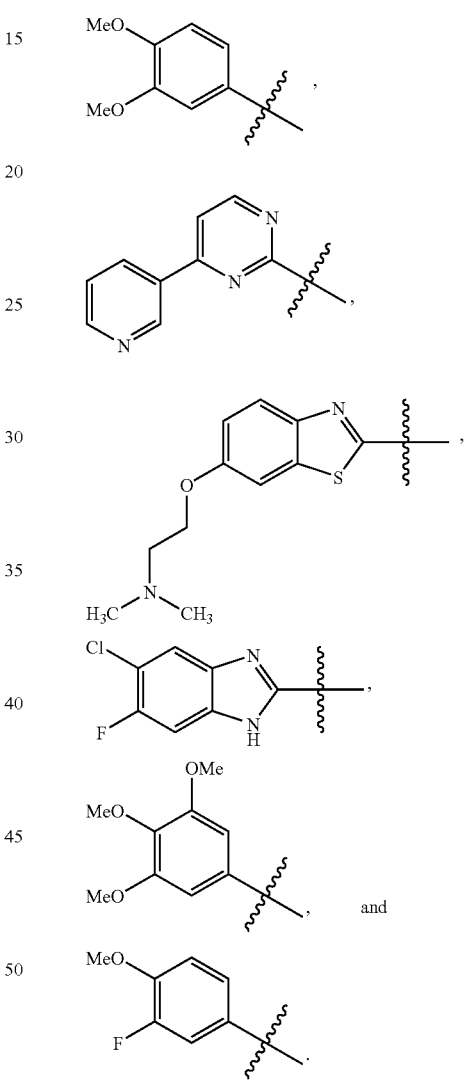

or a pharmaceutically acceptable salt thereof, wherein R$^2$ and R$^3$ are independently selected from the group consisting of hydrogen, trifluoromethyl, butyl, —(CH$_2$)$_3$— OH, chloro, fluoro, amino, phenyl, thienyl, furanyl, —CH═CHC(O)NH$_2$, —C≡CCH$_2$—OH, —C≡CCH$_2$—OCH$_3$; and the A ring is optionally further substituted with from 1 to 3 substituents independently selected from methyl, hydroxy, methoxy, halo, and amino.

In some preferred embodiments (hereinafter collectively referre to as embodiment [0080]), the compounds according to embodiment [0079] are those in which Cy$^2$ is selected from:

In other preferred embodiments (hereinafter collectively referred to as embodiment [0081]) of the compounds according to embodiments [0079] and [0080], the A ring is not further substituted.

In another preferred embodiment (hereinafter embodiment [0082]) of the compounds according to embodiments [0079]-[0081], R$^2$ and R$^3$ are both —H.

In another embodiment of this aspect, the invention comprises compounds of the general formula (3) (hereinafter embodiment [0083]):

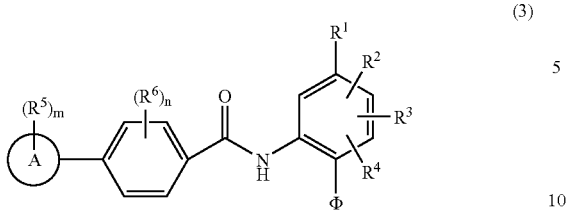

(3)

or a pharmaceutically acceptable salt or in vivo hydrolyzable ester or amide thereof; wherein:

Φ is —NH$_2$ or —OH;

Ring A is a heterocyclyl, wherein if said heterocyclyl contains an —NH— moiety that nitrogen is optionally substituted by a group selected from K;

$R^5$ is a substituent on carbon and is selected from halo, nitro, cyano, hydroxy, trifluoromethyl, trifluoromethoxy, amino, carboxy, carbamoyl, mercapto, sulphamoyl, $C_{1-6}$-alkyl, $C_{2-6}$-alkenyl, $C_{2-6}$-alkynyl, $C_{1-6}$alkoxy, $C_{1-6}$-alkanoyl, $C_{1-6}$-alkanoyloxy, N—($C_{1-6}$-alkyl)amino, N,N—($C_{1-6}$-alkyl)$_2$amino, $C_{1-6}$-alkanoylamino, N—($C_{1-6}$-alkyl)carbamoyl, N,N—($C_{1-6}$-alkyl)$_2$carbamoyl, $C_{1-6}$-alkylS(O)$_a$ wherein a is 0 to 2, $C_{1-6}$-alkoxycarbonyl, N—($C_{1-6}$-alkyl)sulphamoyl, N,N—($C_{1-6}$-alkyl)$_2$sulphamoyl, aryl, aryloxy, arylC$_{1-6}$-alkyl, heterocyclic group, (heterocyclic group) $C_{1-6}$-alkyl, or a group (B-E-); wherein $R^5$, including group (B-E-), is optionally substituted on carbon by one or more W; and wherein if said heterocyclic group contains an —NH— moiety that nitrogen is optionally substituted by J;

W is halo, nitro, cyano, hydroxy, trifluoromethyl, trifluoromethoxy, amino, carboxy, carbamoyl, mercapto, sulphamoyl, $C_{1-6}$-alkyl, $C_{2-6}$-alkenyl, $C_{2-6}$-alkynyl, $C_{1-6}$-alkoxy, $C_{1-6}$-alkanoyl, $C_{1-6}$-alkanoyloxy, N—($C_{1-6}$-alkyl)amino, N,N—($C_{1-6}$-alkyl)$_2$amino, $C_{1-6}$-alkanoylamino, N—($C_{1-6}$-alkyl)carbamoyl, N,N—($C_{1-6}$-alkyl)$_2$carbamoyl, $C_{1-6}$-alkylS(O)$_a$ wherein a is 0 to 2, $C_{1-6}$-alkoxycarbonyl, N—($C_{1-6}$-alkyl)sulphamoyl, N,N—($C_{1-6}$-alkyl)$_2$sulphamoyl, or a group (B'-E'-); wherein W, including group (B'-E'-) is optionally substituted on carbon by one or more Y;

Y and Z are independently selected from halo, nitro, cyano, hydroxy, trifluoromethyl, trifluoromethoxy, amino, carboxy, carbamoyl, mercapto, sulphamoyl, $C_{1-6}$-alkyl, $C_{2-6}$-alkenyl, $C_{2-6}$-alkynyl, $C_{1-6}$-alkoxy, $C_{1-6}$-alkanoyl, $C_{1-6}$-alkanoyloxy, N—($C_{1-6}$-alkyl) amino, N,N—($C_{1-6}$-alkyl)$_2$amino, $C_{1-6}$-alkanoylamino, N—($C_{1-6}$-alkyl)carbamoyl, N,N—($C_{1-6}$-alkyl)$_2$-carbamoyl, $C_{1-6}$-alkylS(O)$_a$ wherein a is 0 to 2, $C_{1-6}$-alkoxycarbonyl, N—($C_{1-6}$-alkyl)sulphamoyl or N,N—($C_{1-6}$-alkyl)$_2$sulphamoyl;

G, J and K are independently selected from $C_{1-8}$-alkyl, $C_{1-8}$-alkenyl, $C_{1-8}$-alkanoyl, $C_{1-8}$-alkylsulphonyl, $C_{1-8}$-alkoxycarbonyl, carbamoyl, N—($C_{1-8}$-alkyl) carbamoyl, N,N—($C_{1-8}$-alkyl)carbamoyl, benzyloxycarbonyl, benzoyl, phenylsulphonyl, aryl, arylC$_{1-6}$-alkyl or (heterocyclic group) $C_{1-6}$-alkyl; wherein G, J, and K are optionally substituted on carbon by one or more Q; and wherein if said heterocyclic group contains an —NH— moiety that nitrogen is optionally substituted by hydrogen or $C_{1-6}$alkyl;

Q is halo, nitro, cyano, hydroxy, trifluoromethyl, trifluoromethoxy, amino, carboxy, carbamoyl, mercapto, sulphamoyl, $C_{1-6}$-alkyl, $C_{2-6}$alkenyl, $C_{2-6}$-alkynyl, $C_{1-6}$-alkoxy, $C_{1-6}$-alkanoyl, $C_{1-6}$-alkanoyloxy, N—($C_{1-6}$-alkyl)amino, N,N—($C_{1-6}$-alkyl)$_2$amino, $C_{1-6}$-alkanoylamino, N—($C_{1-6}$-alkyl)carbamoyl, N,N—($C_{1-6}$-alkyl)$_2$carbamoyl, $C_{1-6}$-alkylS(O)$_a$ wherein a is 0 to 2, $C_{1-6}$-alkoxycarbonyl, $C_{1-6}$-alkoxycarbonylamino, N—($C_{1-6}$-alkyl)sulphamoyl, N,N—($C_{1-6}$-alkyl)$_2$sulphamoyl, aryl, aryloxy, aryl $C_{1-6}$-alkyl, arylC$_{1-6}$-alkoxy, heterocyclic group, (heterocyclic group) $C_{1-6}$-alkyl, (heterocyclic group) $C_{1-6}$-alkoxy, or a group (B"-E"-); wherein Q, including group (B"-E"-), is optionally substituted on carbon by one or more Z;

B, B' and B" are independently selected from $C_{1-6}$-alkyl, $C_{2-6}$-alkenyl, $C_{2-6}$-alkynyl, $C_{3-8}$-cycloalkyl, $C_{3-8}$-cycloalkylC$_{1-6}$-alkyl, aryl, arylC$_{1-6}$-alkyl, heterocyclic group, (heterocyclic group) $C_{1-6}$-alkyl, phenyl or phenylC$_{1-6}$-alkyl; wherein B, B' and B" is optionally substituted on carbon by one or more D; and wherein if said heterocyclic group contains an —NH— moiety that nitrogen is optionally substituted by a group selected from G;

E, E' and E" are independently selected from —N($R^a$), —O—, —C(O)O—, —OC(O)—, —C(O)—, —N($R^a$(O)—, —N($R^a$)C(O)N($R^b$)—, —N($R^a$(O) O—, —OC(O)N($R^a$)—, —C(O)N($R^a$)—, S(O)$_r$, —SO$_2$N($R^a$)—, —N($R^a$)SO$_2$— wherein $R^a$ and $R^b$ are independently selected from hydrogen or $C_{1-6}$-alkyl optionally substituted by one or more F and r is 0-2;

D and F are independently selected from halo, nitro, cyano, hydroxy, trifluoromethyl, trifluoromethoxy, amino, carboxy, carbamoyl, mercapto, sulphamoyl, $C_{1-6}$-alkyl, $C_{2-6}$-alkenyl, $C_{2-6}$-alkynyl, $C_{1-6}$-alkoxy, $C_{1-6}$-alkanoyl, $C_{1-6}$-alkanoyloxy, N—($C_{1-6}$-alkyl) amino, N,N—($C_{1-6}$-alkyl)$_2$amino, $C_{1-6}$-alkanoylamino, N—($C_{1-6}$-alkyl)carbamoyl, N,N—($C_{1-6}$-alkyl)$_2$carbamoyl, $C_{1-6}$-alkylS(O)$_a$ wherein a is 0 to 2, $C_{1-6}$-alkoxycarbonyl, N—($C_{1-6}$-alkyl)sulphamoyl or N,N—($C_{1-6}$-alkyl)$_2$sulphamoyl;

m is 0, 1, 2, 3 or 4; wherein the values of $R^5$ may be the same or different;

$R^6$ is halo;

n is 0, 1 or 2; wherein the values of $R^6$ may be the same or different; and $R^1$, $R^2$, $R^3$, and $R^4$ are as defined in embodiment [0046].

Particular values of Ring A, $R^5$, $R^6$, m, and n (hereinafter embodiment [0084]) include the following:

Ring A:

(a) pyridyl, quinolyl, indolyl, pyrimidinyl, morpholinyl, piperidinyl, piperazinyl, pyridazinyl, pyrazinyl, thiazolyl, thienyl, thienopyrimidinyl, thienopyridinyl, purinyl, triazinyl, oxazolyl, pyrazolyl, or furanyl; wherein if Ring A contains an —NH— moiety that nitrogen is optionally substituted by a group selected from K;

(b) pyridin-4-yl, pyridin-3-yl, pyridin-2-yl, quinolin-8-yl, pyrimidin-6-yl, pyrimidin-5-yl, pyrimidin-4-yl, morpholin-4-yl, piperidin-4-yl, piperidin-3-yl, piperidin-2-yl, piperazin-4-yl, pyridazin-5-yl, pyrazin-6-yl, thiazol-2-yl, thien-2-yl, thieno[3,2b]pyrimidinyl, thieno[3,2b] pyrimidinyl, thieno[3,2b]pyridinyl, purin-6-yl or triazin-6-yl; wherein if Ring A contains an —NH— moiety that nitrogen is optionally substituted by a group selected from K;

(c) pyridyl, quinolyl, pyrimidyl, morpholinyl, piperidinyl, piperazinyl, pyridazinyl, pyrazinyl, thiazoyl or furanyl;

(d) pyridin-4-yl, pyridin-3-yl, pyridin-2-yl, quinoline-8-yl, pyradizin-2-yl, furan-3-yl, morpholinyl, thiazol-2-yl, pyrimidin-6-yl, piperidinyl or piperazinyl; and (e) pyridine-4-yl, pyridine-3-yl, quinoline-8-yl, piperidinyl or piperazin-4-yl.

$R^5$:

(a) a substituent on carbon and is selected from halo, amino, $C_{1-6}$-alkyl, $C_{1-6}$-alkoxy, N—($C_{1-6}$-alkyl)amino, aryl, aryloxy, aryl$C_{1-6}$-alkyl, heterocyclic group, (heterocyclic group) $C_{1-6}$-alkyl, or a group (B-E-); wherein $R^5$, including group (B-E-), is optionally substituted on carbon by one or more W; and wherein if said heterocyclic group contains an —NH— moiety that nitrogen is optionally substituted by J;

W is hydroxy, mercapto, $C_{1-6}$-alkyl, $C_{1-6}$-alkoxy, N,N—($C_{1-6}$-alkyl)$_2$amino or a group (B'-E'-); wherein W, including group (B'-E'-), is optionally substituted on carbon by one or more Y;

Y and Z are independently selected from halo, nitro, cyano, hydroxy, $C_{1-6}$-alkoxy, N,N—($C_{1-6}$-alkyl)$_2$ amino or $C_{1-6}$-alkanoylamino;

G, J, and K are independently selected from $C_{1-8}$-alkyl, $C_{2-8}$-alkenyl, $C_{1-8}$-alkanoyl, aryl, aryl$C_{1-6}$-alkyl or (heterocyclic group) $C_{1-6}$-alkyl; wherein G, J and K are optionally substituted on carbon by one or more Q; and wherein if said heterocyclic group contains an —NH— moiety that nitrogen is optionally substituted by hydrogen or $C_{1-6}$-alkyl;

Q is cyano, hydroxy, $C_{1-6}$-alkoxy, $C_{1-6}$-alkanoyloxy, $C_{1-6}$-alkoxycarbonyl, $C_{1-6}$-alkoxycarbonylamino, aryl, aryloxy or a group (B"-E"-); wherein Q, including group (B"-E"-), is optionally substituted on carbon by one or more Z;

B, B' and B" are independently selected from $C_{1-6}$-alkyl, $C_{2-6}$-alkenyl, $C_{2-6}$alkynyl, $C_{3-8}$-cycloalkyl, $C_{3-8}$-cycloalkyl$C_{1-6}$-alkyl, aryl, aryl$C_{1-6}$-alkyl, heterocyclic group, (heterocyclic group) $C_{1-6}$-alkyl, phenyl or phenyl$C_{1-6}$-alkyl; wherein B, B' and B" are optionally substituted on carbon by one or more D; and wherein if said heterocyclic group contains an —NH— moiety that nitrogen is optionally substituted by a group selected from G;

E, E' and E" are independently selected from —N($R^a$)—, —O—, —C(O)O—, —OC(O)—, —C(O)—, —N($R^a$)C(O)—, —N($R^a$)C(O)N($R^b$)—, —N($R^a$)C(O)O—, —OC(O)N($R^a$)—, —C(O)N ($R^a$)—, S(O)$_r$, —SO$_2$N($R^a$)—, —N($R^a$)SO$_2$—, wherein $R^a$ and $R^b$ are independently selected from hydrogen or $C_{1-6}$-alkyl optionally substituted by one or more F and r is 0-2;

D and F are independently selected from halo, $C_{1-6}$-alkoxy or N,N—($C_{1-6}$-alkyl)$_2$amino.

(b) a substituent on carbon and is selected from fluoro, chloro, amino, methyl, ethyl, propyl, methoxy, N-methylamino, N-ethylamino, N-propylamino, N-butylamino, phenyl, naphthylethyl, piperizin-4-yl, piperidin-1-yl, piperidin-4-yl, 2-(thiomethyl)-pyrimidin-4-yl, tetrahydrofuran-2-ylmethyl, tetrahydropyran-2-ylmethyl, 1,2,5-thiadiazol-3-ylethyl, piperidin-1-ylmethyl, pyridin-2-ylmethyl, or a group (B-B-); wherein $R^5$, including group (B-E-), is optionally substituted on carbon by one or more W; and wherein if said heterocyclic group contains an —NH— moiety that nitrogen is optionally substituted by J;

W is hydroxy, methyl, ethyl, ethoxy, N,N-(diethyl) amino, N,N-(dibutyl)amino, or a group (B'-E'-); wherein W, including group (B'-E'-), is optionally substituted on carbon by one or more Y;

Y and Z are independently selected from fluoro, chloro, bromo, nitro, cyano hydroxy, methoxy, N,N-dimethyl)amino or methylcarbonylamino;

G, J and K are independently selected from methyl, ethyl, propyl, pentyl, 2-methylbutyl, butyl, acetyl, benzyl, 3-(pyrrol-1-yl)propyl or pyrrolidin-2-one-(5S)-methyl; wherein G, J and K are optionally substituted on carbon by one or more Q; and wherein if said heterocyclic group contains an —NH— moiety that nitrogen is optionally substituted by hydrogen or methyl;

Q is cyano, hydroxy, methoxy, ethoxy, methylcarbonyloxy, methoxycarbonyl, t-butoxycarbonylamino, phenyl or a group (B"-E"-); wherein Q, including group (B"-E"-), is optionally substituted on carbon by one or more Z;

B, B' and B" are independently selected from methyl, ethyl, propyl, cyclohexyl, phenyl, benzyl, 1,2,3,4-tetrahydroquinolinyl, 3-morpholinopropyl, 2-morpholinoethyl, 2-pyrrolidin-4-ylethyl, 3-morpholinopropyl, 3-(4-methylpiperazin-1-yl)propyl, 2-piperidin-1-ylethyl, 3-piperidin-1-ylpropyl, pyridin-3-ylmethyl or imidazol-1-ylpropyl; wherein B, B' and B" are optionally substituted on carbon by one or more D; and wherein if said heterocyclic group contains an —NH— moiety that nitrogen is optionally substituted by a group selected from G;

E, E' and E" are independently selected from —N($R^a$)—, —O$_1$—C(O), —, —NHC(O)—, —N($R^a$)C(O)O—; wherein $R^a$ is hydrogen or methyl optionally substituted by one or more F;

D and F are independently selected from fluoro, methoxy or ethoxy;

(c) fluoro, chloro, amino, methyl, methoxy, 3-morpholin-4-ylpropylamino, (3-morpholin-4-yl)ethylamino, acetyl, benzyl, methoxycarbonylmethyl, 2-pyrrolidin-4-ylethoxy, 3-morpholinopropoxy, N-(2-fluorophenyl) propanamide, 4-(diethylamino)phenylcarbonylmethyl, 3-(4-methylpiperazin-4-yl)propylamino, 2-piperidin-1-ylethylamino, 2-[N,N-diethyl)amino-ethylamino, pyridin-3-ylmethylamino, 3-piperidin-1-ylpropylamino, imidazol-1-ylpropylamino, 3-methoxypropylamino, 3-morpholinopropylamino, piperazin-1-yl, N-ethylamino, 4-methylpiperazin-1-yl, 1-(3-phenoxy)propyl, 1-(3-cyanophenyl)methyl, 1-(4-cyanophenyl)methyl, tetrahydrofuran-2-ylmethyl, 1-(3-benzyloxy)propyl, 3-methoxybenzyl, 2,3-dihydroxypropyl, 2-(methylcarbonyloxy)ethyl, 3-(pyrrol-1-yl)propyl, 1-[3-(2-methoxyethoxy)]propyl, 2-(4-acetamidophenyoxy)ethyl, 2-(t-butoxycarbonylamino)ethyl, 2-(t-butoxycarbonylamino)propyl, 2-[(2-methoxyphenyl)oxy]ethyl, (1,2,3,4-tetrahydroquinolin-4-yl)acetyl, 2-[N-(2-fluorophenyl)ylacetamide]ethyl, methoxycarbonylmethyl, 2-(ethoxy)ethyl, 4-methylpent-3-enyl, tetrahydropyran-2-ylmethyl, 1-(2S)-2-methylbutyl, 4-(benzyloxy)butyl, 2-[4-nitro)phenoxy)}ethyl, 2-[N,N-(dibutyl)amino] ethylamino, 3-[(N-methyl-N-phenyl)amino]propylamino, N-3-[2-(dimethylamino)ethoxy]propylamino, 2-[4-(acetamido)phenoxy]ethyl, 2-[4-hydroxyphenoxy)]ethyl, 1,2,5-thiadiazol-3-ylethyl, piperidin-1-ylmethyl, 2-[4-chloro)phenoxy]ethyl, pyrrolidin-2-one-(5S)-methyl, phenylaminocarbonyloxymethyl, cyclohexylaminocarbonyloxymethyl, 2-(thiomethyl)-pyrimidin-4-yl or pyridin-2-ylmethyl;
(d) halo, amino, $C_{1-6}$-alkyl, $C_{1-6}$-alkoxy, $C_{1-3}$-alkanoyloxy, N—($C_{1-3}$-alkyl)amino, N,N—($C_{1-3}$-alkyl)$_2$amino, $C_{1-3}$-alkanoylamino, N—($C_{1-3}$-alkyl)carbamoyl, N,N—($C_{1-3}$-alkyl)$_2$carbamoyl;
(e) halo, amino, $C_{1-6}$-alkyl or $C_{1-6}$-alkoxy; and
(f) halo, amino, methyl or methoxy.

m:
(a) 0, 1, 2, 3 or 4; wherein the values of $R^5$ may be the same or different;
(b) 0, 1, or 2; wherein the values of $R^5$ may be the same or different;
(c) 0 or 1;
(d) 0; and
(e) 1.

$R^6$:
(a) halo;
(b) fluoro or chloro; and
(c) fluoro.

n:
(a) 0, 1 or 2, wherein the values of $R^6$ may be the same or different;
(b) 0 or 1;
(c) 0; and
(d) 1.

Other embodiments (hereinafter collectively referred to as embodiment [0085]) of the compound according to embodiment [0083], include those in which:
Ring A is a heterocyclyl;
$R^5$ is halo, nitro, cyano, hydroxy, trifluoromethyl, trifluoromethoxy, amino, carboxy, carbamoyl, mercapto, sulphamoyl, $C_{1-6}$-alkyl, $C_{2-6}$-alkenyl, $C_{2-6}$-alkynyl, $C_{1-6}$-alkoxy, $C_{1-6}$-alkanoyl, $C_{1-6}$-alkanoyloxy, N—($C_{1-6}$-alkyl)amino, N,N—($C_{1-6}$-alkyl)$_2$amino, $C_{1-6}$-alkanoylamino, N—($C_{1-6}$-alkyl)carbamoyl, N,N—($C_{1-6}$-alkyl)$_2$carbamoyl, $C_{1-6}$-alkylS(O)$_a$ wherein a is 0 to 2, $C_{1-6}$-alkoxycarbonyl, N—($C_{1-6}$-alkyl)sulphamoyl, N,N—($C_{1-6}$alkyl)$_2$sulphamoyl or a group (B-E-); wherein, B is selected from $C_{1-6}$-alkyl, $C_{2-6}$-alkenyl, $C_{2-6}$-alkynyl, $C_{3-8}$-cycloalkyl, $C_{3-8}$-cycloalkyl$C_{1-6}$-alkyl, phenyl, heterocyclyl, phenyl$_{1-6}$-alkyl or heterocyclyl$C_{1-6}$-alkyl; wherein B is optionally substituted on carbon by one or more D; and wherein if said heterocyclyl contains an —NH— moiety that nitrogen is optionally substituted by a group selected from G;
E is —N($R^a$)—, —O—, —C(O)O—, —OC(O)—, —C(O)—, —N($R^a$)C(O)—, —C(O)N($R^a$)—, —S(O)$_r$—, —SO$_2$N($R^a$)—, —N($R^a$)SO$_2$— wherein $R^a$ is hydrogen or $C_{1-6}$-alkyl optionally substituted by one or more D and r is 0-2;
D is independently selected from halo, nitro, cyano, hydroxy, trifluoromethyl, trifluoromethoxy, amino, carboxy, carbamoyl, mercapto, sulphamoyl, $C_{1-6}$-alkyl, $C_{2-6}$-alkenyl, $C_{2-6}$alkynyl, $C_{1-6}$-alkoxy, $C_{1-6}$-alkanoyl, $C_{1-6}$-alkanoyloxy, N—($C_{1-6}$-alkyl)amino, N,N—($C_{1-6}$-alkyl)$_2$amino, $C_{1-6}$-alkanoylamino, N—($C_{1-6}$-alkyl)carbamoyl, N,N—($C_{1-6}$-alkyl)$_2$carbamoyl, $C_{1-6}$-alkylS(O)$_a$ wherein a is 0 to 2, $C_{1-6}$-alkoxycarbonyl, N—($C_{1-6}$-alkyl)sulphamoyl and N,N—($C_{1-6}$-alkyl)$_2$sulphamoyl;
G is selected from $C_{1-4}$-alkyl, $C_{1-4}$-alkanoyl, $C_{1-4}$-alkylsulphonyl, $C_{1-4}$-alkoxycarbonyl, carbamoyl, N—($C_{1-4}$-alkyl)carbamoyl, N,N—($C_{1-4}$-alkyl)carbamoyl, benzyl, benzyloxycarbonyl, benzoyl and phenylsulphonyl;

m is 0, 1, 2, 3 or 4; wherein the values of $R^5$ are the same or different;
$R^6$ is halo; and
n is 0, 1 or 2; wherein the values of $R^6$ can be the same or different.

In another embodiment of the compound according to embodiment [0083] (hereinafter embodiment [0086]),
Ring A is a pyridyl, quinolyl, indolyl, pyrimidinyl, morpholinyl, piperidinyl, piperazinyl, pyridazinyl, pyrazinyl, thiazolyl, thienyl, thienopyrimidinyl, thienopyridinyl, purinyl, triazinyl, oxazolyl, pyrazolyl, or furanyl; wherein if Ring A contains an —NH— moiety that nitrogen is optionally substituted by a group selected from K;
$R^5$ is a substituent on carbon and is selected from halo, amino, $C_{1-6}$-alkyl, $C_{1-6}$-alkoxy, N—($C_{1-6}$-alkyl)amino, aryl, aryloxy, aryl$C_{1-6}$-alkyl, heterocyclic group, (heterocyclic group)$C_{1-6}$-alkyl, or a group (B-E-); wherein $R^5$, including group (B-E-), is optionally substituted on carbon by one or more W; and wherein if said heterocyclic group contains an —NH— moiety that nitrogen is optionally substituted by J;
W is hydroxy, mercapto, $C_{1-6}$-alkyl, $C_{1-6}$-alkoxy, N,N—($C_{1-6}$-alkyl)$_2$amino or a group (B'-E'-);
  wherein W, including group (B'-E'-), is optionally substituted on carbon by one or more Y;
Y and Z are independently selected from halo, nitro, cyano, hydroxy, $C_{1-6}$-alkoxy, N,N—($C_{1-6}$-alkyl)$_2$ amino or $C_{1-6}$-alkanoylamino;
G, J and K are independently selected from $C_{1-6}$-alkyl, $C_{1-6}$-alkenyl, $C_{1-8}$-alkanoyl, aryl, aryl$C_{1-6}$-alkyl or (heterocyclic group) $C_{1-6}$-alkyl; wherein G, J and K are optionally substituted on carbon by one or more Q; and wherein f said heterocyclic group contains an —NH— moiety that nitrogen is optionally substituted by hydrogen or $C_{1-6}$-alkyl;
Q is cyano, hydroxy, $C_{1-6}$-alkoxy, $C_{1-6}$-alkanoyloxy, $C_{1-6}$-alkoxycarbonyl, $C_{1-6}$-alkoxycarbonylamino, aryl, aryloxy or a group (B"-E"-); wherein Q, including group (B"-E"-), is optionally substituted on carbon by one or more Z;
B, B' and B" are independently selected from $C_{1-6}$-alkyl, $C_{2-6}$-alkenyl, $C_{2-6}$alkynyl, $C_{3-8}$-cycloalkyl, $C_{3-8}$-cycloalkyl$C_{1-6}$-alkyl, aryl, aryl$C_{1-6}$-alkyl, heterocyclic group, (heterocyclic group) $C_{1-6}$-alkyl, phenyl or phenyl$C_{1-6}$-alkyl; wherein B, B' and B" are optionally substituted on carbon by one or more D; and wherein if said heterocyclic group contains an —NH— moiety that nitrogen is optionally substituted by a group selected from G;
E, E' and E" are independently selected from —N($R^a$)—, —O—, —C(O)O—, —OC(O)—, —C(O)—, —N($R^a$)C(O)—, —N($R^a$)C(O)N($R^a$)—, N($R^a$)C(O)O—, —OC(O)N($R^a$)—, —C(O)N($R^a$)—, —S(O)$_r$—, —SO$_2$N($R^3$)—, —N($R^a$)SO$_2$— wherein $R^a$ and $R^b$ are independently selected from hydrogen or $C_{1-6}$-alkyl optionally substituted by one or more F and r is 0-2;
D and F are independently selected from halo, $C_{1-6}$-alkoxy or N,N—($C_{1-6}$-alkyl)$_2$amino;
m is 0, 1, 2, 3 or 4; wherein the values of $R^5$ are the same or different;
$R^6$ is fluoro or chloro; and
n is 0, 1 or 2, wherein the values of $R^6$ are the same or different;

In another embodiment of the compound according to embodiment [0083] (hereinafter embodiment [0087]), Ring A is pyridin-4-yl, pyridin-3-yl, pyridin-2-yl, quinolin-8-yl, pyrimidin-6-yl, pyrimidin-5-yl, pyrimidin-4-yl, morpholin-4-yl, piperidin-4-yl, piperidin-3-yl, piperidin-2-yl, piperazin-4-yl, pyridazin-5-yl, pyrazin-6-yl, thiazol-2-yl, thien-2-yl, thieno[3,2-d]pyrimidinyl, thieno[3,2b]pyrimidinyl, thieno[3,2b]pyridinyl, purin-6-yl or triazin-6-yl; wherein if Ring A contains an —NH— moiety that nitrogen is optionally substituted by a group selected from K;

$R^5$ is a substituent on carbon and is selected from fluoro, chloro, amino, methyl, ethyl, propyl, methoxy, N-methylamino, N-ethylamino, N-propylamino, N-butylamino, phenyl, naphthylethyl, piperazin-1-yl, piperidin-1-yl, piperidin-4-yl, 2-thiomethyl)pyrimidin-4-yl, tetrahydrofuran-2-ylmethyl, tetrahydropyran-2-ylmethyl, 1,2,5-thiadiazol-3-ylethyl, piperidin-1-ylmethyl, pyridin-2-ylmethyl, or a group (B-B-); wherein $R^5$, including group (B-B-), is optionally substituted on carbon by one or more W; and wherein if said heterocyclic group contains an —NH— moiety that nitrogen is optionally substituted by J;

W is hydroxy, methyl, ethyl, ethoxy, N,N-(diethyl)amino, N,N-(dibutyl)amino, or a group (B'-E'-); wherein W, including group (B'-E'-), is optionally substituted on carbon by one or more Y;

Y and Z are independently selected from fluoro, chloro, bromo, nitro, cyano, hydroxy, methoxy, N,N-(dimethyl)amino or methylcarbonylamino;

G, J and K are independently selected from methyl, ethyl, propyl, pentyl, 2-methylbutyl, butyl, acetyl, benzyl, 3-pyrrol-1-yl)propyl or pyrrolidin-2-one-(5S)-methyl; wherein G, J and K are optionally substituted on carbon by one or more Q; and wherein if said heterocyclic group contains an —NH— moiety that nitrogen is optionally substituted by hydrogen or methyl;

Q is cyano, hydroxy, methoxy, ethoxy, methylcarbonyloxy, methoxycarbonyl, t-butoxycarbonylamino, phenyl or a group (B"-E"-); wherein Q, including group (B"-E"-), is optionally substituted on carbon by one or more Z;

B, B' and B" are independently selected from methyl, ethyl, propyl, cyclohexyl, phenyl, benzyl, 1,2,3,4-tetrahydroquinolinyl, 3-morpholinopropyl, 2-morpholinoethyl, 2-pyrrolidin-1-ylethyl, 3-morpholinopropyl, 3-(4-methylpiperazin-1-yl)propyl, 2-piperidin-1-ylethyl, 3-piperidin-1-ylpropyl, pyridin-3-ylmethyl or imidazol-1-ylpropyl; wherein B, B' and B" are optionally substituted on carbon by one or more D; and wherein if said heterocyclic group contains an —NH— moiety that nitrogen is optionally substituted by a group selected from G;

E, E' and E" are independently selected from —N($R^a$)—, —O—, —C(O), —NHC(O)—, —N($R^a$)(O)O—;
wherein $R^a$ is hydrogen or methyl optionally substituted by one or more F;

D and F are independently selected from fluoro, methoxy or ethoxy;

m is 0, 1, or 2; wherein the values of $R^5$ are the same or different;

$R^6$ is fluoro; and n is 0 or 1.

In the embodiments of the compounds according to embodiments [0083] and [0085]-[0087], $R^1$, $R^2$, $R^3$, and $R^4$ are as defined in embodiments [0048] and [0049], in other preferred embodiments, the compounds according to embodiment [0083] are the compounds of Tables 1-8 and 13 of WO 03/087057 modified by replacing the terminal moiety:

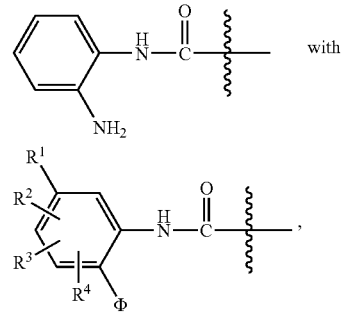

wherein Φ, $R^1$, $R^2$, $R^3$, and $R^4$ are as defined in accordance with embodiments [0046], and preferably embodiments [0048] and [0049]. Such embodiments are hereinafter collectively referred to as embodiment [0088].

The definitions in embodiments [0090]-[0097] apply to $R^5$ and $R^6$ in embodiments [0083]-[0088] and supplement the definitions in embodiments [0020]-[0042]. To the extent there are any inconsistencies between the definitions in embodiments [0020]-[0042] and in embodiment [0090]-[0097], the definitions in embodiments [0090]-[0097] shall take precedence for the compounds of embodiments [0083]-[0088] only.

"Alkyl" includes both straight and branched chain alkyl groups. For example, "$C_{1-8}$-alkyl" and "$C_{1-6}$-alkyl" includes methyl, ethyl, propyl, isopropyl, pentyl, hexyl, heptyl, and t-butyl. However, references to individual alkyl groups such as 'propyl' are specific for the straight-chained version only and references to individual branched chain alkyl groups such as 'isopropyl' are specific for the branched chain version only.

The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A "heterocyclyl" is a saturated, partially saturated or unsaturated, mono or bicyclic ring containing 3-12 atoms of which at least one atom is chosen from nitrogen, sulphur or oxygen, which may, unless otherwise specified, be carbon or nitrogen linked, wherein a ring sulphur atom is optionally oxidized to form the S-oxide(s). Preferably a "heterocyclyl" is a saturated, partially saturated or unsaturated, monocyclic ring containing 5 or 6 atoms of which at least one atom is chosen from nitrogen, sulphur or oxygen or a 8-10 membered bicyclic ring which may, unless otherwise specified, be carbon or nitrogen linked, wherein a ring sulphur atom is optionally oxidized to form S-oxide(s). Examples and suitable values of the term "heterocyclyl" are thiazolidinyl, pyrrolidinyl, 1,3-benzodioxolyl, 1,2,4-oxadiazolyl, 2-azabicyclo[2.2.1]heptyl, morpholinyl, tetrahydrofuranyl, furanyl, tetrahydropyranyl, piperidinyl, piperazinyl, thiomorpholinyl, 1,3-dioxolanyl, homopiperazinyl, thienyl, pyrrolyl, pyrazolyl, oxadiazolyl, tetrazolyl, oxazolyl, thienopyrimidinyl, thienopyridinyl, thieno{3,2-d]pyrimidinyl, 1,3,5-triazinyl, purinyl, 1,2,3,4-tetrahydroquinolinyl, benzimidazolyl, benzthiazolyl, benzoxazolyl, benzothienyl, benzofuranyl, indazolyl, quinazolinyl, cinnolinyl, phthalazinyl, quinoxalinyl, napthyridinyl, benzotriazolyl, pyrrolothienyl, imidazothienyl, isoxazolyl, imidazolyl, thiadiazolyl, isothiazolyl, 1,2,3-triazolyl, 1,2,4- triazolyl, pyranyl, indolyl, pyrimidyl, thiazolyl, pyrazinyl, pyridazinyl, pyridyl, quinolyl, quinazolinyl, and 1-isoquinolinyl.

A "heterocyclic group" is a saturated, partially saturated or unsaturated, mono or bicyclic ring containing 3-12 atoms of which at least one atom is chosen from nitrogen, sulphur or oxygen, which may, unless otherwise specified, be carbon or nitrogen linked, wherein a $CH_2$ group is optionally replaced by a C(O), and wherein a ring sulphur atom is optionally oxidized to form the S-oxide(s). Preferably a "heterocyclic group" is a saturated, partially saturated or unsaturated, monocyclic ring containing 5 or 6 atoms of which at least one atom is chosen from nitrogen, sulphur or oxygen or a 9 or 10 membered bicyclic ring which may, unless otherwise specified, be carbon or nitrogen linked, wherein a $CH_2$ group is optionally replaced by a C(O), and wherein a ring sulphur atom is optionally oxidized to form S-oxide(s). Examples and suitable values of the term "heterocyclic group" are pyrrolidinyl, 2-pyrrolidonyl 2,5-dioxopyrrolidinyl, 2,4-dioxoimidazolidinyl, 2-oxo-1,3,4-triazolinyl, oxazolidinyl, 2-oxazolidonyl, 5,6-dihydro-uracilyl, 1,3-benzodioxolyl, 1,2,4-oxadiazolyl, 2-azabicyclo[2.2.1]heptyl, morpholinyl, 2-oxotetrahydrofuranyl, tetrahydrofuranyl, furanyl, tetrahydropyranyl, piperidinyl, piperazinyl, thiomorpholinyl, 1,1-dioxothiomorpholinyl, 1,3-dioxolanyl, homopiperazinyl, thiophenyl, thienopyridinyl, thienopyrimidinyl, thieno[3,2-d]pyrimidinyl, 1,3,5-triazinyl, purinyl, quinolinyl, isoquinolinyl, 1,2,3,4-tetrahydroquinolinyl, tetrahydroisoquinolinyl, imidazolyl, benzimidazolyl, benzothiazolyl, benzoxazolyl, benzothiophenyl, benzofuranyl, indazolyl, quinazolinyl, cinnolinyl, phthalazinyl, quinoxalinyl, napthyridinyl, oxazolyl, isoxazolyl, pyrrolyl, tetrazolyl, thiadiazolyl, isothiazolyl, 1,2,3-triazolyl, 1,2,4-trazolyl, pyranyl, indolyl, isoindolyl, pyrimidinyl, thiazolyl, pyrazolyl, 3-pyrrolinyl, pyrazinyl, pyridazinyl, pyridinyl, pyridonyl, pyrimidonyl and 1-isoquinolinyl.

An "aryl" group is, for example, phenyl, indenyl, indanyl, naphthyl, tetrahydronaphthyl or fluorenyl, preferably phenyl.

An example of "$C_{1-6}$-alkanoyloxy" is acetoxy. Examples of "$C_{1-8}$-alkoxycarbonyl", "$C_{1-6}$-alkoxycarbonyl" and $C_{1-4}$-alkoxycarbonyl include methoxycarbonyl, ethoxycarbonyl, N- and t-butoxycarbonyl. Examples of $C_{2-6}$-alkynyl are ethynyl and 2-propynyl. Examples of "$C_{1-6}$-alkoxy" include methoxy, ethoxy and propoxy. Examples of "$C_{1-6}$-alkanoylamino" and $C_{1-3}$-alkanoylamino include formamido, acetamido and propionylamino. Examples of "$C_{1-6}$-alkylS(O)$_a$ wherein a is 0 to 2" include $C_{1-6}$-alkyl sulphonyl, $C_{1-3}$-alkylS(O)$_a$, methylthio, ethylthio, methylsulphinyl, ethylsulphinyl, mesyl and ethylsulphonyl. Examples of "$C_{1-8}$-alkanoyl", "$C_{1-6}$-alkanoyl" and $C_{1-4}$-alkanoyl include $C_{1-3}$-alkanoyl, propionyl and acetyl. Examples of "N—$C_{1-6}$-alkylamino" and N—($C_{1-3}$-alkyl)amino include methylamino and ethylamino. Examples of "N,N—($C_{1-6}$-alkyl)$_2$amino" and N,N—($C_{1-2}$-alkyl)$_2$amino include di-N-methylamino, di-(N-ethyl) amino, di-(N-butyl)amino and N-ethyl-N-methylamino. Examples of "$C_{2-8}$-alkenyl" are $C_{1-6}$-alkenyl and $C_{2-3}$-alkenyl, and include vinyl, alkyl, and 1-propenyl. Examples of "N—($C_{1-3}$-alkyl)sulphamoyl" and "N—($C_{1-5}$alkyl)sulphamoyl" are N—($C_{1-3}$-alkyl)sulphamoyl, N-(methyl)sulphamoyl and N-(ethyl)sulphamoyl. Examples of "N—($C_{1-6}$-alkyl)$_2$sulphamoyl" are N,N-$C_{1-3}$-alkyl)$_2$sulphamoyl, N,N-(dimethyl)sulphamoyl and N-(methyl)-N-(ethyl) sulphamoyl. Examples of "N—($C_{1-8}$-alkyl)carbamoyl" and "N—($C_{1-6}$-alkyl)carbamoyl" are N—($C_{1-4}$-alkyl)carbamoyl, N—($C_{1-3}$-alkyl)carbamoyl, methylaminocarbonyl, and ethylaminocarbonyl. Examples of "N,N—$C_{1-8}$-alkyl)$_2$carbamoyl" and "N,N—($C_{1-6}$-alkyl)$_2$carbamoyl" are N,N—($C_{1-4}$-alkyl)$_2$carbamoyl, N,N—($C_{1-2}$-alkyl)$_2$carbamoyl, dimethylaminocarbonyl and methylethylaminocarbonyl. Examples of "(heterocyclic group)$C_{1-6}$-alkyl" include piperidin-1-ylmethyl, piperidin-1-ylethyl, piperidin-1-ylpropyl, pyridylmethyl, 3-morpholinopropyl, 2-morpholinoethyl and 2-pyrimid-2-ylethyl. Examples of "(heterocyclic group)$C_{1-6}$-alkoxy" include (heterocyclic group)methoxy, (heterocyclic group)ethoxy and (heterocyclic group) propoxy. Examples of "aryl$C_{1-6}$-alkyl" include benzyl, 2-phenylethyl, 2-phenylpropyl and 3-phenylpropyl. Examples of "aryloxy" include phenoxy and naphthyloxy. Examples of "$C_{3-8}$-cycloalkyl" include cyclopropyl and cyclohexyl. Examples of "$C_{3-8}$ cycloalkyl$C_{1-6}$-alkyl" include cyclopropylmethyl and 2-cyclohexylpropyl. Examples of "$C_{1-6}$-alkoxycarbonylamino" include methoxycarbonylamino and t-butoxycarbonylamino.

Composite terms are used to describe groups comprising more than one functionality such as aryl$C_{1-4}$-alkyl. Such terms are to be interpreted as is understood by a person skilled in the art. For example aryl$C_{1-6}$-alkyl comprises $C_{1-6}$-alkyl substituted by aryl and such a group includes benzyl, 2-phenylethyl, 2-phenylpropyl and 3-phenylpropyl.

In another embodiment of this aspect, the invention comprises compounds of the following general formula (4) (hereinafter embodiment [0098]):

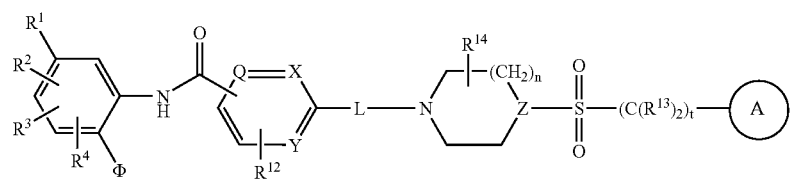

(4)

the N-oxide forms, the pharmaceutically acceptable addition salts and the stereo-chemically isomeric forms thereof, wherein Φ is —NH 2 or —OH;

n is 0, 1, 2 or 3, wherein when n is 0 then a direct bond is intended;

t is 0, 1, 2, 3 or 4, wherein when t is 0 then a direct bond is intended;

Q, X, Y, and Z are independently N or CH;

$R^1$ is H or as defined in embodiment [0046], $R^2$, $R^3$, and $R^4$ are as defined in embodiment [0046];

$R^{12}$ is hydrogen, halo, hydroxy, amino, nitro, $C_{1-6}$-alkyl, $C_{1-6}$-alkyloxy, trifluoromethyl, di($C_{1-6}$-alkyl)amino, hydroxyamino and naphthalenylsulfonylpyrazinyl;

-L- is a direct bond or a bivalent radical selected from $C_{1-6}$-alkanediyl, amino, carbonyl and aminocarbonyl;

each $R^{13}$ is a hydrogen atom, wherein when t is 2, 3, or 4 one of the $R^{13}$ is optionally aryl;

$R^{14}$ is hydrogen, hydroxy, amino, hydroxy$C_{1-6}$-alkyl, $C_{1-6}$-alkyl, $C_{1-6}$-alkyloxy aryl$C_{1-6}$-alkyl, aminocarbonyl, hydroxycarbonyl, amino$C_{1-6}$-alkyl, aminocarbonyl $C_{1-6}$-alkyl, hydroxycarbonyl$C_{1-6}$-alkyl, hydroxyaminocarbonyl, $C_{1-6}$-alkyloxycarbonyl, $C_{1-6}$-alkylamino$C_{1-6}$-alkyl or di($C_{1-6}$-alky)amino$C_{1-6}$-alkyl;
Ring A is selected from
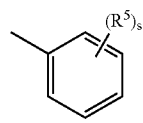 (a-1)
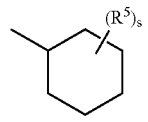 (a-2)
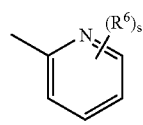 (a-3)
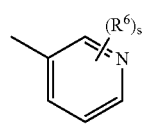 (a-4)
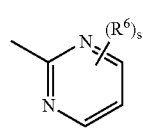 (a-5)
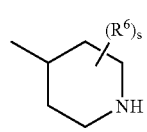 (a-6)
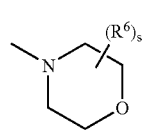 (a-7)
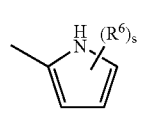 (a-8)
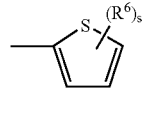 (a-9)
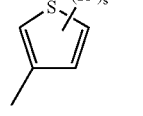 (a-10)
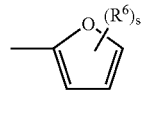 (a-11)
-continued
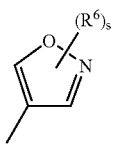 (a-12)
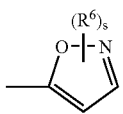 (a-13)
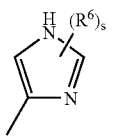 (a-14)
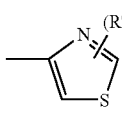 (a-15)
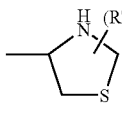 (a-16)
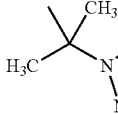 (a-17)
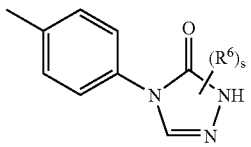 (a-18)
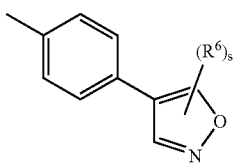 (a-19)
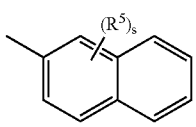 (a-20)
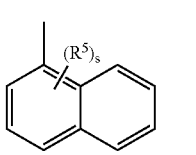 (a-21)
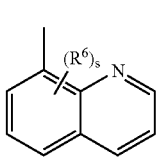 (a-22)

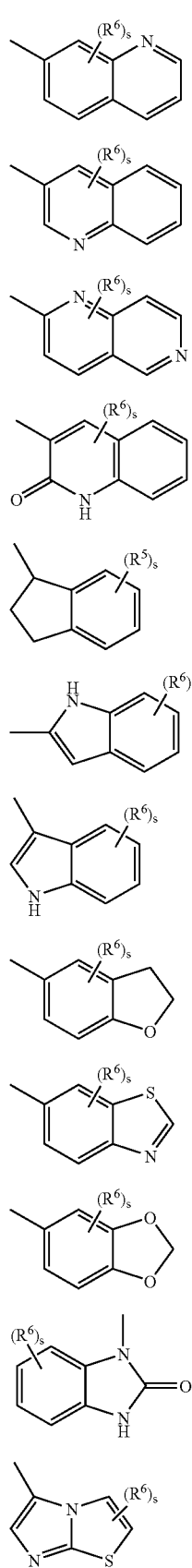
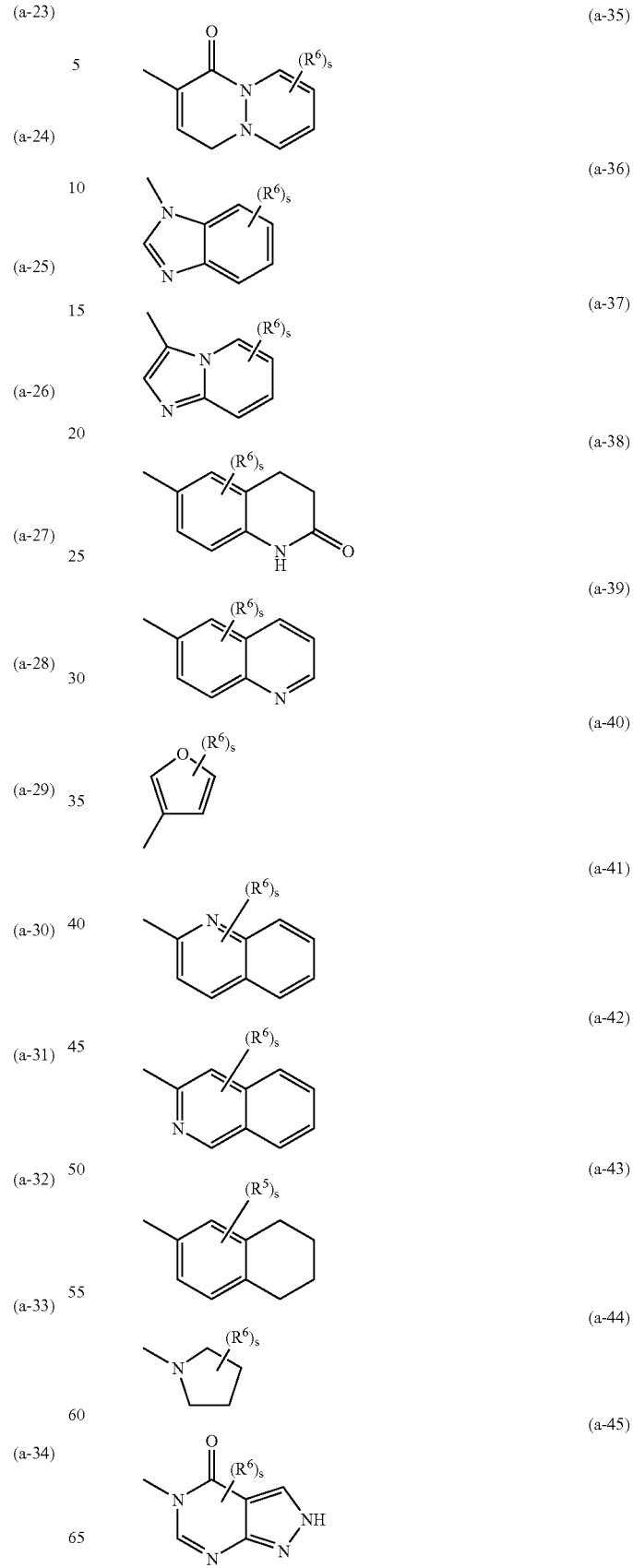

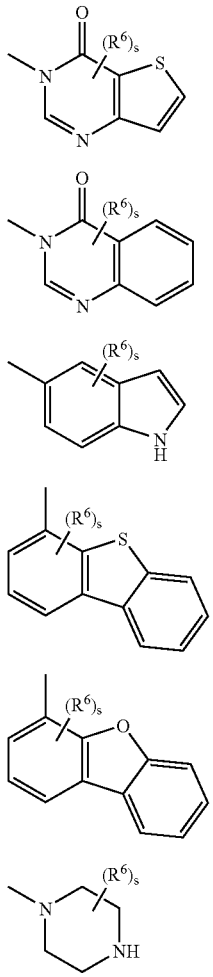

wherein each s is independently 0, 1, 2, 3, 4 or 5;

$R^5$ and $R^6$ are independently selected from hydrogen; halo; hydroxy; amino; nitro; trihalo$C_{1-6}$-alkyl; trihalo$C_{1-6}$-alkyloxy; $C_{1-6}$-alkyl; $C_{1-6}$-alkyl substituted with aryl and $C_{3-10}$-cycloalkyl; $C_{1-6}$-alkyloxy; $C_{1-6}$-alkyloxy$C_{1-6}$-alkyloxy; $C_{1-6}$-alkylcarbonyl; $C_{1-6}$-alkyloxycarbonyl; $C_{1-6}$-alkylsulfonyl; cyano$C_{1-6}$-alkyl; hydroxy$C_{1-6}$-alkyl; hydroxy$C_{1-6}$-alkyloxy; hydroxy$C_{1-6}$-alkylamino; amino$C_{1-6}$-alkyloxy; di($C_{1-6}$-alkyl)aminocarbonyl; di(hydroxy$C_{1-6}$-alkyl)amino; (aryl)($C_{1-6}$-alkyl)amino; di($C_{1-6}$-alkyl)amino$C_{1-6}$-alkyloxy; di($C_{1-6}$-alkyl)amino$C_{1-6}$-alkylamino; di($C_{1-6}$-alkyl)amino$C_{1-6}$-alkylamino$C_{1-6}$-alkyl; arylsulfonyl; arylsulfonylamino; aryloxy; aryloxy$C_{1-6}$-alkyl; aryl$C_{1-6}$-alkenediyl; di($C_{1-6}$-alkyl)amino; di($C_{1-6}$-alkyl)amino$C_{1-6}$-alkyl; di($C_{1-6}$-alkyl)amino($C_{1-6}$-alkyl)amino; di($C_{1-6}$-alkyl)amino($C_{1-6}$-alkyl)amino$C_{1-6}$-alkyl; di($C_{1-6}$-alkyl)amino$C_{1-6}$-alkyl($C_{1-6}$-alkyl)amino; di($C_{1-6}$-alkyl)amino$C_{1-6}$-alkyl($C_{1-6}$-alkyl)amino$C_{1-6}$-alkyl; aminosulfonylamino($C_{1-6}$-alkyl)amino; aminosulfonylamino($C_{1-6}$-alkyl)amino$C_{1-6}$-alkyl; di($C_{1-6}$-alkyl)aminosulfonylamino($C_{1-6}$-alkyl)amino; di($C_{1-6}$-alkyl)aminosulfonylamino($C_{1-6}$-alkyl)amino$C_{1-6}$-alkyl; cyano; thiophenyl; thiophenyl substituted with di($C_{1-6}$-alkyl)amino$C_{1-6}$-alkyl($C_{1-6}$-alkyl)amino$C_{1-6}$-alkyl, di($C_{1-6}$-alkyl)amino$C_{1-6}$-alkyl, $C_{1-6}$-alkylpiperazinyl$C_{1-6}$-alkyl, hydroxy$C_{1-6}$-alkylpiperazinyl$C_{1-6}$-alkyl, hydroxy$C_{1-6}$-alkyloxy$C_{1-6}$-alkylpiperazinyl$C_{1-6}$-alkyl, di($C_{1-6}$-alkyl)aminosulfonylpiperazinyl$C_{1-6}$-alkyl, $C_{1-6}$-alkyloxypiperidinyl, $C_{1-6}$-alkyloxypiperidinyl$C_{1-6}$-alkyl, morpholinyl$C_{1-6}$-alkyl, hydroxy$C_{1-6}$-alkyl($C_{1-6}$-alkyl)amino$C_{1-6}$-alkyl, or di(hydroxy$C_{1-6}$-alkyl)amino$C_{1-6}$-alkyl; furanyl; furanyl substituted with hydroxy$C_{1-6}$-alkyl; benzofuranyl; imidazolyl; oxazolyl; oxazolyl substituted with aryl and $C_{1-6}$-alkyl; $C_{1-6}$-alkyltriazolyl; tetrazolyl; pyrrolidinyl; pyrrolyl; piperidinyl$C_{1-6}$-alkyloxy; morpholinyl; $C_{1-6}$-alkylmorpholinyl; morpholinyl$C_{1-6}$-alkyloxy; morpholinyl$C_{1-6}$-alkyl; morpholinyl$C_{1-6}$-alkylamino; morpholinyl$C_{1-6}$-alkylamino$C_{1-6}$-alkyl; piperazinyl; $C_{1-6}$-alkylpiperazinyl; $C_{1-6}$-alkylpiperazinyl$C_{1-6}$-alkyloxy; piperazinyl$C_{1-6}$-alkyl; naphthalenylsulfonylpiperazinyl; naphthalenylsulfonylpiperidinyl; naphthalenylsulfonyl; $C_{1-6}$-alkylpiperazinyl$C_{1-6}$-alkyl; $C_{1-6}$-alkylpiperazinyl$C_{1-6}$-alkylamino $C_{1-6}$-alkylpiperazinyl$C_{1-6}$-alkylamino$C_{1-6}$-alkyl; $C_{1-6}$-alkylpiperazinylsulfonyl; aminosulfonylpiperazinyl $C_{1-6}$-alkyloxy; aminosulfonylpiperazinyl; aminosulfonylpiperazinyl$C_{1-6}$-alkyl; di($C_{1-6}$-alkyl)aminosulfonylpiperazinyl; di($C_{1-6}$-alkyl)aminosulfonylpiperazinyl$C_{1-6}$-alkyl; hydroxy$C_{1-6}$-alkylpiperazinyl; hydroxy$C_{1-6}$-alkylpiperazinyl$C_{1-6}$-alkyl; $C_{1-6}$-alkyloxyperidinyl; $C_{1-6}$-alkyloxypiperidinyl$C_{1-6}$-alkyl; piperidinylamino$C_{1-6}$-alkylamino; piperidinylamino$C_{1-6}$-alkylamino$C_{1-6}$-alkyl; ($C_{1-6}$-alkylpiperidinyl)(hydroxy$C_{1-6}$-alkyl)amino$C_{1-6}$-alkylamino; ($C_{1-6}$-alkylpiperidinyl)(hydroxy$C_{1-6}$-alkyl)amino$C_{1-6}$-alkylamino$C_{1-6}$-alkyl; hydroxy$C_{1-6}$-alkyloxy$C_{1-6}$-alkyl piperazinyl; hydroxy$C_{1-6}$-alkyloxy$C_{1-6}$-alkylpiperazinyl$C_{1-6}$-alkyl; (hydroxy$C_{1-6}$-alkyl)($C_{1-6}$-alkyl)amino; (hydroxy$C_{1-6}$alkyl)($C_{1-6}$-alkyl)amino$C_{1-6}$-alkyl; hydroxy$C_{1-6}$-alkylamino$C_{1-6}$-alkyl; di(hydroxy$C_{1-6}$-alkyl)amino$C_{1-6}$-alkyl; pyrrolidinyl$C_{1-6}$-alkyl; pyrrolidinyl$C_{1-6}$-alkyloxy; pyrazolyl; thiopyrazolyl; pyrazolyl substituted with two substituents selected from $C_{1-6}$-alkyl and trihalo$C_{1-6}$-alkyl; pyridinyl; pyridinyl substituted with $C_{1-6}$-alkyloxy, aryloxy or aryl; pyrimidinyl; tetrahydropyrimidinylpiperazinyl; tetrahydropyrimidinylpiperazinyl$C_{1-6}$-alkyl; quinolinyl; indolyl; phenyl; phenyl substituted with one, two or three substituents independently selected from halo, amino, nitro, $C_{1-6}$-alkyl, $C_{1-6}$-alkyloxy, hydroxy$C_{1-4}$-alkyl, trifluoromethyl, trifluoromethyloxy, hydroxy$C_{1-4}$-alkyloxy, $C_{1-4}$-alkylsulfonyl, $C_{1-4}$-alkyloxy$C_{1-4}$-alkyloxy, $C_{1-4}$-alkyloxycarbonyl, amino$C_{1-4}$-alkyloxy, di($C_{1-4}$-alkyl)amino$C_{1-4}$-alkyloxy, di($C_{1-4}$-alkyl)amino, di($C_{1-4}$-alkyl)aminocarbonyl, di($C_{1-4}$-alkyl)amino$C_{1-4}$-alkyl, di($C_{1-4}$-alkyl)amino$C_{1-4}$-alkylamino$C_{1-4}$-alkyl, di ($C_{1-4}$-alkyl)amino($C_{1-4}$-alkyl)amino, di($C_{1-4}$-alkyl)amino($C_{1-4}$-alkyl)amino$C_{1-4}$-alkyl, di($C_{1-4}$-alkyl)amino$C_{1-4}$-alkyl($C_{1-4}$-alkyl)amino, di($C_{1-4}$-alkyl)amino$C_{1-4}$-alkyl($C_{1-4}$-alkyl)amino$C_{1-4}$-alkyl, aminosulfonylamino($C_{1-4}$-alkyl)amino, aminosulfonylamino($C_{1-4}$-alkyl)amino$C_{1-4}$-alkyl, di($C_{1-4}$-alkyl)aminosulfonylamino($C_{1-4}$-alkyl)amino, di($C_{1-4}$-alkyl)aminosulfonylamino($C_{1-4}$-alkyl)amino$C_{1-4}$-alkyl, cyano, piperidinyl$C_{1-4}$-alkyloxy, pyrrolidinyl$C_{1-4}$-alkyloxy, aminosulfonylpiperazinyl, aminosulfonylpiperazinyl$C_{1-4}$-alkyl, di($C_{1-4}$-alkyl)aminosulfonylpiperazinyl, di($C_{1-4}$-alkyl)aminosulfonylpiperazinyl$C_{1-4}$-alkyl, hydroxy$C_{1-4}$-alkylpiperazinyl, hydroxy$C_{1-4}$-alkylpiperazinyl$C_{1-4}$-alkyl, $C_{1-4}$-alkyloxypiperidinyl, $C_{1-4}$-alkyloxypiperidinyl$C_{1-4}$-alkyl, hydroxy$C_{1-4}$-alkyloxy$C_{1-4}$- alkylpiperazinyl, hydroxyC$_{1-4}$-alkyloxyC$_{1-4}$-alkylpiperazinylC$_{1-4}$-alkyl, (hydroxyC$_{1-4}$-alkyl)(C$_{1-4}$-alkyl)amino, (hydroxyC$_{1-4}$-alkyl)(C$_{1-4}$-alkyl)amino C$_{1-4}$-alkyl, di(hydroxyC$_{1-4}$-alkyl)amino, di(hydroxy C$_{1-4}$-alkyl)aminoC$_{1-4}$-alkyl, furanyl, furanyl substituted with —CH=CH—CH=CH—, pyrrolidinylC$_{1-4}$-alkyl, pyrrolidinylC$_{1-4}$-alkyloxy, morpholinyl, morpholinylC$_{1-4}$-alkyloxy, morpholinylC$_{1-4}$-alkyl, morpholinylC$_{1-4}$-alkylamino, morpholinylC$_{1-4}$-alkylaminoC$_{1-4}$-alkyl, piperazinyl, C$_{1-4}$-alkylpiperazinyl, C$_{1-4}$-alkylpiperazinylC$_{1-4}$-alkyloxy, piperazinylC$_{1-4}$-alkyl, C$_{1-4}$-alkylpiperazinylC$_{1-4}$-alkyl, C$_{1-4}$-alkylpiperazinylC$_{1-4}$-alkylamino, C$_{1-4}$-alkylpiperazinylC$_{1-4}$-alkylaminoC$_{1-6}$-alkyl, tetrahydropyrimidinylpiperazinyl, tetrahydropyrimidinylpiperazinylC$_{1-4}$-alkyl, piperidinylaminoC$_{1-4}$-alkylamino, piperidinylaminoC$_{1-4}$-alkylaminoC$_{1-4}$-alkyl, (C$_{1-4}$-alkylpiperidinyl)(hydroxyC$_{1-4}$-alkyl)aminoC$_{1-4}$-alkylamino, (C$_{1-4}$-alkylpiperidinyl)(hydroxyC$_{1-4}$-alkyl)aminoC$_{1-4}$-alkylaminoC$_{1-4}$-alkyl, pyridinylC$_{1-4}$-alkyloxy, hydroxyC$_{1-4}$-alkylamino, hydroxyC$_{1-4}$-alkylaminoC$_{1-4}$-alkyl, di(C$_{1-4}$-alkyl)aminoC$_{1-4}$-alkylamino, aminothiadiazolyl, aminosulfonylpiperazinylC$_{1-4}$-alkyloxy, and thiophenylC$_{1-4}$-alkylamino; the central moiety

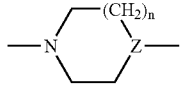

is optionally bridged (i.e., forming a bicyclic moiety) with a methylene, ethylene or propylene bridge;

each $R^5$ and $R^6$ can be placed on the nitrogen in replacement of the hydrogen;

aryl in the above is phenyl, or phenyl substituted with one or more substituents each independently selected from halo, C$_{1-6}$-alkyl, C$_{1-6}$-alkyloxy, trifluoromethyl, cyano, and hydroxycarbonyl.

In one embodiment of the compound according to embodiment [0098] (hereinafter embodiment [0099]), one or more of the following apply:

a) n is 1 or 2;
b) t is 0, 1 or 2;
c) Z is nitrogen;
d) $R^{12}$ is hydrogen, nitro, C$_{1-6}$-alkyloxy, trifluoromethyl, di(C$_{1-6}$-alkyl)amino, hydroxyamino or naphtalenylsulfonylpyrazinyl;
e) -L- is a direct bond or a bivalent radical selected from C$_{1-6}$-alkanediyl, carbonyl and aminocarbonyl;
f) each $R^{13}$ is hydrogen;
g) $R^{14}$ is hydrogen, hydroxyC$_{1-6}$-alkyl, aminocarbonyl, hydroxyaminocarbonyl or di(C$_{1-6}$-alkyl)aminoC$_{1-6}$-alkyl;
h) the A ring is a radical selected from (a-1), (a-7), (a-9), (a-10), (a-12), (a-14), (a-19), (a-20), (a-21), (a-22), (a-23), (a-30), (a-34), (a-49) and (a-50);
i) each s is independently 0, 1, 2 or 5;
j) each $R^5$ and $R^6$ are independently selected from hydrogen; halo; nitro; trihaloC$_{1-6}$-alkyl; trihaloC$_{1-6}$-alkyloxy; C$_{1-6}$-alkyl; C$_{1-6}$-alkyloxy; C$_{1-6}$-alkylsulfonyl; (aryl)(C$_{1-6}$-alkyl)amino; arylsulfonyl; aryloxy; arylC$_{2-6}$-alkenediyl; di(C$_{1-6}$-alkyl)amino; thiophenyl; thiophenyl substituted with di(C$_{1-6}$-alkyl)aminoC$_{1-6}$-alkyl(C$_{1-6}$-alkyl)aminoC$_{1-6}$-alkyl, di(C$_{1-6}$-alkyl)aminoC$_{1-6}$-alkyl, C$_{1-6}$-alkylpiperazinylC$_{1-6}$-alkyl, hydroxydC$_{1-6}$-alkylpiperazinylC$_{1-6}$-alkyl, hydroxyC$_{1-6}$-alkyloxyC$_{1-6}$-alkylpiperazinylC$_{1-6}$-alkyl, di(C$_{1-6}$-alkyl)aminosulfonylpiperazinylC$_{1-6}$-alkyl, C$_{1-6}$-alkyloxypiperidinylC$_{1-6}$-alkyl, morpholinylC$_{1-6}$-alkyl, hydroxyC$_{1-6}$-alkyl(C$_{1-6}$-alkyl)aminoC$_{1-6}$-alkyl, or dKhydroxyC$_{1-6}$-alkyl)aminoC$_{1-6}$-alkyl; furanyl; oxazolyl; pyrrolyl; pyrazolyl; pyridinyl; pyridinyl substituted with C$_{1-6}$-alkyloxy; quinolinyl; indolyl; phenyl; and phenyl substituted with one, two or three substituents independently selected from halo, amino, C$_{1-6}$-alkyl, C$_{1-6}$-alkyloxy, hydroxyC$_{1-4}$-alkyl, trifluoromethyl, trifluoromethyloxy, di(C$_{1-4}$-alkyl)aminoC$_{1-4}$-alkyloxy, di(C$_{1-4}$-alkyl)amino, di(C$_{1-4}$-alkyl)amino C$_{1-4}$-alkyl, di(C$_{1-4}$-alkyl)aminoC$_{1-4}$-alkyl(C$_{1-4}$-alkyl)amino, di(C$_{1-4}$-alkyl)aminoC$_{1-4}$-alkyl(C$_{1-4}$-alkyl)aminoC$_{1-4}$-alkyl, hydroxyC$_{1-4}$-alkylpiperazinylC$_{1-4}$-alkyl, hydroxyC$_{1-4}$-alkyloxyC$_{1-4}$-alkylpiperazinylC$_{1-4}$-alkyl, di(hydroxyC$_{1-4}$-alkyl)aminoC$_{1-4}$-alkyl, pyrrolidinyl C$_{1-4}$-alkyl, pyrrolidinylC$_{1-4}$-alkyloxy, morpholinylC$_{1-4}$-alkyloxy, morpholinylC$_{1-4}$-alkyl, and C$_{1-4}$-alkylpiperazinylC$_{1-4}$-alkyl, and k) the central moiety

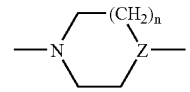

is optionally bridged (i.e., forming a bicyclic moiety) with a methylene bridge.

In another embodiment of the compound according to embodiment [0098] (hereinafter embodiment [0100]), one or more of the following apply:

l) n is 1 or 2;
m) t is 0 or 2;
n) Z is nitrogen;
o) $R^{12}$ is hydrogen;
p) -L- is a direct bond;
q) each $R^{13}$ is hydrogen;
r) $R^{14}$ is hydrogen;
s) the A ring is a radical selected from (a-1), (a-9), (a-19), (a-20), (a-21), (a-22), (a-23), (a-49) and (a-50);
t) each s is independently 0, 1, 2 or 5;
u) each $R^5$ and $R^6$ is independently selected from hydrogen; halo; trihaloC$_{1-6}$-alkyl; trihaloC$_{1-6}$-alkyloxy; C$_{1-6}$-alkyl; C$_{1-6}$-alkyloxy; arylC$_{2-6}$-alkenediyl; di(C$_{1-6}$-alkyl)amino; thiophenyl; thiophenyl substituted with di(C$_{1-6}$-alkyl)aminoC$_{1-6}$-alkyl(C$_{1-6}$-alkyl)aminoC$_{1-6}$-alkyl, di(C$_{1-6}$-alkyl)aminoC$_{1-6}$-alkyl, C$_{1-6}$-alkylpiperazinylC$_{1-6}$-alkyl, hydroxyC$_{1-6}$-alkylpiperazinylC$_{1-6}$-alkyl, hydroxyC$_{1-6}$-alkyloxyC$_{1-6}$-alkylpiperazinylC$_{1-6}$-alkyl, C$_{1-6}$-alkyloxypiperidinylC$_{1-6}$-alkyl, morpholinylC$_{1-6}$-alkyl, hydroxyC$_{1-6}$-alkyl(C$_{1-6}$-alkyl)aminoC$_{1-6}$-alkyl, or diflurohydroxyC$_{1-6}$-alkyl)aminoC$_{1-6}$-alkyl; furanyl; oxazolyl; pyrazolyl; pyridinyl; pyridinyl substituted with C$_{1-6}$-alkyloxy; quinolinyl; indolyl; phenyl; and phenyl substituted with one, two or three substituents independently selected from halo, amino, C$_{1-6}$-alkyl, C$_{1-6}$-alkyloxy, hydroxyC$_{1-6}$-alkyl, trifluoromethyl, trifluoromethyloxy, di(C$_{1-4}$-alkyl)aminoC$_{1-4}$-alkyloxy, di(C$_{1-4}$-alkyl)amino, di(C$_{1-4}$-alkyl)aminoC$_{1-4}$-alkyl, di(C$_{1-4}$-alkyl)aminoC$_{1-4}$-alkyl(C$_{1-4}$-alkyl)aminoC$_{1-4}$-alkyl, hydroxyC$_{1-4}$-alkylpiperazinylC$_{1-4}$-alkyl, hydroxyC$_{1-4}$-alkyloxyC$_{1-4}$-alkylpiperazinylC$_{1-4}$-alkyl, di(hydroxyC$_{1-4}$-alkyl)aminoC$_{1-4}$-alkyl, pyrrolidinyl $C_{1-4}$-alkyl pyrrolidinyl$C_{1-4}$-alkyloxy, morpholinyl$C_{1-4}$-alkyloxy, morpholinyl$C_{1-4}$-alkyl, $C_{1-4}$-alkylpiperazinyl$C_{1-4}$-alkyl, and v) the central moiety

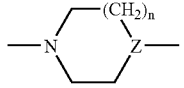

is optionally bridged (i.e., forming a bicyclic moiety) with a methylene bridge.

In another embodiment of the compound according to embodiment [0098] (hereinafter embodiment [0101]), one or more of the following apply:
w) n is 1;
x) t is 0;
y) Z is nitrogen;
z) $R^{12}$ is hydrogen;
aa) -L- is a direct bond;
bb) each $R^{13}$ is hydrogen;
cc) $R^{14}$ is hydrogen;
dd) the A ring is a radical selected from (a-1) and (a-20);
ee) each s is independently 0 or 1;
ff) each $R^5$ and $R^6$ is independently selected from hydrogen; thiophenyl; thiophenyl substituted with di($C_{1-6}$-alkyl)amino$C_{1-6}$-alkyl or $C_{1-6}$-alkylpiperazinyl$C_{1-6}$-alkyl; furanyl; phenyl; and phenyl substituted with one substituents independently selected from di($C_{1-4}$-alkyl)amino$C_{1-4}$-alkyloxy, di($C_{1-4}$-alkyl)amino, di($C_{1-4}$-alkyl)amino$C_{1-4}$-alkyl, di($C_{1-4}$-alkyl)amino$C_{1-4}$-alkyl ($C_{1-4}$-alkyl)amino$C_{1-4}$-alkyl, pyrrolidinyl$C_{1-4}$-alkyl, pyrrolidinyl$C_{1-4}$-alkyloxy and $C_{1-4}$-alkylpiperazinyl $C_{1-4}$-alkyl.

In another embodiment of the compound according to embodiment [0098] (hereinafter embodiment [0102]), L is a direct bond and/or $R^{12}$ is H.

In another embodiment of the compound according to embodiment [0098] (hereinafter embodiment [0103]), one or more of the following apply:
a) t is 0;
b) $R^{12}$ is hydrogen, halo, hydroxy, amino, nitro, $C_{1-6}$-alkyl, $C_{1-6}$-alkyloxy, trifluoromethyl or di($C_{1-6}$-alkyl)amino;
c) -L- is a direct bond or a bivalent radical selected from $C_{1-6}$-alkanediyl, amino, and carbonyl;
d) $R^{14}$ is hydrogen, hydroxy, amino, hydroxyd-$C_{1-6}$-alkyl, $C_{1-6}$-alkyl, $C_{1-6}$alkyloxy, aryl$C_{1-6}$-alkyl, aminocarbonyl, amino$C_{1-6}$-alkyl, $C_{1-6}$-alkylamino$C_{1-6}$-alkyl or di($C_{1-6}$-alkyl)amino$C_{1-6}$-alkyl;
e) the A ring is a radical selected from (a-1), (a-3), (a-4), (a-5), (a-6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-28), (a-29), (a-30), (a-31), (a-32), (a-33), (a-34), (a-35), (a-36), (a-37), (a-38), (a-39), (a-40), (a-41), (a-42), (a-44), (a-45), (a-46), (a-47), (a-48) and (a-51);
f) each s is independently 0, 1, 2, 3 or 4;
g) $R^5$ is hydrogen; halo; hydroxy; amino; nitro; trihalo $C_{1-6}$-alkyl; trihalo$C_{1-6}$-alkyloxy; $C_{1-6}$-alkyl; $C_{1-6}$-alkyloxy; $C_{1-6}$-alkylcarbonyl; $C_{1-6}$-alkyloxycarbonyl; $C_{1-6}$-alkylsulfonyl; hydroxy$C_{1-6}$-alkyl; aryloxy; di($C_{1-6}$-alkyl)amino; cyano; thiophenyl; furanyl; furanyl substituted with hydroxy$C_{1-6}$-alkyl; benzofuranyl; imidazolyl; oxazolyl; oxazolyl substituted with aryl and $C_{1-6}$-alkyl; $C_{1-6}$-alkyltriazolyl; tetrazolyl; pyrrolidinyl; pyrrolyl; morpholinyl; $C_{1-6}$-alkylmorpholinyl; piperazinyl; $C_{1-6}$-alkylpiperazinyl; hydroxy$C_{1-6}$-alkylpiperazinyl; $C_{1-6}$-alkyloxypiperidinyl; pyrazoyl; pyrazolyl substituted with one or two substituents selected from $C_{1-6}$-alkyl and trihalo$C_{1-6}$-alkyl; pyridinyl; pyridinyl substituted with $C_{1-6}$-alkyloxy, aryloxy or aryl; pyrimidinyl; quinolinyl; indole; phenyl; or phenyl substituted with one or two substituents independently selected from halo, $C_{1-6}$-alkyl, $C_{1-6}$-alkyloxy, or trifluoromethyl;
h) $R^6$ is hydrogen; halo; hydroxy; amino; nitro; trihalo $C_{1-6}$-alkyl; trihalo$C_{1-6}$-alkyloxy; $C_{1-6}$-alkyl; $C_{1-6}$-alkyloxy; $C_{1-6}$-alkylcarbonyl; $C_{1-6}$-alkyloxycarbonyl; $C_{1-6}$-alkylsulfonyl; hydroxy$C_{1-6}$-alkyl; aryloxy; di($C_{1-6}$-alkyl)amino; cyano; pyridinyl; phenyl; or phenyl substituted with one or two substituents independently selected from halo, $C_{1-6}$-alkyl, $C_{1-6}$-alkyloxy, and trifluoromethyl, and
i) the central moiety

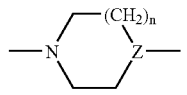

is optionally bridged (i.e., forming a bicyclic moiety) with an ethylene bridge.

In another embodiment of the compound according to embodiment [0098] (hereinafter embodiment [0104]), one or more of the following apply:
a) $R^{12}$ is hydrogen, halo, hydroxy, amino, nitro, $C_{1-6}$-alkyl, $C_{1-6}$-alkyloxy, trifluoromethyl, hydroxyamino or naphthalenylsulfonylpyrazinyl;
b) $R^{14}$ is hydrogen, hydroxy, amino, hydroxy$C_{1-6}$-alkyl, $C_{1-6}$-alkyloxy, aryl$C_{1-6}$-alkyl, aminocarbonyl, hydroxycarbonyl, amino$C_{1-6}$-alkyl, aminocarbonyl$C_{1-6}$-alkyl, hydroxycarbonyl$C_{1-6}$-alkyl, hydroxyaminocarbonyl, $C_{1-6}$-alkyloxycarbonyl, $C_{1-6}$-alkylamino$C_{1-6}$-alkyl or di($C_{1-6}$-alkyl)amino$C_{1-6}$-alkyl;
c) the A ring is a radical selected from (a-1), (a-2), (a-3), (a-4), (a-5), (a-6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-27), (a-28), (a-29), (a-30), (a-31), (a-32), (a-33), (a-34), (a-35), (a-36), (a-37), (a-38), (a-39), (a-40), (a-41), (a-42), (a-43) and (a-44);
d) each $R^5$ and $R^6$ are independently selected from hydrogen; halo; hydroxy; amino; nitro; trihalo$C_{1-6}$-alkyl; trihalo$C_{1-6}$-alkyloxy; $C_{1-6}$-alkyl; $C_{1-6}$-alkyloxy; $C_{1-6}$-alkyloxyd$C_{1-6}$-alkyloxy; $C_{1-6}$-alkylcarbonyl; $C_{1-6}$-alkylsulfonyl; cyano$C_{1-6}$-alkyl; hydroxy$C_{1-6}$-alkyl; hydroxy$C_{1-6}$-alkyloxy; hydroxy$C_{1-6}$-alkylamino; amino$C_{1-6}$-alkyloxy; di($C_{1-6}$-alkyl)aminocarbonyl; di(hydroxy$C_{1-6}$-alkyl)amino; di($C_{1-6}$-alkyl)amino$C_{1-6}$-alkyloxy; di($C_{1-6}$-alkyl)amino$C_{1-6}$-alkylamino; arylsulfonyl; arylsulfonylamino; aryloxy; aryl$C_{2-6}$-alkenediyl; di($C_{1-6}$-alkyl)amino; cyano; thiophenyl; thiophenyl substituted with di($C_{1-6}$-alkyl)amino$C_{1-6}$-alkyl($C_{1-6}$-alkyl)amino$C_{1-6}$-alkyl, di($C_{1-6}$-alkyl)amino$C_{1-6}$-alkyl, $C_{1-6}$-alkylpiperazinyl$C_{1-6}$-alkyl or di(hydroxy$C_{1-6}$-alkyl)amino$C_{1-6}$-alkyl; furanyl; imidazolyl; $C_{1-6}$-alkyltriazolyl; tetrazolyl; piperidinyl$C_{1-6}$-alkyloxy; morpholinyl; $C_{1-6}$-alkylmorpholinyl; morpholinyl$C_{1-6}$-alkyloxy; morpholinyl$C_{1-6}$-alkyl; $C_{1-6}$-alkylpiperazinyl$C_{1-6}$-alkyloxy; $C_{1-6}$-alkylpiperazinyl$C_{1-6}$-alkyl; $C_{1-6}$-alkylpiperazinylsulfonyl; aminosulfonylpiperazinyl$C_{1-6}$-alkyloxy; aminosulfonylpiperazinyl; aminosulfonylpiperazinyl$C_{1-6}$-alkyl;

di($C_{1-6}$-alkyl)aminosulfonylpiperazinyl; di($C_{1-6}$-alkyl) aminosulfonylpiperazinyl$C_{1-6}$-alkyl; hydroxy$C_{1-6}$-alkylpiperazinyl; hydroxy$C_{1-6}$-alkylpiperazinyl$C_{1-6}$-alkyl; $C_{1-6}$-alkyloxypiperidinyl; $C_{1-6}$-alkyloxypiperidinyl$C_{1-6}$-alkyl; hydroxy$C_{1-6}$-alkyloxy$C_{1-6}$-alkylpiperazinyl; hydroxy$C_{1-6}$-alkyloxy$C_{1-6}$-alkylpiperazinyl$C_{1-6}$-alkyl; (hydroxy$C_{1-6}$-alkyl)($C_{1-6}$-alkyl)amino; (hydroxy$C_{1-6}$-alkyl)($C_{1-6}$-alkyl)amino$C_{1-6}$-alkyl; pyrrolidinyl$C_{1-6}$-alkyloxy; pyrazolyl; thiopyrazolyl; pyrazolyl substituted with two substituents selected from $C_{1-6}$-alkyl or trihalo$C_{1-6}$-alkyl; pyridinyl; pyridinyl substituted with $C_{1-6}$-alkyloxy or aryl; pyrimidinyl; quinolinyl; phenyl; and phenyl substituted with one, two or three substituents independently selected from halo, amino, $C_{1-6}$-alkyl, $C_{1-6}$-alkyloxy, hydroxy$C_{1-4}$-alkyl, trifluoromethyl, trifluoromethyloxy, hydroxy$C_{1-4}$-alkoxy, $C_{1-4}$-alkyloxy $C_{1-4}$-alkoxy, amino$C_{1-4}$-alkyloxy, di($C_{1-4}$-alkyl)amino$C_{1-4}$-alkyloxy, di($C_{1-4}$-alkyl)amino, piperidinyl$C_{1-4}$-alkyloxy, pyrrolidinyl$C_{1-4}$-alkyloxy, aminosulfonylpiperazinyl, aminosulfonylpiperazinyl$C_{1-4}$-alkyl, di($C_{1-4}$-alkyl)aminosulfonylpiperazinyl, di($C_{1-4}$-alkyl)aminosulfonylpiperazinyl$C_{1-4}$-alkyl, hydroxy$C_{1-4}$-alkylpiperazinyl, hydroxy$C_{1-4}$-alkylpiperazinyl$C_{1-4}$-alkyl, $C_{1-4}$-alkyloxypiperidinyl, $C_{1-4}$-alkoxypiperidinyl$C_{1-4}$-alkyl, hydroxy$C_{1-4}$-alkyloxy $C_{1-4}$-alkylpiperazinyl, hyroxy$C_{1-4}$-alkoxy$C_{1-4}$-alkylpiperazinyl$C_{1-4}$-alkyl, hydroxy$C_{1-4}$-alkyl)($C_{1-4}$-alkyl) amino, (hydroxy$C_{1-4}$-alkyl)($C_{1-4}$-alkyl)amino$C_{1-4}$-alkyl, pyrrolidinyl$C_{1-4}$-alkoxy, morpholinyl$C_{1-4}$-alkyloxy, morpholinyl$C_{1-4}$-alkyl, CC$_{1-4}$-alkylpiperazinyl$C_{1-4}$-alkoxy, $C_{1-4}$-alkylpiperazinyl $C_{1-4}$-alkyl, hydroxy$C_{1-4}$-alkylamino, di(hydroxy$C_{1-4}$-alkyl)amino, di($C_{1-4}$-alkyl)amino$C_{1-4}$-alkylamino, aminothiadiazolyl, aminosulfonylpiperazinyl$C_{1-4}$-alkyloxy, and thiophenyl$C_{1-4}$-alkylamino.

In another embodiment of the compound according to embodiment [0098] (hereinafter embodiment [0105]), $R^{12}$ is hydrogen, halo, hydroxy, amino, nitro, $C_{1-6}$alkyl, $C_{1-6}$alkoxy, trifluoromethyl, hydroxyamino or naphtalenylsulfonylpyrazinyl;

$R^{14}$ is hydrogen, hydroxy, amino, hyroxy$C_{1-6}$-alkyl, $C_{1-6}$-alkyloxy, aryl$C_{1-6}$-alkyl, aminocarbonyl, hydroxycarbonyl, amino$C_{1-6}$-alkyl, aminocarbonyl$C_{1-6}$-alkyl, hydroxycarbonyl$C_{1-6}$-alkyl, hydroxyaminocarbonyl, $C_{1-6}$-alkyloxycarbonyl, $C_{1-6}$-alkylamino$C_{1-6}$-alkyl or di($C_{1-6}$-alkyl)amino$C_{1-6}$-alkyl;

the A ring is a radical selected from (a-1), (a-2), (a-3), (a-4), (a-5), (a-6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-27), (a-28), (a-29), (a-30), (a-31), (a-32), (a-33), (a-34), (a-35), (a-36), (a-37), (a-38), (a-39), (a-40), (a-41), (a-42) (a-43) and (a-44); and each $R^5$ and $R^6$ is independently selected from hydrogen; halo; hydroxy; amino; nitro; trihalo$C_{1-6}$-alkyl; trihalo$C_{1-6}$-alkyloxy; $C_{1-6}$-alkyl; $C_{1-6}$-alkoxy; $C_{1-6}$-alkyloxy$C_{1-6}$-alkoxy; $C_{1-6}$-alkylcarbonyl; $C_{1-6}$-alkylsulfonyl; cyano$C_{1-6}$-alkyl; hydroxy$C_{1-6}$-alkyl; hydroxy$C_{1-6}$-alkyloxy; hydroxy$C_{1-6}$-alkylamino; amino$C_{1-6}$-alkyloxy; di($C_{1-6}$-alkyl)aminocarbonyl; di(hydroxy $C_{1-6}$-alkyl)amino; di($C_{1-6}$-alkyl)amino$C_{1-6}$-alkyloxy; di($C_{1-6}$-alkyl)amino$C_{1-6}$-alkylamino; arylsulfonyl; arylsulfonylamino; aryloxy; aryl$C_{2-6}$-alkenediyl; di ($C_{1-6}$-alkyl)amino; cyano; thiophenyl; thiophenyl substituted with di($C_{1-6}$-alkyl)amino$C_{1-6}$-alkyl($C_{1-6}$-alkyl) amino$C_{1-6}$-alkyl, di($C_{1-6}$-alkyl)amino$C_{1-6}$-alkyl, $C_{1-6}$-alkylpiperazinyl$C_{1-6}$-alkyl or di(hydroxy$C_{1-6}$-alkyl) amino$C_{1-6}$-alkyl; furanyl; imidazolyl; $C_{1-6}$-alkyltriazolyl; tetrazolyl; piperidinyl$C_{1-6}$-alkyloxy; morpholinyl; $C_{1-6}$-alkylmorpholinyl; morpholinyl$C_{1-6}$-alkyloxy; morpholinyl$C_{1-6}$-alkyl; $C_{1-6}$-alkylpiperazinyl$C_{1-6}$-alkyloxy; $C_{1-6}$-alkylpiperazinyl$C_{1-6}$-alkyl; $C_{1-6}$-alkylpiperazinylsulfonyl; aminosulfonylpiperazinyl$C_{1-6}$-alkyloxy; aminosulfonylpiperazinyl; aminosulfonylpiperazinyl$C_{1-6}$-alkyl; di($C_{1-6}$-alkyl)aminosulfonylpiperazinyl; di($C_{1-6}$-alkyl) aminosulfonylpiperazinyl$C_{1-6}$-alkyl; hydroxy$C_{1-6}$-alkylpiperazinyl; hydroxy$C_{1-6}$-alkylpiperazinyl$C_{1-6}$-alkyl; $C_{1-6}$-alkoxypiperidinyl; $C_{1-6}$-alkyloxypipendinyl$C_{1-6}$-alkyl; hydroxy$C_{1-6}$-alkoxy $C_{1-6}$-alkylpiperazinyl; hydroxy$C_{1-6}$-alkyloxy$C_{1-6}$-alkylpiperazinyl$C_{1-6}$-alkyl; (hydroxy$C_{1-6}$-alkyl)($C_{1-6}$-alkyl) amino; (hydroxy$C_{1-6}$-alkyl)($C_{1-6}$-alkyl)amino$C_{1-6}$-alkyl; pyrrolidinyl$C_{1-6}$-alkoxy; pyrazolyl; thiopyrazolyl; pyrazolyl substituted with two substituents selected from $C_{1-6}$-alkyl and trihalo$C_{1-6}$-alkyl; pyridinyl; pyridinyl substituted with $C_{1-6}$alkoxy or aryl; pyrimidinyl; quinolinyl; phenyl; and phenyl substituted with one, two or three substituents independently selected from halo, amino, $C_{1-6}$-alkyl, $C_{1-6}$-alkoxy, hydroxy$C_{1-6}$-alkyl, trifluoromethyl, trifluoromethyloxy, hydroxyl$C_{1-6}$-alkoxy$C_{1-6}$-alkyloxy, amino$C_{1-4}$-alkyloxy, di($C_{1-4}$-alkyl)amino$C_{1-4}$-alkoxy, di($C_{1-4}$-alkyl) amino, piperidinyi$C_{1-4}$-alkoxy, pyrrolidinyl$C_{1-4}$-alkyloxy, aminosulfonylpiperazinyl, aminosulfonylpiperazinyl$C_{1-4}$-alkyl, di($C_{1-4}$-alkyl)aminosutfonylpiperazinyl, di($C_{1-4}$-alkyl)aminosulfonylpiperazinyl$C_{1-4}$-alkyl, hydroxy$C_{1-4}$-alkylpiperazinyl, hydroxy$C_{1-4}$-alkylpiperazinyl$C_{1-4}$-alkyl, $C_{1-4}$-alkyloxypiperidinyl, $C_{1-4}$-alkyloxypiperidinyl$C_{1-4}$-alkyl, hydroxy$C_{1-4}$-alkyloxy$C_{1-4}$-alkylpiperazinyl, hydroxy$C_{1-4}$-alkoxy$C_{1-4}$-alkylpiperazinyl$C_{1-4}$-alkyl, (hydroxy$C_{1-4}$-alkyl)($C_{1-4}$-alkyl)amino, (hydroxy$C_{1-4}$-alkyl)($C_{1-4}$-alkyl)amino$C_{1-4}$-alkyl, pyrrolidinyl$C_{1-4}$-alkoxy, morpholinyl$C_{1-4}$-alkyloxy, morpholinyl$C_{1-4}$-alkyl, $C_{1-4}$-alkylpiperazinyl$C_{1-4}$-alkoxy, $C_{1-4}$-alkylpiperazinyl$C_{1-4}$-alkyl, hydroxy$C_{1-4}$-alkylamino, di(hydroxy$C_{1-4}$-alkyl)amino, di($C_{1-4}$-alkyl)amino$C_{1-4}$-alkylamino, aminothiadiazolyl, aminosulfonylpiperazinyl$C_{1-4}$-alkyloxy, and thiophenyl$C_{1-4}$-alkylamino.

In another embodiment of the compound according to embodiment [0098] (hereinafter embodiment [0106]), t is 0;

$R^{12}$ is hydrogen, halo, hydroxy, amino, nitro, $C_{1-6}$-alkyl, $C_{1-6}$-alkoxy, trifluoromethyl or di($C_{1-6}$-alkyl)amino;

-L- is a direct bond or a bivalent radical selected from $C_{1-6}$-alkanediyl, amino and carbonyl;

$R^{14}$ is hydrogen, hydroxy, amino, hydroxy$C_{1-6}$-alkyl, $C_{1-6}$-alkyl, $C_{1-6}$-alkoxy, aryl$C_{1-6}$-alkyl, aminocarbonyl, amino$C_{1-6}$-alkyl, $C_{1-6}$-alkylamino$C_{1-6}$-alkyl or di($C_{1-6}$-alkyl)amino$C_{1-6}$-alkyl;

the A ring is a radical selected from (a-1), (a-3), (a-4), (a-5), (a-6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-28), (a-29), (a-30), (a-31), (a-32), (a-33), (a-34), (a-35), (a-36), (a-37), (a-38), (a-39), (a-40), (a-41), (a-42), (a-44), (a-45), (a-46), (a-47), (a-48) and (a-51);

each s is independently 0, 1, 2, 3 or 4;

$R^5$ is hydrogen; halo; hydroxy; amino; nitro; trihalo$C_{1-6}$-alkyl; trihalo$C_{1-6}$-alkyloxy; $C_{1-6}$-alkyl; $C_{1-6}$-alkyloxy; $C_{1-6}$-alkylcarbonyl; $C_{1-6}$-alkyloxycarbonyl; $C_{1-6}$-alkylsulfonyl; hydroxy$C_{1-6}$-alkyl; aryloxy; di($C_{1-6}$-alkyl)

amino; cyano; thiophenyl; furanyl; furanyl substituted with hydroxyC$_{1-6}$-alkyl; benzofuranyl; imidazolyl; oxazolyl; oxazolyl substituted with aryl and C$_{1-6}$alkyl; C$_{1-6}$-alkyltriazolyl; tetrazolyl; pyrrolidinyl; pyrrolyl; morpholinyl; C$_{1-6}$-alkylmorpholinyl; piperazinyl; C$_{1-6}$-alkylpiperazinyl; hydroxyC$_{1-6}$-alkylpiperazinyl; C$_{1-6}$-alkyloxypiperidinyl; pyrazoyl; pyrazolyl substituted with one or two substituents selected from C$_{1-6}$-alkyl and trihaloC$_{1-6}$-alkyl; pyridinyl; pyridinyl substituted with C$_{1-6}$-alkyloxy, aryloxy or aryl; pyrimidinyl; quinolinyl; indole; phenyl; and phenyl substituted with one or two substituents independently selected from halo, C$_{1-6}$-alkyl, C$_{1-6}$-alkyloxy and trifluoromethyl;

R$^6$ is hydrogen; halo; hydroxy; amino; nitro; trihaloC$_{1-6}$-alkyl; trihaloC$_{1-6}$-alkyloxy; C$_{1-6}$-alkyl; C$_{1-6}$-alkyloxy; C$_{1-6}$-alkylcarbonyl; C$_{1-6}$-alkyloxycarbonyl; C$_{1-6}$-alkylsulfonyl; hydroxyC$_{1-6}$-alkyl; aryloxy; di(C$_{1-6}$-alkyl)amino; cyano; pyridinyl; phenyl; or phenyl substituted with one or two substituents independently selected from halo, C$_{1-6}$-alkyl, C$_{1-6}$-alkyloxy and trifluoromethyl; and the central moiety

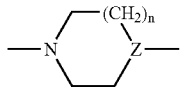

is optionally bridged (i.e., forming a bicyclic moiety) with an ethylene bridge.

In another embodiment of the compound according to embodiment [0098] (hereinafter embodiment [0107], n is 1 or 2;
t is 0, 1 or 2;
Z is nitrogen;
R$^{12}$ is hydrogen, nitro, C$_{1-6}$-alkyloxy, trifluoromethyl, di(C$_{1-6}$-alkyl)amino, hydroxyamino or naphtalenylsulfonylpyrazinyl;
-L- is a direct bond or a bivalent radical selected from C$_{1-6}$-alkanediyl, carbonyl and aminocarbonyl;
each R$^{13}$ represents a hydrogen atom;
R$^{14}$ is hydrogen, hydroxyC$_{1-6}$-alkyl, aminocarbonyl, hydroxyaminocarbonyl or di(C$_{1-6}$-alkyl)aminoC$_{1-6}$-alkyl;
the A ring is a radical selected from (a-1), (a-7), (a-9), (a-10), (a-12), (a-14), (a-19), (a-20), (a-21), (a-22), (a-23), (a-30), (a-34), (a-49) and (a-50);
each s is independently 0, 1, 2 or 5;
each R$^5$ and R$^6$ is independently selected from hydrogen; halo; nitro; trihaloC$_{1-6}$-alkyl; trihaloC$_{1-6}$-alkyloxy; C$_{1-6}$-alkyl; C$_{1-6}$-alkyloxy; C$_{1-6}$-alkylsulfonyl; (aryl)(C$_{1-6}$-alkyl)amino; arylsulfonyl; aryloxy; arylC$_{2-6}$-alkenediyl; di(C$_{1-6}$-alky)amino; thiophenyl; thiophenyl substituted with di(C$_{1-6}$-alkyl)aminoC$_{1-6}$-alkyl(C$_{1-6}$-alkyl)aminoC$_{1-6}$-alkyl, di(C$_{1-6}$-alkyl)aminoC$_{1-6}$-alkyl, C$_{1-6}$-alkylpiperazinylC$_{1-6}$-alkyl, hydroxyC$_{1-6}$-alkylpiperazinylC$_{1-6}$-alkyl, hydroxylC$_{1-6}$-alkyloxyC$_{1-6}$-alkylpiperazinylC$_{1-6}$-alkyl, di(C$_{1-6}$-alkyl)aminosulfonylpiperazinylC$_{1-6}$-alkyl, C$_{1-6}$-alkyloxypiperidinyl C$_{1-6}$-alkyl, morpholinylC$_{1-6}$-alkyl, hydroxyC$_{1-6}$-alkyKC$_{1-6}$-alkyl)aminoC$_{1-6}$-alkyl, or dKhydroxyC$_{1-6}$-alkyl)aminoC$_{1-6}$-alkyl; furanyl; oxazolyl; pyrrolyl; pyrazolyl; pyridinyl; pyridinyl substituted with C$_{1-6}$-alkyloxy; quinolinyl; indolyl; phenyl; and phenyl substituted with one, two or three substituents independently selected from halo, amino, C$_{1-6}$-alkyl, C$_{1-6}$-alkyloxy, hydroxyC$_{1-4}$-alkyl, trifluoromethyl, trifluoromethyloxy, di(C$_{1-4}$-alkyl)aminoC$_{1-4}$-alkyloxy, di(C$_{1-4}$-alkyl)amino, di(C$_{1-4}$-alkyl)aminoC$_{1-4}$-alkyl, di(C$_{1-4}$-alkyl)aminoC$_{1-4}$-alkyl(C$_{1-4}$-alkyl)amino, di (C$_{1-4}$-alkyl)aminoC$_{1-4}$-alkyl(C$_{1-4}$-alkyl)aminoC$_{1-4}$-alkyl, hydroxyl4alkylpiperazinylC$_{1-4}$-alkyl, hydroxyC$_{1-4}$-alkyloxyC$_{1-4}$-alkylpiperazinylC$_{1-4}$-alkyl, di(hydroxyC$_{1-4}$-alkyl)aminoC$_{1-4}$-alkyl, pyrrolidinyl C$_{1-4}$-alkyl, pyrrolidinylC$_{1-4}$-alkoxy, morpholinylC$_{1-4}$-alkyloxy, and morpholinylC$_{1-4}$-alkyl, and C$_{1-4}$alylpiperazinylC$_{1-4}$-alkyl, and
the central moiety

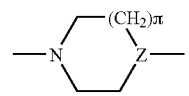

is optionally bridged (i.e., forming a bicyclic moiety) with a methylene bridge.

In another embodiment of the compound according to embodiment [0098] (hereinafter embodiment [0108]), n is 1 or 2;
t is 0 or 2;
Z is nitrogen;
R$^{12}$ is hydrogen;
-L- is a direct bond;
each R$^{13}$ is hydrogen;
R$^{14}$ is hydrogen;
the A ring is a radical selected from (a-1), (a-9), (a-19), (a-20), (a-21), (a-22), (a-23), (a-49) and (a-50);
each s is independently 0, 1, 2 or 5;
each R$^5$ and R$^6$ is independently selected from hydrogen; halo; trihaloC$_{1-6}$-alkyl; trihaloC$_{1-6}$-alkyloxy; C$_{1-6}$-alkyl; C$_{1-6}$-alkyloxy; arylC$_{2-6}$-alkenediyl; di(C$_{1-6}$-alky)amino; thiophenyl; thiophenyl substituted with di(C$_{1-6}$-alkyl)aminoC$_{1-6}$-alkyl(C$_{1-6}$-alkyl)aminoC$_{1-6}$-alkyl di(C$_{1-6}$-alkyl)aminoC$_{1-6}$-alkyl, C$_{1-6}$-alkylpiperazinylC$_{1-6}$-alkyl, hydroxyC$_{1-6}$-alkylpiperazinylC$_{1-6}$-alkyl, hydroxyC$_{1-6}$-alkyloxyC$_{1-6}$-alkylpiperazinylC$_{1-6}$-alkyl, C$_{1-6}$-alkyloxypiperidinylC$_{1-6}$-alkyl, morpholinylC$_{1-6}$-alkyl, hydroxyC$_{1-6}$-alkyl(C$_{1-6}$-alkyl)aminoC$_{1-6}$-alkyl, or di(hydroxyC$_{1-6}$-alkyl)aminoC$_{1-6}$-alkyl; furanyl; oxazolyl; pyrazolyl; pyridinyl; pyridinyl substituted with C$_{1-6}$-alkyloxy; quinolinyl; indolyl; phenyl; and phenyl substituted with one, two or three substituents independently selected from halo, amino, C$_{1-6}$-alkyl, C$_{1-6}$-alkyloxy, hydroxyC$_{1-4}$-alkyl, trifluoromethyl, trifluoromethyloxy, di(C$_{1-4}$-alkyl)aminoC$_{1-4}$-alkyloxy, di(C$_{1-4}$-alkyl)amino, di(C$_{1-4}$-alkyl)aminoC$_{1-4}$-alkyl, di(C$_{1-4}$-alkyl)aminoC$_{1-4}$-alkyl)C$_{1-4}$-alkyl)aminoC$_{1-4}$-alkyl, hydroxyC$_{1-4}$-alkylpiperazinylC$_{1-4}$-alkyl, hyroxyC$_{1-4}$-alkyloxyC$_{1-4}$-alkylpiperazinylC$_{1-4}$-alkyl, di(hydroxyC$_{1-4}$-alkyl)aminoC$_{1-4}$-alkyl, pyrrolidinyl C$_{1-4}$-alkyl, pyrrolidinylC$_{1-4}$-alkyloxy, morpholinylC$_{1-4}$-alkyloxy, morpholinylC$_{1-4}$-alkyl, and C$_{1-4}$-alkylpiperazinylC$_{1-4}$-alkyl, and
the central moiety

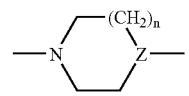

is optionally bridged (i.e., forming a bicyclic moiety) with a methylene bridge.

In another embodiment of the compound according to embodiment [0098] (hereinafter embodiment [0109]),
n is 1;
t is 0;
Z is nitrogen;
$R^{12}$ is hydrogen;
-L- is a direct bond;
each $R^{13}$ is hydrogen;
$R^{14}$ is hydrogen;
the A ring is radical selected from (a-1) and (a-20);
each s is independently 0 or 1;
each $R^5$ and $R^6$ is independently selected from hydrogen; thiophenyl; thiophenyl substituted with di($C_{1-6}$-alkyl)amino$C_{1-6}$-alkyl, or $C_{1-6}$-alkylpiperazinyl$C_{1-6}$-alkyl; furanyl; phenyl; and phenyl substituted with one substituents independently selected from di($C_{1-4}$-alkyl)amino$C_{1-4}$-alkyloxy, di($C_{1-4}$-alkyl)amino, di($C_{1-4}$-alkyl)amino$C_{1-4}$-alkyl, di($C_{1-4}$-alkyl)amino$C_{1-4}$-alkyl ($C_{1-4}$alkyl)amino$C_{1-4}$-alkyl, pyrrolidinyl$C_{1-4}$-alkyl, pyrrolidinyl$C_{1-4}$-alkyloxy and $C_{1-4}$-alkylpiperazinyl $C_{1-4}$-alkyl.

In the compounds of embodiments [0098]-[0109], $R^1$, $R^2$, $R^3$, and $R^4$ are preferably as defined in embodiments [0048] and [0049]. In other embodiments of the compounds of embodiments [0098]-[0109], $R^1$, $R^2$, $R^3$, and $R^4$ are all H. Other preferred embodiments of the compounds of embodiments [0098]-[0109] include the compounds of pages 21 and 22 and Table F-1 of WO 03/076422 in which the terminal hydroxamic acid moiety (HO—NH—C(O)—) is replaced with

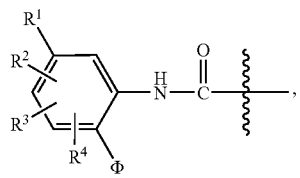

wherein Φ, $R^1$, $R^2$, $R^3$, and $R^4$ are as defined in accordance with embodiment [0046], and preferably embodiments [0048] and [0049]. Such embodiments are hereinafter collectively referred to as embodiment [0110].

In embodiments [0098]-[0110] the definitions in embodiments [0112]-[0114] supplement the definitions in embodiments [0020]-[0042]. To the extent there are any inconsistencies between the definitions in embodiments [0020]-[0042] and in embodiments [0112]-[0114], the definitions in embodiments [0112]-[0114] take precedence for the compounds of embodiments [0098]-[0110] only.

Halo is generic to fluoro, chloro, bromo and iodo; $C_{1-4}$-alkyl defines straight and branched chain saturated hydrocarbon radicals having from 1 to 4 carbon atoms such as, e.g., methyl, ethyl, propyl, butyl, 1-methylethyl, 2-methylpropyl and the like; $C_{1-6}$-alky includes $C_{1-4}$-alkyl and the higher homologues thereof having 5 to 6 carbon atoms such as, for example, pentyl, 2-methylbutyl, hexyl, 2-methylpentyl and the like; $C_{1-6}$-alkanediyl defines bivalent straight and branched chained saturated hydrocarbon radicals having from 1 to 6 carbon atoms such as, for example, methylene, 1,2-ethanediyl, 1,3-propanediyl 1,4-butanediyl, 1,5-pentanediyl, 1,6-hexanediyl and the branched isomers thereof such as, 2-methylpentanediyl, 3-methylpentanediyl, 2,2-dimethylbutanediyl, 2,3-dimethylbutanediyl and the like; trihalo$C_{1-6}$-alkyl defines $C_{1-6}$-alkyl containing three identical or different halo substituents for example trifluoromethyl; $C_{2-6}$-alkenediyl defines bivalent straight and branched chain hydrocarbon radicals containing one double bond and having from 2 to 6 carbon atoms such as, for example, ethenediyl, 2-propenediyl, 3-butenediyl, 2-pentenediyl, 3-pentenediyl, 3-methyl-2-butenediyl, and the like; aryl defines phenyl, and phenyl substituted with one or more substituents each independently selected from halo, $C_{1-6}$-alkyl, $C_{1-6}$-alkyloxy or trifluoromethyl, cyano, hydroxycarbonyl; aminoaryl defines aryl substituted with amino; $C_{3-10}$-cycloalkyl includes cyclic hydrocarbon groups having from 3 to 10 carbons, such as cyclopropyl, cyclobutyl, cyclopentyl, cyclopentenyl, cyclohexyl, cyclohexenyl, cycloheptyl, cyclooctyl and the like.

The term "another Zn-chelating group" refers to a group which is capable of interacting with a $Zn^{2+}$-ion, which can be present at an enzymatic binding site.

The N-oxide forms of the compounds of embodiment [0098] (hereinafter embodiment [0114]) comprise those compounds wherein one or several nitrogen atoms are oxidized to the so-called N-oxide, particularly those N-oxides wherein one or more of the piperidine-, piperazine or pyridazinyl-nitrogens are N-oxidized.

In another embodiment, the invention comprises compounds of the following structural formula (5) (hereinafter embodiment [0115]):

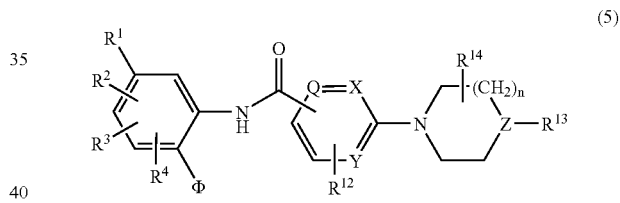

(5)

or a pharmaceutically acceptable salt thereof, wherein
Φ is —NH$_2$ or —OH;
$R^1$ is H or as defined in embodiment [0046];
$R^2$, $R^3$, and $R^4$ are as defined in embodiment [0046];
n is 0, 1, 2 or 3 and when n is 0 then a direct bond is intended;
Q is nitrogen or

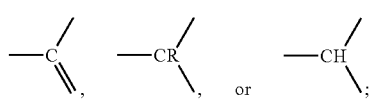

X is nitrogen or

Y is nitrogen or

Z is nitrogen or

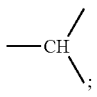

R is selected from the group consisting of hydrogen, halogen, —$NH_2$, nitro, hydroxy, aryl, heterocyclyl, $C_3$-$C_8$-cycloalkyl, heteroaryl, $C_1$-$C_7$alkyl, haloalkyl, $C_1$-$C_7$alkenyl, $C_1$-$C_7$alkynyl, $C_1$-$C_7$-acyl, $C_1$-$C_7$-alkyl-aryloxy, $C_1$-$C_7$alkyl-arylsulfanyl, $C_1$-$C_7$-alkyl-arylsulfinyl, $C_1$-$C_7$alkyl-arylsulfonyl, $C_1$-$C_7$alkyl-arylaminosulfonyl, $C_1$-$C_7$alkyl-arylamine, $C_1$-$C_7$alkynyl-C(O)-amine, $C_1$-$C_7$alkenyl-C(O)-amine, $C_1$-$C_7$-alkynyl-$R^9$, $C_1$-$C_7$alkenyl-$R^9$ wherein $R^9$ is hydrogen, hydroxy, amino, $C_1$-$C_7$alkyl or $C_1$-$C_7$-alkoxy;

$R^{12}$ is hydrogen, halo, hydroxy, amino, nitro, $C_{1-6}$alkyl, $C_{1-6}$alkyloxy, trifluoromethyl, di($C_{1-6}$alkyl)amino, hydroxy no or naphtalenylsulfonylpyrazinyl;

$R^{13}$ is hydrogen, $C_{1-6}$alkyl, aryl$C_{2-6}$alkenediyl, furanylcarbonyl, naphtalenylcarbonyl, —C(O)phenyl$R^9$, $C_{1-6}$alkylaminocarbonyl, aminosulfonyl, arylaminosulfonyl, aminosulfonylamino, di($C_{1-6}$alkyl)aminosulfonylamino, arylaminosulfonylamino, aminosulfonylamino$C_{1-6}$alkyl, di($C_{1-6}$alkyl)aminosulfonylamino$C_{1-6}$alkyl, arylaminosulfonylamino$C_{1-6}$-alkyl, di($C_{1-6}$alkyl)amino$C_{1-6}$alkyl, $C_{1-12}$alkylsulfonyl, di($C_{1-6}$alkyl)aminosulfonyl, trihalo$C_{1-6}$alkylsulfonyl, di(aryl)$C_{1-6}$alkylcarbonyl, thiophenyl$C_{1-6}$alkylcarbonyl, pyridinylcarbonyl or aryl$C_{1-6}$alkylcarbonyl wherein each $R^9$ is independently selected from phenyl; phenyl substituted with one, two or three substituents independently selected from halo, amino, $C_{1-6}$alkyl, $C_{1-6}$alkyloxy, hydroxy$C_{1-4}$alkyl, hydroxy$C_{1-4}$alkyloxy, amino$C_{1-4}$alkyloxy, di($C_{1-4}$alkyl)amino$C_{1-4}$alkyloxy, di($C_{1-6}$alkyl)amino$C_{1-6}$alkyl, di($C_{1-6}$alkyl)amino$C_{1-6}$alkyl($C_{1-6}$alkyl)amino$C_{1-6}$alkyl, hydroxy$C_{1-4}$alkylpiperazinyl$C_{1-4}$alkyl, $C_{1-4}$alkyloxypiperidinyl$C_{1-4}$alkyl, hydroxy$C_{1-4}$alkyloxy$C_{1-4}$alkylpiperazinyl, $C_{1-4}$alkylpiperazinyl$C_{1-4}$alkyl, di(hydroxy$C_{1-4}$alkyl)amino$C_{1-4}$alkyl, pyrrolidinyl$C_{1-4}$alkyl, morpholinyl$C_{1-4}$alkyloxy, or morpholinyl$C_{1-4}$alkyl; thiophenyl; or thiophenyl substituted with di($C_{1-4}$alkyl)amino$C_{1-4}$alkyloxy, di($C_{1-6}$alkyl)amino$C_{1-6}$alkyl, di($C_{1-6}$alkyl)amino$C_{1-6}$alkyl($C_{1-6}$alkyl)amino$C_{1-6}$alkyl, pyrrolidinyl$C_{1-4}$alkyloxy, $C_{1-6}$alkylpiperazinyl$C_{1-6}$alkyl, di(hydroxy$C_{1-4}$alkyl)amino$C_{1-4}$alkyl or morpholinyl$C_{1-4}$alkyloxy.

$R^{14}$ is hydrogen, hydroxy, amino, hydroxy$C_{1-6}$alkyl, $C_{1-6}$alkyl, $C_{1-6}$alkyloxy, aryl$C_{1-6}$alkyl, aminocarbonyl, hydroxycarbonyl, amino$C_{1-6}$alkyl, aminocarbonyl$C_{1-6}$alkyl, hydroxycarbonyl$C_{1-6}$alkyl, hydroxyaminocarbonyl, $C_{1-6}$alkyloxycarbonyl, $C_{1-6}$alkylamino$C_{1-6}$alkyl or di($C_{1-6}$alkyl)amino$C_{1-6}$alkyl;

when $R^{13}$ & $R^{14}$ are present on the same carbon atom, $R^{13}$ & $R^{14}$ together may form a bivalent radical of formula —C(O)—NH—$CH_2$—$NR^{10}$ (a-1)

wherein $R^{10}$ is hydrogen or aryl;

when $R^{13}$ & $R^{14}$ are present on adjacent carbon atoms, $R^{13}$ & $R^{14}$ together may form a bivalent radical of formula =CH—CH=CH= (b-1);

aryl in the above is phenyl, or phenyl substituted with one or more substituents each independently selected from halo, $C_{1-6}$alkyl, $C_{1-6}$alkyloxy, trifluoromethyl, cyano or hydroxycarbonyl.

In some embodiments of the compound according to embodiment [0115] (hereinafter collectively referred to as embodiment [0116]), one or more of the following restrictions apply:

n is 0 or 1;

Q is

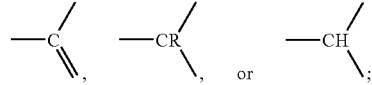

$R^{12}$ is hydrogen or nitro;

$R^{13}$ is $C_{1-6}$alkyl, aryl$C_{2-6}$alkenediyl, furanylcarbonyl, naphtalenylcarbonyl, $C_{1-6}$alkylaminocarbonyl, aminosulfonyl, di($C_{1-6}$alkyl)aminosulfonylamino$C_{1-6}$alkyl, di($C_{1-6}$alkyl)amino$C_{1-6}$alkyl, $C_{1-12}$alkylsulfonyl, di($C_{1-6}$ alkyl)aminosulfonyl, trihalo$C_{1-6}$alkylsulfonyl, di(aryl)$C_{1-6}$alkylcarbonyl, thiophenyl$C_{1-6}$alkylcarbonyl, pyridinylcarbonyl or aryl$C_{1-6}$alkylcarbonyl;

$R^{14}$ is hydrogen;

when $R^{13}$ & $R^{14}$ are present on the same carbon atom $R^{13}$ & $R^{14}$ together may form a bivalent radical of formula (a-1) wherein $R^{10}$ is aryl;

when $R^{13}$ & $R^{14}$ are present on adjacent carbon atoms $R^{13}$ & $R^{14}$ together may form a bivalent radical of formula (b-1).

In another embodiment of the compound according to embodiment [0115] (hereinafter embodiment [0117]), one or more of the following restrictions apply:

n is 1;

Q is

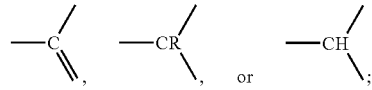

Z is nitrogen;

$R^{12}$ is hydrogen;

$R^{13}$ is naphtalenylcarbonyl, $C_{1-12}$alkylsulfonyl or di(aryl) $C_{1-6}$alkylcarbonyl;

$R^{14}$ is hydrogen.

In another embodiment of the compound according to embodiment [0115] (hereinafter embodiment [0118]), $R^{12}$ is H.

In another embodiment of the compound according to embodiment [0115] (hereinafter embodiment [0119]):

$R^{12}$ is hydrogen, halo, hydroxy, amino, nitro, $C_{1-6}$alkyl, $C_{1-6}$alkyloxy, trifluoromethyl or di($C_{1-6}$alkyl)amino;

R[13] is hydrogen, C$_{1-6}$alkyl, arylC$_{2-6}$alkenediyl, furanylcarbonyl, naphtalenylcarbonyl, —C(O)phenylR[9], C$_{1-6}$alkylaminocarbonyl, aminosulfonyl, arylaminosulfonyl, aminosulfonylamino, di(C$_{1-6}$alkyl)aminosulfonylamino, di(C$_{1-6}$alkyl)aminoC$_{1-6}$alkyl, C$_{1-12}$alkylsulfonyl, di(C$_{1-6}$alkyl)aminosulfonyl or pyridinylcarbonyl wherein each R[9] is independently selected from phenyl; phenyl substituted with one, two or three substituents independently selected from halo, C$_{1-6}$alkyl, C$_{1-6}$alkyloxy; or thiophenyl;

R[14] is hydrogen, hydroxy, amino, hydroxyC$_{1-6}$alkyl, C$_{1-6}$alkyl, C$_{1-6}$alkyloxy, arylC$_{1-6}$alkyl, aminocarbonyl, aminoC$_{1-6}$alkyl, C$_{1-6}$alkylaminoC$_{1-6}$alkyl or di(C$_{1-6}$alkyl)aminoC$_{1-6}$alkyl.

In some embodiments of the compound according to embodiment [0115] (hereinafter collectively referred to as embodiment [0120]), R[12] is hydrogen, halo, hydroxy, amino, nitro, C$_{1-6}$alkyl, C$_{1-6}$alkyloxy, trifluoromethyl or di(C$_{1-6}$alkyl)amino;

R[13] is hydrogen, C$_{1-6}$alkyl, arylC$_{2-6}$alkenediyl, furanylcarbonyl, naphtalenylcarbonyl, —C(O)phenylR[9], C$_{1-6}$alkylaminocarbonyl, aminosulfonyl, arylaminosulfonyl, aminosulfonylamino, di(C$_{1-6}$alkyl)aminosulfonylamino, di(C$_{1-6}$alkyl)aminoC$_{1-6}$alkyl, C$_{1-6}$alkylsulfonyl, di(C$_{1-6}$alkyl)aminosulfonyl or pyridinylcarbonyl wherein each R[9] is independently selected from phenyl; phenyl substituted with one, two or three substituents independently selected from halo, C$_{1-6}$alkyl, C$_{1-6}$alkyloxy; or thiophenyl; and R[14] is hydrogen, hydroxy, amino, hydroxyC$_{1-6}$alkyl, C$_{1-6}$alkyl, C$_{1-6}$alkyloxy, arylC$_{1-6}$alkyl, aminocarbonyl, aminoC$_{1-6}$alkyl, C$_{1-6}$alkylaminoC$_{1-6}$alkyl or di(C$_{1-6}$alkyl)aminoC$_{1-6}$alkyl.

In some embodiments of the compound according to embodiment [0115] (hereinafter collectively referred to as embodiment [0121]), n is 0 or 1; Q is

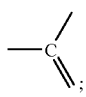

or —NHC(O)C$_{1-6}$alkanediylSH; R[12] is hydrogen or nitro; R[13] is C$_{1-6}$alkyl, arylC$_{2-6}$alkenediyl, furanylcarbonyl, naphtalenylcarbonyl, C$_{1-6}$alkylaminocarbonyl, aminosulfonyl, di(C$_{1-6}$alkyl)aminosulfonylaminoC$_{1-6}$alkyl, di(C$_{1-6}$alkyl)aminoC$_{1-6}$alkyl), C$_{1-12}$alkylsulfonyl, di(C$_{1-6}$alkyl)aminosulfonyl, trihaloC$_{1-6}$alkylsulfonyl, di(aryl)C$_{1-6}$alkylcarbonyl, thiophenylC$_{1-6}$alkylcarbonyl, pyridinylcarbonyl or arylC$_{1-6}$alkylcarbonyl; R[14] is hydrogen; when R[13] and R[14] are present on the same carbon atom R[13] & R[14] together may form a bivalent radical of formula (a-1) wherein R[10] is aryl; or when R[13] & R[14] are present on adjacent carbon atoms R[13] & R[14] together may form a bivalent radical of formula (b-1).

In some embodiments of the compound according to embodiment [0115] (hereinafter collectively referred to as embodiment [0122]), n is 1; Q is

each Z is nitrogen; R[12] is hydrogen; R[13] is naphthalenylcarbonyl, C$_{1-12}$alkylsulfonyl or di(aryl)C$_{1-6}$alkylcarbonyl; and R[14] is hydrogen.

Particular embodiments of the compound according to embodiment [0115] (hereinafter collectively referred to as embodiment [0123]) include the following

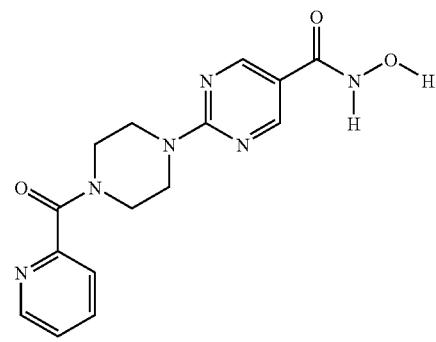

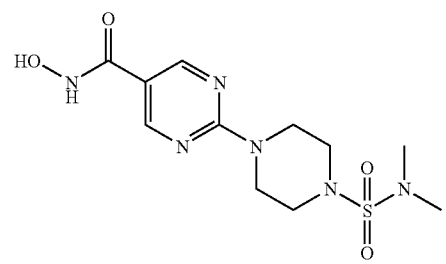

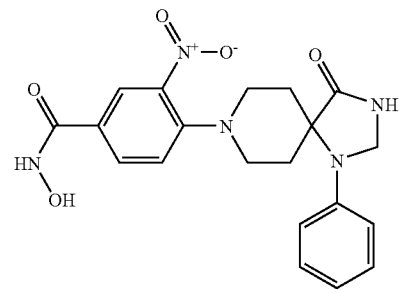

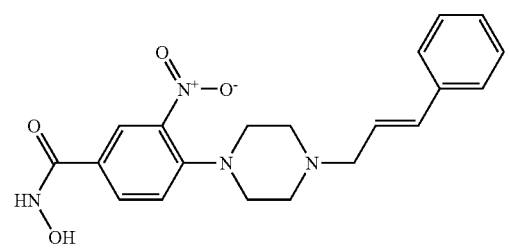

-continued
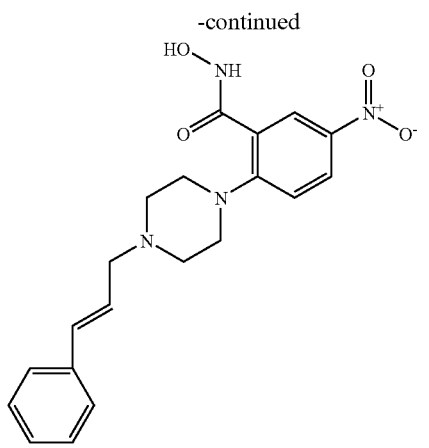
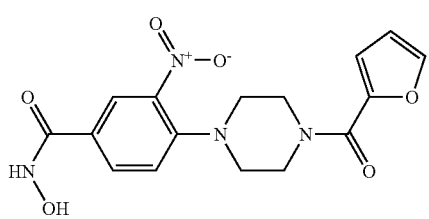
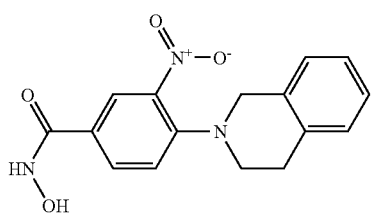
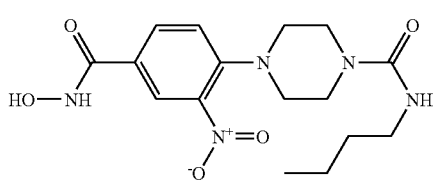
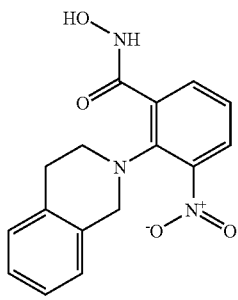
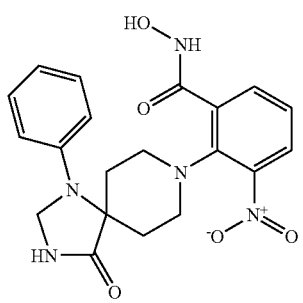
-continued
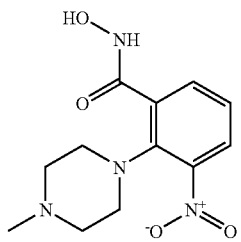
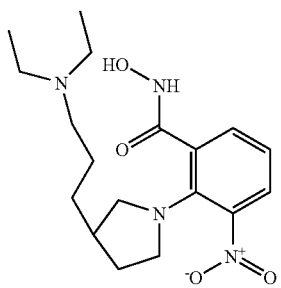
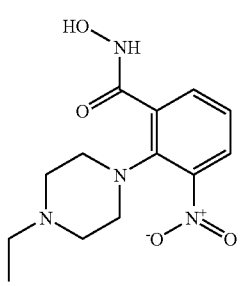
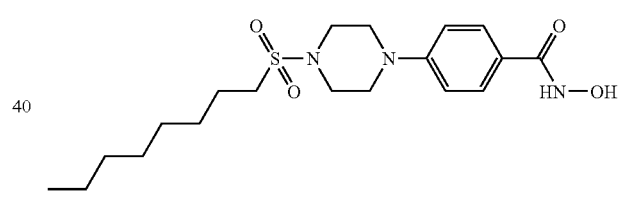
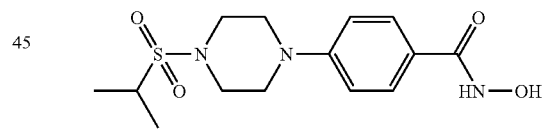
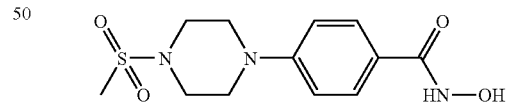
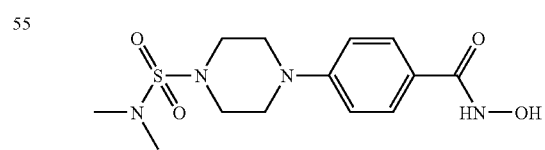
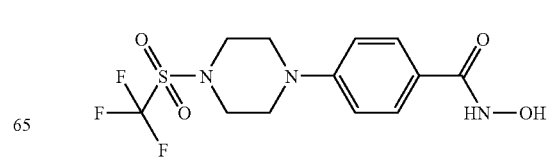

-continued

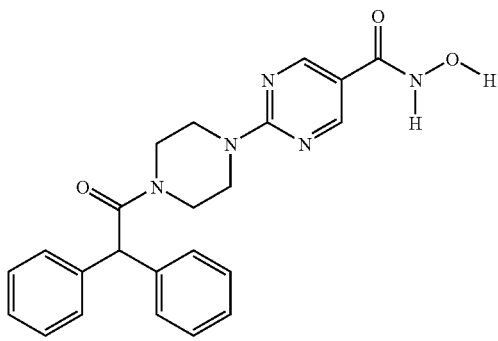

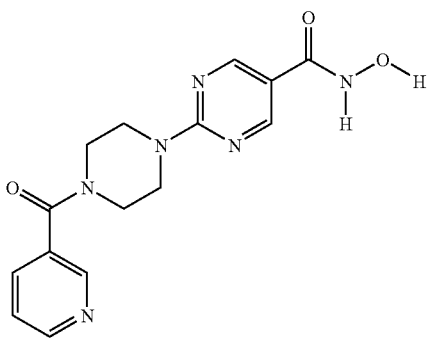

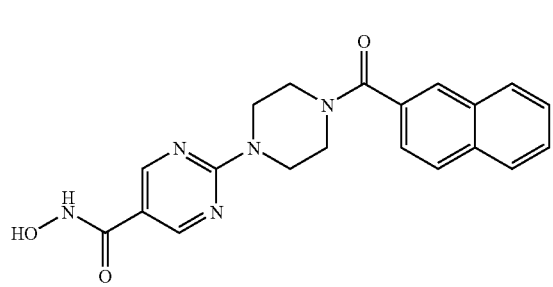

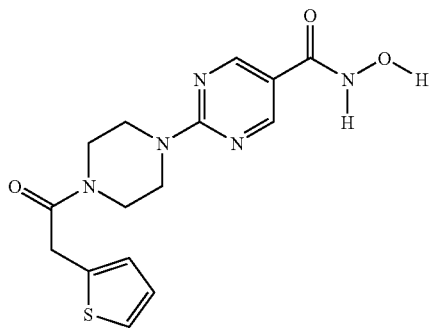

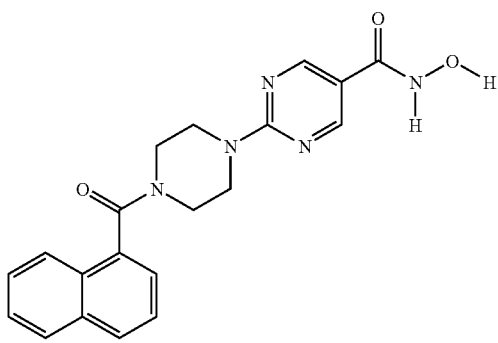

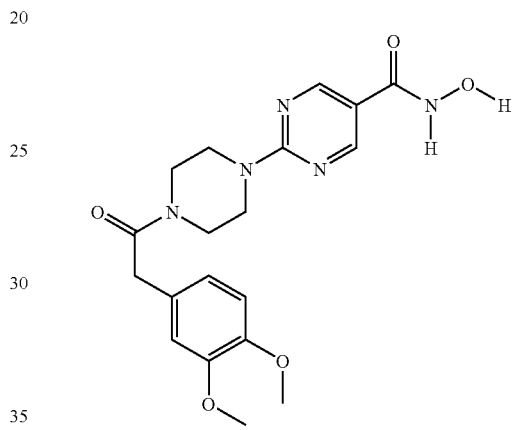

in which the terminal hydroxamic acid moiety (—C(O)NH—OH) is replaced with

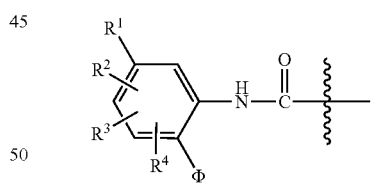

wherein Φ, R¹, R², R³, and R⁴ are as defined in accordance with embodiment [0046], and preferably embodiments [0048] and [0049].

In the compounds of embodiments [0115]-[0123], R¹, R², R³, and R⁴ are preferably as defined in embodiments [0048] and [0049], while in other embodiments of the compounds of embodiments [0115]-[0123], R¹, R², R³, and R⁴ are all H. Such embodiments are hereinafter collectively referred to as embodiment [0124].

In another embodiment, the invention comprises compounds of the following structural formula (6) (hereinafter embodiment [0125]):

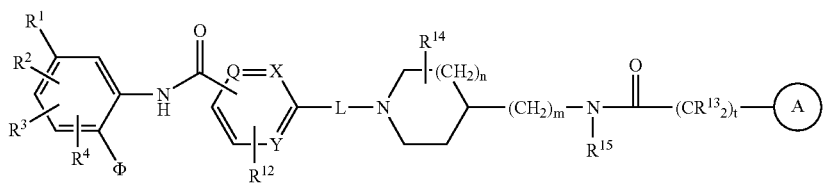

(6)

or a pharmaceutically acceptable salt thereof, wherein
Φ is —NH$_2$ or —OH;
R$^1$ is H or as defined in embodiment [0046];
R$^2$, R$^3$, and R$^4$ are as defined in embodiment [0046];
n is 0, 1, 2 or 3 and when n is 0 then a direct bond is intended;
m is 0 or 1 and when m is 0 then a direct bond is intended;
t is 0, 1, 2, 3 or 4 and when t is 0 then a direct bond is intended;
Q is nitrogen or

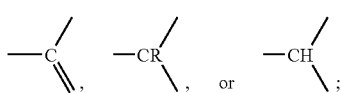

X is nitrogen or

Y is nitrogen or

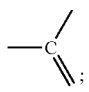

R is selected from the group consisting of hydrogen, halogen, —NH$_2$, nitro, hydroxy, aryl, heterocyclyl, C$_3$-C$_8$-cycloalkyl, heteroaryl, C$_1$-C$_7$alkyl, haloalkyl, C$_1$-C$_7$alkenyl, C$_1$-C$_7$alkynyl, C$_1$-C$_7$-acyl, C$_1$-C$_7$-alkyl-aryloxy, C$_1$-C$_7$-alkyl-arylsulfanyl, C$_1$-C$_7$-alkyl-arylsulfinyl, C$_1$-C$_7$-alkyl-arylsulfonyl, C$_1$-C$_7$alkyl-arylaminosulfonyl, C$_1$-C$_7$-alkyl-arylamine, C$_1$-C$_7$-alkynyl-C(O)-amine, C$_1$-C$_7$alkenyl-C(O)-amine, C$_1$-C$_7$-alkynyl-R$^9$, C$_1$-C$_7$-alkenyl-R$^9$ wherein R$^9$ is hydrogen, hydroxy, amino, C$_1$-C$_7$alkyl or C$_1$-C$_7$alkoxy;
R$^{12}$ is hydrogen, halo, hydroxy, amino, nitro, C$_{1-6}$alkyl, C$_{1-6}$alkyloxy, trifluoromethyl, di(C$_{1-6}$alkyl)amino, hydroxyamino or naphtalenylsulfonylpyazinyl;
-L- is a direct bond or a bivalent radical selected from C$_{1-6}$alkanediyl, C$_{1-6}$alkanediyloxy, amino, carbonyl or aminocarbonyl;
each R$^{13}$ is independently represents a hydrogen atom and one hydrogen atom can be replaced by a substituent selected from aryl;
R$^{14}$ is hydrogen, hydroxy, amino, hydroxyC$_{1-6}$alkyl, C$_{1-6}$alkyl, C$_{1-6}$alkyloxy, arylC$_{1-6}$alkyl, aminocarbonyl, hydroxycarbonyl, aminoC$_{1-6}$alkyl, aminocarbonylC$_{1-6}$alkyl, hydroxycarbonylC$_{1-6}$alkyl, hydroxyaminocarbonyl, C$_{1-6}$alkyloxycarbonyl, C$_{1-6}$alkylaminoC$_{1-6}$alkyl or di(C$_{1-6}$alkyl)aminoC$_{1-6}$alkyl;
R$^{15}$ is hydrogen, C$_{1-6}$alkyl, C$_{3-10}$cycloalkyl, hydroxyC$_{1-6}$alkyl, C$_{1-6}$alkyloxyC$_{1-6}$alkyl, di(C$_{1-6}$alkyl)aminoC$_{1-6}$alkyl or aryl;

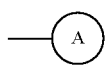

is a radical selected from

 (a-1)

 (a-2)

 (a-3)

 (a-4)

 (a-5)

 (a-6)

 (a-7)

 (a-8)

-continued
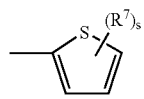 (a-9)
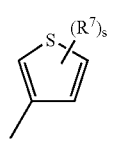 (a-10)
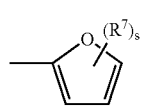 (a-11)
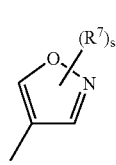 (a-12)
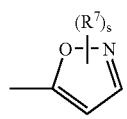 (a-13)
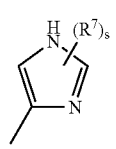 (a-14)
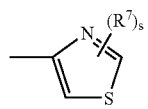 (a-15)
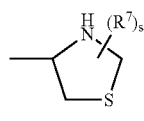 (a-16)
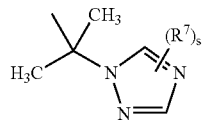 (a-17)
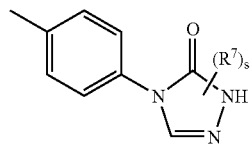 (a-18)
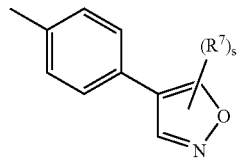 (a-19)
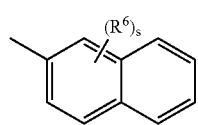 (a-20)
-continued
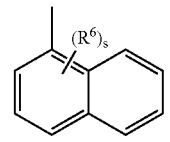 (a-21)
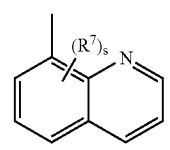 (a-22)
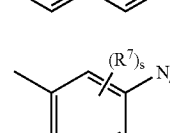 (a-23)
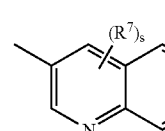 (a-24)
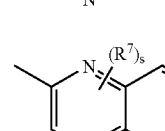 (a-25)
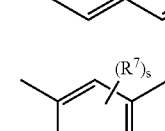 (a-26)
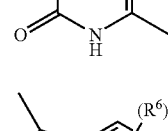 (a-27)
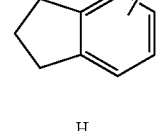 (a-28)
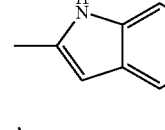 (a-29)
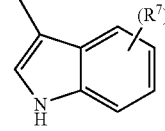 (a-30)
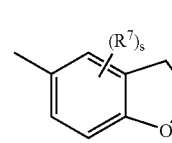 (a-31)

-continued

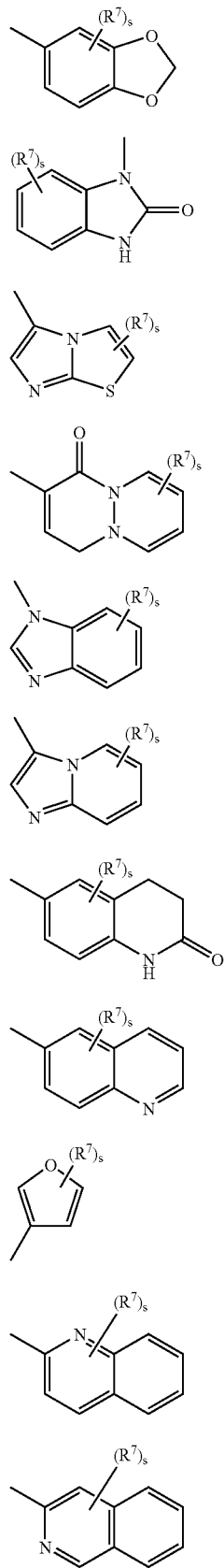

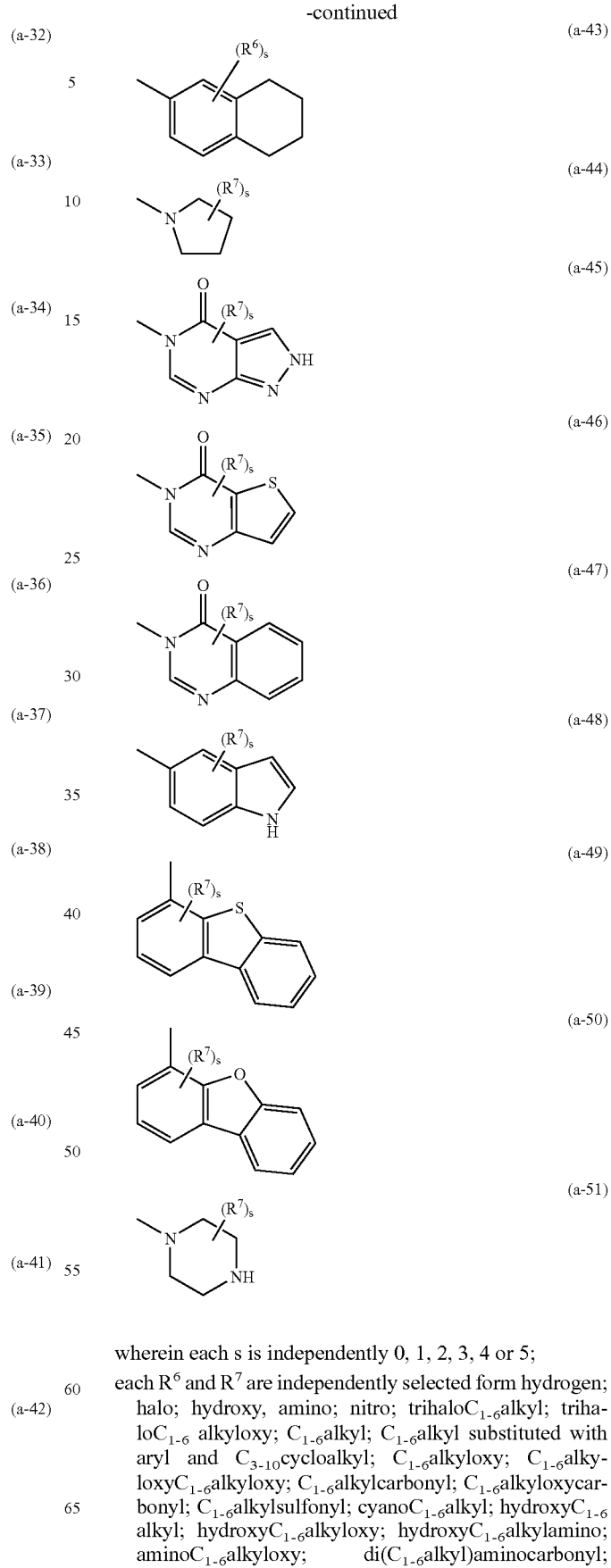

wherein each s is independently 0, 1, 2, 3, 4 or 5;
each $R^6$ and $R^7$ are independently selected form hydrogen; halo; hydroxy, amino; nitro; trihalo$C_{1-6}$alkyl; trihalo$C_{1-6}$ alkyloxy; $C_{1-6}$alkyl; $C_{1-6}$alkyl substituted with aryl and $C_{3-10}$cycloalkyl; $C_{1-6}$alkyloxy; $C_{1-6}$alkyloxy$C_{1-6}$alkyloxy; $C_{1-6}$alkylcarbonyl; $C_{1-6}$alkyloxycarbonyl; $C_{1-6}$alkylsulfonyl; cyano$C_{1-6}$alkyl; hydroxy$C_{1-6}$alkyl; hydroxy$C_{1-6}$alkyloxy; hydroxy$C_{1-6}$alkylamino; amino$C_{1-6}$alkyloxy; di($C_{1-6}$alkyl)aminocarbonyl;

di(hydroxyC$_{1-6}$alkyl)amino; (aryl)(C$_{1-6}$alkyl)amino; di(C$_{1-6}$alkyl)aminoC$_{1-6}$alkyloxy; di(C$_{1-6}$alkyl)aminoC$_{1-6}$alkylamino; di(C$_{1-6}$alkyl)aminoC$_{1-6}$alkylaminoC$_{1-6}$alkyl; arylsulfonyl; arylsulfonylamino; aryloxy; aryloxyC$_{1-6}$alkyl; arylC$_{2-6}$alkenediyl; di(C$_{1-6}$alkyl)amino; di(C$_{1-6}$alkyl)aminoC$_{1-6}$alkyl; di(C$_{1-6}$alkyl)amino(C$_{1-6}$alkyl)amino; di(C$_{1-6}$alkyl)amino(C$_{1-6}$alkyl)aminoC$_{1-6}$alkyl; di(C$_{1-6}$alkyl)aminoC$_{1-6}$alkyl(C$_{1-6}$alkyl)amino; di(C$_{1-6}$alkyl)aminoC$_{1-6}$alkyl(C$_{1-6}$alkyl)aminoC$_{1-6}$alkyl; aminosulfonylamino(C$_{1-6}$alkyl)amino; aminosulfonylamino(C$_{1-6}$alkyl)aminoC$_{1-6}$alkyl; di(C$_{1-6}$alkyl)aminosulfonylamino(C$_{1-6}$alkyl)amino; di(C$_{1-6}$alkyl)aminosulfonylamino(C$_{1-6}$alkyl)aminoC$_{1-6}$alkyl; cyano; thiophenyl; thiophenyl substituted with di(C$_{1-6}$alkyl)aminoC$_{1-6}$alkyl(C$_{1-6}$alkyl)aminoC$_{1-6}$alkyl, di(C$_{1-6}$alkyl)aminoC$_{1-6}$alkyl, C$_{1-6}$alkylpiperazinylC$_{1-6}$alkyl, hydroxyC$_{1-6}$alkylpiperazinylC$_{1-6}$alkyl, hydroxyC$_{1-6}$alkyloxyC$_{1-6}$alkylpiperazinylC$_{1-6}$alkyl, di(C$_{1-6}$alkyl)aminosulfonylpiperazinylC$_{1-6}$alkyl, C$_{1-6}$alkyloxypiperidinyl, C$_{1-6}$alkyloxypiperidinylC$_{1-6}$alkyl, morpholinylC$_{1-6}$alkyl, hydroxyC$_{1-6}$alkyl(C$_{1-6}$alkyl)aminoC$_{1-6}$alkyl, or di(hydroxyC$_{1-6}$alkyl)aminoC$_{1-6}$alkyl; furanyl; furanyl substituted with hydroxyC$_{1-6}$alkyl; benzofuranyl; imidazolyl; oxazolyl; oxazolyl substituted with aryl and C$_{1-6}$alkyl; C$_{1-6}$alkyltriazolyl; tetrazolyl; pyrrolidinyl; pyrrolyl; piperidinylC$_{1-6}$alkyloxy; morpholinyl; C$_{1-6}$alkylmorpholinyl; morpholinylC$_{1-6}$alkyloxy; morpholinylC$_{1-6}$alkyl; morpholinylC$_{1-6}$alkylamino; morpholinylC$_{1-6}$alkylaminoC$_{1-6}$alkyl; piperazinyl; C$_{1-6}$alkylpiperazinyl; C$_{1-6}$alkylpiperazinylC$_{1-6}$alkyloxy; piperazinylC$_{1-6}$alkyl; naphthalenylsulfonylpiperazinyl; naphthalenylsulfonylpiperazinyl; naphtalenylsulfonyl; C$_{1-6}$alkylpiperazinylC$_{1-6}$alkyl; C$_{1-6}$alkylpiperazinylC$_{1-6}$alkylamino; C$_{1-6}$alkylpiperazinylC$_{1-6}$alkylaminoC$_{1-6}$alkyl; C$_{1-6}$alkylpiperazinylsulfonyl; aminosulfonylpiperazinylC$_{1-6}$alkyloxy; aminosulfonylpiperazinyl; aminosulfonylpiperazinylC$_{1-6}$alkyl; di(C$_{1-6}$alkyl)aminosulfonylpiperazinyl; di(C$_{1-6}$alkyl)aminosulfonylpiperazinylC$_{1-6}$alkyl; hydroxyC$_{1-6}$alkylpiperazinyl; hydroxyC$_{1-6}$alkylpiperazinylC$_{1-6}$alkyl; C$_{1-6}$alkyloxypiperidinyl; C$_{1-6}$alkyloxypiperidinylC$_{1-6}$alkyl; piperidinylaminoC$_{1-6}$alkylamino; piperidinylaminoC$_{1-6}$alkylaminoC$_{1-6}$alkyl; (C$_{1-6}$alkylpiperidinyl)(hydroxyC$_{1-6}$alkyl)aminoC$_{1-6}$alkylamino; (C$_{1-6}$alkylpiperidinyl)(hydroxyC$_{1-6}$alkyl)aminoC$_{1-6}$alkylaminoC$_{1-6}$alkyl; hydroxyC$_{1-6}$alkyloxyC$_{1-6}$alkylpiperazinyl; hydroxyC$_{1-6}$alkyloxyC$_{1-6}$alkylpiperazinylC$_{1-6}$alkyl; (hydroxyC$_{1-6}$alkyl)(C$_{1-6}$alkyl)amino; (hydroxyC$_{1-6}$alkyl)(C$_{1-6}$alkyl)aminoC$_{1-6}$alkyl; hydroxyC$_{1-6}$ alkylaminoC$_{1-6}$alkyl; di(hydroxyC$_{1-6}$alkyl)C$_{1-6}$alkyl; pyrrolidinylC$_{1-6}$alkyl; pyrrolidinylC$_{1-6}$alkyloxy; pyrazolyl; thiopyrazolyl; pyrazolyl substituted with two substituents selected from C$_{1-6}$alkyl or trihaloC$_{1-6}$alkyl; pyridinyl; pyridinyl substituted with C$_{1-6}$alkyloxy, aryloxy or aryl; pyrimidinyl; tetrahydropyrimidinylpiperazinyl; tetrahydropyrimidinylpiperazinylC$_{1-6}$alkyl, quinolinyl; indole; phenyl; phenyl substituted with one, two or three substituents independently selected from halo, amino, nitro, C$_{1-6}$alkyl, C$_{1-6}$alkyloxy, hydroxyC$_{1-4}$alkyl, trifluoromethyl trifluoromethyloxy, hydroxyC$_{1-4}$alkyloxy, C$_{1-4}$alkylsulfonyl, C$_{1-4}$alkyloxyC$_{1-4}$alkyloxy, C$_{1-4}$alkyloxycarbonyl, aminoC$_{1-4}$alkyloxy, di(C$_{1-4}$alkyl)aminoC$_{1-4}$alkyloxy, di(C$_{1-4}$alkyl)aminocarbonyl, di(C$_{1-4}$alkyl)aminoC$_{1-4}$alkyl, di(C$_{1-4}$alkyl)aminoC$_{1-4}$alkylaminoC$_{1-4}$alkyl, di(C$_{1-4}$alkyl)amino(C$_{1-4}$alkyl)amino, di(C$_{1-4}$alkyl)amino(C$_{1-4}$alkyl)aminoC$_{1-4}$alkyl, di(C$_{1-4}$alkyl)aminoC$_{1-4}$alkyl(C$_{1-4}$alkyl)amino, di(C$_{1-4}$alkyl)aminoC$_{1-4}$alkyl(C$_{1-4}$alkyl)aminoC$_{1-4}$alkyl, aminosulfonylamino(C$_{1-4}$alkyl)amino, aminosulfonylamino(C$_{1-4}$alkyl)aminoC$_{1-4}$alkyl, di(C$_{1-4}$ alkyl)aminosulfonylamino(C$_{1-4}$alkyl)amino, di(C$_{1-4}$alkyl)aminosulfonylamino(C$_{1-4}$alkyl)aminoC$_{1-6}$alkyl, cyano piperidinylC$_{1-4}$alkyloxy, pyrrolidinylC$_{1-4}$alkyloxy; aminosulfonylpiperazinyl, aminosulfonylpiperazinylC$_{1-4}$alkyl, di(C$_{1-4}$alkyl)aminosulfonylpiperazinyl, di(C$_{1-4}$alkyl)aminosulfonylpiperazinylC$_{1-4}$alkyl, hydroxyC$_{1-4}$alkylpiperazinyl, hydroxyC$_{1-4}$alkylpiperazinylC$_{1-4}$alkyl, C$_{1-4}$alkyloxypiperidinyl, C$_{1-4}$alkyloxypiperidinylC$_{1-4}$alkyl, hydroxyC$_{1-4}$alkyloxyC$_{1-4}$alkylpiperazinyl, hydroxyC$_{1-4}$alkyloxyC$_{1-4}$alkylpiperazinylC$_{1-4}$alkyl, (hydroxyC$_{1-4}$alkyl)(C$_{1-4}$alkyl)amino, (hydroxyC$_{1-4}$alkyl)(C$_{1-4}$alkyl)aminoC$_{1-4}$alkyl, di(hydroxyC$_{1-4}$alkyl)amino, di(hydroxyC$_{1-4}$alkyl)aminoC$_{1-4}$alkyl, furanyl, furanyl substituted with —CH═CH—CH═CH—, pyrrolidinylC$_{1-4}$alkyl, pyrrolidinylC$_{1-4}$alkyloxy, morpholinyl, morpholinylC$_{1-4}$alkyloxy, morpholinylC$_{1-4}$alkyl, morpholinylC$_{1-4}$alkylamino, morpholinylC$_{1-4}$alkylaminoC$_{1-4}$alkyl, piperazinyl, C$_{1-4}$alkylpiperazinyl, C$_{1-4}$alkylpiperazinylC$_{1-4}$alkyloxy, piperazinylC$_{1-4}$alkyl, C$_{1-4}$alkylpiperazinylC$_{1-4}$ alkyl, C$_{1-4}$alkylpiperazinylC$_{1-4}$alkylamino, C$_{1-4}$alkylpiperazinylC$_{1-4}$alkylaminoC$_{1-6}$alkyl, tetrahydropyrimidinylpiperazinyl, tetrahydropyrimidinylpiperazinylC$_{1-4}$alkyl, piperidinylaminoC$_{1-4}$alkylamino, piperidinylaminoC$_{1-4}$alkylaminoC$_{1-4}$alkyl, (C$_{1-4}$alkylpiperidinyl)(hydroxyC$_{1-4}$alkyl)aminoC$_{1-4}$alkylamino, (C$_{1-4}$alkylpiperidinyl)(hydroxyC$_{1-4}$alkyl)aminoC$_{1-4}$alkylaminoC$_{1-4}$alkyl, pyridinylC$_{1-4}$alkyloxy, hydroxyC$_{1-4}$alkylamino, hydroxyC$_{1-4}$alkylaminoC$_{1-4}$alkyl, di(C$_{1-4}$alkyl)aminoC$_{1-4}$alkylamino, aminothiadiazolyl, aminosulfonylpiperazinylC$_{1-4}$alkyloxy, or thiophenylC$_{1-4}$alkylamino;

each R$^6$ and R$^7$ can be placed on the nitrogen in replacement of the hydrogen;

aryl in the above is phenyl or phenyl substituted with one or more substituents each independently selected from halo, C$_{1-6}$alkyl, C$_{1-6}$alkyloxy, trifluoromethyl, cyano or hydroxycarbonyl.

In some embodiments of the compound according to embodiment [0125] (hereinafter collectively referred to as embodiment [0126]), one or more of the following restrictions apply:

n is 1;

m is 0 or 1;

t is 0, 1 or 2:

Q is

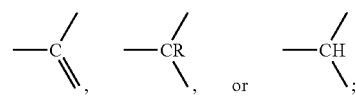

R$^{12}$ is hydrogen or C$_{1-6}$alkyl;

-L- is a dire bond;

R$^{14}$ is hydrogen;

R$^{15}$ is hydrogen;

—

is a radical selected from (a-1), (a-20), (a-25), (a-27), (a-28), (a-29), (a-41) or (a-42);
  each s is independently 0, 1, 2 or 3;
  each $R^6$ is independently selected from hydrogen, halo, $C_{1-6}$alkyl or $C_{1-6}$alkyloxy.

In other embodiments of the compound according to embodiment [0125] (hereinafter collectively referred to as embodiment [0127]), one or more of the following restrictions apply:
  n is 1;
  m is 0 or 1;
  t is 0, 1 or 3;
  Q is

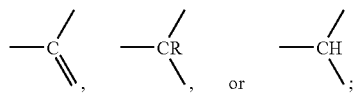

$R^{12}$ is hydrogen;
  -L- is a direct bond;
  $R^{14}$ is hydrogen;
  $R^{15}$ is hydrogen;

—

is a radical selected from (a-1), (a-20), (a-25), (a-27), (a-28), (a-29), (a-41) or (a-42);
  each s is independently 0, 1, 2 or 3;
  each $R^6$ is independently selected from hydrogen, halo, $C_{1-6}$alkyl or $C_{1-6}$alkyloxy.

In other embodiments of the compound according to embodiment [0125] (hereinafter collectively referred to as embodiment [0128]), one or more of the following restrictions apply:
  $R^{15}$ is hydrogen, $C_{1-6}$alkyl, $C_{3-10}$cycloalkyl, hydroxy$C_{1-6}$alkyl, $C_{1-6}$alkyloxy$C_{1-6}$alkyl or di($C_{1-6}$alkyl)amino$C_{1-6}$alkyl;

—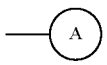

is a radical selected from (a-1), (a-2), (a-3), (a-4), (a-5), (a-6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-27), (a-28), (a-29), (a-30), (a-31), (a-32), (a-33), (a-34), (a-35), (a-36), (a-37), (a-38), (a-39), (a-40), (a-41), (a-42) (a-43) or (a-44);
  each $R^6$ and $R^7$ are independently selected from hydrogen; halo; hydroxy; amino; nitro; trihalo$C_{1-6}$alkyl; trihalo$C_{1-6}$ alkyloxy; $C_{1-6}$alkyl; $C_{1-6}$alkyloxy; $C_{1-6}$alkyloxy$C_{1-6}$alkyloxy; $C_{1-6}$alkylcarbonyl; $C_{1-6}$alkylsulfonyl; cyano$C_{1-6}$alkyl; hydroxy$C_{1-6}$alkyl; hydroxy$C_{1-6}$alkyloxy; hydroxy$C_{1-6}$alkylamino; amino$C_{1-6}$alkyloxy; di($C_{1-6}$alkyl)aminocarbonyl; di(hydroxy$C_{1-6}$alkyl)amino; aryl$C_{1-6}$alkyl)amino; di($C_{1-6}$alkyl)amino$C_{1-6}$alkyloxy; di($C_{1-6}$alkyl)amino$C_{1-6}$alkylamino; arylsulfonyl; arylsulfonylamino; aryloxy; aryl$C_{2-6}$alkenediyl; di($C_{1-6}$alkyl)amino; di($C_{1-6}$alkyl)amino$C_{1-6}$alkyl; di($C_{1-6}$alkyl)amino$C_{1-6}$alkyl($C_{1-6}$alkyl)amino$C_{1-6}$alkyl; cyano; thiophenyl; thiophenyl substituted with di($C_{1-6}$alkyl)amino$C_{1-6}$alkyl($C_{1-6}$alkyl)amino$C_{1-6}$alkyl, di($C_{1-6}$alkyl)amino$C_{1-6}$alkyl, $C_{1-6}$alkylpiperazinyl$C_{1-6}$alkyl or di(hydroxy$C_{1-6}$alkyl)amino$C_{1-6}$alkyl; furanyl; imidazolyl; $C_{1-6}$alkyltriazolyl; tetrazolyl; pyrrolidinyl; piperidinyl$C_{1-6}$alkyloxy; morpholinyl; $C_{1-6}$alkylmorpholinyl; morpholinyl$C_{1-6}$alkyloxy; morpholinyl$C_{1-6}$alkyl; $C_{1-6}$alkylpiperazinyl; $C_{1-6}$alkylpiperazinyl$C_{1-6}$alkyloxy; $C_{1-6}$alkylpiperazinyl$C_{1-6}$alkyl; $C_{1-6}$alkylpiperazinylsulfonyl; aminosulfonylpiperazinyl$C_{1-6}$alkyloxy; aminosulfonylpiperazinyl; aminosulfonylpiperazinyl$C_{1-6}$alkyl; di($C_{1-6}$alkyl)aminosulfonylpiperazinyl; di($C_{1-6}$alkyl)aminosulfonylpiperazinyl$C_{1-6}$alkyl; hydroxy$C_{1-6}$alkylpiperazinyl; hydroxy$C_{1-6}$alkylpiperazinyl$C_{1-6}$alkyl; $C_{1-6}$alkyloxypiperidinyl; $C_{1-6}$alkyloxypiperidinyl$C_{1-6}$alkyl; hydroxy$C_{1-6}$alkyloxy$C_{1-6}$alkylpiperazinyl; hydroxy$C_{1-6}$alkyloxy$C_{1-6}$alkylpiperazinyl$C_{1-6}$alkyl; (hydroxy$C_{1-6}$alkyl)($C_{1-6}$alkyl)amino; (hydroxy$C_{1-6}$alkyl)($C_{1-6}$alkyl)amino$C_{1-6}$alkyl; pyrrolidinyl$C_{1-6}$alkyloxy; pyrazolyl; thiopyrazolyl; pyrazolyl substituted with two substituents selected from $C_{1-6}$alkyl or trihalo$C_{1-6}$alkyl; pyridinyl; pyridinyl substituted with $C_{1-6}$alkyloxy or aryl; pyrimidinyl; quinolinyl; indole; phenyl; phenyl substituted with one, two or three substituents independently selected from halo, amino, $C_{1-6}$alkyl, $C_{1-6}$alkyloxy, hydroxy$C_{1-6}$alkyl, trifluoromethyl, trifluoromethyloxy, hydroxy$C_{1-4}$alkyloxy, $C_{1-4}$alkyloxy$C_{1-4}$alkyloxy, amino$C_{1-4}$alkyloxy, di($C_{1-4}$alkyl)amino$C_{1-4}$alkyloxy, di($C_{1-4}$alkyl)amino, di($C_{1-4}$alkyl)amino$C_{1-4}$alkyl, di($C_{1-4}$alkyl)amino$C_{1-4}$alkyl ($C_{1-4}$ alkyl)amino$C_{1-4}$alkyl, piperidinyl$C_{1-4}$alkyloxy, pyrrolidinyl$C_{1-4}$alkyloxy, aminosulfonylpiperazinyl, aminosulfonylpiperazinyl$C_{1-4}$alkyl, di($C_{1-4}$alkyl)aminosulfonylpiperazinyl, di($C_{1-4}$alkyl)aminosulfonylpiperazinyl$C_{1-4}$alkyl, hydroxy$C_{1-4}$alkylpiperazinyl, hydroxy$C_{1-4}$alkylpiperazinyl$C_{1-4}$alkyl, $C_{1-4}$alkyloxypiperidinyl, $C_{1-4}$alkyloxypiperidinyl$C_{1-4}$alkyl, hydroxy$C_{1-4}$alkyloxy$C_{1-4}$alkylpiperazinyl, hydroxy$C_{1-4}$ alkyloxy$C_{1-4}$alkylpiperazinyl$C_{1-4}$alkyl, (hydroxy$C_{1-4}$alkyl)($C_{1-4}$alkyl)amino, (hydroxy$C_{1-4}$alkyl)($C_{1-4}$alkyl)amino$C_{1-4}$alkyl, pyrrolidinyl$C_{1-4}$alkyloxy, morpholinyl$C_{1-4}$alkyloxy, morpholinyl$C_{1-4}$alkyl, $C_{1-4}$alkylpiperazinyl, $C_{1-4}$alkylpiperazinyl$C_{1-4}$alkyloxy, $C_{1-4}$alkylpiperazinyl$C_{1-4}$alkyl, hydroxy$C_{1-4}$alkylamino, di(hydroxy$C_{1-4}$alkyl)amino, di($C_{1-4}$alkyl)amino$C_{1-4}$alkylamino, aminothiadiazolyl, aminosulfonylpiperazinyl$C_{1-4}$alkyloxy, or thiophenyl$C_{1-4}$alkylamino.

In some embodiments of the compound according to embodiment [0125] (hereinafter collectively referred to as embodiment [0129]), one or more of the following restrictions apply:
  t=0;
  m=0;
  $R^{12}$ is hydrogen, halo, hydroxy, amino, nitro, $C_{1-6}$alkyl, $C_{1-6}$alkyloxy, trifluoromethyl or di($C_{1-6}$alkyl)amino;
  -L- is a direct bond or a bivalent radical selected from $C_{1-6}$alkanediyl, $C_{1-6}$alkylanediyloxy, amino or carbonyl;

R$^{14}$ is hydrogen, hydroxy, amino, hydroxyC$_{1-6}$alkyl, C$_{1-6}$alkyl, C$_{1-6}$alkyloxy, arylC$_{1-6}$alkyl, aminocarbonyl, aminoC$_{1-6}$alkyl, C$_{1-6}$alkylaminoC$_{1-6}$alkyl or di(C$_{1-6}$alkyl)aminoC$_{1-6}$alkyl;

R$^{15}$ is hydrogen;

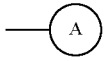

is a radical selected from (a-1), (a-3), (a-4), (a-5), (a-6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-28), (a-29), (a-30), (a-31), (a-32), (a-33), (a-34), (a-35), (a-36), (a-37), (a-38), (a-39), (a-40) (a-41), (a-42), (a-44), (a-45), (a-46), (a-47), (a-48) or (a-51);

each a is independently 0, 1, 2, 3 or 4,

R$^6$ is hydrogen; halo; hydroxy; amino; nitro; trihaloC$_{1-6}$alkyl; trihaloC$_{1-6}$alkyloxy; C$_{1-6}$alkyl; C$_{1-6}$alkyloxy; C$_{1-6}$alkylcarbonyl; C$_{1-6}$alkyloxycarbonyl; C$_{1-6}$alkylsulfonyl; hydroxyC$_{1-6}$alkyl; aryloxy; di(C$_{1-6}$alkyl)amino; cyano; thiophenyl, furanyl; furanyl substituted with hydroxyC$_{1-6}$alkyl; benzofuranyl; imidazolyl; oxazolyl; oxazolyl substituted with aryl and C$_{1-6}$alkyl; C$_{1-6}$alkyltriazolyl; tetrazolyl; pyrrolidinyl; pyrrolyl; morpholinyl; C$_{1-6}$alkylmorpholinyl; piperazinyl; C$_{1-6}$alkylpiperazinyl; hydroxyC$_{1-6}$alkylpiperazinyl; C$_{1-6}$alkyloxypiperidinyl; pyrazoyl; pyrazolyl substituted with one or two substituents selected from C$_{1-6}$alkyl or trihaloC$_{1-6}$alkyl; pyridinyl; pyridinyl substituted with C$_{1-6}$alkyloxy, aryloxy or aryl; pyrimidinyl; quinolinyl; indole; phenyl; or phenyl substituted with one or two substituents independently selected from halo, C$_{1-6}$alkyl, C$_{1-6}$alkyloxy or trifluoromethyl;

R$^7$ is hydrogen; halo; hydroxy, amino; nitro; trihaloC$_{1-6}$alkyl; trihaloC$_{1-6}$alkyloxy; C$_{1-6}$alkyl; C$_{1-6}$alkyloxy; C$_{1-6}$alkylcarbonyl; C$_{1-6}$alkylcarbonyl; C$_{1-6}$alkylsulfonyl; hydroxyC$_{1-6}$alkyl; aryloxy; di(C$_{1-6}$alkyl)amino; cyano; pyridinyl; phenyl; or phenyl substituted with one or two substituents independently selected from halo, C$_{1-6}$alkyl, C$_{1-6}$alkyloxy or trifluoromethyl.

In some embodiments of the compound according to embodiment [0125] (hereinafter collectively referred to as embodiment [0130]):

R$^{15}$ is hydrogen, C$_{1-6}$alkyl, C$_{3-10}$alkylcycloalkyl, hydroxyC$_{1-6}$alkyl, C$_{1-6}$alkyloxyC$_{1-6}$alkyl or di(C$_{1-6}$alkyl)aminoC$_{1-6}$alkyl;

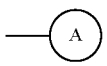

is a radical selected from (a-1), (a-2), (a-3), (a-4), (a-5), (a-6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-27), (a-28), (a-29), (a-30), (a-31), (a-32), (a-33), (a-34), (a-35), (a-36), (a-37), (a-38), (a-39), (a-40), (a-41), (a-42) (a-43) or (a-44); and each R$^6$ and R$^7$ are independently selected from hydrogen; halo; hydroxy; amino; nitro; trihaloC$_{1-6}$alkyl; trihaloC$_{1-6}$ alkyloxy; C$_{1-6}$alkyl; C$_{1-6}$alkyloxy; C$_{1-6}$alkyloxyC$_{1-6}$alkyloxy; C$_{1-6}$alkylcarbonyl; C$_{1-6}$alkylsulfonyl; cyanoC$_{1-6}$alkyl; hydroxyC$_{1-6}$alkyl; hydroxyC$_{1-6}$alkyloxy; hydroxyC$_{1-6}$alkylamino; aminoC$_{1-6}$alkyloxy; di(C$_{1-6}$alkyl)aminocarbonyl; di(hydroxyC$_{1-6}$alkyl)amino; arylC$_{1-6}$alkyl)amino; di(C$_{1-6}$alkyl)aminoC$_{1-6}$alkyloxy; di(C$_{1-6}$alkyl)aminoC$_{1-6}$alkylamino; arylsulfonyl; arylsulfonylamino; aryloxy, arylC$_{2-6}$alkenediyl; di(C$_{1-6}$alkyl)amino; di(C$_{1-6}$alkyl)aminoC$_{1-6}$alkyl; di(C$_{1-6}$alkyl)aminoC$_{1-6}$alkyl(C$_{1-6}$alkyl)aminoC$_{1-6}$alkyl; cyano; thiophenyl; thiophenyl substituted with di(C$_{1-6}$alkyl)aminoC$_{1-6}$alkyl(C$_{1-6}$alkyl)aminoC$_{1-6}$alkyl, di(C$_{1-6}$alkyl)aminoC$_{1-6}$alkyl, C$_{1-6}$alkylpiperazinylC$_{1-6}$alkyl or di(hydroxyC$_{1-6}$alkyl)aminoC$_{1-6}$alkyl; furanyl; imidazolyl; C$_{1-6}$alkyltriazolyl; tetrazolyl; pyrrolidinyl; piperidinylC$_{1-6}$alkyloxy; morpholinyl; C$_{1-6}$alkylmorpholinyl; morpholinylC$_{1-6}$alkyloxy; morpholinylC$_{1-6}$alkyl; C$_{1-6}$alkylpiperapiperazinylC$_{1-6}$alkyloxy; C$_{1-6}$alkylpiperazinylC$_{1-6}$alkyl; C$_{1-6}$alkylpiperazinylsulfonyl; aminosulfonylpiperazinylC$_{1-6}$alkyloxy; aminosulfonylpiperazinyl; aminosulfonylpiperazinylC$_{1-6}$alkyl; di(C$_{1-6}$alkyl)aminosulfonylpiperazinyl; di(C$_{1-6}$alkyl)aminosulfonylpiperazinylC$_{1-6}$alkyl; hydroxyC$_{1-6}$alkylpiperazinyl; hydroxyC$_{1-6}$alkylpiperazinylC$_{1-6}$alkyl; C$_{1-6}$alkyloxypiperidinyl; C$_{1-6}$alkyloxypiperidinylC$_{1-6}$alkyl; hydroxyC$_{1-6}$alkyloxyC$_{1-6}$alkylpiperazinyl; hydroxyC$_{1-6}$alkyloxyC$_{1-6}$alkylpiperazinylC$_{1-6}$alkyl; (hydroxyC$_{1-6}$alkyl)(C$_{1-6}$alkyl)amino; (hydroxyC$_{1-6}$alkyl)(C$_{1-6}$alkyl)aminoC$_{1-6}$alkyl; pyrrolidinylC$_{1-6}$alkyloxy; pyrazolyl; thiopyrazolyl; pyrazolyl substituted with two substituents selected from C$_{1-6}$alkyl or trihaloC$_{1-6}$alkyl; pyridinyl; pyridinyl substituted with C$_{1-6}$alkyloxy or aryl; pyrimidinyl; quinolinyl; indole; phenyl; phenyl substituted with one, two or three substituents independently selected from halo, amino, C$_{1-6}$alkyl, C$_{1-6}$alkyloxy, hydroxyC$_{1-4}$alkyl, trifluoromethyl, trifluoromethyloxy, hydroxyC$_{1-4}$alkyloxy, C$_{1-4}$alkyloxyC$_{1-4}$alkyloxy, aminoC$_{1-4}$alkyloxy, di(C$_{1-4}$alkyl)aminoC$_{1-4}$alkyloxy, di(C$_{1-4}$alkyl)amino, di(C$_{1-4}$alkyl)aminoC$_{1-4}$alkyl, di(C$_{1-4}$alkyl)aminoC$_{1-4}$alkyl(C$_{1-4}$alkyl)aminoC$_{1-4}$alkyl, piperidinylC$_{1-4}$alkyloxy, pyrrolidinylC$_{1-4}$alkyloxy, aminosulfonylpiperazinyl, aminosulfonylpiperazinylC$_{1-4}$alkyl, di(C$_{1-4}$alkyl)aminosulfonylpiperazinyl, di(C$_{1-4}$alkyl)aminosulfonylpiperazinylC$_{1-4}$alkyl, hydroxyC$_{1-4}$alkylpiperazinyl, hydroxyC$_{1-4}$alkylpiperazinylC$_{1-4}$alkyl, C$_{1-4}$alkyloxypiperidinyl, C$_{1-4}$alkyloxypiperidinylC$_{1-4}$alkyl, hydroxyC$_{1-4}$alkyloxyC$_{1-4}$alkylpiperazinyl, hydroxyC$_{1-4}$alkyloxyC$_{1-4}$alkylpiperazinylC$_{1-4}$alkyl, (hydroxyC$_{1-4}$alkyl)(C$_{1-4}$alkyl)amino, (hydroxyC$_{1-4}$alkyl)(C$_{1-4}$alkyl)aminoC$_{1-4}$alkyl pyrrolidinylC$_{1-4}$alkyloxy, morpholinylC$_{1-4}$alkyloxy, morpholinylC$_{1-4}$alkyl, C$_{1-4}$alkylpiperazinyl, C$_{1-4}$alkylpiperazinylC$_{1-4}$alkyloxy, C$_{1-4}$alkylpiperazinylC$_{1-4}$alkyl, hydroxyC$_{1-4}$alkylamino, di(hydroxyC$_{1-4}$alkyl)amino, di(C$_{1-4}$)aminoC$_{1-4}$alkylamino, aminothiadiazolyl aminosulfonylpiperazinylC$_{1-4}$alkyloxy, or thiophenylC$_{1-4}$alkylamino.

In some embodiments of the compound according to embodiment [0125] (hereinafter collectively referred to as embodiment [0131]), t is 0, m is 0 and:

R$^{12}$ is hydrogen, halo, hydroxy, amino, nitro, C$_{1-6}$alkyl, C$_{1-6}$alkyloxy, trifluoromethyl or di(C$_{1-6}$alkyl)amino;

-L- is a direct bond or a bivalent radical selected from C$_{1-6}$alkanediyl, C$_{1-6}$alkanendiyloxy, amino or carbonyl;

R$^{14}$ is hydrogen hydroxy, amino, hydroxyC$_{1-6}$alkyl, C$_{1-6}$alkyl, C$_{1-6}$alkyloxy, arylC$_{1-6}$alkyl, aminocarbonyl, aminoC$_{1-6}$alkyl, C$_{1-6}$alkylaminoC$_{1-6}$alkyl or di(C$_{1-6}$alkyl)aminoC$_{1-6}$alkyl;

R$^{15}$ is H;

is a radical selected from (a-1), (a-3), (a-4), (a-5), (a-6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-28), (a-29), (a-30), (a-31), (a-32), (a-33), (a-34), (a-35), (a-36), (a-37), (a-38), (a-39), (a-4), (a-41), (a-42), (a-44), (a-45), (a-46), (a-47), (a-48) or (a-51);

each s is independently 0, 1, 2, 3 or 4;

$R^6$ is hydrogen; halo; hydroxy; amino; nitro; trihalo$C_{1-6}$ alkyl; trihalo$C_{1-6}$alkyloxy; $C_{1-6}$alkyl; $C_{1-6}$alkyloxy; $C_{1-6}$alkylcarbonyl; $C_{1-6}$alkyloxycarbonyl; $C_{1-6}$alkylsulfonyl; hydroxy$C_{1-6}$alkyl; aryloxy; di($C_{1-6}$alkyl)amino; cyano; thiophenyl; furanyl; furanyl substituted with hydroxy$C_{1-6}$alkyl; benzofuranyl; imidazolyl; oxazolyl; oxazolyl substituted with aryl and $C_{1-6}$alkyl; $C_{1-6}$alkylthiazolyl; tetrazolyl; pyrrolidinyl; pyrrolyl; morpholinyl; $C_{1-6}$alkylmorpholinyl; piperazinyl; $C_{1-6}$alkylpiperazinyl; hydroxy$C_{1-6}$alkylpiperazinyl; $C_{1-6}$alkyloxypiperidinyl; pyrazoyl; pyrazolyl substituted with one or two substituents selected from $C_{1-6}$alkyl or trihalo$C_{1-6}$alkyl; pyridinyl; pyridinyl substituted with $C_{1-6}$alkyloxy or aryl; pyrimidinyl; quinolinyl; indole; phenyl; or phenyl substituted with one or two substituents independently selected from halo, $C_{1-6}$alkyl, $C_{1-6}$alkyloxy or trifluoromethyl;

and $R^7$ is hydrogen; halo; hydroxy; amino; nitro; trihalo$C_{1-6}$ alkyl; trihalo$C_{1-6}$alkoxy; $C_{1-6}$alkyl; $C_{1-6}$alkyloxy; $C_{1-6}$alkylcarbonyl; $C_{1-6}$alkyloxycarbonyl; $C_{1-6}$alkylsulfonyl; hydroxy$C_{1-6}$alkyl; aryloxy; di($C_{1-6}$alkyl)amino; cyano; pyridinyl phenyl; or phenyl substituted with one or two substituents independently selected from halo, $C_{1-6}$alkyl, $C_{1-6}$alkyloxy or trifluoromethyl.

In some embodiments of the compound according to embodiment [0125] (hereinafter collectively referred to as embodiment [0132]), n is 1; m is 0 or 1; t is 0, 1 or 2; Q is

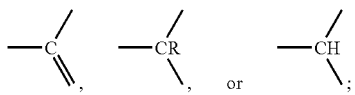

$R^{12}$ is hydrogen or $C_{1-6}$alkyl; -L- is a direct bond; $R^{14}$ and $R^{15}$ are H;

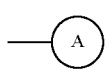

is a radical selected from (a-1), (a-20), (a-25), (a-27), (a-28), (a-29), (a-41) or (a-42); each s is independently 0, 1 or 2; and each $R^6$ is independently selected from hydrogen, halo, $C_{1-6}$alkyl or $C_{1-6}$alkyloxy.

In some embodiments of the compound according to embodiment [0125] (hereinafter collectively referred to as embodiment [0133]), n is 1; m is 0 or 1; t is 0, 1 or 2; Q is

$R^{12}$ is hydrogen; -L- is a direct bond; $R^{14}$ and $R^{15}$ are H;

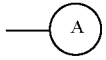

is a radical selected from (a-1), (a-20), (a-27), (a-28), (a-29), (a-41) or (a-42); each s is independently 0, 1 or 2; and each $R^6$ is independently selected from hydrogen, halo, $C_{1-6}$alkyl or $C_{1-6}$alkyloxy.

Particular embodiments of the compound according to embodiment [0125] (hereinafter collectively referred to as embodiment [0134]) include the following

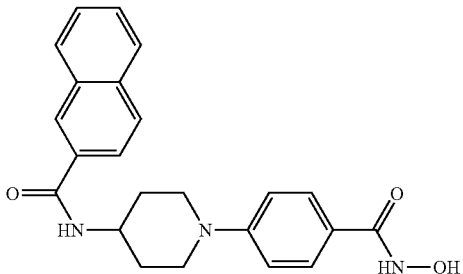

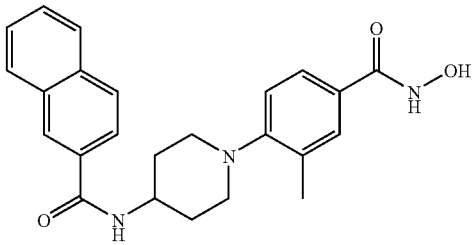

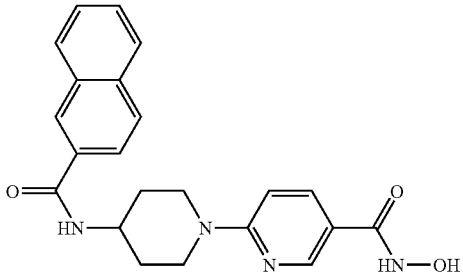

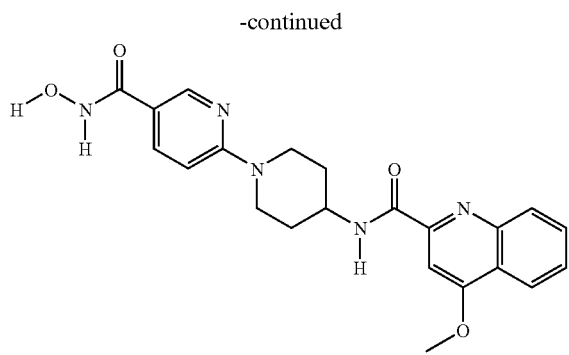
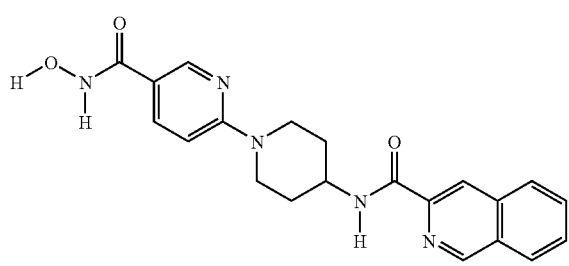
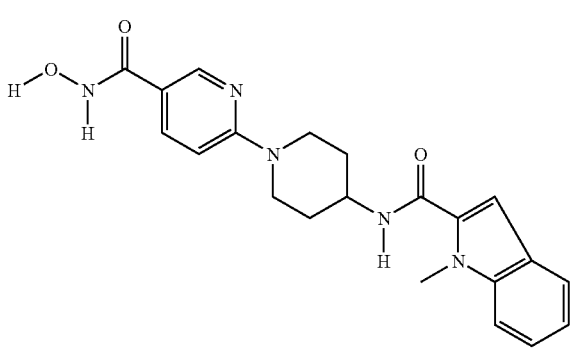
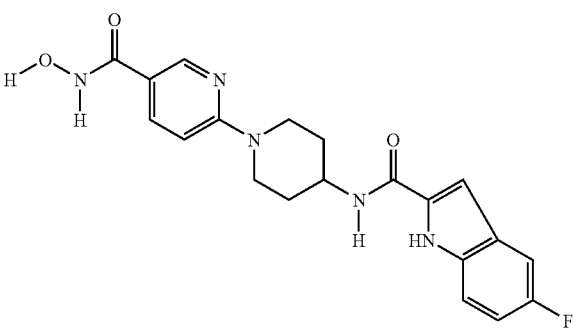
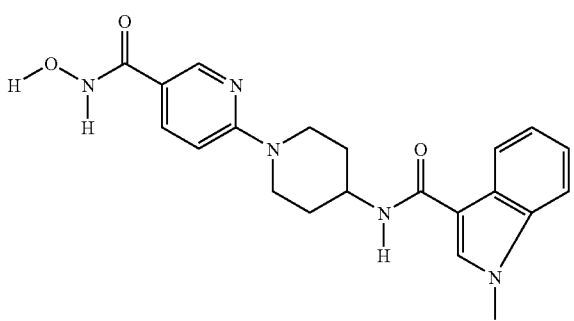
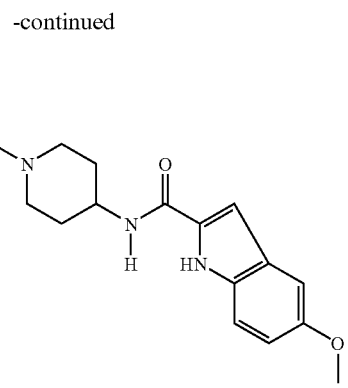
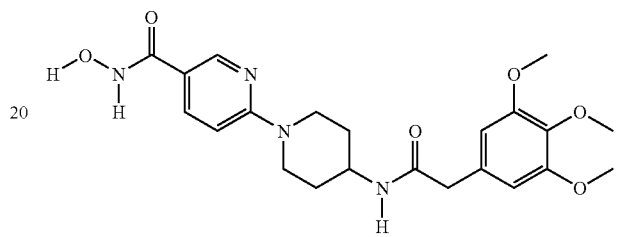
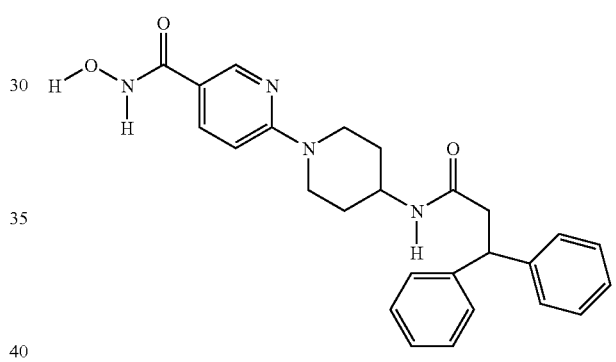
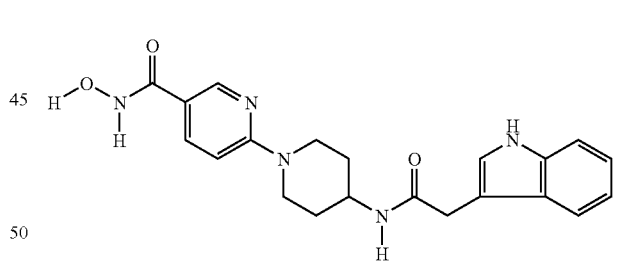
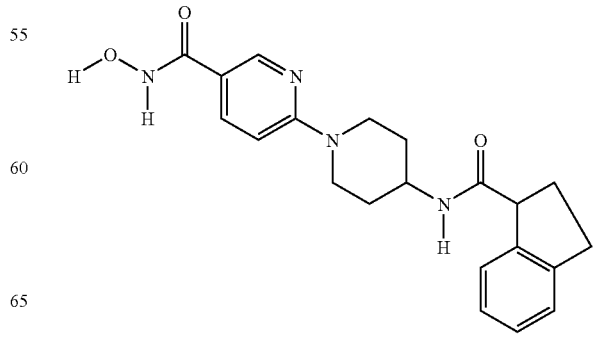

-continued

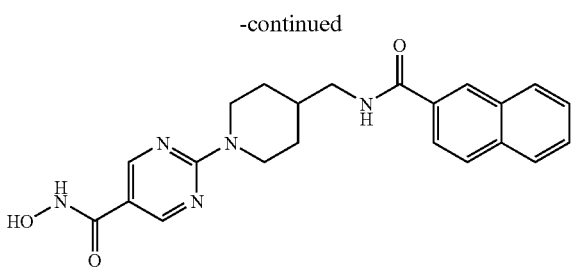

in which the terminal hydroxamic acid moiety (—C(O)NH—OH) is replaced with

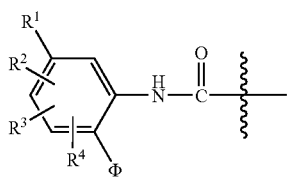

wherein Φ, $R^1$, $R^2$, $R^3$, and $R^4$ are as defined in accordance with embodiment [0046], and preferably embodiments [0048] and [0049]:

In the compounds of embodiments [0125]-[0134], $R^1$, $R^2$, $R^3$, and $R^4$ are preferably as defined in embodiments [0048] and [0049]. In other embodiments of the compounds of embodiments [0125]-[0134], $R^1$, $R^2$, $R^3$, and $R^4$ are all H. Such embodiments are hereinafter collectively referred to as embodiment [0135].

In another embodiment, the invention comprises compounds of the following structural formula (7) (hereinafter embodiment [0136]):

(7)

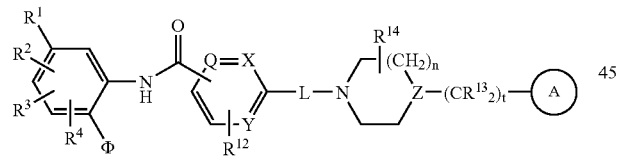

or a pharmaceutically acceptable salt thereof, wherein

Φ is —NH$_2$ or —OH;

$R^1$ is H or as defined in embodiment [0046];

$R^2$, $R^3$, and $R^4$ are as defined in embodiment [0046];

n is 0, 1, 2 or 3 and when n is 0 then a direct bond is intended;

t is 0, 1, 2, 3 or 4 and when t is 0 then a direct bond is intended;

Q is nitrogen or

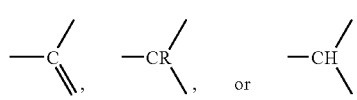

X is nitrogen or

Y is nitrogen or

Z is nitrogen or

R is selected from the group consisting of hydrogen, halogen, —NH$_2$, nitro, hydroxy, aryl, heterocyclyl, $C_3$-$C_8$-cycloalkyl, heteroaryl, $C_1$-$C_7$-alkyl, haloalkyl, $C_1$-$C_7$-alkenyl, $C_1$-$C_7$-alkynyl, $C_1$-$C_7$-acyl, $C_1$-$C_7$-alkyl-aryloxy, $C_1$-$C_7$-alkyl-arylsulfanyl, $C_1$-$C_7$-alkylarylsulfinyl, $C_1$-$C_7$-alkyl-arylsulfonyl, $C_1$-$C_7$-alkyl-arylaminosulfonyl, $C_1$-$C_7$-alkyl-arylamine, $C_1$-$C_7$-alkynyl-C(O)amine, $C_1$-$C_7$-alkenyl-C(O)amine, $C_1$-$C_7$-alkynyl-$R^9$, $C_1$-$C_7$-alkenyl-$R^9$ wherein $R^9$ is hydrogen, hydroxy, amino, $C_1$-$C_7$-alkyl or $C_1$-$C_7$-alkoxy;

$R^{12}$ is hydrogen, halo, hydroxy, amino, nitro, $C_{1-6}$alkyl, $C_{1-6}$alkyloxy, trifluoromethyl, di($C_{1-6}$alkyl)amino, hydroxyamino or naphtalenylsulfonylpyrazinyl;

-L- is a direct bond or a bivalent radical selected from $C_{1-6}$alkanediyl, $C_{1-6}$alkyloxy, amino, cabonyl or aminocarbonyl;

each $R^{13}$ independently represents a hydrogen atom and one hydrogen atom can be replaced by a substituent selected from aryl;

$R^{14}$ is hydrogen, hydroxy, amino, hydroxy$C_{1-6}$alkyl, $C_{1-6}$alkyl, $C_{1-6}$alkyloxy, aryl$C_{1-6}$alkyl, aminocarbonyl, hydroxycarbonyl, amino$C_{1-6}$alkyl, aminocarbonyl$C_{1-6}$alkyl, hydroxycarbonyl$C_{1-6}$alkyl, hydroxyaminocarbonyl, $C_{1-6}$alkyloxycarbonyl, $C_{1-6}$alkylamino$C_{1-6}$alkyl or di($C_{1-6}$alkyl)amino$C_{1-6}$alkyl;

is a radical selected from (a-1)

-continued
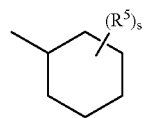 (a-2)
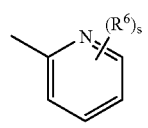 (a-3)
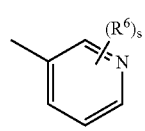 (a-4)
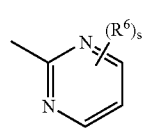 (a-5)
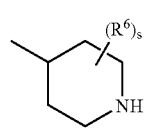 (a-6)
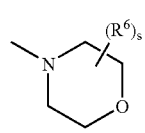 (a-7)
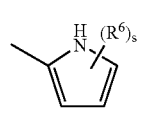 (a-8)
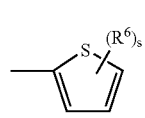 (a-9)
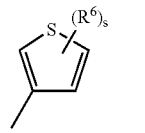 (a-10)
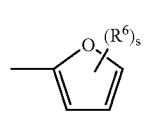 (a-11)
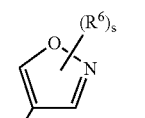 (a-12)
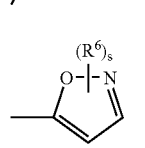 (a-13)
-continued
 (a-14)
 (a-15)
 (a-16)
 (a-17)
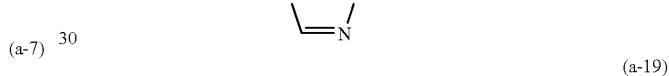 (a-18)
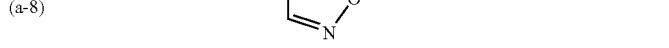 (a-19)
 (a-20)
 (a-21)
 (a-22)
 (a-23)
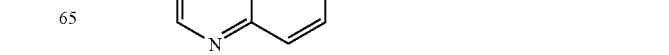 (a-24)

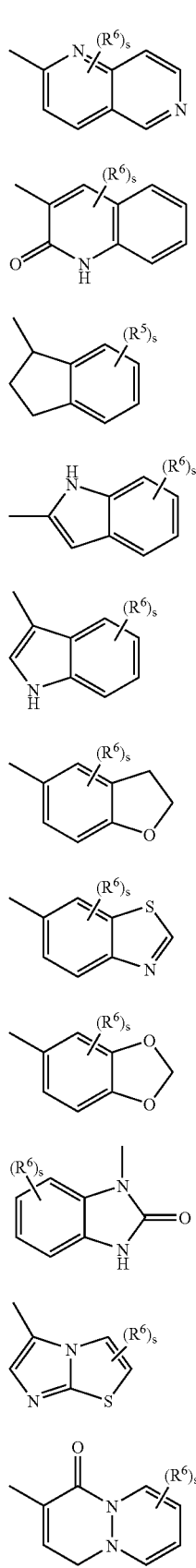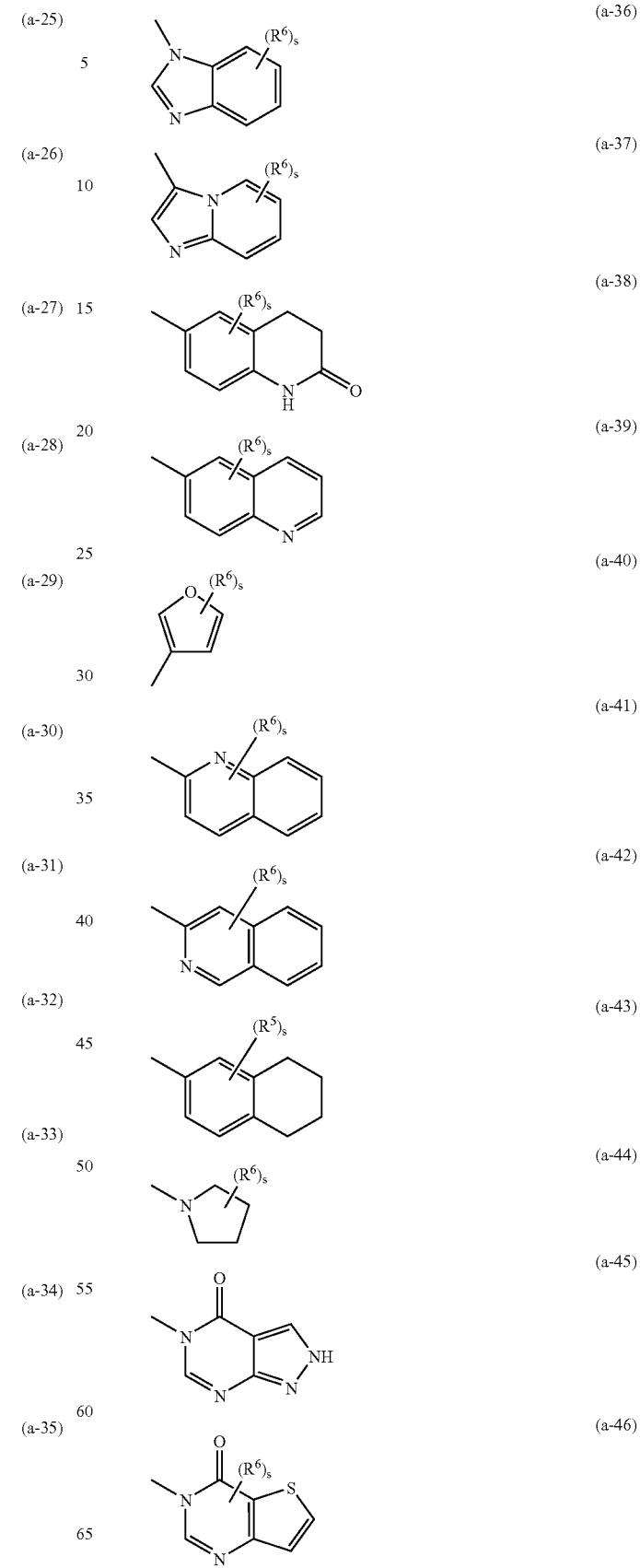

-continued

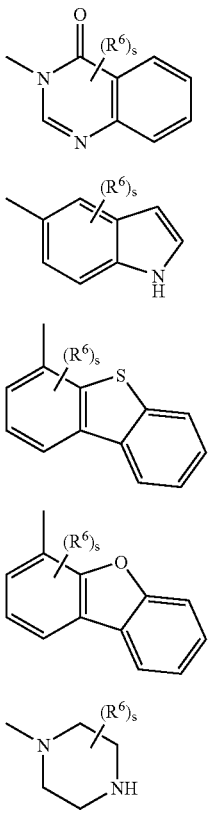

(a-47)
(a-48)
(a-49)
(a-50)
(a-51)

wherein each s is independently 0, 1, 2, 3, 4 or 5;

each $R^5$ and $R^6$ are independently selected from hydrogen; halo; hydroxy; amino; nitro; trihalo$C_{1-6}$alkyl; trihalo$C_{1-6}$ alkyloxy; $C_{1-6}$alkyl; $C_{1-6}$alkyl substituted with aryl and $C_{3-10}$cycloalkyl; $C_{1-6}$alkyloxy; $C_{1-6}$alkyloxy$C_{1-6}$alkyloxy; $C_{1-6}$alkylcarbonyl; $C_{1-6}$alkyloxycarbonyl; $C_{1-6}$alkysulfonyl; cyano$C_{1-6}$alkyl; hydroxy$C_{1-6}$alkyl; hydroxy$C_{1-6}$alkyloxy, hydroxy$C_{1-6}$alkylamino; amino$C_{1-6}$alkyloxy; di($C_{1-6}$alkyl)aminocarbonyl; di(hydroxy$C_{1-6}$alkyl)amino; (aryl)($C_{1-6}$alkyl)amino; di($C_{1-6}$alkyl)amino$C_{1-6}$alkyloxy; di($C_{1-6}$alkyl)amino$C_{1-6}$alkylamino; di($C_{1-6}$alkyl)amino$C_{1-6}$alkylamino$C_{1-6}$alkyl; arylsulfonyl; arylsulfonylamino; aryloxy; aryloxy$C_{1-6}$alkyl; aryl$C_{2-6}$alkenediyl; di($C_{1-6}$alkyl)amino; di($C_{1-6}$alkyl)amino$C_{1-6}$alkyl; di($C_{1-6}$alkyl)amino($C_{1-6}$alkyl)amino; di($C_{1-6}$alkyl)amino($C_{1-6}$alkyl)amino$C_{1-6}$alkyl; di($C_{1-6}$alkyl)amino$C_{1-6}$alkyl($C_{1-6}$alkyl)amino; di($C_{1-6}$alkyl)amino$C_{1-6}$alkyl($C_{1-6}$alkyl)amino$C_{1-6}$alkyl; aminosulfonylamino($C_{1-6}$alkyl)amino; aminosulfonylamino($C_{1-6}$alkyl)amino$C_{1-6}$alkyl; di($C_{1-6}$alkyl)aminosulfonylamino($C_{1-6}$alkyl)amino; di($C_{1-6}$alkyl)aminosulfonylamino($C_{1-6}$alkyl)amino$C_{1-6}$alkyl; cyano; thiophenyl; thiophenyl substituted with di($C_{1-6}$alkyl)amino$C_{1-6}$alkyl($C_{1-6}$alkyl)amino$C_{1-6}$alkyl, di($C_{1-6}$alkyl)amino$C_{1-6}$alkyl, $C_{1-6}$alkylpiperazinyl$C_{1-6}$alkyl, hydroxy$C_{1-6}$alkylpiperazinyl$C_{1-6}$alkyl, hydroxy$C_{1-6}$alkyloxy$C_{1-6}$alkylpiperazinyl$C_{1-6}$alkyl, di($C_{1-6}$alkyl)aminosulfonylpiperazinyl$C_{1-6}$alkyl, $C_{1-6}$alkyloxypiperidinyl, $C_{1-6}$alkyloxypiperidinyl$C_{1-6}$alkyl, morpholinyl$C_{1-6}$alkyl, hydroxy$C_{1-6}$alkyl($C_{1-6}$alkyl)amino$C_{1-6}$alkyl; or di(hydroxy$C_{1-6}$alkyl)amino$C_{1-6}$alkyl; furanyl; furanyl substituted with hydroxy$C_{1-6}$alkyl; benzofuranyl; imidazolyl; oxazolyl; oxazolyl substituted with aryl and $C_{1-6}$alkyl; $C_{1-6}$alkyltriazolyl; tetrazolyl; pyrrolidinyl; pyrrolyl; piperidinyl$C_{1-6}$alkyloxy; morpholinyl; $C_{1-6}$alkylmorpholinyl; morpholinyl$C_{1-6}$alkyloxy; morpholinyl$C_{1-6}$alkyl; morpholinyl$C_{1-6}$alkylamino; morpholinyl$C_{1-6}$alkylamino$C_{1-6}$alkyl; piperazinyl; $C_{1-6}$alkylpiperazinyl; $C_{1-6}$alkylpiperazinyl$C_{1-6}$alkyloxy; piperazinyl$C_{1-6}$alkyl; naphtalenylsulfonylpiperazinyl; naphtalenylsulfonylpiperidinyl; naphtalenylsulfonyl; $C_{1-6}$alkylpiperazinyl$C_{1-6}$alkyl; $C_{1-6}$alkylpiperazinyl$C_{1-6}$alkylamino; $C_{1-6}$alkylpiperazinyl$C_{1-6}$alkylamino$C_{1-6}$alkyl; $C_{1-6}$alkylpiperazinylsulfonyl; aminosulfonylpiperazinyl$C_{1-6}$alkyloxy; aminosulfonylpiperazinyl; aminosulfonylpiperazinyl$C_{1-6}$ alkyl; di($C_{1-6}$alkyl)aminosulfonylpiperazinyl; di($C_{1-6}$alkyl)aminosulfonylpiperazinyl$C_{1-6}$alkyl; hydroxy$C_{1-6}$alkylpiperazinyl; hydroxy$C_{1-6}$alkylpiperazinyl$C_{1-6}$lkyl; $C_{1-6}$alkyloxypiperidinyl; $C_{1-6}$alkyloxypiperidinyl$C_{1-6}$alkyl; piperidinylamino$C_{1-6}$alkylamino; piperidinylamino$C_{1-6}$alkylamino$C_{1-6}$alkyl; ($C_{1-6}$alkylpiperidinyl)hydroxy$C_{1-6}$alkyl)amino$C_{1-6}$alkylamino; ($C_{1-6}$alkylpiperidinyl)(hydroxy$C_{1-6}$alkyl)amino$C_{1-6}$alkylamino$C_{1-6}$alkyl; hydroxy$C_{1-6}$alkyloxy$C_{1-6}$alkylpiperazinyl; hydroxy$C_{1-6}$alkyloxy$C_{1-6}$alkylpiperazinyl$C_{1-6}$ alkyl; (hydroxy$C_{1-6}$alkyl)($C_{1-6}$alkyl)amino; (hydroxy$C_{1-6}$alkyl)$C_{1-6}$alkyl)amino$C_{1-6}$alkyl;

hydroxy$C_{1-6}$ alkylamino$C_{1-6}$alkyl; di(hydroxy$C_{1-6}$alkyl)amino$C_{1-6}$alkyl; pyrrolidinyl$C_{1-6}$alkyl; pyrrolidinyl$C_{1-6}$alkyloxy; pyrazolyl; thiopyrazolyl; pyrazolyl substituted with two substituents selected from $C_{1-6}$alkyl or trihalo$C_{1-6}$alkyl; pyridinyl; pyridinyl substituted with $C_{1-6}$alkyloxy, aryloxy or aryl; pyrimidinyl; tetrahydropyrimidinylpiperazinyl; tetrahydropyrimidinylpiperazinyl$C_{1-6}$alkyl; quinolinyl; indole; phenyl; phenyl substituted with one, two or three substituents independently selected from halo, amino, nitro, $C_{1-6}$alkyl, $C_{1-6}$alkyloxy, hydroxy$C_{1-4}$alkyl, trifluoromethyl, trifluoromethyloxy, hydroxy$C_{1-4}$alkyloxy, $C_{1-4}$alkylsulfonyl, $C_{1-4}$alkyloxy$C_{1-4}$alkyloxy, $C_{1-4}$alkyloxycarbonyl, amino$C_{1-4}$alkyloxy, di($C_{1-4}$alkyl)amino$C_{1-4}$alkyloxy, di($C_{1-4}$alkyl)amino, di($C_{1-4}$alkyl)aminocarbonyl, di($C_{1-4}$alkyl)amino$C_{1-4}$alkyl, di($C_{1-4}$alkyl)amino$C_{1-4}$alkylamino$C_{1-4}$alkyl, di($C_{1-4}$alkyl)amino($C_{1-4}$alkyl)amino, di($C_{1-4}$alkyl)amino($C_{1-4}$alkyl)amino$C_{1-4}$alkyl, di($C_{1-4}$alkyl)amino$C_{1-4}$alkyl($C_{1-4}$alkyl)amino, di($C_{1-4}$alkyl)amino$C_{1-4}$alkyl($C_{1-4}$alkyl)amino$C_{1-4}$alkyl, aminosulfonylamino($C_{1-4}$alkyl)amino, aminosulfonylamino($C_{1-4}$alkyl)amino$C_{1-4}$alkyl, di($C_{1-4}$ alkyl)aminosulfonylamino($C_{1-4}$alkyl)amino, di($C_{1-4}$alkyl)aminosulfonylamino($C_{1-4}$alkyl)amino$C_{1-6}$ alkyl, cyano, piperidinyl$C_{1-4}$alkyloxy, pyrrolidinyl$C_{1-4}$alkyloxy, aminosulfonylpiperazinyl, aminosulfonylpiperazinyl$C_{1-4}$alkyl, di($C_{1-4}$alkyl)aminosulfonylpiperazinyl, di($C_{1-4}$alkyl)aminosulfonylpiperazinyl$C_{1-4}$alkyl, hydroxy$C_{1-4}$alkylpiperazinyl, hydroxy$C_{1-4}$alkylpiperazinyl$C_{1-4}$alkyl, $C_{1-4}$alkyloxypiperidinyl, $C_{1-4}$alkyloxypiperidinyl$C_{1-4}$alkyl, hydroxy$C_{1-4}$alkyloxy$C_{1-4}$alkylpiperazinyl, hydroxy$C_{1-4}$alkyloxy$C_{1-4}$alkylpiperazinyl$C_{1-4}$alkyl, (hydroxy$C_{1-4}$alkyl)($C_{1-4}$alkyl)amino, (hydroxy$C_{1-4}$alkyl)($C_{1-4}$alkyl)amino$C_{1-4}$alkyl, di(hydroxy$C_{1-4}$alkyl)amino, di(hydroxy$C_{1-4}$alkyl)amino$C_{1-4}$alkyl, furanyl, furanyl substituted with —CH=CH—CH=CH—, pyrrolidinyl$C_{1-4}$alkyl, pyrrolidinyl$C_{1-4}$alkyloxy, morpholinyl, morpholinyl$C_{1-4}$alkyloxy, morpholinyl$C_{1-4}$alkyl, morpholinyl$C_{1-4}$alkylamino, morpholinyl$C_{1-4}$alkylamino$C_{1-4}$alkyl, piperazinyl, $C_{1-4}$alkylpiperazinyl, ($C_{1-4}$alkylpiperazinyl$C_{1-4}$alkyloxy, piperazinyl$C_{1-4}$alkyl, $C_{1-4}$alkylpiperazinyl$C_{1-4}$alkyl, $C_{1-4}$alkylpiperazinyl$C_{1-4}$alkylamino, $C_{1-4}$alkylpiperazinyl$C_{1-4}$alkylamino$C_{1-4}$alkyl, tetrahydropyrimidinylpiperazinyl, tetrahydropyrimidinylpiperazinyl$C_{1-4}$alkyl, piperidinylamino$C_{1-4}$alkylamino, piperidinylamino$C_{1-4}$alkylamino$C_{1-4}$alkyl, ($C_{1-4}$alkylpiperidinyl)(hydroxy$C_{1-4}$alkyl)amino$C_{1-4}$alkylamino, ($C_{1-4}$alkylpiperidinyl)(hydroxy$C_{1-4}$alkyl)amino$C_{1-4}$alkylamino$C_{1-4}$alkyl, pyridinyl$C_{1-4}$alkyloxy, hydroxy$C_{1-4}$alkylamino, hydroxy$C_{1-4}$alkylamino$C_{1-4}$alkyl, di($C_{1-4}$alkyl)amino$C_{1-4}$alkylamino, aminothiadiazolyl, aminosulfonylpiperazinyl$C_{1-4}$alkyloxy, or thiophenyl$C_{1-4}$alkylamino;

each $R^5$ and $R^6$ can be placed on the nitrogen in replacement of the hydrogen;

aryl in the above is phenyl, or phenyl substituted with one or more substituents each independently selected from halo, $C_{1-6}$alkyl, $C_{1-6}$alkyloxy, trifluoromethyl, cyano or hydroxycarbonyl.

Other embodiments of the compound according to embodiment [0136] (hereinafter collectively referred to as embodiment [0137]) are those in which one or more of the following apply (wherein each of $R^2$, $R^3$, and $R^4$ in this embodiment corresponds to $R^{12}$, $R^{13}$, and $R^{14}$, respectively, in embodiment [0136]):

n is 1 or 2;
t is 0, 1, 2 or 4;
Q is

$R^2$ is hydrogen or nitro;
-L- is a direct bond or a bivalent radical selected from $C_{1-6}$alkanediyl;
$R^4$ is hydrogen;

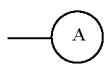

is a radical selected from (a-1), (a-2), (a-3), (a-5), (a-6), (a-11), (a-18), (a-20), (a-21), (a-32), (a-33), (a-47) or (a-51);
each s is independently 0, 1, 2, or 4;
each $R^5$ and $R^6$ are independently selected from hydrogen; halo; trihalo$C_{1-6}$alkyl; $C_{1-6}$alkyl; $C_{1-6}$alkyl substituted with aryl and $C_{3-10}$alkylcycloalkyl; $C_{1-6}$alkyloxy$C_{1-6}$alkylcarbonyl; benzofuranyl; naphtalenylsulfonyl; pyridinyl substituted with aryloxy, phenyl; or phenyl substituted with one substituent independently selected from hydroxy$C_{1-4}$alkyl or morpholinyl$C_{1-4}$alkyl.

Other embodiments of the compound according to embodiment [0136] (hereinafter collectively referred to as embodiment [0138]) are those in which one or more of the following apply (wherein each of $R^2$, $R^3$, and $R^4$ in this embodiment corresponds to $R^{12}$, $R^{13}$, and $R^{14}$, respectively, in embodiment [0136]):

n is 1;
t is 0, 1 or 2;

Q is

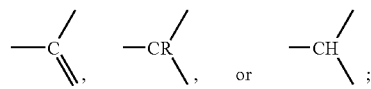

X is nitrogen;
Y is nitrogen;
$R^2$ is hydrogen;
-L- is a direct bond;
each $R^3$ independently represents a hydrogen atom;
$R^4$ is hydrogen;

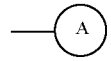

is a radical selected from (a-6), (a-11), (a-20), (a-47) or (a-51);
each s is independently 0, 1, or 4;
each $R^5$ and $R^6$ are independently selected from hydrogen; $C_{1-6}$alkyl; $C_{1-6}$alkyloxy; naphtalenylsulfonyl; or phenyl substituted with hydroxy$C_{1-4}$alkyl or morpholinyl$C_{1-4}$alkyl.

Other embodiments of the compound according to embodiment [0136] (hereinafter collectively referred to as embodiment [0139]) L is a direct bond.

Other embodiments of the compound according to embodiment [0136] (hereinafter collectively referred to as embodiment [0140]) are those in which one or more of the following apply (wherein each of $R^2$, $R^3$, and $R^4$ in this embodiment corresponds to $R^{12}$, $R^{13}$, and $R^{14}$, respectively, in embodiment [0136]:

t is 1, 2, 3, or 4;
$R^2$ is hydrogen, halo, hydroxy, amino, nitro, $C_{1-6}$alkyl, $C_{1-6}$alkyloxy, trifluoromethyl or di($C_{1-6}$alkyl)amino;
-L- is a direct bond or a bivalent radical selected from $C_{1-6}$alkanediyl, $C_{1-6}$alkanediyloxy, amino or carbonyl;
$R^4$ is hydrogen, hydroxy, amino, hydroxy$C_{1-6}$alkyl, $C_{1-6}$alkyl, $C_{1-6}$alkyloxy, aryl$C_{1-6}$alkyl, aminocarbonyl, amino$C_{1-6}$alkyl, $C_{1-6}$alkylamino$C_{1-6}$alkyl or di($C_{1-6}$alkyl)amino$C_{1-6}$alkyl;

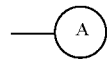

is a radical selected from (a-1), (a-3), (a-4) (a-5) (a-6), (a-7), (a-8), (a-9), (a-10), (a-11), (a-12), (a-13), (a-14), (a-1), (a-16), (a-17), (a-18), (a-19), (a-20), (a-21), (a-22), (a-23), (4-24); (a-25), (a-26), (a-28), (a-29), (a-30), (a-31), (a-32), (a-33), (a-34), (a-35), (a-36), (a-37), (a-38), (ea-39); (a-40), (a-41), (a-42), (a-44), (a-45), (a-46), (a-47), (a-8) and (a-51);
each s is independently 0, 1, 2, 3 or 4;
$R^5$ is hydrogen; halo; hydroxy; amino; nitro; trihalo$C_{1-6}$alkyl; trihalo$C_{1-6}$alkyloxy; $C_{1-6}$alkyl; $C_{1-6}$alkyloxy; $C_{1-6}$alkylcarbonyl; $C_{1-6}$alkyloxycarbonyl; $C_{1-6}$alkylsulfonyl; hydroxy$C_{1-6}$alkyl, aryloxy; di($C_{1-6}$alkyl)amino; cyano; thiophenyl; furanyl; furanyl substituted with hydroxy$C_{1-6}$alkyl; benzofuranyl; imidazolyl; oxazolyl; oxazolyl substituted with aryl and $C_{1-6}$alkyl; $C_{1-6}$alkyltriazolyl; tetrazolyl; pyrrolidinyl; pyrrolyl; morpholinyl;

$C_{1-6}$alkylmorpholinyl; piperazinyl; $C_{1-6}$alkylpiperidinyl; hydroxy$C_{1-6}$alkylpiperazinyl; $C_{1-6}$alkyloxypiperidinyl; pyrazolyl; pyrazolyl substituted with one or two substituents selected from $C_{1-6}$alkyl or trihalo$C_{1-6}$alkyl; pyridinyl; pyridinyl substituted with $C_{1-6}$alkyloxy, aryloxy or aryl; pyrimidinyl; quinolinyl; indole; phenyl; or phenyl substituted with one or two substituents independently selected from halo, $C_{1-6}$alkyl, $C_{1-6}$alkoxy or trifluoromethyl;

$R^6$ is hydrogen; halo; hydroxy; amino; nitro; trihalo$C_{1-6}$alkyl; trihalo$C_{1-6}$alkyloxy; $C_{1-6}$alkyl; $C_{1-6}$alkyloxy; $C_{1-6}$alkylcarbonyl; $C_{1-6}$alkyloxycarbonyl; $C_{1-6}$alkylsulfonyl; hydroxy$C_{1-6}$alkyl; aryloxy; di($C_{1-6}$alkyl)amino; cyano; pyridinyl; phenyl; or phenyl substituted with one or two substituents independently selected from halo, $C_{1-6}$alkyl, $C_{1-6}$alkyloxy or trifluoromethyl.

Other embodiments of the compound according to embodiment [0136] (hereinafter collectively referred to as embodiment [0141]) include those in which the following are true (wherein each of $R^2$, $R^3$, and $R^4$ in this embodiment corresponds to $R^{12}$, $R^{13}$, and $R^{14}$, respectively, in embodiment [0136]):

t is 1, 2, 3, or 4;
$R^2$ is hydrogen, halo, hydroxy, amino, nitro, $C_{1-6}$alkyl, $C_{1-6}$alkyloxy, trifluoromethyl or di($C_{1-6}$alkyl)amino;
-L- is a direct bond or a bivalent radical selected from $C_{1-6}$alkanediyl, $C_{1-6}$alkanediyloxy, amino or carbonyl;
$R^4$ is hydrogen, hydroxy, amino, hydroxy$C_{1-6}$alkyl, $C_{1-6}$alkyl, $C_{1-6}$alkyloxy, aryl$C_{1-6}$alkyl, aminocarbonyl, amino$C_{1-6}$alkyl, $C_{1-6}$alkylamino$C_{1-6}$alkyl or di($C_{1-6}$alkyl)amino$C_{1-6}$alkyl;

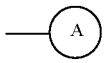

is a radical selected from (a-1), (a-3), (a-4), (a-5), (a-6), (a-7), (a-8, (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-28), (a-29), (a-30), (a-31), (a-32), (a-33), (a-34), (a-35), (a-36), (a-37), (a-38), (a-39), (a-40), (a-41), (a-42), (a-44), (a-45), (a-46), (a-47); (a-48) and (a-51);

each s is independently 0, 1, 2, 3 or 4;

$R^5$ is hydrogen; halo; hydroxy; amino; nitro; trihalo$C_{1-6}$alkyl; trihalo$C_{1-6}$alkyloxy; $C_{1-6}$alkyl; $C_{1-6}$alkyloxy; $C_{1-6}$alkylcarbonyl; $C_{1-6}$alkyloxycarbonyl; $C_{1-6}$alkylsulfonyl; hydroxy$C_{1-6}$alkyl; aryloxy; di($C_{1-6}$alkyl)amino; cyano; thiophenyl; furanyl; furanyl substituted with hydroxy$C_{1-6}$alkyl; benzofuranyl; imidazolyl; oxazolyl; oxazolyl substituted with aryl and $C_{1-6}$alkyl; $C_{1-6}$alkyltriazolyl; tetrazolyl; pyrrolidinyl; pyrrolyl; morpholinyl; $C_{1-6}$alkylmorpholinyl; piperazinyl; $C_{1-6}$alkylpiperazinyl; hydroxy$C_{1-6}$alkylpiperazinyl; $C_{1-6}$alkyloxypiperidinyl; pyrazolyl; pyrazolyl substituted with one or two substituents selected from $C_{1-6}$alkyloxy or trihalo$C_{1-6}$alkyl; pyridinyl; pyridinyl substituted with $C_{1-6}$alkyloxy, aryloxy or aryl; pyrimidinyl; quinolinyl; indole; phenyl; or phenyl substituted with one or two substituents independently selected from halo, $C_{1-6}$alkyl, $C_{1-6}$alkyloxy or trifluoromethyl;

$R^6$ is hydrogen; halo; hydroxy; amino; nitro; trihalo$C_{1-6}$alkyl; trihalo$C_{1-6}$alkyloxy; $C_{1-6}$alkyl; $C_{1-6}$alkyloxy; $C_{1-6}$alkylcarbonyl; $C_{1-6}$alkyloxycarbonyl; $C_{1-6}$alkylsulfonyl; hydroxy$C_{1-6}$alkyl; aryloxy; di($C_{1-6}$alkyl)amino; cyano; pyridinyl; phenyl; or phenyl substituted with one or two substituents independently selected from halo, $C_{1-6}$alkyl, $C_{1-6}$alkyloxy or trifluoromethyl.

Other embodiments of the compound according to embodiment [0136] (hereinafter collectively referred to as embodiment [0142]) are the following (wherein each of $R^2$, $R^3$, and $R^4$ in this embodiment corresponds to $R^{12}$, $R^{13}$, and $R^{14}$, respectively, in embodiment [0136]):

n is 1 or 2;
t is 1, 2, 3, or 4;
Q is

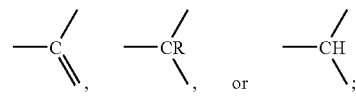

$R^2$ is H or nitro:
-L- is a direct bond or a bivalent radical selected from $C_{1-6}$alkanediyl; $R^4$ is hydrogen;

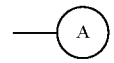

is a radical selected from (a-1), (a-2), (a-3), (a-5), (a-6), (a-11), (a-18), (a-20), (a-21), (a-32), (a-33), (a-47) or (a-51); each s is independently 0, 1, 2, or 4; each $R^5$ and $R^6$ independently selected from hydrogen; halo; trihalo$C_{1-6}$alkyl; $C_{1-6}$alkyl; $C_{1-6}$alkyl substituted with aryl and $C_{3-10}$cycloalkyl; $C_{1-6}$alkyloxy, $C_{1-6}$alkylcarbonyl; benzofuranyl; naphtalenylsulfonyl; pyridinyl substituted with aryloxy phenyl; or phenyl substituted with one substituent independently selected from hydroxy$C_{1-4}$alkyl or morpholinyl$C_{1-4}$alkyl.

Other embodiments of the compound according to embodiment [0136] (hereinafter collectively referred to as embodiment [0143]) are the following (wherein each of $R^2$, $R^3$, and $R^4$ in this embodiment corresponds to $R^{12}$, $R^{13}$, and $R^{14}$, respectively, in embodiment [0136]):

n is 1;
t is 0 or 1; X is nitrogen; Y is nitrogen;
Q is

$R^2$ is hydrogen; -L- is a direct bond; each $R^3$ independently represents a hydrogen atom; $R^4$ is hydrogen;

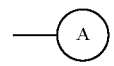

is a radical selected from (a-6), (a-11), (a-20), (a-47) or (a-51); each s is independently 0, 1, or 4; and each $R^5$ and $R^6$ are independently selected from hydrogen; $C_{1-6}$alkyl; $C_{1-6}$alkyloxy; naphtalenylsulfonyl; or aryl substituted with hydroxy$C_{1-4}$alkyl or morpholinyl$C_{1-4}$alkyl.

Particular embodiments of the compound according to embodiment [0136] (hereinafter collectively referred to as embodiment [0144]) include the following 89
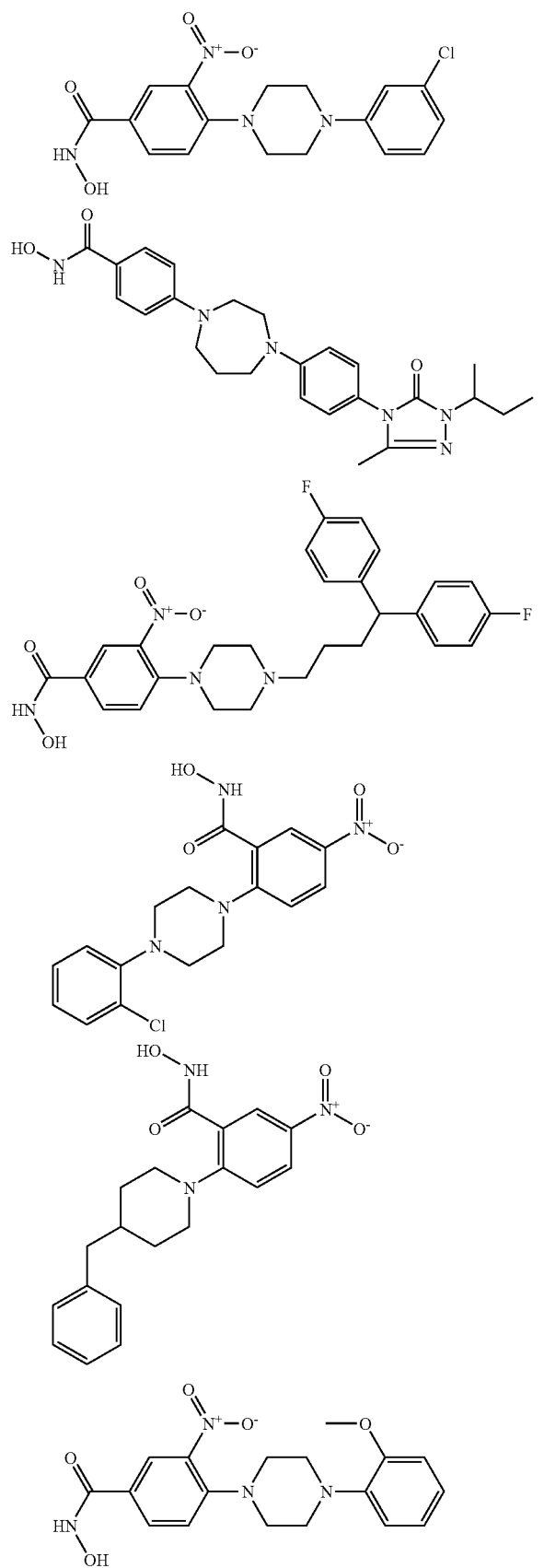
90
-continued
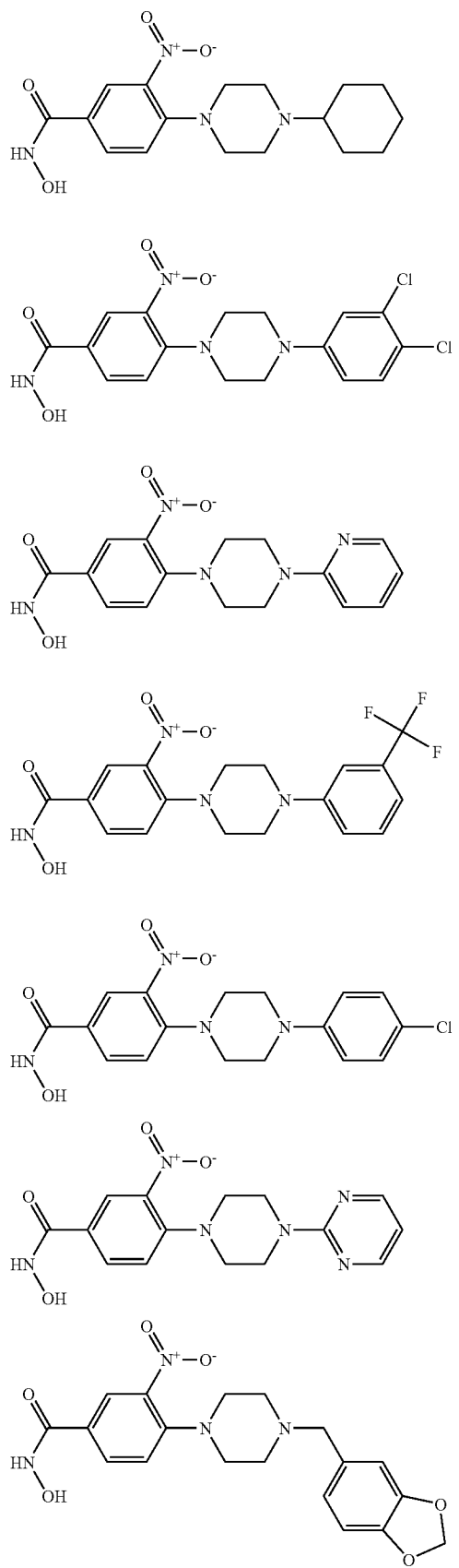

-continued
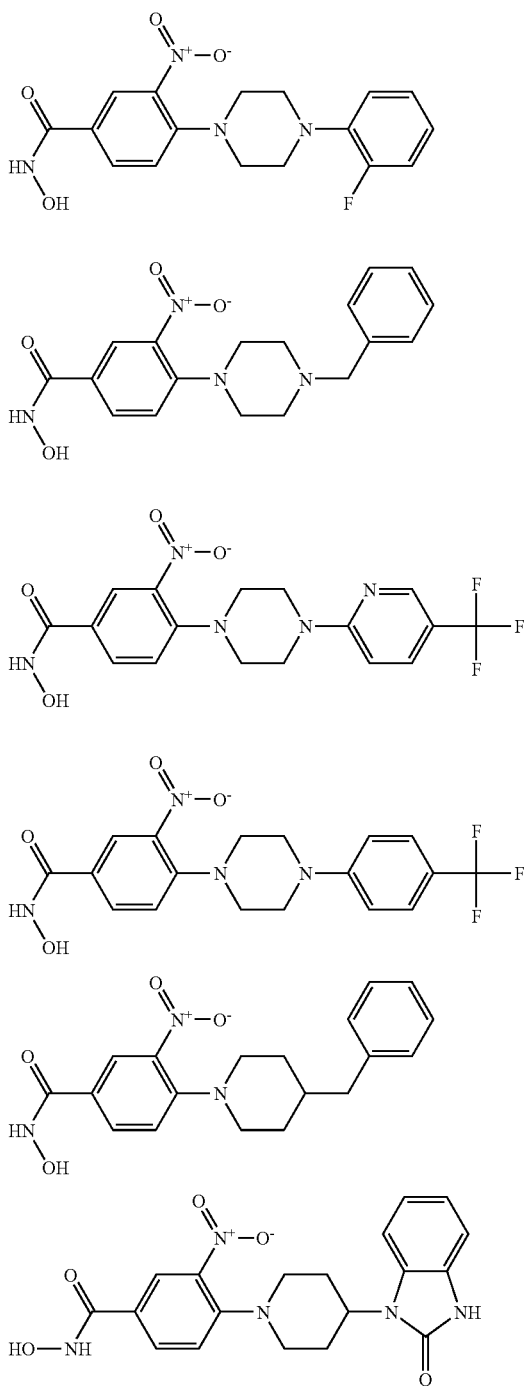
-continued
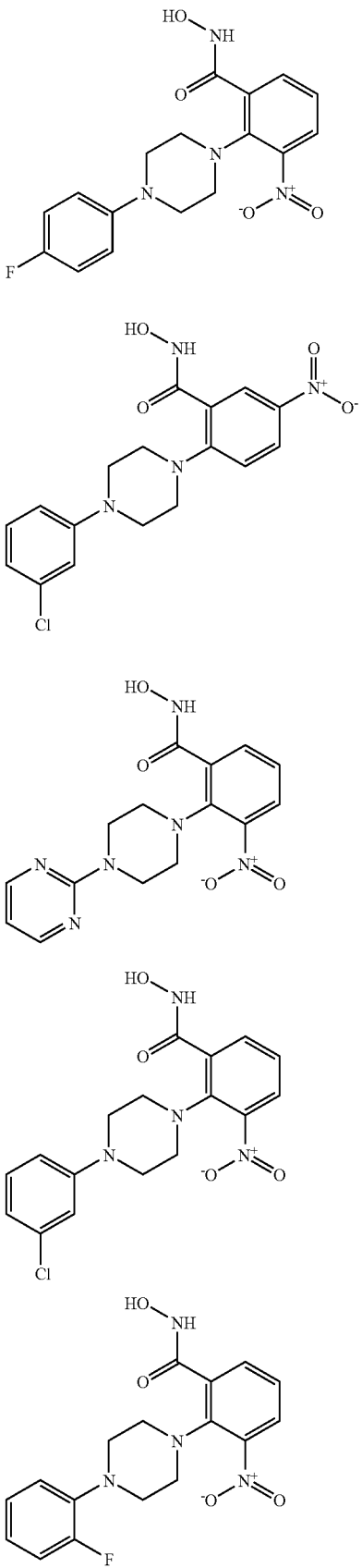

-continued
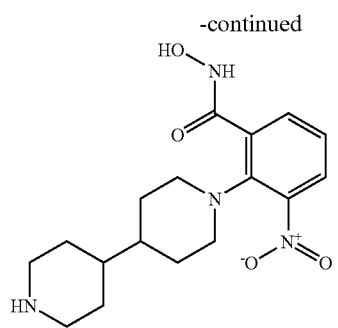
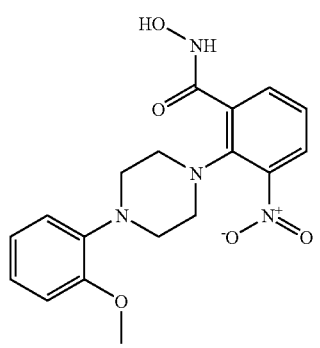
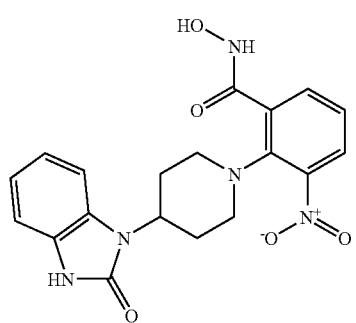
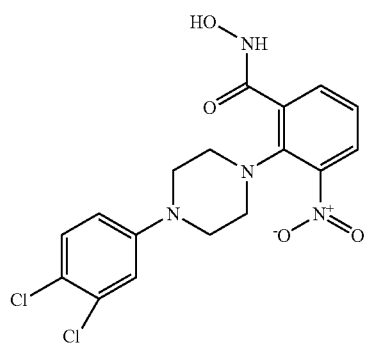
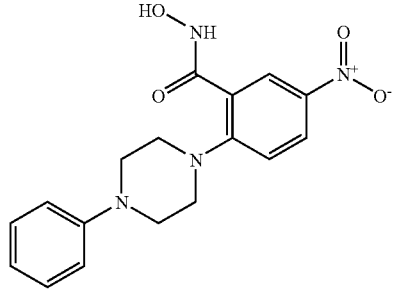
-continued
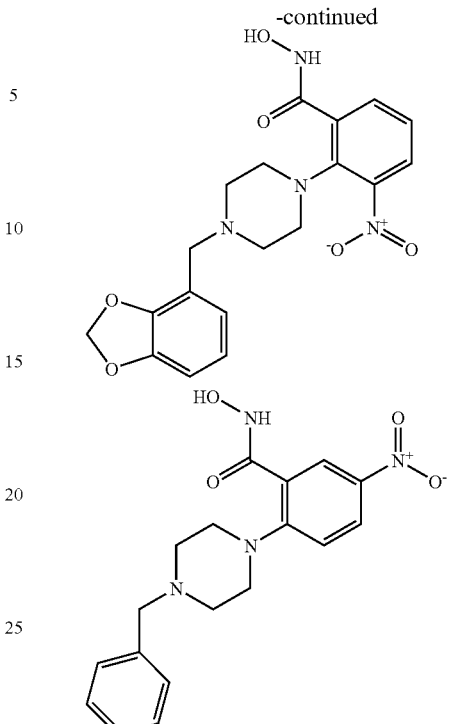
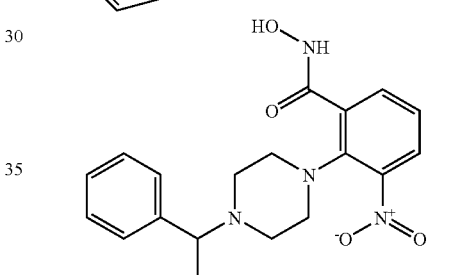
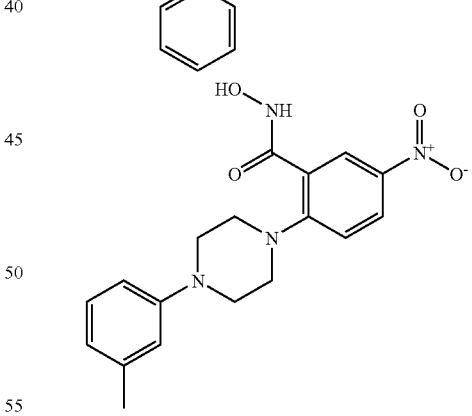
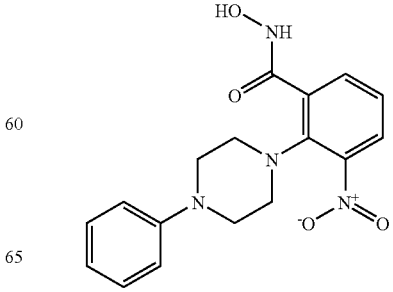

-continued
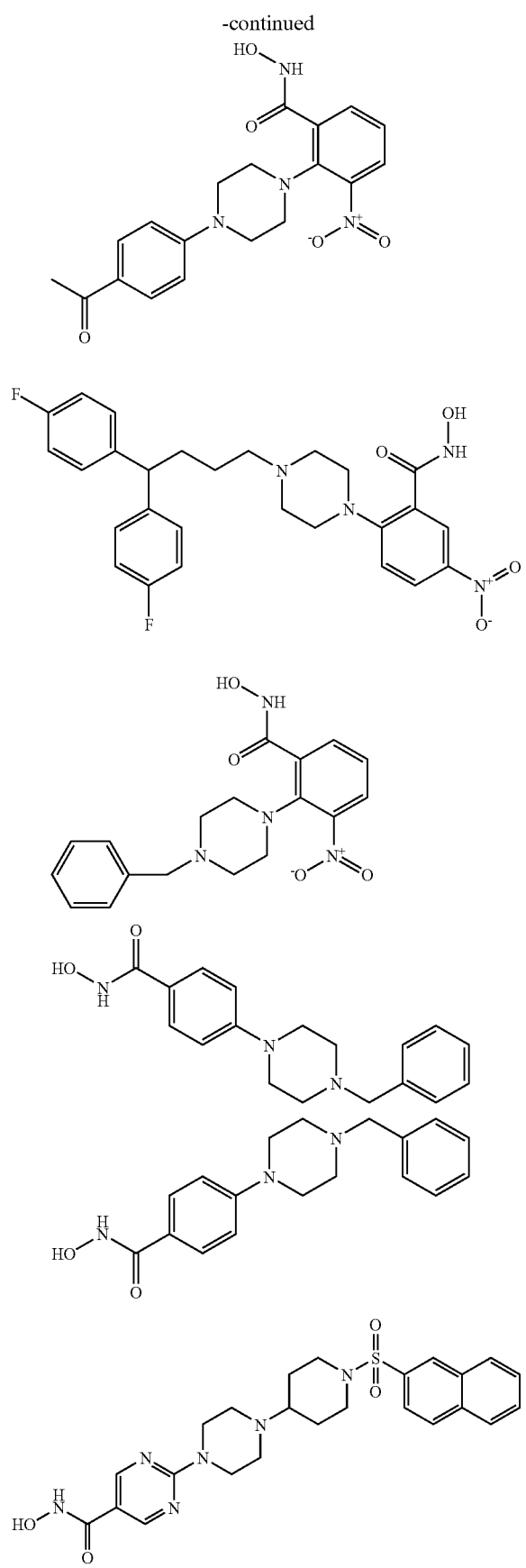
-continued
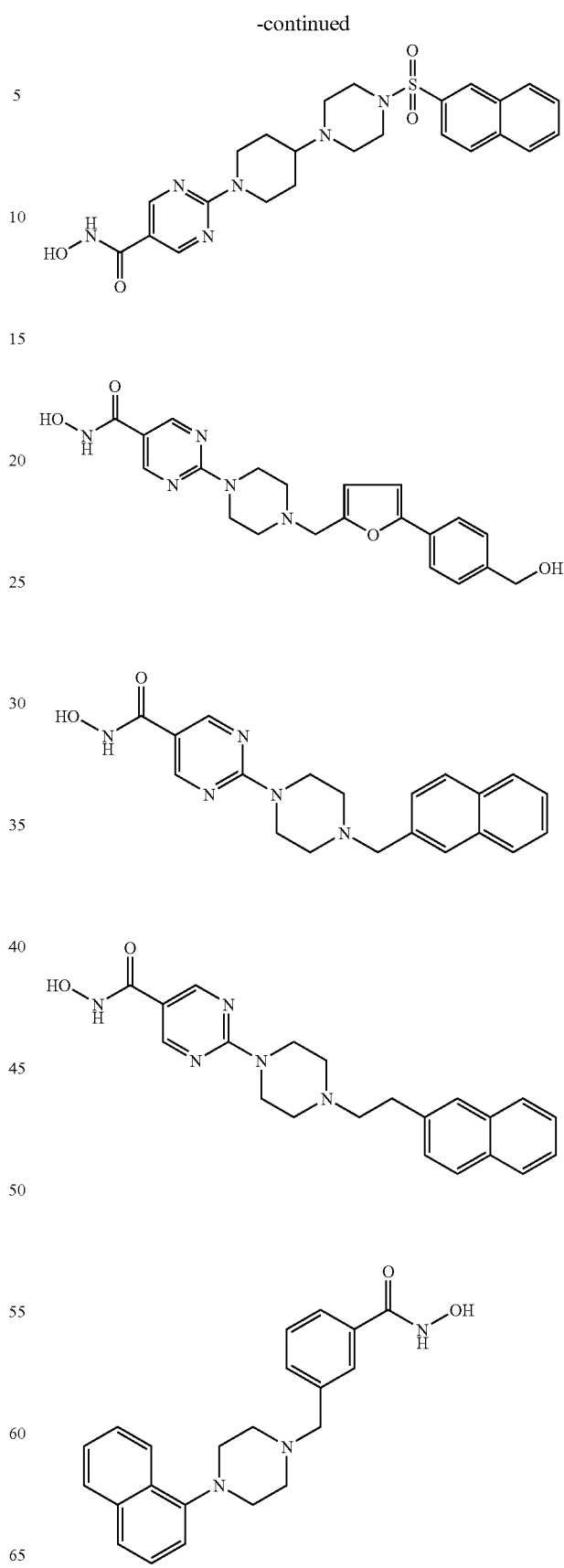

-continued

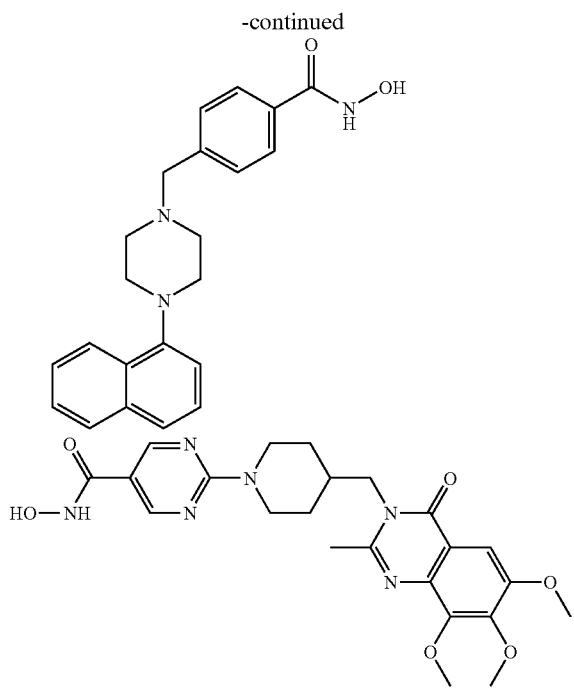

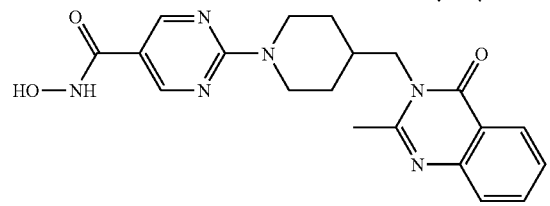

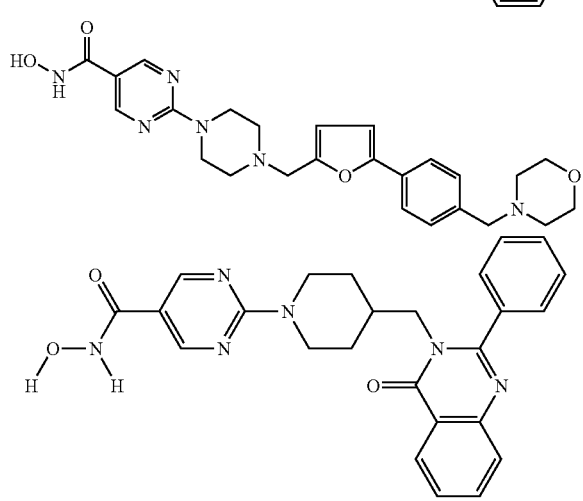

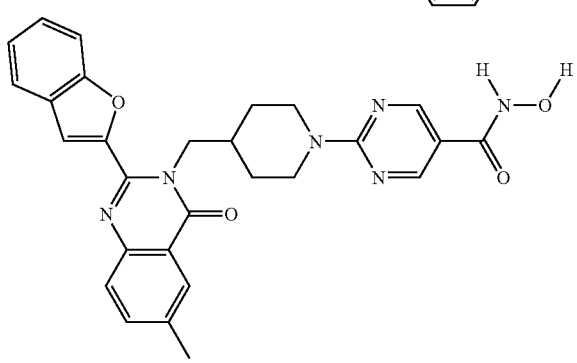

-continued

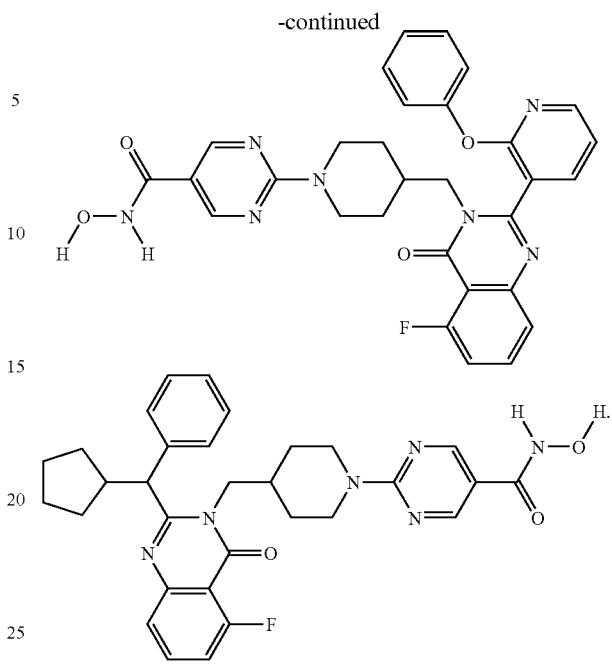

in which the terminal hydroxamic acid moiety (—C(O)—NH—OH) is replaced with

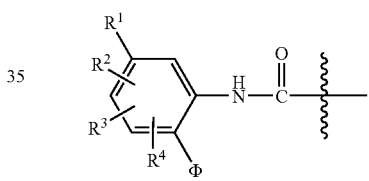

wherein Φ, $R^1$, $R^2$, $R^3$, and $R^4$ are as defined in accordance with embodiment [0046], and preferably embodiments [0048] and [0049]:

In the compounds of embodiments [0136]-[0144], $R^1$, $R^2$, $R^3$, and $R^4$ are preferably as defined in embodiments [0048] and [0049]. In other embodiments of the compounds of embodiments [0136]-[0144], $R^1$, $R^2$, $R^3$, and $R^4$ are all H. Such embodiments are hereinafter collectively referred to as embodiment [0145].

In another embodiment, the invention comprises compounds of the following structural formula (8) (hereinafter embodiment [0146]):

(8)

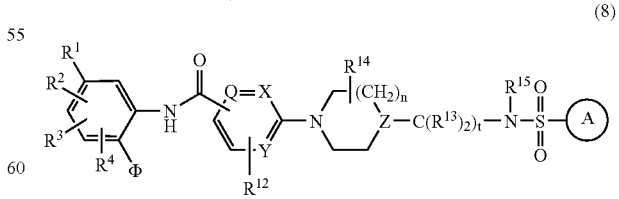

or a pharmaceutically acceptable salt thereof, wherein
Φ is —$NH_2$ or —OH;
$R^1$ is H or as defined in embodiment [0046];
$R^2$, $R^3$, and $R^4$ are as defined in embodiment [0046];

n is 0, 1, 2 or 3 and when n is 0 then a direct bond is intended;

t is 0, 1, 2, 3 or 4 and when t is 0 then a direct bond is intended;

Q is nitrogen or

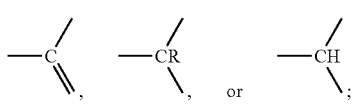

X is nitrogen or

Y is nitrogen or

Z is nitrogen or

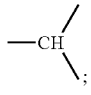

R is selected from the group consisting of hydrogen, halogen, —NH$_2$, nitro, hydroxy, aryl, heterocyclyl, C$_3$-C$_8$-cycloalkyl, heteroaryl, C$_1$-C$_7$alkyl, haloalkyl, C$_1$-C$_7$-alkenyl, C$_1$-C$_7$-alkynyl, C$_1$-C$_7$-acyl, C$_1$-C$_7$-alkyl-aryloxy, C$_1$-C$_7$-alkyl-arylsulfanyl, C$_1$-C$_7$-alkyl-arylsulfinyl, C$_1$-C$_7$-alkyl-arylsulfonyl, C$_1$-C$_7$-alkyl-arylaminosulfonyl, C$_1$-C$_7$-alkyl-arylamine, C$_1$-C$_7$-alkynyl-C(O)-amine, C$_1$-C$_7$-alkenyl-C(O)-amine, C$_1$-C$_7$-alkynyl-R$^9$, C$_1$-C$_7$-alkenyl-9 wherein R$^9$ is hydrogen, hydroxy, amino, C$_1$-C$_7$-alkyl or C$_1$-C$_7$-alkoxy;

R$^{12}$ is hydrogen, halo, hydroxy, amino, nitro, C$_{1-6}$alkyl, C$_{1-6}$alkyloxy, trifluoromethyl, di(C$_{1-6}$alkyl)amino, hydroxyamino or naphtalenylsulfonylpyrazinyl;

each R$^{13}$ independently represents a hydrogen atom and one hydrogen atom can be replaced by a substituent selected from aryl;

R$^{14}$ is hydrogen, hydroxy, amino, hydroxyC$_{1-6}$alkyl, C$_{1-6}$alkyl, C$_{1-6}$alkyloxy, arylC$_{1-6}$alkyl, aminocarbonyl, hydroxycarbonyl, aminoC$_{1-6}$alkyl, aminocarbonylC$_{1-6}$alkyl, hydroxycarbonylC$_{1-6}$alkyl, hydroxyaminocarbonyl, C$_{1-6}$alkyloxycarbonyl, C$_{1-6}$alkylaminoC$_{1-6}$alkyl or di(C$_{1-6}$alkyl)aminoC$_{1-6}$alkyl;

R$^{15}$ is hydrogen, C$_{1-6}$alkyl, C$_{3-10}$cycloalkyl, hydroxyC$_{1-6}$alkyl, C$_{1-6}$alkyloxyC$_{1-6}$alkyl, di(C$_{1-6}$alkyl)aminoC$_{1-6}$alkyl or aryl;

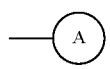

is a radical selected from

(a-1)

(a-2)

(a-3)

(a-4)

(a-5)

(a-6)

(a-7)

(a-8)

(a-9)

(a-10)

(a-11)

(a-12)

-continued
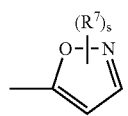 (a-13)
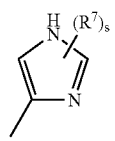 (a-14)
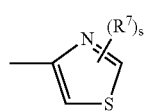 (a-15)
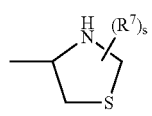 (a-16)
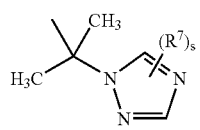 (a-17)
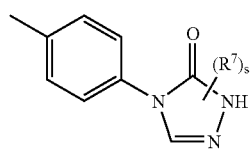 (a-18)
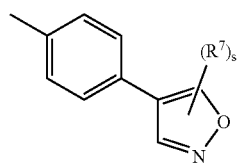 (a-19)
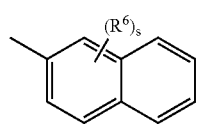 (a-20)
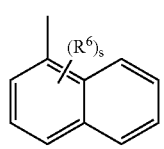 (a-21)
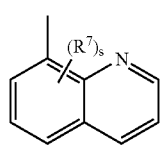 (a-22)
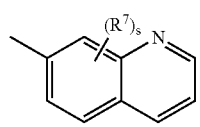 (a-23)
-continued
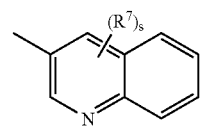 (a-24)
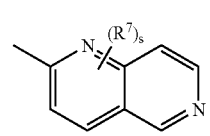 (a-25)
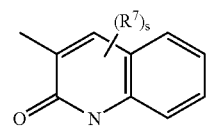 (a-26)
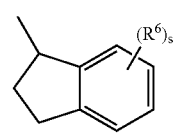 (a-27)
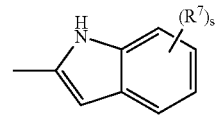 (a-28)
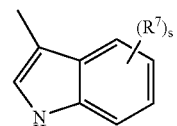 (a-29)
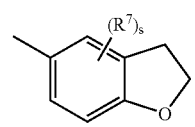 (a-30)
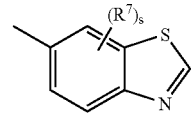 (a-31)
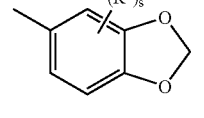 (a-32)
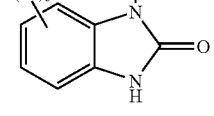 (a-33)
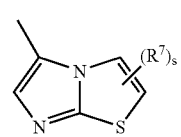 (a-34)

-continued

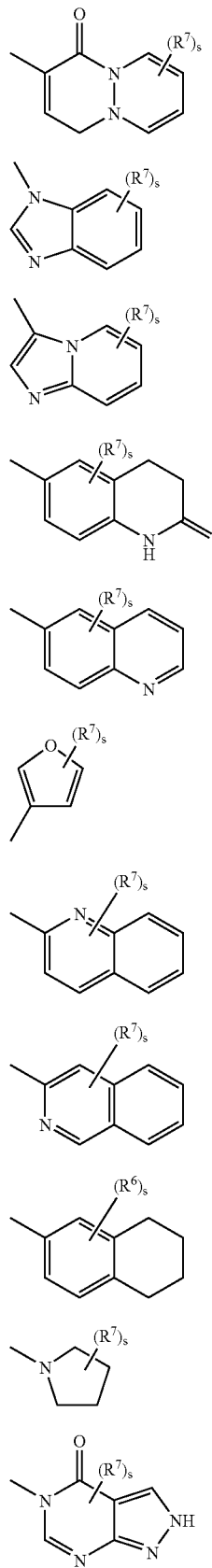

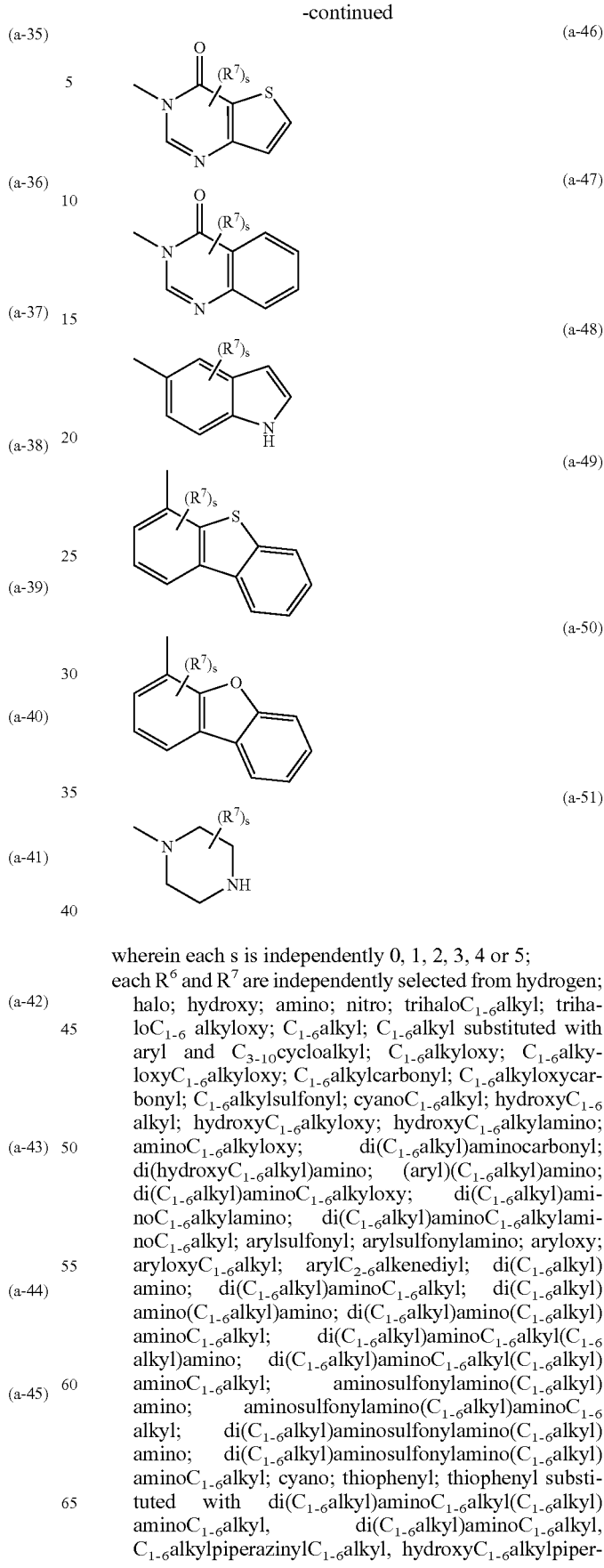

wherein each s is independently 0, 1, 2, 3, 4 or 5;
each $R^6$ and $R^7$ are independently selected from hydrogen; halo; hydroxy; amino; nitro; trihalo$C_{1-6}$alkyl; trihalo$C_{1-6}$ alkyloxy; $C_{1-6}$alkyl; $C_{1-6}$alkyl substituted with aryl and $C_{3-10}$cycloalkyl; $C_{1-6}$alkyloxy; $C_{1-6}$alkyloxy$C_{1-6}$alkyloxy; $C_{1-6}$alkylcarbonyl; $C_{1-6}$alkyloxycarbonyl; $C_{1-6}$alkylsulfonyl; cyano$C_{1-6}$alkyl; hydroxy$C_{1-6}$alkyl; hydroxy$C_{1-6}$alkyloxy; hydroxy$C_{1-6}$alkylamino; amino$C_{1-6}$alkyloxy; di($C_{1-6}$alkyl)aminocarbonyl; di(hydroxy$C_{1-6}$alkyl)amino; (aryl)($C_{1-6}$alkyl)amino; di($C_{1-6}$alkyl)amino$C_{1-6}$alkyloxy; di($C_{1-6}$alkyl)amino$C_{1-6}$alkylamino; di($C_{1-6}$alkyl)amino$C_{1-6}$alkylamino$C_{1-6}$alkyl; arylsulfonyl; arylsulfonylamino; aryloxy; aryloxy$C_{1-6}$alkyl; aryl$C_{2-6}$alkenediyl; di($C_{1-6}$alkyl)amino; di($C_{1-6}$alkyl)amino$C_{1-6}$alkyl; di($C_{1-6}$alkyl)amino($C_{1-6}$alkyl)amino; di($C_{1-6}$alkyl)amino($C_{1-6}$alkyl)amino$C_{1-6}$alkyl; di($C_{1-6}$alkyl)amino$C_{1-6}$alkyl($C_{1-6}$alkyl)amino; di($C_{1-6}$alkyl)amino$C_{1-6}$alkyl($C_{1-6}$alkyl)amino$C_{1-6}$alkyl; aminosulfonylamino($C_{1-6}$alkyl)amino; aminosulfonylamino($C_{1-6}$alkyl)amino$C_{1-6}$alkyl; di($C_{1-6}$alkyl)aminosulfonylamino($C_{1-6}$alkyl)amino; di($C_{1-6}$alkyl)aminosulfonylamino($C_{1-6}$alkyl)amino$C_{1-6}$alkyl; cyano; thiophenyl; thiophenyl substituted with di($C_{1-6}$alkyl)amino$C_{1-6}$alkyl($C_{1-6}$alkyl)amino$C_{1-6}$alkyl, di($C_{1-6}$alkyl)amino$C_{1-6}$alkyl, $C_{1-6}$alkylpiperazinyl$C_{1-6}$alkyl, hydroxy$C_{1-6}$alkylpiperazinyl$C_{1-6}$alkyl, hydroxy$C_{1-6}$alkyloxy$C_{1-6}$alkylpiperazinyl$C_{1-4}$alkyl, di($C_{1-6}$alkyl)aminosulfonylpiperazinyl$C_{1-6}$alkyl, $C_{1-6}$alkyloxypiperidinyl, $C_{1-6}$alkyloxypiperidinyl$C_{1-6}$alkyl, morpholinyl$C_{1-6}$alkyl, hydroxy$C_{1-6}$alkyl($C_{1-6}$alkyl)amino$C_{1-6}$alkyl, or di(hydroxy$C_{1-6}$alkyl)amino$C_{1-6}$alkyl; furanyl; furanyl substituted with hydroxy$C_{1-6}$alkyl; benzofuranyl; imidazolyl; oxazolyl; oxazolyl substituted with aryl and $C_{1-6}$alkyl; $C_{1-6}$alkyltriazolyl; tetrazolyl; pyrrolidinyl; pyrrolyl; piperidinyl$C_{1-6}$alkyloxy; morpholinyl; $C_{1-6}$alkylmorpholinyl; morpholinyl$C_{1-6}$alkyloxy; morpholinyl$C_{1-6}$alkyl; morpholinyl$C_{1-6}$alkylamino; morpholinyl$C_{1-6}$alkylamino$C_{1-6}$alkyl; piperazinyl; $C_{1-6}$alkylpiperazinyl; $C_{1-6}$alkylpiperazinyl$C_{1-6}$alkyloxy; piperazinyl$C_{1-6}$alkyl; naphtalenylsulfonylpiperazinyl; naphtalenylsulfonylpiperidinyl; naphtalenylsulfonyl; $C_{1-6}$alkylpiperazinyl$C_{1-6}$alkyl; $C_{1-6}$alkylpiperazinyl$C_{1-6}$alkylamino; $C_{1-6}$alkylpiperazinyl$C_{1-6}$alkylamino$C_{1-6}$alkyl; $C_{1-6}$alkylpiperazinylsulfonyl; aminosulfonylpiperazinyl$C_{1-6}$alkyloxy; aminosulfonylpiperazinyl; aminosulfonylpiperazinyl$C_{1-6}$alkyl; di($C_{1-6}$alkyl)aminosulfonylpiperazinyl; di($C_{1-6}$alkyl)aminosulfonylpiperazinyl$C_{1-6}$alkyl; hydroxy$C_{1-6}$alkylpiperazinyl; hydroxy$C_{1-6}$alkylpiperazinyl$C_{1-6}$alkyl; $C_{1-6}$alkyloxypiperidinyl; $C_{1-6}$alkyloxypiperidinyl$C_{1-6}$alkyl; piperidinylamino$C_{1-6}$alkylamino; piperidinylamino$C_{1-6}$alkylamino$C_{1-6}$alkyl; ($C_{1-6}$alkylpiperidinyl)(hydroxy$C_{1-6}$alkyl)amino$C_{1-6}$alkylamino; ($C_{1-6}$ alkylpiperidinyl)(hydroxy$C_{1-6}$alkyl)amino$C_{1-6}$alkylamino$C_{1-6}$alkyl; hydroxy$C_{1-6}$alkyloxy$C_{1-6}$alkylpiperazinyl; hydroxy$C_{1-6}$alkyloxy$C_{1-6}$alkylpiperazinyl$C_{1-6}$alkyl; (hydroxy$C_{1-6}$alkyl)($C_{1-6}$alkyl)amino; (hydroxy$C_{1-6}$alkyl)($C_{1-6}$alkyl)amino$C_{1-6}$alkyl; hydroxy$C_{1-6}$alkylamino$C_{1-6}$alkyl; di(hydroxy$C_{1-6}$alkyl)amino$C_{1-6}$alkyl; pyrrolidinyl$C_{1-6}$alkyl; pyrrolidinyl$C_{1-6}$alkyloxy; pyrazolyl; thiopyrazolyl; pyrazolyl substituted with two substituents selected from $C_{1-6}$alkyl or trihalo$C_{1-6}$alkyl; pyridinyl; pyridinyl substituted with $C_{1-6}$alkyloxy, aryloxy or aryl; pyrimidinyl; tetrahydropyrimidinylpiperazinyl; tetrahydropyrimidinylpiperazinyl$C_{1-6}$alkyl; quinolinyl; indole; phenyl; phenyl substituted with one, two or three substituents independently selected from halo, amino, nitro, $C_{1-6}$alkyl, $C_{1-6}$alkyloxy, hydroxy$C_{1-4}$alkyl, trifluoromethyl, trifluoromethyloxy, hydroxy$C_{1-4}$alkyloxy, $C_{1-4}$alkylsulfonyl, $C_{1-4}$alkyloxy$C_{1-4}$alkyloxy, $C_{1-4}$alkyloxycarbonyl, amino$C_{1-4}$alkyloxy, di($C_{1-4}$alkyl)amino$C_{1-4}$alkyloxy, di($C_{1-4}$alkyl)amino, di($C_{1-4}$alkyl)aminocarbonyl, di($C_{1-4}$alkyl)amino$C_{1-4}$alkyl, di($C_{1-4}$alkyl)amino$C_{1-4}$alkylamino$C_{1-4}$alkyl, di($C_{1-4}$alkyl)amino($C_{1-4}$alkyl)amino, di($C_{1-4}$alkyl)amino($C_{1-4}$alkyl)amino$C_{1-4}$alkyl, di($C_{1-4}$alkyl)amino$C_{1-4}$alkyl($C_{1-4}$alkyl)amino, di($C_{1-4}$alkyl)amino$C_{1-4}$alkyl($C_{1-4}$alkyl)amino$C_{1-4}$alkyl, aminosulfonylamino($C_{1-4}$alkyl)amino, aminosulfonylamino($C_{1-4}$alkyl)amino$C_{1-4}$alkyl, di($C_{1-4}$ alkyl)aminosulfonylamino($C_{1-4}$alkyl)amino, di($C_{1-4}$alkyl)aminosulfonylamino($C_{1-4}$alkyl)amino$C_{1-6}$alkyl, cyano, piperidinyl$C_{1-4}$alkyloxy, pyrrolidinyl$C_{1-4}$alkyloxy, aminosulfonylpiperazinyl, aminosulfonylpiperazinyl$C_{1-4}$alkyl, di($C_{1-4}$alkyl)aminosulfonylpiperazinyl, di($C_{1-4}$alkyl)aminosulfonylpiperazinyl$C_{1-4}$alkyl, hydroxy$C_{1-4}$alkylpiperazinyl, hydroxy$C_{1-4}$alkylpiperazinyl$C_{1-4}$alkyl, $C_{1-4}$alkyloxypiperidinyl, $C_{1-4}$alkyloxypiperidinyl$C_{1-4}$alkyl, hydroxy$C_{1-4}$alkyloxy$C_{1-4}$alkylpiperazinyl, hydroxy$C_{1-4}$alkyloxy$C_{1-4}$alkylpiperazinyl$C_{1-4}$alkyl, (hydroxy$C_{1-4}$alkyl)($C_{1-4}$alkyl)amino, (hydroxy$C_{1-4}$alkyl)($C_{1-4}$alkyl)amino$C_{1-4}$alkyl, di(hydroxy$C_{1-4}$alkyl)amino, di(hydroxy$C_{1-4}$alkyl)amino$C_{1-4}$alkyl, furanyl, furanyl substituted with —CH—CH=CH—, pyrrolidinyl$C_{1-4}$alkyl, pyrrolidinyl$C_{1-4}$alkyloxy, morpholinyl, morpholinyl$C_{1-4}$ alkyloxy, morpholinyl$C_{1-4}$alkyl, morpholinyl$C_{1-4}$alkylamino, morpholinyl$C_{1-4}$alkylamino$C_{1-4}$alkyl, piperazinyl, $C_{1-4}$alkylpiperazinyl, $C_{1-4}$alkylpiperazinyl$C_{1-4}$alkyloxy, piperazinyl$C_{1-4}$alkyl, $C_{1-4}$alkylpiperazinyl$C_{1-4}$alkyl, $C_{1-4}$alkylpiperazinyl$C_{1-4}$alkylamino, $C_{1-4}$alkylpiperazinyl$C_{1-4}$alkylamino$C_{1-4}$alkyl, tetrahydropyrimidinylpiperazinyl, tetrahydropyrimidinylpiperazinyl$C_{1-4}$alkyl, piperidinylamino$C_{1-4}$alkylamino, piperidinylamino$C_{1-4}$alkylamino$C_{1-4}$alkyl, ($C_{1-4}$alkylpiperidinyl)(hydroxy$C_{1-4}$alkyl)amino$C_{1-4}$alkylamino, ($C_{1-4}$alkylpiperidinyl)(hydroxy$C_{1-4}$alkyl)amino$C_{1-4}$ alkylamino$C_{1-4}$alkyl, pyridinyl$C_{1-4}$alkyloxy, hydroxy$C_{1-4}$alkylamino, hydroxy$C_{1-4}$alkylamino$C_{1-4}$alkyl, di($C_{1-4}$alkyl)amino$C_{1-4}$alkylamino, aminothiadiazolyl, aminosulfonylpiperazinyl$C_{1-4}$alkyloxy, or thiophenyl$C_{1-4}$alkylamino;

each $R^6$ and $R^7$ can be placed on the nitrogen in replacement of the hydrogen;

aryl in the above is phenyl, or phenyl substituted with one or more substituents each independently selected from halo, $C_{1-6}$alkyl, $C_{1-6}$alkyloxy, trifluoromethyl, cyano or hydroxycarbonyl.

Other embodiments of the compound according to embodiment [0146] (hereinafter collectively referred to as embodiment [0147]) are those in which one or more of the following apply (wherein each of $R^2$, $R^3$, $R^4$ and $R^5$ in this embodiment corresponds to $R^{12}$, $R^{13}$, $R^{14}$, and $R^{15}$, respectively, in embodiment [0146]):

n is 0, 1 or 2;

t is 0, 1, 2 or 3

Q is

$R^2$ is hydrogen, $C_{1-6}$alkyl or naphtalenylsulfonylpyrazinyl;

each $R^3$ independently represents a hydrogen atom;

$R^4$ is hydrogen, hydroxy, hydroxy$C_{1-6}$alkyl or $C_{1-6}$alkyloxy;

$R^5$ is hydrogen, $C_{1-6}$alkyl, hydroxy$C_{1-6}$alkyl or $C_{1-6}$alkyloxy$C_{1-6}$alkyl;

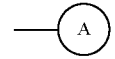

is a radical selected from (a-1), (a-7) or (a-20);

each s is independently 0 or 1;

each $R^6$ is independently selected from hydrogen; thiophenyl; furanyl; benzofuranyl; phenyl; or phenyl substituted with one substituents independently selected from $C_{1-6}$alkyl, $C_{1-6}$alkyloxy, hydroxy$C_{1-4}$alkyl, $C_{1-4}$alkylsulfonyl or di($C_{1-4}$alkyl)amino; each $R^7$ is independently selected from hydrogen.

Other embodiments of the compound according to embodiment [0146] (hereinafter collectively referred to as embodiment [0148]) are those in which one or more of the following apply (wherein each of $R^2$, $R^3$, $R^4$ and $R^5$ in this embodiment corresponds to $R^{12}$, $R^{13}$, $R^{14}$, and $R^{15}$, respectively, in embodiment [0146]):

n is 1 or 2;
t is 0, 1, 2 or 3:
Q is

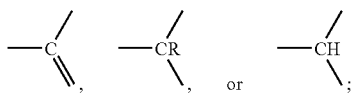

$R^2$ is hydrogen or $C_{1-6}$alkyl;
each $R^3$ independently represents a hydrogen atom;
$R^4$ is hydrogen;
$R^5$ is hydrogen or $C_{1-6}$alkyloxy$C_{1-6}$alkyl;

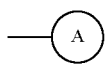

is a radical selected from (a-1) or (a-20);
each s is independently 0 or 1;
each $R^6$ is independently selected from hydrogen; thiophenyl; furanyl; benzofuranyl; phenyl; or phenyl substituted with one substituents independently selected from $C_{1-6}$alkyl, $C_{1-6}$alkyloxy, hydroxy$C_{1-4}$alkyl or di($C_{1-4}$ alkyl)amino.

Other embodiments of the compound according to embodiment [0146] (hereinafter collectively referred to as embodiment [0149]) are those in which $R^{12}$ is H.

Other embodiments of the compound according to embodiment [0146] (hereinafter collectively referred to as embodiment [0150]) are those in which one or more of the following apply (wherein each of $R^2$, $R^3$, $R^4$ and $R^5$ in this embodiment corresponds to $R^{12}$, $R^{13}$, $R^{14}$, and $R^{15}$, respectively, in embodiment [0146]):

t is 0;
$R^2$ is hydrogen, halo, hydroxy, amino, nitro, $C_{1-4}$alkyl, $C_{1-6}$alkyloxy, trifluoromethyl or di($C_{1-6}$alkyl)amino;
$R^4$ is hydrogen, hydroxy, amino, hydroxy$C_{1-6}$alkyl, $C_{1-6}$alkyl, $C_{1-6}$alkyloxy, aryl$C_{1-6}$alkyl, aminocarbonyl, amino$C_{1-6}$alkyl, $C_{1-6}$alkylamino$C_{1-6}$alkyl or di($C_{1-6}$alkyl)amino$C_{1-6}$alkyl;
$R^5$ is hydrogen

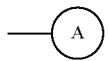

is a radical selected from (a-1), (a-3), (a-4), (a-5), (a-6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-28), (a-29), (a-30), (a-31), (a-32), (a-33), (a-34), (a-35), (a-36), (a-37), (a-38), (a-39), (a-40), (a-41), (a-42), (a-44), (a-45), (a-46), (a-47), (a-48) or (a-51);
each s is independently 0, 1, 2, 3 or 4;
$R^6$ is hydrogen; halo; hydroxy; amino; nitro; trihalo$C_{1-6}$alkyl; trihalo$C_{1-6}$alkyloxy; $C_{1-6}$alkyl; $C_{1-6}$alkyloxy; $C_{1-6}$alkylcarbonyl; $C_{1-6}$alkyloxycarbonyl; $C_{1-6}$alkylsulfonyl; hydroxy$C_{1-6}$alkyl; aryloxy; di($C_{1-4}$alkyl)amino; cyano; thiophenyl; furanyl; furanyl substituted with hydroxy$C_{1-6}$alkyl; benzofuranyl; imidazolyl; oxazolyl; oxazolyl substituted with aryl and $C_{1-6}$alkyl; $C_{1-6}$alkyltriazolyl; tetrazolyl; pyrrolidinyl; pyrrolyl; morpholinyl; $C_{1-6}$alkylmorpholinyl; piperazinyl; $C_{1-6}$alkylpiperazinyl; hydroxy$C_{1-6}$alkylpiperazinyl; $C_{1-6}$alkyloxypiperidinyl; pyrazoyl; pyrazolyl substituted with one or two substituents selected from $C_{1-6}$alkyl or trihalo$C_{1-6}$alkyl; pyridinyl; pyridinyl substituted with $C_{1-6}$alkyloxy, aryloxy or aryl; pyrimidinyl; quinolinyl; indole; phenyl; or phenyl substituted with one or two substituents independently selected from halo, $C_{1-6}$alkyl, $C_{1-6}$alkyloxy or trifluoromethyl;
$R^7$ is hydrogen; halo; hydroxy; amino; nitro; trihalo$C_{1-6}$alkyl; trihalo$C_{1-6}$alkyloxy; $C_{1-6}$alkyl; $C_{1-6}$alkyloxy; $C_{1-6}$alkylcarbonyl; $C_{1-6}$alkyloxycarbonyl; $C_{1-6}$alkylsulfonyl; hydroxy$C_{1-6}$alkyl; aryloxy; di($C_{1-6}$alkyl)amino; cyano; pyridinyl; phenyl; or phenyl substituted with one or two substituents independently selected from halo, $C_{1-6}$alkyl, $C_{1-6}$alkyloxy or trifluoromethyl.

Other embodiments of the compound according to embodiment [0146] (hereinafter collectively referred to as embodiment [0151]) are those in which one or more of the following apply (wherein each of $R^2$, $R^3$, $R^4$ and $R^5$ in this embodiment corresponds to $R^{12}$, $R^{13}$, $R^{14}$, and $R^{15}$, respectively, in embodiment [0146]):

$R^5$ is hydrogen, $C_{1-6}$alkyl, $C_{3-10}$cycloalkyl, hydroxy$C_{1-6}$alkyl, $C_{1-6}$alkyloxy$C_{1-6}$alkyl or di($C_1$-(alkyl)amino$C_{1-6}$alkyl;

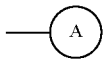

is a radical selected from (a-1), (a-2), (a-3), (a-4), (a-5), (a-6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-27), (a-28), (a-29), (a-30), (a-31), (a-32), (a-33), (a-34), (a-35), (a-36), (a-37), (a-38), (a-39), (a-40), (a-41), (a-42) (a-43) or (a-44);
1) each $R^6$ and $R^7$ are independently selected from hydrogen; halo; hydroxy; amino; nitro; trihalo$C_{1-6}$alkyl; trihalo$C_{1-6}$alkyloxy; $C_{1-6}$alkyl; $C_{1-6}$alkyloxy, $C_{1-6}$alkyloxy$C_{1-6}$alkyloxy; $C_{1-6}$alkylcarbonyl; $C_{1-6}$alkylsulfonyl; cyano$C_{1-6}$alkyl; hydroxy$C_{1-6}$alkyl; hydroxy$C_{1-6}$alkyloxy; hydroxy$C_{1-6}$alkylamino; amino$C_{1-6}$alkyloxy; di($C_{1-6}$alkyl)aminocarbonyl; di(hydroxy$C_{1-6}$alkyl)amino; aryl$C_{1-6}$alkylamino; di($C_{1-6}$alkyl)amino$C_{1-6}$alkyloxy; di($C_{1-6}$alkyl)amino$C_{1-6}$alkylamino; arylsulfonyl; arylsulfonylamino; aryloxy, arylC$_{2-6}$alkenediyl; di(C$_{1-6}$alkyl)amino; di(C$_{1-6}$alkyl)aminoC$_{1-6}$alkyl; di(C$_{1-6}$alkyl)aminoC$_{1-6}$alkyl(C$_{1-6}$alkyl)aminoC$_{1-6}$alkyl; cyano; thiophenyl; thiophenyl substituted with di(C$_{1-6}$alkyl)aminoC$_{1-6}$alkyl(C$_{1-6}$alkyl)aminoC$_{1-6}$alkyl, di(C$_{1-6}$alkyl)aminoC$_{1-6}$alkyl, C$_{1-6}$alkylpiperazinylC$_{1-6}$alkyl or di(hydroxyC$_{1-6}$alkyl)aminoC$_{1-6}$alkyl; furanyl; imidazolyl; C$_{1-6}$alkyltriazolyl; tetrazolyl; pyrrolidinyl; piperidinylC$_{1-6}$alkyloxy; morpholinyl; C$_{1-6}$alkylmorpholinyl; morpholinylC$_{1-6}$alkyloxy; morpholinylC$_{1-6}$alkyl; C$_{1-6}$alkylpiperazinyl; C$_{1-6}$alkylpiperazinylC$_{1-6}$alkyloxy; C$_{1-6}$alkylpiperazinylC$_{1-6}$alkyl; C$_{1-6}$alkylpiperazinylsulfonyl; aminosulfonylpiperazinylC$_{1-6}$alkyloxy; aminosulfonylpiperazinyl; aminosulfonylpiperazinylC$_{1-6}$alkyl; di(C$_{1-6}$alkyl)aminosulfonylpiperazinyl; di(C$_{1-6}$alkyl)aminosulfonylpiperazinylC$_{1-6}$alkyl; hydroxyC$_{1-6}$alkylpiperazinyl; hydroxyC$_{1-6}$alkylpiperazinylC$_{1-6}$alkyl; C$_{1-6}$alkyloxypiperidinyl; C$_{1-6}$alkyloxypiperidinylC$_{1-6}$alkyl; hydroxyC$_{1-6}$alkyloxyC$_{1-6}$alkylpiperazinyl; hydroxyC$_{1-6}$alkyloxyC$_{1-6}$alkylpiperazinylC$_{1-6}$alkyl; (hydroxyC$_{1-6}$alkyl)(C$_{1-6}$alkyl)amino, (hydroxyC$_{1-6}$alkyl)(C$_{1-6}$alkyl)aminoC$_{1-6}$alkyl; pyrrolidinylC$_{1-6}$alkyloxy; pyrazolyl; thiopyrazolyl; pyrazolyl substituted with two substituents selected from C$_{1-6}$alkyl or trihaloC$_{1-6}$alkyl; pyridinyl; pyridinyl substituted with C$_{1-6}$alkyloxy or aryl; pyrimidinyl; quinolinyl; indole; phenyl; phenyl substituted with one, two or three substituents independently selected from halo, amino, C$_{1-6}$alkyl, C$_{1-6}$alkyloxy, hydroxyC$_{1-4}$alkyl, trifluoromethyl, trifluoromethyloxy, hydroxyC$_{1-4}$alkyloxy, C$_{1-4}$alkyloxyC$_{1-4}$alkyloxy, aminoC$_{1-4}$alkyloxy, di(C$_{1-4}$alkyl)aminoC$_{1-4}$alkyloxy, di(C$_{1-4}$alkyl)amino, di(C$_{1-4}$alkyl)aminoC$_{1-4}$alkyl, di(C$_{1-4}$alkyl)aminoC$_{1-4}$alkyl(C$_{1-4}$ alkyl)aminoC$_{1-4}$alkyl, piperidinylC$_{1-4}$alkyloxy, pyrrolidinylC$_{1-4}$alkyloxy, aminosulfonylpiperazinyl, aminosulfonylpiperazinylC$_{1-4}$alkyl, di(C$_{1-4}$alkyl)aminosulfonylpiperazinyl, di(C$_{1-4}$alkyl)aminosulfonylpiperazinylC$_{1-4}$alkyl, hydroxyC$_4$alkylpiperazinyl, hydroxyC$_{1-4}$alkylpiperazinylC$_{1-4}$alkyl, C$_{1-4}$alkyloxypiperidinyl, C$_{1-4}$alkyloxypiperidinylC$_{1-4}$alkyl, hydroxyC$_{1-4}$alkyloxy, C$_{1-4}$alkylpiperazinyl hydroxyC$_{1-4}$ alkyloxyC$_{1-4}$alkylpiperazinylC$_{1-4}$alkyl, hydroxyC$_{1-4}$alkyl)(C$_{1-4}$alkyl)amino, (hydroxyC$_{1-4}$alkyl)(C$_{1-4}$alkyl)aminoC$_{1-4}$alkyl, pyrrolidinylC$_{1-4}$alkyloxy, morpholinylC$_{1-4}$alkyloxy, morpholinylC$_{1-4}$alkyl, C$_{1-4}$alkylpiperazinyl, C$_{1-4}$alkylpiperazinylC$_{1-4}$alkyloxy, C$_{1-4}$alkylpiperazinylC$_{1-4}$alkyl, hydroxyC$_{1-4}$alkylamino, di(hydroxyC$_{1-4}$alkyl)amino, di(C$_{1-4}$alkyl)aminoC$_{1-4}$alkylamino, aminothiadiazolyl, aminosulfonylpiperazinylC$_{1-4}$alkyloxy, or thiophenylC$_{1-4}$alkylamino.

Other embodiments of the compound according to embodiment [0146] (hereinafter collectively referred to as embodiment [0152]) include those in which the following are true (wherein each of R$^2$, R$^3$, R$^4$ and R$^5$ in this embodiment corresponds to R$^{12}$, R$^{13}$, R$^{14}$, and R$^{15}$, respectively, in embodiment [0146]):

R$^5$ is hydrogen, C$_{1-6}$alkyl, C$_{3-10}$cycloalkyl, hydroxyC$_{1-6}$alkyl, C$_{1-6}$alkyloxyC$_{1-6}$alkyl or di(C$_{1-6}$alkyl)aminoC$_{1-6}$alkyl;

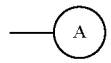

is a radical selected from (a-1), (a-2), (a-3), (a-4), (a-5), (a-6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-27), (a-28), (a-29), (a-30), (a-31), (a-32), (a-33), (a-34), (a-35), (a-36), (a-37), (a-38), (a-39), (a-40), (a-41), (a-42) (a-43) or (a-44);

each R$^6$ and R$^7$ are independently selected from hydrogen; halo; hydroxy, amino; nitro; trihaloC$_{1-6}$alkyl; trihaloC$_{1-6}$ alkyloxy, C$_{1-6}$alkyl; C$_{1-6}$alkyloxy; C$_{1-6}$alkyloxyC$_{1-6}$alkyloxy; C$_{1-6}$alkylcarbonyl; C$_{1-6}$alkylsulfonyl; cyanoC$_{1-6}$alkyl; hydroxyC$_{1-6}$alkyl; hydroxyC$_{1-6}$alkyloxy; hydroxyC$_{1-6}$alkylamino; aminoC$_{1-6}$alkyloxy; di(C$_{1-6}$alkyl)aminocarbonyl; di(hydroxyC$_{1-6}$alkyl)amino; arylC$_{1-6}$alkyl)amino; di(C$_{1-6}$alkyl)aminoC$_{1-6}$alkyloxy; di(C$_{1-6}$alkyl)aminoC$_{1-6}$alkylamino; arylsulfonyl; arylsulfonylamino; aryloxy; arylC$_{2-6}$alkenediyl; di(C$_{1-6}$alkyl)amino; di(C$_{1-6}$alkyl)aminoC$_{1-6}$alkyl; di(C$_{1-6}$alkyl)aminoC$_{1-6}$alkyl(C$_{1-6}$alkyl)aminoC$_{1-6}$alkyl; cyano; thiophenyl; thiophenyl substituted with di(C$_{1-6}$alkyl)aminoC$_{1-6}$alkyl(C$_{1-6}$alkyl)aminoC$_{1-6}$alkyl, di(C$_{1-6}$alkyl)aminoC$_{1-6}$alkyl, C$_{1-6}$alkylpiperazinylC$_{1-6}$alkyl or di(hydroxyC$_{1-6}$alkyl)aminoC$_{1-6}$alkyl; furanyl; imidazolyl; C$_{1-6}$alkyltriazolyl; tetrazolyl; pyrrolidinyl; piperidinylC$_{1-6}$alkyloxy; morpholinyl; C$_{1-6}$alkylmorpholinyl; morpholinylC$_{1-6}$alkyloxy; morpholinylC$_{1-6}$alkyl; C$_{1-6}$alkylpiperazinyl; C$_{1-6}$alkylpiperazinylC$_{1-6}$alkyloxy; C$_{1-6}$alkylpiperazinylC$_{1-6}$alkyl; C$_{1-6}$alkylpiperazinylsulfonyl; aminosulfonylpiperazinylC$_{1-6}$alkyloxy, aminosulfonylpiperazinyl; aminosulfonylpiperazinylC$_{1-6}$alkyl; di(C$_{1-6}$alkyl)aminosulfonylpiperazinyl; di(C$_{1-6}$alkyl)aminosulfonylpiperazinylC$_{1-6}$alkyl; hydroxyC$_{1-6}$alkylpiperazinyl; hydroxyC$_{1-6}$alkylpiperazinylC$_{1-6}$alkyl; C$_{1-6}$alkyloxypiperidinyl; C$_{1-6}$alkyloxypiperidinylC$_{1-6}$alkyl; hydroxyC$_{1-6}$alkyloxyC$_{1-6}$alkylpiperazinyl; hydroxyC$_{1-6}$alkyloxyC$_{1-6}$alkylpiperazinylC$_{1-6}$alkyl; (hydroxyC$_{1-6}$alkyl)(C$_{1-6}$alkyl)amino; (hydroxyC$_{1-6}$alkyl)(C$_{1-6}$alkyl)aminoC$_{1-6}$alkyl; pyrrolidinylC$_{1-6}$alkyloxy; pyrazolyl; thiopyrazolyl; pyrazolyl substituted with two substituents selected from C$_{1-6}$alkyl or trihaloC$_{1-6}$alkyl; pyridinyl; pyridinyl substituted with C$_{1-6}$alkyloxy or aryl; pyrindinyl; quinolinyl; indole; phenyl; phenyl substituted with one, two or three substituents independently selected from halo, amino, C$_{1-6}$alkyl, C$_{1-6}$alkyloxy, hydroxyC$_{1-4}$alkyl; trifluoromethyl, trifluoromethyloxy, hydroxyC$_{1-4}$alkyloxy, C$_{1-4}$alkyloxyC$_{1-4}$alkyloxy, aminoC$_{1-4}$alkyloxy, di(C$_{1-4}$alkyl)aminoC$_{1-4}$alkyloxy, di(C$_{1-4}$alkyl)amino, di(C$_{1-4}$alkyl)aminoC$_{1-4}$alkyl, di(C$_{1-4}$alkyl)aminoC$_{1-4}$alkyl(C$_{1-4}$ alkyl)aminoC$_{1-4}$alkyl, piperidinylC$_{1-4}$alkyloxy, pyrrolidinylC$_{1-4}$alkyloxy; aminosulfonylpiperazinyl, aminosulfonylpiperazinylC$_{1-4}$alkyl, di(C$_{1-4}$alkyl)aminosulfonylpiperazinyl, di(C$_{1-4}$alkyl)aminosulfonylpiperazinylC$_{1-4}$alkyl, hydroxyC$_{1-4}$alkylpiperazinyl, hydroxyC$_{1-4}$alkylpiperazinylC$_{1-4}$alkyl, C$_{1-4}$alkyloxypiperidinyl, C$_{1-4}$alkyloxypiperidinylC$_{1-4}$alkyl, hydroxyC$_{1-4}$alkyloxyC$_{1-4}$alkylpiperazinyl, hydroxyC$_{1-4}$ alkyloxyC$_{1-4}$alkylpiperazinylC$_{1-4}$alkyl, (hydroxyC$_{1-4}$alkyl)(C$_{1-4}$alkyl)amino, (hydroxyC$_{1-4}$alkyl)(C$_{1-4}$alkyl)aminoC$_{1-4}$alkyl, pyrrolidinylC$_{1-4}$alkyloxy, morpholinylC$_{1-4}$alkyloxy, morpholinylC$_{1-4}$alkyl, C$_{1-4}$alkylpiperazinyl, C$_{1-4}$alkylpiperazinylC$_{1-4}$alkyloxy, C$_{1-4}$alkylpiperazinylC$_{1-4}$alkyl, hydroxyC$_{1-4}$alkylamino, di(hydroxyC$_{1-4}$alkyl)amino, di(C$_{1-4}$alkyl)aminoC$_{1-4}$alkylamino, aminothiadiazolyl, aminosulfonylpiperazinylC$_{1-4}$alkyloxy, or thiophenylC$_{1-4}$alkylamino.

Other embodiments of the compound according to embodiment [0146] (hereinafter collectively referred to as embodiment [0153]) include those in which the following are true (wherein each of $R^2$, $R^3$, $R^4$ and $R^5$ in this embodiment corresponds to $R^{12}$, $R^{13}$, $R^{14}$, and $R^{15}$, respectively, in embodiment [0146]):

t is 0;

$R^2$ is hydrogen, halo, hydroxy, amino, nitro, $C_{1-6}$alkyl, $C_{1-6}$alkyloxy, trifluoromethyl or di($C_{1-6}$alkyl)amino;

$R^4$ is hydrogen, hydroxy, amino, hydroxy$C_{1-6}$alkyl, $C_{1-6}$alkyl, $C_{1-6}$alkyloxy, aryl$C_{1-6}$alkyl, aminocarbonyl, amino$C_{1-6}$alkyl, $C_{1-6}$alkylamino$C_{1-6}$alkyl or di($C_{1-6}$alkyl)amino$C_{1-6}$alkyl;

$R^5$ is hydrogen;

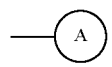

is a radical selected from (a-1), (a-3), (a-4), (a-5), (a-6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-28), (a-29), (a-30), (a-31), (a-32), (a-33), (a-34), (a-35), (a-36), (a-37), (a-38), (a-39), (a-40), (a-41), (a-42), (a-44), (a-45), (a-46), (a-47), (a-48) or (a-51);

each s is independently 0, 1, 2, 3 or 4;

$R^6$ is hydrogen; halo; hydroxy; amino; nitro; trihalo$C_{1-6}$alkyl; trihalo$C_{1-6}$alkyloxy; $C_{1-6}$alkyl; $C_{1-6}$alkyloxy; $C_{1-6}$alkylcarbonyl; $C_{1-6}$alkyloxycarbonyl; $C_{1-6}$alkylsulfonyl; hydroxy$C_{1-6}$alkyl; aryloxy; di($C_{1-6}$alkyl)amino; cyano; thiophenyl; furanyl; furanyl substituted with hydroxy$C_{1-6}$alkyl; benzofuranyl; imidazolyl; oxazolyl; oxazolyl substituted with aryl and $C_{1-6}$alkyl; $C_{1-6}$alkyltriazolyl; tetrazolyl; pyrrolidinyl; pyrrolyl; morpholinyl; $C_{1-6}$alkylmorpholinyl; piperazinyl; $C_{1-6}$alkylpiperazinyl; hydroxy$C_{1-6}$alkylpiperazinyl; $C_{1-6}$alkyloxypiperidinyl; pyrazoyl; pyrazolyl substituted with one or two substituents selected from $C_{1-6}$alkyl or trihalo$C_{1-6}$alkyl; pyridinyl; pyridinyl substituted with $C_{1-6}$alkyloxy, aryloxy or aryl; primidinyl; quinolinyl; indole; phenyl; or phenyl substituted with one or two substituents independently selected from halo, $C_{1-6}$alkyl, $C_{1-6}$alkyloxy or trifluoromethyl; and $R^7$ is hydrogen; halo; hydroxy; amino; nitro; trihalo$C_{1-6}$alkyl; trihalo$C_{1-6}$alkyloxy; $C_{1-6}$alkyl; $C_{1-6}$alkyloxy; $C_{1-6}$alkylcarbonyl; $C_{1-6}$alkyloxycarbonyl; $C_{1-6}$alkylsulfonyl; hydroxy$C_{1-6}$alkyl; aryloxy; di($C_{1-6}$alkyl)amino; cyano; pyridinyl; phenyl; or phenyl substituted with one or two substituents independently selected from halo, $C_{1-6}$alkyl, $C_{1-6}$alkyloxy or trifluoromethyl.

Other embodiments of the compound according to embodiment [0146] (hereinafter collectively referred to as embodiment [0154]) include those in which the following are true (wherein each of $R^2$, $R^3$, $R^4$ and $R^5$ in this embodiment corresponds to $R^{12}$, $R^{13}$, $R^{14}$, and $R^{15}$, respectively, in embodiment [0146]):

n is 0, 1 or 2; t is 0, 1, 2 or 3; Q is

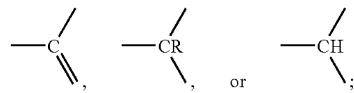

$R^2$ is hydrogen, $C_{1-6}$alkyl or naphtalenylsulfonylpyrazinyl; each $R^3$ independently represents a hydrogen atom; $R^4$ is hydrogen, hydroxy, hydroxy$C_{1-6}$alkyl or $C_{1-6}$alkyloxy, $R^5$ is hydrogen, $C_{1-6}$alkyl, hydroxy$C_{1-6}$alkyl or $C_{1-6}$alkyloxy$C_{1-6}$alkyl;

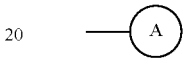

is a radical selected from (a-1), (a-7) or (a-20); each s is independently 0 or 1; each $R^6$ is independently selected from hydrogen; thiophenyl; furanyl; benzofuranyl; phenyl; or phenyl substituted with one substituents independently selected from $C_{1-6}$alkyl, $C_{1-6}$alkyloxy, hydroxy$C_{1-4}$alkyl, $C_{1-4}$alkylsulfonyl or di($C_{1-4}$alkyl)amino and each $R^7$ is independently selected from hydrogen.

Other embodiments of the compound according to embodiment [0146] (hereinafter collectively referred to as embodiment [0155]) include those in which the following are true (wherein each of $R^2$, $R^3$, $R^4$ and $R^5$ in this embodiment corresponds to $R^{12}$, $R^{13}$, $R^{14}$, and $R^{15}$, respectively, in embodiment [0146]):

n is 1 or 2; t is 0, 1, 2 or 3; Q is

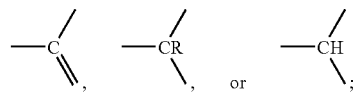

$R^2$ is hydrogen or $C_{1-6}$alkyl; each $R^3$ independently represents a hydrogen atom; $R^4$ is hydrogen; $R^5$ is hydrogen or $C_{1-6}$alkyloxy$C_{1-6}$alkyl;

is a radical selected from (a-1) or (a-20); each s is independently 0 or 1; and each $R^6$ is independently selected from hydrogen; thiophenyl; furanyl; benzofuranyl; phenyl; or phenyl substituted with one substituents independently selected from $C_{1-6}$alkyl, $C_{1-6}$alkyloxy, hydroxy$C_{1-4}$alkyl or di($C_{1-4}$alkyl)amino.

Particular embodiments of the compound according to embodiment [0136] (hereinafter collectively referred to as embodiment [0156]) include the following 113 114
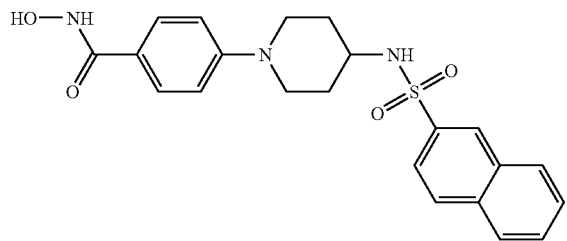
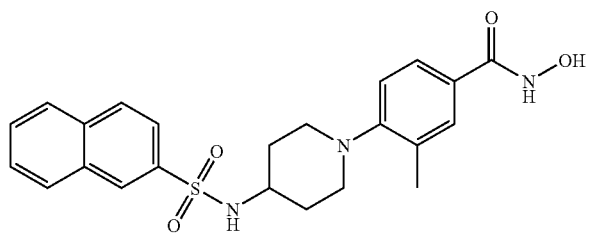
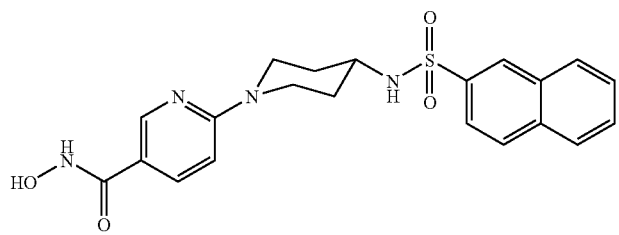
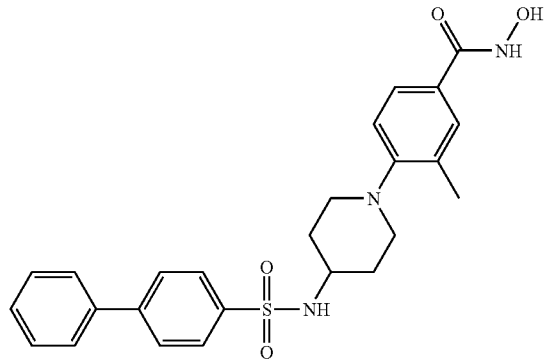
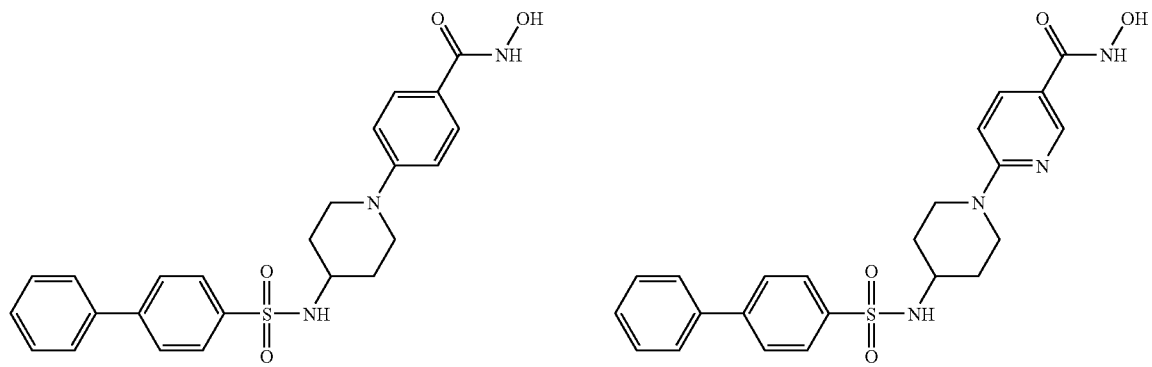

115 116
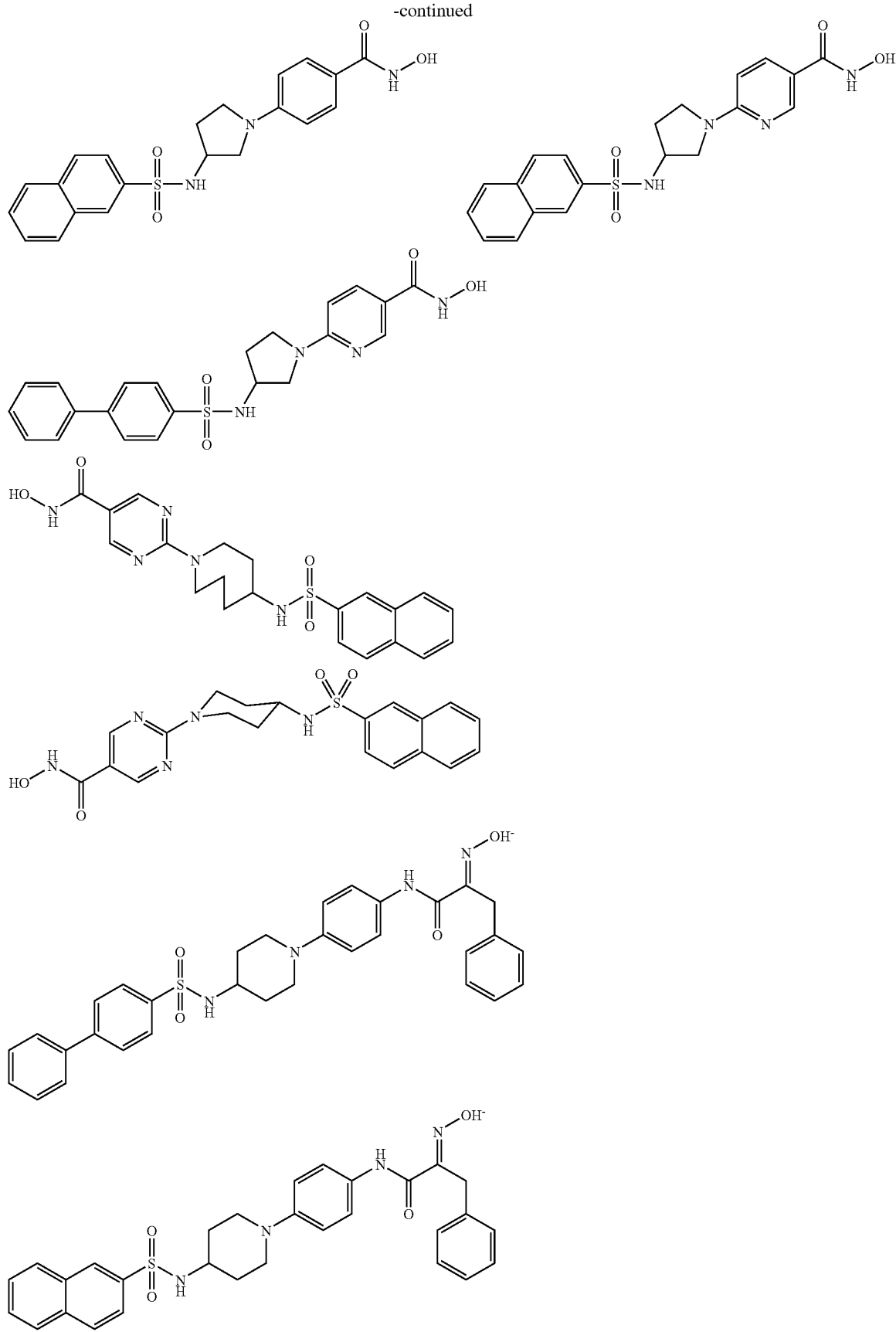
-continued

-continued
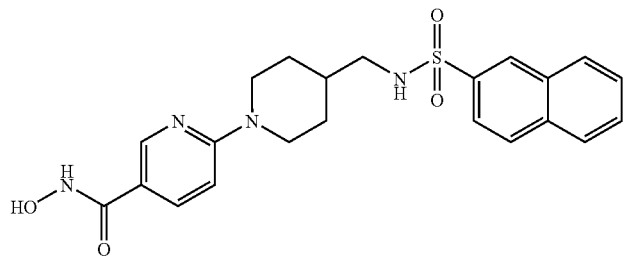
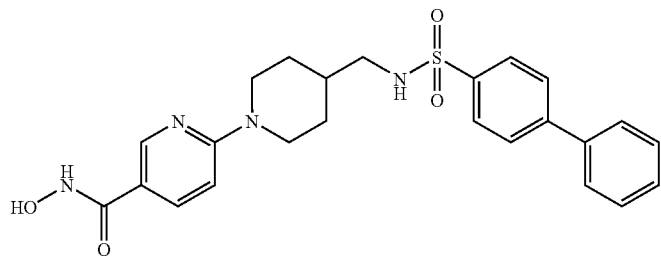
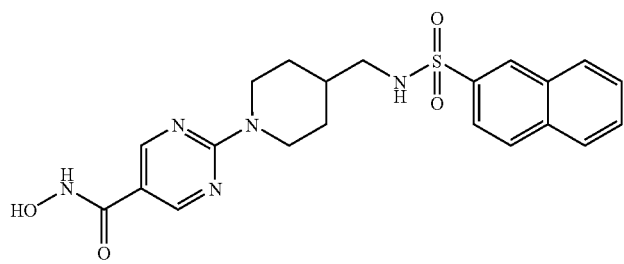
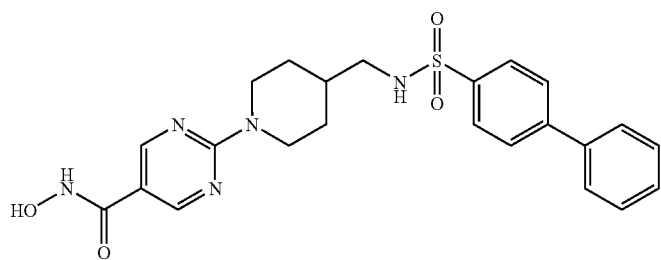
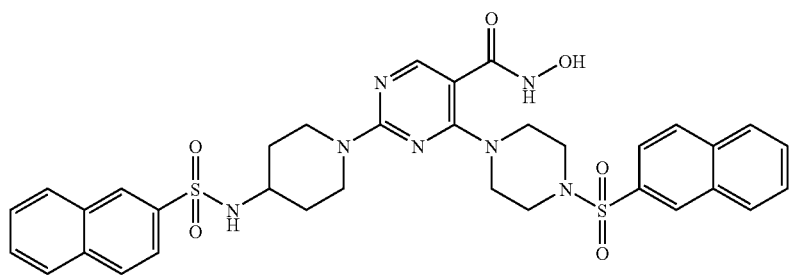
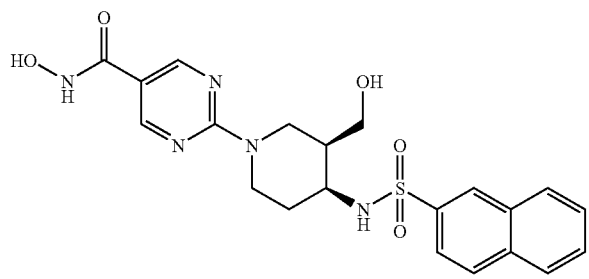

-continued
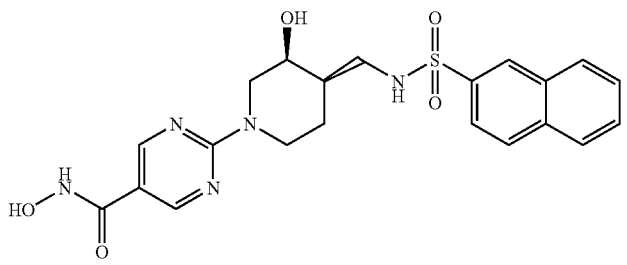
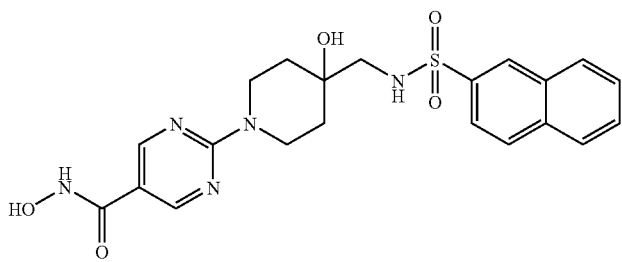
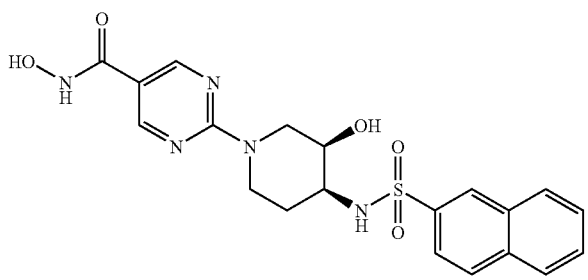
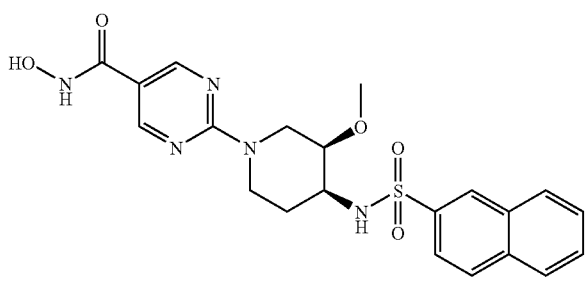
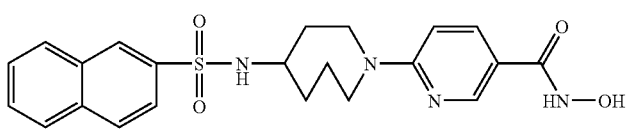
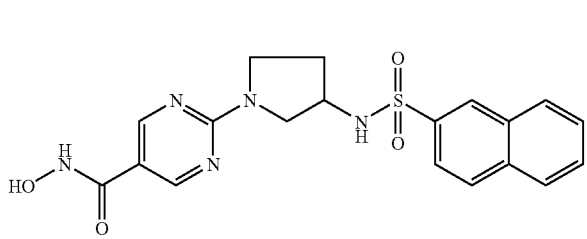
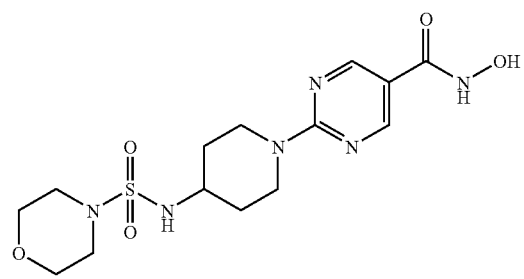

-continued
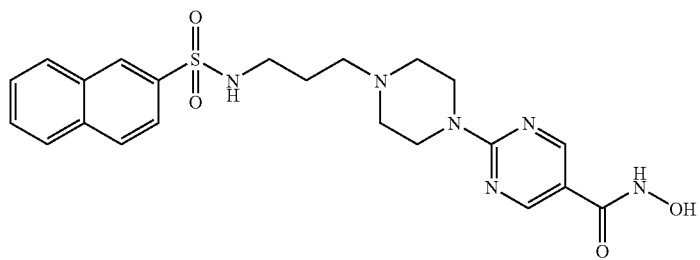
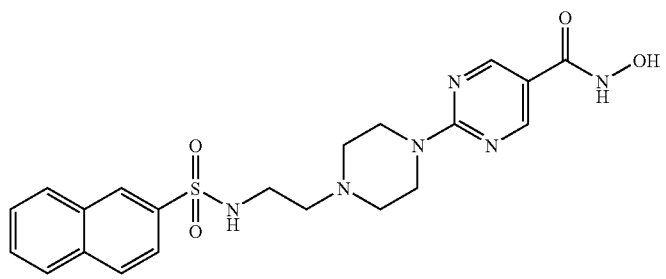
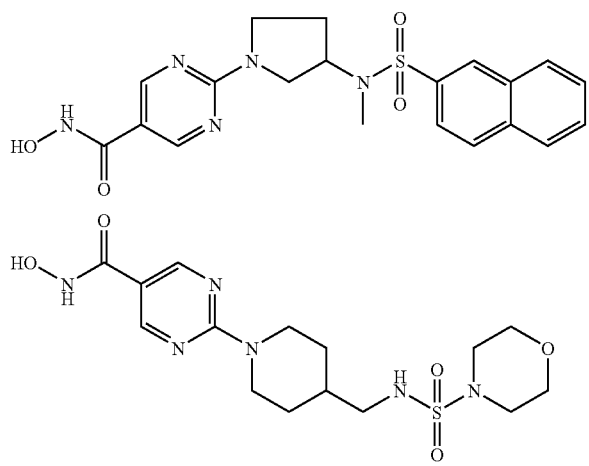
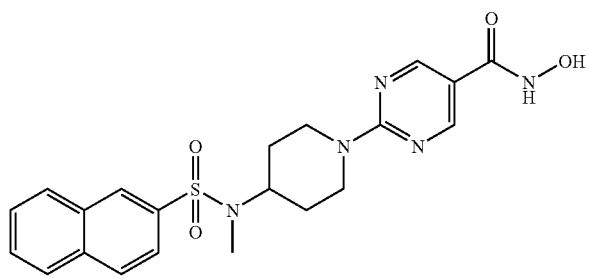
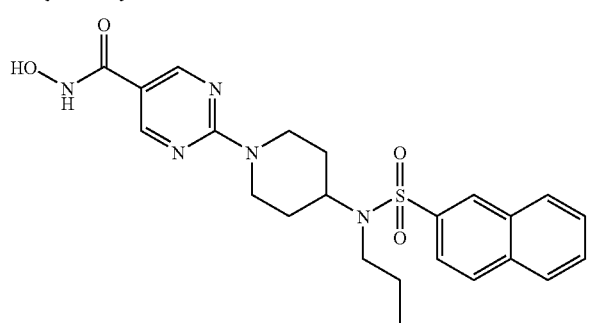

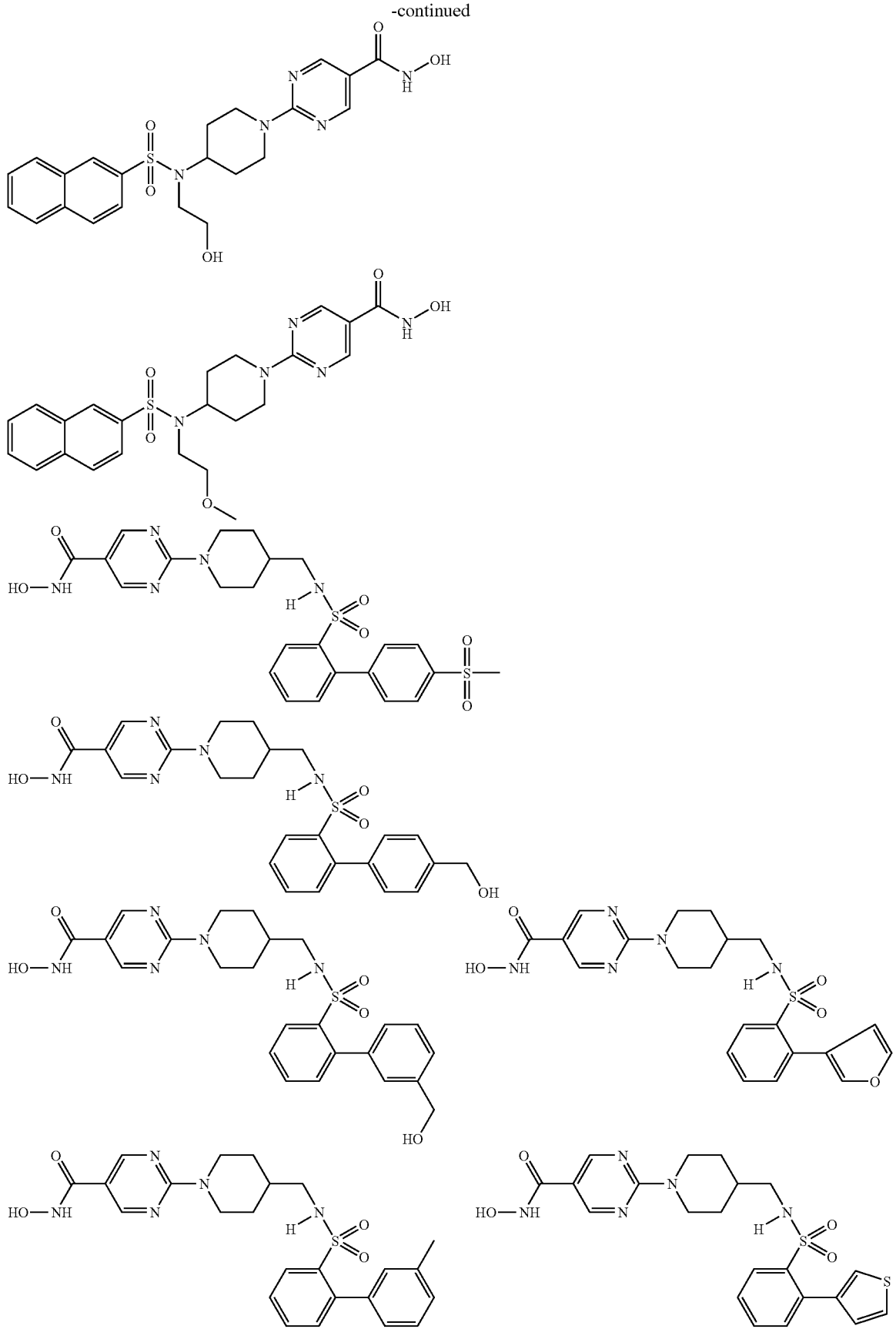

-continued

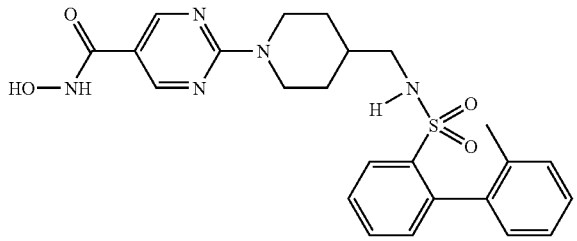

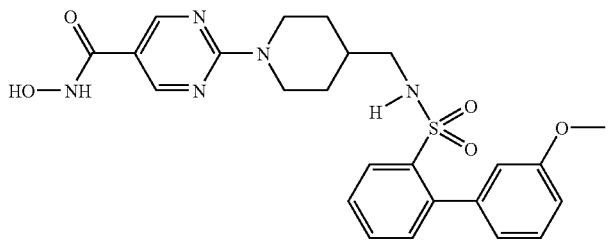

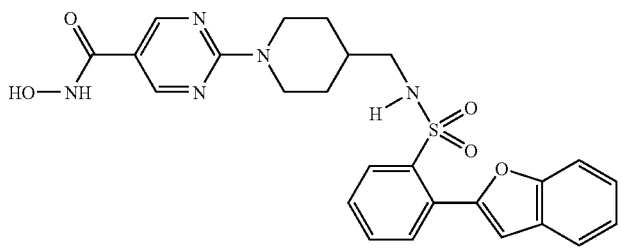

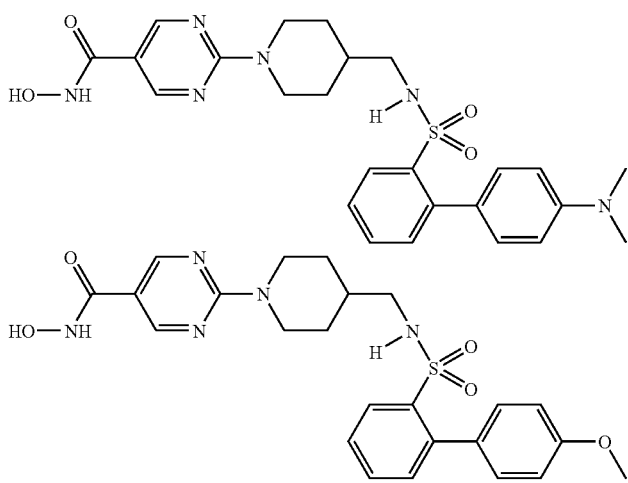

in which the terminal hydroxamic acid moiety (—C(O)NH—OH) is replaced with

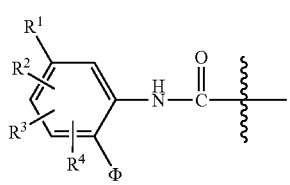

wherein Φ, R¹, R², R³, and R⁴ are as defined in accordance with embodiment [0046], and preferably embodiments [0048] and [0049].

In the compounds of embodiments [0146]-[0156], $R^1$, $R^2$, $R^3$, and $R^4$ are preferably as defined in embodiments [0048] and [0049]. In other embodiments of the compounds of embodiments [0146]-[0156], $R^1$, $R^2$, $R^3$, and $R^4$ are all H. Such embodiments are hereinafter collectively referred to as embodiment [0157].

In another embodiment, the invention comprises compounds of the following structural formula (9) (hereinafter embodiment [0158]):

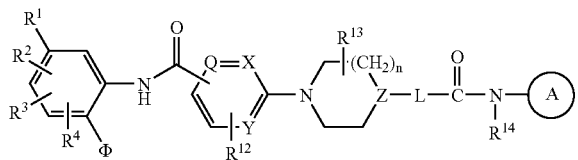
(9)

or a pharmaceutically acceptable salt thereof, wherein
Φ is —NH$_2$ or —OH;
R$^1$ is H or as defined in embodiment [0046];
R$^2$, R$^3$, and R$^4$ are as defined in embodiment [0046];
n is 0, 1, 2 or 3 and when n is 0 then a direct bond is intended;
Q is nitrogen or

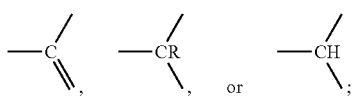

X is nitrogen or

Y is nitrogen or

Z is nitrogen or

R is selected from the group consisting of hydrogen, halogen, —NH$_2$, nitro, hydroxy, aryl, heterocyclyl, C$_3$-C$_8$-cycloalkyl, heteroaryl, C$_1$-C$_7$-alkyl, haloalkyl, C$_1$-C$_7$-alkenyl, C$_1$-C$_7$-alkynyl, C$_1$-C$_7$-acyl, C$_1$-C$_7$-alkyl-aryloxy, C$_1$-C$_7$-alkyl-arylsulfanyl, C$_1$-C$_7$-alkyl-arylsulfinyl, C$_1$-C$_7$-alkyl-arylsulfonyl, C$_1$-C$_7$-alkyl-arylaminosulfonyl, C$_1$-C$_7$-alkyl-arylamine, C$_1$-C$_7$-alkynyl-C(O)-amine, C$_1$-C$_7$-alkenyl-C(O)-amine, C$_1$-C$_7$-alkynyl-R$^9$, CrC$_7$alkenyl-R$^9$ wherein R$^9$ is hydrogen, hydroxy, amino, C$_1$-C$_7$-alkyl or C$_1$-C$_7$-alkoxy;
R$^{12}$ is hydrogen, halo, hydroxy, amino, nitro, C$_{1-6}$alkyl, C$_{1-6}$alkyloxy, trifluoromethyl, di(C$_{1-6}$alkyl)amino, hydroxyamino or naphtalenylsulfonylpyrazinyl;
R$^{13}$ is hydrogen, hydroxy, amino, hydroxyC$_{1-6}$alkyl, C$_{1-6}$alkyl, C$_{1-6}$alkyloxy, arylC$_{1-6}$alkyl, aminocarbonyl, hydroxycarbonyl, aminoC$_{1-6}$alkyl, aminocarbonylC$_{1-6}$alkyl, hydroxycarbonylC$_{1-6}$alkyl, hydroxyaminocarbonyl, C$_{1-6}$alkyloxycarbonyl, C$_{1-6}$alkylaminoC$_{1-6}$alkyl or di(C$_{1-6}$alkyl)aminoC$_{1-6}$alkyl;
when Z is equal to nitrogen, then -L- is a direct bond;
when Z is equal to

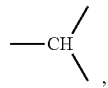

then -L- is —NH— or the bivalent radical —C$_{1-6}$alkanediylNH—;
R$^{14}$ is hydrogen, C$_{1-6}$alkyl, C$_{3-10}$cycloalkyl, hydroxyC$_{1-6}$alkyl, C$_{1-6}$alkyloxyC$_{1-6}$alkyl, di(C$_{1-6}$alkyl)aminoC$_{1-6}$alkyl or aryl;

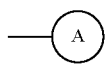

is a radical selected from

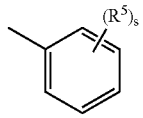
(a-1)

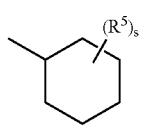
(a-2)

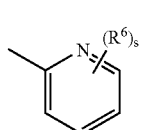
(a-3)

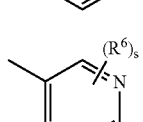
(a-4)

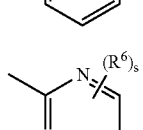
(a-5)

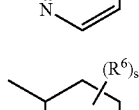
(a-6)

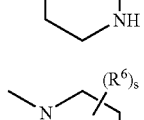
(a-7)

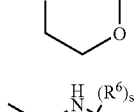
(a-8)

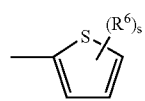
(a-9)
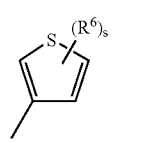
(a-10)
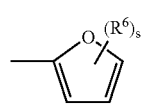
(a-11)
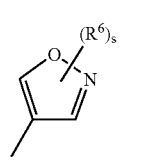
(a-12)
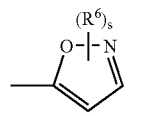
(a-13)
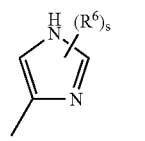
(a-14)
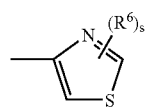
(a-15)
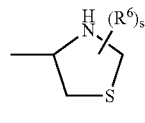
(a-16)
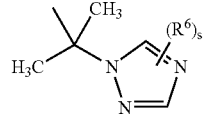
(a-17)
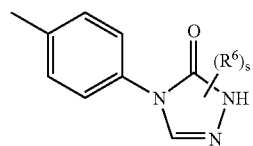
(a-18)
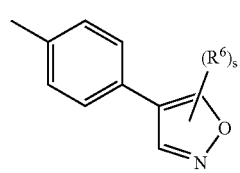
(a-19)
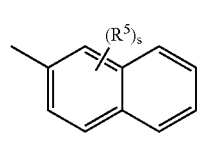
(a-20)
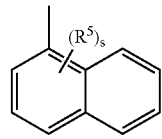
(a-21)
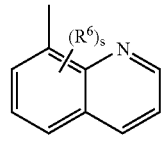
(a-22)
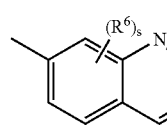
(a-23)
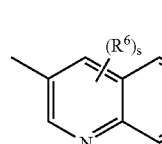
(a-24)
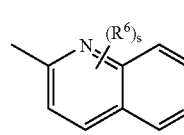
(a-25)
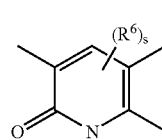
(a-26)
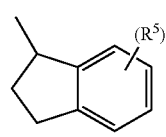
(a-27)
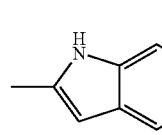
(a-28)
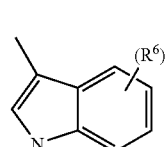
(a-29)
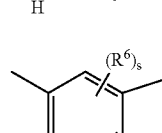
(a-30)
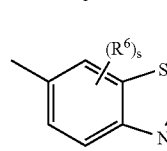
(a-31)

-continued

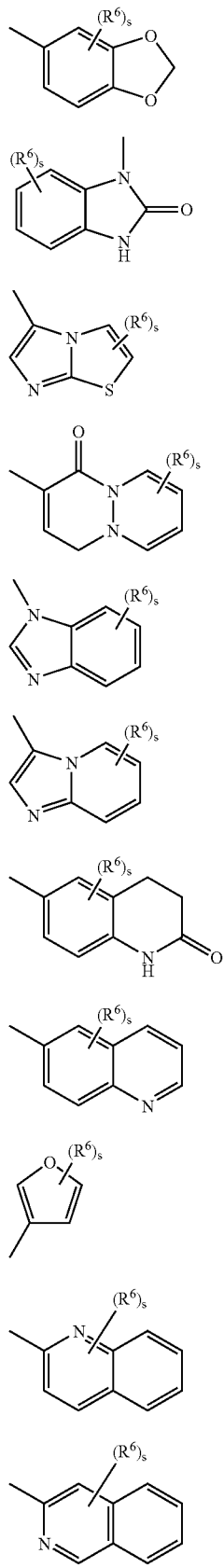

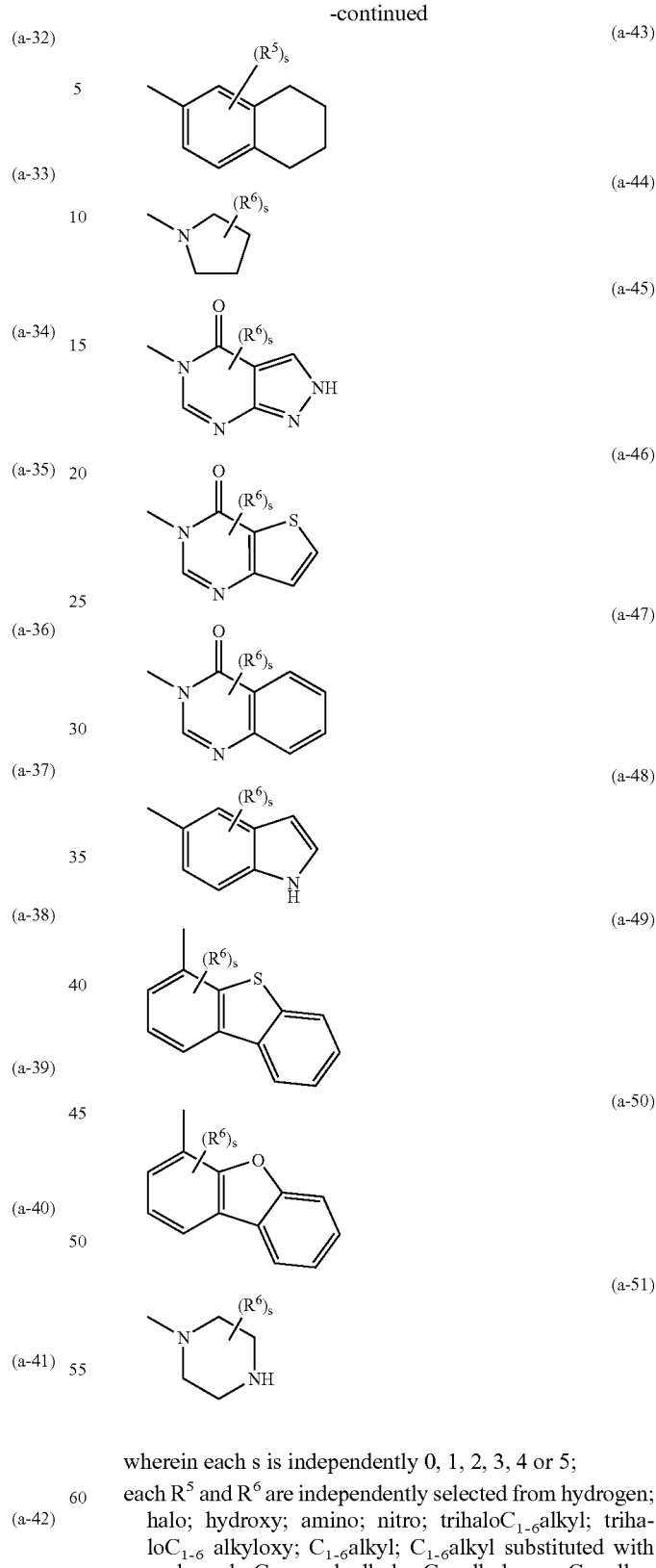

wherein each s is independently 0, 1, 2, 3, 4 or 5;
each $R^5$ and $R^6$ are independently selected from hydrogen; halo; hydroxy; amino; nitro; trihalo$C_{1-6}$alkyl; trihalo$C_{1-6}$ alkyloxy; $C_{1-6}$alkyl; $C_{1-6}$alkyl substituted with aryl and $C_{3-10}$cycloalkyl; $C_{1-6}$alkyloxy; $C_{1-6}$alkyloxy$C_{1-6}$alkyloxy; $C_{1-6}$alkylcarbonyl; $C_{1-6}$alkyloxycarbonyl; $C_{1-6}$alkylsulfonyl; cyano$C_{1-6}$alkyl; hydroxy$C_{1-6}$alkyl; hydroxy$C_{1-6}$alkyloxy; hydroxy$C_{1-6}$alkylamino; amino$C_{1-6}$alkyloxy; di($C_{1-6}$alkyl)aminocarbonyl;

di(hydroxyC$_{1-6}$alkyl)amino; (aryl)(C$_{1-6}$alkyl)amino; di(C$_{1-6}$alkyl)aminoC$_{1-6}$alkyloxy; di(C$_{1-6}$alkyl)aminoC$_{1-6}$alkylamino; di(C$_{1-6}$alkyl)aminoC$_{1-6}$alkylaminoC$_{1-6}$alkyl; arylsulfonyl; arylsulfonylamino; aryloxy; aryloxyC$_{1-6}$alkyl; arylC$_{2-6}$alkenediyl; di(C$_{1-6}$alkyl) amino; di(C$_{1-6}$alkyl)aminoC$_{1-6}$alkyl; di(C$_{1-6}$alkyl) amino(C$_{1-6}$alkyl)amino; di(C$_{1-6}$alkyl)amino(C$_{1-6}$alkyl) aminoC$_{1-6}$alkyl; di(C$_{1-6}$alkyl)aminoC$_{1-6}$alkyl(C$_{1-6}$ alkyl)amino, di(C$_{1-6}$alkyl)aminoC$_{1-6}$alkyl(C$_{1-6}$alkyl) aminoC$_{1-6}$alkyl; aminosulfonylamino(C$_{1-6}$alkyl) amino; aminosulfonylamino(C$_{1-6}$alkyl)aminoC$_{1-6}$ alkyl; di(C$_{1-6}$alkyl)aminosulfonylamino(C$_{1-6}$alkyl) amino; di(C$_{1-6}$alkyl)aminosulfonylamino(C$_{1-6}$alkyl) aminoC$_{1-6}$alkyl; cyano; thiophenyl; thiophenyl substituted with di(C$_{1-6}$alkyl)aminoC$_{1-6}$alkyl(C$_{1-6}$alkyl) aminoC$_{1-6}$alkyl, di(C$_{1-6}$alkyl)aminoC$_{1-6}$alkyl, C$_{1-6}$alkylpiperazinylC$_{1-6}$alkyl, hydroxyC$_{1-6}$alkylpiperazinylC$_{1-6}$alkyl, hydroxyC$_{1-6}$alkyloxyC$_{1-6}$alkylpiperazinylC$_{1-6}$alkyl, di(C$_{1-6}$alkyl)aminosulfonylpiperazinylC$_{1-6}$alkyl, C$_{1-6}$alkyloxypiperidinyl, C$_{1-6}$alkyloxypiperidinylC$_{1-6}$alkyl, morpholinylC$_{1-6}$ alkyl, hydroxyC$_{1-6}$alkyl(C$_{1-6}$alkyl)aminoC$_{1-6}$alkyl, or di(hydroxyC$_{1-6}$alkyl)aminoC$_{1-6}$alkyl; furanyl; furanyl substituted with hydroxyC$_{1-6}$alkyl; benzofuranyl; imidazolyl; oxazolyl; oxazolyl substituted with aryl and C$_{1-6}$alkyl; C$_{1-6}$alkyltriazolyl; tetrazolyl; pyrrolidinyl; pyrrolyl; piperidinylC$_{1-6}$alkyloxy; morpholinyl; C$_{1-6}$alkylmorpholinyl; morpholinylC$_{1-6}$alkyloxy; morpholinylC$_{1-6}$alkyl; morpholinylC$_{1-6}$alkylamino; morpholinylC$_{1-6}$alkylaminoC$_{1-6}$alkyl; piperazinyl; C$_{1-6}$alkylpiperazinyl; C$_{1-6}$alkylpiperazinylC$_{1-6}$alkyloxy; piperazinylC$_{1-6}$alkyl; naphtalenylsulfonylpiperidinyl; naphtalenylsulfonylpiperidinyl; naphtalenylsulfonyl C$_{1-6}$alkylpiperazinylC$_{1-6}$alkyl; C$_{1-6}$alkylpiperazinylC$_{1-6}$alkylamino; C$_{1-6}$alkylpiperazinylC$_{1-6}$alkylaminoC$_{1-6}$alkyl; C$_{1-6}$alkylpiperazinylsulfonyl; aminosulfonylpiperazinylC$_{1-6}$alkyloxy; aminosulfonylpiperazinyl; aminosulfonylpiperazinylC$_{1-6}$ alkyl; di(C$_{1-6}$alkyl)aminosulfonylpiperazinyl; di(C$_{1-6}$ alkyl)aminosulfonylpiperazinylC$_{1-6}$alkyl; hydroxyC$_{1-6}$ alkylpiperazinyl; hydroxyC$_{1-6}$alkylpiperazinylC$_{1-6}$ alkyl; C$_{1-6}$alkyloxypiperidinyl; C$_{1-6}$alkyloxypiperidinylC$_{1-6}$alkyl; piperidinylaminoC$_{1-6}$alkylamino; piperidinylaminoC$_{1-6}$alkylaminoC$_{1-6}$alkyl; (C$_{1-6}$alkylpiperidinyl)(hydroxyC$_{1-6}$alkyl)aminoC$_{1-6}$alkylamino; (C$_{1-6}$ alkylpiperidinyl)(hydroxyC$_{1-6}$alkyl)aminoC$_{1-6}$ alkylaminoC$_{1-6}$alkyl; hydroxyC$_{1-6}$alkyloxyC$_{1-6}$alkylpiperazinyl; hydroxyC$_{1-6}$alkyloxyC$_{1-6}$alkylpiperazinylC$_{1-6}$alkyl; (hydroxyC$_{1-6}$alkyl)(C$_{1-6}$alkyl)amino; (hydroxyC$_{1-6}$alkyl)(C$_{1-6}$alkyl)aminoC$_{1-6}$alkyl; hydroxyC$_{1-6}$alkylaminoC$_{1-6}$alkyl; di(hydroxyC$_{1-6}$ alkyl)(C$_{1-6}$alkyl)aminoC$_{1-6}$alkyl; pyrrolidinylC$_{1-6}$ alkyl; pyrrolidinylC$_{1-6}$alkyloxy; pyrazolyl; thiopyrazolyl; pyrazolyl substituted with two substituents selected from C$_{1-6}$alkyl or trihaloC$_{1-6}$alkyl; pyridinyl; pyridinyl substituted with C$_{1-6}$alkyloxy, aryloxy or aryl; pyrimidinyl; tetrahydropyrimidinylpiperazinyl; tetrahydropyrimidinylpiperazinylC$_{1-6}$alkyl; quinolinyl; indolyl; phenyl; phenyl substituted with one, two or three substituents independently selected from halo, amino, nitro, C$_{1-6}$alkyl, C$_{1-6}$alkyloxy, hydroxyC$_{1-4}$ alkyl, trifluoromethyl, trifluoromethyloxy, hydroxyC$_{1-4}$ alkyloxy, C$_{1-4}$alkylsulfonyl, C$_{1-4}$alkyloxyC$_{1-4}$alkyloxy, C$_{1-4}$alkyloxycarbonyl, aminoC$_{1-4}$alkoxy, di(C$_{1-4}$alkyl) aminoC$_{1-4}$alkyloxy, di(C$_{1-4}$alkyl)amino, di(C$_{1-4}$alkyl) aminocarbonyl, di(C$_{1-4}$alkyl)aminoC$_{1-4}$alkyl, di(C$_{1-4} $ alkyl)aminoC$_{1-4}$alkyl)aminoC$_{1-4}$alkyl, di (C$_{1-4}$alkyl)amino(C$_{1-4}$alkyl)amino, di(C$_{1-4}$alkyl)amino (C$_{1-4}$alkyl)aminoC$_{1-4}$alkyl di(C$_{1-4}$alkyl)aminoC$_{1-4}$ alkyl(C$_{1-4}$alkyl)amino, di(C$_{1-4}$alkyl)aminoC$_{1-4}$alkyl (C$_{1-4}$alkyl)aminoC$_{1-4}$alkyl, aminosulfonylamino(C$_{1-4}$ alkyl)amino, aminosulfonylamino(C$_{1-4}$alkyl)aminoC$_{1-4}$ alkyl, di(C$_{1-4}$alkyl)aminosulfonylamino(C$_{1-4}$ alkyl)amino, di(C$_{1-4}$alkyl)aminosulfonylamino(C$_{1-4}$ alkyl)aminoC$_{1-4}$alkyl, cyano, piperidinylC$_{1-4}$alkyloxy, pyrrolidinylC$_{1-4}$alkyloxy, aminosulfonylpiperazinyl, aminosulfonylpiperazinylC$_{1-4}$alkyl, di(C$_{1-4}$alkyl)aminosulfonylpiperazinyl, di(C$_{1-4}$alkyl)aminosulfonylpiperazinylC$_{1-4}$alkyl, hydroxyC$_{1-4}$alkylpiperazinyl, hydroxyC$_{1-4}$alkylpiperazinylC$_{1-4}$alkyl, C$_{1-4}$alkyloxypiperidinyl, C$_{1-4}$alkyloxypiperidinylC$_{1-4}$alkyl, hydroxyC$_{1-4}$alkyloxyC$_{1-4}$alkylpiperazinyl, hydroxyC$_{1-4}$ alkyloxyC$_{1-4}$alkylpiperazinylC$_{1-4}$alkyl, (hydroxyC$_{1-4}$alkyl)(C$_{1-4}$alkyl)amino, (hydroxyC$_{1-4}$ alkyl)(C$_{1-4}$alkyl)aminoC$_{1-4}$alkyl, di(hydroxyC$_{1-4}$alkyl) amino, di(hydroxyC$_{1-4}$alkyl)aminoC$_{1-4}$alkyl, furanyl, furanyl substituted with —CH═CH—CH═CH—, pyrrolidinylC$_{1-4}$alkyl, pyrrolidinylC$_{1-4}$alkyloxy, morpholinyl, morpholinylC$_{1-4}$alkyloxy, morpholinylC$_{1-4}$ alkyl, morpholinylC$_{1-4}$alkylamino, morpholinylC$_{1-4}$ alkylaminoC$_{1-4}$alkyl, piperazinyl, C$_{1-4}$alkylpiperazinyl, C$_{1-4}$alkylpiperazinylC$_{1-4}$alkyloxy, piperazinylC$_{1-4}$ alkyl, C$_{1-4}$alkylpiperazinylC$_{1-4}$alkyl, C$_{1-4}$alkylpiperazinylC$_{1-4}$alkylamino, C$_{1-4}$alkylpiperazinylC$_{1-4}$alkylaminoC$_{1-4}$alkyl, tetrahydropyrimidinylpiperazinyl, tetrahydropyrimidinylpiperazinylC$_{1-4}$alkyl, piperidinylaminoC$_{1-4}$alkylamino, (C$_{1-4}$alkylpiperidinyl)(hydroxyC$_{1-4}$alkyl)aminoC$_{1-4}$alkylamino, (C$_{1-4}$ alkylpiperidinyl)(hydroxyC$_{1-4}$alkyl)aminoC$_{1-4}$alkylaminoC$_{1-4}$alkyl, pyridinylC$_{1-4}$alkyloxy, hydroxyC$_{1-4}$ alkylamino, hydroxyC$_{1-4}$alkylaminoC$_{1-4}$alkyl, di(C$_{1-4}$ alkyl)aminoC$_{1-4}$alkylamino, aminothiadiazolyl, aminosulfonylpiperazinylC$_{1-4}$alkyloxy, or thiophenylC$_{1-4}$ alkylamino;

each R$^5$ and R$^6$ can be placed one the nitrogen in replacement of the hydrogen;

aryl in the above is phenyl, or phenyl substituted with one or more substituents each independently selected from halo, C$_{1-6}$alkyl, C$_{1-6}$alkyloxy, trifluoromethyl, cyano or hydroxycarbonyl.

Other embodiments of the compound according to embodiment [0158] (hereinafter collectively referred to as embodiment [0159]) are those in which one or more of the following apply (wherein each of R$^2$, R$^3$, and R$^4$ in this embodiment corresponds to R$^{12}$, R$^{13}$, and R$^{14}$, respectively, in embodiment [0158]):

n is 1;

Q is

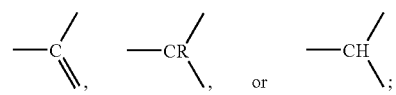

R$^2$ is hydrogen or nitro;
R$^3$ is hydrogen;
when Z is equal to

then -L- is the bivalent radical —$C_{1-6}$alkanediylNH—;
$R^4$ is hydrogen, $C_{1-6}$alkyl or aryl;

is a radical selected from (a-1) or (a-21);
each s is independently 0, 1 or 2;
each 10 is independently selected f hydrogen; halo; trihalo$C_{1-6}$alkyl; trihalo$C_{1-6}$alkyloxy; $C_{1-6}$alkyl; $C_{1-6}$alkyloxy; $C_{1-6}$alkylcarbonyl; aryloxy; cyano or phenyl.

Other embodiments of the compound according to embodiment [0158] (hereinafter collectively referred to as embodiment [0160]) are those in which one or more of the following apply (wherein each of $R^2$, $R^3$, and $R^4$ in this embodiment corresponds to $R^{12}$, $R^{13}$, and $R^{14}$, respectively, in embodiment [0158]):

n is 1;
Q is

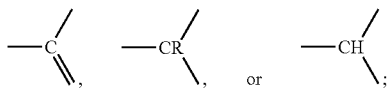

X is nitrogen;
Y is nitrogen;
$R^2$ is hydrogen;
$R^3$ is hydrogen;
when Z is equal to

then -L- is the bivalent radical —$C_{1-6}$alkanediyl NH—;
$R^4$ is hydrogen, $C_{1-6}$alkyl or aryl;

is the radical (a-1);
each s is independently 0 or 1;
each $R^5$ is independently selected from hydrogen or phenyl.

Other embodiments of the compound according to embodiment [0158] (hereinafter collectively referred to as embodiment [0161]) are those in which one or more of the following apply (wherein each of $R^2$, $R^3$, and $R^4$ in this embodiment corresponds to $R^{12}$, $R^{13}$, and $R^{14}$, respectively, in embodiment [0158]):

Z is N;
$R^2$ is hydrogen, halo, hydroxy, amino, nitro, $C_{1-6}$alkyl, $C_{1-6}$alkyloxy, trifluoromethyl or di($C_{1-6}$alkyl)amino;
$R^3$ is hydrogen, hydroxy, amino, hydroxy$C_{1-6}$alkyl, $C_{1-6}$alkyl, $C_{1-6}$alkyloxy, aryl$C_{1-6}$alkyl, aminocarbonyl, amino$C_{1-6}$alkyl, $C_{1-6}$alkylamino$C_{1-6}$alkyl or di($C_{1-6}$alkyl)amino$C_{1-6}$alkyl;
$R^4$ is hydrogen;

is a radical selected form (a-1), (a-3), (a-4), (a-5), (a-6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-28), (a-29), (a-30), (a-31), (a-32), (a-33), (a-34), (a-36), (a-37), (a-38), (a-39), (a-40), (a-41), (a-42), (a-44), (a-45), (a-46), (a-47), (a-48) or (a-51);
each s is independently 0, 1, 2, 3 or 4;
$R^5$ is hydrogen; halo; hydroxy; amino; nitro; trihalo$C_{1-6}$alkyl; trihalo$C_{1-6}$alkyloxy; $C_{1-6}$alkyl; $C_{1-6}$alkyloxy; $C_{1-6}$alkylcarbonyl; $C_{1-6}$alkyloxycarbonyl; $C_{1-6}$alkylsulfonyl; hydroxy$C_{1-6}$alkyl; aryloxy; di($C_{1-6}$alkyl)amino; cyano; thiophenyl; furanyl; furanyl substituted with hydroxy$C_{1-6}$alkyl; benzofuranyl; imidazolyl; oxazolyl; oxazolyl substituted with aryl and $C_{1-6}$alkyl; $C_{1-6}$alkylthiazolyl, tetrazolyl; pyrrodinyl; pyrrolyl; morpholinyl; $C_{1-6}$alkylmorpholinyl; piperazinyl; $C_{1-6}$alkylpiperazinyl; hydroxy$C_{1-6}$alkylpiperazinyl; $C_{1-6}$alkyloxypiperidinyl; pyrazolyl; pyrazolyl substituted with one or two substituents selected from $C_{1-6}$alkyl or trihalo$C_{1-6}$alkyl; pyridinyl; pyridinyl substituted with $C_{1-6}$alkyloxy, aryloxy or aryl; pyrimidinyl, quinolinyl; indole; phenyl; or phenyl substituted with one or two substituents independently selected from halo, $C_{1-6}$alkyl, $C_{1-6}$alkyloxy or trifluoromethyl;
$R^6$ is hydrogen; halo; hydroxy; amino; nitro; trihalo$C_{1-6}$alkyl; trihalo$C_{1-6}$alkyloxy; $C_{1-6}$alkyl; $C_{1-6}$alkyloxy; $C_{1-6}$alkylcarbonyl; $C_{1-6}$alkyloxycarbonyl; $C_{1-6}$alkylsulfonyl; hydroxy$C_{1-6}$alkyl; aryloxy; di($C_{1-6}$alkyl)amino; cyano; pyridinyl; phenyl; or phenyl substituted with one or two substituents independently selected from halo, $C_{1-6}$alkyl, $C_{1-6}$alkyloxy or trifluoromethyl.

Other embodiments of the compound according to embodiment [0158] (hereinafter collectively referred to as embodiment [0162]) include the following (wherein each of $R^2$, $R^3$, and $R^4$ in this embodiment corresponds to $R^{12}$, $R^{13}$, and $R^{14}$, respectively, in embodiment [0158]):

Z is N;
$R^2$ is hydrogen, halo, hydroxy, amino, nitro, $C_{1-6}$alkyl, $C_{1-6}$alkyloxy, trifluoromethyl or di($C_{1-6}$alkyl)amino;
$R^3$ is hydrogen, hydroxy, amino, hydroxy$C_{1-6}$alkyl, $C_{1-6}$alkyl, $C_{1-6}$alkyloxy, aryl$C_{1-6}$alkyl, aminocarbonyl, amino$C_{1-6}$alkyl, $C_{1-6}$alkylamino$C_{1-6}$alkyl or di($C_{1-6}$alkyl)amino$C_{1-6}$alkyl;
$R^4$ is hydrogen;

is a radical selected from (a-1), (a-3), (a-4), (a-5), (a-6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-28), (a-29), (a-30), (a-31), (a-32), (a-33), (a-34), (a-35), (a-36), (a-37), (a-38), (a-39), (a-40), (a-41), (a-42), (a-44), (a-45), (a-46), (a-47), (a-48) or (a-51);
  each s is independently 0, 1, 2, 3 or 4;
  $R^5$ is hydrogen; halo; hydroxy; amino; nitro; trihalo$C_{1-6}$alkyl; trihalo$C_{1-6}$alkyloxy; $C_{1-6}$alkyl; $C_{1-6}$alkyloxy; $C_{1-6}$alkylcarbonyl; $C_{1-6}$alkyloxycarbonyl; $C_{1-6}$alkylsulfonyl; hydroxy$C_{1-6}$alkyl; aryloxy; di($C_{1-6}$alkyl)amino; cyano; thiophenyl; furanyl; furanyl substituted with hydroxy$C_{1-6}$alkyl; benzofuranyl; imidazolyl; oxazolyl; oxazolyl substituted with aryl and $C_{1-6}$alkyl; $C_{1-6}$alkyltriazolyl; tetrazolyl; pyrrolidinyl; pyrrolyl; morpholinyl; $C_{1-6}$alkylmorpholinyl; piperazinyl; $C_{1-6}$alkylpiperazinyl; hydroxy$C_{1-6}$alkylpiperazinyl; $C_{1-6}$alkyloxypiperidinyl; pyrazolyl; pyrazolyl substituted with one or two substituents selected from $C_{1-6}$alkyl or trihalo$C_{1-6}$alkyl; pyridinyl; pyridinyl substituted with $C_{1-6}$alkyloxy, aryloxy or aryl; pyrimidinyl; quinolinyl; indole; phenyl; or phenyl substituted with one or two substituents independently selected from halo, $C_{1-6}$alkyl, $C_{1-6}$alkyloxy or trifluoromethyl; and
  $R^6$ is hydrogen; halo; hydroxy, amino; nitro; trihalo$C_{1-6}$alkyl; trihalo$C_{1-6}$alkyloxy; $C_{1-6}$alkyl; $C_{1-6}$alkyloxy; $C_{1-6}$alkylcarbonyl; $C_{1-6}$alkyloxycarbonyl; $C_{1-6}$alkylsulfonyl; hydroxy$C_{1-6}$alkyl; aryloxy; di($C_{1-6}$alkyl)amino; cyano; pyridinyl; phenyl; or phenyl substituted with one or two substituents independently selected form halo, $C_{1-6}$alkyl, $C_{1-6}$alkyloxy or trifluoromethyl.

Other embodiments of the compound according to embodiment [0158] (hereinafter collectively referred to as embodiment [0163]) include the following (wherein each of $R^2$, $R^3$, and $R^4$ in this embodiment corresponds to $R^{12}$, $R^3$, and $R^{14}$, respectively, in embodiment [0158]):
  n is 1; Q is

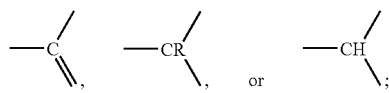

$R^2$ is hydrogen or nitro; $R^3$
hydrogen; when Z is equal

to then -L- is the bivalent radical —$C_{1-6}$alkanediylNH—; $R^4$ is hydrogen, $C_{1-6}$alkyl or aryl;

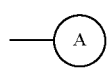

is a radical selected from (a-1) or (a-21); each s is independently 0, 1 or 2; and each $R^5$ is independently selected from hydrogen; halo; trihalo$C_{1-6}$alkyl; trihalo$C_{1-6}$alkyloxy;
  $C_{1-6}$alkyl; $C_{1-6}$alkyloxy;
  $C_{1-6}$alkylcarbonyl; aryloxy; cyano or phenyl.

Other embodiments of the compound according to embodiment [0158] (hereinafter collectively referred to as embodiment [0164]) include the following (wherein each of $R^2$, $R^3$, and $R^4$ in this embodiment corresponds to $R^{12}$, $R^{13}$, and $R^{14}$, respectively, in embodiment [0158]):
  n is 1; X is nitrogen; Y is nitrogen;
  Q is

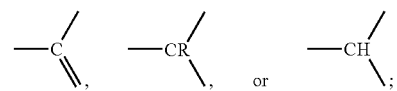

$R^2$ is hydrogen; $R^3$ is hydrogen; when Z is equal to

then
  -L- is the bivalent radical —$C_{1-6}$alkanediylNH—; $R^4$ is hydrogen, $C_{1-6}$alkyl or aryl;

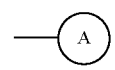

is the radical (a-1); each s is independently 0 or 1; and each $R^1$ is independently selected from hydrogen or phenyl.

Particular embodiments of the compound according to embodiment [0158] (hereinafter collectively referred to as embodiment [0165]) include the following

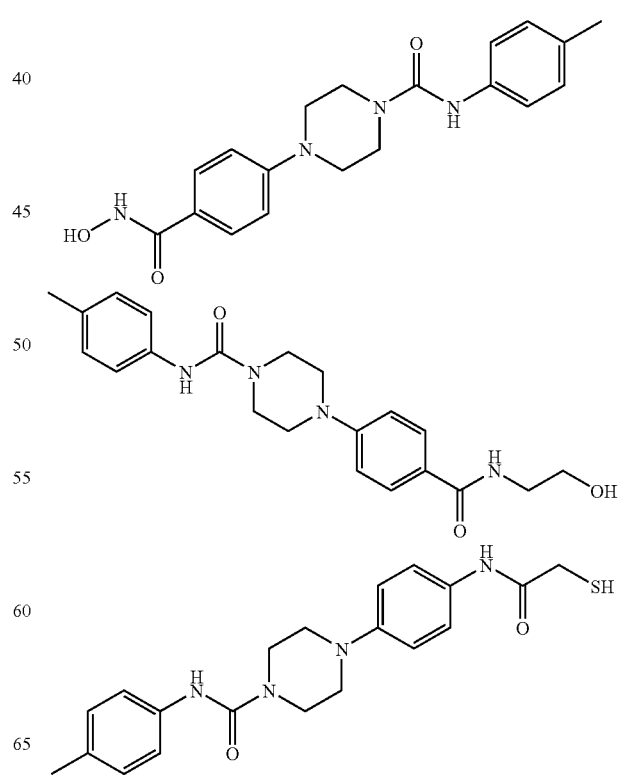

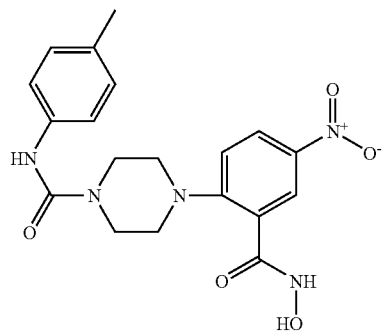
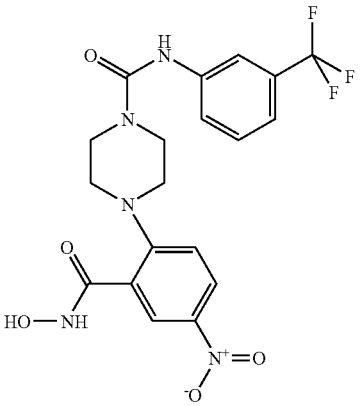
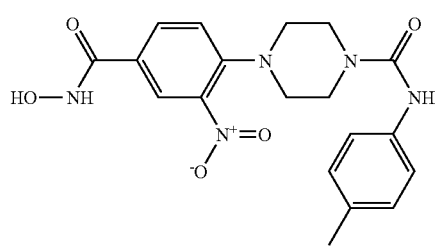
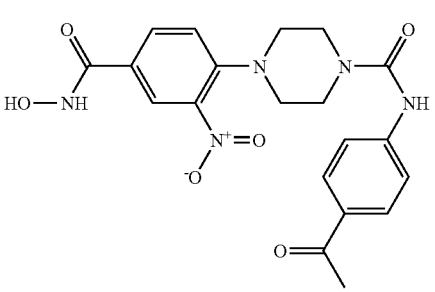
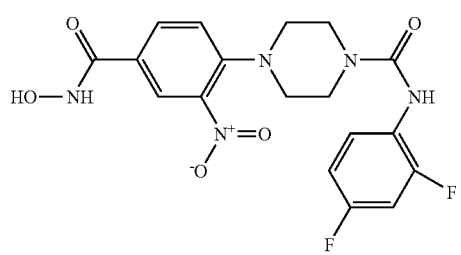
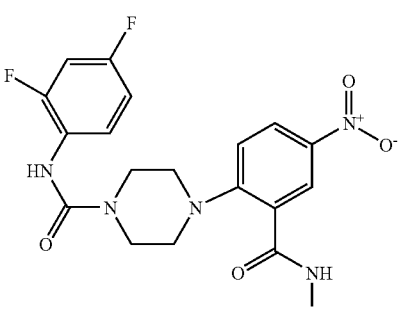
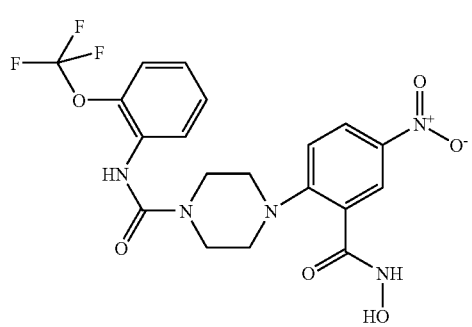
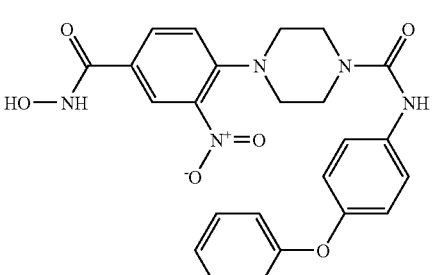
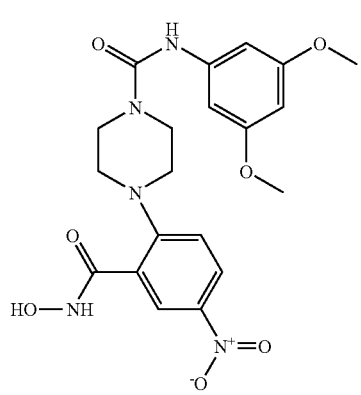
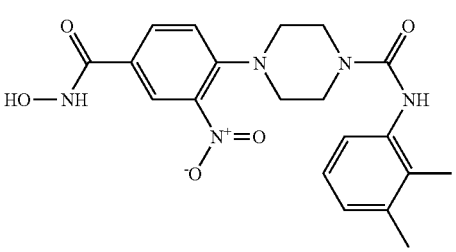

-continued
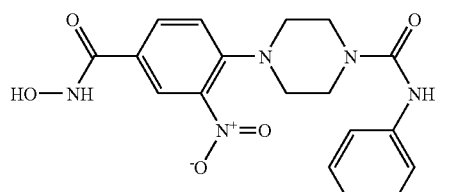
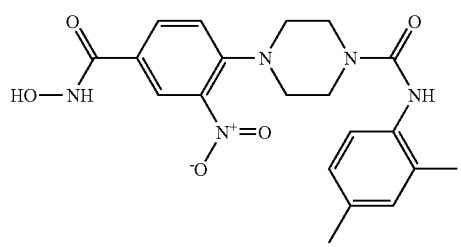
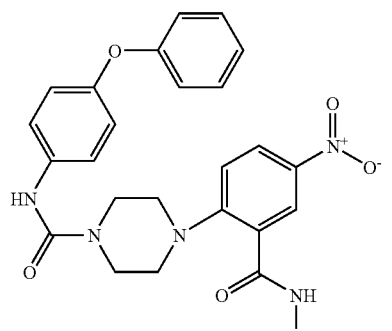
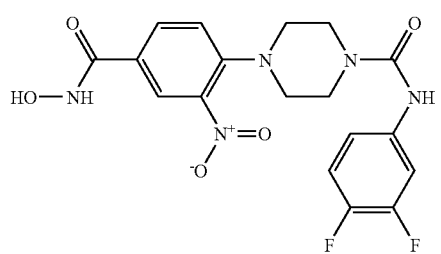
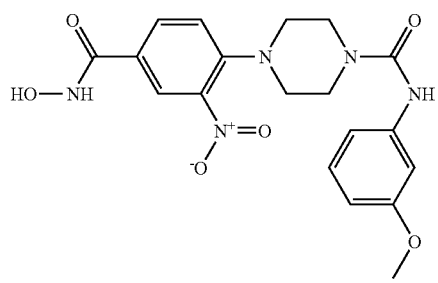
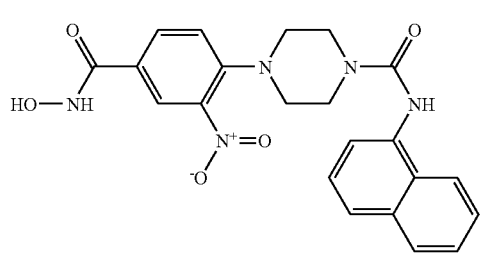
-continued
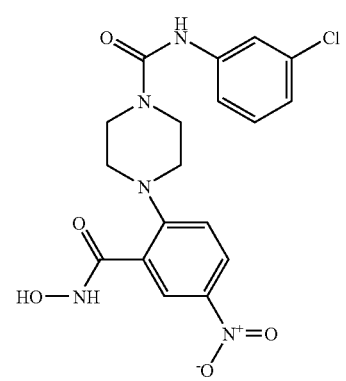
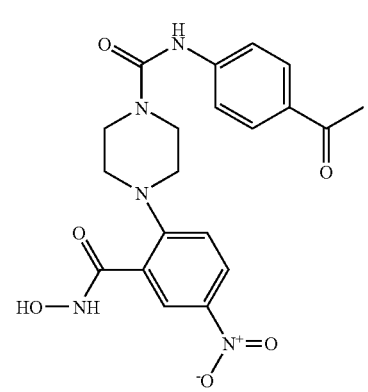
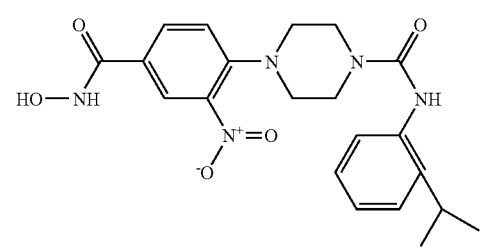
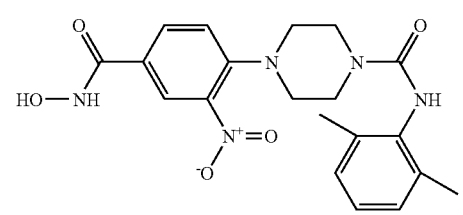
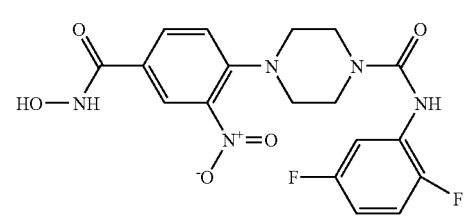

-continued
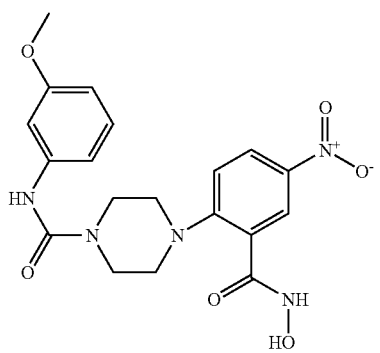
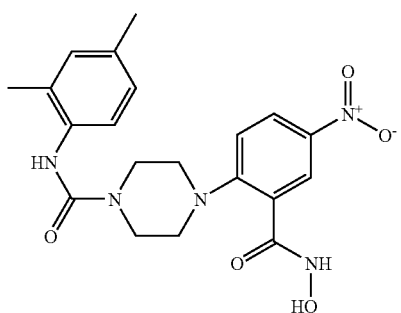
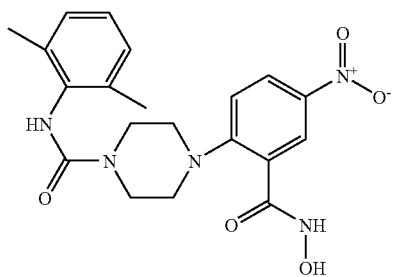
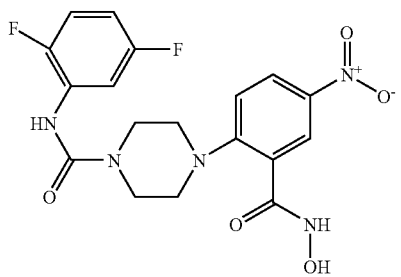
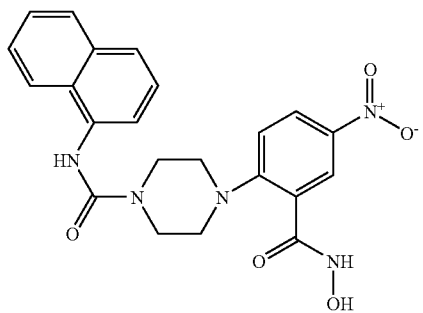
-continued
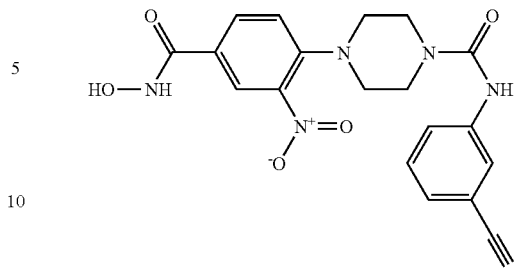
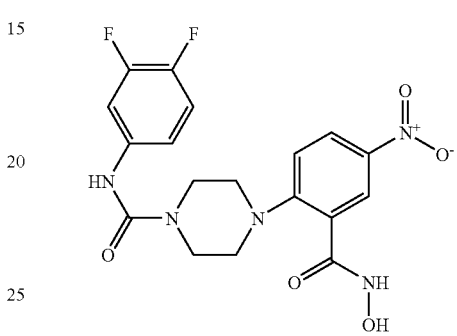
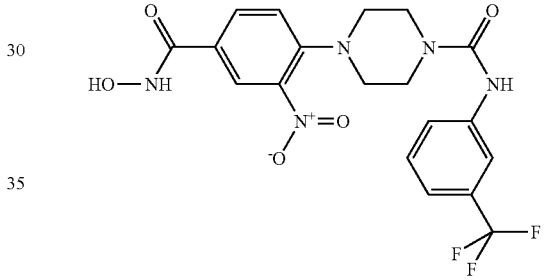
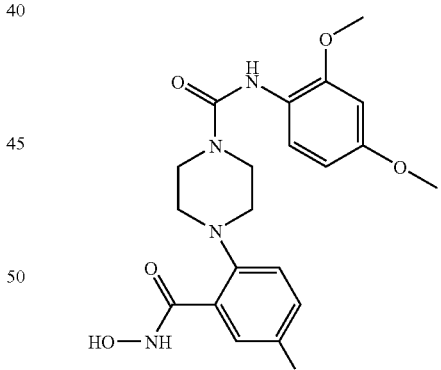
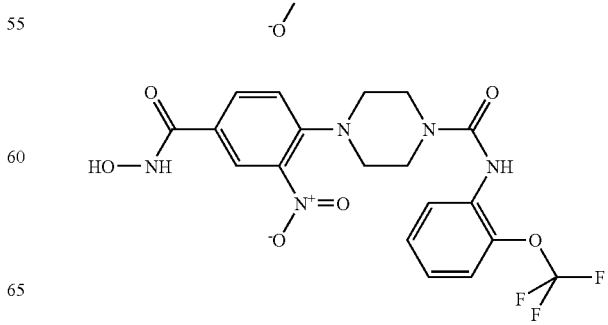

145
-continued
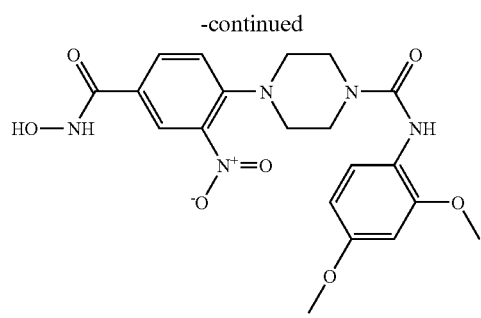
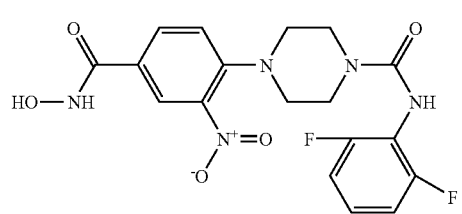
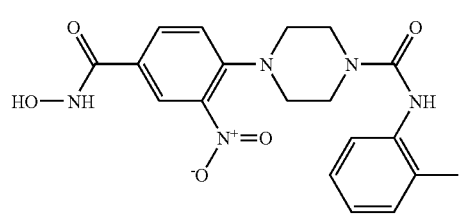
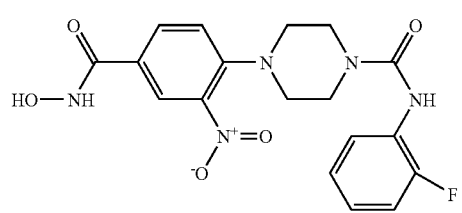
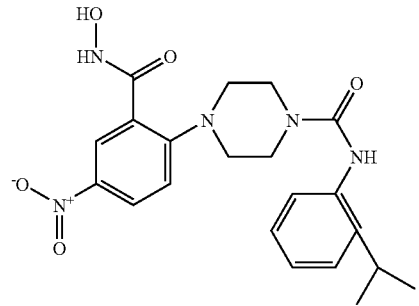
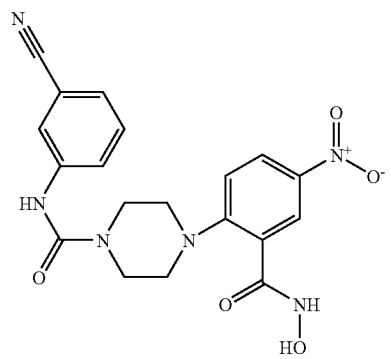
146
-continued
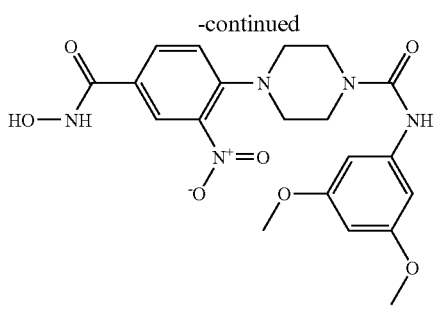
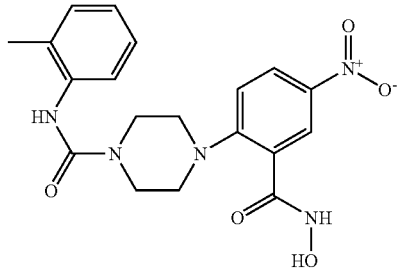
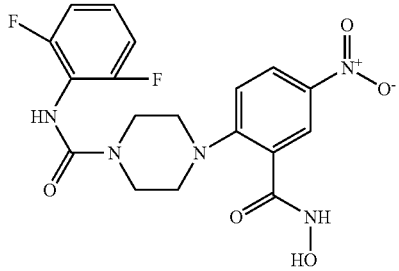
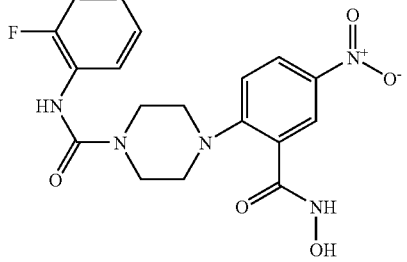
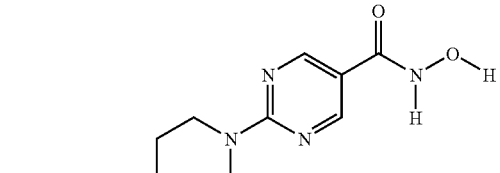
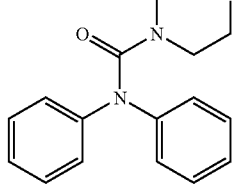
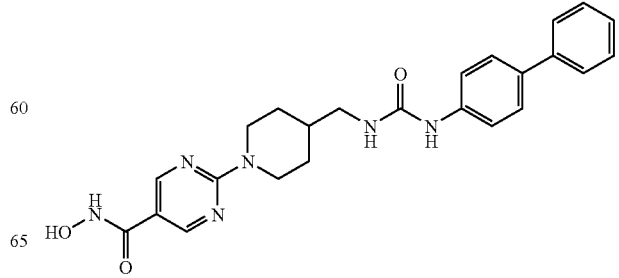

-continued

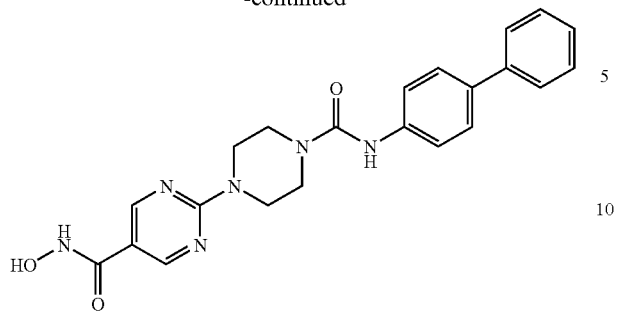

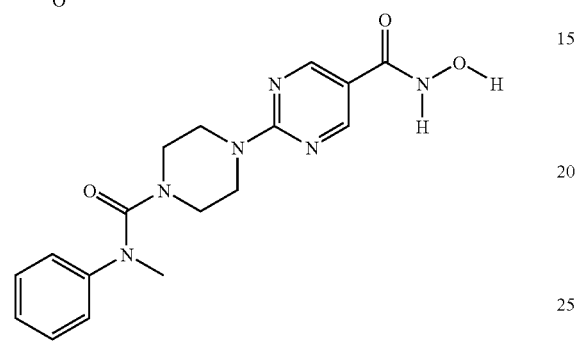

in which the terminal hydroxamic acid moiety (C(O)—NH—OH) is replaced with

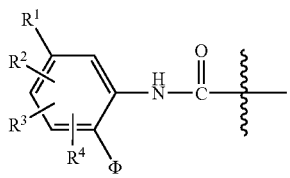

wherein Φ, $R^1$, $R^2$, $R^3$, and $R^4$ are as defined in accordance with embodiment [0046], and preferably embodiments [0048] and [0049].

In the compounds of embodiments [0158]-[0165], $R^1$, $R^2$, $R^3$, and $R^4$ are preferably as defined in embodiments [0048] and [0049]. In other embodiments of the compounds of embodiments [0158]-[0165], $R^1$, $R^2$, $R^3$, and $R^4$ are all H. Such embodiments are hereinafter collectively referred to as embodiment [0166].

In another embodiment, the invention comprises compounds of the following structural formula (10) (hereinafter embodiment [0167]):

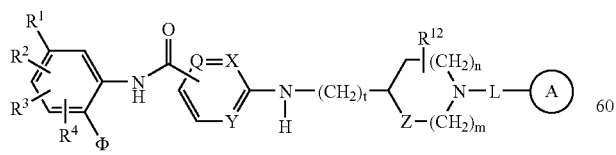

(10)

or a pharmaceutically acceptable salt thereof, wherein
Φ is —NH₂ or —OH;
$R^1$ is H or as defined in embodiment [0046];
$R^2$, $R^3$, and $R^4$ are as defined in embodiment [0046];
n is 0, 1, 2 or 3 and when n is 0 then a direct bond is intended;
m is 0, 1, 2 or 3 and when m is 0 then a direct bond is intended;
t is 0 or 1 and when t is 1 then at bond is intended;
Q is nitrogen or

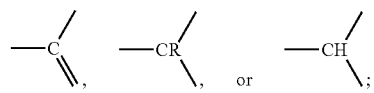

X is nitrogen or

Y is nitrogen or

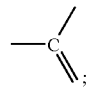

Z is CH₂— or —O—;
R is selected from the group consisting of hydrogen, halogen, —NH₂, nitro, hydroxy, aryl, heterocyclyl, $C_3$-$C_8$-cycloalkyl, heteroaryl, $C_1$-$C_7$-alkyl, haloalkyl, $C_1$-$C_7$-alkenyl, $C_1$-$C_7$-alkynyl, $C_1$-$C_7$-acyl, $C_1$-$C_7$-alkyl-aryloxy, $C_1$-$C_7$-alkyl-arylsulfanyl, $C_1$-$C_7$-alkyl-arylsulfinyl, $C_1$-$C_7$-alkyl-arylsulfonyl, $C_1$-$C_7$-alkyl-arylaminosulfonyl, $C_1$-$C_7$-alkyl-arylamine, $C_1$-$C_7$-alkynyl-C(O)amine, $C_1$-$C_7$-alkenyl-C(O)amine, $C_1$-$C_7$-alkynyl-$R^9$, $C_1$-$C_7$-alkenyl-$R^9$ wherein $R^9$ is hydrogen, hydroxy, amino, $C_1$-$C_7$-alkyl or $C_1$-$C_7$-alkoxy;
$R^{12}$ is hydrogen, hydroxy, amino, hydroxy$C_{1-6}$alkyl, $C_{1-6}$alkyl, $C_{1-6}$alkyloxy, aryl$C_{1-6}$alkyl, aminocarbonyl, hydroxycarbonyl, amino$C_{1-6}$alkyl, aminocarbonyl$C_{1-6}$alkyl, hydroxycarbonyl$C_{1-6}$alkyl, hydroxyaminocarbonyl, $C_{1-6}$alkyloxycarbonyl, $C_{1-6}$alkylamino$C_{1-6}$alkyl or di($C_{1-6}$alkyl)amino$C_{1-6}$alkyl;
-L- is a bivalent radical selected from $C_{1-6}$alkanediyl, carbonyl, sulfonyl, or $C_{1-6}$alkanediyl substituted with phenyl;

is a radical selected from

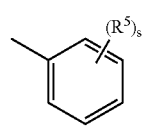

(a-1)

-continued
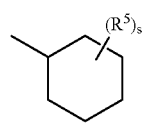 (a-2)
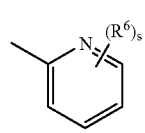 (a-3)
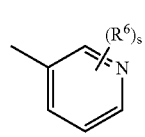 (a-4)
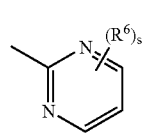 (a-5)
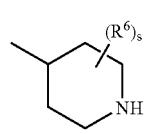 (a-6)
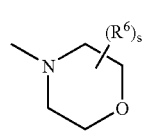 (a-7)
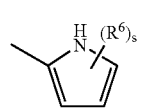 (a-8)
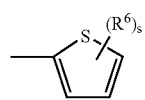 (a-9)
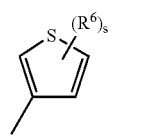 (a-10)
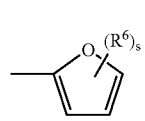 (a-11)
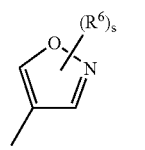 (a-12)
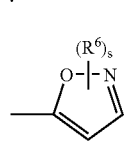 (a-13)
-continued
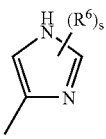 (a-14)
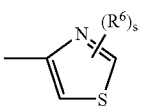 (a-15)
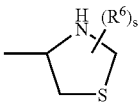 (a-16)
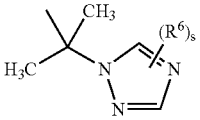 (a-17)
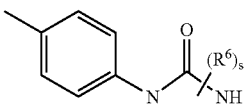 (a-18)
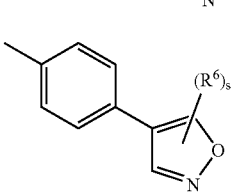 (a-19)
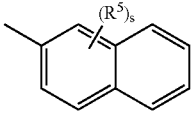 (a-20)
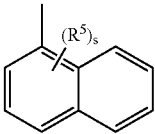 (a-21)
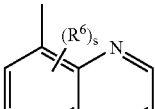 (a-22)
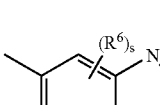 (a-23)
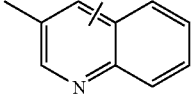 (a-24)

(a-25) 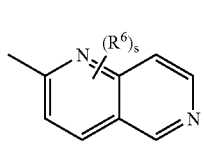
(a-26) 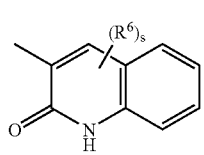
(a-27) 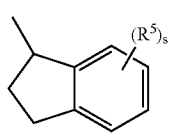
(a-28) 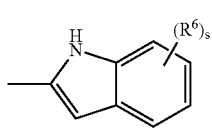
(a-29) 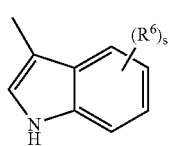
(a-30) 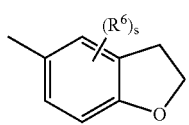
(a-31) 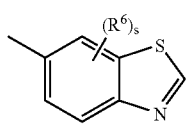
(a-32) 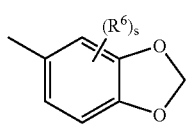
(a-33) 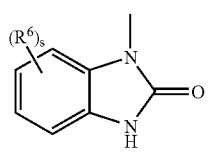
(a-34) 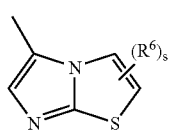
(a-35) 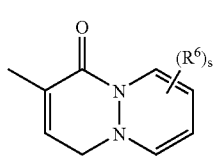
(a-36) 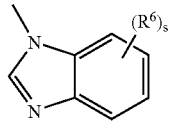
(a-37) 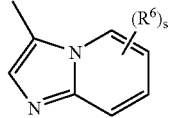
(a-38) 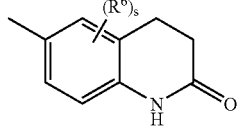
(a-39) 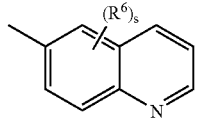
(a-40) 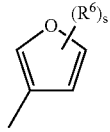
(a-41) 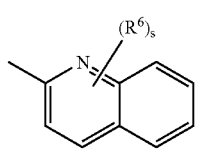
(a-42) 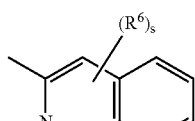
(a-43) 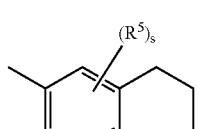
(a-44) 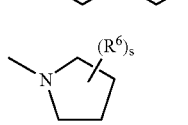
(a-45) 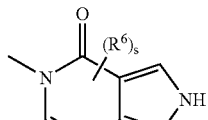
(a-46) 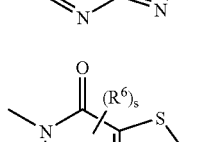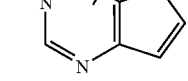

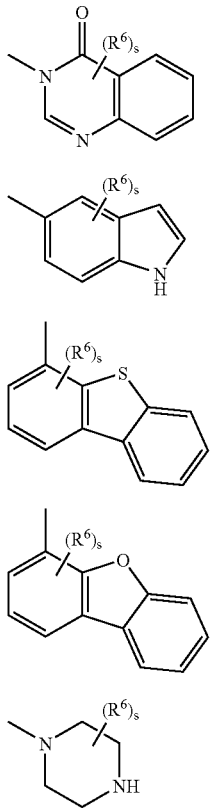

wherein each s is independently 0, 1, 2, 3, 4 or 5;
each $R^5$ and $R^6$ are independently selected from hydrogen; halo; hydroxy; amino; nitro; trihalo$C_{1-6}$alkyl; trihalo$C_{1-6}$ alkyloxy; $C_{1-6}$alkyl; $C_{1-6}$alkyl substituted with aryl and $C_{3-10}$cycloalkyl; $C_{1-6}$alkyloxy; $C_{1-6}$alkyloxy$C_{1-6}$alkyloxy; $C_{1-6}$alkylcarbonyl; $C_{1-6}$alkyloxycarbonyl; $C_{1-6}$alkylsulfonyl; cyano$C_{1-6}$alkyl; hydroxy$C_{1-6}$alkyl; hydroxy$C_{1-6}$alkyloxy; hydroxy$C_{1-6}$alkylamino; amino$C_{1-6}$alkyloxy; di($C_{1-6}$alkyl)aminocarbonyl; di(hydroxy$C_{1-6}$alkyl)amino; (aryl)($C_{1-6}$alkyl)amino; di($C_{1-6}$alkyl)amino$C_{1-6}$alkyloxy; di($C_{1-6}$alkyl)amino$C_{1-6}$alkylamino; di($C_{1-6}$alkyl)amino$C_{1-6}$alkylamino$C_{1-6}$alkyl; arylsulfonyl; arylsulfonylamino; aryloxy; aryloxy$C_{1-6}$alkyl; aryl$C_{2-6}$alkenediyl; di($C_{1-6}$alkyl)amino; di($C_{1-6}$alkyl)amino$C_{1-6}$alkyl; di($C_{1-6}$alkyl)amino($C_{1-6}$alkyl)amino; di($C_{1-6}$alkyl)amino($C_{1-6}$alkyl)amino$C_{1-6}$alkyl; di($C_{1-6}$alkyl)amino$C_{1-6}$alkyl($C_{1-6}$alkyl)amino; di($C_{1-6}$alkyl)amino$C_{1-6}$alkyl($C_{1-6}$alkyl)amino$C_{1-6}$alkyl; aminosulfonylamino($C_{1-6}$alkyl)amino; aminosulfonylamino($C_{1-6}$alkyl)amino$C_{1-6}$alkyl; di($C_{1-6}$alkyl)aminosulfonylamino($C_{1-6}$alkyl)amino; di($C_{1-6}$alkyl)aminosulfonylamino($C_{1-6}$alkyl)amino$C_{1-6}$alkyl; cyano; thiophenyl; thiophenyl substituted with di($C_{1-6}$alkyl)amino$C_{1-6}$alkyl($C_{1-6}$alkyl)amino$C_{1-6}$alkyl, di($C_{1-6}$alkyl)amino$C_{1-6}$alkyl, $C_{1-6}$alkylpiperazinyl$C_{1-6}$alkyl, hydroxy$C_{1-6}$alkylpiperazinyl$C_{1-6}$alkyl, hydroxy$C_{1-6}$alkyloxy$C_{1-6}$alkylpiperazinyl$C_{1-6}$alkyl, di($C_{1-6}$alkyl)aminosulfonylpiperazinyl$C_{1-6}$alkyl, $C_{1-6}$alkyloxypiperidinyl, $C_{1-6}$alkyloxypiperidinyl$C_{1-6}$alkyl, morpholinyl$C_{1-6}$alkyl, hydroxy$C_{1-6}$alkyl($C_{1-6}$alkyl)amino$C_{1-6}$alkyl, or di(hydroxy$C_{1-6}$alkyl)amino$C_{1-6}$alkyl; furanyl; furanyl substituted with hydroxy$C_{1-6}$alkyl; benzofuranyl; imidazolyl; oxazolyl; oxazolyl substituted with aryl and $C_{1-6}$alkyl, $C_{1-6}$alkyltriazolyl; tetrazolyl; pyrrolidinyl; pyrrolyl; piperidinyl$C_{1-6}$alkyloxy; morpholinyl; $C_{1-6}$alkylmorpholinyl; morpholinyl$C_{1-6}$alkyloxy; morpholinyl$C_{1-6}$alkyl; morpholinyl$C_{1-6}$alkylamino; morpholinyl$C_{1-6}$alkylamino$C_{1-6}$alkyl; piperazinyl; $C_{1-6}$alkylpiperazinyl; $C_{1-6}$alkylpiperazinyl$C_{1-6}$alkyloxy; piperazinyl$C_{1-6}$alkyl; naphtalenylsulfonylpiperazinyl; naphtalenylsulfonylpiperidinyl; naphtalenylsulfonyl; $C_{1-6}$alkylpiperazinyl$C_{1-6}$alkyl; $C_{1-6}$alkylpiperazinyl$C_{1-6}$alkylamino; $C_{1-6}$alkylpiperazinyl$C_{1-6}$alkylamino$C_{1-6}$alkyl; $C_{1-6}$alkylpiperazinylsulfonyl; aminosulfonylpiperazinyl$C_{1-6}$alkyloxy; aminosulfonylpiperazinyl; aminosulfonylpiperazinyl$C_{1-6}$alkyl; di($C_{1-6}$alkyl)aminosulfonylpiperazinyl; di($C_{1-6}$alkyl)aminosulfonylpiperazinyl$C_{1-6}$alkyl; hydroxy$C_{1-6}$alkylpiperazinyl; hydroxy$C_{1-6}$alkylpiperazinyl$C_{1-6}$alkyl; $C_{1-6}$alkyloxypiperidinyl; $C_{1-6}$alkyloxypiperidinyl$C_{1-6}$alkyl; piperidinylamino$C_{1-6}$alkylamino; piperidinylamino$C_{1-6}$alkylamino$C_{1-6}$alkyl; ($C_{1-6}$alkylpiperidinyl)(hydroxy$C_{1-6}$alkyl)amino$C_{1-6}$alkylamino; ($C_{1-6}$ alkylpiperidinyl)(hydroxy$C_{1-6}$alkyl)amino$C_{1-6}$alkylamino$C_{1-6}$alkyl; hydroxy$C_{1-6}$alkyloxy$C_{1-6}$alkylpiperazinyl; hydroxy$C_{1-6}$alkyloxy$C_{1-6}$alkylpiperazinyl$C_{1-6}$alkyl; (hydroxy$C_{1-6}$alkyl)($C_{1-6}$alkyl)amino; (hydroxy$C_{1-6}$alkyl)($C_{1-6}$alkyl)amino$C_{1-6}$alkyl; hydroxy$C_{1-6}$alkylamino$C_{1-6}$alkyl; di(hydroxy$C_{1-6}$alkyl)amino$C_{1-6}$alkyl; pyrrolidinyl$C_{1-6}$alkyl; pyrrolidinyl$C_{1-6}$alkyloxy, pyrazolyl; thiopyrazolyl; pyrazolyl substituted with two substituents selected from $C_{1-6}$alkyl or trihalo$C_{1-6}$alkyl; pyridinyl; pyridinyl substituted with $C_{1-6}$alkyloxy, aryloxy or aryl; pyrimidinyl; tetrahydropyrimidinylpiperazinyl; tetrahydropyrimidinylpiperazinyl$C_{1-6}$alkyl; quinolinyl; indolyl; phenyl; phenyl substituted with one, two or three substituents independently selected from halo, amino, nitro, $C_{1-6}$alkyl, $C_{1-6}$alkyloxy, hydroxy$C_{1-4}$alkyl, trifluoromethyl, trifluoromethyloxy, hydroxy$C_{1-4}$alkyloxy, $C_{1-4}$alkylsulfonyl, $C_{1-4}$alkyloxy$C_{1-4}$alkyloxy, $C_{1-4}$alkyloxycarbonyl, amino$C_{1-4}$alkyloxy, di($C_{1-4}$alkyl)amino$C_{1-4}$alkyloxy, di($C_{1-4}$alkyl)amino, di($C_{1-4}$alkyl)aminocarbonyl, di($C_{1-4}$alkyl)amino$C_{1-4}$alkyl, di($C_{1-4}$alkyl)amino$C_{1-4}$alkylamino$C_{1-4}$alkyl, di($C_{1-4}$alkyl)amino($C_{1-4}$alkyl)amino, di($C_{1-4}$alkyl)amino($C_{1-4}$alkyl)amino$C_{1-4}$alkyl, di($C_{1-4}$alkyl)amino$C_{1-4}$alkyl($C_{1-4}$alkyl)amino, di($C_{1-4}$alkyl)amino$C_{1-4}$alkyl($C_{1-4}$alkyl)amino$C_{1-4}$alkyl, aminosulfonylamino($C_{1-4}$alkyl)amino, aminosulfonylamino($C_{1-4}$alkyl)amino$C_{1-4}$alkyl,
di($C_{1-4}$ alkyl)aminosulfonylamino($C_{1-4}$alkyl)amino, di($C_{1-4}$alkyl)aminosulfonylamino($C_{1-4}$alkyl)
amino$C_4$alkyl, cyano, piperidinyl$C_{1-4}$alkyloxy, pyrrolidinyl$C_{1-4}$alkyloxy, aminosulfonylpiperazinyl, aminosulfonylpiperazinyl$C_{1-4}$alkyl, di($C_{1-4}$alkyl)aminosulfonylpiperazinyl, di($C_{1-4}$alkyl)aminosulfonylpiperazinyl$C_{1-4}$alkyl, hydroxy$C_{1-4}$alkylpiperazinyl, hydroxy$C_{1-4}$alkylpiperazinyl$C_{1-4}$alkyl, $C_{1-4}$alkyloxypiperidinyl, $C_{1-4}$alkyloxypiperidinyl$C_{1-4}$alkyl, hydroxy$C_{1-4}$alkyloxy$C_{1-4}$alkylpiperazinyl, hydroxy$C_{1-4}$alkyloxy$C_{1-4}$alkylpiperazinyl$C_{1-4}$alkyl, (hydroxy$C_{1-4}$alkyl)($C_{1-4}$alkyl)amino, (hydroxy$C_{1-4}$alkyl)($C_{1-4}$alkyl)amino$C_{1-4}$alkyl, di(hydroxy$C_{1-4}$alkyl)amino, di(hydroxy$C_{1-4}$alkyl)amino$C_{1-4}$ alkyl, furanyl, furanyl substituted with —CH=CH—CH=CH—, pyrrolidinyl$C_{1-4}$alkyl, pyrrolidinyl$C_{1-4}$alkyloxy, morpholinyl, morpholinyl$C_{1-4}$alkyloxy, morpholinyl$C_{1-4}$alkyl, morpholinyl$C_{1-4}$alkylamino, morpholinylC$_{1-4}$alkylaminoC$_{1-4}$alkyl, piperazinyl, C$_{1-4}$alkylpiperazinyl, C$_{1-4}$alkylpiperazinylC$_{1-4}$alkyloxy, piperazinylC$_{1-4}$alkyl, C$_{1-4}$alkylpiperazinylC$_{1-4}$alkyl, C$_{1-4}$alkylpiperazinylC$_{1-4}$alkylamino, C$_{1-4}$alkylpiperazinylC$_{1-4}$alkylaminoC$_{1-6}$alkyl, tetrahydropyrimidinylpiperazinyl, tetrahydropyrimidinylpiperazinylC$_{1-4}$ alkyl, piperidinylaminoC$_{1-4}$alkylamino, piperidinylaminoC$_{1-4}$alkylaminoC$_{1-4}$alkyl, (C$_{1-4}$alkylpiperidinyl)(hydroxyC$_{1-4}$alkyl)aminoC$_{1-4}$alkylamino, (C$_{1-4}$alkylpiperidinyl)(hydroxyC$_{1-4}$alkyl)aminoC$_{1-4}$ alkylaminoC$_{1-4}$alkyl, pyridinylC$_{1-4}$alkyloxy, hydroxyC$_{1-4}$alkylamino, hydroxyC$_{1-4}$alkylaminoC$_{1-4}$alkyl, di(C$_{1-4}$alkyl)aminoC$_{1-4}$alkylamino, aminothiadiazolyl, aminosulfonylpiperazinylC$_{1-4}$alkyloxy, or thiophenylC$_{1-4}$alkylamino;

each R$^5$ and R$^6$ can be placed on the nitrogen in replacement of the hydrogen;

aryl in the above is phenyl, or phenyl substituted with one or more substituents each independently selected from halo, C$_{1-4}$alkyl, C$_{1-6}$alkyloxy, trifluoromethyl, cyano or hydroxycarbonyl.

Other embodiments of the compound according to embodiment [0167] (hereinafter collectively referred to as embodiment [0168]) are those in which one or more of the following apply (wherein each of R$^2$, R$^3$, and R$^4$ in this embodiment corresponds to R$^{12}$, R$^{13}$, and R$^{14}$, respectively, in embodiment [0167]):

n is 0, 1 or 2;
m is 0, 1 or 2;
Q is

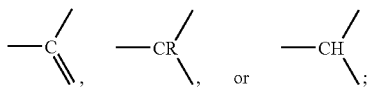

X is nitrogen;
R$^2$ is hydrogen;
-L- is a bivalent radical selected from carbonyl, sulfonyl, or C$_{1-4}$alkanediyl substituted with phenyl;

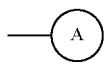

is a radical selected from (a~1), (a-20) or (a-43);
each s is independently 0 or 1;
each R$^5$ is independently selected from hydrogen or phenyl, Other embodiments of the compound according to embodiment [0167] (hereinafter collectively referred to as embodiment [0169]) are those in which one or more of the following apply (wherein each of R$^2$, R$^3$, and R$^4$ in this embodiment corresponds to R$^{12}$, R$^{13}$, and R$^{14}$, respectively, in embodiment [0167]):

n is 0, 1 or 2;
m is 1 or 2
Q is

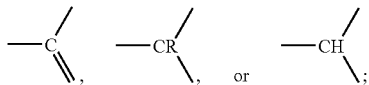

X is nitrogen;

R$^2$ is hydrogen;
-L- is a bivalent radical selected from carbonyl or sulfonyl;

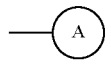

is a radical selected from (a-1) or (a-20);
each s is independently 0 or 1;
each R$^5$ is independently selected from hydrogen or aryl.

Other embodiments of the compound according to embodiment [0167] (hereinafter collectively referred to as embodiment [0170]) are those in which one or more of the following apply (wherein each of R$^2$, R$^3$, and R$^4$ in this embodiment corresponds to R$^{12}$, R$^{13}$, and R$^{14}$, respectively, in embodiment [0167]):

t is o;
R$^2$ is hydrogen, hydroxy, amino, hydroxyC$_{1-6}$alkyl, C$_{1-6}$alkyl, C$_{1-6}$alkyloxy, arylC$_{1-6}$alkyl, aminocarbonyl, aminoC$_{1-6}$alkyl, C$_{1-6}$alkylaminoC$_{1-6}$alkyl or di(C$_{1-6}$alkyl)aminoC$_{1-6}$alkyl;
-L- is a bivalent radical selected from C$_{1-6}$alkanediyl, carbonyl or sulfonyl;

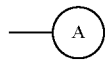

is a radical selected from (a-1), (a-3), (a-4), (a-5), (a-6), (a-7), (a-4), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-28), (a-29), (a-30), (a-31), (a-32), (a-33), (a-34), (a-35), (a-36), (a-37), (a-38), (a-39), (a-40), (a-1), (a-42), (a-44), (a-45), (a-46), (a 47), (a-48) or (a-51);

each s is independently 0, 1, 2, 3 or 4;
R$^5$ is hydrogen; halo; hydroxy; amino; nitro; trihaloC$_{1-6}$alkyl; trihaloC$_{1-6}$alkyloxy; C$_{1-6}$alkyl; C$_{1-6}$alkyloxy; C$_{1-6}$alkylcarbonyl; C$_{1-6}$alkyloxycarbonyl; C$_{1-6}$alkylsulfonyl; hydroxyC$_{1-6}$alkyl; aryloxy; di(C$_{1-6}$alkyl)amino; cyano; thiophenyl; furanyl; furanyl substituted with hydroxyC$_{1-6}$alkyl; benzofuranyl; imidazolyl; oxazolyl; oxazolyl substituted with aryl and C$_{1-6}$alkyl; C$_{1-6}$alkyltriazolyl; tetrazolyl; pyrrolidinyl; pyrrolyl; morpholinyl; C$_{1-6}$alkylmorpholinyl; piperazinyl; C$_{1-6}$alkylpiperazinyl; hydroxyC$_{1-6}$alkylpiperazinyl; C$_{1-6}$alkyloxypiperidinyl; pyrazoyl; pyrazolyl substituted with one or two substituents selected from C$_{1-6}$alkyl or trihaloC$_{1-6}$alkyl; pyridinyl; pyridinyl substituted with C$_{1-6}$alkyloxy, aryloxy or aryl; pyrimidinyl; quinolinyl; indole; phenyl; or phenyl substituted with one or two substituents independently selected from halo, C$_{1-6}$alkyl, C$_{1-6}$alkyloxy or trifluoromethyl;
R$^6$ is hydrogen; halo; hydroxy; amino; nitro; trihaloC$_{1-6}$alkyl; trihaloC$_{1-6}$alkyloxy; C$_{1-6}$alkyl; C$_{1-6}$alkyloxy; C$_{1-6}$alkylcarbonyl; C$_{1-6}$alkyloxycarbonyl; C$_{1-6}$alkylsulfonyl; hydroxyC$_{1-6}$alkyl; aryloxy; di(C$_{1-6}$alkyl)amino; cyano; pyridinyl; phenyl; or phenyl substituted with one or two substituents independently selected from halo, C$_{1-6}$alkyl, C$_{1-6}$alkyloxy or trifluoromethyl.

Other embodiments of the compound according to embodiment [0167] (hereinafter collectively referred to as embodiment [0171]) include the following (wherein each of $R^2$, $R^3$, and $R^4$ in this embodiment corresponds to $R^{12}$, $R^{13}$, and $R^{14}$, respectively, in embodiment [0167]):

t is 0;

$R^2$ is hydrogen, hydroxy, amino, hydroxy$C_{1-6}$alkyl, $C_{1-6}$alkyl, $C_{1-6}$alkyloxy, aryl$C_{1-6}$alkyl, aminocarbonyl, amino$C_{1-6}$alkyl, $C_{1-6}$alkylamino$C_{1-6}$alkyl or di($C_{1-6}$alkyl)amino$C_{1-6}$alkyl;

-L- is a bivalent radical selected from $C_{1-6}$alkanediyl, carbonyl or sulfonyl;

is a radical selected from (a-1), (a-3), (a-4), (a-5), (a-6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-28), (a-29), (a-30), (a-31), (a-32), (a-33), (a-34), (a-35), (a-36), (a-37), (a-38), (a-39), (a-40), (a-41), (a-42), (a-44), (a-45), (a-46), (a-47), (a-48) or (a-51);

s is 0, 1, 2, 3 or 4;

$R^5$ is hydrogen, halo; hydroxy; amino; nitro; trihalo$C_{1-6}$alkyl; trihalo$C_{1-6}$alkyloxy; $C_{1-6}$alkyl; $C_{1-6}$alkyloxy; $C_{1-6}$alkylcarbonyl; $C_{1-6}$alkyloxycarbonyl; $C_{1-6}$alkylsulfonyl; hydroxy$C_{1-6}$alkyl; aryloxy; di($C_{1-6}$alkyl)amino; cyano; thiophenyl; furanyl; furanyl substituted with hydroxy$C_{1-6}$alkyl; benzofuranyl; imidazolyl; oxazolyl; oxazolyl substituted with aryl and $C_{1-6}$alkyl; $C_{1-6}$alkylthiazolyl; tetrazolyl; pyrrolidinyl; pyrrolyl; morpholinyl; $C_{1-6}$alkylmorpholinyl; piperazinyl; $C_{1-6}$alkylpiperazinyl; hydroxy$C_{1-6}$alkylpiperazinyl; $C_{1-6}$alkyloxypiperidinyl; pyrazoyl; pyrazolyl substituted with one or two substituents selected from $C_{1-6}$alkyl or trihalo$C_{1-6}$alkyl; pyridinyl; pyridinyl substituted with $C_{1-6}$alkyloxy, aryloxy or aryl; pyrimidinyl; quinolinyl; indole; phenyl; or phenyl substituted with one or two substituents independently selected from halo, $C_{1-6}$alkyl, $C_{1-6}$alkyloxy or trifluoromethyl; and $R^6$ is hydrogen; halo; hydroxy; amino; nitro; trihalo$C_{1-6}$alkyl; trihalo$C_{1-6}$alkyloxy; $C_{1-6}$alkyl; $C_{1-6}$alkyloxy; $C_{1-6}$alkylcarbonyl; $C_{1-6}$alkyloxycarbonyl; $C_{1-6}$alkylsulfonyl; hydroxy$C_{1-6}$alkyl; aryloxy; di($C_{1-6}$alkyl)amino; cyano; pyridinyl; phenyl; or phenyl substituted with one or two substituents independently selected from halo, $C_{1-6}$alkyl, $C_{1-6}$alkyloxy or trifluoromethyl.

Other embodiments of the compound according to embodiment [0167] (hereinafter collectively referred to as embodiment [0172]) include the following (wherein each of $R^2$, $R^3$, and $R^4$ in this embodiment corresponds to $R^{12}$, $R^{13}$, and $R^{14}$, respectively, in embodiment [0167]):

n is 0, 1 or 2; m is 0, 1, or 2; Q is

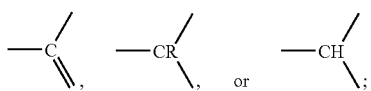

X is nitrogen sulfonyl, or $C_{1-6}$alkanediyl substituted with phenyl;

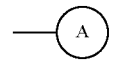

is a radical selected from (a-1), (a-20) or (a-43); s is 0 or 1; and each $R^5$ is independently selected from hydrogen or phenyl.

Other embodiments of the compound according to embodiment [0167] (hereinafter collectively referred to as embodiment [0173]) include the following (wherein each of $R^2$, $R^3$, and $R^4$ in this embodiment corresponds to $R^{12}$, $R^{13}$, and $R^{14}$, respectively, in embodiment [0167]):

n is 0, 1 or 2; m is 0, 1, or 2; Q is

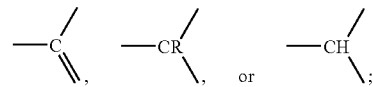

X is nitrogen $R^2$ is hydrogen; -L- is a bivalent radical selected from carbonyl or sulfonyl;

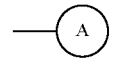

is a radical selected from (a-1) or (a-20); each s is independently 0 or 1; and each $R^5$ is independently selected from hydrogen or aryl.

Particular embodiments of the compound according to embodiment [0167] (hereinafter collectively referred to as embodiment [0174]) include the following

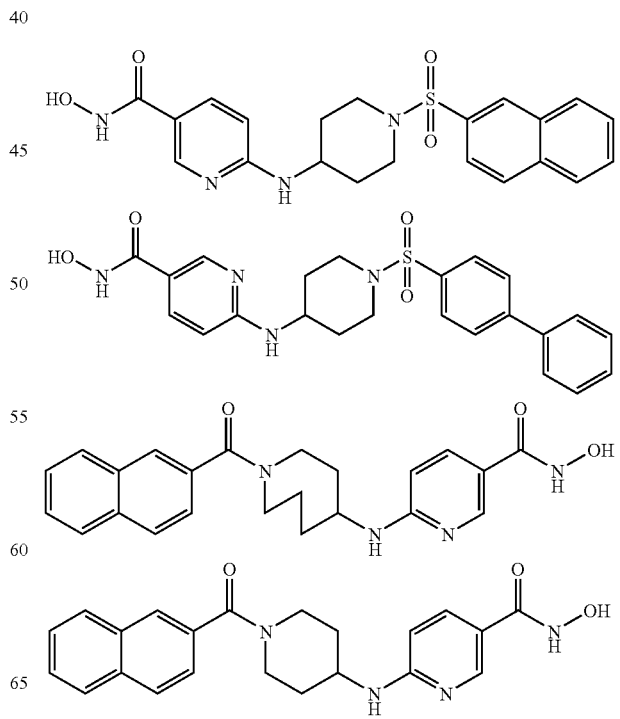

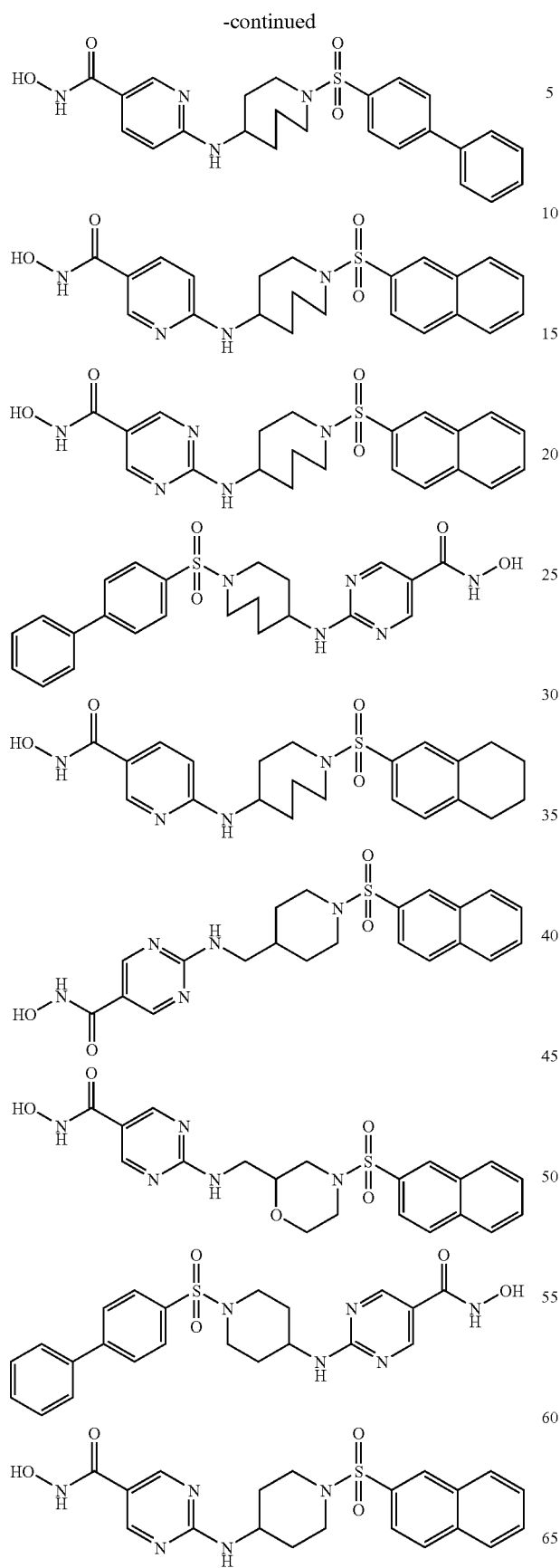

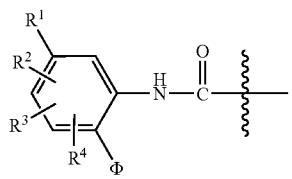

in which the terminal hydroxamic acid moiety (—C(O)—NH—OH) is replaced with

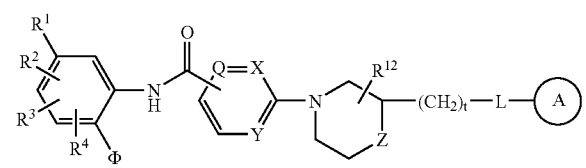

wherein Φ, $R^1$, $R^2$, $R^3$, and $R^4$ are as defined in accordance with embodiment [0046], and preferably [0048] and [0049].

In the compounds of embodiments [0167]-[0174], $R^1$, $R^2$, $R^3$, and $R^4$ are preferably as defined in embodiments [0048] and [0049]. In other embodiments of the compounds of embodiments [0167]-[0174], $R^1$, $R^2$, $R^3$, and $R^4$ are all H. Such embodiments are hereinafter collectively referred to as embodiment [0175].

In another embodiment, the invention comprises compounds of the following structural formula (11) (hereinafter embodiment [0176]):

(11)

or a pharmaceutically acceptable salt thereof, wherein

Φ is —$NH_2$ or —OH;

$R^1$ is H or as defined in embodiment [0046];

$R^2$, $R^3$, and $R^4$ are as defined in embodiment [0046];

t is 0, 1, 2, 3 or 4 and when t is 0 then a direct bond is intended;

Q is nitrogen or

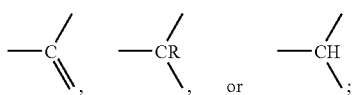

X is nitrogen or

Y is nitrogen or

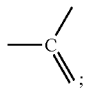

Z is —NH—, —O— or —CH$_2$—;

R is selected from the group consisting of hydrogen, halogen, —NH$_2$, nitro, hydroxy, aryl, heterocyclyl, C$_3$-C$_8$-cycloalkyl, heteroaryl, C$_1$-C$_7$-alkyl, haloalkyl, C$_1$-C$_7$-alkenyl, C$_1$-C$_7$-alkynyl, C$_1$-C$_7$-acyl, C$_1$-C$_7$-alkyl-aryloxy, C$_1$-C$_7$-alkyl-arylsulfanyl, C$_1$-C$_7$-alkyl-arylsulfinyl, C$_1$-C$_7$-alkyl-arylsulfonyl, C$_1$-C$_7$-alkyl-arylaminosulfonyl, C$_1$-C$_7$-alkyl-arylamine, C$_1$-C$_7$-alkynyl-C(O)-amine, C$_1$-C$_7$-alkenyl-C(O)amine, C$_1$-C$_7$-alkynyl-R$^9$, C$_1$-C$_7$-alkenyl-R$^9$ wherein R$^9$ is hydrogen, hydroxy, amino, C$_1$-C$_7$-alkyl or C$_1$-C$_7$-alkoxy;

R$^{12}$ is hydrogen, hydroxy, amino, hydroxyC$_{1-6}$, C$_{1-6}$alkyl, C$_{1-6}$alkyloxy, arylC$_{1-6}$alkyl, aminocarbonyl, hydroxycarbonyl, aminoC$_{1-6}$alkyl, aminocarbonylC$_{1-6}$alkyl, hydroxycarbonylC$_{1-6}$alkyl, hydroxyaminocarbonyl, C$_{1-6}$alkyloxycarbonyl, C$_{1-6}$alkylaminoC$_{1-6}$alkyl or di(C$_{1-6}$alkyl)aminoC$_{1-6}$alkyl;

-L- is a bivalent radical selected from —NR$^9$C(O)—, —NR$^9$SO$_2$— or —NR$^9$CH$_2$— wherein R$^9$ is hydrogen, C$_{1-6}$alkyl, C$_{3-10}$cycloalkyl, hydroxyC$_{1-6}$alkyl, C$_{1-6}$alkyloxyC$_{1-6}$alkyl or di(C$_{1-6}$alkyl)aminoC$_{1-6}$alkyl;

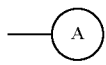

is a radical selected from

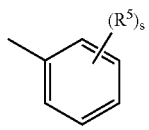
(a-1)

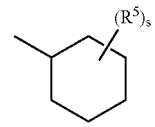
(a-2)

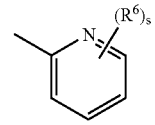
(a-3)

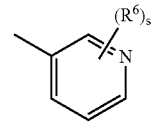
(a-4)

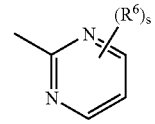
(a-5)

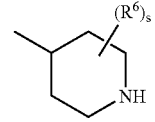
(a-6)

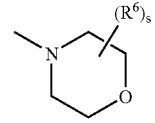
(a-7)

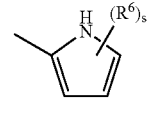
(a-8)

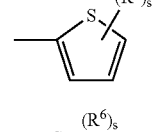
(a-9)

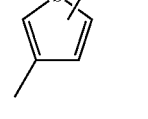
(a-10)

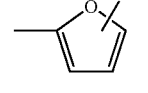
(a-11)

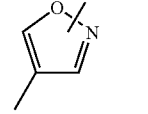
(a-12)

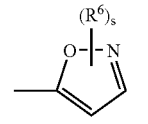
(a-13)

-continued
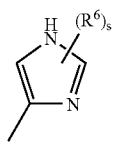 (a-14)
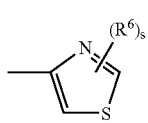 (a-15)
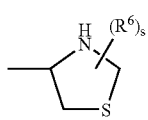 (a-16)
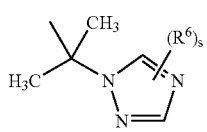 (a-17)
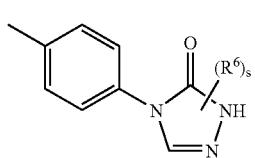 (a-18)
 (a-19)
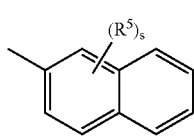 (a-20)
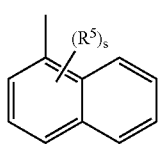 (a-21)
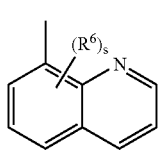 (a-22)
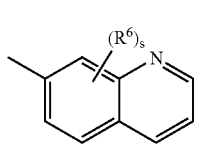 (a-23)
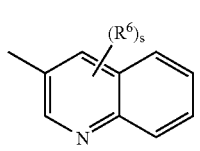 (a-24)
-continued
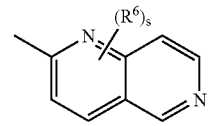 (a-25)
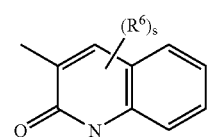 (a-26)
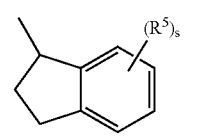 (a-27)
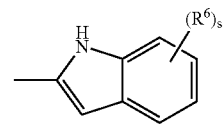 (a-28)
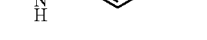 (a-29)
 (a-30)
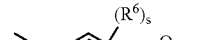 (a-31)
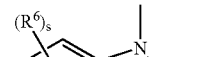 (a-32)
 (a-33)
 (a-34)
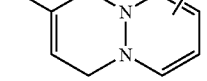 (a-35)

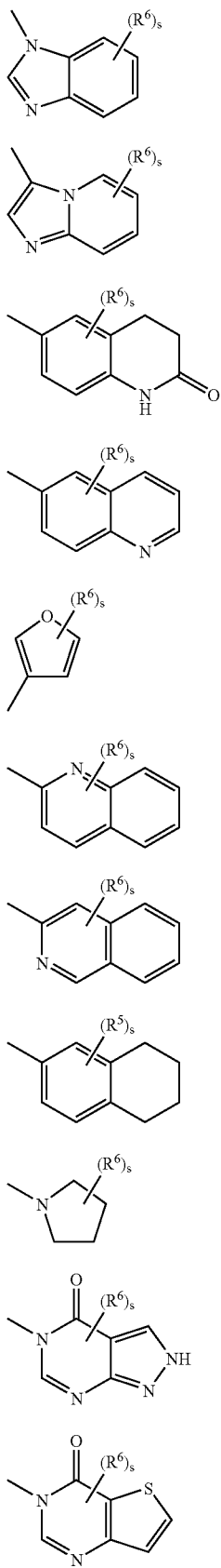

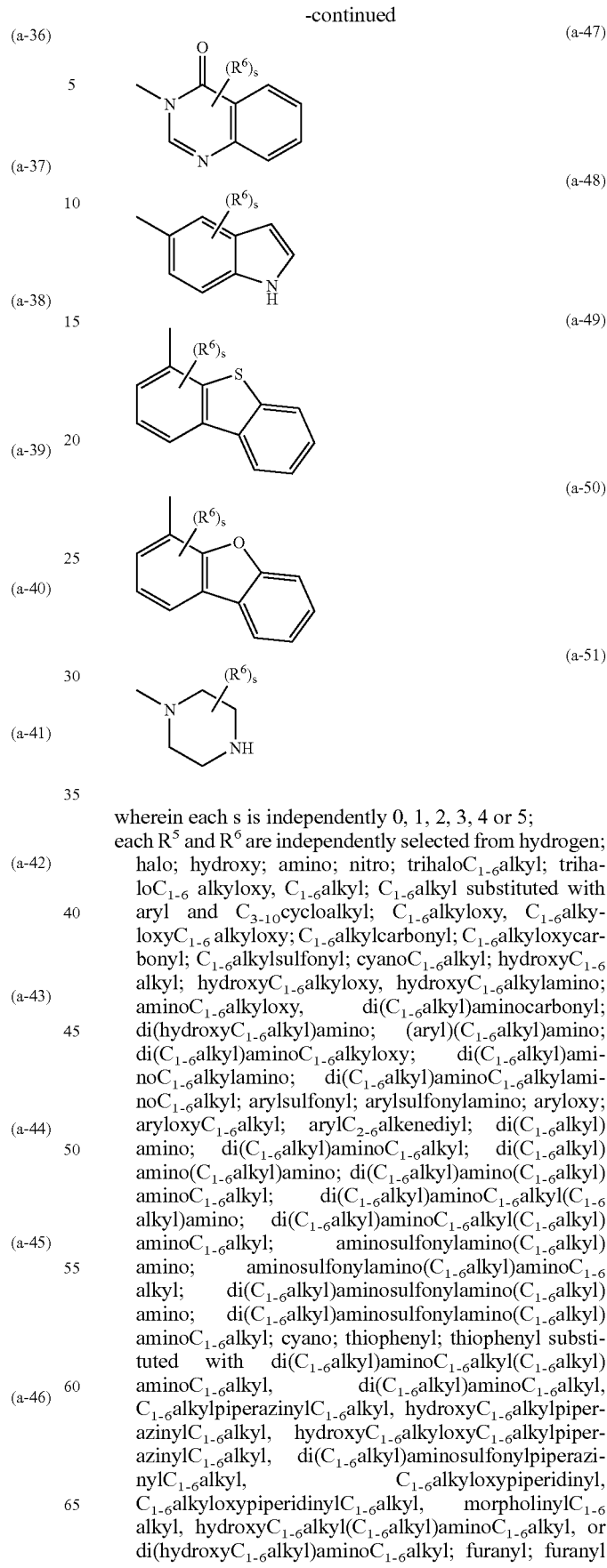

wherein each s is independently 0, 1, 2, 3, 4 or 5;
each $R^5$ and $R^6$ are independently selected from hydrogen; halo; hydroxy; amino; nitro; trihalo$C_{1-6}$alkyl; trihalo$C_{1-6}$ alkyloxy, $C_{1-6}$alkyl; $C_{1-6}$alkyl substituted with aryl and $C_{3-10}$cycloalkyl; $C_{1-6}$alkyloxy, $C_{1-6}$alkyloxy$C_{1-6}$ alkyloxy; $C_{1-6}$alkylcarbonyl; $C_{1-6}$alkyloxycarbonyl; $C_{1-6}$alkylsulfonyl; cyano$C_{1-6}$alkyl; hydroxy$C_{1-6}$ alkyl; hydroxy$C_{1-6}$alkyloxy, hydroxy$C_{1-6}$alkylamino; amino$C_{1-6}$alkyloxy, di($C_{1-6}$alkyl)aminocarbonyl; di(hydroxy$C_{1-6}$alkyl)amino; (aryl)($C_{1-6}$alkyl)amino; di($C_{1-6}$alkyl)amino$C_{1-6}$alkyloxy; di($C_{1-6}$alkyl)amino$C_{1-6}$alkylamino; di($C_{1-6}$alkyl)amino$C_{1-6}$alkylamino$C_{1-6}$alkyl; arylsulfonyl; arylsulfonylamino; aryloxy; aryloxy$C_{1-6}$alkyl; aryl$C_{2-6}$alkenediyl; di($C_{1-6}$alkyl) amino; di($C_{1-6}$alkyl)amino$C_{1-6}$alkyl; di($C_{1-6}$alkyl)amino($C_{1-6}$alkyl)amino; di($C_{1-6}$alkyl)amino($C_{1-6}$alkyl)amino$C_{1-6}$alkyl; di($C_{1-6}$alkyl)amino$C_{1-6}$alkyl($C_{1-6}$ alkyl)amino; di($C_{1-6}$alkyl)amino$C_{1-6}$alkyl($C_{1-6}$alkyl)amino$C_{1-6}$alkyl; aminosulfonylamino($C_{1-6}$alkyl) amino; aminosulfonylamino($C_{1-6}$alkyl)amino$C_{1-6}$ alkyl; di($C_{1-6}$alkyl)aminosulfonylamino($C_{1-6}$alkyl) amino; di($C_{1-6}$alkyl)aminosulfonylamino($C_{1-6}$alkyl) amino$C_{1-6}$alkyl; cyano; thiophenyl; thiophenyl substituted with di($C_{1-6}$alkyl)amino$C_{1-6}$alkyl($C_{1-6}$alkyl) amino$C_{1-6}$alkyl, di($C_{1-6}$alkyl)amino$C_{1-6}$alkyl, $C_{1-6}$alkylpiperazinyl$C_{1-6}$alkyl, hydroxy$C_{1-6}$alkylpiperazinyl$C_{1-6}$alkyl, hydroxy$C_{1-6}$alkyloxy$C_{1-6}$alkylpiperazinyl$C_{1-6}$alkyl, di($C_{1-6}$alkyl)aminosulfonylpiperazinyl$C_{1-6}$alkyl, $C_{1-6}$alkyloxypiperidinyl, $C_{1-6}$alkyloxypiperidinyl$C_{1-6}$alkyl, morpholinyl$C_{1-6}$ alkyl, hydroxy$C_{1-6}$alkyl($C_{1-6}$alkyl)amino$C_{1-6}$alkyl, or di(hydroxy$C_{1-6}$alkyl)amino$C_{1-6}$alkyl; furanyl; furanyl substituted with hydroxyC$_{1-6}$alkyl; benzofuranyl; imidazolyl; oxazolyl; oxazolyl substituted with aryl and C$_{1-6}$alkyl; C$_{1-6}$alkyltriazolyl; tetrazolyl; pyrrolidinyl; pyrrolyl; piperidinylC$_{1-6}$alkyloxy; morpholinyl; C$_{1-6}$alkylmorpholinyl; morpholinylC$_{1-6}$alkyloxy; morpholinylC$_{1-6}$alkyl; morpholinylC$_{1-6}$alkylamino; morpholinylC$_{1-6}$alkylaminoC$_{1-6}$alkyl; piperazinyl; C$_{1-6}$alkylpiperazinyl; C$_{1-6}$alkylpiperazinylC$_{1-6}$alkyloxy; piperazinylC$_{1-6}$alkyl; naphtalenylsulfonylpiperazinyl; naphtalenylsulfonylpiperidinyl; naphtalenylsulfonyl; C$_{1-6}$alkylpiperazinylC$_{1-6}$alkyl; C$_{1-6}$alkylpiperazinylC$_{1-6}$alkylamino; C$_{1-6}$alkylpiperazinylC$_{1-6}$alkylaminoC$_{1-6}$alkyl; C$_{1-6}$alkylpiperazinylsulfonyl; aminosulfonylpiperazinylC$_{1-6}$alkyloxy; aminosulfonylpiperazinyl; aminosulfonylpiperazinylC$_{1-6}$alkyl; di(C$_{1-6}$alkyl)aminosulfonylpiperazinyl; di(C$_{1-6}$alkyl)aminosulfonylpiperazinylC$_{1-6}$alkyl; hydroxyC$_{1-6}$alkylpiperazinyl; hydroxyC$_{1-6}$alkylpiperazinylC$_{1-6}$alkyl; C$_{1-6}$alkyloxypiperidinyl; C$_{1-6}$alkyloxypiperidinylC$_{1-6}$alkyl; piperidinylaminoC$_{1-6}$alkylamino; piperidinylaminoC$_{1-6}$alkylaminoC$_{1-6}$alkyl; (C$_{1-6}$alkylpiperidinyl)(hydroxyC$_{1-6}$alkyl)aminoC$_{1-6}$alkylamino; (C$_{1-6}$ alkylpiperidinyl)(hydroxyC$_{1-6}$alkyl)aminoC$_{1-6}$alkylaminoC$_{1-6}$alkyl; hydroxyC$_{1-6}$alkyloxyC$_{1-6}$alkylpiperazinyl; hydroxyC$_{1-6}$alkyloxyC$_{1-6}$alkylpiperazinylC$_{1-6}$alkyl; (hydroxyC$_{1-6}$alkyl)(C$_{1-6}$alkyl)amino; (hydroxyC$_{1-6}$alkyl)(C$_{1-6}$alkyl)aminoC$_{1-6}$alkyl; hydroxyC$_{1-6}$alkylaminoC$_{1-6}$alkyl; di(hydroxyC$_{1-6}$alkyl)aminoC$_{1-6}$alkyl; pyrrolidinylC$_{1-6}$alkyl; pyrrolidinylC$_{1-6}$alkyloxy, pyrazolyl; thiopyrazolyl; pyrazolyl substituted with two substituents selected from C$_{1-6}$alkyl or trihaloC$_{1-6}$alkyl; pyridinyl; pyridinyl substituted with C$_{1-6}$alkyloxy, aryloxy or aryl; pyrimidinyl; tetrahydropyrimidinylpiperazinyl; tetrahydropyrimidinylpiperazinylC$_{1-6}$alkyl; quinolinyl; indole; phenyl; phenyl substituted with one, two or tee substituents independently selected from halo, amino, nitro, C$_{1-6}$alkyl, C$_{1-6}$alkyloxy, hydroxyC$_{1-4}$alkyl, trifluoromethyl, trifluoromethyloxy, hydroxyC$_{1-4}$alkyloxy, C$_{1-4}$alkylsulfonyl, C$_{1-4}$alkyloxyC$_{1-4}$alkyloxy, C$_{1-4}$alkyloxycarbonyl, aminoC$_{1-4}$alkyloxy, di(C$_{1-4}$alkyl)aminoC$_{1-4}$alkyloxy, di(C$_{1-4}$alkyl)amino, di(C$_{1-4}$alkyl)aminocarbonyl, di(C$_{1-4}$alkyl)aminoC$_{1-4}$alkyl, di(C$_{1-4}$alkyl)aminoC$_{1-4}$alkylaminoC$_{1-4}$alkyl, di(C$_{1-4}$alkyl)amino(C$_{1-4}$alkyl)amino, di(C$_{1-4}$alkyl)amino(C$_{1-4}$alkyl)aminoC$_{1-4}$alkyl, di(C$_{1-4}$alkyl)aminoC$_{1-4}$alkyl(C$_{1-4}$alkyl)amino, di(C$_{1-4}$alkyl)aminoC$_{1-4}$alkyl(C$_{1-4}$alkyl)aminoC$_{1-4}$alkyl, aminosulfonylamino(C$_{1-4}$alkyl)amino, aminosulfonylamino(C$_{1-4}$alkyl)aminoC$_{1-4}$alkyl, di(C$_{1-4}$alkyl)aminosulfonylamino(C$_{1-4}$alkyl)amino, di(C$_{1-4}$alkyl)aminosulfonylamino(C$_{1-4}$alkyl)aminoC$_{1-6}$alkyl, cyano, piperidinylC$_{1-4}$alkyloxy, pyrrolidinylC$_{1-4}$alkyloxy, aminosulfonylpiperazinyl, aminosulfonylpiperazinylC$_{1-4}$alkyl, di(C$_{1-4}$alkyl)aminosulfonylpiperazinyl, di(C$_{1-4}$alkyl)aminosulfonylpiperazinylC$_{1-4}$alkyl, hydroxyC$_{1-4}$alkylpiperazinyl, hydroxyC$_{1-4}$alkylpiperazinylC$_{1-4}$alkyl, C$_{1-4}$alkyloxypiperidinyl, C$_{1-4}$alkyloxypiperidinylC$_{1-4}$alkyl, hydroxyC$_{1-4}$alkyloxyC$_{1-4}$alkylpiperazinyl, hydroxyC$_{1-4}$alkyloxyC$_{1-4}$alkylpiperazinylC$_{1-4}$alkyl, (hydroxyC$_{1-4}$alkyl)(C$_{1-4}$alkyl)amino, (hydroxyC$_{1-4}$alkyl)(C$_{1-4}$alkyl)aminoC$_{1-4}$alkyl, di(hydroxyC$_{1-4}$alkyl)amino, di(hydroxyC$_{1-4}$alkyl)aminoC$_{1-4}$alkyl, furanyl, furanyl substituted with —CH=CH—CH=CH—, pyrrolidinylC$_{1-4}$alkyl, pyrrolidinylC$_{1-4}$alkyloxy, morpholinyl, morpholinylC$_{1-4}$alkyloxy, morpholinylC$_{1-4}$alkyl, morpholinylC$_{1-4}$alkylamino, morpholinylC$_{1-4}$alkylaminoC$_{1-4}$alkyl, piperazinyl, C$_{1-4}$alkylpiperazinyl, C$_{1-4}$alkylpiperazinylC$_{1-4}$alkyloxy, piperazinylC$_{1-4}$alkyl, C$_{1-4}$alkylpiperazinylC$_{1-4}$alkyl, C$_{1-4}$alkylpiperazinylC$_{1-4}$alkylamino, C$_{1-4}$alkylpiperazinylC$_{1-4}$alkylaminoC$_{1-4}$alkyl, tetrahydropyrimidinylpiperazinyl, tetrahydropiperazinylpiperazinylC$_{1-4}$alkyl, piperidinylaminoC$_{1-4}$alkylamino, piperidinylaminoC$_{1-4}$alkylaminoC$_{1-4}$alkyl, (C$_{1-4}$alkylpiperidinyl)(hydroxyC$_{1-4}$alkyl)aminoC$_{1-4}$alkylamino, (C$_{1-4}$alkylpiperidinyl)(hydroxyC$_{1-4}$alkyl)aminoC$_{1-4}$alkylaminoC$_{1-4}$alkyl, pyridinylC$_{1-4}$alkyloxy, hydroxyC$_{1-4}$alkylamino, hydroxyC$_{1-4}$alkylaminoC$_{1-4}$alkyl, di(C$_{1-4}$alkyl)aminoC$_{1-4}$alkylamino, aminothiadiazolyl, aminosulfonylpiperazinylC$_{1-4}$alkyloxy, or thiophenylC$_{1-4}$alkylamino;

each R$^5$ and R$^6$ can be placed on the nitrogen in replacement of the hydrogen;

aryl in the above is phenyl, or phenyl substituted with one or more substituents each independently selected from halo, C$_{1-6}$alkyl, C$_{1-6}$alkyloxy, trifluoromethyl, cyano or hydroxycarbonyl.

Other embodiments of the compound according to embodiment [0176] (hereinafter collectively referred to as embodiment [0177]) are those in which one or more of the following apply (wherein each of R$^2$, R$^3$, and R$^4$ in this embodiment corresponds to R$^{12}$, R$^{13}$, and R$^{14}$, respectively, in embodiment [0176]):

t is 0 or 17

Q is

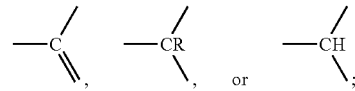

X is nitrogen;

R$^{12}$ is hydrogen, hydroxy, C$_{1-6}$alkyl, or arylC$_{1-6}$alkyl;

-L- is a bivalent radical selected form —NHC(O)— or —NHSO$_3$—;

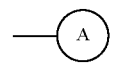

is a radical selected from (a-1) or (a-20);

each s is independently 0 or 1;

each R$^5$ is independently selected f hydrogen or phenyl.

Other embodiments of the compound according to embodiment [0176] (hereinafter collectively referred to as embodiment [0178]) are those in which one or more of the following apply (wherein each of R$^2$, R$^3$, and R$^4$ in this embodiment corresponds to R$^{12}$, R$^{13}$, and R$^{14}$, respectively, in embodiment [0176]):

t is 1;

Q is

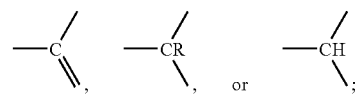

X is nitrogen;
Y is nitrogen;
Z is —O— or CH$_2$—;

$R^{12}$ is H;

-L- is a bivalent radical selected from —NHC(O)— or —NHSO$_2$—;

—(A)

is a radical selected from (a-1) or (a-20);

each s is independently 0 or 1;

each $R^5$ is independently selected from hydrogen or phenyl.

Other embodiments of the compound according to embodiment [0176] (hereinafter collectively referred to as embodiment [0179]) are those in which one or more of the following apply (wherein each of $R^2$, $R^3$, and $R^4$ in this embodiment corresponds to $R^{12}$, $R^{13}$, and $R^{14}$, respectively, in embodiment [0176]):

t is 0;

$R^{12}$ is hydrogen, hydroxy, amino, hydroxyC$_{1-6}$alkyl, C$_{1-6}$alkyl, C$_{1-6}$alkyloxy, arylC$_{1-6}$alkyl, aminocarbonyl, aminoC$_{1-6}$alkyl, C$_{1-6}$alkylaminoC$_{1-6}$alkyl or di(C$_{1-6}$alkyl)aminoC$_{1-6}$alkyl;

-L- is a bivalent radical selected from —NHC(O)— or —NHSO$_2$—;

—(A)

is a radical selected from (a-1), (a-3), (a-4), (a-5), (a-6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-28), (a-29), (a-30), (a-31), (a-32), (a-33), (a-34), (a-35), (a-36), (a-37), (a-38), (a-39), (a-480), (a-41), (a-42), (a-44), (a-45), (a-46), (a-47), (a-48) or (a-51);

each s is independently 0, 1, 2, 3 or 4;

$R^5$ is hydrogen; halo; hydroxy, amino; nitro; trihaloC$_{1-6}$alkyl; trihaloC$_{1-6}$alkyloxy; C$_{1-6}$alkyl; C$_{1-6}$alkyl; C$_{1-6}$alkylcarbonyl; C$_{1-6}$alkyloxycarbonyl; C$_{1-6}$alkylsulfonyl; hydroxyC$_{1-6}$alkyl; aryloxy; di(C$_{1-6}$alkyl)amino; cyano; thiophenyl; furanyl; furanyl substituted with hydroxyC$_{1-6}$alkyl; benzofuranyl; imidazolyl; oxazolyl; oxazolyl substituted with aryl and C$_{1-6}$alkyl; C$_{1-6}$alkyltriazolyl; tetrazolyl; pyrrolidinyl; pyrrolyl; morpholinyl; C$_{1-6}$alkylmorpholinyl; piperazinyl; C$_{1-6}$alkylpiperazinyl; hydroxyC$_{1-6}$alkylpiperazinyl; C$_{1-6}$alkyloxypiperidinyl; pyrazoyl; pyrazolyl substituted with one or two substituents selected from C$_{1-6}$alkyl or trihaloC$_{1-6}$alkyl; pyridinyl; pyridinyl substituted with C$_{1-6}$alkyloxy, aryloxy or aryl; pyridinyl; quinolinyl; indole; phenyl; or phenyl substituted with one or two substituents independently selected from halo, C$_{1-6}$alkyl, C$_{1-6}$alkyloxy or trifluoromethyl;

$R^6$ is hydrogen; halo; hydroxy; amino; nitro; trihaloC$_{1-6}$alkyl; trihaloC$_{1-6}$alkyloxy; C$_{1-6}$alkyl; C$_{1-6}$alkyloxy; C$_{1-6}$alkylcarbonyl; C$_{1-6}$alkyloxycarbonyl, C$_{1-6}$alkylsulfonyl; hydroxyC$_{1-6}$alkyl; aryloxy; di(C$_{1-6}$alkyl)amino; cyano; pyridinyl; phenyl; or phenyl substituted with one or two substituents independently select from halo, C$_{1-6}$alkyl, C$_{1-6}$alkyloxy or trifluoromethyl.

Other embodiments of the compound according to embodiment [0176] (hereinafter collectively referred to as embodiment [0180]) are those in which one or more of the following apply (wherein each of $R^2$, $R^3$, and $R^4$ in this embodiment corresponds to $R^{12}$, $R^{13}$, and $R^{14}$, respectively, in embodiment [0176]):

$R^3$ and $R^4$ are each independently selected from hydrogen, hydroxy, hydroxyC$_{1-6}$alkyl, aminoC$_{1-6}$alkyl or aminoaryl;

—(A)

is a radical selected from (a-1), (a-2), (a-3), (a-4), (a-5), (a-6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-27), (a-28), (a-29), (a-30), (a-31), (a-32), (a-33), (a-34), (a-35), (a-36), (a-37), (a-38), (a-39), (a-40), (a-41), (a-42) (a-43) or (a-44);

each $R^5$ and $R^6$ are independently selected from hydrogen; halo; hydroxy; amino; nitro; trihaloC$_{1-6}$alkyl; trihaloC$_{1-6}$ alkyloxy; C$_{1-6}$alkyl; C$_{1-6}$alkyloxy; C$_{1-6}$alkyloxyC$_{1-6}$alkyloxy; C$_{1-6}$alkylcarbonyl; C$_{1-6}$alkylsulfonyl; cyanoC$_{1-6}$alkyl; hydroxyC$_{1-6}$alkyl; hydroxyC$_{1-6}$ alkyloxy; hydroxyC$_{1-6}$alkylamino; aminoC$_{1-6}$alkyloxy; di(C$_{1-6}$alkyl)aminocarbonyl; di(hydroxyC$_{1-6}$alkyl) amino; arylC$_{1-6}$alkylamino; di(C$_{1-6}$alkyl)aminoC$_{1-6}$alkyloxy, di(C$_{1-6}$alkyl)aminoC$_{1-6}$alkylamino; arylsulfonyl; arylsulfonylamino; aryloxy; arylC$_{2-6}$alkenediyl, di(C$_{1-6}$alkyl)amino di(C$_{1-6}$alkyl)aminoC$_{1-6}$alkyl; di(C$_{1-6}$ alkyl)aminoC$_{1-6}$alkyl(C$_{1-6}$alkyl)aminoC$_{1-6}$ alkyl; cyano; thiophenyl; thiophenyl substituted with di(C$_{1-6}$alkyl)aminoC$_{1-6}$alkyl(C$_{1-6}$alkyl)aminoC$_{1-6}$ alkyl, di(C$_{1-6}$alkyl)aminoC$_{1-6}$alkyl, C$_{1-6}$alkylpiperazinylC$_{1-6}$alkyl or di(C$_{1-6}$alkyl)aminoC$_{1-6}$alkyl; furanyl; imidazolyl; C$_{1-6}$alkyltriazolyl; tetrazolyl; pyrrolidinyl; piperidinylC$_{1-6}$alkyloxy; morpholinyl; C$_{1-6}$alkylmorpholinyl; morpholinylC$_{1-6}$alkyloxy; morpholinylC$_{1-6}$ alkyl; C$_{1-6}$alkylpiperazinyl; C$_{1-6}$alkylpiperazinylC$_{1-6}$ alkyloxy; C$_{1-6}$alkylpiperazinylC$_{1-6}$alkyl; C$_{1-6}$alkylpiperazinylsulfonyl; aminosulfonylpiperazinylC$_{1-6}$alkyloxy; aminosulfonylpiperazinyl; aminosulfonylpiperazinylC$_{1-6}$alkyl; di(C$_{1-6}$alkyl) aminosulfonylpiperazinyl; di(C$_{1-6}$alkyl) aminosulfonylpiperazinylC$_{1-6}$alkyl; hydroxyC$_{1-6}$ alkylpiperazinyl; hydroxyC$_{1-6}$alkylpiperazinylC$_{1-6}$ alkyl; C$_{1-6}$alkyloxypiperidinyl; C$_{1-6}$alkyloxypiperidinylC$_{1-6}$alkyl; hydroxyC$_{1-6}$alkyloxyC$_{1-6}$alkylpiperazinyl; hydroxyC$_{1-6}$alkylpiperazinylC$_{1-6}$alkyl; (hydroxyC$_{1-6}$alkyl)(C$_{1-6}$alkyl)amino; (hydroxyC$_{1-6}$alkyl) (C$_{1-6}$alkyl)aminoC$_{1-6}$alkyl; pyrrolidinylC$_{1-6}$alkyloxy; pyrazolyl; thiopyrazolyl; pyrazolyl substituted with two substituents selected from C$_{1-6}$alkyl or trihaloC$_{1-6}$alkyl; pyridinyl; pyridinyl substituted with C$_{1-6}$alkyloxy or aryl; pyrimidinyl; quinolinyl; indole; phenyl; phenyl substituted with one, two or three substituents independently selected from halo, amino, C$_{1-6}$alkyl, C$_{1-6}$alkyloxy, hydroxyC$_{1-6}$alkyl, trifluoromethyl, trifluoromethyloxy, hydroxyC$_{1-4}$alkyloxy, C$_{1-4}$alkyloxyC$_{1-4}$alkyloxy, aminoC$_{1-4}$alkyloxy, di(C$_{1-4}$alkyl)aminoC$_{1-4}$ alkyloxy, di(C$_{1-4}$alkyl)amino, di(C$_{1-4}$alkyl)aminoC$_{1-4}$ alkyl, di(C$_{1-4}$alkyl)aminoC$_{1-4}$alkyl(C$_{1-4}$alkyl)aminoC$_{1-4}$ alkyl, piperidinylC$_{1-4}$alkyloxy, pyrrolidinylC$_{1-4}$ alkyloxy, aminosulfonylpiperazinyl, aminosulfonylpiperazinylC$_{1-4}$alkyl, di(C$_{1-4}$alkyl)aminosulfonylpiperazinyl, di(C$_{1-4}$alkyl)aminosulfonylpiperazinylC$_{1-4}$alkyl, hydroxyC$_{1-4}$alkylpiperazinyl, hydroxyC$_{1-4}$alkylpiperazinylC$_{1-4}$alkyl, C$_{1-4}$alkyloxypiperidinyl, C$_{1-4}$alkyloxypiperidinylC$_{1-4}$alkyl, hydroxyC$_{1-4}$alkyloxyC$_{1-4}$alkylpiperazinyl, hydroxyC$_{1-4}$alkyloxyC$_{1-4}$alkylpiperazinylC$_{1-4}$alkyl, (hydroxyC$_{1-4}$alkyl)(C$_{1-4}$alkyl)amino, (hydroxyC$_{1-4}$alkyl)(C$_{1-4}$alkyl)aminoC$_{1-4}$alkyl, pyrrolidinylC$_{1-4}$alkyloxy, morpholinylC$_{1-4}$alkyloxy, morpholinylC$_{1-4}$alkyl, C$_{1-4}$alkylpiperazinyl, C$_{1-4}$alkylpiperazinylC$_{1-4}$alkyloxy, C$_{1-4}$alkylpiperazinylC$_{1-4}$alkyl, hydroxyC$_{1-4}$alkylamino, di(hydroxyC$_{1-4}$alkyl)amino, di(C$_{1-4}$alkyl-aminoC$_{1-4}$alkylamino, aminothiadiazolyl, aminosulfonylpiperazinylC$_{1-4}$alkyloxy, or thiophenylC$_{1-4}$alkylamino.

Other embodiments of the compound according to embodiment [0176] (hereinafter collectively referred to as embodiment [0181]) include the following (wherein each of R$^2$, R$^3$, and R$^4$ in this embodiment corresponds to R$^{12}$, R$^3$, and R$^{14}$, respectively, in embodiment [0176]):

R$^3$ and R$^4$ are each independently selected from hydrogen, hydroxy, hydroxyC$_{1-6}$alkyl, aminoC$_{1-6}$alkyl or aminoaryl;

is a radical selected from (a-1), (a-2), (a-3), (a-4), (a-5), (a 6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-27), (a-28), (a-29), (a-30), (a-31), (a-32), (a-33), (a-34), (a-35), (a-36), (a-37), (a-3), (a-39), (a-40), (a-41), (a-42) (a-43) or (a-44);

each R$^5$ and R$^6$ are independently selected from hydrogen; halo; hydroxy; amino; nitro; trihaloC$_{1-6}$alkyl; trihaloC$_{1-6}$ alkyloxy; C$_{1-6}$alkyl; C$_{1-6}$alkyloxy; C$_{1-6}$alkyloxyC$_{1-6}$alkyloxy; C$_{1-6}$alkylcarbonyl; C$_{1-6}$alkylsulfonyl; cyanoC$_{1-6}$alkyl; hydroxyC$_{1-6}$alkyl; hydroxyC$_{1-6}$alkyloxy, hydroxyC$_{1-6}$alkylamino; aminoC$_{1-6}$alkyloxy; di(C$_{1-6}$alkyl)aminocarbonyl; di(hydroxyC$_{1-6}$alkyl)amino; arylC$_{1-6}$alkyl)amino; di(C$_{1-6}$alkyl)aminoC$_{1-6}$alkyloxy; di(C$_{1-6}$alkyl)aminoC$_{1-6}$alkylamino; arylsulfonyl; arylsulfonylamino; aryloxy; arylC$_{2-6}$alkenediyl; di(C$_{1-6}$alkyl)amino; di(C$_{1-6}$alkyl)aminoC$_{1-6}$alkyl; di(C$_{1-6}$alkyl)aminoC$_{1-6}$alkyl(C$_{1-6}$alkyl)aminoC$_{1-6}$alkyl; cyano; thiophenyl; thiophenyl substituted with di(C$_{1-6}$alkyl)aminoC$_{1-6}$alkyl(C$_{1-6}$alkyl)aminoC$_{1-6}$alkyl, di(C$_{1-6}$alkyl)aminoC$_{1-6}$alkyl, C$_{1-6}$alkylpiperazinylC$_{1-6}$alkyl or di(hydroxyC$_{1-6}$alkyl)aminoC$_{1-6}$alkyl; furanyl; imidazolyl; C$_{1-6}$alkyltriazolyl; tetrazolyl; pyrrolidinyl; piperidinylC$_{1-6}$alkyloxy; morpholinyl; C$_{1-6}$alkylmorpholinyl; morpholinylC$_{1-6}$alkyloxy; morpholinylC$_{1-6}$alkyl; C$_{1-6}$alkylpiperazinyl; C$_{1-6}$alkylpiperazinylC$_{1-6}$alkyloxy; C$_{1-6}$alkylpiperazinylC$_{1-6}$alkyl; C$_{1-6}$alkylpiperazinylsulfonyl; aminosulfonylpiperazinylC$_{1-6}$alkyloxy, aminosulfonylpiperazinyl; aminosulfonylpiperazinylC$_{1-6}$alkyl; di(C$_{1-6}$alkyl)aminosulfonylpiperazinyl; di(C$_{1-6}$alkyl)aminosulfonylpiperazinylC$_{1-6}$alkyl; hydroxyC$_{1-6}$alkylpiperazinyl; hydroxyC$_{1-6}$alkylpiperazinylC$_{1-6}$alkyl; C$_{1-6}$alkyloxypiperidinyl; C$_{1-6}$alkyloxypiperidinylC$_{1-6}$alkyl; hydroxyC$_{1-6}$alkyloxyC$_{1-6}$alkylpiperazinyl; hydroxyC$_{1-6}$alkyloxyC$_{1-6}$alkylpiperazinylC$_{1-6}$alkyl; (hydroxyC$_{1-6}$alkyl)(C$_{1-6}$alkyl)amino; (hydroxyC$_{1-6}$alkyl)(C$_{1-6}$alkyl)aminoC$_{1-6}$alkyl; pyrrolidinylC$_{1-6}$alkyloxy; pyrazolyl; thiopyrazolyl; pyrazolyl substituted with two substituents selected from C$_{1-6}$alkyl or trihaloC$_{1-6}$alkyl; pyridinyl; pyridinyl substituted with C$_{1-6}$alkyloxy or aryl; pyrimidinyl; quinolinyl; indole; phenyl; phenyl substituted with one, two or three substituents independently selected from halo, amino, C$_{1-6}$alkyl, C$_{1-6}$alkyloxy, hydroxyC$_{1-6}$alkyl, trifluoromethyl, trifluoromethyloxy, hydroxyC$_{1-4}$alkyloxy, C$_{1-4}$alkyloxyC$_{1-4}$alkyloxy, aminoC$_{1-4}$alkyloxy, di(C$_{1-4}$alkyl)aminoC$_{1-4}$alkyloxy, di(C$_{1-4}$alkyl)amino, di(C$_{1-4}$alkyl)aminoC$_{1-4}$alkyl, di(C$_{1-4}$alkyl)aminoC$_{1-4}$alkyl (C$_{1-4}$ alkyl)aminoC$_{1-4}$alkyl, piperidinylC$_{1-4}$alkyloxy, pyrrolidinylC$_{1-4}$alkyloxy, aminosulfonylpiperazinyl, aminosulfonylpiperazinylC$_{1-4}$alkyl, di(C$_{1-4}$alkyl)aminosulfonylpiperazinyl, di(C$_{1-4}$alkyl)aminosulfonylpiperazinylC$_{1-4}$alkyl, hydroxyC$_{1-4}$alkylpiperazinyl, hydroxyC$_{1-4}$alkylpiperazinylC$_{1-4}$alkyl, C$_{1-4}$alkyloxypiperidinyl, C$_{1-4}$alkyloxypiperidinylC$_{1-4}$alkyl, hydroxyC$_{1-4}$alkyloxyC$_{1-4}$alkylpiperazinyl, hydroxyC$_{1-4}$ alkyloxyC$_{1-4}$alkylpiperazinylC$_{1-4}$alkyl, (hydroxyC$_{1-4}$alkyl)(C$_{1-4}$alkyl)amino, (hydroxyC$_{1-4}$alkyl)(C$_{1-4}$alkyl)aminoC$_{1-4}$alkyl, pyrrolidinylC$_{1-4}$alkyloxy, morpholinylC$_{1-4}$alkyloxy, morpholinylC$_{1-4}$alkyl, C$_{1-4}$alkylpiperazinyl, C$_{1-4}$alkylpiperazinylC$_{1-4}$alkyloxy, C$_{1-4}$alkylpiperazinylC$_{1-4}$alkyl, hydroxyC$_{1-4}$alkylamino, di(hydroxyC$_{1-4}$alkyl)amino, di(C$_{1-4}$alkyl)aminoC$_{1-4}$alkylamino, aminothiadiazolyl, aminosulfonylpiperazinylC$_{1-4}$alkyloxy, or thiophenylC$_{1-4}$alkylamino.

Other embodiments of the compound according to embodiment [0176] (hereinafter collectively referred to as embodiment [0182]) include the following (wherein each of R$^2$, R$^3$, and R$^4$ in this embodiment corresponds to R$^{12}$, R$^{13}$, and R$^{14}$, respectively, in embodiment [0176]):

t is 0;

-L- is a bivalent radical selected from —NHC(O)— or —NHSO$_2$—;

is a radical selected from (a-1), (a-3), (a-4), (a-5), (a-6), (a-7), (a-8), (a-9), (a-10), (a-11), (a-12), (a-13), (a-14), (a-15), (a-16), (a-17), (a-18), (a-19), (a-20), (a-21), (a-22), (a-23), (a-24), (a-25), (a-26), (a-28), (a-29), (a-30), (a-31), (a-32), (a-33), (a-34), (a-35), (a-36), (a-37), (a-38), (a-39), (a-40), (a-41), (a-42), (a-44), (a-45), (a-46), (a-47), (a-48) or (a-51);

each s is independently 0, 1, 2, 3 or 4;

R$^5$ is hydrogen; halo; hydroxy; amino; nitro; trihaloC$_{1-6}$alkyl; trihaloC$_{1-6}$alkyloxy; C$_{1-6}$alkyl; C$_{1-6}$alkyloxy; C$_{1-6}$alkylcarbonyl; C$_{1-6}$alkyloxycarbonyl; C$_{1-6}$alkylsulfonyl); hydroxyC$_{1-6}$alkyl; aryloxy, di(C$_{1-6}$alkyl)amino; cyano; thiophenyl; furanyl; furanyl substituted with hydroxyC$_{1-6}$alkyl; benzofuranyl; imidazolyl; oxazolyl; oxazolyl substituted with aryl and C$_{1-6}$alkyl; C$_{1-6}$alkyltriazolyl; tetrazolyl; pyrrolidinyl; pyrrolyl; morpholinyl; C$_{1-6}$alkylmorpholinyl; piperazinyl; C$_{1-6}$alkylpiperazinyl; hydroxyC$_{1-6}$alkylpiperazinyl; C$_{1-6}$alkyloxypiperidinyl; pyrazoyl; pyrazolyl substituted with one or two substituents selected from C$_{1-6}$alkyl or trihaloC$_{1-6}$alkyl; pyridinyl; pyridinyl substituted with C$_{1-6}$alkyloxy or aryl; pyrimidinyl; quinolinyl; indole; phenyl; or phenyl substituted with one or two substituents independently selected from halo, $C_{1-6}$alkyl, $C_{1-6}$alkyloxy or trifluoromethyl;

and $R^6$ is hydrogen; halo; hydroxy; amino; nitro; trihalo$C_{1-6}$ alkyl; trihalo$C_{1-6}$alkyloxy; $C_{1-6}$alkyl; $C_{1-6}$alkyloxy; $C_{1-6}$alkylcarbonyl; $C_{1-6}$alkyloxycarbonyl; $C_{1-6}$alkylsulfonyl; hydroxy$C_{1-6}$alkyl; aryloxy; di($C_{1-6}$alkyl)amino; cyano; pyridinyl; phenyl; or phenyl substituted with one or two substituents independently selected from halo, $C_{1-6}$alkyl, $C_{1-6}$alkyloxy or trifluoromethyl.

Other embodiments of the compound according to embodiment [0176] (hereinafter collectively referred to as embodiment [0183]) include the following (wherein each of $R^2$, $R^3$, and $R^4$ in this embodiment corresponds to $R^{12}$, $R^{13}$, and $R^{14}$ respectively, in embodiment [0176]):

t is 0 or 1; Q is

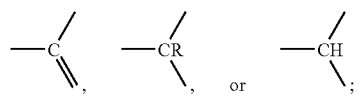

X is nitrogen
$R^{12}$ is hydrogen, hydroxy, $C_{1-6}$alkyl or $C_{1-6}$alkyl; -L- is a bivalent radical selected from
—NHC(O)— or —NHSO$_2$—;

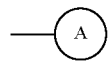

is a radical selected from (a-1) or (a-20); each s is independently 0 or 1; and each $R^5$ is independently selected from hydrogen or phenyl.

Other embodiments of the compound according to embodiment [0176] (hereinafter collectively referred to as embodiment [0184]) include the following (wherein each of $R^2$, $R^3$, and $R^4$ in this embodiment corresponds to $R^{12}$, $R^{13}$, and $R^{14}$, respectively, in embodiment [0176]):

t is 1; Q is

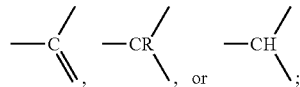

X is nitrogen; Y is nitrogen; Z is —O— or —CH$_2$—;
$R^2$ is hydrogen; -L- is a bivalent radical selected from
—NHC(O)— or —NHSO$_2$—;

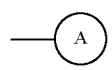

is a radical selected from (a-1) or (a-20); each s is independently 0 or 1; and each $R^5$ is independently selected from hydrogen or phenyl.

Particular embodiments of the compound according to embodiment [0176] (hereinafter collectively referred to as embodiment [0185]) include the following

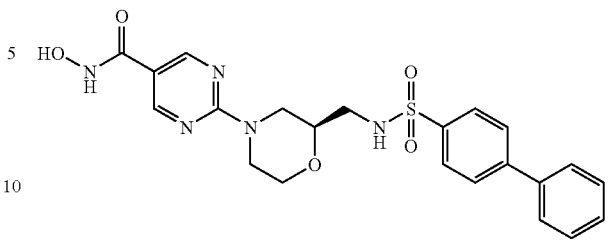

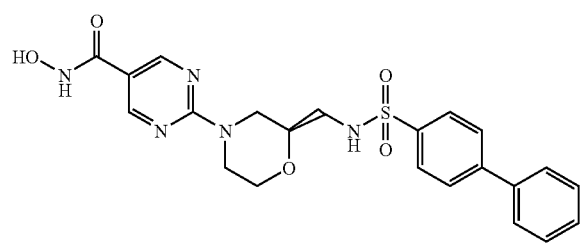

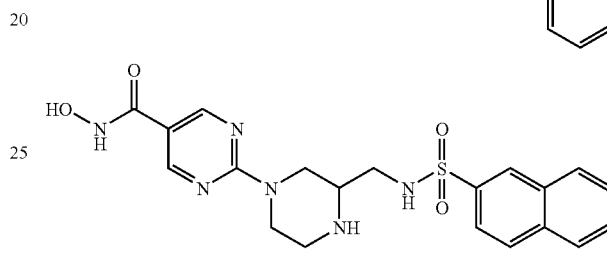

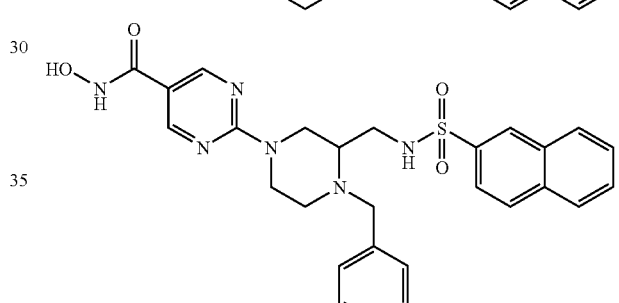

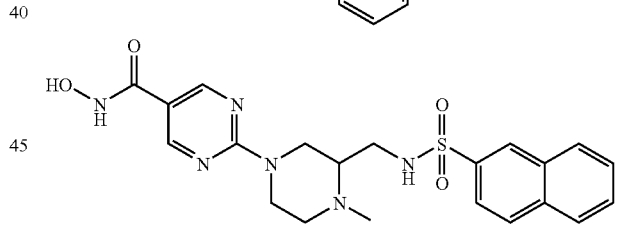

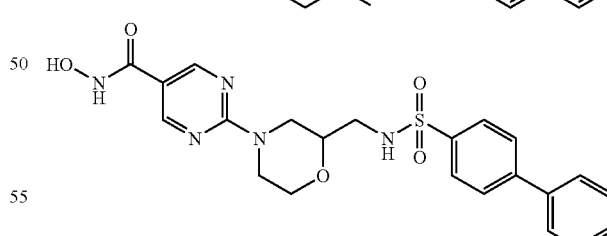

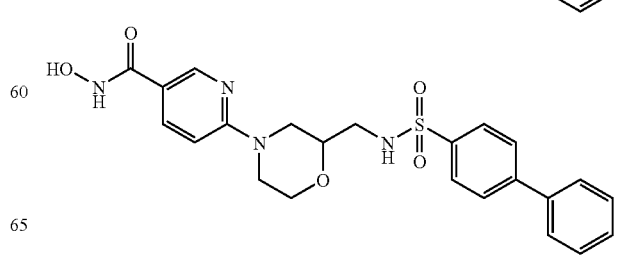

-continued

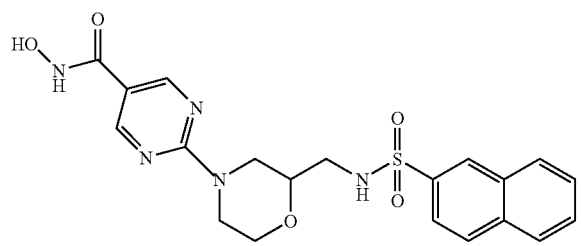
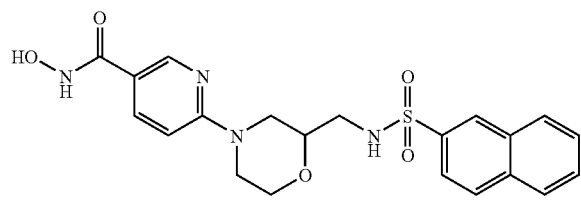
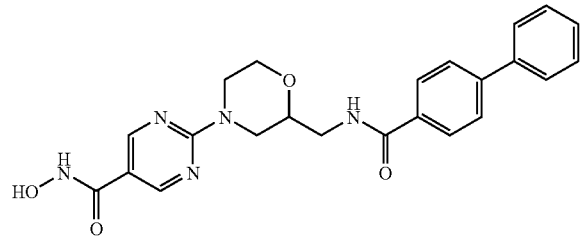
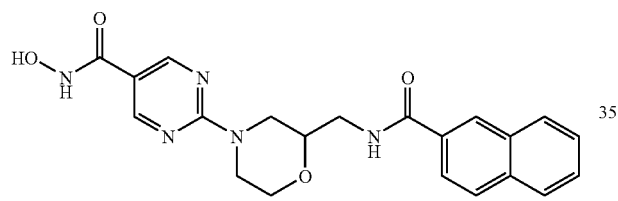
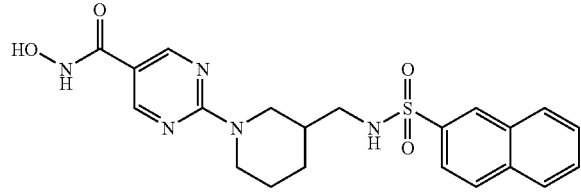
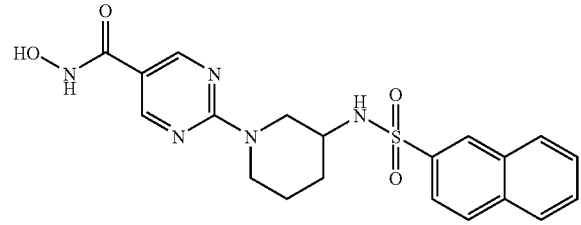
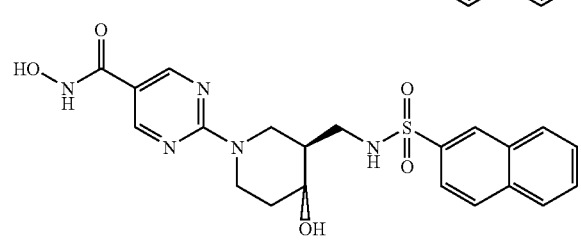

in which the terminal hydroxamic acid moiety (—C(O)NH—OH) is replaced with

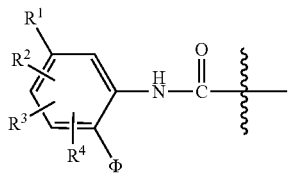

wherein Φ, $R^1$, $R^2$, $R^3$, and $R^4$ are as defined in accordance with embodiment [0046], and preferably embodiments [0048] and [0049].

In the compounds of embodiments [0176]-[0185], $R^1$, $R^2$, $R^3$, and $R^{41}$ are preferably as defined in embodiments [0048] and [0049]. In other embodiments of the compounds of embodiments [0176]-[0185], $R^1$, $R^2$, $R^3$, and $R^4$ are all H. Such embodiments are hereinafter collectively referred to as embodiment [0186].

In another embodiment, the invention comprises compounds of the following structural formula (12) (hereinafter embodiment [0187]):

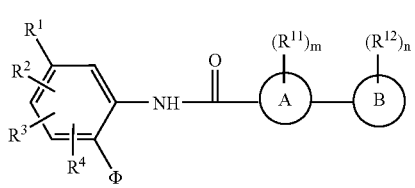

(12)

or a pharmaceutically acceptable salt thereof, wherein
Φ is —$NH_2$ or —OH;
$R^1$ is H or as defined in embodiment [0046];
$R^2$, $R^3$, and $R^4$ are as defined in embodiment [0046];
Ring A is a heterocyclyl, wherein if said heterocyclyl contains an —NH— moiety that nitrogen may be optionally substituted by a group selected from G;
$R^{11}$ is a substituent on carbon and is selected from halo, nitro, cyano, hydroxy, oxo, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkyloxy, $C_{1-6}$alkanoyl, $C_{1-6}$alkanoyloxy, N—($C_{1-6}$alkyl)amino, N,N—($C_{1-6}$alkyl)amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, aryl, aryloxy, aryl$C_{1-6}$alkyl, heterocyclic group, (heterocyclic group)$C_{1-6}$alkyl or a group (D-E-); wherein $R^1$, including group (D-E-), may be optionally substituted on carbon by one or more V; and wherein, if said heterocyclic group contains an —NH— moiety that nitrogen may be optionally substituted by a group selected from J;
V is halo, nitro, cyano, hydroxy, oxo, trifluoromethyl, trifluoromethoxy, amino, carboxy, carbamoyl, mercapto, sulphamoyl, $C_{1-6}$alkyl, $C_{2-4}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—$C_{1-6}$alkyl)carbamoyl, N,N—($C_{1-6}$alkyl) carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl or a group (D'-E'-);

wherein V, including group (D'-E'-), may be optionally substituted on carbon by one or more W;

W and Z are independently selected from halo, nitro, cyano, hydroxy, oxo, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)carbamoyl, $C_{1-6}$alkylS(O)$_a$ wherein a is 0 to 2, $C_{1-6}$alkoxycarbonyl, N—($C_{1-6}$alkyl)sulphamoyl or N,N—($C_{1-6}$alkyl)$_2$sulphamoyl;

G, J and K are independently selected from $C_{1-8}$alkyl, $C_{2-8}$alkenyl, $C_{2-8}$alkynyl, $C_{1-8}$alkanoyl, $C_{1-8}$alkylsulphonyl, $C_{1-8}$alkoxycarbonyl, carbamoyl, N—($C_{1-8}$alkyl)carbamoyl, N,N—($C_{1-8}$alkyl)carbamoyl, benzyloxycarbonyl, benzoyl and phenylsulphonyl, aryl, aryl$C_{1-6}$alkyl or (heterocyclic group)$C_{1-6}$alkyl; wherein G, J and K may be optionally substituted on carbon by one or more Q; and wherein if said heterocyclic group contains an —NH— moiety that nitrogen may be optionally substituted by a group selected from hydrogen or $C_{1-6}$alkyl;

Q is halo, nitro, cyano, hydroxy, oxo, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkyloxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, aryl, aryloxy, aryl$C_{1-6}$alkyl, aryl$C_{1-6}$alkyloxy, heterocyclic group, (heterocyclic group)$C_{1-6}$alkyl, (heterocyclic group)$C_{1-6}$alkyloxy, or a group (D"-E"-); wherein Q, including group (D"-E"-), may be optionally substituted on carbon by one or more Z;

D, D' and D" are independently selected from $C_{1-6}$alkyl, $C_{1-6}$alkenyl, $C_{1-6}$alkynyl, $C_{3-8}$cycloalkyl, $C_{3-8}$cycloalkyl$C_{1-6}$alkyl, aryl, aryl$C_{1-6}$alkyl, heterocyclic group, (heterocyclic group) $C_{1-6}$alkyl; wherein D, D' and D" may be optionally substituted on carbon by one or more F'; and wherein if said heterocyclic group contains an —NH— moiety that nitrogen may be optionally substituted by a group selected from K;

E, E' and E" are independently selected from —N(R$^a$)—, —O—, —C(O)O, —OC(O)—, —C(O)—, —N(R$^a$)C(O)—, —N(R$^a$)C(O)N(R$^b$)—, —N(R$^a$)C(O)O—, —OC(O)N(R$^a$)—, —C(O)N(R$^a$)—, —S(O)$_r$, —SO$_2$N(R$^a$)—, —N(R$^a$)SO$_2$—; wherein R$^a$ and R$^b$ are independently selected from hydrogen or $C_{1-6}$alkyl optionally substituted by one or more F and r is 0-2;

F and F' are independently selected from halo, nitro, cyano, hydroxy, trifluoromethyl, trifluoromethoxy, amino, carboxy, carbamoyl, mercapto, sulphamoyl, $C_{1-6}$alkyl, $C_{1-6}$alkenyl, $C_{2-6}$alkynyl, $C_{1-6}$alkyloxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl;

m is 0, 1, 2, 3 or 4; wherein the values of R$^1$ may be the same or different;

Ring B is a ring selected from

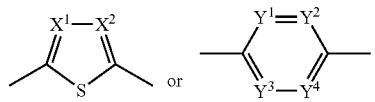

wherein,
$X^1$ and $X^2$ are selected from CH or N, and
$Y^1, Y^2, Y^3$ and $Y^4$ are selected from CH or N provided that at least one of $Y^1, Y^2, Y^3$ and $Y^4$ is N
$R^{12}$ is halo;
n is 0, 1, or 2, wherein the values of $R^{12}$ are the same or different.

In some embodiments of the compound according to embodiment [0187] (hereinafter collectively referred to as embodiment [0188]), Ring A is a pyridyl, quinolyl, indolyl pyrimidinyl, morpholinyl, piperidinyl, piperazinyl, pyridazinyl, pyrazinyl, thiazolyl, thienyl, thienopyrimidinyl, thienopyridinyl, purinyl, 1',2',3',6'-tetrahydropyridinyl, triazinyl, oxazolyl, pyrazolyl, or furanyl; wherein if Ring A contains an —NH— moiety that nitrogen may be optionally substituted by a group selected from G.

Ring A is pyridin-4-yl, pyridin-3-yl, pyridin-2-yl, quinolin-8-yl, pyrimidin-6-yl, pyrimidin-5-yl, pyrimidin-4-yl, morpholin-4-yl, piperidin-4-yl, piperidin-3-yl, piperidin-2-yl, piperazin-4-yl, pyridazin-5-yl, pyrazin-6-yl, thiazol-2-yl, thien-2-yl, thieno[3,2d]pyrimidinyl, thieno[3,2b]pyrimidinyl, thieno[3,2b]pyridinyl, purin-6-yl, 1',2',3',6'-tetrahydropyridin-4-yl Ring A is pyridinyl, pyridin-3-yl, pyridin-2-yl, quinolin-8-yl, pyrimidin-6-yl, pyrimidin-5-yl, pyrimidin-4-yl, morpholin-4-yl, piperidin-4-yl, piperidin-3-yl, piperidin-2-yl, piperazin-4-yl, pyridazin-5-yl, pyrazin-6-yl, thiazol-2-yl, thien-2-yl, thieno[3,2-d]pyrimidinyl, thieno[3,2b]pyridinyl, thieno[3,2b]pyridinyl, purin-6-yl, 1',2',3',6'-tetrahydropyridin-4-yl or triazin-6-yl; wherein if Ring A contains an —NH— moiety that nitrogen may be optionally substituted by a group selected from G.

Ring A is pyridin-4-yl, pyridin-3-yl, pyridin-2-yl, morpholin-4-yl, piperidin-4-yl, piperidin-3-yl, piperidin-2-yl, piperazin-4-yl, thiazol-2-yl, thien-2-yl, furan-3-yl, pyrrolidin-1-yl, piperidin-1-yl, thiazol-1-yl or 1',2',3',6'-tetrahydropyridinyl wherein if Ring A contains an —NH— moiety that nitrogen may be optionally substituted by a group selected form G.

Ring A is a pyridyl, pyrimidyl, morpholinyl, piperidinyl, piperazinyl, pyridazinyl, thienyl, pyrazinyl, thiazolyl, 1,2,4-triazolyl or furanyl.

Ring A is pyridin-4-yl, pyridin-3-yl, pyridin-2-yl or 1,2,4-triazolyl.

Ring B is thienyl, thiadiazolyl, thiazolyl, pyrimidyl, pyrazinyl, pyridazinyl or pyridyl.

Ring B is thienyl, thiazolyl, pyrimidyl, pyrazinyl, pyridazinyl or pyridyl.

Ring B is thienyl or pyridyl.

Ring B is thienyl or pyridyl wherein both the thienyl and the pyridyl are attached to Ring A in the 2-position of the thienyl or pyridyl ring and to the amide group of formula (I) in the 5-position of the thienyl or pyridyl ring.

$R^{11}$ is halo, amino, $C_{1-6}$alkyl, $C_{1-6}$alkoxy, $C_{1-3}$alkanoyloxy, N—($C_{1-3}$alkyl)amino, N,N—($C_{1-3}$alkyl)$_2$amino, $C_{1-3}$alkanoylamino, N—($C_{1-3}$alkyl)carbamoyl, N—($C_{1-3}$alkyl)carbamoyl.

$R^{11}$ is halo, amino, $C_{1-6}$alkyl or $C_{1-6}$alkoxy.

$R^{11}$ is halo, amino, methyl or methoxy.

$R^{11}$ is A substituent on carbon and is selected from halo, nitro, cyano, hydroxy, oxo, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, aryl, aryloxy, aryl$C_{1-6}$alkyl, heterocyclic group, (heterocyclic group)$C_{1-6}$alkyl or a group (D-E-); wherein $R^1$, including group (D-E-), may be optionally substituted on carbon by one or more V; and wherein, if said heterocyclic group contains an —NH— moiety that nitrogen may be optionally substituted by a group selected from J;

V is halo, nitro, cyano, hydroxy, oxo, trifluoromethyl, trifluoromethoxy, amino, carboxy, carbamoyl, mercapto, sulphamoyl, $C_{1-6}$alkyl, $C_{2-6}$alkenyl, $C_{1-6}$alkynyl, $C_{1-6}$alkyloxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl or a group (D'-E'-); wherein V, including group (D'-E'-), may be optionally substituted on carbon by one or more W;

W and Z are independently selected from halo, nitro, cyano, hydroxy, oxo, trifluoromethyl, trifluoromethoxy, amino, carboxy, carbamoyl, mercapto, sulphamoyl, $C_{1-6}$alkyl, $C_{2-6}$alkenyl, $C_{1-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl or N,N—($C_{1-6}$alkyl)sulphamoyl;

G, J and K are independently selected from $C_{1-8}$alkyl, $C_{2-8}$alkenyl, $C_{2-8}$alkynyl, $C_{1-8}$alkanoyl, $C_{1-8}$alkylsulphonyl, $C_{1-8}$alkoxycarbonyl, carbamoyl, N—($C_{1-8}$alkyl)carbamoyl N,N—($C_{1-8}$alkyl)carbamoyl, benzyloxycarbonyl, benzoyl and phenylsulphonyl, aryl, aryl$C_{1-6}$alkyl or (heterocyclic group)$C_{1-6}$alkyl; wherein G, J and K may be optionally substituted on carbon by one or more Q; and wherein if said heterocyclic group contains an —NH— moiety that nitrogen may be optionally substituted by a group selected from hydrogen or $C_{1-6}$alkyl;

Q is halo, nitro, cyano, hydroxy, oxo, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, aryl, aryloxy, aryl$C_{1-6}$alkyl, aryl$C_{1-6}$alkoxy, heterocyclic group, (heterocyclic group)$C_{1-6}$alkyl, (heterocyclic group)$C_{1-6}$alkyloxy, or a group (D'-E'-); wherein Q, including group (D'-E'-), may be optionally substituted on carbon by one or more Z;

D, D' and D" are independently selected from $C_{1-6}$alkyl, $C_{1-6}$alkenyl, $C_{1-6}$alkynyl, $C_{3-8}$cycloalkyl, $C_{3-8}$cycloalkyl, aryl, aryl$C_{1-6}$alkyl, heterocyclic group, (heterocyclic group)$C_{1-6}$alkyl; wherein D, D' and D" may be optionally substituted on carbon by one or more F'; and wherein if said heterocyclic group contains an —NH— moiety that nitrogen may be optionally substituted by a group selected from K;

E, E' and E" are independently selected from —N($R^a$)—, —O—, —C(O)O—, —OC(O)—, —C(O)—, —N($R^a$)C(O)—, —N($R^a$)C(O)N($R^b$)—, —N(O)C(O)O—, —OC(O)N($R^a$)—, —C(O)N($R^a$)—, —S(O)$_r$—, —SO$_2$N($R^a$)—, —N($R^a$)SO$_2$—; wherein $R^a$ and $R^b$ are independently selected from hydrogen or $C_{1-6}$alkyl optionally substituted by one or more F and r is 0-2; and F and F' are independently selected from halo, nitro, cyano, hydroxy, trifluoromethyl, trifluoromethoxy, amino, carboxy, carbamoyl, mercapto, sulphamoyl, $C_{1-6}$alkyl, $C_{2-4}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl.

$R^{11}$ is a substituent on carbon and is selected from cyano, hydroxy, $C_{1-6}$alkyl or a group (D-E); wherein $R^{11}$ including group (D-E), may be optionally substituted on carbon by one or more V;

V is cyano, hydroxy or a group (D'-E'-); wherein V, including group (D'-E'-), may be optionally substituted an carbon by one or more W;

W and Z are independently selected from cyano, $C_{1-6}$alkyl or $C_{1-6}$alkyloxy;

G and K a independently selected from $C_{1-8}$alkyl, $C_{2-8}$alkenyl, $C_{2-8}$alkynyl, aryl$C_{1-6}$alkyl or (heterocyclic group) $C_{1-6}$alkyl; wherein G and K may be optionally substituted on carbon by one or more Q, Q is cyano, hydroxy, oxo, $C_{1-6}$alkyl, $C_{1-6}$alkenyl, $C_{1-6}$alkoxy, $C_{1-6}$alkanoyl, $C_{1-6}$alkanoyloxy, N—($C_{1-6}$ alkyl)carbamoyl, N,N—($C_{1-6}$alkyl)$_2$carbamoyl, $C_{1-6}$alkoxycarbonyl, $C_{1-6}$alkoxycarbonylamino, aryl, aryloxy or a group (D"-E"-); wherein Q, including group (D"-E"-), may be optionally substituted on carbon by one or more Z;

D, D' and D" are independently selected from aryl, aryl$C_{1-6}$alkyl or heterocyclic group; wherein D, D' and D" may be optionally substituted on carbon by one or more F'; an wherein if said heterocyclic group contains an —NH— moiety that nitrogen may be optionally substituted by a group selected from K;

E, E' and E" are independently selected from —O—, —C(O)O—, —OC(O)—, (O)—, —N($R^a$)(C(O), —C(O)N($R^a$)—, —S(O)$_r$: wherein $R^a$ is selected from hydrogen or $C_{1-6}$alkyl optionally substituted by one or more F and r is 0-2; and F and F' are independently selected from nitro, hydroxy, $C_{1-6}$alkyl, $C_{1-6}$alkoxy, $C_{1-6}$alkanoyl, N—($C_{1-6}$alkyl)amino, N,N—($C_{1-6}$alkyl)$_2$amino, $C_{1-6}$alkanoylamino or $C_{1-6}$alkoxycarbonyl.

m is 0, 1, 2, 3 or 4; whereto the values of $R^{11}$ are the same or different m is 0, 1, or 2; wherein the values of $R^{11}$ are the same or different.

m is 0.

m is 1.

$R^{12}$ is halo.

a $R^{12}$ is fluoro.

$R^{12}$ is chloro.

n is 0, 1, or 2; wherein the values of $R^{12}$ are the same or different;

n is 0;

n is 1.

Other embodiments of the compound according to embodiment [0187] (hereinafter collectively referred to as embodiment [0189]) include the following (wherein each of $R^2$ in this embodiment corresponds to $R^{12}$ in embodiment [0187]):

Ring A is a pyridyl, indolyl, pyrimidyl, morpholinyl, piperidinyl, piperazinyl, pyridazinyl, thienyl, pyrazinyl, thiazolyl, oxazolyl, 1,2,4-thiazolyl, isoxazolyl, isothiazolyl, pyrazolyl, or furanyl;

Ring B is thienyl, thiadiazolyl, thiazolyl, pyrimidyl, pyrazinyl, pyridazinyl or pyridyl;

$R^{11}$ is halo, amino, $C_{1-6}$alkyl, $C_{1-6}$alkoxy, $C_{1-3}$alkanoyloxy, N—($C_{1-3}$alkyl)amino, N,N—($C_{1-6}$alkyl)amino, $C_{1-3}$alkanoylamino, N—($C_{1-3}$alkyl)carbonyl, N,N—($C_{1-3}$alkyl)$_2$carbamoyl;

m is 0, 1, 2, wherein the values of $R^{11}$ are the same or different.

n is 0, 1, 2, wherein the values of $R^{12}$ are the same or different;

$R^{12}$ is F or Cl.

Other embodiments of the compound according to embodiment [0187] (hereinafter collectively referred to as embodiment [0190]) include the following (wherein each of $R^2$ in this embodiment corresponds to $R^{12}$ in embodiment [0187]):

Ring A is pyridin-4-yl, pyridin-3-yl, pyridin-2-yl or 1,2,4-triazolyl;

Ring B is thienyl or pyridyl;

$R^{11}$ is halo, amino, methyl or methoxy;

m is 0, 1, 2, wherein the values of $R^{11}$ are the same or different.

n is 0 or 1;

$R^{12}$ is F.

Other embodiments of the compound according to embodiment [0187] (hereinafter collectively referred to as embodiment [0191]) include the following (wherein each of $R^2$ in this embodiment corresponds to $R^{12}$ in embodiment [0187]):

Ring A is a pyridyl, quinolyl, indolyl, pyrimidinyl, morpholinyl, piperidinyl, piperazinyl, pyridazinyl, pyrazinyl, thiazolyl, thienyl, thienopyrimidinyl, thienopyridinyl, purinyl, 1',2',3',6'-tetrahydropyridinyl, triazinyl, oxazolyl, pyrazolyl, or furanyl; wherein if Ring A contains an —NH— moiety that nitrogen may be optionally substituted by a group selected from G;

Ring B is thienyl, thiadiazolyl, thiazolyl, pyrimidyl, pyrazinyl, pyridazinyl or pyridyl;

$R^{11}$ is a substituent on carbon and is selected from halo, nitro, cyano, hydroxy, oxo, trifluoromethyl, trifluoromethoxy, amino, carboxy, carbamoyl, mercapto, sulphamoyl $C_{1-6}$alkyl, $C_{2-6}$alkenyl, $C_{1-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, aryl, aryloxy, aryl$C_{1-6}$alkyl, heterocyclic group, (heterocyclic group)$C_{1-6}$alkyl or a group (D-E-); wherein $R^1$, including group (D-E-), may be optionally substituted on carbon by one or more V; and wherein, if said heterocyclic group contains an —NH— moiety that nitrogen may be optionally substituted by a group selected from J;

V is halo, nitro, cyano, hydroxy, oxo, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—$C_{1-6}$alkyl)carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl or a group (D'-E'-); wherein V, including group (D'-E'-), may be optionally substituted on carbon by one or more W;

W and Z are independently selected from halo, nitro, cyano, hydroxy, oxo, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl or N,N—($C_{1-6}$alkyl)$_2$sulphamoyl;

G, J and K are independently selected from $C_{1-8}$alkyl, $C_{2-8}$-alkenyl, $C_{2-8}$alkynyl, $C_{1-8}$alkanoyl, $C_{1-8}$alkylsulphonyl, $C_{1-8}$alkoxycarbonyl, carbamoyl, N—($C_{1-8}$alkyl)carbamoyl, N,N—($C_{1-8}$alkyl)carbamoyl, benzyloxycarbonyl benzoyl and phenylsulphonyl, aryl, aryl$C_{1-6}$alkyl or (heterocyclic group)$C_{1-6}$alkyl; wherein G, J and K may be optionally substituted on carbon by one or more Q; and wherein if said heterocyclic group contains an —NH— moiety that nitrogen may be optionally substituted by a group selected from hydrogen or $C_{1-6}$alkyl;

Q is halo, nitro, cyano, hydroxy, oxo, trifluoromethyl, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, $C_{1-6}$alkoxycarbonylamino, N—($C_{1-6}$alkyl)sulphamoyl, N,N—($C_{1-6}$alkyl)$_2$sulphamoyl, aryl, aryloxy, aryl$C_{1-6}$alkyl, aryl$C_{1-6}$alkoxy, heterocyclic group, (heterocyclic group)$C_{1-6}$alkyl, (heterocyclic group)$C_{1-6}$alkoxy, or a group (D'-E'-); wherein Q, including group (D''-E''-), may be optionally substituted on carbon by one or more Z;

D, D' and D'' are independently selected from $C_{1-6}$alkyl, $C_{1-6}$alkenyl, $C_{2-6}$alkynyl, $C_{3-8}$cycloalkyl, $C_{3-8}$cycloalkyl$C_{1-6}$alkyl, aryl, aryl$C_{1-6}$alkyl, heterocyclic group, heterocyclic group)$C_{1-6}$alkyl; wherein D, D' and D'' may be optionally substituted on carbon by one or more F'; and wherein if said heterocyclic group contains an —NH— moiety that nitrogen may be optionally substituted by a group selected from K;

E, E' and E'' are independently selected from —N($R^a$)—, —O—, —C(O)O, —OC(O)—, —C(O)—, —N($R^a$)C(O)—, —N($R^a$)C(O)N($R^b$)—, —N($R^a$)C(O)O—, —OC(O)N($R^a$)—, —C(O)N($R^a$)—, S(O)$_r$—, —SO$_2$N($R^a$)—, —N($R^a$)SO$_2$—; wherein $R^a$ and $R^b$ are independently selected from hydrogen or $C_{1-6}$alkyl optionally substituted by one or more F and r is 0-2;

F and F' are independently selected from halo, nitro, cyano, hydroxy, trifluoromethyl, trifluoromethoxy, amino, carboxy, carbamoyl, mercapto, sulphamoyl, $C_{1-6}$alkyl, $C_{1-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl;

m is 0, 1, 2, 3, or 4, wherein the values of $R^{11}$ are the same or different;

$R^{12}$ is F or Cl;

n is 0, 1, or 2, wherein the values of $R^{12}$ are the same or different.

Other embodiments of the compound according to embodiment [0187] (hereinafter collectively referred to as embodiment [0192]) include the following (wherein each of $R^2$ in this embodiment corresponds to $R^{12}$ in embodiment [0187]):

Ring A is pyridinyl, pyridin-3-yl, pyridin-2-yl, morpholin-4-yl, piperidin-4-yl, piperidin-3-yl, piperidin-2-yl, piperazin-4-yl, thiazol-2-yl, thien-2-yl, furan-3-yl, pyrrolidin-1-yl, piperidin-1-yl, thiazol-1-yl or 1',2',3',6'-tetrahydropyridinyl wherein if Ring A contains an —NH— moiety that nitrogen may be optionally substituted by a group selected from G;

Ring B is thienyl, thiazolyl, pyrimidyl pyrazinyl, pyridazinyl or pyridyl;

$R^{11}$ is a substituent on carbon and is selected from cyano, hydroxy, $C_{1-6}$alkyl or a group (D-E-); wherein $R^{11}$, including group (D-E-), may be optionally substituted on carbon by one or more V;

W and Z are independently selected from cyano, $C_{1-6}$alkyl or $C_{1-6}$alkoxy;

G and K are independently selected from $C_{1-8}$alkyl, $C_{2-8}$alkenyl, $C_{2-8}$alkynyl, aryl$C_{1-6}$alkyl or (heterocyclic group) $C_{1-6}$alkyl; wherein G and K may be optionally substituted on carbon by one or more Q;

Q is cyano, hydroxy, oxo, $C_{1-6}$alkyl, $C_{2-6}$alkenyl, $C_{1-6}$alkoxy, $C_{1-6}$alkanoyl, $C_{1-6}$alkanoyloxy, N—($C_{1-6}$alkyl)carbamoyl, N,N—($C_{1-6}$alkyl)carbamoyl, $C_{1-6}$alkoxycarbonyl, $C_{1-6}$alkoxycarbonylamino, aryl, aryloxy or a group (D"-E"-); wherein Q, including group (D"-F"-), may be optionally substituted on carbon by one or more Z;

D, D' and D" are independently selected from aryl, aryl$C_{1-6}$alkyl or heterocyclic group; wherein D, D' and D" may be optionally substituted on carbon by one or more F'; and wherein if said heterocyclic group contains an —NH— moiety that nitrogen may be optionally substituted by a group selected from K;

E, E' and E" are independently selected from —O—, —C(O)O—, —OC(O)—, —C(O)—, —N($R^a$)C(O)—, —C(O)N($R^a$)—, —S(O)$_r$—; wherein $R^a$ is selected from hydrogen or $C_{1-6}$alkyl optionally substituted by one or more F and r is 0-2;

F and F' are independently selected from nitro, hydroxy, $C_{1-6}$alkyl, $C_{1-6}$alkoxy, $C_{1-6}$alkanoyl, N—($C_{1-6}$alkyl)amino, N,N—($C_{1-6}$alkyl)amino, $C_{1-6}$alkanoylamino or $C_{1-6}$alkoxycarbonyl;

m is 0, 1, or 2, wherein the values of $R^{11}$ are the same or different;

$R^{12}$ is F;

n is 0 or 1.

The following are particular embodiments of the compounds according to embodiment [0187] (hereinafter collectively referred to as embodiment [0193]):

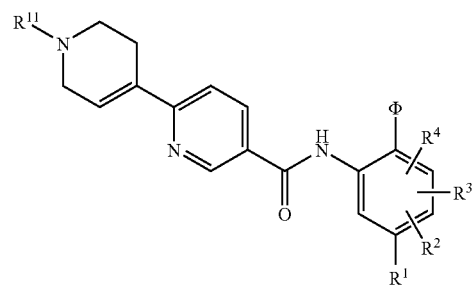

wherein $R^{11}$ is selected from:

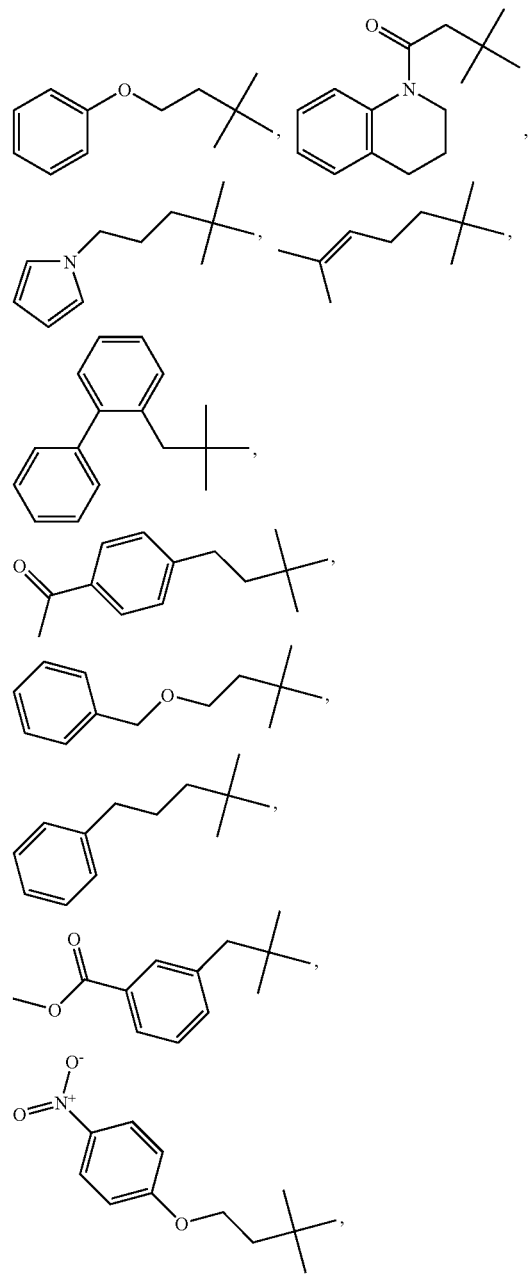

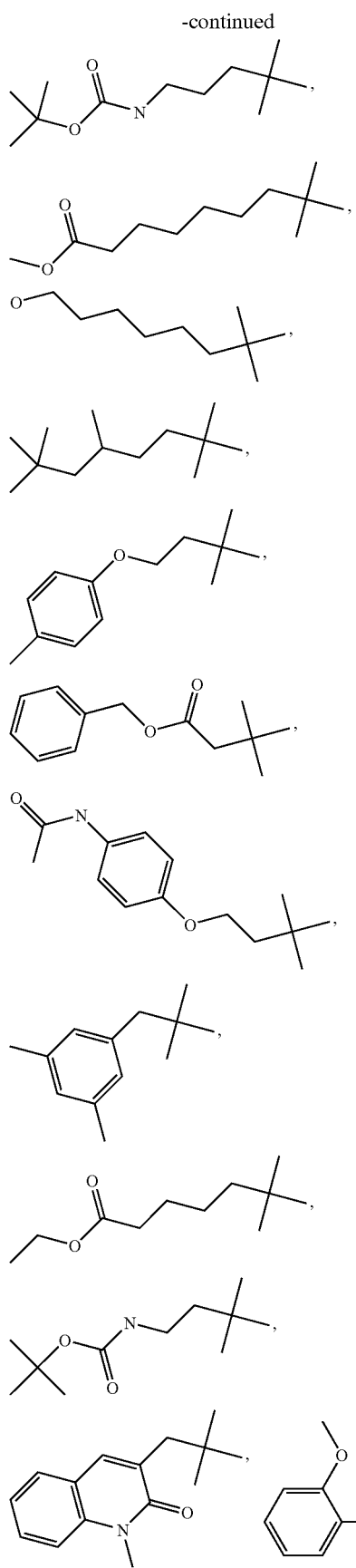
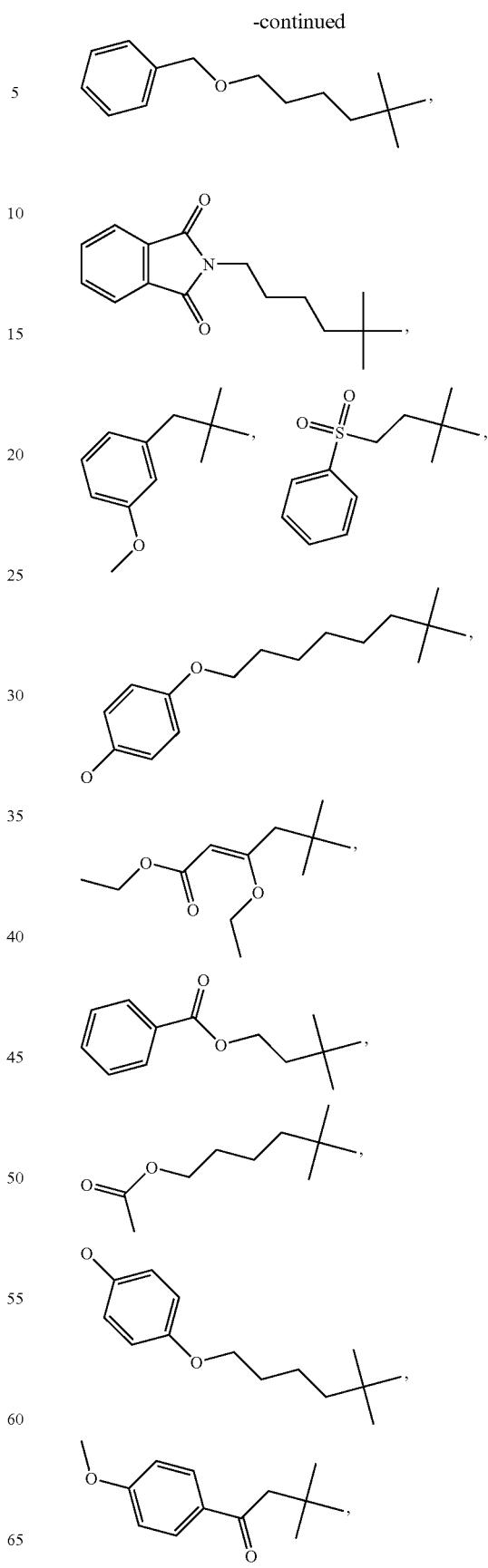

-continued

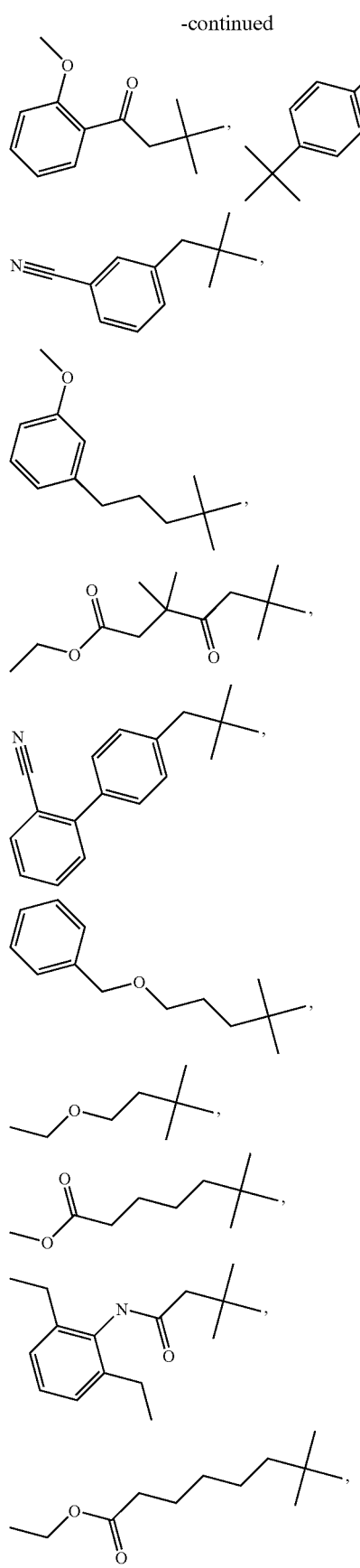

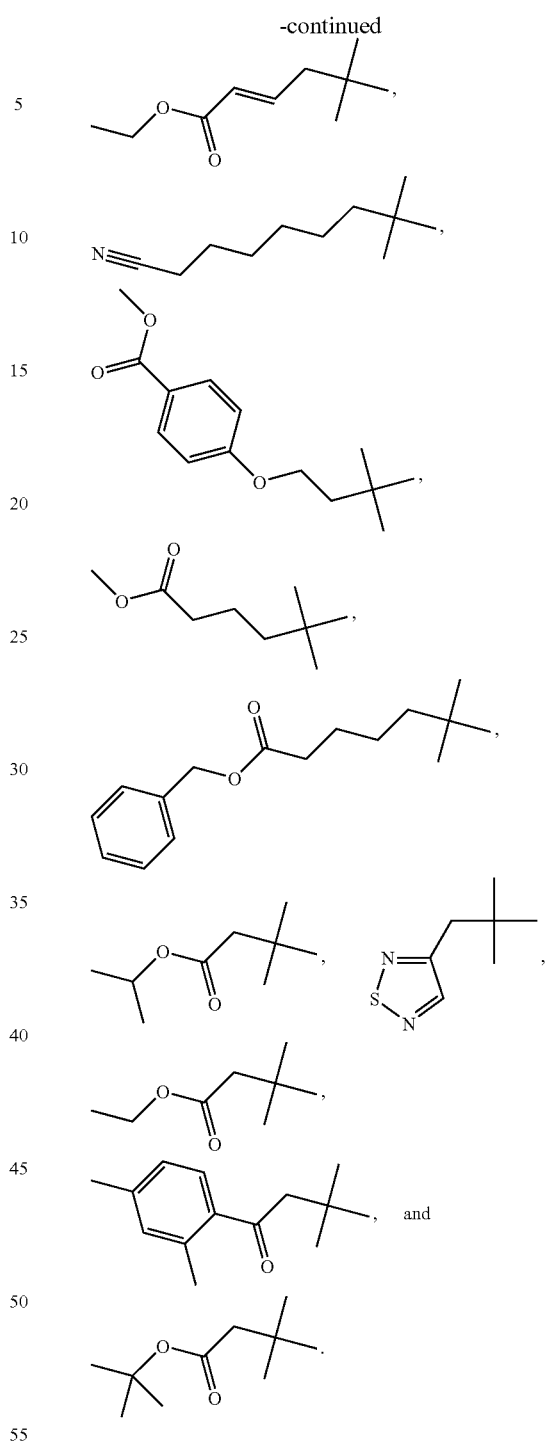

In the compounds of embodiment [0187]-[0193], $R^1$, $R^2$, $R^3$, and $R^4$ are preferably as defined in embodiments [0048] and [0049]. In other embodiments of the compounds of embodiments [0187]-[0193], $R^1$, $R^2$, $R^3$, and $R^4$ are all H. Such embodiments are hereinafter collectively referred to as embodiment [0194].

In another embodiment (hereinafter embodiment [0195]), the invention comprises the compounds of WO 03/024448 in which the terminal moieties —C(O)—NH-Ay$^1$, —C(O)NH-Ay$^2$, —C(O)NH—Ar$^a$—NH$_2$, and:

are replaced with the moiety:

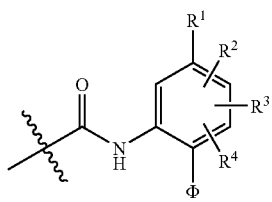

wherein Φ, $R^1$, $R^2$, $R^3$, and $R^4$ are as defined in accordance with embodiment [0046], and preferably embodiments [0048] and [0049].

In another embodiment, (hereinafter embodiment [0196]), the invention comprises compounds of the following structural formula (13):

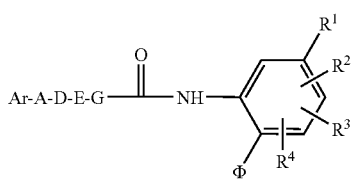

(13)

or a pharmaceutically acceptable salt thereof, wherein
Φ is —$NH_2$ or —OH;
$R^1$ is H or as defined in embodiment [0046];
$R^2$, $R^3$, and $R^4$ are as defined in embodiment [0046]; and
Ar, A, D, E, and G are as defined in JP 2003137866.

In the compounds of embodiment [0196], $R^1$, $R^2$, $R^3$, and $R^4$ are preferably as defined in embodiments [0048] and [0049]. In other embodiments of the compounds of embodiment [0196], $R^1$, $R^2$, $R^3$, and $R^4$ are all H. Particular embodiments of the compounds of embodiment [0196] are those obtained by substituting the terminal moiety:

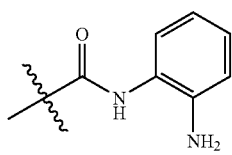

of the compounds of JP 2003137866 with the moiety:

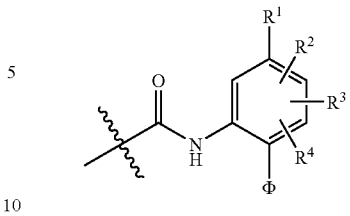

wherein Φ, $R^1$, $R^2$, $R^3$, and $R^4$ are as defined in accordance with embodiment [0046], and preferably embodiments [0048] and [0049]. Such embodiments are hereinafter collectively referred to as embodiment [0197].

In another embodiment, the invention comprises compounds of the following structural formula (14) (hereinafter embodiment [0198]):

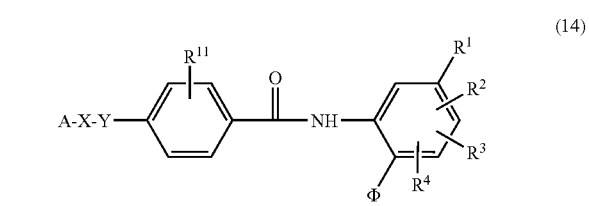

(14)

or a pharmaceutically acceptable salt thereof, wherein
Φ is —$NH_2$ or —OH;
$R^1$ is H or as defined in embodiment [0046];
$R^2$, $R^3$, and $R^4$ are as defined in embodiment [0046];
X, Y, and A are as defined in JP 11-269146 (1999); and
$R^{11}$ is the same as $R^1$ of JP 11-269146 (1999).

In the compounds of embodiment [0198], $R^1$, $R^2$, $R^3$, and $R^4$ are preferably as defined in embodiments [0048] and [0049]. In other embodiments of the compounds of embodiment [0198], $R^1$, $R^2$, $R^3$, and $R^4$ are all H. Particular embodiments of the compounds of embodiment [0198] are those obtained by substituting the terminal moiety:

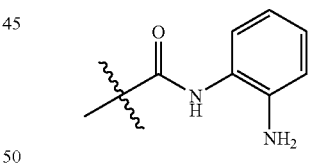

of compounds 1-50 of Tables 24 of JP 11-269146 (1999) with the moiety:

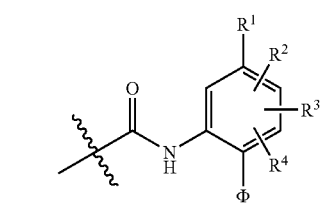

wherein φ, $R^1$, $R^2$, $R^3$, and $R^4$ are as defined in accordance with embodiment [0046], and preferably embodiments

[0048] and [0049]. Such embodiments are hereinafter collectively referred to as embodiment [0199].

In another embodiment, the invention comprises compounds of the following structural formula (15) (hereinafter embodiment [0200]):

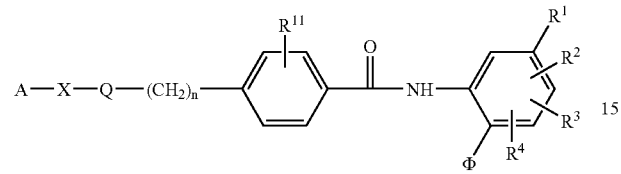

(15)

or a pharmaceutically acceptable salt thereof, wherein

Φ is —NH$_2$ or —OH;

R$^1$ is H or as defined in embodiment [0046];

R$^2$, R$^3$, and R$^4$ are as defined in embodiment [0046];

n, X, Q, and A are as defined in JP 11-302173 (1999); and

R$^{11}$ is the same as R$^1$ of JP 11-302173 (1999).

In the compounds of embodiment [0200], R$^1$, R$^2$, R$^3$, and R$^4$ are preferably as defined in embodiments [0048] and [0049]. In other embodiments of the compounds of embodiment [0200], R$^1$, R$^2$, R$^3$, and R$^4$ are all H. Particular embodiments of the compounds of embodiment [0200] are those obtained by substituting the terminal moiety:

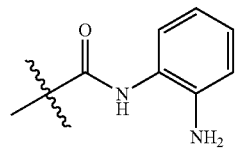

of the compounds 1-67 of JP 11-302173 (1999) with the moiety:

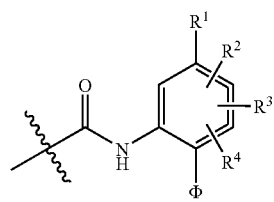

wherein Φ, R$^1$, R$^2$, R$^3$, and R$^4$ are as defined in accordance with embodiment [0046], and preferably embodiments [0048] and [0049]. Such embodiments are hereinafter collectively referred to as embodiment [0201].

In another embodiment, the invention comprises compounds of the following structural formula (16) (hereinafter embodiment [0202]):

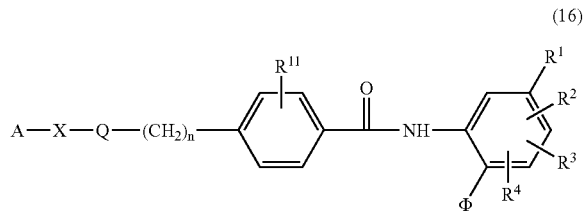

(16)

or a pharmaceutically acceptable salt thereof, wherein

Φ is —NH$_2$ or —OH;

R$^1$ is H or as defined in embodiment [0046];

R$^2$, R$^3$, and R$^4$ are as defined in embodiment [0046];

n, Q, X, and A are as defined in JP 2001131130; and

R$^{11}$ is the same as R$^1$ of JP 2001131130.

In the compounds of embodiment [0202], R$^1$, R$^2$, R$^3$, and R$^4$ are preferably as defined in embodiments [0048] and [0049]. In other embodiments of the compounds of embodiment [0202], R$^1$, R$^2$, R$^3$, and R$^4$ are all H. Particular embodiments of the compounds of embodiment [0202] are those obtained by substituting the terminal moieties:

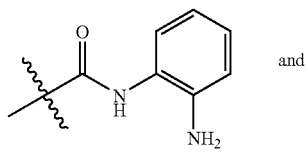

and

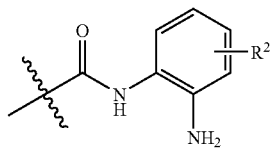

of the compounds of JP 2001131130 with the moiety:

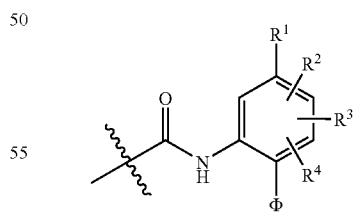

wherein Φ, R$^1$, R$^2$, R$^3$, and R$^4$ are as defined in accordance with embodiment [0046], and preferably embodiments [0048] and [0049]. Such embodiments are hereinafter collectively referred to as embodiment [0203].

In another embodiment, the invention comprises compounds of the following structural formula (17) (hereinafter embodiment [0204]):

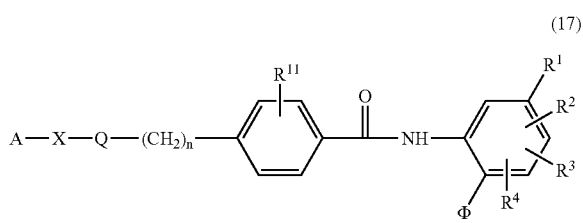
(17)

or a pharmaceutically acceptable salt thereof, wherein
Φ is —NH$_2$ or —OH;
R$^1$ is H or as defined in embodiment [0046];
R$^2$, R$^3$, and R$^4$ are as defined in embodiment [0046];
n, X, Q, and A are as defined in JP 10152462, JP 2002332267, and JP 11-302173; and
R$^{11}$ is the same as R$^1$ of JP 10152462, JP 2002332267, and JP 11-302173.

In the compounds of embodiment [0204], R$^1$, R$^2$, R$^3$, and R$^4$ are preferably as defined in embodiments [0048] and [0049]. In other embodiments of the compounds of embodiment [0204], R$^1$, R$^2$, R$^3$, and R$^4$ are all H. Particular embodiments of the compounds of embodiment [0204] are those obtained by substituting the terminal moiety:

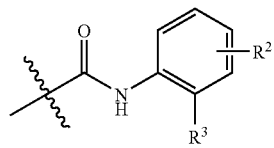

(particularly 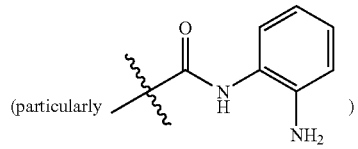 )

of the compounds of JP 10152462, JP 2002332267, and JP 11-302173 with the moiety:

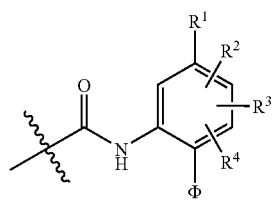

wherein Φ, R$^1$, R$^2$, R$^3$, and R$^4$ are as defined in accordance with embodiment [0046], and preferably embodiments [0048] and [0049]. Such embodiments are hereinafter collectively referred to as embodiment [0205].

In another embodiment, the invention comprises compounds of the following structural formula (18) (hereinafter embodiment [0206]):

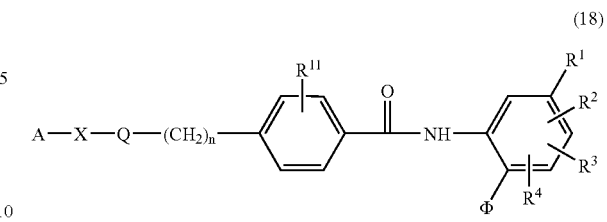
(18)

or a pharmaceutically acceptable salt thereof, wherein
Φ is —NH$_2$ or —OH;
R$^1$ is H or as defined in embodiment [0046];
R$^2$, R$^3$, and R$^4$ are as defined in embodiment [0046];
n, X, Q, and A are as defined in U.S. Pat. No. 6,174,905; and
R$^{11}$ is the same as R$^1$ of U.S. Pat. No. 6,174,905.

In the compounds of embodiment [0206], R$^1$, R$^2$, R$^3$, and R$^4$ are preferably as defined in embodiments [0048] and [0049]. In other embodiments of the compounds of embodiment [0206], R$^1$, R$^2$, R$^3$, and R$^4$ are all H. Particular embodiments of the compounds of embodiment [0206] are those obtained by substituting the terminal moiety:

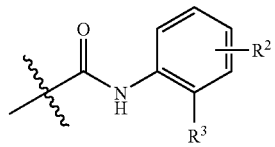

of the compounds of Table 1 of U.S. Pat. No. 6,174,905 and the terminal moiety:

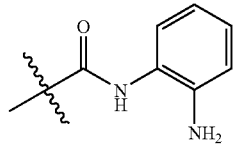

of the compounds of Tables 2-4 of U.S. Pat. No. 6,174,905 with the moiety:

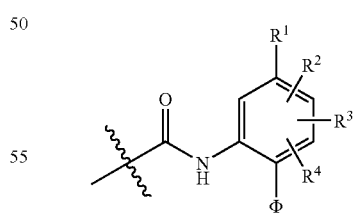

wherein Φ, R$^1$, R$^2$, R$^3$, and R$^4$ are as defined in accordance with embodiment [0046], and preferably [0048] and [0049]. Such embodiments are hereinafter collectively referred to as embodiment [0207].

In another embodiment according to embodiment [0046], the invention comprises compounds of WO01/70675 wherein the terminal moiety —C(O)—NHOH, —C(O)—CH$_2$—SC(O)CH$_3$, —C(O)—CH$_2$—SH, —C(O)—CH$_2$—SCH$_3$, —C(O)—CH₂—SCH₂-phenyl, —C(O)—CH₂—S-phenyl, —C(O)CH₂—SC(O)-phenyl and

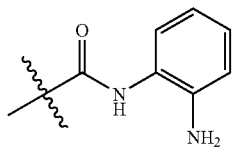

of the compounds of Tables 2 and 3 are replaced by the moiety

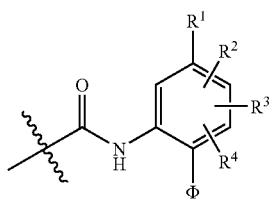

wherein Φ, $R^1$, $R^2$, $R^3$, and $R^4$ are as defined in accordance with embodiment [0046], and preferably [0048] and [0049]. Such embodiments are hereinafter collectively referred to as embodiment [0208].

In the second aspect (hereinafter embodiment [0209]), the invention provides a composition comprising a compound according to any one of embodiments [0046]-[0088], [0098]-[0110], and [0115]-[0207], or as depicted in any of the tables herein together with a pharmaceutically acceptable excipient.

The third aspect of the invention (hereinafter embodiment [0210]) provides a method of inhibiting histone deacetylase, the method comprising contacting the histone deacetylase with a compound according to any one of embodiments [0046]-[0088], [0098]-[0110], and [0115]-[0207] or as depicted in any of the tables herein, or with a composition according to embodiment [0209]. Inhibition of the histone deacetylase can be in a cell or a multicellular organism. If in a multicellular organism, the method according to this aspect of the invention comprises administering to the organism a compound according any one of embodiments [0046]-[0088], [0098]-[0110], and [0115]-[0207] or as depicted in any of the tables herein, or a composition according to embodiment [0209]. Preferably the organism is a mammal, more preferably a human.

The data presented herein demonstrate the anti-tumor effects of the HDAC inhibitors of the invention. Recent publications reporting on HDAC inhibitor human clinical trials suggest that these inhibitors can effectively treat human solid tumors or cancer (lung, colon, prostrate, stomach, breast, leukemia), including complete remissions of transformed lymphoma (SAHA, ASCO Abstract No. 2321, 2003) and peripheral T-cell lymphoma (depsipeptide/FR901228 ASCO Abstract No. 88, 2002). Together with the data presented herein demonstrating surprising efficacy at inhibiting HDAC-1 and tumor growth inhibition in vivo, these data lead on to reasonably expect that the HDAC-1 inhibitors of the invention are useful not only for inhibition of HDAC, but as therapeutic agents for the treatment of cancer as well.

Preferred compounds according to the invention include those in the Table 1, which were prepared essentially using the methods described herein and illustrated below in the schemes. All of the compounds in this application were named using Chemdraw Ultra version 6.0.2, which is available through Cambridgesoft. co, 100 Cambridge Park Drive, Cambridge, Mass. 02140, Namepro version 5.09, which is available from ACD labs, 90 Adelaide Street West, Toronto, Ontario, M5H, 3V9, Canada, or were derived therefrom.

TABLE 1

| Compound | Name | Structure |
|---|---|---|
| C | N-[2-amino-5-(2-thienyl)phenyl]-4{[(5-chloro-6-fluoro-1H-benzimidazol-2-yl)amino]methyl}benzamide | 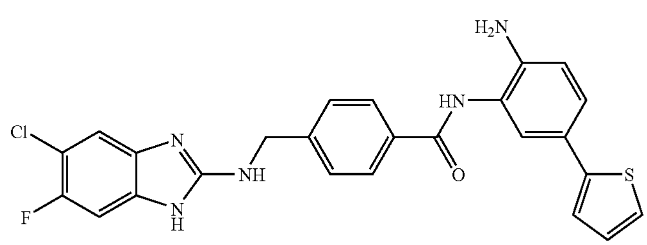 |
| 6 | N-[2-amino-5-(2-thienyl)phenyl]-4{[(3,4-dimethoxyphenyl)amino]methyl}benzamide | 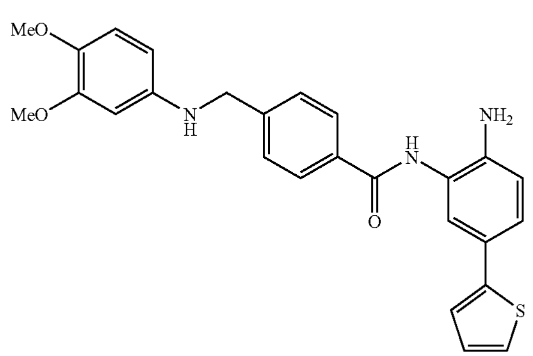 |

TABLE 1-continued
| Compound | Name | Structure |
|---|---|---|
| 12 | N-[2-amino-5-(2-thienyl)phenyl]-4{[(3-fluoro-4-methoxyphenyl)amino]methyl}benzamide | 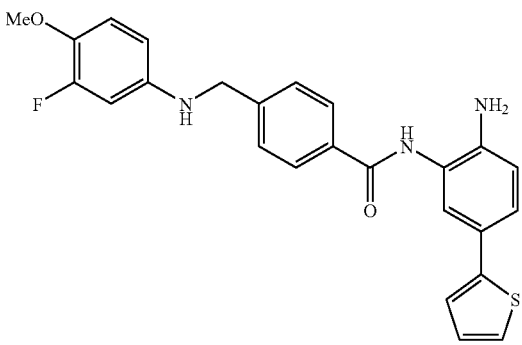 |
| 23 | N-[2-amino-5-(2-thienyl)phenyl]-1-(3,4,5-trimethoxybenzyl)indoline-6-carboxamide | 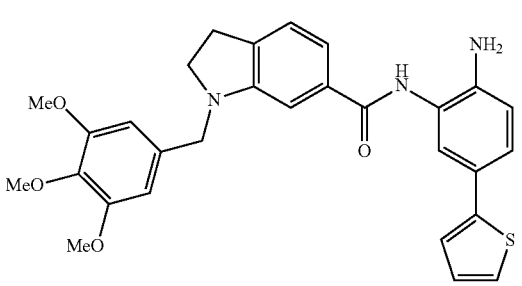 |
| 29 | N-[2-amino-5-(2-thienyl)phenyl]-5-{[(3,4,5-trimethoxyphenyl)amino]methyl}-1-benzofuran-2-carboxamide | 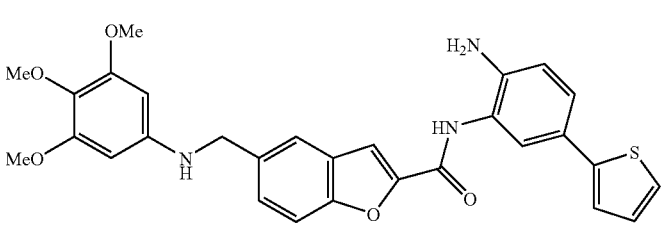 |
| 43 | N-[2-amino-5-(2-thienyl)phenyl]-4{[(4-pyridin-3-ylpyrimidin-2-yl)amino]methyl}benzamide | 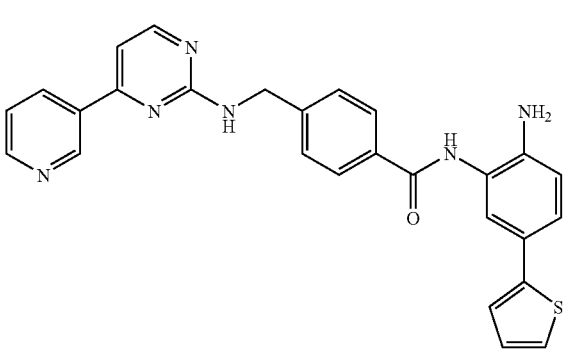 |

TABLE 1-continued

| Compound | Name | Structure |
|---|---|---|
| 50 | N-[2-amino-5-(2-thienyl)phenyl]-4[({6-[2-(dimethylamino)ethoxy]-1H-benzimidazol-2-yl}thio)methyl]benzamide | 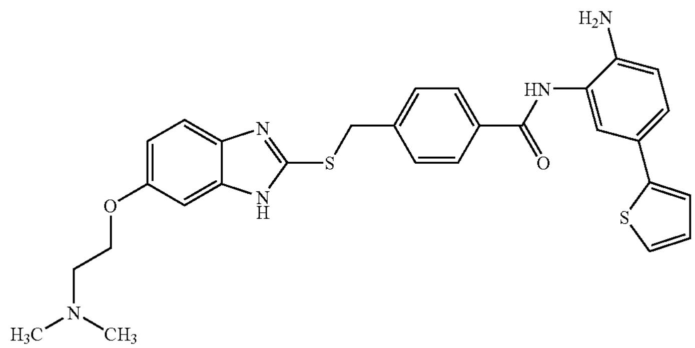 |
| 55 | N-[2-amino-5-(2-thienyl)phenyl]-4-{[(6-chloro-5-fluoro-1H-benzimidazol-2-yl)thio]methyl}benzamide | 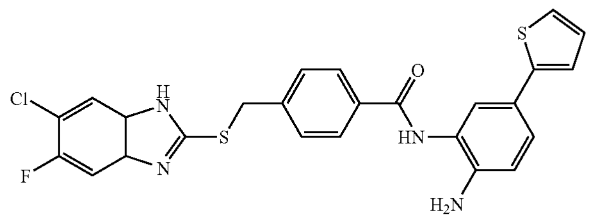 |
| 67 | trans-N-[2-amino-5-(2-thienyl)phenyl]-3-(4-{[(3,4,5-trimethoxyphenyl)amino]methyl}phenyl)acrylamide | 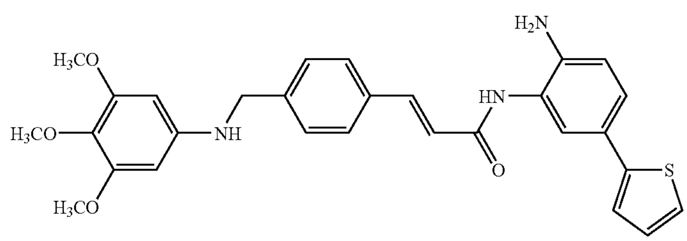 |

We have unexpectedly found that when HDAC inhibitors including within them the benzamide moiety:

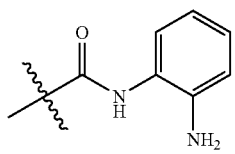

are substituted on the aniline ring at the 5-position (para to the —NH$_2$ group) with a substantially planar ring or ring system (aryl or heteroaryl), the compound's HDAC inhibitory activity (as measured by the human HDAC-1 inhibition assay described below) increases by a factor of from 3 to 10 or more compared to similar compounds in which the aniline ring is unsubstituted or substituted with a smaller, non-planar moiety, or if the planar moiety is at other than the 5-position of the aninlinyl ring. Additionally, we have found that the planar moiety itself can be substituted. Accordingly, R$^1$ in the compounds of the invention is a mono-, bi-, or tri-cyclic aryl or heteroaryl moiety, which moiety is optionally substituted. In some preferred embodiments R$^1$ is not further substituted. In other preferred embodiments, R$^1$ is substituted with a moiety of from 1-5 atoms, e.g., methyl, hydroxymethyl, halomethyl, halo, hydroxy, amino, etc. In other embodiments, R$^1$ is substituted with a larger moiety, e.g., from 6-25 atoms.

This is surprising in view of T. Suzuki et. al., *J. Med. Chem.*, 1999, 42, 3001-3003, which teaches that the substitution pattern on the aniline ring of the benzamide fragment of known HDACs (wherein the amino group is ortho to the amide nitrogen) is highly sensitive to substitutions. Substituents such as Me and OMe ortho- or meta-relative to the amino group are detrimental to HDAC inhibitory activity, causing complete loss of HDAC potency. The same type of substituents in the para-position relative to the amino group did not cause significant drop of potency which allowed assuming that only small substituents such as Me, MeO, F, Cl might be tolerated.

Furthermore, we have surprisingly found that the HDAC inhibitory activity of such compounds (i.e., compounds comprising the chemical moiety of embodiment [0046] and having a substantially planar ring or ring system at the 5-position of the aniline ring) is substantially independent of the identity of the chemical moiety bound to the carbonyl of the amide in embodiment [0046]. Accordingly, in compounds of formula 1 Y is any chemical moiety (preferably physiologically non-reactive) consisting of 1 to 50 atoms.

The following are representative examples of the compounds according to the embodiments described above.

TABLE Ia

| Ex | Cpd | Structure | Name | Characterization | Scheme |
|---|---|---|---|---|---|
| 15aa | 76aa | 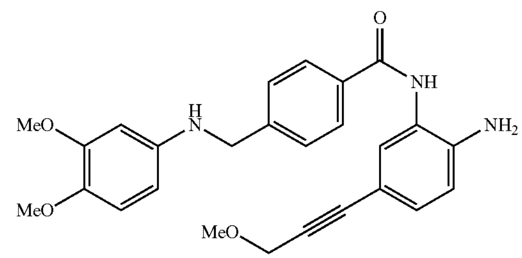 | N-(2-amino-5-(3-methoxyprop-1-ynyl)phenyl)-4-((3,4-dimethoxyphenylamino)methyl)benzamide | $^1$H NMR: (DMSO) δ (ppm): 9.52 (s, 1H); 7.89 (d, J = 8.2, 2H); 7.46 (d, J = 8.2, 2H); 7.25 (d, J = 1.9, 1H); 7.04 (dd, J = 1.9, 8.2, 1H); 6.70 (d, J = 8.2, 1H); 6.64 (d, J = 8.6, 1H); 6.31 (d, J = 2.5, 1H); 5.98 (m, 2H); 5.35 (bs, 2H); 4.29 (d, J = 6.1, 2H); 4.26 (s, 2H); 3.65 (s, 3H); 3.58 (s, 3H); 3.29 (s, 3H). MS: calc: 445.5; found: 446.4 (M + H) | 13 |
| 19 | 93 | 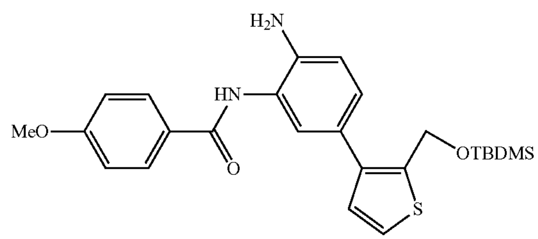 | N-(2-amino-5-(2-((tert-butyl)dimethylsilyloxy)methyl)thiophen-3-yl)phenyl)-4-methoxybenzamide | $^1$H NMR: (DMSO) δ (ppm): 9.54 (s, 1H), 7.96 (d, J = 8.8 Hz, 2H), 7.43 (d, J = 5.1 Hz, 1H), 7.28 (d, J = 1.8 Hz, 1H), 7.09-7.02 (m, 4H), 6.81 (d, J = 8.2 Hz, 1H), 5.05 (s, 2H), 4.82 (s, 2H), 3.83 (s, 3H), 0.87 (s, 9H), 0.06 (s, 6H). MS: (calc.) 468.2; (obt.) 491.2 (M + Na)$^+$. | 17 |
| 19aa | 93aa | 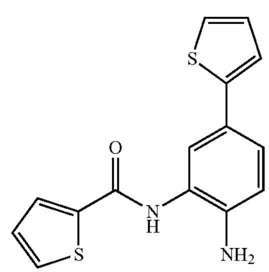 | N-(2-amino-5-(thiophen-2-yl)phenyl)thiophene-2-carboxamide | $^1$H NMR: (DMSO) δ (ppm): 9.76 (s, 1H), 7.99 (d, J = 2.9 Hz, 1H), 7.82 (d, J = 4.9 Hz, 1H), 7.40 (s, 1H), 7.34 (d, J = 5.1 hz, 1H), 7.29 (d, J = 8.2 Hz, 1H), 7.24 (d, J = 3.9 Hz, 1H), 7.20 (t, J = 3.9 Hz, 1H), 7.03 (t, J = 3.5 Hz, 1H), 6.79 (d, J = 8.2 Hz, 1H), 5.17 (s, 2H). MS: 300.04 (calc) 301.1 (obs) | 17 |

TABLE Ia-continued

| Ex | Cpd | Structure | Name | Characterization | Scheme |
|---|---|---|---|---|---|
| 19bb | 93bb | 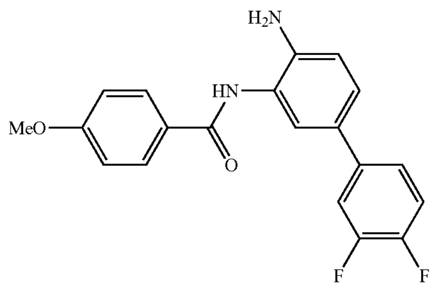 | N-(2-amino-5-(3,4-difluorophenyl)phenyl)-4-methoxybenzamide | ¹H NMR: (DMSO) δ (ppm): 9.59 (s, 1H), 7.97 (d, J = 8.8, Hz, 2H), 7.59 (ddd, J = 12.7, 7.8, 2.3, 1H), 7.49 (d, J = 2.3 Hz, 1H), 7.45-7.36 (m, 2H), 6.32 (dd, J = 8.2, 2.2 Hz, 1H), 7.04 (d, J = 8.8, Hz, 2H), 6.84 (d, 8.2, Hz, 1H), 5.15 (s, 1H), 3.83 (s, 3H). MS: (calc.) 354.1; (obt.) 355.2 (MH)⁺. | 17 |
| 19cc | 93cc | 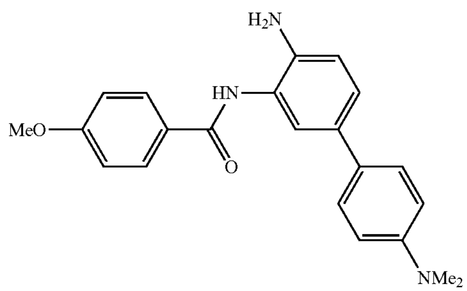 | N-(2-amino-5-(4-N,N-dimethylaminophenyl)phenyl)-4-methoxybenzamide | ¹H NMR: (DMSO) δ (ppm): 9.61 (s, 1H), 7.97 (d, J = 9.0, Hz, 2H), 7.38-7.36 (m, 3H), 7.21, (dd, J = 8.2, 2.2 Hz, 1H), 7.04 (d, J = 8.8 Hz, 2H), 6.80 (d, J = 8.4 Hz, 1H), 6.75 (d, J = 9.0 Hz, 2H), 4.89 (sb, 2H), 3.83 (s, 3H), 2.90 (s, 6H). MS: (calc.) 361.1; (obt.) 362.3 (MH)⁺. | 17 |
| 19dd | 93dd | 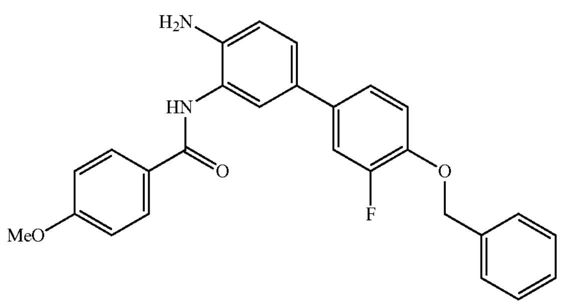 | N-(2-amino-5-(3-fluoro-4-benzyloxyphenyl)phenyl)-4-methoxybenzamide | ¹H NMR: (DMSO) δ (ppm): 9.59 (s, 1H), 7.97 (d, J = 8.8, Hz, 2H), 7.47-7.22 (m, 10H), 7.04 (d, J = 9.0 Hz, 2H), 6.82 (d, J = 8.4 Hz, 1H), 5.18 (s, 2H), 5.06 (sb, 2H), 3.83 (s, 3H). MS: (calc.) 442.2; (obt.) 443.4 (MH)⁺. | 17 |

TABLE Ia-continued

| Ex | Cpd | Structure | Name | Characterization | Scheme |
|---|---|---|---|---|---|
| 19ee | 93ee | (structure) | N-(2-amino-5-(3-methoxyphenyl)phenyl)-4-methoxybenzamide | ¹H NMR: (DMSO) δ (ppm): 9.61 (s, 1H), 7.98 (d, J = 8.8 Hz, 2H), 7.47 (d, J = 2.2 Hz, 1H), 7.32-7.26 (m, 2H), 7.12-7.10 (m, 1H), 7.05-7.02 (m, 3H), 6.84 (d, J = 8.2 Hz, 1H), 6.80 (ddd, J = 8.2, 2.5, 0.8 Hz, 1H), 5.07 (sb, 2H), 3.84 (s, 3H), 3.79 (s, 3H). MS: (calc.) 348.2; (obt.) 349.2 (MH)⁺. | 17 |
| 19ff | 93ff | (structure) | N-(2-amino-5-(thiophen-2-yl)phenyl)-2,2-difluorobenzo[d][1,3]dioxole-5-carboxamide | ¹H NMR: (DMSO) δ (ppm): 9.67 (s, 1H), 7.94 (d, J = 1.6 Hz, 1H), 7.83 (dd, J = 8.6, 1.8 Hz, 1H), 7.48 (d, J = 8.4 Hz, 1H), 7.35 (d, J = 2.2 Hz, 1H), 7.26 (dd, J = 5.0, 1.2 Hz, 1H), 7.22 (dd, J = 8.2, 2.3 Hz, 1H), 7.15 (dd, J = 3.6, 1.2 Hz, 1H), 6.96 (dd, J = 5.0, 3.5 Hz, 1H), 6.71 (d, J = 8.4 Hz, 1H), 5.14 (s, 2H). MS: 374.05 (calc), 375.0 (obs). | 17 |
| 19gg | 93gg | (structure) | N-(2-amino-5-(thiophen-2-yl)phenyl)benzo[c][1,2,5]oxadiazole-5-carboxamide | ¹H NMR: (DMSO) δ (ppm): 10.03 (s, 1H), 8.74 (s, 1H), 8.15 (d, J = 9.4 Hz, 1H), 8.02 (d, J = 9.4 Hz, 1H), 7.48 (d, J = 2.0 Hz, 1H), 7.33 (d, J = 5.1 Hz, 1H), 7.30 (dd, J = 8.4, 2.0 Hz, 1H), 7.23 (d, J = 3.5 Hz, 1H), 7.03 (t, J = 4.9 Hz, 1H), 6.79 (d, J = 8.2 Hz, 1H), 5.32 (s, 2H). MS: 336.07 (calc) 337.0 (obs). | 17 |

| Ex | Cpd | Structure | Name | Characterization | Scheme |
|---|---|---|---|---|---|
| 19hh | 93hh | 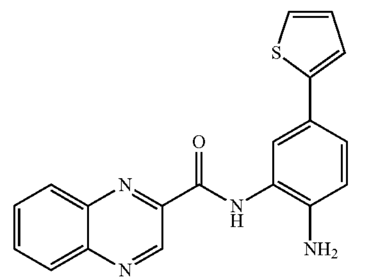 | N-(2-amino-5-(thiophen-2-yl)phenyl)quinoxaline-2-carboxamide | ¹H NMR: (DMSO) δ (ppm): 10.25 (s, 1H), 9.52 (s, 1H), 8.27 to 8.21 (m, 2H), 8.20 to 7.99 (m, 2H), 7.66 (d, J = 2.2 Hz, 1H), 7.35 (dd, J = 5.1, 0.98 Hz, 1H), 7.31 (dd, J = 8.2, 2.2 Hz, 1H), 7.25 (dd, J = 3.5, 0.98 Hz, 1H), 7.04 (dd, J = 5.1, 3.5 Hz, 1H), 6.83 (d, J = 8.4 Hz, 1H), 5.28 (s, 2H). MS: 346.09 (calc), 347.1 (obs). | 17 |
| 20 | 94 | 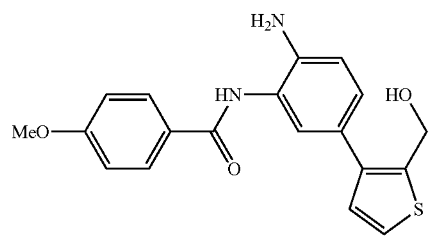 | N-(2-amino-5-(2-(hydroxymethyl)thiophen-3-yl)phenyl)-4-methoxybenzamide | ¹H NMR: (DMSO) δ (ppm): 9.57 (s, 1H), 7.96 (d, J = 8.8 Hz, 2H), 7.40 (d, J = 5.1 Hz, 1H), 7.23 (d, J = 1.8 Hz, 1H), 7.09-7.02 (m, 4H), 6.81 (d, J = 8.0 Hz, 1H), 5.51 (t, J = 5.4 Hz, 1H), 5.01 (s, 2H), 4.64 (d, J = 5.3 Hz, 2H), 3.83 (s, 3H). MS: (calc.) 354.1; (obt.) 354.1 (M + Na)⁺. | 17 |
| 20aa | 94aa | 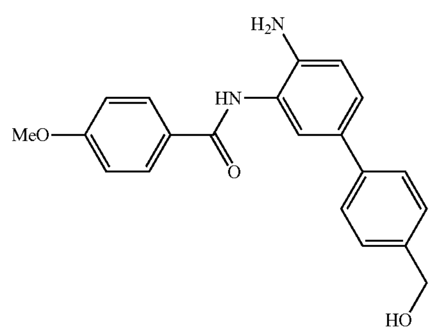 | N-(2-amino-5-(4-hydroxymethylphenyl)phenyl)-4-methoxybenzamide | ¹H NMR: (DMSO) δ (ppm): 9.61 (s, 1H), 7.98 (d, J = 8.8 Hz, 2H), 7.51-7.47 (m, 3H), 7.32-7.28 (m, 3H), 7.04 (d, J = 8.8 Hz, 2H), 6.84 (d, J = 8.2 Hz, 1H), 5.15 (t, J = 5.8 Hz, 2H), 5.04 (sb, 2H), 4.49 (d, J = 5.7 Hz, 2H), 3.84 (s, 3H). MS: (calc.) 348.1; (obt.) 349.1 (MH)⁺. | 17 |

TABLE Ia-continued

| Ex | Cpd | Structure | Name | Characterization | Scheme |
|---|---|---|---|---|---|
| 20bb | 94bb | 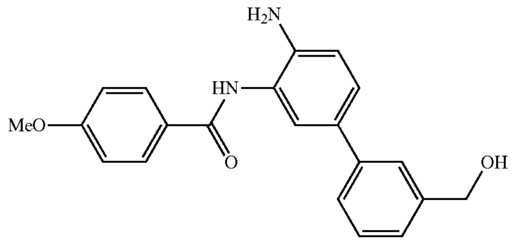 | N-(2-amino-5-(3-hydroxymethyl)phenyl)phenyl)-4-methoxybenzamide | ¹H NMR: (DMSO) δ (ppm): 9.61 (s, 1H), 7.98 (d, J = 9.0 Hz, 2H), 7.50-7.49 (m, 2H), 7.40 (d, J = 8.0 Hz, 1H), 7.34-7.29 (m, 2H), 7.17 (d, J = 8.0 Hz, 1H), 7.04 (d, J = 9.0 Hz, 2H), 6.85 (d, J = 8.4 Hz, 1H), 5.19 (t, J = 5.8 Hz, 1H), 5.06 (sb, 2H), 5.52 (d, J = 2.8 Hz, 2H), 3.84 (s, 3H). MS: (calc.) 348.2; (obt.) 349.1 (MH)⁺. | 17 |
| 20cc | 94dd | 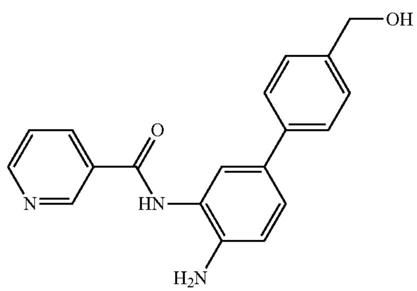 | N-(2-amino-5-(4-hydroxymethyl)phenyl)phenyl)-4-methoxybenzamide | ¹H NMR: (DMSO) δ (ppm): 9.89 (s, 1H), 9.14 (d, J = 1.6 Hz, 1H), 8.73 (dd, J = 4.9, 1.8 Hz, 1H), 8.33 (dt, J = 8.0, 1.9 Hz, 1H), 6.54 (dd, J = 7.4, 5.2 Hz, 1H), 7.51-7.49 (m, 3H), 7.34-7.30 (m, 3H), 6.84 (d, J = 8.4 Hz, 1H), 5.18 (sb, 3H), 4.49 (d, J = 5.5 Hz, 2H). MS: (calc.) 319.1; (obt.) 320.2 (MH)⁺. | 17 |
| 20dd | 94dd | 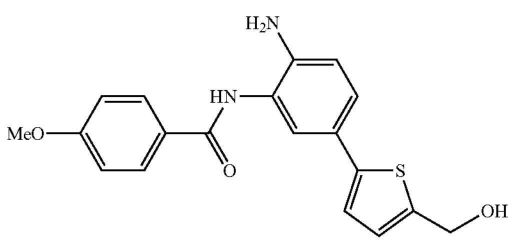 | N-(2-amino-5-(5-(hydroxymethyl)thiophen-2-yl)phenyl)-4-methoxybenzamide | ¹H NMR: (DMSO) δ (ppm): 9.60 (s, 1H), 7.97 (d, J = 9.0 Hz, 2H), 7.40 (d, J = 2.2 Hz, 1H), 7.23 (dd, J = 8.2, 2.2 Hz, 1H), 7.06-7.02 (m, 3H), 6.85 (d, J = 3.5 Hz, 1H), 6.78 (d, J = 8.4 Hz, 1H), 7.41 (s, 1H), 5.10 (sb, 2H), 4.57 (sb, 2H), 3.83 (s, 3H). MS: (calc.) 354.1; (obt.) 355.1 (MH)⁺. | 17 |

| Ex | Cpd | Structure | Name | Characterization | Scheme |
|---|---|---|---|---|---|
| 21 | 99 | 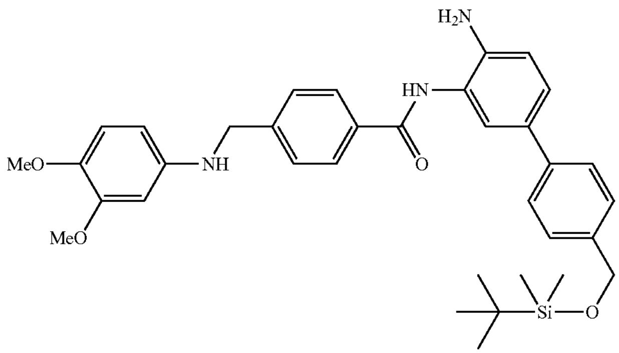 | N-(2-amino-5-(4-((tert-butyl)dimethylsilyl)oxy)methyl)phenyl)phenyl)-4-((3,4-dimethoxyphenyl)amino)methyl)benzamide | ¹H NMR: (DMSO) δ (ppm): 9.66 (s, 1H), 7.93 (d, J = 8.0 Hz, 2H), 7.52-7.46 (m, 5H), 7.31-7.29 (m, 3H), 6.84 (d, J = 7.6 Hz, 1H), 6.64 (d, J = 8.6 Hz, 1H), 6.32 (s, 1H), 6.00-5.98 (m, 2H), 5.06 (s, 2H), 4.70 (s, 2H), 4.30 (d, J = 5.9 Hz, 2H), 3.66 (s, 3H), 3.59 (s, 3H), 0.91 (s, 9H), 0.10 (s, 6H). MS: (calc.) 597.2 (obt.) 598.5 (MH)⁺. | 18 |
| 21-1 | 100 | 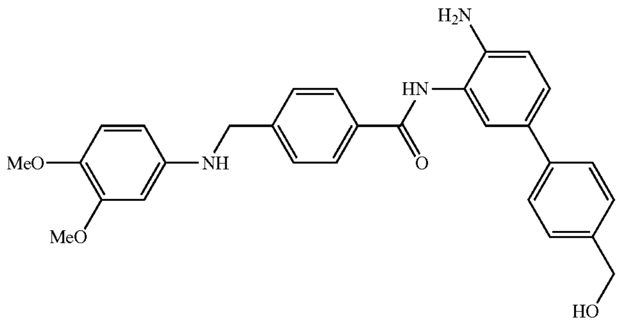 | N-(2-amino-5-(4-(hydroxymethyl)phenyl)phenyl)-4-((3,4-dimethoxyphenyl)amino)methyl)benzamide | ¹H NMR: (DMSO) δ (ppm): 9.67 (s, 1H), 7.93 (d, J = 7.8 Hz, 2H), 7.50-7.46 (m, 5H), 7.31-7.29 (m, 3H), 6.84 (d, J = 8.0 Hz, 1H), 6.64 (d, J = 8.4 Hz, 1H), 6.32 (d, J = 2.0 Hz, 1H), 6.00-5.98 (m, 2H), 5.15 (t, J = 5.5 Hz, 1H), 5.06 (s, 2H), 4.49 (d, J = 5.7 Hz, 2H), 4.31 (d, J = 5.9 Hz, 2H), 3.66 (s, 3H), 3.59 (s, 3H). MS: (calc.) 483.2; (obt.) 484.4 (MH)⁺. | 18 |
| 22 | 104 | 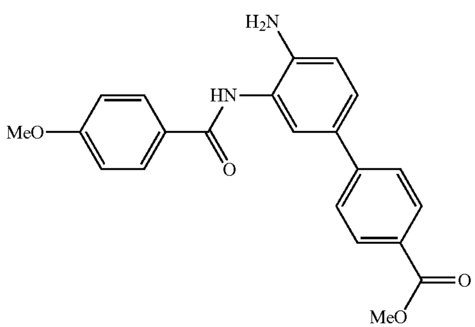 | N-(2-amino-5-(4-methoxycarbonyl)phenyl)phenyl)-4-methoxybenzamide | ¹H NMR: (DMSO) δ (ppm): 9.61 (s, 1H), 7.98 (d, J = 8.8, Hz, 2H), 7.95 (d, J = 8.4 Hz, 2H), 7.71, (d, J = 8.4 Hz, 2H), 7.60 (d, J = 2.2 Hz, 1H), 7.43 (dd, J = 8.4, 2.2 Hz, 1H), 7.04 (d, J = 8.8 Hz, 2H), 6.86 (d, J = 8.4 Hz, 1H), 5.27 (sb, 2H), 3.85 (s, 3H), 3.84 (s, 3H). MS: (calc.) 376.1; (obt.) 377.1 (MH)⁺. | 19 |

TABLE Ia-continued

| Ex | Cpd | Structure | Name | Characterization | Scheme |
|---|---|---|---|---|---|
| 23 | 105 | 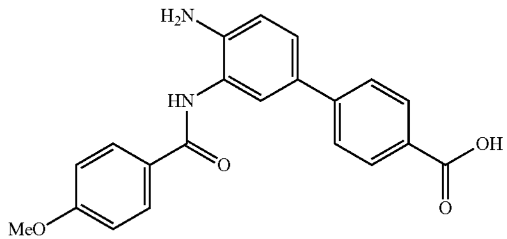 | N-(2-amino-5-(4-carboxyphenyl)phenyl)-4-methoxybenzamide | $^1$H NMR: (DMSO) δ (ppm): 9.61 (s, 1H), 7.98 (d, J = 8.6, Hz, 2H), 7.93 (d, J = 8.2 Hz, 2H), 7.66 (d, J = 8.2 Hz, 2H), 7.58 (d, J = 2.0 Hz, 1H), 7.40 (dd, J = 8.2, 2.0 Hz, 1H), 7.04 (d, J = 8.8 Hz, 2H), 6.86 (d, J = 8.4 Hz, 1H), 5.23 (sb, 2H), 3.84 (s, 3H). MS: (calc.) 362.1; (obt.) 363.1 (MH)$^+$. | 19 |
| 24 | 107 | 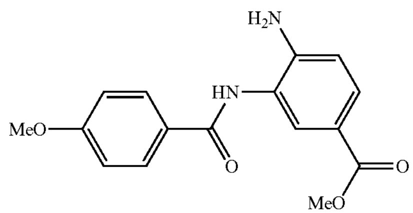 | methyl 4-amino-3-(4-methoxybenzamido)benzoate | $^1$H NMR: (DMSO) δ (ppm): 9.51 (s, 1H), 7.96 (d, J = 8.8 Hz, 2H), 7.75 (d, J = 2.0 Hz, 1H), 7.56 (dd, J = 8.4, 2.0 Hz, 1H), 7.03 (d, J = 9.0 Hz, 2H), 6.75 (d, J = 8.4 Hz, 1H), 5.80 (s, 2H), 3.83 (s, 3H), 3.75 (s, 3H). MS: (calc.) 300.1; (obt.) 301.1 (MH)$^+$. | 20 |
| 24aa | 107aa | 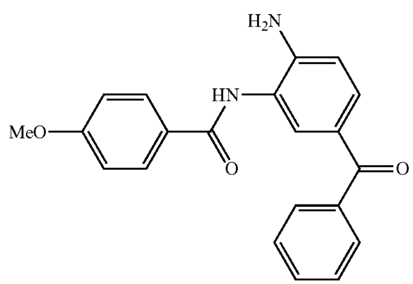 | N-(2-amino-5-benzoylphenyl)-4-methoxybenzamide | $^1$H NMR: (DMSO) δ (ppm): 9.55 (s, 1H), 7.95 (d, J = 8.8 Hz, 2H), 7.63-7.47 (m, 7H), 7.02 (d, J = 8.8 Hz, 2H), 6.80 (d, J = 8.4 Hz, 1H), 5.98 (s, 2H), 3.83 (s, 3H). MS: (calc.) 346.1; (obt.) 347.1 (MH)$^+$. | 20 |
| 25 | 108 | 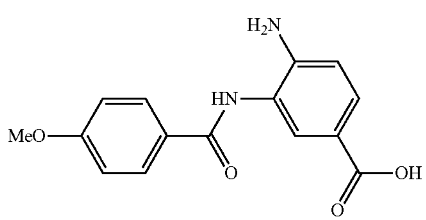 | 4-amino-3-(4-methoxybenzamido)benzoic acid | $^1$H NMR: (DMSO) δ (ppm): 9.52 (s, 1H), 7.96 (d, J = 8.8 Hz, 2H), 7.71 (d, J = 2.0 Hz, 1H), 7.54 (dd, J = 8.4, 2.0 Hz, 1H), 7.02 (d, J = 9.0 Hz, 2H), 6.74 (d, J = 8.4 Hz, 1H), 5.69 (s, 2H), 3.83 (s, 3H). MS: (calc.) 361.1; (obt.) 362.3 (MH)$^+$. | 20 |

| Ex | Cpd | Structure | Name | Characterization | Scheme |
|---|---|---|---|---|---|
| 26 | 109 | 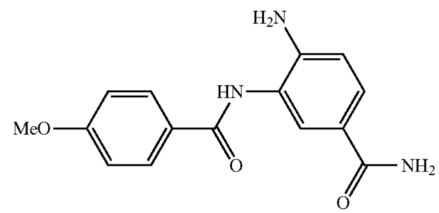 | N-(2-amino-5-carbamoylphenyl)-4-methoxybenzamide | ¹H NMR: (DMSO) δ (ppm): 9.57 (s, 1H), 7.96 (d, J = 8.8 Hz, 2H), 7.67 (d, J = 2.2 Hz, 1H), 7.59 (sb, 1H), 7.52 (dd, J = 8.2, 2.0 Hz, 1H), 7.02 (d, J = 8.8 Hz, 2H), 6.90 (sb, 1H), 6.72 (d, J = 8.4 Hz, 1H), 5.41 (s, 2H), 3.83 (s, 3H). MS: (calc.) 285.1; (obt.) 286.1 (MH)⁺. | 20 |
| 27 | 112 | 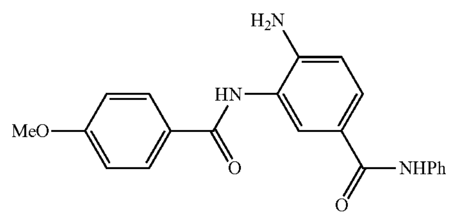 | N-(2-amino-5-phenylcarbamoylphenyl)-4-methoxybenzamide | ¹H NMR: (DMSO) δ (ppm): 9.83 (s, 1H), 9.62 (s, 1H), 7.99 (d, J = 8.8 Hz, 2H), 7.82 (d, J = 2.0 Hz, 1H), 7.73 (dd, J = 8.8, 1.2 Hz, 2H), 7.67 (dd, J = 8.4, 2.2 Hz, 1H), 7.31-7.27 (m, 2H), 7.05-7.01 (m, 3H), 6.80 (d, J = 8.4 Hz, 1H), 3.84 (s, 3H). MS: (calc.) 361.1; (obt.) 362.1 (MH)⁺. | 20 |
| 27aa | 112aa | 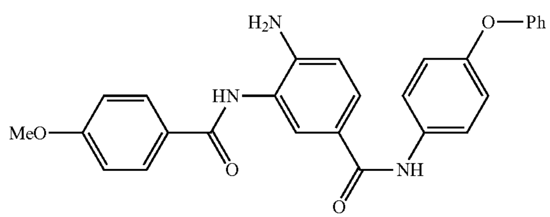 | N-(2-amino-5-(phenoxyphenyl)carbamoylphenyl)-4-methoxybenzamide | ¹H NMR: (DMSO) δ (ppm): 9.87 (s, 1H), 9.62 (s, 1H), 7.99 (d, J = 8.8 Hz, 2H), 7.82 (d, J = 2.2 Hz, 1H), 7.75 (dt, J = 9.0, 2.7 Hz, 2H), 7.67 (dd, J = 8.4, 2.2 Hz, 1H), 7.38-7.32 (m, 2H), 7.10-6.94 (m, 7H), 6.80 (d, J = 8.4 Hz, 1H), 5.56 (sb, 2H), 3.84 (s, 3H). MS: (calc.) 453.2; (obt.) 454.2 (MH)⁺. | 20 |
| 28 | 114 | 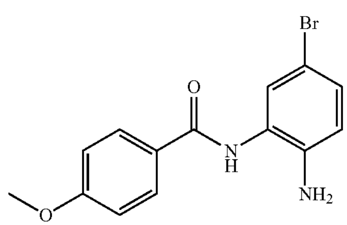 | N-(2-amino-5-bromophenyl)-4-methoxybenzamide | ¹H NMR: (DMSO) δ (ppm): 9.52 (s, 1H), 7.93 (d, J = 9.0 Hz, 2H), 7.34 (d, J = 2.3 Hz, 1H), 7.08 (dd, J = 8.6, 2.3 Hz, 1H), 7.02 (d, J = 9.0 Hz, 2H), 6.71 (d, J = 8.6 Hz, 1H), 5.10 (s, 2H), 3.82 (s, 3H). MS: 321.17 (calc) 321.0/323.0 (found). | 21 |

TABLE Ia-continued

| Ex | Cpd | Structure | Name | Characterization | Scheme |
|---|---|---|---|---|---|
| 29 | 115 | (structure: 3-chloro-4-fluorobiphenyl with H₂N and NHC(O)-C₆H₄-OMe) | N-(2-amino-5-(3-chloro-4-fluorophenyl)phenyl)-4-methoxybenzamide | ¹H NMR: (DMSO) δ (ppm): 9.59 (s, 1H), 7.97 (d, J = 8.8 Hz, 2H), 7.71 (dd, J = 7.2, 2.3 Hz, 1H), 7.56-7.52 (m, 1H), 7.51 (d, J = 2.2 Hz, 1H), 7.40 (t, J = 9.0 1H), 7.33 (dd, J = 8.2, 2.3, 1H), 7.04 (d, J = 9.0 Hz, 2H), 6.84 (d, J = 8.4 Hz, 1H), 5.16 (sb, 2H), 3.84 (s, 3H). MS: (calc.) 370.1; (obt.) 371.1 (MH)⁺. | 21 |
| 29aa | 115aa | (structure: 4-fluorobiphenyl with H₂N and NHC(O)-C₆H₄-OMe) | N-(2-amino-5-(4-fluorophenyl)phenyl)-4-methoxybenzamide | ¹H NMR: (DMSO) d (ppm): 400 MHz, (DMSO) δ (ppm): 9.59 (s, 1H), 7.97 (d, J = 8.4 Hz, 2H), 7.58-7.54 (m, 2H), 7.46 (bs, 1H), 7.27 (d, J = 8.0 Hz, 1H), 7.19 (t, J = 8.8 Hz, 2H), 7.04 (d, J = 8.8 Hz, 2H), 6.84 (d, J = 8.4 Hz, 1H), 5.07 (sb, 2H), 3.83 (s, 3H). MS: (calc.) 336.1; (obt.) 337.2 (MH)⁺. | 21 |
| 29bb | 115bb | (structure: 4-trifluoromethoxybiphenyl with H₂N and NHC(O)-C₆H₄-OMe) | N-(2-amino-5-(4-(trifluoromethoxy)phenyl)phenyl)-4-methoxybenzamide | ¹H NMR: (DMSO) δ (ppm): 9.60 (s, 1H), 7.97 (d, J = 8.6 Hz, 2H), 7.65 (d, J = 8.8 Hz, 2H), 7.50 (s, 1H), 7.36-7.31 (m, 3H), 7.04 (d, J = 8.6 Hz, 2H), 6.85 (d, J = 8.4 Hz, 1H), 5.15 (sb, 2H), 3.83 (s, 3H). MS: (calc.) 402.1; (obt.) 403.4 (MH)⁺. | 21 |

TABLE Ia-continued

| Ex | Cpd | Structure | Name | Characterization | Scheme |
|---|---|---|---|---|---|
| 29cc | 115cc | 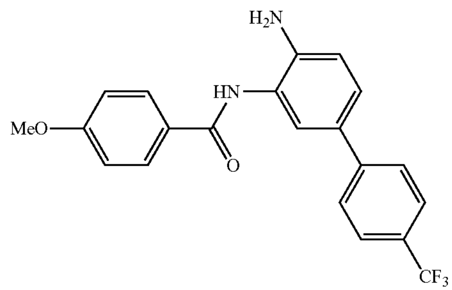 | N-(2-amino-5-(4-(trifluoromethyl)phenyl)phenyl)-4-methoxybenzamide | ¹H NMR: (DMSO) δ (ppm): 9.61 (s, 1H), 7.98 (d, J = 8.6 Hz, 2H), 7.77 (d, J = 8.2 Hz, 2H), 7.71 (d, J = 8.2 Hz, 2H), 7.58 (s, 1H), 7.40 (d, J = 8.6 Hz, 1H), 7.04 (d, J = 8.8 Hz, 2H), 6.87 (d, J = 8.4 Hz, 1H), 5.25 (sb, 2H), 3.84 (s, 3H). MS: (calc.) 386.1; (obt.) 387.4 (MH)⁺. | 21 |
| 30 | 116 | 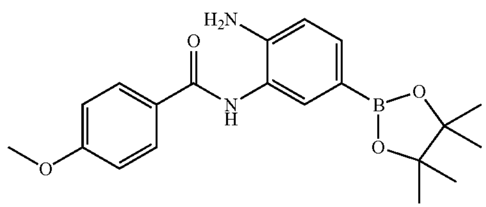 | N-(2-amino-5-(4,4,5,5-tetramethyl-1,3,2-dioxaborolan-2-yl)phenyl)-4-methoxybenzamide | ¹H NMR: (DMSO) δ (ppm): 9.47 (s, 1H), 7.95 (d, J = 8.8 Hz, 2H), 7.41 (d, J = 1.4 Hz, 1H), 7.24 (dd, J = 7.8, 1.4 Hz, 1H), 7.01 (d, J = 8.8 Hz, 2H), 6.70 (d, J = 7.8 Hz, 1H), 5.31 (s, 2H), 3.82 (s, 3H), 1.25 (s, 12H). MS: 368.24 (calc) 369.1 (found) | 21 |
| 31 | 117 | 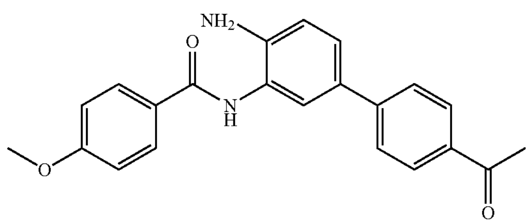 | N-(4-amino-4'-acetylbiphen-3-yl)-4-methoxybenzamide | ¹H NMR: (DMSO) δ (ppm): 9.61 (s, 1H), 7.96 (dd, J = 12.8, 8.8 Hz, 4H), 7.70 (d, J = 8.8 Hz, 2H), 7.60 (d, J = 2.1 Hz, 1H), 7.42 (dd, J = 8.4, 2.3 Hz, 1H), 7.04 (d, J = 8.8 Hz, 2H), 6.86 (d, J = 8.2 Hz, 1H), 5.26 (s, 2H), 3.84 (s, 3H), 2.58 (s, 3H). MS: 360.41 (calc) 361.1 (MH+) (found) | 21 |
| 31aa | 117aa | 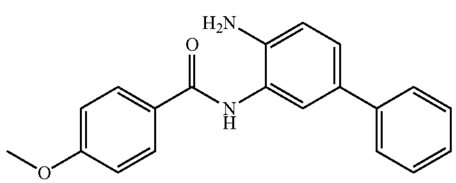 | N-(4-aminobiphenyl)-3-methoxybenzamide | ¹H NMR: (DMSO) δ (ppm): 9.64 (s, 1H), 8.01 (d, J = 8.8 Hz, 2H), 7.57 (dd, J = 8.4, 1.2 Hz, 2H), 7.51 (d, J = 2.0 Hz, 1H), 7.40 (t, J = 7.8 Hz, 2H), 7.34 (dd, J = 8.2, 2.0 Hz, 1H), 7.25 (t, J = 7.2 Hz, 1H), 7.07 (d, J = 8.8 Hz, 2H), 6.88 (d, J = 8.2 Hz, 1H), 5.10 (s, 2H), 3.87 (s, 3H). MS: 318.37 (calc) 319.1 (found) | 21 |

TABLE Ia-continued

| Ex | Cpd | Structure | Name | Characterization | Scheme |
|---|---|---|---|---|---|
| 31bb | 117bb | 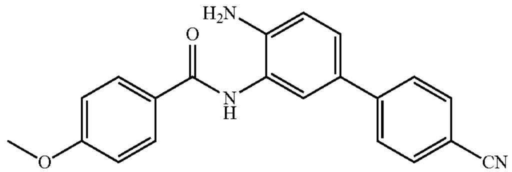 | N-(4-amino-4'-cyanobiphen-3-yl)-4-methoxybenzamide | ¹H NMR: (DMSO) δ (ppm): 9.59 (s, 1H), 7.98 (d, J = 9.0 Hz, 2H), 7.81-7.73 (m, 4H), 7.61 (d, J = 2.2 Hz, 1H), 7.43 (dd, J = 8.4, 2.3 Hz, 1H), 7.04 (d, J = 8.8 Hz, 2H), 6.86 (d, J = 8.4 Hz, 1H), 5.32 (s, 2H), 3.84 (s, 3H). MS: 343.38 (calc) 344.1 (MH+) (found) | 21 |
| 31cc | 117cc | 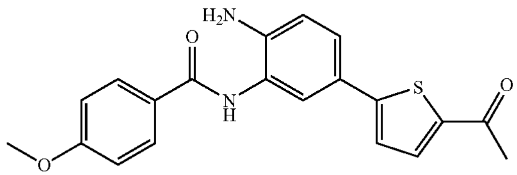 | N-(2-amino-5-(5-acetylthiophen-2-yl)phenyl)-4-methoxybenzamide | ¹H NMR: (DMSO) δ (ppm): 9.59 (s, 1H), 7.97 (d, J = 8.8 Hz, 2H), 7.84 (d, J = 4.1 Hz, 1H), 7.57 (d, J = 2.2 Hz, 1H), 7.39 (dd, J = 8.3, 2.3 Hz, 1H), 7.37 (d, J = 3.9 Hz, 1H), 7.04 (d, J = 8.8 Hz, 2H), 6.81 (d, J = 8.4 Hz, 1H), 5.42 (s, 2H), 3.84 (s, 3H), 2.50 (s, 3H). MS: 366.43 (calc) 367.1 (MH+) (found) | 21 |
| 31dd | 117dd | 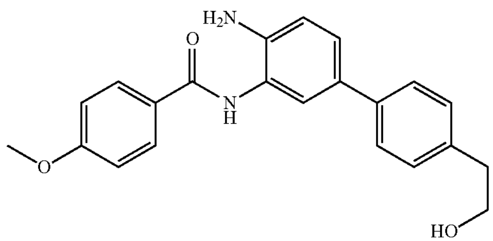 | N-(4-amino-4'-(2-hydroxyethyl)biphen-3-yl)-4-methoxybenzamide | ¹H NMR: (DMSO) δ (ppm): 9.60 (s, 1H), 7.97 (d, J = 8.8 Hz, 2H), 7.44 (d, J = 8.4 Hz, 3H), 7.27 (d, J = 8.4 Hz, 2H), 7.21 (d, J = 8.4 Hz, 2H), 7.03 (d, J = 9.0 Hz, 2H), 6.83 (d, J = 8.4 Hz, 1H), 5.01 (d, J = 10.4 Hz, 2H), 4.64 (t, J = 5.3 Hz, 1H), 3.84 (s, 3H), 3.63-3.58 (m, 2H), 2.72 (t, J = 7.0 Hz, 2H). MS: 362.43 (calc) 363.1 (MH+) (found) | 21 |
| 31ee | 117ee | 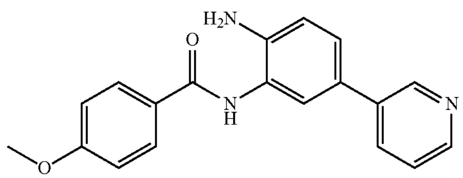 | N-(2-amino-5-(pyridin-3-yl)phenyl)-4-methoxybenzamide | ¹H NMR: (DMSO) δ (ppm): 9.62 (s, 1H), 8.77 (s, 1H), 8.42 (d, J = 4.7 Hz, 1H), 7.98 (d, J = 7.0 Hz, 2H), 7.93 (d, J = 7.9 Hz, 1H), 7.53 (s, 1H), 7.40-7.36 (m, 2H), 7.04 (d, J = 8.8 Hz, 2H), 6.87 (d, J = 8.2 Hz, 2H), 5.16 (d, J = 9.7 Hz, 2H), 3.84 (s, 3H). MS: 319.36 (calc) 320.1 (MH+) (found) | 21 |
| 31ff | 117ff | 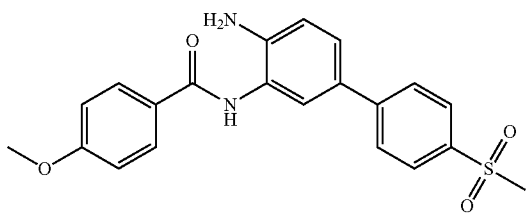 | N-(4-amino-4'-methylsulfonylbiphen-3-yl)-4-methoxybenzamide | ¹H NMR: (DMSO) δ (ppm): (DMSO-d6) d(ppm): 9.61 (s, 1H), 7.98 (d, J = 9.0 Hz, 2H), 7.89 (d, J = 8.6 Hz, 2H), 7.81 (d, J = 8.8 Hz, 2H), 7.62-7.61 (m, 1H), 7.43 (dd, J = 8.4, 2.3 Hz, 1H), 7.04 (d, J = 8.8 Hz, 2H), 6.88 (d, J = 8.4 Hz, 1H), 5.30 (s, 2H), 3.84 (s, 3H), 3.22 (s, 3H). MS: 396.46 (calc) 397.2 (MH+) (found) | 21 |

TABLE Ia-continued

| Ex | Cpd | Structure | Name | Characterization | Scheme |
|---|---|---|---|---|---|
| 31gg | 117gg | 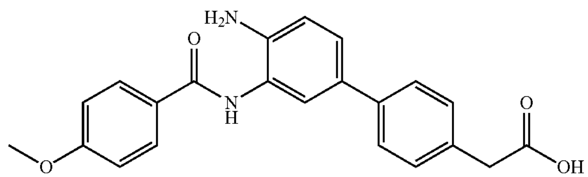 | 4-(4'-amino-N-3'-(4-methoxybenzamido)biphenyl)acetic acid | ¹H NMR: (DMSO) δ (ppm): 9.61 (s, 1H), 7.98 (d, J = 9.0 Hz, 2H), 7.48 (d, J = 6.5 Hz, 3H), 7.29 (dd, J = 8.4, 2.2 Hz, 1H), 7.25 (d, J = 8.2 Hz, 2H), 7.04 (d, J = 8.8 Hz, 2H), 6.84 (d, J = 8.4 Hz, 1H), 5.05 (s, 2H), 3.84 (s, 3H), 3.56 (s, 3H). MS: 376.41 (calc) 377.2 (MH+) (found) | 21 |
| 31hh | 117hh | 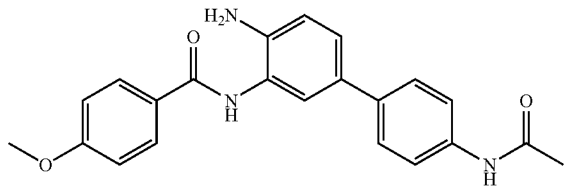 | N-(4-amino-4'-N-acetamidobiphen-3-yl)-4-methoxybenzamide | ¹H NMR: (DMSO) δ (ppm): 9.92 (s, 1H), 9.60 (s, 1H), 7.97 (d, J = 8.8 Hz, 2H), 7.57 (d, J = 8.8 Hz, 2H), 7.48–7.44 (m, 3H), 7.27 (d, J = 8.4 Hz, 1H), 7.04 (d, J = 8.8 Hz, 2H), 6.83 (d, J = 8.2 Hz, 1H), 5.00 (d, J = 10.2 Hz, 2H), 3.84 (s, 3H), 2.04 (s, 3H). MS: 375.43 (calc) 376.3 (MH+) (found) | 21 |
| 31ii | 117ii | 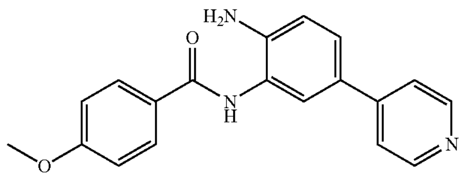 | N-(2-amino-5-(pyridin-4-yl)phenyl)-4-methoxybenzamide | ¹H NMR: (DMSO) δ (ppm): 9.61 (s, 1H), 8.49 (d, J = 5.9 Hz, 2H), 7.98 (d, J = 8.8 Hz, 2H), 7.65 (d, J = 2.2 Hz, 1H), 7.57 (dd, J = 4.5, 1.6 Hz, 2H), 7.49 (dd, J = 8.4, 2.2 Hz, 1H), 7.04 (d, J = 9.0 Hz, 2H), 6.87 (d, J = 8.4 Hz, 1H), 5.34 (d, J = 8.6 Hz, 2H), 3.84 (s, 3H). MS: 319.36 (calc) 320.2 (MH+) (found) | 21 |
| 31jj | 117jj | 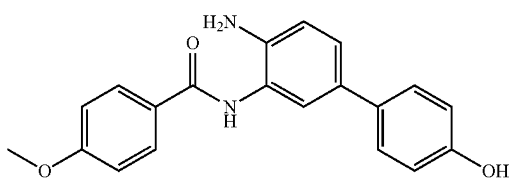 | N-(4-amino-4'-hydroxybiphen-3-yl)-4-methoxybenzamide | ¹H NMR: (DMSO) δ (ppm): 9.59 (s, 1H), 9.32 (s, 1H), 7.97 (d, J = 9.0 Hz, 2H), 7.37 (d, J = 2.2 Hz, 1H), 7.33 (d, J = 8.8 Hz, 2H), 7.19 (dd, J = 8.2, 2.2 Hz, 1H), 7.03 (d, J = 9.0 Hz, 2H), 6.80 (d, J = 8.4 Hz, 1H), 6.76 (d, J = 8.6 Hz, 2H), 4.92 (s, 2H), 3.83 (s, 3H). MS: 334.37 (calc) 335.1 (MH+) (found) | 21 |
| 31kk | 117kk | 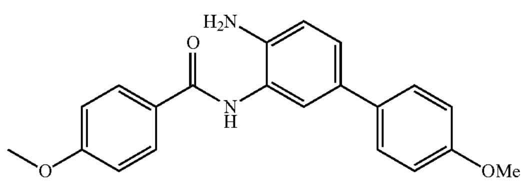 | N-(4-amino-4'-methoxybiphen-3-yl)-4-methoxybenzamide | ¹H NMR: (DMSO) δ (ppm): 9.60 (s, 1H), 7.97 (d, J = 8.8 Hz, 2H), 7.46 (d, J = 8.8 Hz, 2H), 7.41 (d, J = 2.3 Hz, 1H), 7.23 (dd, J = 8.2, 2.1 Hz, 1H), 7.03 (d, J = 9.1 Hz, 2H), 6.94 (d, J = 8.8 Hz, 2H), 6.82 (d, J = 8.5 Hz, 1H), 4.97 (s, 2H), 3.83 (s, 3H), 3.76 (s, 3H). MS: 348.40 (calc) 349.2 (MH+) (found) | 21 |

| Ex | Cpd | Structure | Name | Characterization | Scheme |
|---|---|---|---|---|---|
| 31ll | 117ll | 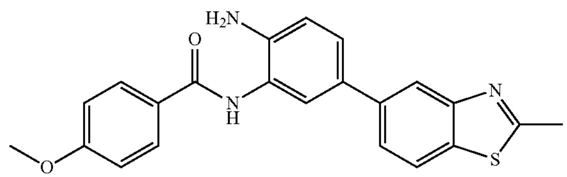 | N-(2-amino-5-(2-methylbenzo[d]thiazol-5-yl)phenyl)-4-methoxybenzamide | 1H NMR: (DMSO) δ (ppm): 9.63 (s, 1H), 8.02-7.97 (m, 4H), 7.60-7.57 (m, 2H), 7.40 (dd, J = 8.2, 2.1 Hz, 1H), 7.04 (d, J = 8.8 Hz, 2H), 6.87 (d, J = 8.5 Hz, 1H), 5.11 (s, 2H), 3.84 (s, 3H), 2.80 (s, 3H). MS: 389.47 (calc) 390.2 (MH+) (found) | 21 |
| 31mm | 117mm | 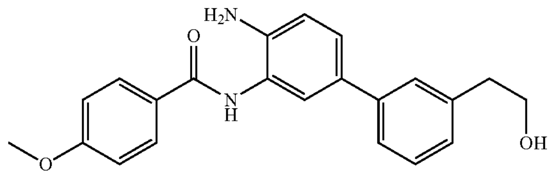 | N-(4-amino-3'-(2-hydroxyethyl)biphen-3-yl)-4-methoxybenzamide | 1H NMR: (DMSO) δ (ppm): 9.61 (s, 1H), 7.98 (d, J = 8.8 Hz, 2H), 7.47 (d, J = 2.0 Hz, 1H), 7.38-7.34 (m, 2H), 7.30-7.25 (m, 2H), 7.07 (d, J = 7.4 Hz, 2H), 7.04 (d, J = 9.0 Hz, 1H), 6.84 (d, J = 8.2 Hz, 1H), 5.04 (s, 2H), 4.64 (t, J = 5.3 Hz, 1H), 3.84 (s, 3H), 3.63 (quad, J = 7.0 Hz, 2H), 2.76 (t, J = 7.0 Hz, 2H). MS: 362.43 (calc) 363.3 (MH+) (found) | 21 |
| 31nn | 117nn | 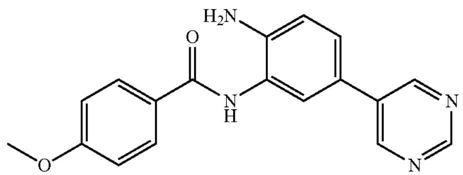 | N-(2-amino-5-(pyrimidin-5-yl)phenyl)-4-methoxybenzamide | 1H NMR (DMSO) δ (ppm): 9.64 (s, 1H), 9.02 (s, 1H), 9.00 (s, 2H), 7.98 (d, J = 8.6 Hz, 2H), 7.61 (d, J = 1.6 Hz, 1H), 7.46 (dd, J = 8.4, 1.8 Hz, 1H), 7.04 (d, J = 8.6 Hz, 2H), 6.90 (d, J = 8.2 Hz, 1H), 5.30 (s, 2H), 3.84 (s, 3H). MS: 320.35 (calc) 321.2 (MH+) (found) | 21 |
| 31oo | 117oo | 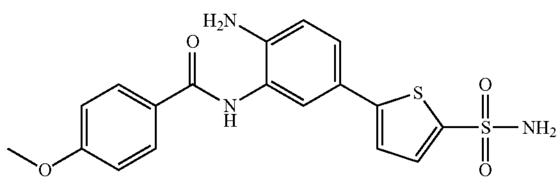 | N-[2-Amino-5-(5-sulfamoyl-thiophen-2-yl)-phenyl]-4-methoxybenzamide | 1H NMR (DMSO) δ (ppm): 9.58 (s, 1H), 7.97 (d, J = 8.4 Hz, 2H), 7.61 (s, 2H), 7.51 (d, J = 1.2 Hz, 1H), 7.43 (dd, J = 3.9, 1.0 Hz, 1H), 7.32 (dd, J = 8.4, 1.4 Hz, 1H), 7.23 (d, J = 3.9 Hz, 1H), 7.04 (d, J = 8.2 Hz, 2H), 6.81 (d, J = 8.2 Hz, 1H), 5.35 (s, 2H), 3.84 (s, 3H). MS: 403.47 (calc) 404.2 (MH+) (found) | 21 |
| 31pp | 117pp | 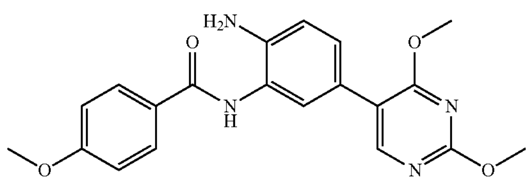 | N-(2-amino-5-(2,4-dimethoxypyrimidin-5-yl)phenyl)-4-methoxybenzamide | 1H NMR (DMSO) δ (ppm): 9.60 (s, 1H), 8.24 (s, 1H), 7.96 (d, J = 8.2 Hz, 2H), 7.31 (s, 1H), 7.13 (d, J = 9.4 Hz, 1H), 7.03 (d, J = 8.2 Hz, 2H), 6.81 (d, J = 7.9 Hz, 1H), 5.06 (s, 2H), 3.92 (s, 3H), 3.91 (s, 3H), 3.83 (s, 3H). MS: 380.40 (calc) 381.4 (MH+) (found) | 21 |

TABLE Ia-continued

| Ex | Cpd | Structure | Name | Characterization | Scheme |
|---|---|---|---|---|---|
| 31qq | 117qq | 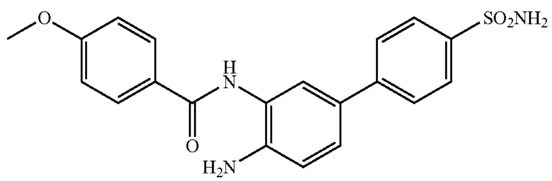 | N-(4-amino-4'-sulfamoylbiphen-3-yl)-4-methoxybenzamide | ¹H NMR (DMSO) δ (ppm): 9.64 (s, 1H), 8.01 (d, J = 9.0 Hz, 2H), 7.82 (d, J = 8.6 Hz, 2H), 7.76 (d, J = 8.8 Hz, 2H), 7.60 (d, J = 2.2 Hz, 1H), 7.43 (dd, J = 8.6, 6.3 Hz, 1H), 7.33 (s, 2H), 7.07 (d, J = 9.0 Hz, 2H), 6.89 (d, J = 8.2 Hz, 1H), 5.27 (s, 2H), 3.86 (s, 3H). MS: 397.45 (calc) 398.4 (found) | 21 |
| 31rr | 117rr | 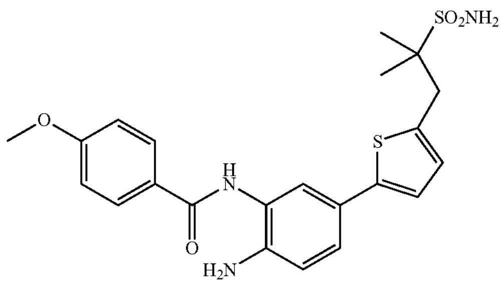 | N-(2-amino-5-(5-(2-methyl-2-sulfamoylpropyl)thiophen-2-yl)phenyl)-4-methoxybenzamide | ¹H NMR (DMSO) δ (ppm): 9.58 (s, 1H), 7.97 (d, J = 8.8 Hz, 2H), 7.66 (s, 1H), 7.49 (d, J = 2.3 Hz, 1H), 7.44 (d, J = 3.9 Hz, 1H), 7.32 (dd, J = 8.2, 2.2 Hz, 1H), 7.22 (d, J = 3.9 Hz, 1H), 7.03 (d, J = 9.0 Hz, 2H), 6.80 (d, J = 8.2 Hz, 1H), 5.36 (s, 2H), 3.83 (s, 3H), 1.99 (s, 2H), 1.17 (s, 6H). MS: 459.59 (calc) 460.4 (found) | 21 |
| 31ss | 117ss | 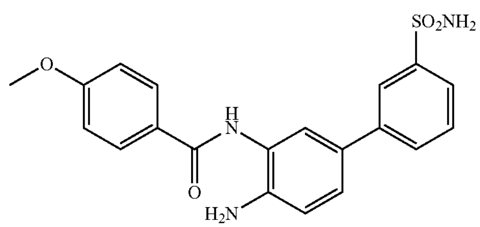 | N-(4-amino-3'-sulfamoylbiphen-3-yl)-4-methoxybenzamide | ¹H NMR (DMSO) δ (ppm): 9.62 (s, 1H), 7.99 (d, J = 8.8 Hz, 2H), 7.77 (d, J = 8.6 Hz, 1H), 7.64 (d, J = 7.8 Hz, 1H), 7.55 (t, J = 7.8 Hz, 1H), 7.54 (d, J = 2.5 Hz, 1H), 7.36 (dd, J = 8.2, 2.0 Hz, 1H), 7.35 (s, 2H), 7.03 (d, J = 8.8 Hz, 2H), 6.87 (d, J = 8.4 Hz, 1H), 5.20 (s, 2H), 3.83 (s, 3H), MS: 397.45 (calc) 398.3 (found) | 21 |
| 31tt | 117tt | 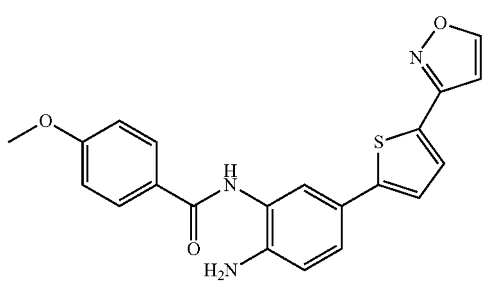 | N-(2-amino-5-(5-(isoxazol-3-yl)thiophen-2-yl)phenyl)-4-methoxybenzamide | ¹H NMR (Acetone-d6) d(ppm): 7.89 (d, J = 8.8 Hz, 2H), 7.77 (d, J = 4.1 Hz, 1H), 7.61 (d, J = 2.2 Hz, 1H), 7.31 (dd, J = 8.4, 2.3 Hz, 1H), 7.26 (d, J = 4.1 Hz, 1H), 6.91 (d, J = 9.0 Hz, 2H), 6.80 (d, J = 8.4 Hz, 1H), 3.75 (s, 3H). MS: 391.45 (calc) 392.3 (found) | 21 |

TABLE Ia-continued

| Ex | Cpd | Structure | Name | Characterization | Scheme |
|---|---|---|---|---|---|
| 31uu | 117uu | (structure) | N-(2-amino-5-(6-fluoropyridin-3-yl)phenyl)-4-methoxybenzamide | ¹H NMR (Acetone-d6) d(ppm): 9.08 (bs, 1H), 8.40 (d, J = 2.2 Hz, 1H), 8.12 (ddd, J = 8.4, 7.8, 2.7 Hz, 1H), 8.04 (d, J = 8.6 Hz, 2H), 7.64 (t, J = 2.3 Hz, 1H), 7.36 (ss, J = 8.2, 2.2 Hz, 1H), 7.10 (ddd, J = 8.6, 2.5, 0.6 Hz, 1H), 7.06 (d, J = 9.0 Hz, 2H), 7.00 (d, J = 8.2 Hz, 1H), 4.89 (bs, 2H), 3.90 (s, 3H). MS: 337.35 (calc) 338.1 (found) | 21 |
| 31vv | 117vv | (structure) | N-[2-Amino-5-(5-carbamido-thiophen-2-yl)-phenyl]-4-methoxybenzamide | ¹H NMR (Acetone-d6) δ (ppm): 8.04 (d, J = 9.0 Hz, 2H), 7.68 (t, J = 2.2 Hz, 1H), 7.63 (d, J = 3.9 Hz, 1H), 7.05 (d, J = 9.0 Hz, 2H), 6.92 (d, J = 8.4 Hz, 1H), 3.90 (s, 3H). MS: 367.43 (calc) 368.1 (found) | 21 |
| 31ww | 117ww | (structure) | N-(2-amino-5-(5-(1-hydroxyethyl(thiophen-2-yl)phenyl)-4-methoxybenzamide | ¹H NMR: (DMSO) δ (ppm): 9.58 (s, 1H), 7.97 (d, J = 8.8 Hz, 2H), 7.40 (d, J = 2.2 Hz, 1H), 7.22 (dd, J = 8.2, 2.2 Hz, 1H), 7.05-7.02 (m, 3H), 6.81 (dd, J = 3.5, 0.8 Hz, 1H), 6.77 (d, J = 8.2 Hz, 1H), 5.48 (d, J = 4.7 Hz, 1H), 5.09 (s, 2H), 4.88 (quint, J = 5.3 Hz, 1H), 3.83 (s, 3H), 1.42 (d, J = 6.3 Hz, 3H). MS: 368.45 (calc) 369.1 (MH+) (found) | 21 |
| 31xx | 117xx | (structure) | N-[2-Amino-5-(5-(N,N-dimethyl)sulfamoyl-thiophen-2-yl)phenyl]-4-methoxybenzamide | ¹H NMR (DMSO) δ (ppm): 9.56 (s, 1H), 7.97 (d, J = 8.8 Hz, 2H), 7.54 (d, J = 2.2 Hz, 1H), 7.52 (d, J = 3.9 Hz, 1H), 7.38 (d, J = 3.9 Hz, 1H), 7.37 (dd, J = 8.4, 2.2 Hz, 1H), 7.03 (d, J = 9.0 Hz, 2H), 6.81 (d, J = 8.4 Hz, 1H), 5.41 (s, 2H), 3.83 (s, 3H), 2.67 (s, 6H). MS: 431.53 (calc) 432.2 (found) | 21 |

| Ex | Cpd | Structure | Name | Characterization | Scheme |
|---|---|---|---|---|---|
| 32 | 122 | 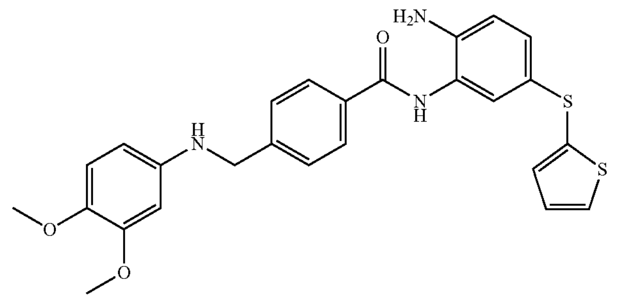 | N-(2-amino-5-(thiophen-2-ylthio)phenyl)-4-((3,4-dimethoxyphenylamino)methyl)benzamide | 1H NMR: (DMSO) δ (ppm): 9.57 (s, 1H), 7.87 (d, J = 8.4 Hz, 2H), 7.57 (dd, J = 5.3, 1.2 Hz, 1H), 7.44 (d, J = 8.4 Hz, 2H), 7.27 (d, J = 2.0 Hz, 1H), 7.19 (dd, J = 3.5, 1.2 Hz, 1H), 7.05 (dd, J = 8.2, 2.2 Hz, 1H), 7.01 (dd, J = 5.3, 3.5 Hz, 1H), 6.72 (d, J = 8.2 Hz, 1H), 6.63 (d, J = 8.6 Hz, 1H), 6.30 (dd, J = 2.5 Hz, J = 6.5 Hz, 1H), 5.97 (dd, J = 8.4, 2.5 Hz, 1H), 5.96 (d, J = 6.5 Hz, 1H), 5.20 (s, 2H), 4.28 (d, J = 6.3 Hz, 2H), 3.65 (s, 3H), 3.58 (s, 3H). MS: 491.63 (calc) 492.5 (found) | 22 |
| 33 | 123 | 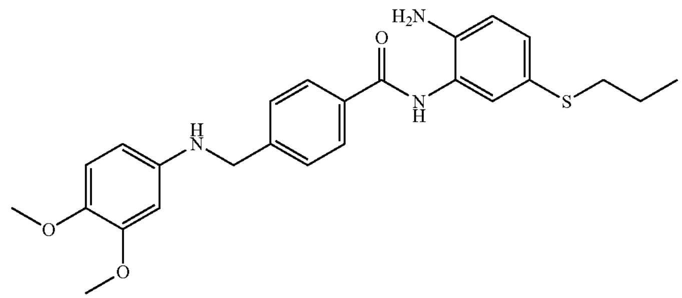 | N-(2-amino-5-(propylthio)phenyl)-4-((3,4-dimethoxyphenylamino)methyl)benzamide | 1H NMR (DMSO-d6) d(ppm): 9.57 (s, 1H), 7.89 (d, J = 8.2 Hz, 2H), 7.45 (d, J = 8.0 Hz, 2H), 7.23 (d, J = 0.4 Hz, 1H), 7.01 (dd, J = 8.4, 2.2 Hz, 1H), 6.71 (d, J = 8.4 Hz, 1H), 6.63 (d, J = 8.6 Hz, 1H), 6.31 (d, J = 2.3 Hz, 1H), 5.98 (dd, J = 8.2, 2.5 Hz, 1H), 5.97 (d, J = 5.9 Hz, 1H), 5.04 (s, 2H), 4.29 (d, J = 5.9 Hz, 2H), 3.65 (s, 3H), 3.58 (s, 3H), 2.71 (t, J = 7.0 Hz, 2H), 1.50 (sext, J = 7.0 Hz, 2H), 0.93 (t, J = 7.2 Hz, 3H). LRMS: 451.59 (calc) 452.5 (found) | 22 |
| 34 | 125 | 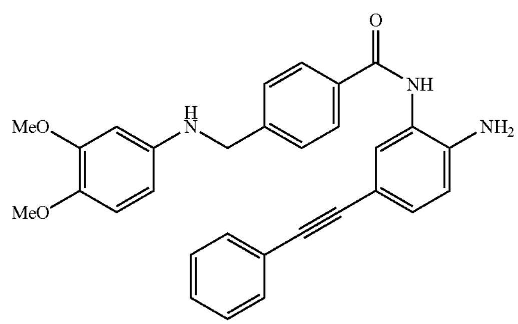 | N-(2-amino-5-(2-phenylethynyl)phenyl)-4-((3,4-dimethoxyphenylamino)methyl)benzamide | 1H NMR: (CD3OD) d(ppm): 7.93 (d, J = 8.4 Hz, 2H), 7.52 (d, J = 8.2 Hz, 2H), 7.44 (dd, J = 8.2, 1.8 Hz, 2H), 7.35-7.29 (m, 4H), 7.21 (dd, J = 8.2, 2.0 Hz, 1H), 6.85 (d, J = 8.4 Hz, 1H), 6.71 (d, J = 8.4 Hz, 1H), 6.36 (d, J = 2.7 Hz, 1H), 6.13 (dd, J = 8.4, 2.5 Hz, 1H), 4.39 (s, 2H), 3.75 (s, 3H), 3.71 (s, 3H). MS: 477.56 (calc) 478.5 (found) | 23 |

| Ex | Cpd | Structure | Name | Characterization | Scheme |
|---|---|---|---|---|---|
| 34aa | 125aa | 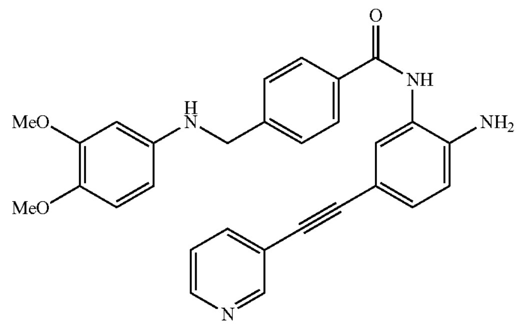 | N-(2-amino-5-(2-(pyridin-3-yl)ethynyl)phenyl)-4-((3,4-dimethoxyphenylamino)methyl)benzamide | 1H NMR: (DMSO) δ (ppm): 9.55 (s, 1H); 8.65 (dd; J = 0.9, 2.2 Hz; 1H); 8.49 (dd; J = 1.6, 4.8 Hz, 1H); 7.91 (d, J = 8.2, 2H); 7.87 (m, 1H); 7.46 (d, J = 8.2, 2H); 7.40 (dd; J = 0.9, 4.8 Hz; 1H); 7.39 (m, 1H); 7.17 (dd; J = 2.0, 8.3 Hz; 1H); 6.76 (d, J = 8.3, 1H); 6.64 (d, J = 8.6, 1H); 6.31 (d, J = 2.7, 1H); 5.98 (m, 2H); 5.51 (bs, 2H); 4.30 (d, J = 6.3, 2H); 3.66 (s, 3H); 3.58 (s, 3H). MS: calc 478.5; found: 478.5 (M + H) | 23 |
| 34-1 | 127 | 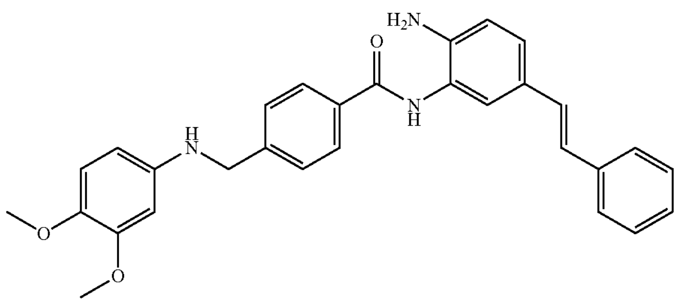 | (E)-N-(2-amino-5-styrylphenyl)-4-((3,4-dimethoxyphenylamino)methyl)benzamide | 1H NMR: (Acetone-d6) d(ppm): 9.07 (s, 1H), 8.01 (d, J = 8.2 Hz, 2H), 7.55 (d, J = 8.2 Hz, 2H), 7.55-7.52 (m, 3H), 7.32 (t, J = 7.4 Hz, 2H), 7.28 (dd, J = 8.2, 2.2 Hz, 1H), 7.19 (t, J = 7.2 Hz, 1H), 7.13 (d, J = 16.4 Hz, 1H), 7.0 (d, J = 16.2 Hz, 1H), 6.89 (d, J = 8.2 Hz, 1H), 6.70 (d, J = 8.4 Hz, 1H), 6.41 (d, J = 2.7 Hz, 1H), 6.12 (dd, J = 8.6, 2.7 Hz, 1H), 5.33 (bs, 1H), 4.85 (bs, 2H), 4.43 (s, 2H), 3.72 (s, 3H), 3.67 (s, 3H). MS: 479.58 (calc) 480.5 (found) | 24 |
| 35 | 128 | 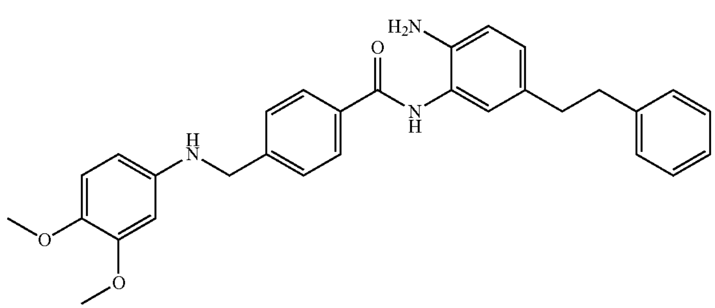 | N-(2-amino-5-phenethylphenyl)-4-((3,4-dimethoxyphenylamino)methyl)benzamide | 1H NMR (Acetone-d6) d(ppm): 9.07 (s, 1H), 7.99 (d, J = 8.2 Hz, 2H), 7.53 (d, J = 8.6 Hz, 2H), 7.27-7.22 (m, 5H), 7.19-7.14 (m, 1H), 6.87 (dd, J = 8.0, 2.0 Hz, 1H), 6.79 (d, J = 8.0 Hz, 1H), 6.70 (d, J = 8.4 Hz, 1H), 6.40 (d, J = 2.8 Hz, 1H), 6.11 (dd, J = 8.4, 2.5 Hz, 1H), 5.33 (bs, 1H), 4.51 (bs, 2H), 4.42 (s, 2H), 3.72 (s, 3H), 3.67 (s, 3H). MS: 481.59 (calc) 482.2 (found) | 24 |

TABLE Ia-continued

| Ex | Cpd | Structure | Name | Characterization | Scheme |
|---|---|---|---|---|---|
| 36 | 129 | (structure) | N-(2-amino-5-phenethylphenyl)-4-methylbenzamide | $^1$H NMR (Acetone-d6) d(ppm): 9.03 (bs, 1H), 7.94 (d, J = 8.0 Hz, 2H), 7.33 (d, J = 7.8 Hz, 2H), 7.28-7.23 (m, 5H), 7.18-7.13 (m, 1H), 6.87 (dd, J = 8.0, 2.0 Hz, 1H), 6.79 (d, J = 8.2 Hz, 1H), 4.48 (bs, 2H), 2.90-2.86 (m, 2H), 2.83-2.78 (m, 2H), 2.42 (s, 3H). MS: LRMS: 330.43 (calc) 331.1 (found) | 24 |
| 37 | 131 | (structure) | N-(2-amino-5-(thiophen-2-yl)phenyl)-4-((6-(2-(dimethylamino)ethoxy)-5-fluoro-1H-benzo[d]imidazol-2-ylthio)methyl)benzamide | $^1$H NMR (Acetone-d6) d(ppm): 9.16 (bs, 1H), 7.97 (d, J = 8.4 Hz, 2H), 7.62 (d, J = 2.9 Hz, 1H), 7.61 (d, J = 8.4 Hz, 2H), 7.32 (dd, J = 8.2, 2.2 Hz, 1H), 7.28 (bs, 0.5 H), 7.27 (dd, J = 5.1, 1.0 Hz, 1H), 7.26 (bs, 0.5 H), 7.22 (dd, J = 3.5, 1.0 Hz, 1H), 7.21 (bs, 1H), 7.03 (dd, J = 5.1, 3.5 Hz, 1H), 6.89 (d, J = 8.2 Hz, 1H), 4.87 (bs, 2H), 4.65 (s, 2H), 4.16 (t, J = 5.7 Hz, 2H), 2.73 (t, J = 5.9 Hz, 2H), 2.30 (s, 6H). MS: 561.70 (calc) 562.3 (found) | 25 |
| 38 | 134 | (structure) | 4-acetamido-N-(2-amino-5-(4,4,5,5-tetramethyl-1,3,2-dioxaborolan-2-yl)phenyl)benzamide | $^1$H NMR (Acetone-d6) d(ppm): 9.42 (bs, 1H), 9.03 (bs, 1H), 8.03 (d, J = 8.8 Hz, 2H), 7.77 (d, J = 8.8 Hz, 2H), 7.60 (d, J = 1.6 Hz, 1H), 7.39 (dd, J = 8.0, 1.6 Hz, 1H), 6.84 (d, J = 7.8 Hz, 1H), 5.01 (bs, 2H), 2.13 (s, 3H), 1.31 (s, 12H). MS: (calc) 395.3 (calc) 396.1 (found) | 26 |
| 39 | 136 | (structure) | N-(2-amino-5-(thiophene-2-carbonyl)phenyl)-4-methoxybenzamide | $^1$H NMR: (DMSO) δ (ppm): 9.61 (s, 1H), 8.02 (d, J = 6.3 Hz, 1H), 8.01 (d, J = 8.6 Hz, 2H), 7.83 (d, J = 2.0 Hz, 1H), 7.75 (d, J = 3.2 Hz, 1H), 7.63 (dd, J = 8.4, 2.0 Hz, 1H), 7.29 (dd, J = 4.9, 3.2 Hz, 1H), 7.08 (d, J = 8.8 Hz, 2H), 6.87 (d, J = 8.6 Hz, 1H), 6.01 (s, 2H), 3.88 (s, 3H). MS: 352.41 (calc) 353.1 (found) | 27 |
| 40 | 140 | (structure) | N-(2-amino-5-thiophen-2-ylphenyl)-4-(2-(N,N-dimethylamino)acetamido)benzamide | $^1$H NMR: (DMSO) δ (ppm): (CD3OD) d(ppm): 7.99 (d, J = 8.8 Hz, 2H), 7.77 (d, J = 8.8 Hz, 2H), 7.48 (d, J = 2.2 Hz, 1H), 7.35 (dd, J = 8.2, 2.2 Hz, 1H), 7.22 (dd, J = 5.1, 1.2 Hz, 1H), 7.20 (td, J = 3.5, 1.2 Hz, 1H), 7.01 (dd, J = 5.1, 3.7 Hz, 1H), 6.90 (d, J = 8.6 Hz, 1H), 3.24 (s, 2H), 2.43 (s, 6H). MS: 394.5 (calc) 395.1 (found) | 28 |

TABLE Ia-continued

| Ex | Cpd | Structure | Name | Characterization | Scheme |
|---|---|---|---|---|---|
| 41a | 143a | 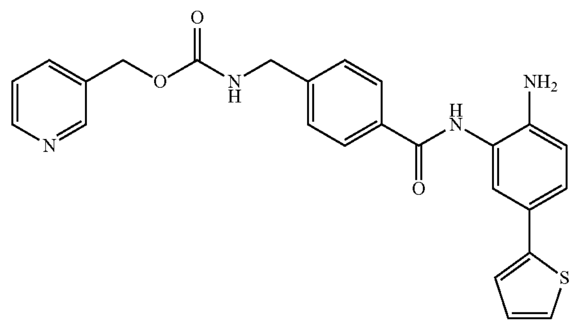 | Pyridin-3-ylmethyl 4-((2-amino-5-(thiophen-2-yl)phenyl)carbamoyl)benzylcarbamate | ¹H NMR (DMSO) δ (ppm): 9.69 (bs, 1H), 8.58 (s, 1H), 8.53-8.51 (m, 1H), 7.98-7.96 (m, 1H), 7.94 (d, J = 7.8 Hz, 2H), 7.78-7.76 (m, 1H), 7.46 (s, 1H), 7.40-7.38 (m, 1H), 7.37 (d, J = 8.4 Hz, 2H), 7.29 (d, J = 8.8 Hz, 1H), 7.24-7.23 (m, 1H), 7.05-7.03 (m, 1H), 6.80 (d, J = 8.4 Hz, 1H), 5.15 (bs, 2H), 5.10 (s, 2H), 4.29 (d, J = 6.1 Hz, 2H). MS: 458.54 (calc) 459.2 (found) | 29 |
| 41b | 143b | 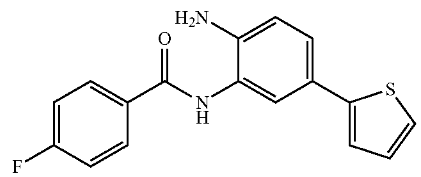 | N-(2-amino-5-(thiophen-2-yl)phenyl)-4-fluorobenzamide | ¹H NMR (DMSO) δ (ppm): 9.73 (s, 1H), 8.06 (dd, J = 8.6, 5.5 Hz, 2H), 7.43 (d, J = 1.8 Hz, 1H), 7.35 (d, J = 8.8 Hz, 2H), 7.33 (dd, J = 6.3, 5.1 Hz, 2H), 7.22 (dd, J = 3.7, 1.2 Hz, 1H), 7.03 (dd, J = 5.1, 3.5 Hz, 1H), 6.78 (d, J = 8.2 Hz, 1H), 5.17 (s, 2H), MS: 312.36 (calc) 313.1 (found) | 29 |
| 41c | 143c | 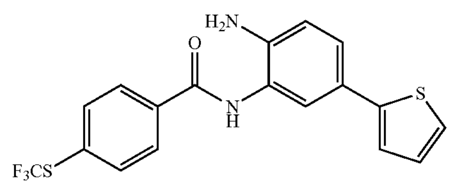 | N-(2-amino-5-(thiophen-2-yl)phenyl)-4-(trifluoromethylthio)benzamide | ¹H NMR (DMSO) δ (ppm): 8.09 (d, J = 8.6 Hz, 2H), 7.84 (d, J = 8.2 Hz, 2H), 7.58 (d, J = 2.2 Hz, 1H), 7.36 (dd, J = 8.2, 2.2 Hz, 1H), 7.23 (dd, J = 5.1, 3.9 Hz, 1H), 7.21 (dd, J = 3.7, 1.2 Hz, 1H), 7.01 (dd, J = 5.1, 3.7 Hz, 1H), 6.90 (d, J = 8.4 Hz, 1H). MS: 394.44 (calc) 395.1 (found) | 29 |
| 41d | 143d | 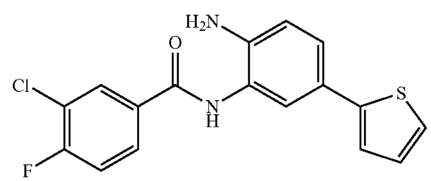 | N-(2-amino-5-(thiophen-2-yl)phenyl)-3-chloro-4-flurobenzamide | ¹H NMR (Acetone-d6) d(ppm): 8.22 (d, J = 7.2 Hz, 1H), 8.08 (bs, 2H), 7.61 (s, 1H), 7.48 (t, J = 8.8 Hz, 1H), 7.35 (dd, J = 8.6, 2.0 Hz, 1H), 7.29 (d, J = 5.1 Hz, 1H), 7.23 (d, J = 3.7 Hz, 2H), 7.04 (dd, J = 7.5, 4.3 Hz, 1H), 6.91 (d, J = 8.2 Hz, 1H), 4.88 (bs, 1H). MS: 346.86 (calc) 347.1 (found) | 29 |

TABLE Ia-continued

| Ex | Cpd | Structure | Name | Characterization | Scheme |
|---|---|---|---|---|---|
| 41aa | 143aa | 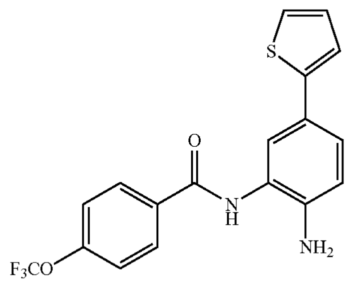 | N-(2-amino-5-(thiophen-2-yl)phenyl)-4-(trifluoromethoxy)benzamide | $^1$H NMR: (DMSO) δ (ppm): 9.79 (s, 1H), 8.10 (d, J = 8.8 Hz, 2H), 7.50 (d, J = 8.4 Hz, 2H), 7.43 (bs, 1H), 7.32 (d, J = 5.2 Hz, 1H), 7.28 (dd, J = 8.4, 2.0 Hz 1H), 7.22 (bd, J = 3.6 Hz, 1H), 7.02 (dd, J = 3.6, 5.2 Hz, 1H), 6.78 (d, J = 8.4 Hz, 1H). MS: (calc.) 378; (obt.) 379 (MH)$^+$. | 29 |
| 41bb | 143bb | 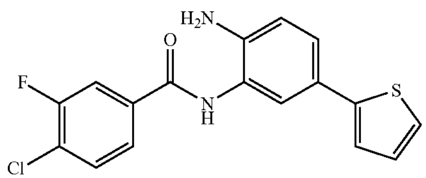 | N-(2-amino-5-(thiophen-2-yl)phenyl)-4-chloro-3-fluorobenzamide | $^1$H NMR (DMSO) δ (ppm): 9.82 (s, 1H), 8.01 (d, J = 10.4 Hz, 1H), 7.85 (d, J = 7.2 Hz, 1H), 7.75 (t, J = 7.6 Hz, 1H), 7.41 (d, J = 2.2 Hz, 1H), 7.33 (d, J = 5.1 Hz, 1H), 7.28 (dd, J = 8.4, 1.8 Hz, 1H), 7.22 (d, J = 3.5 Hz, 1H), 7.02 (dd, J = 4.9, 3.5 Hz, 1H), 6.78 (d, J = 8.4 Hz, 1H), 5.23 (s, 2H). MS: 346.86 (calc) 347.1/349.1 (found) | 29 |
| 41cc | 143cc | 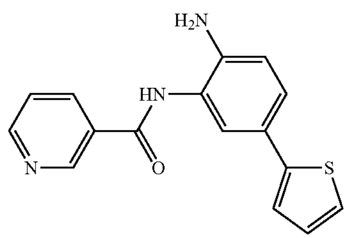 | N-(2-amino-5-(thiophen-2-yl)phenyl)nicotinamide | $^1$H NMR: (DMSO) δ (ppm): 9.87 (s, 1H), 9.14 (d, J = 1.8, Hz, 1H), 8.73 (dd, J = 4.9, 1.8 Hz, 1H), 8.32 (dt, J = 8.0, 2.0 Hz, 1H), 7.54 (dd, J = 7.8, 5.3 Hz, 1H), 7.46 (d, J = 2.2 Hz, 1H), 7.34 (dd, J = 5.1, , 1.2 Hz, 1H), 7.29 (dd, J = 8.4, 2.3 Hz, 1H), 723 (dd, J = 3.5, 1.0 Hz, 1H), 7.03 (dd, J = 5.1, 3.7 Hz, 1H), 6.79 (d, J = 8.4 Hz, 1H), 5.24 (sb, 2H). MS: (calc.) 295.1; (obt.) 296.3 (MH)$^+$. | 29 |
| 41dd | 143dd | 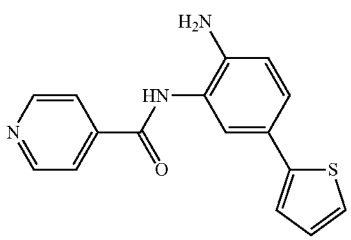 | N-(2-amino-5-(thiophen-2-yl)phenyl)isonicotinamide | $^1$H NMR: (DMSO) δ (ppm): 9.95 (s, 1H), 7.76 (d, J = 6.1, Hz, 2H), 7.90 (d, J = 6.1 Hz, 1H), 7.44 (d, J = 2.2 Hz, 1H), 7.34 (dd, J = 5.1, 1.2 Hz, 1H), 7.30 (dd, J = 8.4, 2.3 Hz, 1H), 7.23 (dd, J = 3.7, 1.2 Hz, 1H), 7.03 (dd, J = 5.1, 3.7 Hz, 1H), 6.79 (d, J = 8.4 Hz, 1H), 5.24 (sb, 2H). MS: (calc.) 295.1; (obt.) 296.3 (MH)$^+$. | 29 |

TABLE Ia-continued

| Ex | Cpd | Structure | Name | Characterization | Scheme |
|---|---|---|---|---|---|
| 41ee | 143ee | 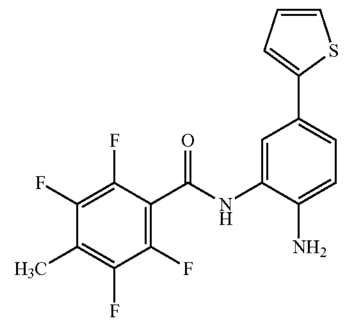 | N-(2-amino-5-(thiophen-2-yl)phenyl)-2,3,5,6-tetrafluoro-4-methylbenzamide | $^1$H NMR: (DMSO) δ (ppm): 10.18 (s, 1H), 7.60 (d, J = 2.4 Hz, 1H), 7.36 (dd, J = 1.2, 5.2 Hz, 1H), 7.30 (dd, J = 2.4, 8.0 Hz, 1H), 7.23 (dd, J = 1.2, 3.2 Hz, 1H), 7.04 (dd, J = 3.6, 5.2 Hz, 1H), 6.81 (d, J = 8.0 Hz, 1H), 5.15 (bs, 2H), 2.32 (s, 3H) MS: (calc.) 380.36; (obt.) 381.2 (MH)$^+$. | 29 |
| 42 | 146 | 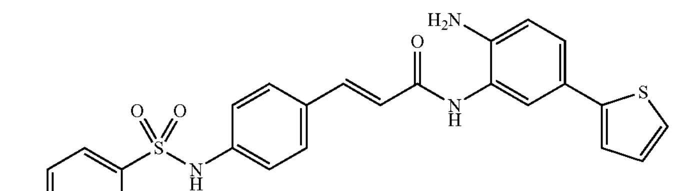 | (E)-N-(2-amino-5-(thiophen-2-yl)phenyl)-3-(4-(4-methylphenylsulfonamido)phenyl)acrylamide | $^1$H NMR (Acetone-d6) d(ppm): 9.20 (bs, 1H), 8.84 (bs, 1H), 7.72 (d, J = 8.0 Hz, 3H), 7.58 (d, J = 15.7 Hz, 1H), 7.54 (d, J = 8.4 Hz, 2H), 7.34 (d, J = 8.6 Hz, 2H), 7.29-7.27 (m, 4H), 7.22 (d, J = 3.5 Hz, 1H), 7.04 (t, J = 4.9 Hz, 1H), 6.88 (d, J = 8.4 Hz, 1H), 6.86 (d, J = 15.3 Hz, 1H), 4.84 (bs, 2H), 2.38 (s, 3H). MS: 489.62 (calc) 490.1 (found) | 30 |
| 43 | 153 | 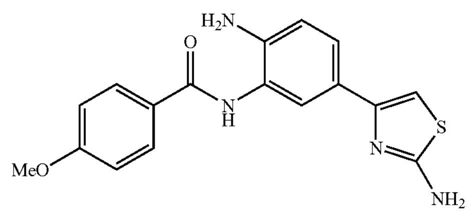 | N-(2-amino-5-(2-aminothiazol-4-yl)phenyl)-4-methoxybenzamide | $^1$H NMR: (DMSO) δ (ppm): 9.55 (s, 1H), 7.96 (d, J = 9.0 Hz, 2H), 7.60 (d, J = 2.2 Hz, 1H), 7.39 (d, J = 8.2, 2.0 Hz, 1H), 7.02 (d, J = 9.0 Hz, 2H), 6.90 (s, 2H), 6.73 (d, J = 8.4 Hz, 1H), 6.63 (s, 1H), 4.98 (s, 2H), 3.83 (s, 3H). MS: 340.4 (calc) 341.2 (found) | 31 |
| 44 | 157 | 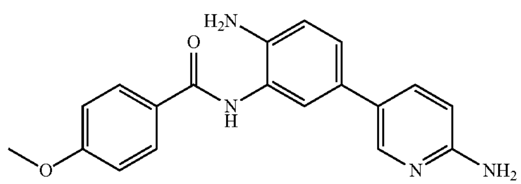 | N-(2-amino-5-(6-aminopyridin-3-yl)phenyl)-4-methoxybenzamide | $^1$H NMR (Acetone-d6) d(ppm): 8.94 (bs, 1H), 8.03 (d, J = 1.8 Hz, 1H), 7.88 (d, J = 8.8 Hz, 1H), 7.47 (dd, J = 8.9, 2.5 Hz, 1H), 7.36 (d, J = 2.3 Hz, 1H), 7.07 (dd, J = 8.2, 2.3 Hz, 1H), 6.89 (d, J = 8.8 Hz, 2H), 6.77 (d, J = 8.2 Hz, 1H), 6.45 (dd, J = 8.4, 0.6 Hz, 1H), 5.29 (bs, 2H), 3.74 (s, 3H). MS: 334.38 (calc) 335.1 (found) | 32 |

| Ex | Cpd | Structure | Name | Characterization | Scheme |
|---|---|---|---|---|---|
| 44a | 157a | 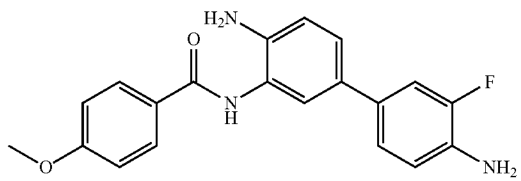 | N-(4,4'-diamino-3'-fluoro-biphenyl-3-yl)-4-methoxybenzamide | ¹H NMR (CD3OD) d(ppm): 7.97 (d, J = 8.6 Hz, 2H), 7.37 (d, J = 1.6 Hz, 1H), 7.28 (dd, J = 8.4, 2.2 Hz, 1H), 7.20-7.13 (m, 2H), 7.03 (d, J = 8.6 Hz, 2H), 6.94 (d, J = 8.2 Hz, 1H), 6.85 (t, J = 9.0 Hz, 1H), 3.88 (s, 3H). MS: 351.38 (calc) 352.3 (MS+) (found) | 32 |
| 45 | 160 | 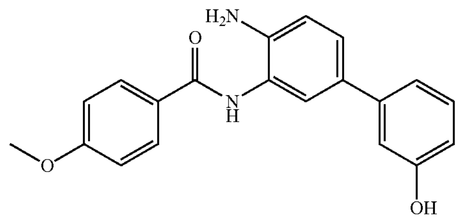 | N-(4-amino-3'-hydroxybiphen-3-yl)-4-methoxybenzamide | ¹H NMR (DMSO) δ (ppm): 9.58 (s, 1H), 9.35 (s, 1H), 7.97 (d, J = 8.4 Hz, 2H), 7.43 (s, 1H), 7.23 (dd, J = 8.2, 1.4 Hz, 1H), 7.16 (t, J = 7.6 Hz, 1H), 7.04 (d, J = 8.4 Hz, 2H), 6.95 (d, J = 7.6 Hz, 1H), 6.91 (s, 1H), 6.82 (d, J = 8.4 Hz, 1H), 6.62 (dt, J = 8.0, 1.0 Hz, 1H), 5.05 (s, 2H), 3.84 (s, 3H). MS: 334.37 (calc) 335.2 (MH+) (found) CHECK NMR | 33 |
| 45aa | 160aa | 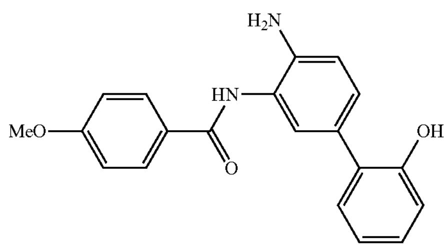 | N-(2-amino-5-(3-hydroxyphenyl)phenyl)-4-methoxybenzamide | ¹H NMR (DMSO) δ (ppm): 9.59 (s, 1H), 9.31 (s, 1H), 7.96 (d, J = 8.8 Hz, 2H), 7.36 (d, J = 2.0 Hz, 1H), 7.18 (td, J = 8.4, 2.0 Hz, 2H), 7.06-7.02 (m, 3H), 6.87 (dd, J = 7.8, 0.8 Hz, 1H), 6.82-6.77 (m, 2H), 4.92 (s, 2H), 3.83 (s, 3H). MS: 334.37 (calc) 335.1 (MH+) (found) CHECK NMR | 33 |
| 46 | 164 | 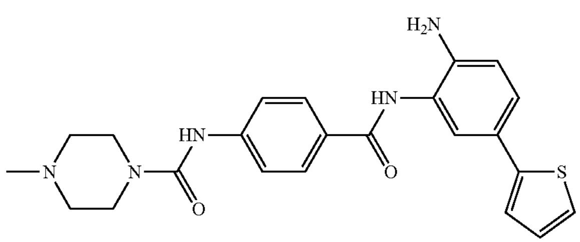 | N-(4-((2-amino-5-(thiophen-2-yl)phenyl)carbamoyl)phenyl)-4-methylpiperazine-1-carboxamide | ¹H NMR: (DMSO) δ (ppm): 400 MHz, (DMSO) d (ppm): 9.57 (s, 1H), 8.80 (s, 1H), 7.89 (d, J = 8.8 Hz, 2H), 7.59 (d, J = 8.8 Hz, 2H), 7.44 (d, J = 2.2 Hz, 1H), 7.34 (dd, J = 5.1, 1.0 Hz, 1H), 7.27 (dd, J = 8.2, 2.2 Hz, 1H), 7.23 (dd, J = 3.5, 1.2 Hz, 1H), 7.03 (dd, J = 5.1, 3.5 Hz, 1H), 6.79 (d, J = 8.4 Hz, 1H), 5.12 (sb, 2H), 3.46 (t, J = 4.8 Hz, 4H), 2.33 (t, J = 4.9 Hz, 4H). MS: (calc.) 435.2; (obt.) 436.4 (MH)⁺. | 34 |

TABLE Ia-continued

| Ex | Cpd | Structure | Name | Characterization | Scheme |
|---|---|---|---|---|---|
| 46aa | 164aa | 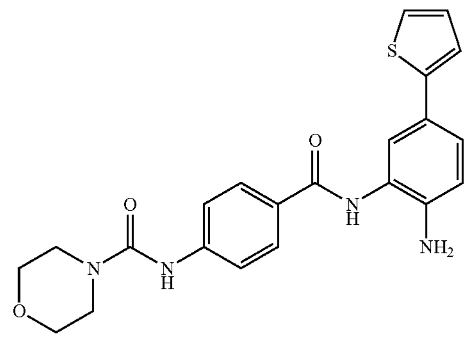 | N-(4-((2-amino-5-(thiophen-2-yl)phenyl)carbamoyl)phenyl)morpholine-4-carboxamide | $^1$H NMR: (DMSO) δ (ppm): 9.57 (1H, s), 8.81 (1H, s), 7.90 (2H, d, 8.8 Hz), 7.60 (2H, d, 9.0 Hz), 7.45 (1H, d, 2.2 Hz), 7.34 (1H, dd, 3.9 and 1.2 Hz), 7.27 (1H, dd, 6.1 and 2.2 Hz), 7.22 (1H, dd, 2.3 and 1.2 Hz), 7.03 (1H, m), 6.78 (1H, d, 8.2 Hz), 5.12 (2H, s), 3.62 (4H, t, 4.5 Hz), 3.45 (4H, t, 5.1 Hz) MS: 422.14 (calc), 423.3 (obs). | 34 |
| 46bb | 164bb | 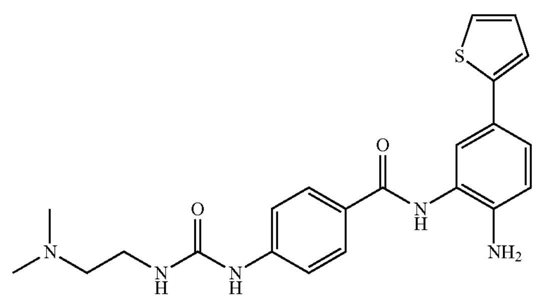 | 1-(4-((2-amino-5-(thiophen-2-yl)phenyl)carbamoyl)phenyl)-3-(2-(dimethylamino)ethyl)urea | $^1$H NMR: (DMSO) δ (ppm): 9.54 (1H, s), 9.10 (1H, s), [8.37 (2H, s) comes from formic salt], 7.87 (2H, d, 8.6), 7.49 (2H, d, 8.8 Hz), 7.44 (1H, d, 2.2 Hz), 7.34 (1H, dd, 3.9 and 1.2 Hz), 7.27 (1H, dd, 6.1 and 2.2 Hz), 7.23 (1H, dd, 2.5 and 1.0), 7.03 (1H, dd, 3.5 and 1.6), 6.79 (1H, d, 8.2 Hz), 6.36 to 6.34 (1H, m), 5.11 (2H, s), 3.2 to 3.1 (2H, m), 2.33 (2H, s), 2.18 (6H, s) MS: 423.2 (calc), 424.2 (obs). | 34 |
| 46cc | 164cc | 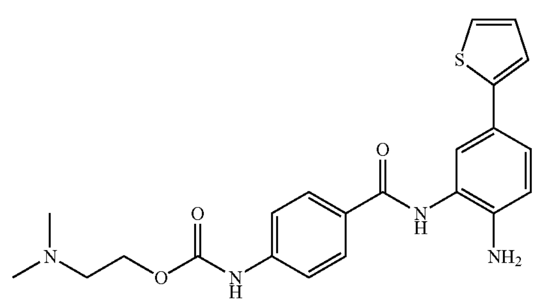 | 2-(dimethylamino)ethyl 4-((2-amino-5-(thiophen-2-yl)phenyl)carbamoyl)phenylcarbamate | $^1$H NMR: (DMSO) δ (ppm): 9.99 (1H, s), 9.59 (1H, s), [8.28 (1H, s) comes from formic acid salt], 7.92 (2H, d, 8.8), 7.57 (2H, d, 9.0 Hz), 7.44 (1H, d, 2.0 Hz), 7.34 (1H, dd, 3.7 and 1.2 Hz), 7.27 (1H, dd, 6.1 and 2.2 Hz), 7.23 (1H, dd, 2.3 and 1.2), 7.03 (1H, dd, 3.3 and 1.8), 6.79 (1H, d, 8.6 Hz), 4.18 (2H, t, 5.7 Hz), 2.20 (6H, s) MS: 424.2 (calc), 425.2 (obs). | 34 |

TABLE Ia-continued

| Ex | Cpd | Structure | Name | Characterization | Scheme |
|---|---|---|---|---|---|
| 46dd | 164dd | 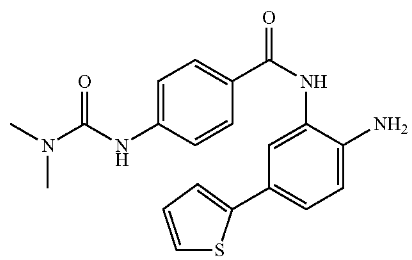 | 3-(4-((2-amino-5-(thiophen-2-yl)phenyl)carbamoyl)phenyl)-1,1-dimethylurea | ¹H NMR: (DMSO) δ (ppm): 9.56 (s, 1H); 8.56 (s, 1H); 7.88 (d, J = 8.8 Hz; 2H); 7.60 (d; J = 8.8 Hz; 2H); 7.44 (d; J = 2.2 Hz; 1H); 7.34 (dd; J = 1.2, 5.1 Hz; 1H); 7.27 (dd; J = 2.2, 8.4 Hz; 1H); 7.22 (dd; J = 1.2, 3.5 Hz; 1H); 7.03 (dd; J = 3.5, 5.1 Hz; 1H); 6.79 (d, J = 8.4 Hz; 1H); 5.12 (bs, 2H); 2.95 (s, 6H). MS: calc: 380.4; found: 381.2 (M + H) | 34 |
| 47 | 168 | 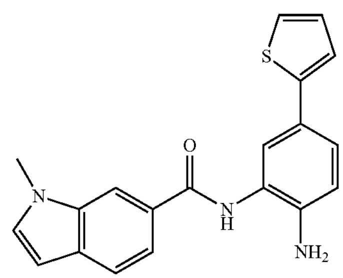 | N-(2-amino-5-(thiophen-2-yl)phenyl)-1-methyl-1H-indole-6-carboxamide | ¹H NMR: (DMSO) δ (ppm): 9.72 (s, 1H), 8.19 (s, 1H), 7.67 (abq, J = 29.4, 7.6, Hz, 2H), 7.52 (d, J = 7.6 Hz, 2H), 7.36 (s, 1H), 7.31 (d, J = 6.5 Hz, 1H), 7.26 (s, 1H), 7.06 (s, 1H), 6.83 (d, J = 8.0 Hz, 1H), 6.52 (s, 1H), 5.16 (s, 2H), 3.90 (s, 3H). MS: 347.1 (calc), 348.1 (obs). | 35 |
| 48 | 172 | 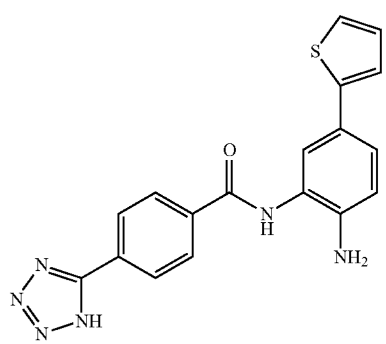 | N-(2-amino-5-(thiophen-2-yl)phenyl)-4-(1H-tetrazol-5-yl)benzamide | ¹H NMR: (DMSO) δ (ppm): 9.71 (s, 1H), 8.07 (d, J = 8.2 Hz, 2H), 8.00 (d, J = 8.2 Hz, 2H), 7.48 (s, 1H), 7.34 (d, J = 5.1 Hz, 1H), 7.28 (dd, J = 8.2, 2.0 Hz, 1H), 7.24 (d, J = 3.5 Hz, 1H), 7.03 (t, J = 3.7 Hz, 1H), 6.79 (d, J = 8.4 Hz, 1H), 5.17 (s, 2H). MS: 362.09 (calc), 363.1 (obs) | 36 |

| Ex | Cpd | Structure | Name | Characterization | Scheme |
|---|---|---|---|---|---|
| 49 | 173 | 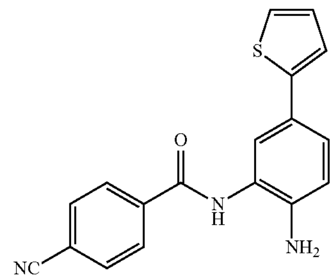 | N-(2-amino-5-(thiophen-2-yl)phenyl)-4-cyanobenzamide | $^1$H NMR: (DMSO) δ (ppm): 9.92 (s, 1H), 8.14 (d, J = 8.4 Hz, 2H), 8.00 (d, J = 8.4 Hz, 2H), 7.44 (d, J = 2.0 Hz, 1H), 7.34 (dd, J = 5.1, 0.98 Hz, 1H), 7.30 (dd, J = 8.2, 2.2 Hz, 1H), 7.23 (d, J = 3.5 Hz, 1H), 7.03 (dd, J = 5.1, 3.5 Hz, 1H), 6.79 (d, J = 8.4 Hz, 1H), 5.24 (s, 2H). MS: 319.08 (calc), 320.1 (obs). | 36 |
| 50 | 174 | 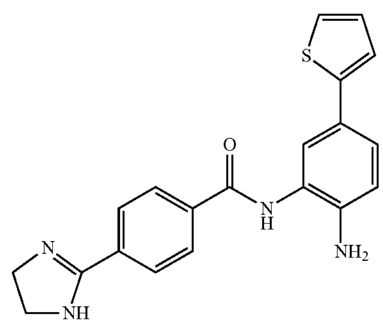 | N-(2-amino-5-(thiophen-2-yl)phenyl)-4-(4,5-dihydro-1H-imidazol-2-yl)benzamide | $^1$H NMR: (DMSO) δ (ppm): 9.78 (s, 1H), 8.02 (d, J = 8.0 Hz, 2H), 7.92 (d, J = 8.0 Hz, 2H), 7.45 (s, 1H), 7.33 (d, J = 5.1 Hz, 1H), 7.28 (d, J = 8.2 Hz, 1H), 7.22 (d, J = 3.3 Hz, 1H), 7.03 (t, J = 3.9 Hz, 1H), 6.79 (d, J = 8.2 Hz, 1H), 5.18 (s, 2H), 3.63 (s, 4H). MS: 362.12 (calc), 363.1 (obs). | 36 |
| 51 | 181 | 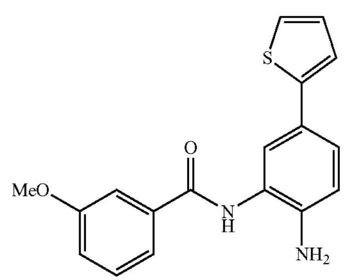 | N-(2-amino-5-(thiophen-2-yl)phenyl)-3-methoxybenzamide | $^1$H NMR: (DMSO) δ (ppm): 9.96 (1H, s), 7.59-7.52 (3H, m), 7.46-7.41 (3H, m), 7.39 (1H, d, 2.2 Hz), 7.33 (1H, dd, 2.5 and 1.0 Hz), 7.16 (1H, dd, 5.7 and 1.8 Hz), 6.98 (1H, d, 8.4 Hz), 3.84 (3H, s) MS: 324.1 (calc), 325.1 (obs). | 37 |

TABLE Ia-continued

| Ex | Cpd | Structure | Name | Characterization | Scheme |
|---|---|---|---|---|---|
| 51aa | 181aa | (thiophene-phenyl-NH-C(O)-phenyl-NO2 at para; phenyl has NH2) | N-(2-amino-5-(thiophen-2-yl)phenyl)-4-nitrobenzamide | $^1$H NMR: (DMSO) δ (ppm): 10.05 (s, 1H), 8.35 (d, J = 8.6 Hz, 2H), 8.22 (d, J = 8.6 Hz, 2H), 7.46 (s, 1H), 7.36 (d, J = 4.1 Hz, 1H), 7.33 (d, J = 8.2 Hz, 1H), 7.25 (d, J = 2.5 Hz, 1H), 7.04 (t, J = 3.5 Hz, 1H), 6.83 (d, J = 8.4 Hz, 1H), (missing NH$_2$). MS: 339.07 (calc), 340.1 (obs). | 37 |
| 51bb | 181bb | (thiophene-phenyl-NH-C(O)-phenyl-NO2 at meta; phenyl has NH2) | N-(2-amino-5-(thiophen-2-yl)phenyl)-3-nitrobenzamide | $^1$H NMR: (DMSO) δ (ppm): 10.14 (1H, s), 8.82 (1H, s), 8.43 (2H, d, 6.3 Hz), 7.82 (1H, t, 7.8 Hz), 7.46 (1H, d, 2.0 Hz), 7.37-7.33 (2H, m), 7.27 (1H, d, 3.3), 7.05 (1H, dd, 3.5 and 1.4 Hz), 6.85 (1H, d, 8.4 Hz) MS: 339.1 (calc) 340.1 (obs). | 37 |
| 51cc | 181cc | (thiophene-phenyl-NH-C(O)-phenyl-CN at meta; phenyl has NH2) | N-(2-amino-5-(thiophen-2-yl)phenyl)-3-cyanobenzamide | $^1$H NMR: (DMSO) δ (ppm): 9.97 (1H, s), 8.45 (1H, s), 8.27 (1H, d, 8.0 Hz), 8.05 (1H, d, 7.8 Hz), 7.74 (1H, t, 8.0 Hz), 7.48 (1H, d, 1.8 Hz), 7.38-7.3 (1H, d, 8.4 Hz) 7.38-7.33 (2H, m), 7.27 (1H, d, 3.52 Hz), 7.05 (1H, dd, 3.5 and 1.4 Hz), 6.86 (1H, d, 8.4). MS: 320.1 (calc) 320.1 (obs). | 37 |

| Ex | Cpd | Structure | Name | Characterization | Scheme |
|---|---|---|---|---|---|
| 51dd | 181dd | 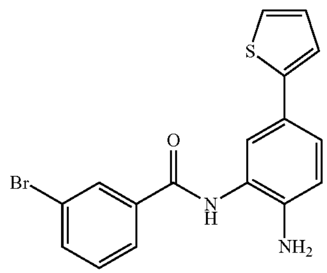 | N-(2-amino-5-(thiophen-2-yl)phenyl)-3-bromobenzamide | ¹H NMR: (DMSO) δ (ppm): 9.90 (1H, s), 8.18 (1H, s), 7.98 (1H, d, 7.4 Hz), 7.50-7.45 (2H, m), 7.37-7.32 (2H, m), 7.27 (1H, d, 3.3 Hz), 7.05 (1H, dd, 3.5 and 1.6 Hz), 6.85 (1H, d, 8.4 Hz) MS: 371.9 (calc) 373.0 (obs). | 37 |
| 51ee | 181ee | 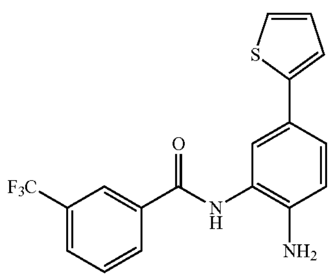 | N-(2-amino-5-(thiophen-2-yl)phenyl)-3-(trifluoromethyl)benzamide | ¹H NMR: (DMSO) δ (ppm): 10.00 (1H, s), 8.34 (1H, s), 8.29 (1H, d, 8.0 Hz), 7.95 (1H, d, 8.0 Hz), 7.76 (1H, t, 7.6 Hz), 7.44 (1H, s), 7.36-7.31 (2H, m), 7.25 (1H, d, 3.3 Hz), 7.04 (1H, t, 3.7 Hz), 6.82 (1H, d, 8.2 Hz) MS: 362.1 (calc) 363.1 (obs) | 37 |
| 52 | 184 | 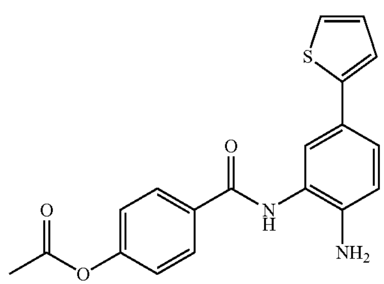 | 4-(2-amino-5-(thiophen-2-yl)phenylcarbamoyl)phenyl acetate | ¹H NMR: (DMSO) δ (ppm): 9.73 (1H, s), 8.03 (2H, d, 8.4), 7.45 (1H, s.), 7.34 (1H, d, 9.0 Hz), 7.30-7.22 (4H, m), 7.04 (1H, dd, 3.5 and 1.6 Hz), 6.79 (1H, d, 8.4 Hz), 5.18 (2H, s), 2.31 (3H, s) MS: 352.1 (calc), 353.1 (obs). | 37 |

| Ex | Cpd | Structure | Name | Characterization | Scheme |
|---|---|---|---|---|---|
| 52aa | 184aa | 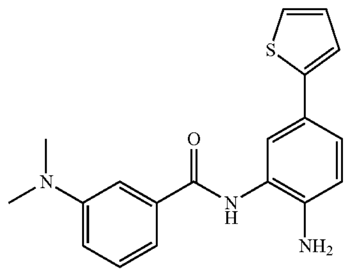 | N-(2-amino-5-(thiophen-2-yl)phenyl)-3-(dimethylamino)benzamide | $^1$H NMR: (DMSO) δ (ppm): 9.64 (1H, s), 7.45 (1H, s), 7.34 (1H, dd, 3.9 and 1.2 Hz), 7.29-7.26 (4H, m), 7.24-7.22 (1H, m), 7.03 (1H, dd, 3.7 and 1.4 Hz), 6.90 (1H, d, 8.2 Hz), 6.80 (1H, d, 8.2 Hz), 5.10 (2H, s), 2.96 (6H, s) MS: 337.1 (calc) 338.1 (obs). | 37 |
| 52bb | 184bb | 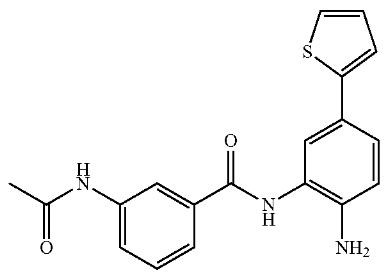 | 3-acetamido-N-(2-amino-5-(thiophen-2-yl)phenyl)benzamide | $^1$H NMR: (DMSO) δ (ppm): 10.11 (1H, s), 9.83 (1H, s), 8.11 (1H, s), 7.79 (1H, d, 6.7 Hz), 7.67 (1H, d, 7.6 Hz), 7.49 (1H, s), 7.43 (1H, t, 7.8 Hz), 7.38 (1H, d, 4.9 Hz), 7.34 (1H, d, 8.4 Hz), 7.28 (1H, d, 3.3 Hz), 7.05 (1H, t, 3.7 Hz), 6.89 (1H, d, 8.4 Hz), 2.07 (3H, s) MS: 351.1 (calc) 352.1 (obs) | 37 |
| 53 | 190 | 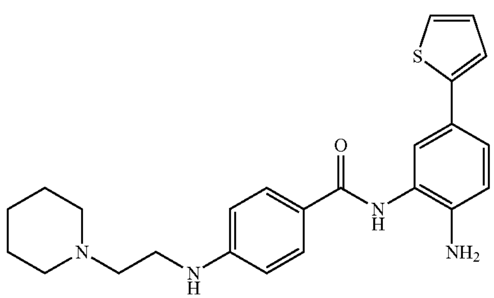 | N-(2-amino-5-(thiophen-2-yl)phenyl)-4-(2-(piperidin-1-yl)ethylamino)benzamide | $^1$H NMR: (DMSO) δ (ppm): 9.34 (1H, s), [8.25 (2H, s) comes from formic salt], 7.77 (2H, d, 8.8), 7.44 (1H, d, 2.2 Hz), 7.34 (1H, dd, 4.0 and 1.2 Hz), 7.26-7.21 (2H, m), 7.03 (1H, dd, 3.5 and 1.4), 6.78 (1H, d, 8.2), 6.62 (1H, d, 8.8 Hz), 6.09 (1H, m), 3.25-3.15 (8H, m), 1.53 to 1.49 (4H, m), 1.39 (2H, m) MS: 420.2 (calc), 421.3 (obs). | 38 |

| Ex | Cpd | Structure | Name | Characterization | Scheme |
|---|---|---|---|---|---|
| 54 | 197 | 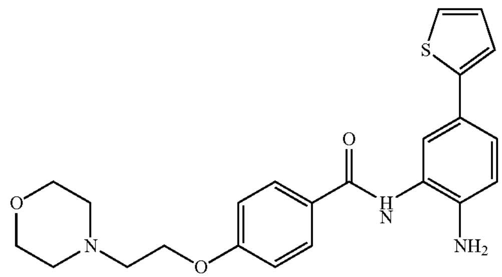 | N-(2-amino-5-(thiophen-2-yl)phenyl)-4-(2-morpholinoethoxy)benzamide | 1H NMR: (DMSO) δ (ppm): 9.67 (1H, s), 8.01 (2H, d, 8.8), 7.44 (1H, d, 2.0 Hz), 7.36 (1H, dd, 4.1 and 1.0 Hz), 7.30 (1H, dd, 6.1 and 2.2 Hz), 7.24 (1H, dd, 2.5 and 1.2), 7.12 (2H, d, 8.8), 7.04 (1H, dd, 3.5 and 1.6 Hz), 6.82 (1H, d, 8.4 Hz), 4.44 (2H, t, 4.1), 3.65 to 3.15 (10H, m) MS: 423.2 (calc), 424.2 (obs). | 39 |
| 55 | 199 | 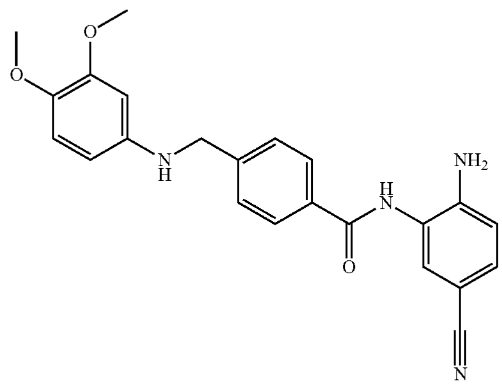 | 4-((3,4-dimethoxyphenyl(amino)methyl)-N-(2-amino-5-cyanophenyl)benzamide | 1H NMR: (DMSO) δ (ppm): 9.56 (bs, 1H), 7.89 (d, J = 8.0 Hz, 2H), 7.52 (bs, 1H), 7.45 (d, J = 8.4 Hz, 2H), 6.77 (d, J = 8.4 Hz, 1H), 6.63 (d, J = 8.4 Hz, 1H), 6.30 (d, J = 2.4 Hz, 1H), 5.99-5.95 (m, 2H), 5.74 (bs, 1H), 4.92 (bs, 2H), 3.64 (s, 3H), 3.32 (s, 3H). MS: (calc.); 402.5 (obt.) 403.4 (MH)+. | 40 |
| 56 | 205 | 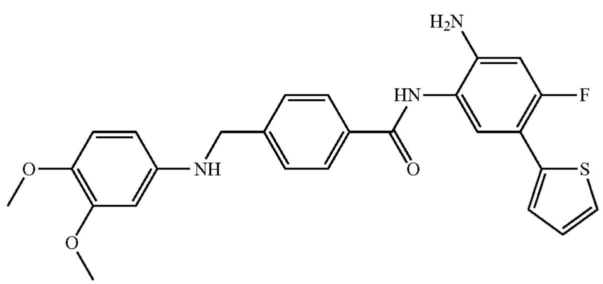 | 4-((3,4-dimethoxyphenyl(amino)methyl)-N-(2-amino-4-fluoro-5-(thiophen-2-yl)phenyl)benzamide | 1H NMR: (DMSO) δ (ppm): 9.65 (s, 1H), 7.96 (d, J = 8.0 Hz, 2H), 7.48-7.51 (m, 4H), 7.31 (d, J = 4.0 Hz, 1H), 7.11 (d, J = 4.0 Hz, 1H), 6.80 (d, J = 8.8 Hz, 1H), 6.50 (d, J = 13.6 Hz, 1H), 6.35 (d, J = 2.8 Hz, 1H), 6.03-6.01 (m, 2H), 5.50 (bs, 2H), 4.34 (d, J = 6.0 Hz, 2H), 3.70 (s, 3H), 3.62 (s, 3H). MS: (calc.) 477.6; (obt.) 478.4 (MH)+. | 41 |

TABLE Ia-continued

| Ex | Cpd | Structure | Name | Characterization | Scheme |
|---|---|---|---|---|---|
| 57a | 209a | 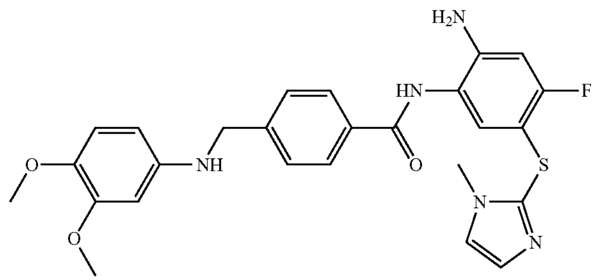 | N-(5-(1-methyl-1H-imidazol-2-ylthio)-2-amino-4-fluorophenyl)-4-((3,4-dimethoxyphenylamino)methyl)benzamide | ¹H NMR: (DMSO) δ (ppm): 9.5 (s, 1H), 7.86 (d, J = 8.4 Hz, 2H), 7.43 (d, J = 8.4 Hz, 2H), 7.2 (s, 1H), 7.10 (d, J = 8.4 Hz, 1H), 6.90 (s, 1H), 6.6 (d, J = 8.8 Hz, 1H), 6.56 (d, J = 11.6 Hz, 1H), 6.29 (d, J = 2.4 Hz, 1H), 5.95 (dd, J = 2.4, 8.8 Hz, 2H), 5.52 (bs, 2H), 4.28 (bs, 2H), 3.64 (s, 6H), 3.57 (s, 3H). MS: (calc.) 507.6; (obt.) 508.4 (MH)⁺. | 42 |
| 57b | 209b | 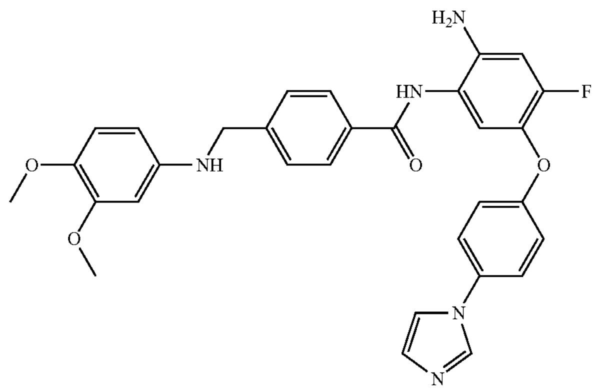 | 4-((3,4-dimethoxyphenylamino)methyl)-N-(5-(4-(1H-imidazol-1-yl)phenoxy)-2-amino-4-fluorophenyl)benzamide | ¹H NMR: (DMSO) δ (ppm): 7.87 (d, J = 8.4 Hz, 2H), 7.75 (bs, 1H), 7.60 (d, J = 8.0 Hz, 2H), 7.44 (d, J = 8.4 Hz, 2H), 7.26 (bs, 1H), 7.14 (d, J = 8.0 Hz, 1H), 7.03 (d, J = 8.0 Hz, 2H), 6.723 (d, J = 13.2 Hz, 1H), 6.62 (d, J = 8.4 Hz, 1H), 6.29 (d, J = 2.4 Hz, 1H), 5.96 (dd, J = 2.4, 8.8 Hz, 2H), 4.28 (bs, 2H), 3.64 (s, 3H), 3.57 (s, 3H) MS: (calc.) 553.6; (obt.) 554.5 (MH)⁺. | 42 |
| 58 | 213 | 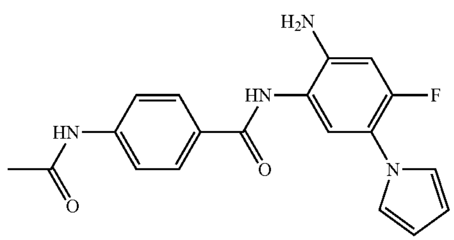 | 4-acetamido-N-(2-amino-4-fluoro-5-(1H-pyrrol-1-yl)phenyl)benzamide | ¹H NMR: (DMSO) δ (ppm): 10.11 (s, 1H), 9.48 (s, 1H), 7.83 (d, J = 8.4 Hz, 2H), 7.56 (d, J = 8.8 Hz, 2H), 7.20 (d, J = 8.4 Hz, 1H), 6.86 (dd, J = 2.0, 4.0 Hz, 2H), 6.62 (d, J = 12.8 Hz, 1H), 6.10 (2H, dd, J = 2.0, 4.0 Hz, 2H), 5.28 (bs, 2H), 2.09 (s, 3H). MS: (calc.) 352.36; (obt.) 353.2 (MH)⁺. | 42 |

TABLE Ia-continued

| Ex | Cpd | Structure | Name | Characterization | Scheme |
|---|---|---|---|---|---|
| 59 | 218 | 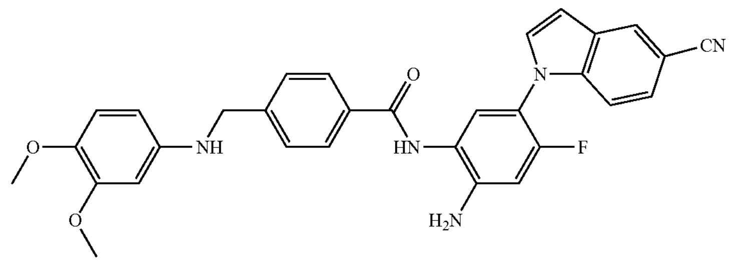 | 4-((3,4-dimethoxyphenylamino)methyl)-N-(2-amino-4-fluoro-5-indole-5-carbonitrile)benzamide | $^1$H NMR: (DMSO) δ (ppm): 8.08 (bs, 1H), 7.96 (d, J = 8.0 Hz, 2H), 7.54 (d, J = 8.0 Hz, 2H), 7.41-7.50 (m, 2H), 7.40 (d, J = 8.0 Hz, 1H), 7.35 (d, J = 7.6 Hz, 1H), 6.83 (d, J = 8.0 Hz, 1H), 6.80 (d, J = 2.4 Hz, 1H), 6.72 (d, J = 8.8 Hz, 1H), 6.38 (d, J = 2.4 Hz, 1H), 6.15 (dd, J = 2.4, 8.8 Hz, 1H), 4.41 (bs, 2H), 3.76 (s, 3H), 3.73 (s, 3H) MS: (calc.) 535.5; (obt.) 536.3 (MH)$^+$. | 43 |
| 60 | 223 | 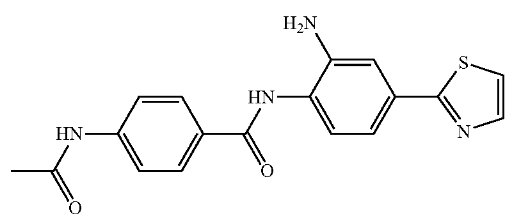 | 4-acetamido-N-(2-amino-4-(thiazol-2-yl)phenyl)benzamide | $^1$H NMR: (CD3OD) δ (ppm): 7.95 (d, J = 8.8 Hz, 2H), 7.60 (d, J = 3.2 Hz, 1H), 7.73-7.71 (m, 2H), 7.56 (d, J = 3.2 Hz, 1H), 7.48 (bs, 1H), 7.32 (bs, 2H), 2.17 (s, 3H) MS: (calc.) 352.4; (obt.) 353.2 (MH)$^+$. | 44 |
| 61a | 224a | 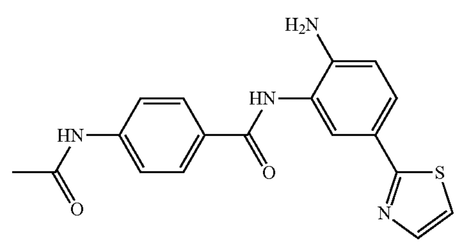 | 4-acetamido-N-(2-amino-5-(thiazol-2-yl)phenyl)benzamide | $^1$H NMR: (CD3OD) δ (ppm): 7.97 (d, J = 8.4 Hz, 2H), 7.77 (d, J = 2.0 Hz, 1H), 7.71-7.73 (m, 3H), 7.56 (d, J = 3.20 Hz, 1H), 7.48 (bs, 1H), 7.32 (bs, 2H), 6.92 (d, J = 8.8 Hz, 1H), 2.17 (s, 3H) MS: (calc.) 352.41; (obt.) 353.2 (MH)$^+$. | 44 |

TABLE Ia-continued

| Ex | Cpd | Structure | Name | Characterization | Scheme |
|---|---|---|---|---|---|
| 61b | 224b | 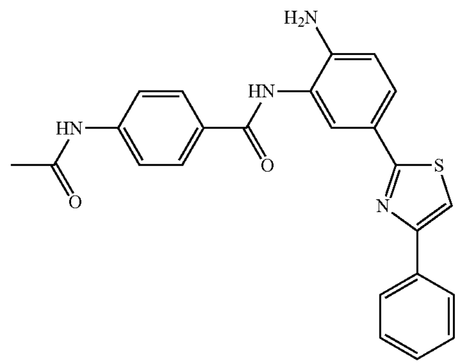 | 4-acetamido-N-(2-amino-5-(4-phenylthiazol-2-yl)phenyl)benzamide | $^1$H NMR: (DMSO) δ (ppm): 10.18 (s, 1H), 9.64 (s, 1H), 8.00-7.94 (m, 5H), 7.84 (d, J = 2.0 Hz, 1H), 7.68 (dd, J = 1.6, 7.2 Hz, 2H), 7.61 (dd, J = 2.0, 8.4 Hz, 1H), 7.42 (dt, J = 1.6, 7.2 Hz, 2H), 7.32 (d, J = 1.6, 7.2 Hz, 1H), 6.84 (d, J = 8.4 Hz, 1H), 5.52 (bs, 2H), 2.09 (s, 3H). MS: (calc.) 428.5; (obt.) 429.1 (MH)$^+$. | 44 |
| 61c | 224c | 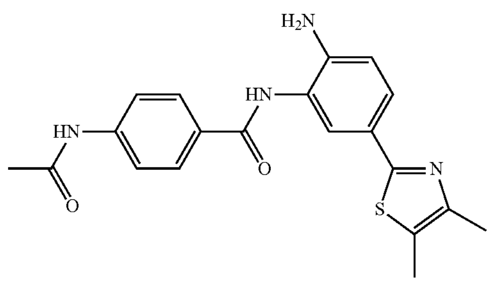 | 4-Acetamido-N-(2-amino-5-(4,5-dimethylthiazol-2-yl)phenyl)benzamide | $^1$H NMR: (DMSO) δ (ppm): 10.25 (s, 1H), 9.63 (s, 1H), 7.93 (d, J = 8.8 Hz, 2H), 7.68-7.67 (m, 3H), 7.41 (dd, J = 2.0, 8.4 Hz, 1H), 6.77 (d, J = 8.4 Hz, 1H), 5.40 (bs, 2H), 2.32 (s, 3H), 2.24 (s, 3H), 2.08 (s, 3H) MS: (calc.) 380.4; (obt.) 381.1 (MH)$^+$. | 44 |
| 62 | 228 | 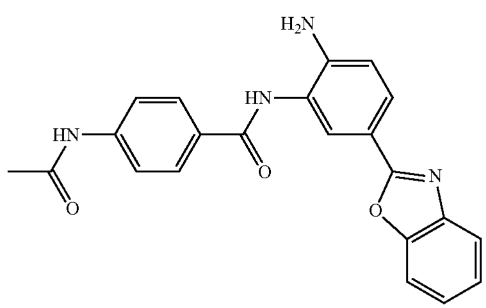 | 4-Acetamido-N-(2-amino-5-(benzo[d]oxazol-2-yl)phenyl)benzamide | $^1$H NMR: (DMSO) δ (ppm): 10.22 (s, 1H), 9.62 (s, 1H), 8.05 (d, J = 2.4 Hz, 1H), 7.89 (d, J = 8.4 Hz, 2H), 7.80 (1H, dd, J = 2.0, 8.4 Hz, 1H), 7.68-7.73 (m, 4H), 7.33-7.35 (m, 2H), 6.91 (d, J = 8.4 Hz, 1H), 5.86 (bs, 2H), 2.12 (s, 3H) MS: (calc.) 386.41; (obt.) 387.1 (MH)$^+$. | 45 |

TABLE Ia-continued

| Ex | Cpd | Structure | Name | Characterization | Scheme |
|---|---|---|---|---|---|
| 63 | 232 | 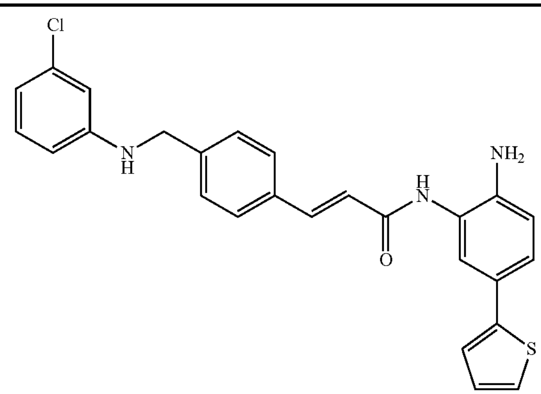 | (E)-3-(4-((3-Chlorophenylamino)methyl)phenyl)-N-(2-amino-5-(thiophen-2-yl)phenyl)acrylamide | ¹H NMR: (DMSO) δ (ppm): 9.42 (bs, 1H), 7.66-7.32 (m, 7H), 7.22-7.14 (m, 2H), 7.10-7.00 (m, 2H), 6.87-6.74 (m, 1H), 6.62-6.50 (m, 4H), 5.19 (bs, 1H), 4.29 (d, J = 5.6 Hz, 2H), MS: (calc.) 459.2; (obt.) 460.3 (MH)⁺. | 46 |
| 64 | 235 | 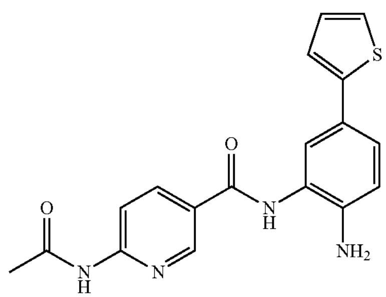 | 6-Acetamido-N-(2-amino-5-(thiophen-2-yl)phenyl)pyridine-3-carboxamide | ¹H NMR: (DMSO) δ (ppm)10.79 (br s, 1H), 9.75 (br s, 1H), 8.90 (s, 1H), 8.31 (d, J = 9.4 Hz, 1H), 8.15 (d, J = 8.5 Hz, 1H), 7.42 (s, 1H), 7.33 (m, 1H), 7.28 (d, J = 8.5 Hz, 1H), 7.22 (s, 1H), 7.02 (m, 1H), 6.78 (d, J = 8.0 Hz, 1H), 5.20 (br s, 2H), 2.13 (s, 3H). MS: (calc.) 352.1; (obt.) 353.2 (MH)⁺. | 47 |
| 65a | 238a | 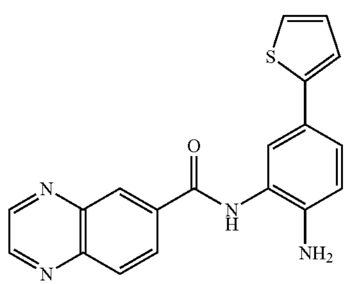 | N-(2-amino-5-(thiophen-2-yl)phenyl)quinoxaline-6-carboxamide | ¹H NMR: (DMSO) δ (ppm): 10.09 (br s, 1H), 9.04 (dd, J = 6.7, 1.8 Hz, 2H), 8.79 (d, J = 1.8 Hz, 1H), 8.37 (dd, J = 8.9, 2.0 Hz, 1H), 8.20 (d, J = 8.6 Hz, 1H), 7.51 (d, J = 2.2 Hz, 1H), 7.34 (dd, J = 4.9, 1.0 Hz, 1H), 7.30 (dd, J = 2.1, 8.1 Hz, 1H), 7.24 (dd, J = 3.5, 1.2 Hz, 1H), 7.04 (dd, J = 4.9, 3.5 Hz, 1H), 6.81 (d, J = 8.2 Hz, 1H), 5.28 (br s, 2H). MS: (calc.) 346.1 (obt.) 347.1 (MH)⁺. | 48 |

| Ex | Cpd | Structure | Name | Characterization | Scheme |
|---|---|---|---|---|---|
| 65b | 238b | 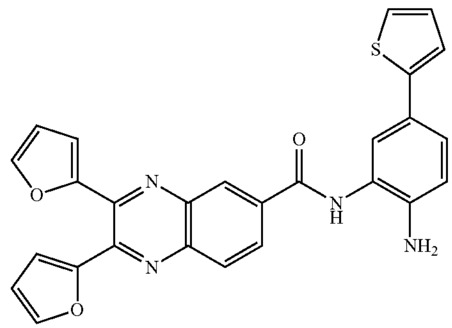 | N-(2-amino-5-(thiophen-2-yl)phenyl)-2,3-di(furan-2-yl)quinoxaline-6-carboxamide | $^1$H NMR: (CD$_3$OD) δ (ppm): 8.56 (s, 1H), 8.21 (d, J = 8.6 Hz, 1H), 8.03 (d, J = 8.8 Hz, 1H), 7.63 (s, 2H), 7.45 (d, J = 1.7 Hz, 1H), 7.27 (d, J = 8.4 Hz, 1H), 7.13-7.12 (m, 2H), 6.90 (t, J = 4.1 Hz, 1H), 6.83 (d, J = 8.4 Hz, 1H), 6.69 (t, J = 3.9 Hz, 2H), 6.55-6.56 (m, 2H). MS: (calc.) 478.1; (obt.) 479.1 (MH)$^+$. | 48 |
| 65c | 238c | 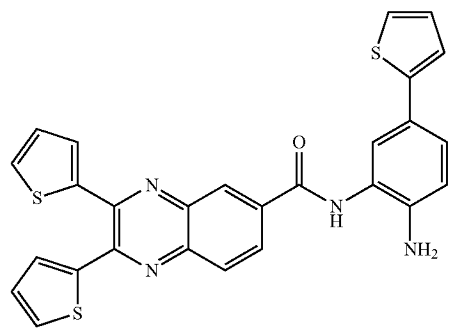 | N-(2-amino-5-(thiophen-2-yl)phenyl)-2,3-di(thiophen-2-yl)quinoxaline-6-carboxamide | $^1$H NMR: (DMSO) δ (ppm): 10.09 (s, 1H), 8.75 (d, J = 1.8 Hz, 1H), 8.32 (dd, J = 8.6, 2.0 Hz, 1H), 8.12 (d, J = 8.6 Hz, 1H), 7.84-7.82 (m, 2H), 7.52 (d, J = 2.0 Hz, 1H), 7.35-7.24 (m, 5H), 7.14-7.11 (m, 2H), 7.03 (dd, J = 5.0, 3.5 Hz, 1H), 6.81 (d, J = 8.4 Hz, 1H), 5.29 (s, 2H). MS: (calc.) 510.1; (obt.) 511.1 (MH)$^+$. | 48 |
| 66 | 242 | 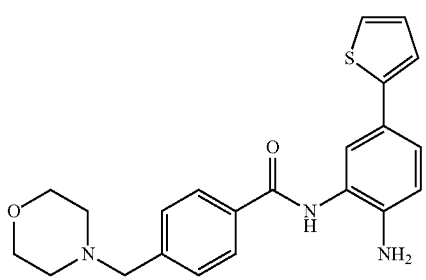 | N-(2-amino-5-(thiophen-2-yl)phenyl)-4-(morpholinomethyl)benzamide | $^1$H NMR: (CDCl$_3$) δ 8.61-8.59 (m, 1H), 8.02 (br s, 1H), 7.86 (d, J = 8.0 Hz, 2H), 7.53 (br s, 1H), 7.44 (d, J = 8.0 Hz, 2H), 7.33 (dd, J = 8.2, 2.2 Hz, 1H), 7.30-7.26 (m, 2H), 7.17 (dd, J = 5.1, 1.2 Hz, 1H), 7.15-7.14 (m, 1H), 7.01 (dd, J = 5.1, 3.5 Hz, 1H), 6.82 (d, J = 8.2 Hz, 1H), 3.73 (t, J = 4.7 Hz, 4H), 3.57 (s, 2H), 2.47 (t, J = 4.3 Hz, 4H). MS: (calc.) 393.2; (obt.) 394.2 (MH)$^+$. | 49 |

TABLE Ia-continued

| Ex | Cpd | Structure | Name | Characterization | Scheme |
|---|---|---|---|---|---|
| 67a | 245a | 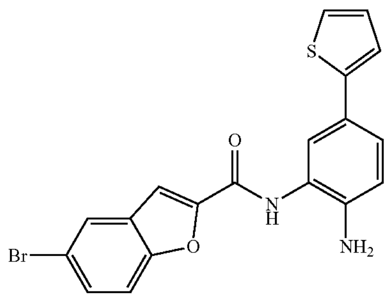 | N-(2-amino-5-(thiophen-2-yl)phenyl)-5-bromobenzofuran-2-carboxamide | $^1$H NMR: (DMSO) δ (ppm): 10.01 (s, 1H), 8.05 (d, J = 1.6 Hz, 1H), 7.69-7.67 (m, 2H), 7.61 (dd, J = 8.8, 2.0 Hz, 1H), 7.44 (d, J = 2.2 Hz, 1H), 7.34 (dd, J = 5.1, 1.2 Hz, 1H), 7.30 (dd, J = 8.4, 2.2 Hz, 1H), 7.23 (dd, J = 3.6, 1.2 Hz, 1H), 7.02 (dd, J = 4.9, 3.6 Hz, 1H), 6.79 (d, J = 8.4 Hz, 1H), 5.24 (s, 2H). MS: (calc.) 413.0 (d); (obt.) 414.0 (d) (MH)$^+$. | 50 |
| 67b | 245b | 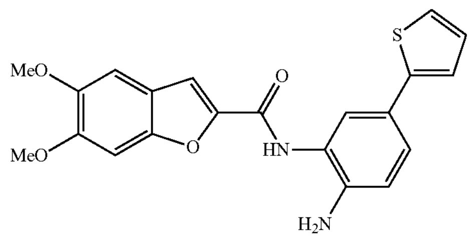 | N-(2-amino-5-(thiophen-2-yl)phenyl)-5,6-dimethoxybenzofuran-2-carboxamide | $^1$H NMR: (DMSO) δ (ppm) 9.77 (s, 1H), 7.64 (s, 1H), 7.51 (d, J = 2.1 Hz, 1H), 7.37 (dd, J = 5.1, 1.2 Hz, 1H), 7.33 (d, J = 2.2 Hz, 1H), 7.31-7.30 (m, 2H), 7.26 (dd, J = 3.7, 1.2 Hz, 1H), 7.06 (dd, J = 5.1, 3.5 Hz, 1H), 6.83 (d, J = 8.5 Hz, 1H), 5.22 (s, 2H), 3.88 (s, 3H), 3.85 (s, 3H). MS: (calc.) 394.1; (obt.) 395.1 (MH)$^+$. | 50 |
| 67c | 245c | 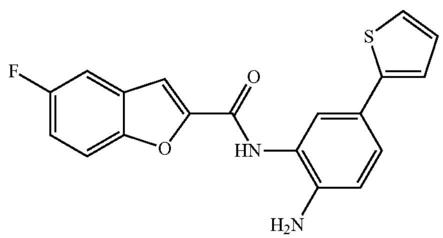 | N-(2-amino-5-(thiophen-2-yl)phenyl)-5-fluorobenzofuran-2-carboxamide | $^1$H NMR: (DMSO) δ (ppm): 9.98 (s, 1H), 7.75-7.71 (m, 2H), 7.63 (dd, J = 9.0, 2.8 Hz, 1H), 7.44 (d, J = 2.0 Hz, 1H), 7.36-7.29 (m, 3H), 7.23 (dd, J = 3.5, 1.1 Hz, 1H), 7.03 (dd, J = 5.1, 3.7 Hz, 1H), 6.79 (d, J = 8.4 Hz, 1H), 5.24 (s, 2H). MS: (calc.) 352.1; (obt.) 353.1 (MH)$^+$. | 50 |
| 67d | 245d | 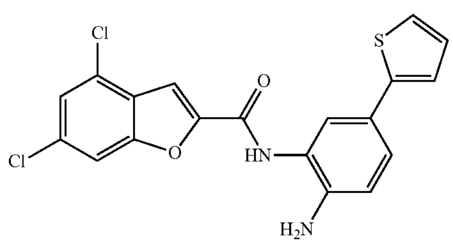 | N-(2-amino-5-(thiophen-2-yl)phenyl)-4,6-dichlorobenzofuran-2-carboxamide | $^1$H NMR: (DMSO) δ (ppm): 10.04 (s, 1H), 7.95 (dd, J = 1.6, 1.0 Hz, 1H), 7.85 (s, 1H), 7.63 (d, J = 1.6 Hz, 1H), 7.43 (d, J = 2.2 Hz, 1H), 7.34 (dd, J = 5.1, 1.2 Hz, 1H), 7.30 (dd, J = 8.4, 2.3 Hz, 1H), 7.23 (dd, J = 3.5, 1.2 Hz, 1H), 7.03 (dd, J = 5.1, 3.5 Hz, 1H), 6.78 (d, J = 8.3 Hz, 1H), 5.28 (s, 2H) MS: (calc.) 403.0 (d); (obt.) 404.0 (d) (MH)$^+$. | 50 |

TABLE Ia-continued

| Ex | Cpd | Structure | Name | Characterization | Scheme |
|---|---|---|---|---|---|
| 67e | 245e | 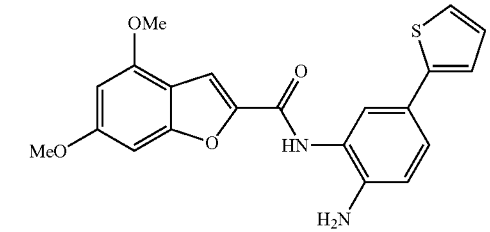 | N-(2-amino-5-(thiophen-2-yl)phenyl)-4,6-dimethoxybenzofuran-2-carboxamide | ¹H NMR: (DMSO) δ (ppm): 9.68 (s, 1H), 7.64 (s, 1H), 7.46 (d, J = 2.0 Hz, 1H), 7.32 (d, J = 1.0 Hz, 1H), 7.27 (dd, J = 8.2, 2.1 Hz, 1H), 7.22 (dd, J = 3.5, 1.0 Hz, 1H), 7.02 (dd, J = 4.9, 3.5 Hz, 1H), 6.84 (s, 1H), 6.78 (d, J = 8.4 Hz, 1H), 6.47 (d, J = 1.7 Hz, 1H), 5.20 (s, 2H), 3.90 (s, 3H), 3.83 (s, 3H). MS: (calc.) 394.1; (obt.) 395.1 (MH)⁺. | 50 |
| 67f | 245f | 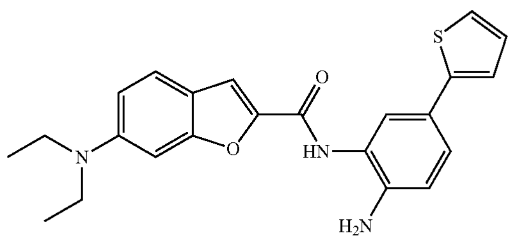 | N-(2-amino-5-(thiophen-2-yl)phenyl)-6-(diethylamino)benzofuran-2-carboxamide | ¹H NMR: (DMSO) δ (ppm): 9.60 (s, 1H), 7.51-7.49 (m, 3H), 7.33 (dd, J = 5.1, 1.2 Hz, 1H), 7.27 (dd, J = 8.2, 2.1 Hz, 1H), 7.22 (dd, J = 3.5, 1.2 Hz, 1H), 7.02 (dd, J = 5.0, 3.5 Hz, 1H), 6.80-6.76 (m, 3H), 5.17 (s, 2H), 3.40 (q, J = 6.8 Hz, 4H), 1.13 (t, J = 7.0 Hz, 6H). MS: (calc.) 405.1; (obt.) 406.1 (MH)⁺. | 50 |
| 68 | 250 | 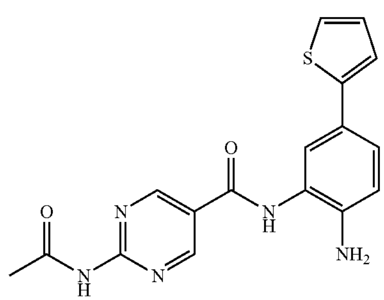 | 2-acetamido-N-(2-amino-5-(thiophen-2-yl)phenyl)pyrimidine-5-carboxamide | ¹H NMR: (DMSO) δ (ppm): 10.90 (s, 1H), 9.87 (s, 1H), 9.16 (s, 2H), 7.47 (d, J = 2.2 Hz, 1H), 7.36 (dd, J = 5.1, 1.2 Hz, 1H), 7.32 (d, J = 8.4, 2.2 Hz, 1H), 7.25 (dd, J = 3.5, 1.1 Hz, 1H), 7.05 (dd, J = 5.1, 3.7 Hz, 1H), 6.81 (d, J = 8.4 Hz, 1H), 5.33 (br s, 2H), 2.26 (s, 3H). MS: (calc.) 353.1; (obt.) 354.1 (MH)⁺. | 51 |

| Ex | Cpd | Structure | Name | Characterization | Scheme |
|---|---|---|---|---|---|
| 69a | 253a | 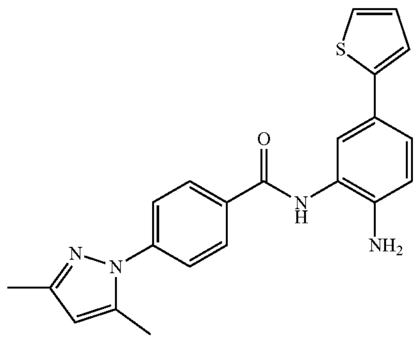 | N-(2-amino-5-(thiophen-2-yl)phenyl)-4-(3,5-dimethyl-1H-pyrazol-1-yl)benzamide | $^1$H NMR: (DMSO) δ (ppm): 9.81 (s, 1H), 8.09 (d, J = 8.4 Hz, 2H), 7.64 (d, J = 8.6 Hz, 2H), 7.46 (d, J = 2.0 Hz, 1H), 7.33 (dd, J = 5.1, 1.2 Hz, 1H), 7.28 (dd, J = 8.2, 2.2 Hz, 1H), 7.23 (dd, J = 3.5, 1.0 Hz, 1H), 7.03 (dd, J = 5.1, 3.5 Hz, 1H), 6.80 (d, J = 8.3 Hz, 1H), 6.12 (s, 1H), 5.19 (s, 2H), 2.38 (s, 3H), 2.20 (s, 3H). MS: (calc.) 388.1; (obt.) 389.1 (MH)$^+$. | 52 |
| 69b | 253b | 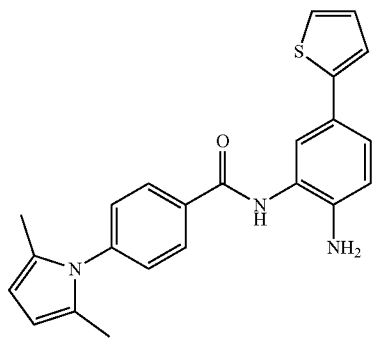 | N-(2-amino-5-(thiophen-2-yl)phenyl)-4-(2,5-dimethyl-1H-pyrrol-1-yl)benzamide | $^1$H NMR: (DMSO) δ (ppm): 9.85 (s, 1H), 8.14 (d, J = 8.4 Hz, 2H), 7.49 (d, J = 2.0 Hz, 1H), 7.44 (d, J = 8.4 Hz, 2H), 7.37 (dd, J = 5.1, 1.2 Hz, 1H), 7.32 (dd, J = 8.5, 2.4 Hz, 1H), 7.26 (dd, J = 3.6, 1.0 Hz, 1H), 7.07 (dd, J = 5.1, 3.5 Hz, 1H), 6.83 (d, J = 8.4 Hz, 1H), 5.86 (s, 2H), 5.24 (s, 2H), 2.05 (s, 6H). MS: (calc.) 387.1; (obt.) 388.1 (MH)$^+$. | 52 |
| 70a | 256a | 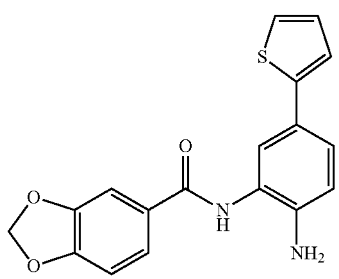 | N-(2-amino-5-(thiophen-2-yl)phenyl)benzo[d][1,3]dioxole-5-carboxamide | $^1$H NMR: (DMSO) δ (ppm): 9.59 (s, 1H), 7.60 (dd, J = 8.0, 1.6 Hz, 1H), 7.55 (d, J = 1.6 Hz, 1H), 7.43 (d, J = 2.2 Hz, 1H), 7.35 (dd, J = 4.9, 0.6 Hz, 1H), 7.29 (dd, J = 8.2, 2.2 Hz, 1H), 7.24 (dd, J = 3.7, 1.0 Hz, 1H), 7.06–7.04 (m, 2H), 6.79 (d, J = 8.2 Hz, 1H), 6.13 (s, 2H), 5.15 (br s, 2H). MS: (calc.) 338.1; (obt.) 339.1 (MH)$^+$. | 53 |

TABLE Ia-continued

| Ex | Cpd | Structure | Name | Characterization | Scheme |
|---|---|---|---|---|---|
| 70b | 256b | 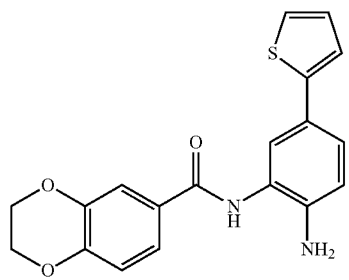 | N-(2-amino-5-(thiophen-2-yl)phenyl)-2,3-dihydrobenzo[b][1,4]dioxine-6-carboxamide | $^1$H NMR: (DMSO) δ (ppm): 9.57 (s, 1H), 7.54 (d, J = 2.1 Hz, 1H), 7.51 (dd, J = 8.4, 2.1 Hz, 1H), 7.42 (d, J = 2.1 Hz, 1H), 7.33 (dd, J = 5.1, 1.2 Hz, 1H), 7.26 (dd, J = 8.4, 2.3 Hz, 1H), 7.22 (dd, J = 3.5, 1.2 Hz, 1H), 7.02 (dd, J = 5.1, 3.5 Hz, 1H), 6.95 (d, J = 8.2 Hz, 1H), 6.79 (d, J = 8.4 Hz, 1H), 5.11 (s, 2H), 4.31-4.28 (m, 4H). MS: (calc.) 352.1; (obt.) 353.1 (MH)$^+$. | 53 |
| 70c | 256c | 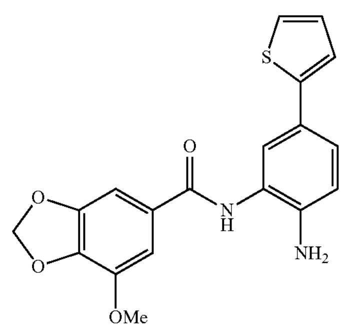 | N-(2-amino-5-(thiophen-2-yl)phenyl)-7-methoxybenzo[d][1,3]dioxole-5-carboxamide | $^1$H NMR: (DMSO) δ (ppm): 9.60 (s, 1H), 7.41 (d, J = 2.2 Hz, 1H), 7.36 (d, J = 1.4 Hz, 1H), 7.34 (dd, J = 5.2, 1.2 Hz, 1H), 7.30-7.26 (m, 2H), 7.23 (dd, J = 3.6, 1.2 Hz, 1H), 7.04 (dd, J = 4.9, 3.5 Hz, 1H), 6.79 (d, J = 8.4 Hz, 1H), 6.10 (s, 2H), 5.14 (br s, 2H), 3.91 (s, 3H). MS: (calc.) 368.1; (obt.) 369.1 (MH)$^+$. | 53 |
| 71a | 258a | 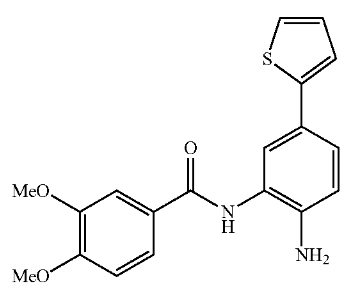 | N-(2-amino-5-(thiophen-2-yl)phenyl)-3,4-dimethoxybenzamide | $^1$H NMR: (DMSO) δ (ppm): 9.64 (s, 1H), 7.63 (dd, J = 8.2, 2.0 Hz, 1H), 7.57 (d, J = 2.2 Hz, 1H), 7.42 (d, J = 2.2 Hz, 1H), 7.33 (dd, J = 5.1, 1.2 Hz, 1H), 7.28 (dd, J = 8.3, 2.3 Hz, 1H), 7.23 (dd, J = 3.5, 1.2 Hz, 1H), 7.05 (d, J = 8.6 Hz, 1H), 7.02 (dd, J = 5.1, 3.6 Hz, 1H), 6.79 (d, J = 8.3 Hz, 1H), 5.12 (br s, 2H), 3.83 (s, 3H), 3.82 (s, 3H). MS: (calc.) 354.1; (obt.) 355.1 (MH)$^+$. | 54 |

TABLE Ia-continued

| Ex | Cpd | Structure | Name | Characterization | Scheme |
|---|---|---|---|---|---|
| 71b | 258b | 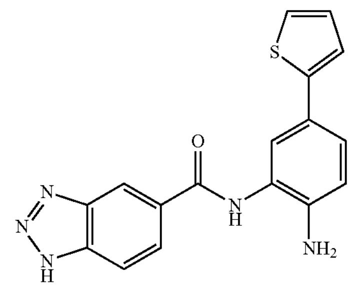 | N-(2-amino-5-(thiophen-2-yl)phenyl)-1H-benzo[d][1,2,3]triazole-5-carboxamide | $^1$H NMR: (DMSO) δ (ppm9.90 (s, 1H), 8.66 (s, 1H), 8.05 (d, J = 9.8 Hz, 1H), 7.96 (d, J = 8.6 Hz, 1H), 7.49 (d, J = 2.0 Hz, 1H), 7.33 (dd, J = 5.1, 1.2 Hz, 1H), 7.30 (dd, J = 8.2, 2.2 Hz, 1H), 7.23 (dd, J = 3.5, 1.1 Hz, 1H), 7.03 (dd, J = 5.0, 3.7 Hz, 1H) 6.81 (d, J = 8.4 Hz, 1H), 5.23 (br s, 2H). MS: (calc.) 335.1; (obt.) 336.0 (MH)$^+$. | 54 |
| 71c | 258c | 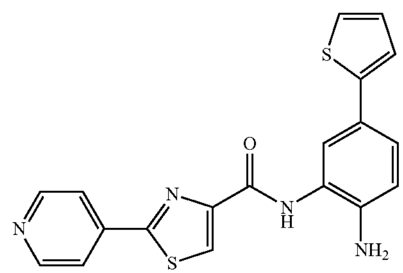 | N-(2-amino-5-(thiophen-2-yl)phenyl)-2-(pyridin-4-yl)thiazole-4-carboxamide | $^1$H NMR: (DMSO) δ (ppm): 9.94 (s, 1H), 8.78 (m, 3H), 8.11 (dd, J = 4.3, 1.6 Hz, 2H), 7.64 (d, J = 2.2 Hz, 1H), 7.38 (dd, J = 5.1, 1.0 Hz, 1H), 7.33 (dd, J = 8.2, 2.1 Hz, 1H), 7.28 (dd, J = 3.7, 1.2 Hz, 1H), 7.07 (dd, J = 5.1, 3.7 Hz, 1H), 6.86 (d, J = 8.4 Hz, 1H), 5.23 (s, 2H). MS: (calc.) 378.0; (obt.) 379.0 (MH)$^+$. | 54 |
| 71d | 258d | 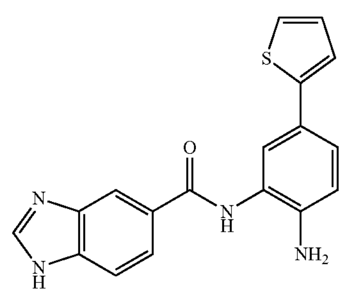 | N-(2-amino-5-(thiophen-2-yl)phenyl)-1H-benzo[d]imidazole-5-carboxamide | $^1$H NMR: (DMSO) δ (ppm): 9.72 (s, 1H), 8.34 (s, 2H), 7.87-7.85 (m, 2H), 7.48 (d, J = 1.8 Hz, 1H), 7.34 (dd, J = 5.1, 1.0 Hz, 1H), 7.28 (dd, J = 8.1, 5.2 Hz, 1H), 7.23 (dd, J = 3.5, 1.2 Hz, 1H), 7.03 (dd, J = 5.1, 3.6 Hz, 1H), 6.80 (d, J = 8.4 Hz, 1H), 5.15 (s, 2H). MS: (calc.) 334.1; (obt.) 335.0 (MH)$^+$. | 54 |

| Ex | Cpd | Structure | Name | Characterization | Scheme |
|---|---|---|---|---|---|
| 71e | 258e | 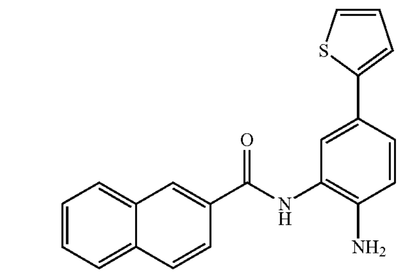 | N-(2-amino-5-(thiophen-2-yl)phenyl)-2-naphthamide | $^1$H NMR: (DMSO) δ (ppm): 9.90 (s, 1H), 8.62 (s, 1H), 8.07-7.98 (m, 4H), 7.63-7.60 (m, 2H), 7.51 (d, J = 2.1 Hz, 1H), 7.34 (dd, J = 5.1, 1.2 Hz, 1H), 7.30 (dd, J = 8.4, 2.2 Hz, 1H), 7.24 (dd, J = 3.5, 1.2 Hz, 1H), 7.04 (dd, J = 5.1, 3.7 Hz, 1H), 6.81 (d, J = 8.4 Hz, 1H), 5.21 (s, 2H). MS: (calc.) 344.1; (obt.) 345.1 (MH)$^+$. | 54 |
| 71f | 258f | 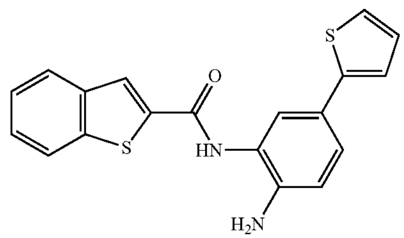 | N-(2-amino-5-(thiophen-2-yl)phenyl)benzo[b]thiophene-2-carboxamide | $^1$H NMR: (DMSO) δ (ppm): 9.99 (s, 1H), 8.32 (s, 1H), 8.03 (dd, J = 8.4, 2.0 Hz, 1H), 7.97 (dd, J = 6.6, 2.7 Hz, 1H), 7.49-7.43 (m, 3H), 7.33 (dd, J = 5.0, 1.1 Hz, 1H), 7.30 (dd, J = 8.2, 2.2 Hz, 1H), 7.24 (dd, J = 3.6, 1.0 Hz, 1H), 7.03 (dd, J = 5.2, 3.7 Hz, 1H), 6.80 (d, J = 8.4 Hz, 1H), 5.24 (s, 2H). MS: (calc.) 350.0; (obt.) 351.0 (MH)$^+$. | 54 |
| 71g | 258g | 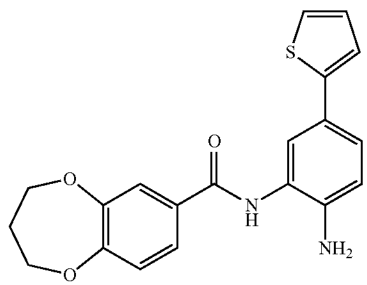 | N-(2-amino-5-(thiophen-2-yl)phenyl)-3,4-dihydro-2H-benzo[b][1,4]dioxepine-7-carboxamide | $^1$H NMR: (DMSO) δ (ppm): 9.61 (s, 1H), 7.63 (d, J = 2.2 Hz, 1H), 7.59 (dd, J = 8.4, 2.2 Hz, 1H), 7.41 (d, J = 2.0 Hz, 1H), 7.33 (d, J = 5.1, 1.2 Hz, 1H), 7.27 (dd, J = 8.2, 2.2 Hz, 1H), 7.22 (dd, J = 3.5, 1.0 Hz, 1H), 7.06-7.01 (m, 2H), 6.78 (d, J = 8.4 Hz, 1H), 5.12 (br s, 2H), 4.22-4.17 (m, 4H), 2.16 (quintet, J = 5.5 Hz, 2H) MS: (calc.) 366.1; (obt.) 367.1 (MH)$^+$. | 54 |
| 71aa | 258aa | 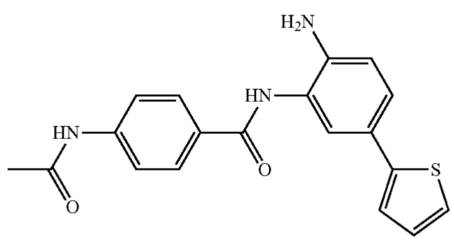 | 4-acetamido-N-(2-amino-5-(thiophen-2-yl)phenyl)benzamide | $^1$H NMR: (DMSO) δ (ppm): 10.19 (s, 1H), 9.61 (s, 1H), 7.94 (d, J = 8.6 Hz, 2H), 7.68 (d, J = 8.6 Hz, 2H), 7.44 (d, J = 2.2 Hz, 1H), 7.34 (dd, J = 5.1, 1.2 Hz, 1H), 7.27 (dd, J = 8.2, 2.2 Hz, 1H), 7.23 (dd, J = 3.7, 1.2 Hz, 1H), 7.03 (dd, J = 5.1, 4.1 Hz, 1H), 6.79 (d, J = 8.4 Hz, 1H), 5.13 (s, 2H), 2.09 (s, 3H). MS: (calc.) 351.1; (obt.) 352.3 (MH)$^+$. | 54 |

TABLE Ia-continued

| Ex | Cpd | Structure | Name | Characterization | Scheme |
|---|---|---|---|---|---|
| 71bb | 258bb | 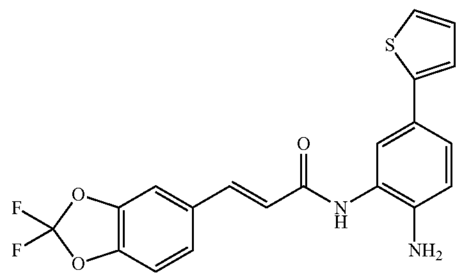 | (E)-N-(2-amino-5-(thiophen-2-yl)phenyl)-3-(2,2-difluorobenzo[d][1,3]dioxol-5-yl)acrylamide | $^1$H NMR: (DMSO) δ (ppm): 9.46 (s, 1H), 7.68 (s, 1H), 7.65 (d, J = 2.2 Hz, 1H), 7.57 (d, J = 7.8 Hz, 1H), 7.48 (s, 2H), 7.34 (dd, J = 5.2, 1.0 Hz, 1H), 7.23 (dd, J = 8.4, 2.2 Hz, 1H), 7.20 (dd, J = 3.6, 1.2 Hz, 1H), 7.03 (dd, J = 5.1, 3.7 Hz, 1H), 6.85 (d, J = 15.7 Hz, 1H), 6.76 (d, J = 8.4 Hz, 1H), 5.20 (s, 2H). MS: 400.07 (calc), 401.1 (obs). | 54 |
| 71cc | 258cc | 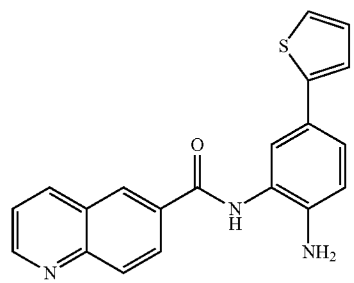 | N-(2-amino-5-(thiophen-2-yl)phenyl)quinoline-6-carboxamide | $^1$H NMR: (DMSO) δ (ppm): 9.97 (s, 1H), 8.99 (dd, J = 4.1, 1.6 Hz, 1H), 8.68 (d, J = 1.8 Hz, 1H), 8.50 (d, J = 8.2 Hz, 1H), 8.29 (dd, J = 8.8, 2.0, 1H), 8.10 (d, J = 8.8 Hz, 1H), 7.62 (dd, J = 8.2, 4.3 Hz, 1H), 7.50 (d, J = 2.2 Hz, 1H), 7.34 (dd, J = 4.9, 0.98 Hz, 1H), 7.30 (dd, J = 8.2, 2.2 Hz, 1H), 7.24 (dd, J = 3.5, 1.2 Hz, 1H), 7.04 (dd, J = 5.1, 3.5 Hz, 1H), 6.82 (d, J = 8.2 Hz, 1H), 5.24 (s, 2H). MS: 345.09 (calc), 346.0 (obs). | 54 |
| 71dd | 258dd | 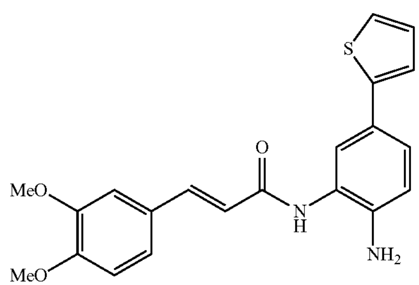 | (E)-N-(2-amino-5-(thiophen-2-yl)phenyl)-3-(3,4-dimethoxyphenyl)acrylamide | $^1$H NMR: (DMSO) δ (ppm): 9.33 (s, 1H), 7.68 (d, J = 1.6 Hz, 1H), 7.49 (d, J = 15.5 Hz, 1H), 7.33 (dd, J = 5.1, 0.98 Hz, 1H), 7.22 (d, J = 2.2 Hz, 1H), 7.20 (d, J = 0.98 Hz, 2H), 7.19 (d, J = 1.2 Hz, 1H), 7.16 (d, J = 8.2 Hz, 1H), 7.02 (dd, J = 5.1, 3.7 Hz, 1H), 7.00 (d, J = 8.4 Hz, 1H), 6.76 (t, J = 8.6 Hz, 1H), 5.19 (s, 2H), 3.81 (s, 3H), 3.79 (s, 3H). MS: 380.12 (calc), 381.1 (obs). | 54 |

TABLE Ia-continued

| Ex | Cpd | Structure | Name | Characterization | Scheme |
|---|---|---|---|---|---|
| 71ee | 258ee | (structure) | N-(2-amino-5-(thiophen-2-yl)phenyl)-4-(1H-pyrrol-1-yl)benzamide | ¹H NMR: (DMSO) δ (ppm): 9.73 (s, 1H), 8.07 (d, J = 8.4 Hz, 2H), 7.73 (d, J = 8.4 Hz, 2H), 7.51 (d, J = 1.8 Hz, 2H), 7.44 (s, 1H), 7.33 (d, J = 5.1 Hz, 1H), 7.28 (dd, J = 8.2, 1.6 Hz, 1H), 7.23 (d, J = 3.5 Hz, 1H), 7.03 (t, J = 4.1 Hz, 1H), 6.79 (d, J = 8.4 Hz, 1H), 6.30 (s, 2H), 5.16 (s, 2H). MS: 359.11 (calc), 360.1 (obs). | 54 |
| 71ff | 258ff | (structure) | N-(2-amino-5-(thiophen-2-yl)phenyl)-4-(1H-imidazol-1-yl)benzamide | ¹H NMR: (DMSO) δ (ppm): 9.79 (s, 1H), 8.40 (s, 1H), 8.12 (d, J = 8.4 Hz, 2H), 7.88 (s, 1H), 7.82 (d, J = 8.6 Hz, 2H), 7.45 (d, J = 1.8 Hz, 1H), 7.33 (dd, J = 4.9, 0.78 Hz, 1H), 7.29 (d, J = 8.2, 2.2 Hz, 1H), 7.23 (d, J = 3.5 Hz, 1H), 7.13 (s, 1H), 7.04 to 7.02 (m, 1H), 6.79 (d, J = 8.4 Hz, 1H), 5.19 (s, 2H). MS: 360.1 (calc), 361.1 (obs). | 54 |
| 71gg | 258gg | (structure) | N-(2-amino-5-(thiophen-2-yl)phenyl)-3,5-dimethoxybenzamide | ¹H NMR: (DMSO) δ (ppm): 9.68 (s, 1H), 7.40 (d, J = 2.0 Hz, 1H), 7.32 (dd, J = 5.1, 1.2 Hz, 1H), 7.27 (dd, J = 8.2, 2.2 Hz, 1H), 7.21 (dd, J = 3.5, 1.2 Hz, 1H), 7.13 (d, J = 2.2 Hz, 2H), 7.01 (dd, J = 5.1, 3.5 Hz, 1H), 6.78 (d, J = 8.2 Hz, 1H), 6.66 (t, J = 2.2 Hz, 1H), 5.11 (s, 2H), 3.79 (s, 6H). MS: 354.1 (calc), 355.1 (obs). | 54 |

| Ex | Cpd | Structure | Name | Characterization | Scheme |
|---|---|---|---|---|---|
| 71hh | 258hh | 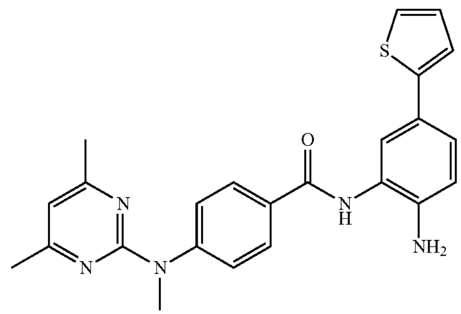 | N-(2-amino-5-(thiophen-2-yl)phenyl)-4-((4,6-dimethyl)pyrimidin-2-yl)(methyl)amino)benzamide | ¹H NMR: (DMSO) δ (ppm): 9.72 (1H, s), 7.97 (2H, d, 8.6 Hz), 7.50 to 7.46 (3H, m,), 7.34 (1H, dd, 3.9 and 1.2 Hz), 7.28 (1H, dd, 6.1 and 2.3 Hz), 7.23 (1H, dd, 2.3 and 1.2 Hz), 7.04 (1H, dd, 3.5 and 1.4 Hz), 6.79 (1H, d, 8.4 Hz), 6.59 (1H, s), 5.18 (2H, s), 3.52 (3H, s), 2.25 (6H, s,) MS: 429.2 (calc), 430.2 (obs) | 54 |
| 71ii | 258ii | 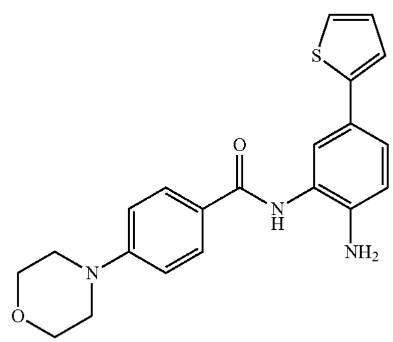 | N-(2-amino-5-(thiophen-2-yl)phenyl)-4-morpholinobenzamide | ¹H NMR: (DMSO) δ (ppm): 9.49 (1H, s), 7.88 (2H, d, 8.6 Hz), 7.43 (1H, s), 7.35 (1H, d, 8.0 Hz), 7.26 to 7.21 (2H, m), 7.04 to 6.99 (3H, m), 6.78 (1H, d, 8.4), 5.1 (2H, s), 3.74 to 3.73 (4H, m), 3.29 to 3.23 (4H, m) MS: 379.1 (calc), 380.1 (obs) | 54 |
| 71jj | 258jj | 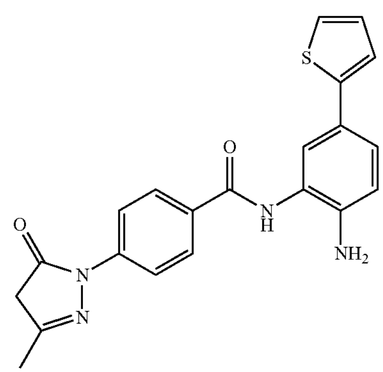 | N-(2-amino-5-(thiophen-2-yl)phenyl)-4-(3-methyl-5-oxo-4,5-dihydropyrazol-1-yl)benzamide | ¹H NMR: (DMSO) δ (ppm): 9.70 (1H, s), 8.03 (2H, d, 8.8 Hz), 7.93 (1H, d, 8.8), 7.70-7.62 (1H, m), 7.46 (1H, d, 2.2 Hz), 7.34 (1H, dd, 4.1 and 1.0 Hz), 7.28 (1H, dd, 6.1 and 2.2 Hz), 7.24 (1H, dd, 2.5 and 1.0), 7.03 (1H, dd, 3.5 and 1.6), 6.80 (1H, d, 8.4 Hz), 5.14 (1H, s), 4.19 (2H, s), 2.12 (3H, s) MS: 390.1 (calc), 391.2 (obs) | 54 |

TABLE Ia-continued

| Ex | Cpd | Structure | Name | Characterization | Scheme |
|---|---|---|---|---|---|
| 71kk | 258kk | 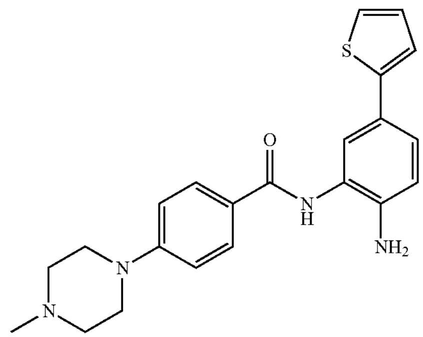 | N-(2-amino-5-(thiophen-2-yl)phenyl)-4-(4-methylpiperazin-1-yl)benzamide | ¹H NMR: (DMSO) δ (ppm): 9.48 (s, 1H), 7.87 (d, J = 9.0 Hz, 2H), 7.44 (d, J = 2.2 Hz, 1H), 7.34 (d, J = 4.9 Hz, 1H), 7.26 (dd, J = 8.4, 2.2 Hz, 1H), 7.23 (d, J = 3.5 Hz, 1H), 7.03 (dd, J = 5.1, 3.7 Hz, 1H), 6.99 (d, J = 9.0 Hz, 2H), 6.79 (d, J = 8.2 Hz, 1H), 5.09 (s, 2H), 3.36 (t, J = 6.7 Hz, 4H), 2.45 (t, J = 4.9 Hz, 4H), 2.23 (s, 3H). MS: 392.17 (calc) 393.2 (obs). | 54 |
| 71ll | 258ll | 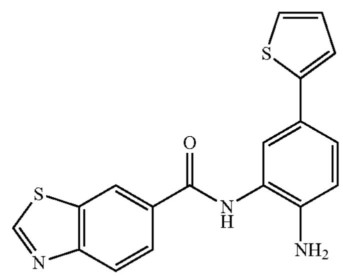 | N-(2-amino-5-(thiophen-2-yl)phenyl)benzo[d]thiazole-6-carboxamide | ¹H NMR: (DMSO) δ (ppm): 9.87 (s, 1H), 9.55 (s, 1H), 8.83 (s, 1H), 8.17 (q, J = 8.4 Hz, 2H), 7.50 (s, 1H), 7.35 (d, J = 5.1 Hz, 1H), 7.30 (dd, J = 8.2, 1.8 Hz, 1H), 7.24 (d, J = 3.3 Hz, 1H), 7.04 (t, J = 4.5 Hz, 1H), 6.84 (d, J = 8.4 Hz, 1H), 5.23 (s, 2H). MS: 351.05 (calc), 352.0 (obs). | 54 |
| 71mm | 258mm | 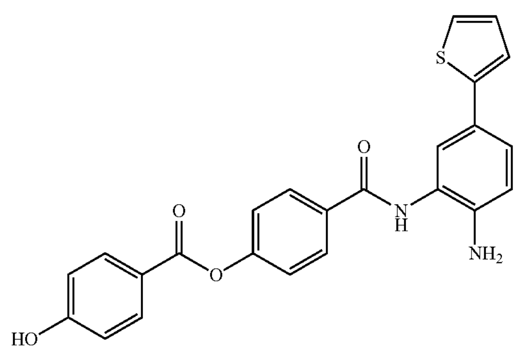 | 4-((2-amino-5-(thiophen-2-yl)phenyl)carbamoyl)phenyl 4-hydroxybenzoate | ¹H NMR: (DMSO) δ (ppm): 9.76 (1H, s), 8.07 (2H, d, 8.6), 7.97 (2H, d, 8.4 Hz), 7.46 (1H, s), 7.39-7.33 (3H, m), 7.29 (1H, dd, 6.1 and 2.2), 7.24 (1H, d, 3.5), 7.04 (1H, dd, 3.5 and 1.6 Hz), 6.91-6.89 (2H, m), 6.80 (1H, d, 8.4), 5.19 (2H, s), 4.15 (1H, s). MS: 430.1 (calc), 431.1 (obs). | 54 |

TABLE Ia-continued

| Ex | Cpd | Structure | Name | Characterization | Scheme |
|---|---|---|---|---|---|
| 71nn | 258nn | 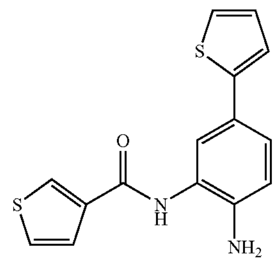 | N-(2-amino-5-(thiophen-2-yl)phenyl)thiophene-3-carboxamide | ¹H NMR: (DMSO) δ (ppm): 9.58 (s, 1H), 8.32 (s, 1H), 7.62 (d, J = 2.0 Hz, 2H), 7.42 (d, J = 2.0 Hz, 1H), 7.34 (d, J = 5.1 Hz, 1H), 7.28 (dd, J = 8.2, 2.0 Hz, 1H), 7.23 (d, J = 2.9 Hz, 1H), 7.03 (dd, J = 5.1, 3.7 Hz, 1H), 6.79 (d, J = 8.4 Hz, 1H), 5.15. (s, 2H), MS: 300.04 (calc) 301.1 (obs) | 54 |
| 71oo | 258oo | 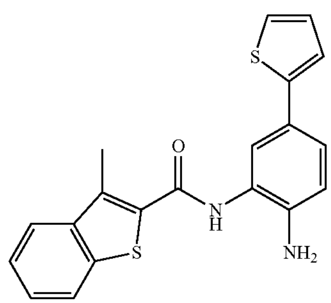 | N-(2-amino-5-(thiophen-2-yl)phenyl)-3-methylbenzo[b]thiophene-2-carboxamide | ¹H NMR: (DMSO) δ (ppm): 9.58 (s, 1H), 7.97 (dt, J = 41.5, 3.7 Hz, 2H), 7.54 (s, 1H), 7.49 (t, J = 5.1 Hz, 1H), 7.29 (dd, J = 8.2, 2.0 Hz, 1H), 7.24 (d, J = 2.9 Hz, 1H), 7.04 (t, J = 4.9 Hz, 1H), 6.82 (d, J = 8.4 Hz, 1H), 5.17 (s, 2H), 2.68 (s, 3H), MS: 364.07 (calc) 365.1 (obs) | 54 |
| 71pp | 258pp | 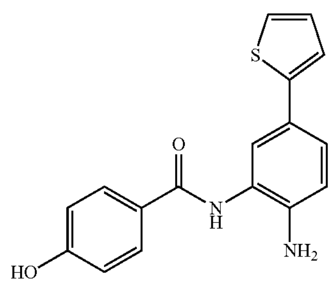 | N-(2-amino-5-(thiophen-2-yl)phenyl)-4-hydroxybenzamide | ¹H NMR: (DMSO) δ (ppm): 9.49 (1H, s), 7.85 (2H, d, 8.6), 7.43 (1H, s), 7.34 (1H, d, 5.1 Hz), 7.26 (1H, d, 6.1 Hz), 7.22 (1H, d, 3.5 Hz), 7.03 (1H, dd, 5.1 and 0 Hz), 6.84-6.77 (3H, m), 5.09 (2H, s) MS: 310.1 (calc), 311.1 (obs). | 54 |

| Ex | Cpd | Structure | Name | Characterization | Scheme |
|---|---|---|---|---|---|
| 71qq | 258qq | 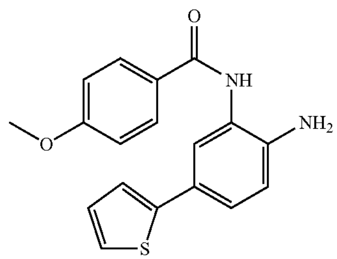 | N-(2-amino-5-(thiophen-2-yl)phenyl)-4-methoxybenzamide | ¹H NMR: (DMSO) δ (ppm): 9.59 (s, 1H); 7.97 (d, J = 8.8 Hz, 2H); 7.43 (d; J = 2.2 Hz; 1H); 7.34 (dd; J = 1.2, 5.1 Hz; 1H); 7.27 (dd; J = 2.2, 8.2 Hz; 1H); 7.23 (dd; J = 1.2, 3.5 Hz; 1H); 7.04 (d; J = 8.8 Hz; 2H); 7.03 (m, 1H); 6.79 (d; J = 8.2 Hz; 1H); 5.12 (bs, 2H); 3.84 (s, 3H). MS: calc: 324.4; found: 325.2 (M + H) | 54 |
| 71rr | 258rr | 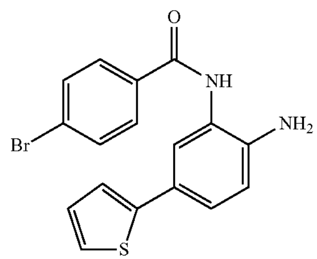 | N-(2-amino-5-(thiophen-2-yl)phenyl)-4-bromobenzamide | ¹H NMR: (DMSO) δ (ppm): 9.78 (s, 1H); 7.93 (d, J = 8.5 Hz, 2H); 7.71 (d, J = 8.5 Hz, 2H); 7.43 (d; J = 1.9 Hz; 1H); 7.33 (dd; J = 1.2, 5.1 Hz; 1H); 7.28 (dd; J = 1.9, 8.3 Hz; 1H); 7.23 (dd; J = 1.2, 3.5 Hz; 1H); 7.03 (dd; J = 3.5, 5.1 Hz; 1H); 6.78 (d; J = 8.3 Hz; 1H); 5.20 (bs, 2H). MS: calc: 371.9 and 373.9; found: 373.1 and 375.1 (M + H) | 54 |
| 71ss | 258ss | 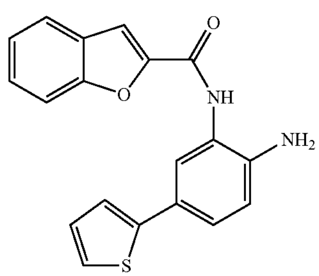 | N-(2-amino-5-(thiophen-2-yl)phenyl)benzofuran-2-carboxamide | ¹H NMR: (DMSO) δ (ppm): 9.73 (s, 1H); 7.99 (s, 1H); 7.97 (s, 1H); 7.56 (d, J = 7.2 Hz; 1H); 7.50 (m, 2H); 7.45 (d; J = 2.1 Hz; 1H); 7.33 (dd; J = 1.0, 5.1 Hz; 1H); 7.28 (dd; J = 2.1, 8.2 Hz; 1H); 7.23 (dd; J = 1.0, 3.5 Hz; 1H); 7.03 (dd; J = 3.5, 5.1 Hz; 1H); 6.79 (d; J = 8.1 Hz; 1H); 5.12 (bs, 2H). MS: calc: 334.4; found: 335.1 (M + H) | 54 |

TABLE Ia-continued

| Ex | Cpd | Structure | Name | Characterization | Scheme |
|---|---|---|---|---|---|
| 71tt | 258tt | 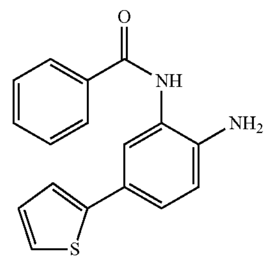 | N-(2-amino-5-(thiophen-2-yl)phenyl)benzamide | ¹H NMR: (CD3OD) δ (ppm): 8.52 (s, 1H); 7.76 (d; J = 7.4 Hz; 1H); 7.65 (d; J = 8.4 Hz; 1H); 7.63 (s, 1H); 7.56 (d; J = 2.0 Hz; 1H); 7.49 (m, 1H); 7.37 (dd; J = 2.1, 8.3 Hz; 1H); 7.34 (m, 1H); 7.23 (m, 2H); 7.02 (dd; J = 3.7, 5.3 Hz; 1H); 6.91 (d; J = 8.3 Hz; 1H). MS: calc: 294.4; found: 295.2 (M + H) | 54 |
| 71uu | 258uu | 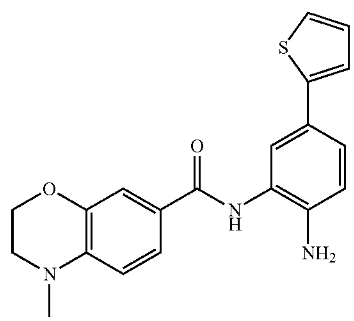 | N-(2-amino-5-(thiophen-2-yl)phenyl)-3,4-dihydro-4-methyl-2H-benzo[b][1,4]oxazine-7-carboxamide | ¹H NMR: (DMSO) δ (ppm): 9.40 (s, 1H); 7.50 (d, J = 8.4 Hz, 1H), 7.42 (s, 1H), 7.34 (d, J = 5.3 Hz, 2H), 7.25 (d, J = 8.2 Hz, 1H), 7.22 (d, J = 2.7 Hz, 1H), 7.03 (t, J = 4.9 Hz, 1H), 6.78 (d, J = 8.4 Hz, 1H), 6.73 (d, J = 8.6 Hz, 1H), 5.06 (s, 2H), 4.23 (d, J = 4.1 Hz, 2H), 3.30 (m, 2H), 2.93 (s, 3H) MS: 365.12 (calc) 366.1 (obs) | 54 |
| 71ww | 258ww | 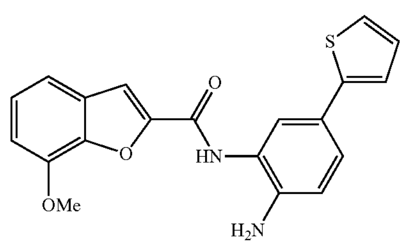 | N-(2-amino-5-(thiophen-2-yl)phenyl)-7-methoxybenzofuran-2-carboxamide | ¹H NMR: (DMSO) δ (ppm): 9.90 (s, 1H); 7.71 (s, 1H); 7.46 (d, J = 2.0 Hz; 1H); 7.35 (s, 1H); 7.34 (m, 1H); 7.30 (dd; J = 2.0, 8.4 Hz; 1H); 7.27 (d; J = 7.9 Hz; 1H); 7.24 (m, 1H); 7.08 (d; J = 7.9 Hz; 1H); 7.04 (dd; J = 3.7, 5.1 Hz; 1H); 6.80 (d; J = 8.2 Hz; 1H); 5.12 (bs, 2H); 3.98 (s; 3H). MS: calc: 364.4; found: 365.1 (M + H) | 54 |

| Ex | Cpd | Structure | Name | Characterization | Scheme |
|---|---|---|---|---|---|
| 72a | 261a | 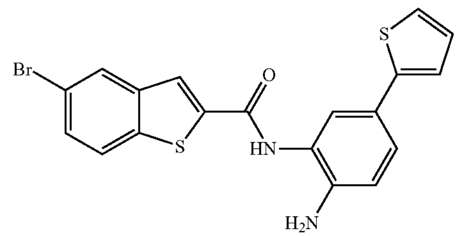 | N-(2-amino-5-(thiophen-2-yl)phenyl)-5-bromobenzo[b]thiophene-2-carboxamide | $^1$H NMR: (DMSO) δ (ppm): 10.08 (s, 1H), 8.27 (s, 1H), 8.23 (d, J = 1.8 Hz, 1H), 8.02 (d, J = 8.6 Hz, 1H), 7.60 (dd, J = 8.6, 2.0 Hz, 1H), 7.43 (d, J = 2.3 Hz, 1H), 7.34 (dd, J = 5.0, 1.2 Hz, 1H), 7.30 (dd, J = 8.2, 2.2 Hz, 1H), 7.24 (dd, J = 3.5, 1.2 Hz, 1H), 7.03 (dd, J = 5.1, 3.5 Hz, 1H), 6.79 (d, J = 8.2 Hz, 1H), 5.25 (s, 2H). MS: (calc.) 429.0 (d); (obt.) 430.0 (d) (MH)$^+$. | 55 |
| 72b | 261b | 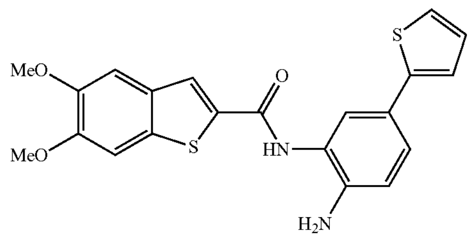 | N-(2-amino-5-(thiophen-2-yl)phenyl)-5,6-dimethoxybenzo[b]thiophene-2-carboxamide | $^1$H NMR: (DMSO) δ (ppm): 9.87 (s, 1H), 8.14 (s, 1H), 7.58 (s, 1H), 7.44 (d, J = 2.2 Hz, 1H), 7.41 (s, 1H), 7.34 (dd, J = 5.1, 1.1 Hz, 1H), 7.29 (dd, J = 8.4, 2.3 Hz, 1H), 7.03 (dd, J = 4.9, 3.5 Hz, 1H), 6.80 (d, J = 8.4 Hz, 1H), 5.20 (s, 2H), 3.85 (s, 3H), 3.84 (s, 3H). MS: (calc.) 410.1; (obt.) 411.1 (MH)$^+$. | 55 |
| 73 | 262 | 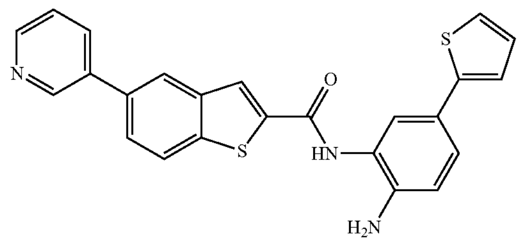 | N-(2-amino-5-(thiophen-2-yl)phenyl)-5-(pyridin-3-yl)benzo[b]thiophene-2-carboxamide | $^1$H NMR: (DMSO) δ (ppm): 10.09 (s, 1H), 8.99 (dd, J = 2.3, 0.8 Hz, 1H), 8.58 (dd, J = 4.7, 1.6 Hz, 1H), 8.38 (s, 1H), 8.33 (d, J = 1.4 Hz, 1H), 8.17 (ddd, J = 9.6, 3.9, 1.8 Hz, 1H), 7.83 (dd, J = 8.5, 1.8 Hz, 1H), 7.53-7.50 (m, 2H), 7.46 (d, J = 2.2 Hz, 1H), 7.34 (dd, J = 5.1, 1.2 Hz, 1H), 7.31 (dd, J = 8.2, 2.2 Hz, 1H), 7.25 (dd, J = 3.5, 1.2 Hz, 1H), 7.03 (dd, J = 5.1, 3.7 Hz, 1H), 6.81 (d, J = 8.4 Hz, 1H), 5.74 (s, 2H). MS: (calc.) 427.1; (obt.) 428.1 (MH)$^+$. | 57 |
| 74 | 264 | 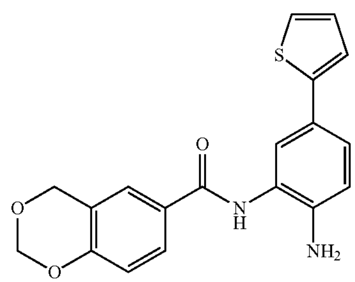 | N-(2-amino-5-(thiophen-2-yl)phenyl)-4H-benzo[d][1,3]dioxine-6-carboxamide | $^1$H NMR: (DMSO) δ (ppm): 9.60 (s, 1H), 7.82 (dd, J = 8.6, 2.2 Hz, 1H), 7.74 (d, J = 2.1 Hz, 1H), 7.41 (d, J = 2.1 Hz, 1H), 7.33 (dd, J = 5.1, 1.2 Hz, 1H), 7.26 (dd, J = 8.4, 2.3 Hz, 1H), 7.21 (dd, J = 3.5, 1.2 Hz, 1H), 7.02 (dd, J = 5.1, 3.8 Hz, 1H), 6.94 (d, J = 8.6 Hz, 1H), 6.77 (d, J = 8.4 Hz, 1H), 5.32 (s, 2H), 5.11 (s, 2H), 4.94 (s, 2H). MS: (calc.) 352.1; (obt.) 353.1 (MH)$^+$. | 57 |

TABLE Ia-continued

| Ex | Cpd | Structure | Name | Characterization | Scheme |
|---|---|---|---|---|---|
| 75 | 269 | 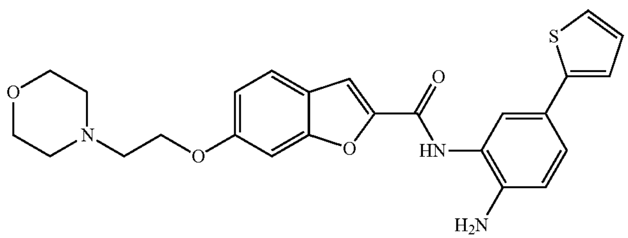 | 6-(2-morpholinoethoxy)-N-(2-amino-5-(thiophen-2-yl)phenyl)benzofuran-2-carboxamide | ¹H NMR: (DMSO) δ (ppm): 7.21 (d, 1H), 7.14 (d, 2H), 6.95 (d, 1H), 6.84-6.79 (m, 3H), 6.62-6.57 (m, 2H), 6.49 (d, 1H), 3.80 (m, 2H), 3.30 (m, 4H), 2.46 (m, 2H), 2.21 (m, 4H). MS: (calc.) 463.2; (obt.) 464.2 (MH)⁺. | 58 |
| 76 | 273 | 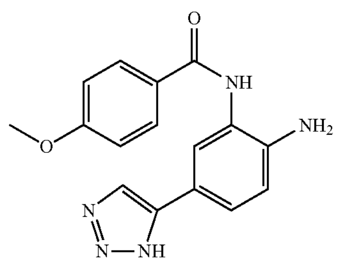 | N-(2-amino-5-(3H-1,2,3-triazol-4-yl)phenyl)-4-methoxybenzamide | ¹H NMR: (DMSO) δ (ppm): 9.62 (s, 1H); 8.08 (bs, 2H); 7.97 (d, J = 8.5 Hz; 2H); 7.62 (s, 1H); 7.45 (d, J = 8.2 Hz; 1H); 7.03 (d, J = 8.5 Hz; 2H); 6.82 (d, J = 8.2 Hz; 1H); 5.11 (bs, 2H); 3.83 (s, 3H). MS: calc: 309.3; found: 310.1 (M + H) | 59 |
| 77 | 277 | 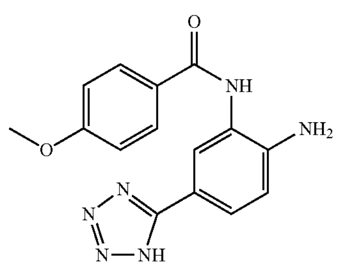 | N-(2-amino-5-(1H-tetrazol-5-yl)phenyl)-4-methoxybenzamide | ¹H NMR: (DMSO) δ (ppm): 9.63 (s, 1H); 7.98 (d, J = 8.8 Hz; 2H); 7.81 (d, J = 2.0 Hz; 1H); 7.61 (dd; J = 2.0, 8.4 Hz; 1H); 7.04 (d, J = 8.8 Hz; 2H); 6.85 (d, J = 8.4 Hz; 1H); 3.85 (s, 3H). MS: calc: 310.3; found: 311.1 (M + H) | 61 |

| Ex | Cpd | Structure | Name | Characterization | Scheme |
|---|---|---|---|---|---|
| 78 | 283 | 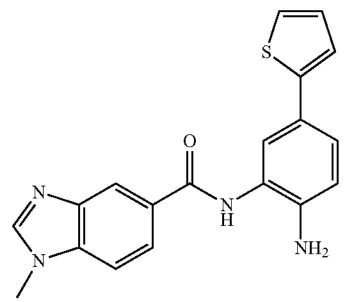 | N-(2-amino-5-(thiophen-2-yl)phenyl)-1-methyl-1H-benzo[d]imidazole-5-carboxamide | ¹H NMR: (DMSO) δ (ppm): 9.75 (s, 1H); 8.38 (d, J = 1.0 Hz, 1H), 8.34 (s, 1H), 7.95 (dd; J = 1.4, 8.4 Hz; 1H); 7.68 (d, J = 8.4 Hz, 1H), 7.50 (d; J = 2.2 Hz; 1H); 7.34 (dd; J = 1.0, 5.0 Hz; 1H); 7.28 (dd; J = 2.2, 8.4 Hz; 1H); 7.24 (dd; J = 1.4, 3.6 Hz; 1H); 7.04 (dd; J = 3.6, 5.0 Hz; 1H); 6.81 (d; J = 8.4 Hz; 1H); 3.90 (s, 3H). MS: calc: 348.4; found: 349.1 (M + H) | 62 |
| 79 | 286 | 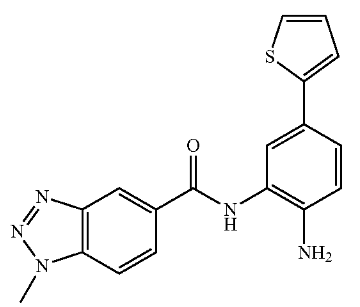 | N-(2-amino-5-(thiophen-2-yl)phenyl)-1-methyl-1H-benzo[d][1,2,3]triazole-5-carboxamide | ¹H NMR: (DMSO) δ (ppm): 9.88 (s, 1H); 8.75 (s, 1H), 8.15 (dd; J = 1.0, 8.6 Hz; 1H); 7.95 (dd, J = 1.0, 8.6 Hz, 1H), 7.49 (d, J = 2.0 Hz, 1H), 7.34 (dd; J = 1.2, 5.1 Hz; 1H); 7.30 (dd; J = 2.0, 8.3 Hz; 1H); 7.24 (dd; J = 1.2, 3.5 Hz; 1H); 7.04 (dd; J = 3.5, 5.1 Hz; 1H); 6.81 (d; J = 8.3 Hz; 1H); 5.24 (bs, 2H); 4.37 (s, 3H). MS: calc: 349.4; found: 350.1 (M + H) | 62 |
| 79aa | 286aa | 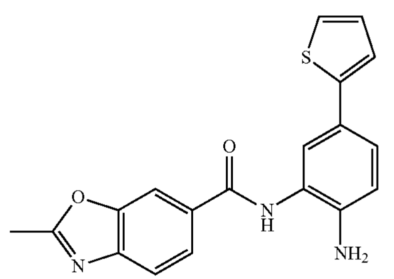 | N-(2-amino-5-(thiophen-2-yl)phenyl)-2-methylbenzo[d]oxazole-6-carboxamide | ¹H NMR: (DMSO) δ (ppm): 9.80 (s, 1H); 8.29 (d, J = 1.4 Hz, 1H), ), 8.00 (dd; J = 1.4, 8.4 Hz, 1H); 7.76 (d, J 32 8.2 Hz, 1H), 7.46 (d; J = 2.0 Hz; 1H); 7.34 (dd; J = 1.0, 5.0 Hz; 1H); 7.30 (dd; J = 2.0, 8.4 Hz; 1H); 7.23 (dd; J = 1.0, 3.5 Hz; 1H); 7.04 (dd; J = 3.5, 5.0 Hz; 1H); 6.80 (d; J = 8.2 Hz; 1H); 5.20 (bs, 2H); 2.67 (s, 3H). MS: calc: 349.4; found: 350.0 (M + H) | 62 |

| Ex | Cpd | Structure | Name | Characterization | Scheme |
|---|---|---|---|---|---|
| 80 | 291 | 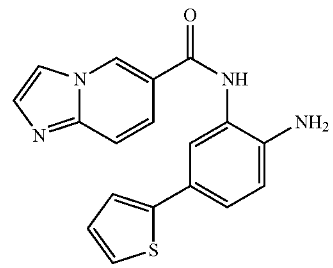 | N-(2-amino-5-(thiophen-2-yl)phenyl)H-imidazo[1,2-a]pyridine-6-carboxamide | ¹H NMR: (CD3OD) δ (ppm): 9.19 (s, 1H); 7.99 (s, 1H); 7.86 (d; J = 8.5 Hz; 1H); 7.67 (s, 1H), 7.64 (d; J = 8.5 Hz; 1H); 7.50 (s, 1H); 7.37 (d; J = 8.5 Hz; 1H); 7.22 (d; J = 4.9 Hz; 1H); 7.21 (m, 1H); 7.01 (t; J = 4.9 Hz; 1H); 6.91 (d; J = 8.5 Hz; 1H). MS: calc: 334.4; found: 335.1 (M + H) | 63 |
| 81 | 296 | 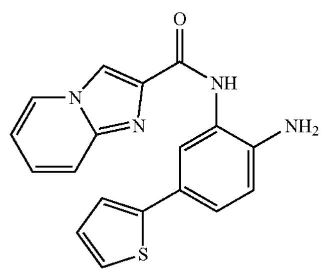 | N-(2-amino-5-(thiophen-2-yl)phenyl)H-imidazo[1,2-a]pyridine-2-carboxamide | ¹H NMR: (DMSO) δ (ppm): 9.73 (s, 1H), 8.62 (dt, J = 1.2; 6.8 Hz, 1H), 8.50 (d, J = 0.7 Hz; 1H); 7.76 (d; J = 2.2 Hz; 1H); 7.66 (d, J = 0.7 Hz, 1H), 7.39 (dd; J = 1.6, 6.8 Hz; 1H); 7.36 (dt; J = 1.6, 4.9 Hz; 1H); 7.26 (dd; J = 2.2, 8.2 Hz; 1H); 7.24 (dd; J = 1.2, 3.6 Hz; 1H); 7.05 (m; 1H); 7.01 (dd; J = 1.2, 6.8 Hz; 1H); 6.84 (d; J = 8.2 Hz; 1H); 5.13 (bs, 2H). MS: calc: 334.4; found: 335.1 (M + H). | 64 |
| 82 | 301 | 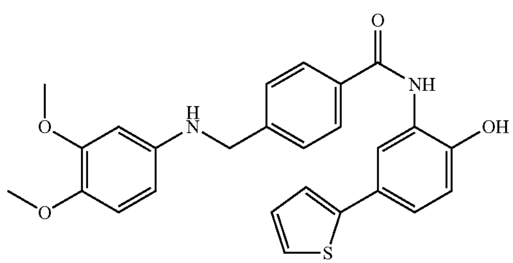 | 4-((3,4-dimethoxyphenyl)amino)methyl)-N-(2-hydroxy-5-(thiophen-2-yl)phenyl)benzamide | ¹H NMR: (DMSO) δ (ppm): 10.1 (s, 1H); 9.52 (s, 1H); 8.00 (s, 1H); 7.92 (d, J = 7.0, 2H); 7.49 (d, J = 7.0, 2H); 7.42 (m, 1H); 7.33 (d, J = 8.0, 1H); 7.29 (s, 1H); 7.07 (s, 1H); 6.93 (d, J = 8.0, 1H); 6.65 (d, J = 8.5, 1H); 6.32 (s, 1H); 5.98 (m, 2H); 4.30 (s, 2H); 3.65 (s, 3H); 3.58 (s, 3H). MS: calc: 460.5; found: 461.1 (M + H) | 65 |

TABLE Ia-continued

| Ex | Cpd | Structure | Name | Characterization | Scheme |
|---|---|---|---|---|---|
| 83 | 302 | 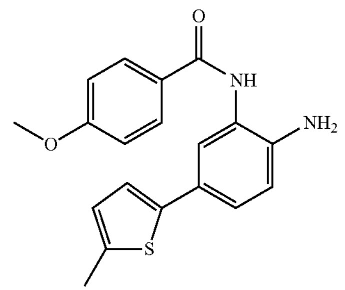 | N-(2-amino-5-(5-methylthiophen-2-yl)phenyl)-4-methoxybenzamide | ¹H NMR: (DMSO) δ (ppm): 9.60 (s, 1H), 7.96 (d, J = 8.0, Hz, 2H); 7.36 (d, J = 2.1 Hz, 1H); 7.20 (dd, J = 2.1, 8.3 Hz, 1H); 7.03 (d, J = 8.0, Hz, 2H); 7.00 (d, J = 3.5 Hz, 1H); 6.78 (d, J = 8.3 Hz, 1H); 6.70 (dd, J = 1.1, 3.5 Hz, 1H); 3.83 (s, 3H); 2.42 (d, J = 1.1 Hz, 3H). MS: calc: 338.4; found: 338.4 (M + H). | 66 |
| 84 | 308 | 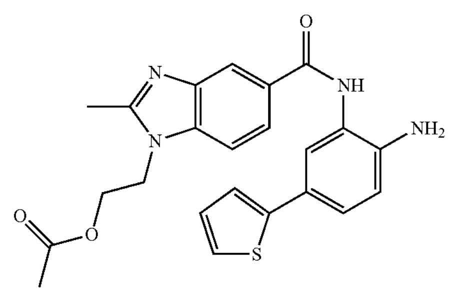 | 2-(5-((2-amino-5-(thiophen-2-yl)phenyl)carbamoyl)-2-methyl-1H-benzo[d]imidazol-1-yl)ethyl acetate | ¹H NMR: (DMSO) δ (ppm): 9.70 (s, 1H), 8.23 (s, 1H); 7.87 (dd, J = 1.0, 8.4 Hz; 1H); 7.62 (d, J = 8.4 Hz, 1H); 7.48 (d; J = 2.0 Hz; 1H); 7.34 (dd; J = 0.8, 4.8 Hz; 1H); 7.28 (dd; J = 2.0, 8.0 Hz; 1H); 7.23 (dd; J = 0.8, 3.6 Hz; 1H); 7.03 (dd; J = 1.2, 4.8 Hz; 1H); 6.81 (d; J = 8.0 Hz; 1H); 5.15 (bs, 2H); 4.52 (t; J = 4.8 Hz; 2H); 4.35 (t; J = 4.8 Hz; 2H); 2.60 (s, 3H); 1.91 (s, 3H). MS: calc: 434.5; found: 435.2 (M + H) | 67 |
| 85 | 309 | 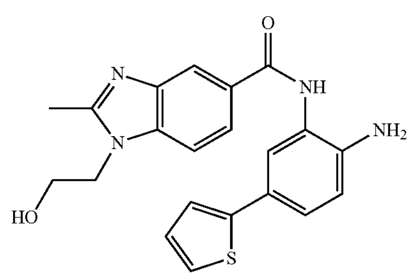 | N-(2-amino-5-(thiophen-2-yl)phenyl)-1-(2-hydroxyethyl)-2-methyl-1H-benzo[d]imidazole-5-carboxamide | ¹H NMR: (DMSO) δ (ppm): 9.70 (s, 1H), 8.22 (s, 1H); 7.84 (dd; J = 1.4, 8.2 Hz; 1H); 7.57 (d; J = 8.4 Hz, 1H); 7.49 (d; J = 2.2 Hz; 1H); 7.34 (dd; J = 1.4, 5.1 Hz; 1H); 7.28 (dd; J = 2.2, 8.2 Hz; 1H); 7.23 (dd; J = 1.0, 3.5 Hz; 1H); 7.04 (dd; J = 3.5, 5.1 Hz; 1H); 6.80 (d; J = 8.4 Hz; 1H); 5.14 (bs, 2H); 5.00 (bs, 1H); 4.28 (t; J = 5.4 Hz; 2H); 3.72 (t; J = 5.4 Hz; 2H); 2.59 (s, 3H); MS: calc: 392.5; found: 393.2 (M + H) | 67 |

TABLE Ia-continued

| Ex | Cpd | Structure | Name | Characterization | Scheme |
|---|---|---|---|---|---|
| 86 | 312 | 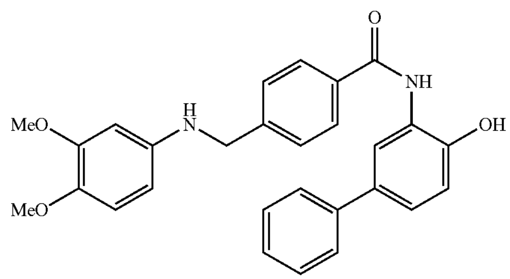 | 4-((3,4-dimethoxyphenyl)amino)methyl)-N-(2-hydroxy-5-(phenyl)phenyl)benzamide | ¹H NMR: (DMSO) δ (ppm): 3.62 (s, 3H), 3.69 (s, 3H), 4.34 (d, J = 5.7 Hz, 2H), 6.03 (m, 2H), 6.35 (d, J = 2.2 Hz, 1H), 6.68 (d, J = 8.4 Hz, 1H), 7.03 (d, J = 8.4 Hz, 1H), 7.32 (t, J = 7.2 Hz, 1H), 7.37 (dd, J = 10.4, 1.6 Hz, 1H), 7.45 (t, J = 7.6 Hz, 2H), 7.52 (d, J = 8.0 Hz, 2H), 7.59 (d, J = 7.6 Hz, 2H), 7.95 (d, J = 8.0 Hz, 2H), 8.03 (br s, 1H), 9.58 (br s, 1H), 10.00 (br s, 1H) MS: (calc.) 454.5; (obt.) 455.4 (MH)⁺ | 68 |
| 87 | 313 | 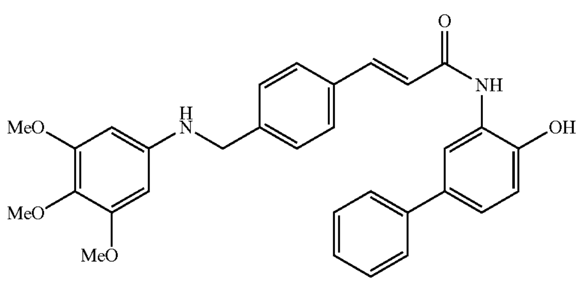 | (E)-3-(4-((3,4,5-trimethoxyphenyl)amino)methyl-phenyl)-N-(2-hydroxy-5-(phenyl)phenyl)acrylamide | ¹H NMR: (DMSO) δ (ppm): 3.54 (s, 3H), 3.68 (s, 3H), 4.30 (d, J = 5.9 Hz, 2H), 5.92 (s, 2H), 6.13 (t, J = 6.3 Hz, 1H), 7.01 (d, J = 8.2 Hz, 1H), 7.21 (d, J = 15.7 Hz, 1H), 7.29 (dd, J = 8.4, 2.3 Hz, 1H), 7.33 (d, J = 7.2 Hz, 1H), 7.42-7.50 (m, 4H), 7.54-7.64 (m, 4H), 8.34 (s, 1H), 9.55 (br s, 1H), 10.21 (br s, 1H) MS: (calc.) 510.6; (obt.) 511.2 (MH)⁺ | 68 |
| 88 | 314 | 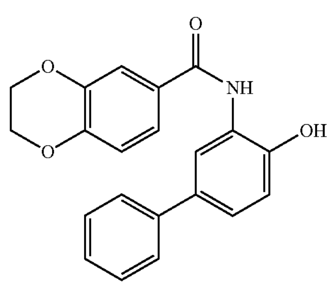 | 2,3-dihydro-N-(2-hydroxy-5-(phenyl)phenyl)benzo[b][1,4]dioxine-6-carboxamide | ¹H NMR: (DMSO) δ (ppm): 4.30 (d, J = 5.9 Hz, 2H), 6.98 (d, J = 8.3 Hz, 1H), 7.26-7.36 (m, 2H), 7.42 (t, J = 7.3 Hz, 2H), 7.50-7.60 (m, 2H), 7.97 (br s, 1H), 9.47 (br s, 1H), 9.93 (br s, 1H) MS: (calc.) 347.4; (obt.) 348.1 (MH)⁺ | 68 |

| Ex | Cpd | Structure | Name | Characterization | Scheme |
|---|---|---|---|---|---|
| 89 | 315 | 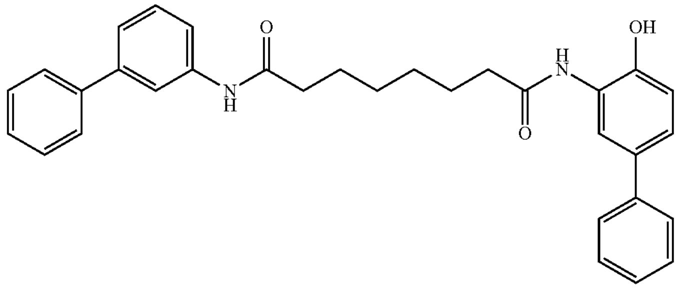 | $N^1$-(2-hydroxy-5-(phenyl)phenyl)-$N^8$-(3-(phenyl)phenyl)octanediamide | $^1$H NMR: (DMSO) δ (ppm): 1.34-1.46 (m, 4H), 1.60-1.74 (m, 4H), 2.38 (t, J = 6.8 Hz, 2H), 2.47 (t, J = 7.0 Hz, 2H), 6.98 (d, J = 8.2 Hz, 1H), 7.20-7.70 (m, 15H), 7.96 (s, 1H), 8.10 (s, 1H), 9.34 (br s, 1H), 10.00 (br s, 1H) MS: (calc.) 492.6; (obt.) 493.5 (MH)$^+$ | 69 |
| 90 | 320 | 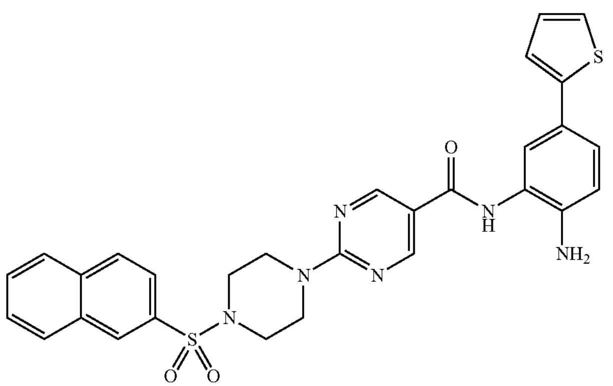 | 2-[4-(Naphthalene-2-sulfonyl)-piperazin-1-yl]-pyrimidine-5-carboxylic acid (2-amino-5-thiophen-2-yl-phenyl)-amide | $^1$H NMR: (400.2 MHz, DMSO) δ (ppm): 9.52 (bs, 1H); 8.83 (s, 2H); 8.44 (s, 1H); 8.20 (d, J = 7.6 Hz, 1H); 8.15 (d, J = 8.6 Hz, 1H); 8.05 (d, J = 8.0 Hz, 1H); 7.75 (dd; J = 1.8, 8.6 Hz; 1H); 7.69 (m, 2H); 7.37 (d, J = 1.8 Hz, 1H); 7.31 (dd; J = 1.2, 5.1 Hz; 1H); 7.25 (dd; J = 2.2, 8.4 Hz; 1H); 7.19 (dd; J = 1.2, 3.5 Hz; 1H); 7.01 (dd; J = 3.5, 5.1 Hz; 1H); 6.74 (d, J = 8.2 Hz, 1H); 5.16 (bs, 2H); 3.96 (t, J = 4.3 Hz, 4H); 3.07 (t, J = 4.3 Hz, 4H); MS: calc: 570.7; found: 571.3 (M + H) | 70 |

| Ex | Cpd | Structure | Name | Characterization | Scheme |
|---|---|---|---|---|---|
| 91 | 323 | 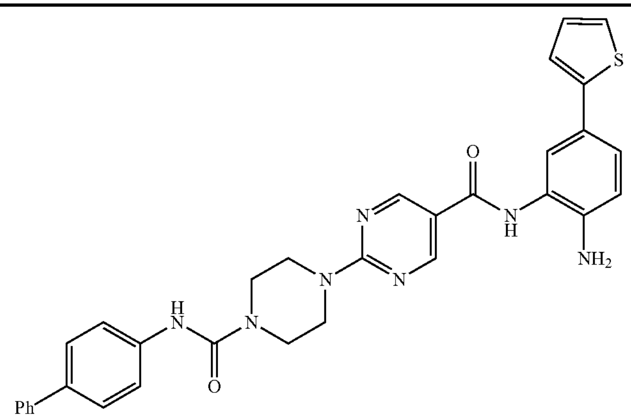 | 2-[4-(Biphenyl-4-ylcarbamoyl)-piperazin-1-yl]-pyrimidine-5-carboxylic acid (2-amino-5-thiophen-2-yl-phenyl)-amide | $^1$H NMR: (400.2 MHz, DMSO) δ (ppm): 9.59 (bs, 1H); 8.92 (s, 2H); 8.75 (bs, 1H); 7.63 (d, J = 1.2 Hz, 1H); 7.61 (m, 1H); 7.57 (m, 4H); 7.41 (m, 3H); 7.33 (dd; J = 1.2, 5.1 Hz; 1H); 7.29 (m, 2H); 7.23 (dd; J = 1.2, 2.5 Hz; 1H); 7.03 (dd; J = 3.7, 5.1 Hz; 1H); 6.78 (d, J = 8.2 Hz, 1H); 5.22 (bs, 2H); 3.93 (t, J = 3.9 Hz, 4H); 3.60 (t, J = 3.9 Hz, 4H). MS: calc: 575.7; found: 576.3 (M + H) | 71 |
| 92 | 327 | 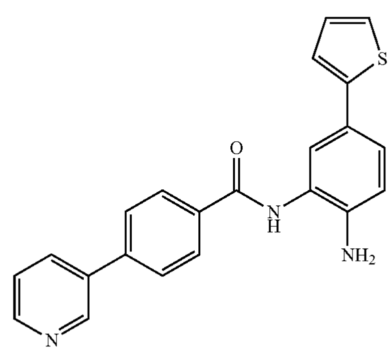 | N-(2-Amino-5-(thiophen-2-yl)phenyl)-4-(pyridin-3-yl)benzamide | $^1$H NMR: (400 MHz, DMSO-d$_6$) δ (ppm): 9.80 (s, 1H), 8.98 (d, J = 2.2 Hz, 1H), 8.60 (dd, J = 4.7, 1.6 Hz, 1H), 8.17 (d, J = 8.6 Hz, 1H), 8.12 (d, J = 8.0 Hz, 2H), 7.90 (d, J = 8.6 Hz, 2H), 7.52 (dd, J = 7.2, 4.1 Hz, 1H), 7.48 (s, 1H), 7.35 (d, J = 4.1 Hz, 1H), 7.29 (dd, J = 8.4, 2.3 Hz, 1H), 7.24 (d, J = 3.3 Hz, 1H), 7.04 (dd, J = 5.1, 1.4, 1H), 6.80 (d, J = 8.2 Hz, 1H), 5.19 (s, 2H). LRMS: (m/z): 372.3 (MH$^+$). | 72 |

TABLE Ia-continued

| Ex | Cpd | Structure | Name | Characterization | Scheme |
|---|---|---|---|---|---|
| 93 | 333 | 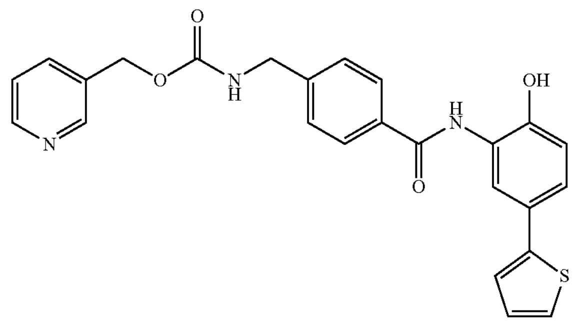 | (Pyridin-3-yl)methyl 4-(2-hydroxy-5-(thiophen-2-yl)phenylcarbamoyl)benzylcarbamate | ¹H NMR: (Acetone-d₆) δ (ppm): 9.37 (bs, 1H), 9.35 (bs, 1H), 8.47 (d, 1.2 Hz, 8.38 (d, J = 3.9 Hz, 1H), 7.97 (s, 1H), 7.87 (d, J = 8.4 Hz, 2H), 7.64 (d, J = 7.4 Hz, 1H), 7.35 (d, J = 8.2 Hz, 2H), 7.25 (dd, J = 8.4, 2.3 Hz, 1H), 7.22 (dd, J = 5.1, 1.2 Hz, 1H), 7.16 (dd, J = 3.7, 1.2 Hz, 1H), 6.93 (d, J = 8.1 Hz, 1H), 6.93 (d, J = 1.6 Hz, 1H), 6.86 (d, J = 8.4 Hz, 1H), 5.01 (s, 2H), 4.31 (d, J = 6.3 Hz, 2H). LRMS: (m/z): 460.2 (MH⁺). | 73 |
| 94 | 341 | 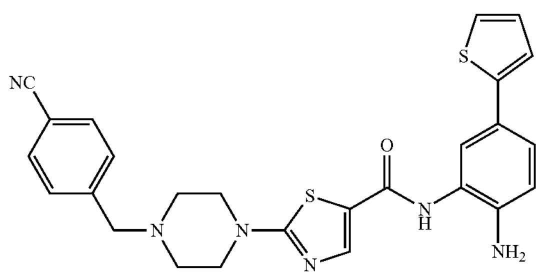 | 2-(4-(4-Cyanobenzyl)piperazin-1-yl)-N-(2-amino-5-(thiophen-2-yl)phenyl)thiazole-5-carboxamide | ¹H NMR: (400.2 MHz, CD₃OD) δ (ppm): 7.95 (br.s, 1H), 7.75 (m, 1H), 7.68 (m, 2H), 7.53 (t, 1H, J = 7.6 Hz), 7.42 (s, 1H), 7.33 (d, 1H, J = 8.2 Hz), 7.20 (m, 2H), 7.00 (m, 1H), 6.87 (d, 1H, J = 8.3 Hz), 3.72 (s, 2H), 3.60 (m, 4H), 2.68 (m, 4H). MS: calc: 500.1; found: 501.2 (M + H) | 74 |
| 95 | 344 | 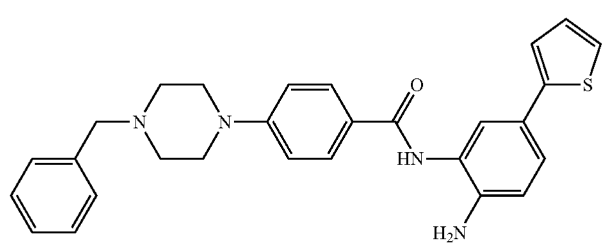 | N-(2-Amino-5-(thiophen-2-yl)phenyl)-4-(4-benzylpiperazin-1-yl)benzamide | ¹H NMR: (400.2 MHz, CDCl₃) δ (ppm): 2.625 (t, J = 5 Hz, 4H), 3.35 (t, J = 5 Hz, 4H), 3.59 (s, 2H), 4.00 (s, 2H), 6.84 (d, J = 8 Hz, 1H), 6.90 (d, J = 9 Hz, 2H), 7.01 (m, 1H), 7.16 (m, 2H), 7.25 (m, 6H), 7.50 (s, 1H), 7.75 (s, 1H), 7.81 (d, J = 9 Hz, 2H). MS: calc: 468.0; found: 469.0 (M + H) | 75 |

TABLE Ia-continued

| Ex | Cpd | Structure | Name | Characterization | Scheme |
|---|---|---|---|---|---|
| 96 | 347 | 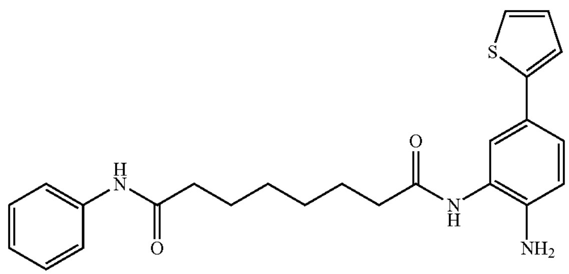 | N1-(2-amino-5-(thiophen-2-yl)phenyl)-N8-phenyloctanediamide | $^1$H NMR: (400.2 MHz, CD$_3$OD) δ (ppm): 7.51 (br.s, 2H), 7.38 (s, 1H), 7.16-7.27 (m, 5H), 6.9-7.1 (m, 2H), 6.84 (m, 1H), 2.42 (m, 4H), 1.76 (m, 4H), 1.49 (m, 4H). MS: calc: 421.2; found: 422.2 (M + H) | 76 |
| 97 | 349 | 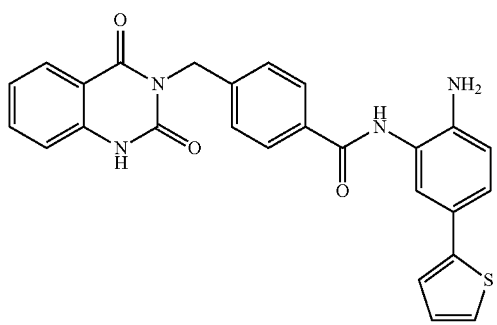 | N-(2-Amino-5-(thiophen-2-yl)phenyl)-4-((1,2-dihydro-2,4-dioxoquinazolin-3(4H)-yl)methyl)benzamide | $^1$H NMR (DMSO-d$_6$) D(ppm): 11.57 (s, 1H), 9.81 (s, 1H), 7.95-7.92 (m, 3H), 7.68 (td, J = 7.2, 1.4 Hz, 1H), 7.48 (d, J = 1.8 Hz, 1H), 7.42 (d, J = 8.2 Hz, 2H), 7.38 (d, J = 5.1 Hz, 1H), 7.34 (dd, J = 8.2, 2.0 Hz, 1H), 7.27 (d, J = 3.3 Hz, 1H), 7.24-7.20 (m, 2H), 7.05 (dd, J = 4.9, 3.5 Hz, 1H), 6.89 (d, J = 8.4 Hz, 1H), 5.17 (s, 2H). (The NH$_2$ group is missing, overlapped by H$_2$O). MS (m/z): 468.53 (calc) 469.2 (MH+) (found). | 77 |
| 98 | 355 | 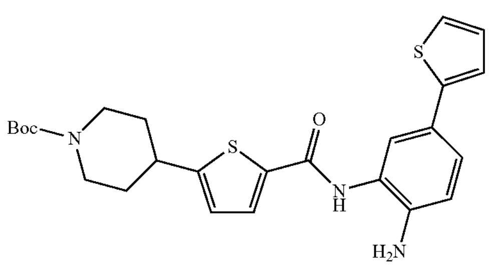 | tert-Butyl 4-(5-(2-amino-5-(thiophen-2-yl)phenylcarbamoyl)thiophen-2-yl)piperidine-1-carboxylate | $^1$H NMR: (CD$_3$OD) δ (ppm) 7.73 (d, J = 3.3 Hz, 1H), 7.45 (d, J = 2.1 Hz, 1H), 7.34 (dd, J = 8.2, 2.2 Hz, 1H), 7.23-7.19 (m, 2H), 7.01 (dd, J = 4.7, 3.7 Hz, 1H), 6.96 (d, J = 3.9 Hz, 1H), 6.88 (d, J = 8.1 Hz, 1H), 4.17 (d, J = 13.1 Hz, 2H), 3.00-2.90 (m, 2H), 2.04 (d, J = 12.1 Hz, 2H), 1.60-1.54 (m, 2H). | 78 |

| Ex | Cpd | Structure | Name | Characterization | Scheme |
|---|---|---|---|---|---|
| 99 | 358 | [structure] | N-(2-amino-5-(thiophen-2-yl)phenyl)-2-(2-morpholinoethyl)-1,3-dioxoisoindoline-5-carboxamide | $^1$H NMR: (DMSO) δ (ppm): 10.03 (s, 1H), 8.45 (s, 1H), 8.38 (d, J = 7.6 Hz, 1H), 7.99 (d, J = 7.6 Hz, 1H), 7.44 (d, J = 2.0 Hz, 1H), 7.32 (dd, J = 11.9, 5.1 Hz, 1H), 7.28 (d, J = 2.0 Hz, 1H), 7.03 (d, J = 4.9 Hz, 1H), 6.78 (d, J = 8.2 Hz, 1H), 5.27 (s, 2H), 3.73 (t, J = 6.3 Hz, 2H), 3.48 (m, 4H), 2.54 (t, J = 6.5 Hz, 2H), 2.41 (m, 4H). MS: 476.15 (calc), 477.2 (obs). | 79 |
| 100 | 361 | [structure] | N-(2-amino-5-(1H-imidazol-1-yl)phenyl)-4-methoxybenzamide | $^1$H NMR: (DMSO) δ (ppm): 9.62 (s, 1H), 7.96 (d, J = 9.0 Hz, 3H), 7.52 (m, 1H), 7.42 (d, J = 2.5 Hz, 1H), 7.19 (dd, J = 8.6, 2.5 Hz, 1H), 7.04 (d, J = 8.8 Hz, 2H), 7.03 (s, 1H), 6.85 (d, J = 8.4 Hz, 1H), 5.11 (s, 2H), 3.83 (s, 3H). MS: 308.13 (calc), 309.2 (obs). | 80 |

SYNTHETIC SCHEMES AND EXPERIMENTAL PROCEDURES

The compounds of the invention can be prepared according to the reaction schemes for the examples illustrated below utilizing methods known to one of ordinary skill in the art. These schemes serve to exemplify some procedures that can be used to make the compounds of the invention. One skilled in the art will recognize that other general synthetic procedures may be used.

The compounds of the invention can be prepared from starting components that are commercially available. Any kind of substitutions can be made to the starting components to obtain the compounds of the invention according to procedures that are well known to those skilled in the art.

The compounds according to embodiments [0083]-[0088] can be routinely synthesized using techniques described herein in conjunction with the teachings of WO 03/087057.

The compounds according to embodiments [0098]-[0110] can be routinely synthesized using techniques described herein in conjunction with the teachings of WO 03/076422.

The compounds according to embodiments [0115]-[0124] can be routinely synthesized using techniques described herein in conjunction with the teachings of WO 03/075929.

The compounds according to embodiments [0125]-[0135] can be routinely synthesized using techniques described herein in conjunction with the teachings of WO 03/076395.

The compounds according to embodiments [0136]-[0145] can be routinely synthesized using techniques described herein in conjunction with the teachings of WO 03/076400.

The compounds according to embodiments [0146]-[0157] can be routinely synthesized using techniques described herein in conjunction with the teachings of WO 03/076401.

The compounds according to embodiments [0158]-[0166] can be routinely synthesized using techniques described herein in conjunction with the teachings of WO 03/076421.

The compounds according to embodiments [0167]-[0175] can be routinely synthesized using techniques described herein in conjunction with the teachings of WO 03/076430.

The compounds according to embodiments [0176]-[0186] can be routinely synthesized using techniques described herein in conjunction with the teachings of WO 03/076438.

The compounds according to embodiments [0187]-[0194] can be routinely synthesized using techniques described herein in conjunction with the teachings of WO 03/92686.

The compounds according to embodiment [0195] can be routinely synthesized using techniques described herein in conjunction with the teachings of WO 03/024448.

The compounds according to embodiments [0196]-[0197] can be routinely synthesized using techniques described herein in conjunction with the teachings of JP 2003137866.

The compounds according to embodiment [0198]-[0199] can be routinely synthesized using techniques described herein in conjunction with the teachings of JP 11-269146 (1999).

The compounds according to embodiments [0200]-[0201] can be routinely synthesized using techniques described herein in conjunction with the teachings of JP 11-302173 (1999).

The compounds according to embodiments [0202]-[0203] can be routinely synthesized using techniques described herein in conjunction with the teachings of JP 2001131130.

The compounds according to embodiments [0204]-[0205] can be routinely synthesized using techniques described herein in conjunction with the teachings of JP 10152462, JP 2002332267, and JP 11-302173.

The compounds according to embodiments [0206]-[0207] can be routinely synthesized using techniques described herein in conjunction with the teachings of U.S. Pat. No. 6,174,905.

The compounds according to embodiment [0206] can be routinely synthesized using techniques described herein in conjunction with the teachings of WO01/70675.

Example 1

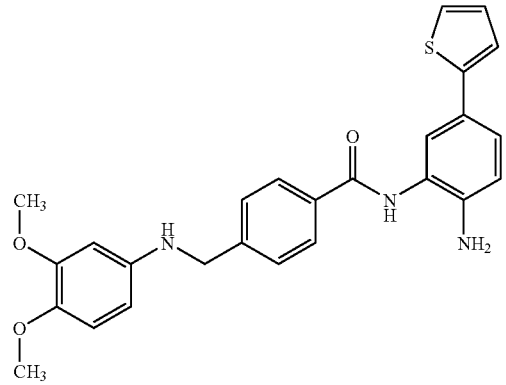

N-[2-amino-5-(2-thienyl)phenyl]-4-{[(3,4-dimethoxyphenyl)amino]methyl}ben2amide (6)

Scheme 1

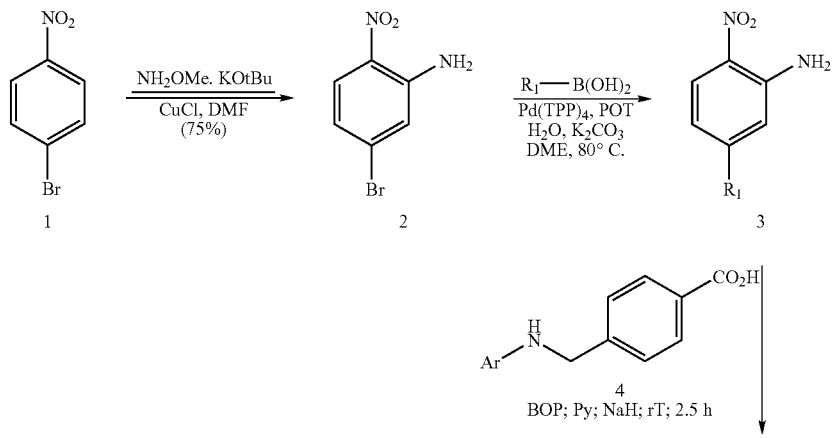

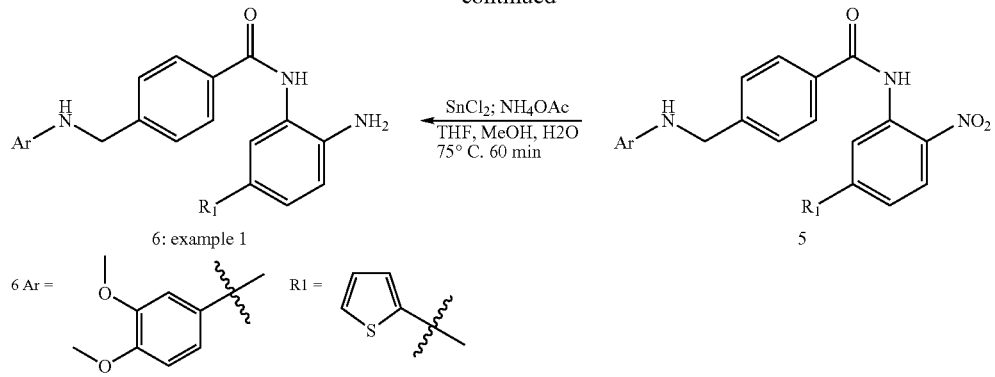

Step 1. 5-Brom0-2-nitro-phenylamine (2)

To a solution of potassium tert-butoxide (14.5 g; 129.2 mmol) and copper(I) chloride (301 mg; 3.04 mmol) in ethyleneglycol dimethylether (120 mL), stirred at 0° C. under nitrogen, a solution of 1-bromo-4-nitro-benzene (1, 6.141 g; 30.4 mmol) and O-methyl-hydroxylamine hydrochloride (3.174 g; 38 mmol) in N,N-dimethylformamide (65 mL) was added drop wise over 103 min, the cooling bath was removed and the mixture was allowed to react at room temperature for 3 h, diluted with ethyl acetate (600 mL) and washed with saturated aqueous ammonium chloride. The organic layer was dried ($MgSO_4$), filtered and concentrated. After purification by flash chromatography (eluent 25% ethyl acetate in hexane), 4.96 g (75% yield) of compound 2 were obtained.

$^1$H NMR: (400.2 MHz, $CDCl_3$) δ (ppm): 7.98 (d, J=9.24, 1H); 7.02 (d, J=1.98, 1H); 6.82 (dd, J=1.98 and 9.24, 1H); 6.12 (bs, 2H).

Step 2. 2-Nitro-5-(thiophen-2-yl-phenylamine (3)

A suspension of bromoarene 2 (5.85 g; 26.9 mmol) (or any other haloarene of choice); 2-thiopheneboronic acid (4.56 g, 35.6 mmol); (or the any other arylboronic acid of choice), tri-o-tolyl-phosphine (2.69 g; 8.8 mmol) and potassium carbonate (11.1 g; 80 mmol) in degassed ethyleneglycol dimethylether (70 mL) and water (35 mL), was treated with tetrakis (triphenylphosphine)palladium(0) (2.04 g, 1.77 mmol) and the mixture stirred on a preheated oil bath at 80° C. for 18 h, diluted with dichloromethane (300 mL), washed with water, dried ($MgSO_4$) and concentrated. Purification by flash chromatography (eluent 50% ether in hexane) afforded compound 3 (5.63 g, 95% yield).

$^1$H NMR: (400.2 MHz, DMSO) δ (ppm): 7.97 (d, J=9.0, 1H); 7.69 (dd, J=1.2 and 5.1, 1H); 7.60 (dd, J=1.2 and 3.6, 1H); 7.49 (bs, 2H); 7.27 (d, J=2.0, 1H); 7.18 (dd, J=3.6 and 5.1, 1H); 6.97 (dd, J=2.0 and 9.0, 1H).

Step 3. 4-[(3,4-Dimethoxy-phenylamino)-methyl]-N-(2-nitro-5-(thiophen-2-yl-phenyl)-benzamide (5)

To a solution of nitrophenylamine (3, 460 mg, 2.1 mmol), (or any other nitrophenylamine of choice, 1 eq); 4-[(3,4-dimethoxy-phenylamino-4-methyl]-benzoic acid (4, see below), 761 mg, 2.65 mmol) (or any other acid of choice, 1.3 eq) and benzotriazol-1-yloxytris(dimethylamino)phosphonium hexafluorophosphate (BOP) (1095 mg, 2.47 mmol) in pyridine (15 mL), 60% sodium hydride in oil (563 mg, 14.1 mmol) was added portion wise under a stream of nitrogen, and the reaction was allowed to progress at room temperature for 2.5 h and diluted with toluene. Excess of NaH was quenched with acetic acid and the whole mixture was concentrated, re-dissolved in ethyl acetate and washed with a solution of $NaHCO_3$ in brine, dried ($MgSO_4$) and concentrated. After purification by flash chromatography (eluent 30% to 75% AcOEt in hexane), 883 mg (1.80 mmol, 86% yield) of amide 5 were obtained.

$^1$H NMR: (400.2 MHz, DMSO) δ (ppm): 10.8 (s, 1H); 8.10 (d, J=2.0, 1H); 8.06 (d, J=8.6, 1H); 7.90 (d, J=8.2, 2H); 7.74 (dd, J=1.0 and 4.9, 1H); 7.72 (dd, J=1.0 and 3.5, 1H); 7.69 (dd, J=2.2 and 8.7, 1H); 7.53 (d, J=8.2, 2H); 7.22 (dd, J=3.5 and 4.9, 1H); 6.64 (d, J=8.6, 1H); 6.31 (d, J=2.0, 1H); 6.01 (t, J=6.1, 1H); 5.98 (dd, J=2.2 and 8.4, 1H); 4.32 (d, J=6.1, 2H); 3.66 (s, 3H); 3.59 (s, 3H).

4-[(3,4-Dimethoxy-phenylamino)-methyl]-benzoic acid (4)

To a solution of 3,4-dimethoxy-phenylamine (786 mg; 5.13 mmol) and dibutyltridichloride (219 mg; 0.72 mmol) in ethyleneglycol dimethylether (7 mL), 4-formyl-benzoic acid (748 mg; 4.98 mmol) was added. The suspension was stirred at room temperature for 10 min, treated with phenylsilane (1.0 mL; 7.9 mmol) and the mixture stirred at the same temperature for 12 h. Methanol and a few drops of water were added, stirred for 5 h, concentrated under vacuum, suspended in dichloromethane and stirred for one day at room temperature. After filtration, pure acid 4 (1.13 g; 79% yield) was obtained as a beige solid.

$^1$H NMR: (400.2 MHz, DMSO) δ (ppm): 7.86 (d, J=8.2, 2H); 7.44 (d, J=8.2, 2H); 6.63 (d, J=8.5, 1H); 6.29 (d, J=2.3, 1H); 5.96 (dd, J=2.3, 8.5, 1H); 5.96 (bs, 1H); 4.28 (s, 2H); 3.64 (s, 3H); 3.58 (s, 3H).

Step 4. N-(2-Amino-5-(thiophen-2-yl-phenyl)-4-[(3,4-dimethoxy-phenylamino)-methyl]-benzamide (6)

A suspension of compound 5 (250 mg, 0.511 mmol) (or any other nitroamide of choice, 1 eq) and tin(II) chloride dihydrate (2.30 g, 10.2 mmol) in a 1:1:1 mixture THF/MeOH/water (18 mL) was stirred at 75° C. in a sealed tube for 1 h, diluted with ethyl acetate and washed with saturated aqueous solution of $NaHCO_3$, dried over $Na_2SO_4$ and purified by flash chromatography, eluent 20% EtOAc in dichloromethane, to afford 138 mg (59% yield) of the title compound 6.

$^1$H NMR: (400.2 MHz, DMSO) δ (ppm): 9.66 (s, 1H); 7.92 (d, J=8.4, 2H); 7.46 (d, J=8.4, 2H); 7.44 (d, J=2.0, 1H); 7.34 (dd, J=1.1; 5.0, 1H); 7.27 (dd, J=2.0; 8.2, 1H); 7.22 (dd, J=1.1 and 3.6, 1H); 7.03 (dd, J=3.6, 5.0, 1H); 6.78 (d, J=8.5, 1H); 6.64 (d, J=8.5, 1H); 6.31 (d, J=2.5, 1H); 6.01-5.97 (m, 2H); 5.14 (bs, 2H); 4.30 (d, J=6.1, 2H); 3.66 (s, 3H); 3.58 (s, 3H).

TABLE 2

Characterization of compounds prepared according to Scheme 1

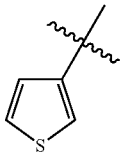

| Cpd | Ex | R | Ar | Name | Characterization |
|---|---|---|---|---|---|
| 7 | 1a | OMe | 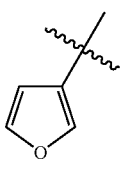 | N-(2-Amino-5-thiophen-3-yl-phenyl)-4-[(3,4-dimethoxy-phenylamino)-methyl]-benzamide | $^1$H NMR: (DMSO) δ (ppm): 9.66 (s, 1H), 7.93 (d, J = 8.4 Hz, 2H), 7.55-7.53 (m, 2H), 7.49-7.43 (m, 3H), 7.39 (dd, J = 4.7, 1.6 Hz, 1H), 7.33 (dd, J = 8.2, 2.2 Hz, 1H), 6.79 (d, J = 8.4 Hz, 1H), 6.64 (d, J = 8.6 Hz, 1H), 6.31 (d, J = 2.7 Hz, 1H), 6.00-5.75 (m, 2H), 5.01 (s, 2H), 4.30 (d, J = 6.1 Hz, 2H), 3.66 (s, 3H), 3.59 (s, 3H). MS: (calc.) 459.2; (obt.) 460.5 (MH)$^+$. |
| 8 | 1b | OMe | 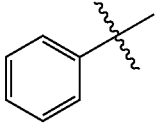 | N-(2-Amino-5-furan-3-yl-phenyl)-4-[(3,4-dimethoxy-phenylamino)-methyl]-benzamide | $^1$H NMR: (DMSO) δ (ppm): 9.65 (s, 1H), 7.94-7.91 (m, 3H), 7.64 (s, 1H), 7.46 (d, J = 7.4 Hz, 2H), 7.36 (s, 1H), 7.21 (d, J = 7.4 Hz, 1H), 6.79-6.76 (m, 2H), 6.64 (d, J = 8.4 Hz, 1H), 6.31 (s, 1H), 6.01-5.97 (m, 2H), 4.96 (s, 2H), 4.30 (d, J = 4.3 Hz, 2H), 3.66 (s, 3H), 3.59 (s, 3H). MS: (calc.) 443.2; (obt.) 444.5 (MH)$^+$. |
| 9 | 1c | OMe | 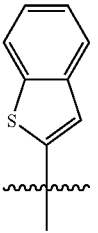 | N-(4-Amino-biphenyl-3-yl)-4-[(3,4-dimethoxy-phenylamino)-methyl]-benzamide | $^1$H NMR: (DMSO) δ (ppm): 9.66 (s, 1H), 7.93 (d, J = 8.0 Hz, 2H), 7.54-7.46 (m, 5H), 7.37 (dd, J = 7.7, 7.7 Hz, 2H), 7.31 (dd, J = 8.4, 2.3 Hz, 1H), 7.22 (dd, J = 7.2, 7.2 Hz, 1H), 6.84 (d, J = 8.4 Hz, 1H), 6.64 (d, J = 8.6 Hx, 1H), 6.31 (d, J = 2.5 Hz, 1H), 6.00-5.97 (m, 2H), 5.08 (s, 2H), 4.30 (d, J = 6.1 Hz, 2H), 3.66 (s, 3H), 3.59 (s, 3H). MS: (calc.) 453.2; (obt.) 454.5 (MH)$^+$. |
| 10 | 1d | OMe | 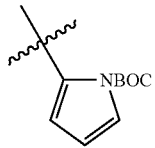 | N-(2-Amino-5-benzo[b]thiophen-2-yl-phenyl)-4-[(3,4-dimethoxy-phenylamino)-methyl]-benzamide | $^1$H NMR: (DMSO) δ (ppm): 9.67 (s, 1H), 7.94 (d, J = 8.4 Hz, 2H), 7.87 (d, J = 8.0 Hz, 1H), 7.73 (d, J = 7.6 Hz, 1H), 7.58 (d, J = 2.3 Hz, 1H), 7.55 (s, 1H), 7.48 (d, J = 8.0 Hz, 2H), 7.41 (dd, J = 8.3, 2.3 Hz, 1H), 7.32 (ddd, J = 7.4, 7.4, 1.2 Hz, 1H), 7.25 (ddd, J = 7.5, 7.5, 1.2 Hz, 1H), 6.83 (d, J = 8.4 Hz, 1H), 6.64 (d, J = 8.6 Hz, 1H), 6.32 (d, J = 2.5 Hz, 1H), 6.00-5.97 (m, 2H), 5.32 (s, 2H), 4.31 (d, J = 6.3 Hz, 2H), 3.66 (s, 3H), 3.59 (s, 3H). MS: (calc.) 509.2; (obt.) 510.5 (MH)$^+$. |
| 11 | 1e | OMe | 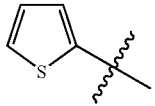 | 2-(4-Amino-3-{4-[(3,4-dimethoxy-phenylamino)-methyl]-benzoylamino}-phenyl)-pyrrole-1-carboxylic acid tert-butyl ester | $^1$H NMR: (DMSO) δ (ppm): 9.60 (s, 1H), 7.89 (d, J = 8.2 Hz, 2H), 7.46 (d, J = 8.2 Hz, 2H), 7.23 (dd, J = 3.3, 1.8 Hz, 1H), 7.14 (d, J = 2.0 Hz, 1H), 6.91 (dd, J = 8.2, 2.2 Hz, 1H), 6.74 (d, J = 8.2 Hz, 1H), 6.64 (d, J = 8.6 Hz, 1H), 6.31 (d, J = 2.5 Hz, 1H), 6.20 (t, J = 6.5 Hz, 1H), 6.08 (dd, J = 3.3, 1.8 Hz, 1H), 5.99-5.96 (m, 2H), 5.00 (s, 2H), 4.29 (d, J = 6.1 Hz, 2H), 3.65 (s, 3H), 3.58 (s, 3H), 1.35 (s, 9H). MS: (calc.) 542.3; (obt.) 543.5 (MH)$^+$. |
| 12 | 1f | F |  | N-(2-Amino-5-thiophen-2-yl-phenyl)-4-[(3-fluoro-4-methoxy-phenylamino)-methyl]-benzamide | $^1$H NMR (400 MHz, DMSO d$_6$): 9.64 (s, 1H); 7.92 (d, 2H, J = 8.2 Hz); 7.45 (d, 2H, J = 8.2 Hz); 7.43 (s, 1H); 7.35 (dd, 1H, J = 1.0, 5.1 Hz); 7.27 (dd, 1H, J = 2.2, 8.4 Hz); 7.21 (dd, 1H, J = 1.2, 3.5 Hz); 7.02 (dd, 1H; J = 3.7, 5.1 Hz); 6.85 (t, 1H, J = 8.9 Hz); 6.78 (d, 1H, J = 8.2 Hz); 6.40 (dd, 1H, J = 2.7, 14.0 Hz); 6.31-6.28 (m, 1H); 6.23 (bt, 1H, J = 6.2 Hz); 5.13 (s, 2H); 4.30 (d, 2H, J = 6.0 Hz), 3.66 (s, 3H). |

Example 2

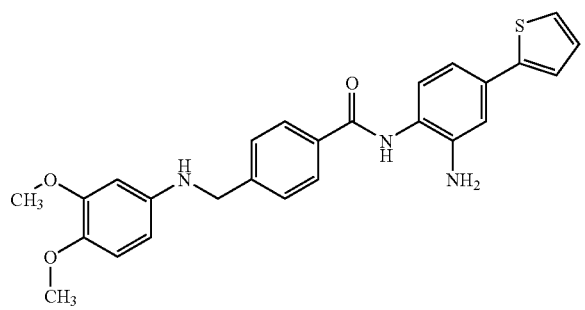

N-[2-amino-4-(2-thienyl)phenyl]-4-{[(3,4-dimethoxyphenyl)amino]methyl}benzamide (16)

Scheme 2

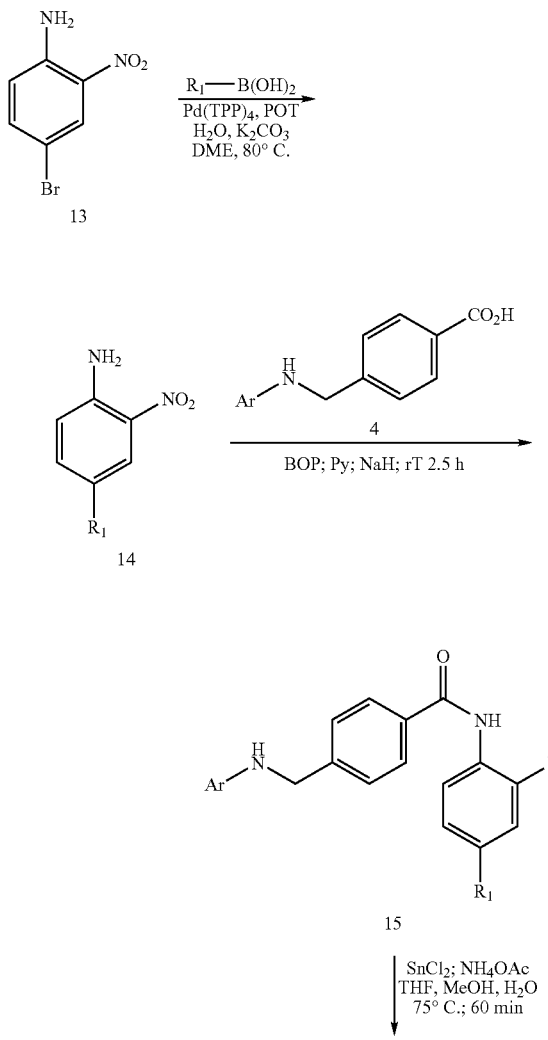

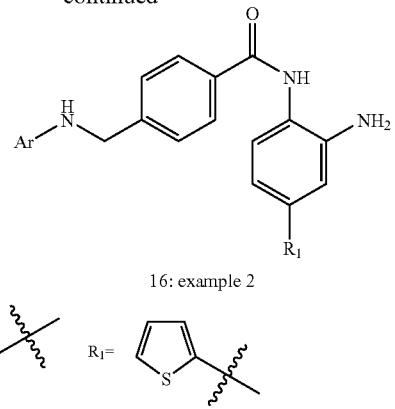

16: example 2

Ar = 3,4-dimethoxyphenyl;   R₁ = 2-thienyl

Step 1. 2-Nitro-4-thiophen-2-yl-phenylamine (14)

Following the same procedure as described in Example 1, Step 2, but substituting compound 1 for compound 13, the title compound 14 was obtained in 89% yield.
¹H NMR: (400.2 MHz, DMSO) δ (ppm): 8.11 (d, J=2.15, 1H); 7.73 (dd, J=2.15, 8.8, 1H); 7.59 (bs, 2H); 7.45 (dd, J=1.1, 5.4, 1H); 7.40 (dd, J=1.1, 3.8, 1H); 7.09 (m, 1H); 7.08 (dd, J=5.6, 8.8, 1H).

Step 2. 4-[(3,4-Dimethoxy-phenylamino)-methyl]-N-(2-nitro-4-thiophen-2-yl-phenyl)-benzamide (15)

Following the same procedure as described in Example 1, Step 3, but substituting compound 3 for compound 14, the title compound was obtained in 68% yield. ¹H NMR: (400.2 MHz, DMSO) δ (ppm): 10.7 (s, 1H); 8.19 (d, J=2.0, 1H); 8.00 (dd, J=1.7, 8.6, 1H); 7.89 (d, J=8.0, 2H); 7.80 (d, J=8.4, 1H); 7.67 (d, J=3.8, 1H); 7.64 (d, J=5.1, 1H); 7.51 (d, J=8.0, 2H); 7.18 (t, J=3.8, 1H); 6.64 (d, J=8.6, 1H); 6.31 (d, J=2.4, 1H); 6.31-5.96 (m, 2H); 4.31 (d, J=6.1, 2H); 3.66 (s, 3H); 3.59 (s, 3H).

Step 3. N-(2-Amino-4-thiophen-2-yl-phenyl)-4-[(3,4-dimethoxy-phenylamino)-methyl]-benzamide (16)

Following the same procedure as described in Example 1, Step 4, but substituting compound 5 for compound 15, the title compound was obtained in 47% yield. ¹H NMR: (400.2 MHz, DMSO) δ (ppm): 9.59 (s, 1H); 7.90 (d, J=8.0, 2H); 7.46 (d, J=8.0, 2H); 7.45 (d, J=1.1, 1H); 7.34 (dd, J=1.1, 3.5, 1H); 7.20 (d, J=8.1, 1H); 7.09 (dd, J=3.5, 4.9, 1H); 6.89 (dd, J=2.2, 8.1, 1H); 6.64 (d, J=8.6, 1H); 6.32 (d, J=2.5, 1H); 6.00-5.97 (m, 2H); 5.07 (bs, 2H); 4.30 (d, J=6.1, 2H); 3.66 (s, 3H); 3.59 (s, 3H).

Example 3

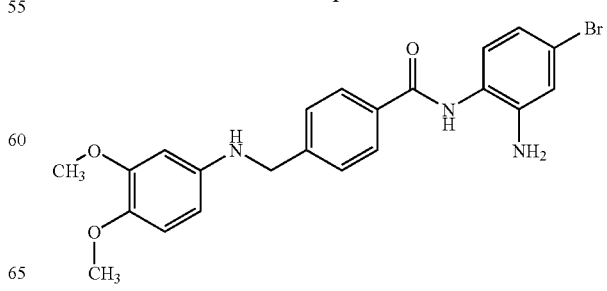

N-4-(2-amino-4-bromophenyl)-4-{[(3,4-dimethoxyphenyl)amino]methyl}benzamide (18)

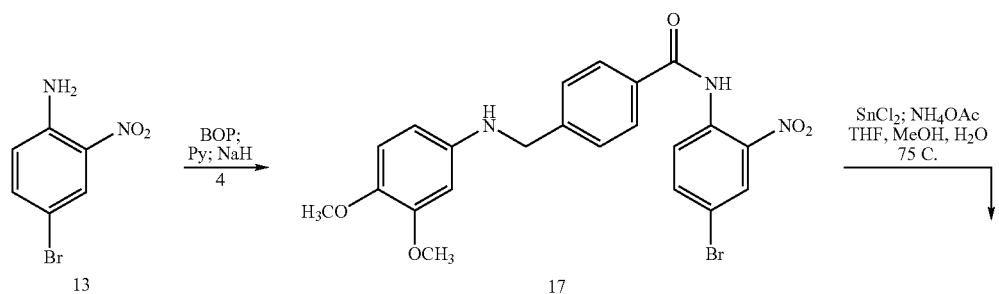

Scheme 2a $R_1 = Br$

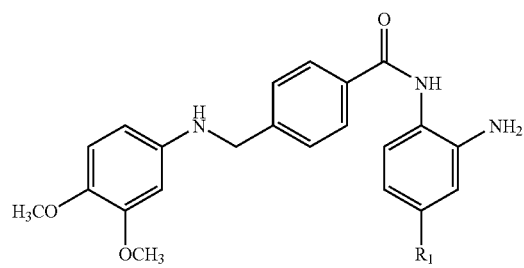

18: example 3

N-(4-Bromo-2-nitro-phenyl)-4-[(3,4-dimethoxyphenylamino)-methyl]-benzamide (17)

Following the same procedure as described in Example 2, Step 2, but substituting compound 14 for compound 13, the compound 17 was obtained in 92% yield. $^1$H NMR: (400.2 MHz, DMSO) δ (ppm): 10.72 (s, 1H); 8.17 (d, J=2.0, 1H); 7.96 (dd, J=2.0, 8.6, 1H); 7.86 (d, J=7.9, 2H); 7.69 (d, J=8.6, 1H); 7.51 (d, J=7.9, 2H); 6.63 (d, J=8.4, 1H); 6.32 (d, J=2.0, 1H); 6.01-5.96 (m, 2H); 4.31 (d, J=5.9, 2H); 3.65 (s, 3H); 3.58 (s, 3H).

N-(2-Amino-4-bromo-phenyl)-4-[(3,4-dimethoxyphenylamino)-methyl]-benzamide (18)

Following the same procedures as described in Example 2, Steps 3, but substituting compound 15 for compound 17, the compound 18 was obtained in 46% yield.

$^1$H NMR, (400.2 MHz, DMSO) δ (ppm): 9.55 (s, 1H), 7.89 (d, J=8.2 Hz, 2H), 7.45 (d, J=8.4 Hz, 2H), 7.07 (d, J=8.4 Hz, 1H), 6.92 (d, J=2.3 Hz, 1H), 6.69 (dd, J=8.4, 2.3 Hz, 1H), 6.63 (d, J=8.4 Hz, 1H), 6.30 (d, J=2.5 Hz, 1H), 6.00-5.96 (m, 2H), 5.22 (s, 2H), 4.29 (d, J=6.3 Hz, 2H), 3.65 (s, 3H), 3.58 (s, 3H). MS: (calc.) 455.1; (obt.) 456.4, 458.4 (MH)$^+$.

Example 4

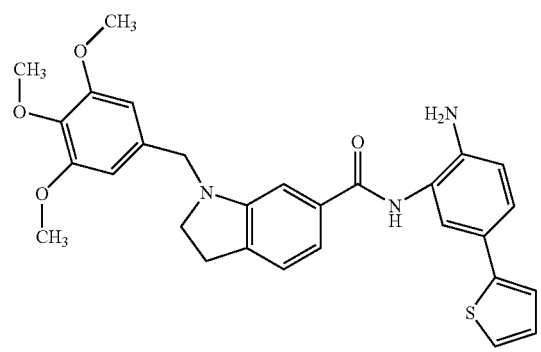

N-[2-amino-5-(2-thienyl)phenyl]-1-(3,4,5-tri-
methoxybenzyl)indoline-6-carboxamide (23)

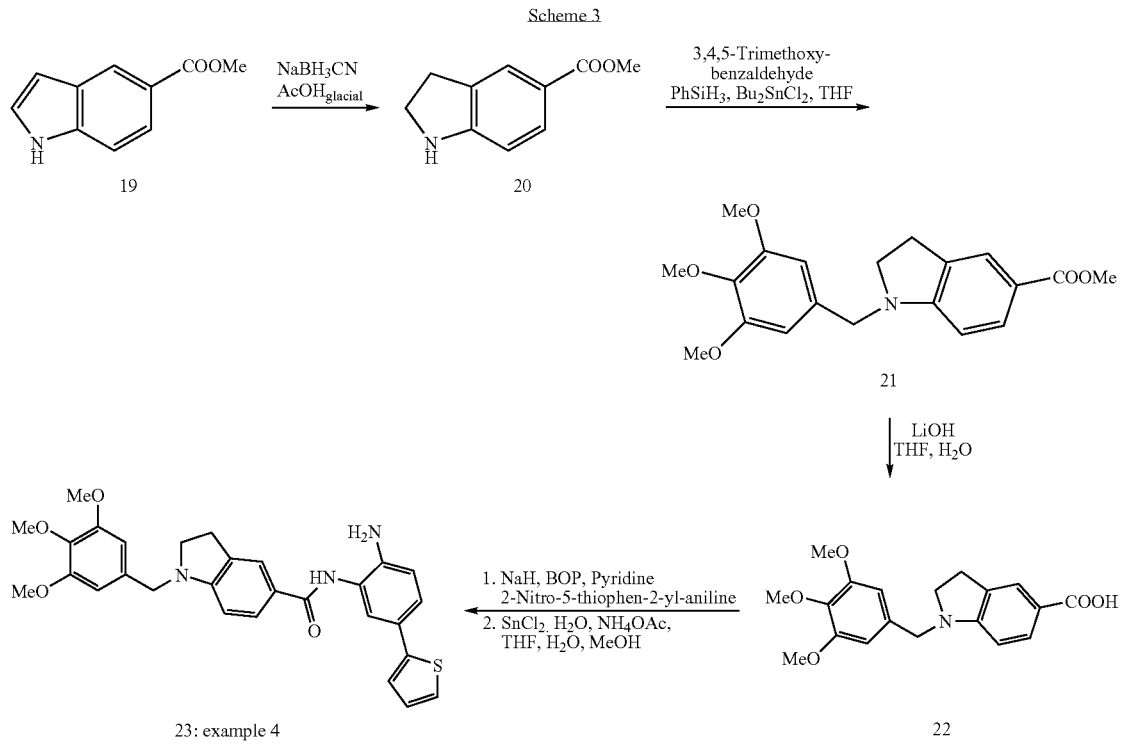

Step 1: Methyl 2,3-Dihydro-1H-indole-5-carboxylate (20)

To a cold solution of methyl indole-5-carboxylate (2 g, 11.4 mmol) in glacial acetic acid at 0° C. (15 ml) sodium cyanoborohydride (1.075 g, 17.1 mmol) was slowly added. The mixture was allowed to warm-up and stirred at room temperature for one more hour, cooled again to 0° C. and quenched with H$_2$O. The pH of the resultant solution was adjusted to the value of 12 by adding aqueous NaOH, extracted with DCM, washed with brine and dried over MgSO$_4$. The dried extract was concentrated in vacuum and purified by flash chromatography (eluent 30% EtOAc in hexane) to give the title compound 20 (1.62 g, 80%) as a beige solid. $^1$H-NMR (DMSO) δ: 2.94 (t, J=8.6 Hz, 2H); 3.51 (dt, J=1.2, 8.6 Hz, 2H); 3.71 (s, 3H); 6.42 (d, J=8.0 Hz, 2H); 7.54 (m, 2H).

Step 2: Methyl 1-(3,4,5-Trimethoxy-benzyl)-2,3-dihydro-1H-indole-5-carboxylate (21)

To a solution of 20 (300 mg, 1.69 mmol), 3,4,5-trimethoxy-benzaldehyde (365 mg, 1.86 mmol) and dibutyltin dichloride (51 mg, 0.17 mmol) in THF (8 mL) was added phenylsilane (229 μl, 1.86 mmol). The mixture was stirred overnight at room temperature under nitrogen. Additional aldehyde and phenylsilane were added and the stirring continued until starting material was consumed. THF was evaporated in vacuum and the residue was purified by flash chromatography (eluent 20% EtOAc in hexane). The compound was further purified by re-crystallization in a mixture EtOAc/hexane and finally by a second flash chromatography (eluent 20% EtOAc in hexane) to give the title compound 21 (428 mg, 71%) as a white solid. $^1$H-NMR (DMSO) δ: 2.96 (t, J=8.4 Hz, 2H); 3.45 (t, J=8.7 Hz, 2H); 3.61 (s, 3H); 3.71 (s, 6H); 3.72 (s, 3H); 4.30 (s, 2H); 6.59 (s, 2H); 6.61 (d, J=8.4 Hz, 1H), 7.54 (d, J=1.6 Hz, 1H); 7.63 (dd, J=1.8, 8.4 Hz, 1H).

Step 3: 1-(3,4,5-Trimethoxy-benzyl)-2,3-dihydro-1H-indole-S-carboxylic acid (22)

A solution of LiOH×H$_2$O (75 mg, 1.78 mmol) in H$_2$O (5 ml) was added to a solution of ester 21 (426 mg, 1.19 mmol) in THF (5 ml). The mixture was stirred at room temperature overnight. THF was removed in vacuum and the remained aqueous solution was acidified to pH 1 using 1N HCl. A precipitate formed which was collected by filtration, washed with H$_2$O and dried to give the title compound 22 as a white solid, (320 mg, 78%). $^1$H-NMR (DMSO) δ: 2.96 (t, J=8.6 Hz, 2H); 3.43 (t, J=8.6 Hz, 2H); 3.62 (s, 3H); 3.72 (s, 6H); 4.29 (s, 2H); 6.58 (s, 1H); 6.60 (s, 2H); 7.53 (s, 1H); 7.61 (d, J=8.8 Hz, 1H).

Steps 4 and 5. 1-(3,4,5-Trimethoxy-benzyl)-2,3-dihydro-1H-indole-6-carboxylic acid (2-amino-5-(thiophen-2-yl-phenyl)-amide (23)

Following the procedures described in Example 1, steps 3 and 4, the title compound 23 was obtained as a yellow solid (294 mg, 41%). $^1$H NMR: (DMSO) δ (ppm): 9.37 (s, 1H), 7.73 (d, J=8.4 Hz, 1H), 7.70 (s, 1H), 7.44 (d, J=2.0 Hz, 1H), 7.33 (d, J=5.1 Hz, 1H), 7.25 (dd, J=8.2, 2.0 Hz, 1H), 7.22 (d, J=3.3 Hz, 1H), 7.03 (dd, J=4.2, 4.2 Hz, 1H), 6.78 (d, J=8.4 Hz, 1H), 6.66 (d, J=8.2 Hz, 1H), 6.64 (s, 2H), 5.06 (s, 2H), 4.32 (s, 2H), 3.75 (s, 6H), 3.64 (s, 3H), 3.45 (t, J=8.3 Hz, 2H), 3.00 (t, J=8.5 Hz, 2H). MS: (calc.) 515.2; (obt.) 513.7 (MH)+.

Example 5

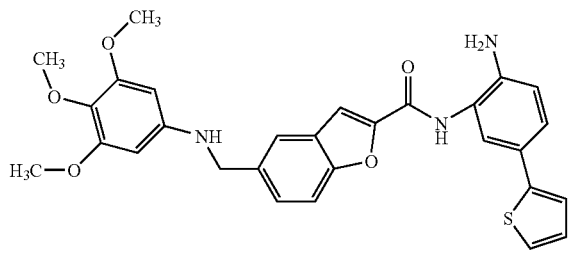

N-[2-amino-5-(2-thienyl)phenyl]-5-{[(3,4,5-trimethoxyphenyl)amino]methyl}-1-benzofuran-2-carboxamide (29)

Step 1: Ethyl 5-Methyl-benzofuran-2-carboxylate (25)

To a stirred suspension of 2-hydroxy-5-methylbenzaldehyde (5 g, 36.7 mmol) and $K_2CO_3$ (12.7 g, 91.8 mmol) in DMF (30 mL), ethyl bromoacetate (4.07 ml, 36.7 mmol) was added drop-wise. This mixture was allowed to stir for two hours under nitrogen at room temperature, and was then heated to 80° C. and stirred overnight. The reaction was quenched with $H_2O$ to form a precipitate which was collected by filtration and purified by flash chromatography (eluent 5% EtOAc in hexane) to give the title compound 25 (2.30 g, 31%). $^1$H-NMR (CDCl$_3$) δ: 1.45 (t, J=7.0 Hz, 3H); 2.47 (s, 3H); 4.45 (q, J=7.0 Hz, 2H); 7.26 (m, 1H); 7.46 (m, 3H).

Steps 2-3.
5-Hydroxymethyl-benzofuran-2-carboxylic acid ethyl ester (26)

A mixture of the ester 25 (2.26 g, 11.1 mmol), N-bromosuccinimide (2.37 g, 13.3 mmol) and VAZO (271 mg, 1.11 mmol) was refluxed overnight in CCl$_4$ (50 mL) under nitro-

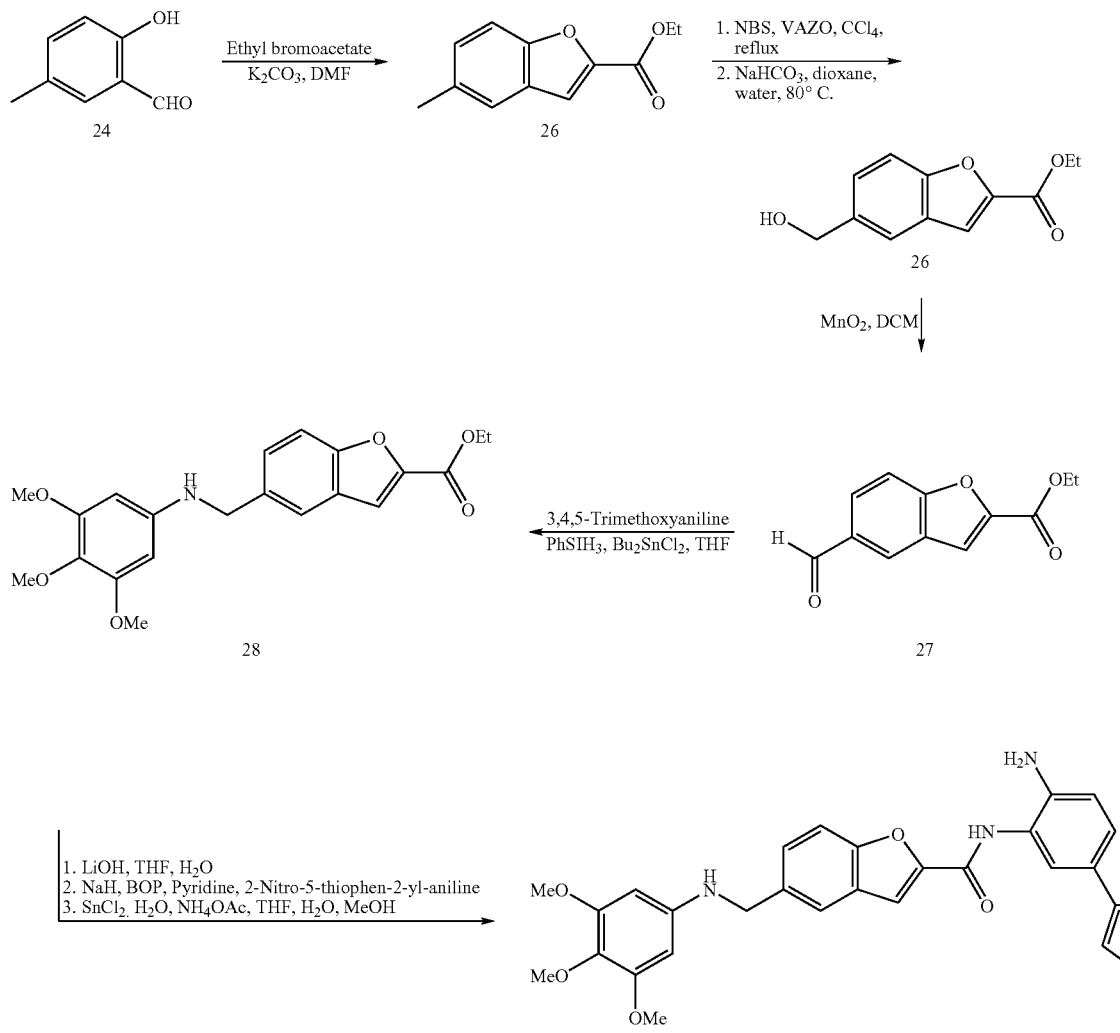

Scheme 4

29: example 5 gen. The reaction mixture was cooled to the room temperature, diluted with dichloromethane and washed with water. The organic layer was dried over anhydrous MgSO₄ and concentrated in vacuum. The residue was purified by flash chromatography (eluent 5% EtOAc in hexane) to give ethyl 5-bromomethyl-benzofuran-2-carboxylate. This compound was dissolved in dioxane (20 ml) and a solution of NaHCO₃ (1.76 g, 20.9 mmol) in water (20 ml) was added. The reaction was stirred at 80° C. during 16 h. The solvent was evaporated and the product was dissolved in EtOAc and washed with brine. The organic layer was dried over anhydrous MgSO₄ and concentrated in vacuum. The residue was purified by flash chromatography (eluent 20-40% EtOAc in hexane to give the title compound 26 (2.55 g, 61%) as a white solid. ¹H-NMR (DMSO) δ: 7.74 (d, J=1.0 Hz, 1H), 7.71-7.70 (m, 1H), 7.65 (d, J=8.6 Hz, 1H), 7.44 (dd, J=8.6, 1.8 Hz, 1H), 5.31 (t, J=5.8 Hz, 1H), 4.59 (d, J=5.7 Hz, 2H), 4.35 (q, J=7.1 Hz, 2H); 1.34 (t, J=7.0, 3H).

Step 4: Ethyl 5-Formyl-benzofuran-2-carboxylate (27)

To a solution of the compound 26 (2.53 g, 11.49 mmol) in DCM (70 ml) was added MnO₂ (9.99 g, 114.9 mmol). The reaction mixture was stirred at room temperature for 16 h and then filtered through a celite pad. The filtrate was concentrated in vacuum to give the title compound 27 (2.19 g, 87%) as a white solid. ¹H-NMR (DMSO) δ: 10.07 (s, 1H), 8.40-8.39 (m, 1H), 8.03 (dd, J=8.6, 1.6 Hz, 1H), 7.93-7.92 (m, 2H), 4.38 (q, J=7.1 Hz, 2H); 1.35 (t, J=7.0, 3H).

Step 5: 5-[(3,4,5-Trimethoxy-phenylamino)-methyl]-benzofuran-2-carboxylic acid ethyl ester (28)

Following the same procedure as described in Example 4, Step 2, but substituting compound 20 and 3,4,5-trimethoxy-benzaldehyde for 3,4,5-trimethoxyaniline and compound 27, the title compound was obtained in 99% yield. ¹H NMR: (DMSO) δ (ppm): 7.75 (d, J=1.0 Hz, 1H), 7.73 (d, J=1.0 Hz, 1H), 7.66 (d, J=8.6 Hz, 1H), 7.51 (dd, J=8.6, 1.8 Hz, 1H), 6.11 (t, J=6.1 Hz, 1H), 5.89 (s, 2H), 4.37-4.32 (m, 4H), 3.63 (s, 6H), 3.49 (s, 3H), 1.33 (t, J=7.0, 3H).

Steps 6-8: 5-[(3,4,5-Trimethoxy-phenylamino)-methyl]-benzofuran-2-carboxylic acid (2-amino-5-(thiophen-2-yl-phenyl)-amide (29)

Following the same procedure as described in Example 4 step 3 and then the procedures described in Example 1, steps 3 and 4, the title compound 29 was obtained as an orange solid in 73% yield. ¹H NMR: (DMSO) δ (ppm): 9.92 (s, 1H), 7.77 (d, J=1.0 Hz, 1H), 7.70 (s, 1H), 7.65 (d, J=8.6 Hz, 1H), 7.49 (dd, J=8.6, 1.8 Hz, 1H), 7.46 (d, J=2.2 Hz, 1H), 7.34 (dd, J=5.1, 1.0 Hz, 1H), 7.30 (dd, J=8.2, 2.2 Hz, 1H), 7.23 (dd, J=3.5, 1.2 Hz, 1H), 7.04 (dd, J=5.1, 3.5 Hz, 1H), 6.80 (d, J=8.4 Hz, 1H), 6.12 (t, J=5.8 Hz, 1H), 5.91 (s, 2H), 4.35 (d, J=5.9 Hz, 2H), 3.64 (s, 6H), 3.50 (s, 3H). MS: (calc.) 529.2; (obt.) 530.7 (MH)⁺.

Example 6

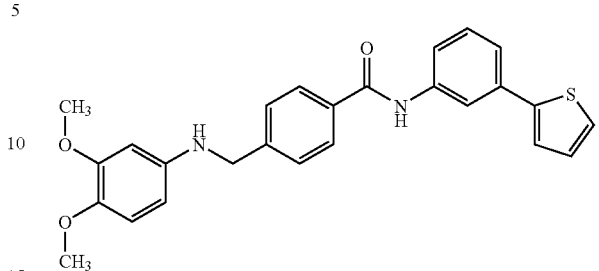

4-{[(3,4-dimethoxyphenyl)amino]methyl}-N-[3-(2-thienyl)phenyl]benzamide (32)

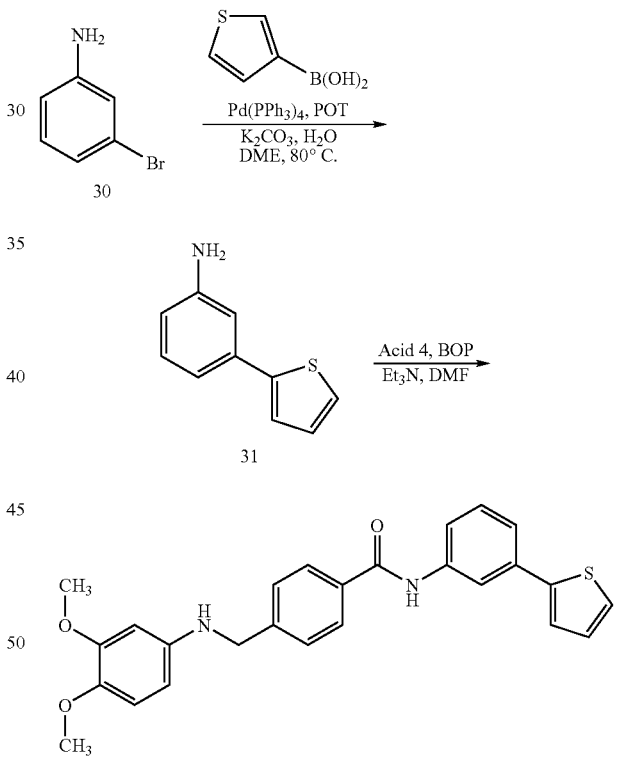

32: example 6

Step 1: 3-Thiophen-2-yl-phenylamine (31)

Following the same procedure as described in Example 1 step 2, but substituting compound 2 for compound 30, the title compound 31 was obtained in 50% yield. ¹H NMR: (DMSO) δ (ppm): 7.45 (dd, J=5.1, 1.2 Hz, 1H), 7.32 (dd, J=3.7, 1.2 Hz, 1H), 7.07 (dd, J=3.7, 1.2 Hz, 1H), 7.02 (dd, J=7.7, 7.7 Hz, 1H), 6.81 (dd, J=1.9, 1.9 Hz, 1H), 6.78 (ddd, J=7.4, 1.6, 0.8 Hz, 1H), 6.48 (ddd, J=8.0, 2.3, 1.0 Hz, 1H), 5.20 (s, 2H). MS: (calc.) 176.4; (obt.) 175.1 (MH)⁺.

Step 2: 4-[(3,4-Dimethoxy-phenylamino)-methyl]-N-(3-thiophen-2-yl-phenyl)-benzamide (32)

To a stirred solution of 31 (122 mg, 0.696 mmol), acid 4 (182 mg, 0.633 mmol) and BOP (308 mg, 0.696 mmol) in DMF (4 ml) was added $B_3N$ (265 μl, 1.90 mmol). The reaction was stirred 3 h at room temperature under nitrogen, quenched with $H_2O$ and evaporated. The residue was extracted with ethyl acetate, washed with saturated solutions of $NH_4Cl$, $NaHCO_3$ and brine. The organic layer was dried over anhydrous $MgSO_4$ and concentrated in vacuum to form a material which was purified by flash chromatography (eluent 40% EtOAc in hexane) to give the title compound 32 (70 mg, 25%) as a yellow solid. $^1$H NMR: (DMSO) δ (ppm): 10.25 (s, 1H), 8.09-8.08 (m, 1H), 7.73 (ddd, J=7.6, 3.7, 3.7 Hz, 1H), 7.54 (dd, J=5.1, 1.0 Hz, 1H), 7.49 (d, J=8.2 Hz, 2H), 7.45 (dd, J=3.7, 1.2 Hz, 1H), 7.42-7.32 (m, 2H), 7.13 (dd, J=5.1, 3.7 Hz, 1H), 6.64 (d, J=8.6 Hz, 1H), 6.31 (d, J=2.5 Hz, 1H), 6.00-5.97 (m, 2H), 4.31 (d, J=6.1 Hz, 2H), 3.65 (s, 3H), 3.59 (s, 3H). MS: (calc), 444.2; (obt.) 445.5 (MH)$^+$.

TABLE 3

Characterization of compounds prepared according to Scheme 5

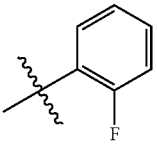

| Cpd | Example | W | Name | Characterization |
|---|---|---|---|---|
| 33 | 6a | 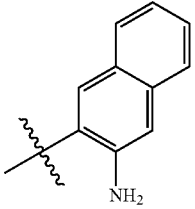 | 4-[(3,4-Dimethoxy-phenylamino)-methyl]-N-(2-fluoro-phenyl)-benzamide | $^1$H NMR (400 MHz, DMSO d$_6$): 10.07 (s, 1H); 7.98 (d, 2H, J = 8.3 Hz); 7.64 (t, 1H, J = 7.5 Hz); 7.55 (d, 2H, J = 8.0 Hz); 7.35-7.27 (m, 3H); 6.71 (d, 1H, J = 8.8 Hz); 6.38 (s, 1H); 6.05 (d, 1H, J = 8.8 Hz); 5.80 (d, 1H, J = 3.5 Hz); 4.36 (s, 2H), 3.71 (s, 3H); 3.65 (s, 3H). |
| 34 | 6b | 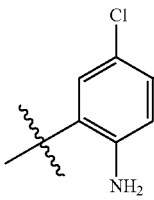 | N-(3-Amino-naphthalen-2-yl)-4-[(3,4-dimethoxy-phenylamino)-methyl]-benzamide | $^1$H NMR (400 MHz, DMSO d$_6$): 9.71 (s, 1H); 7.94 (d, 2H, J = 8.2 Hz); 7.82 (s, 1H); 7.63 (d, 1H, J = 7.6 Hz); 7.52 (d, 1H; J = 7.82 Hz); 7.48 (d, 2H, J = 8.4 Hz); 7.28-7.24 (m, 1H); 7.14-7.10 (m, 1H); 7.05 (s, 1H); 6.64 (d, 1H, J = 8.6 Hz); 6.32 (d, 1H, J = 2.5 Hz); 6.03-5.97 (m, 2H); 5.24 (s, 2H); 4.30 (d, 2H, J = 6.26 Hz), 3.65 (s, 3H); 3.58 (s, 3H). |
| 35 | 6c | 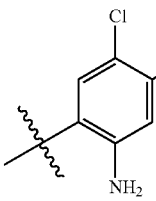 | N-(2-Amino-5-chloro-4-fluoro-phenyl)-4-[(3,4-dimethoxy-phenylamino)-methyl]-benzamide | $^1$H NMR (400 MHz, DMSO d$_6$): 9.53 (s, 1H); 7.88 (d, 2H, J = 8.2 Hz); 7.45 (d, 2H, J = 8.4 Hz); 7.27 (d, 1H, J = 8.0 Hz); 6.67 (d, 1H, J = 11.5 Hz); 6.30 (d, 1H, J = 2.5 Hz); 5.98-5.95 (m, 2H); 5.40 (s, 2H); 4.29 (d, 2H, J = 6.4 Hz), 3.64 (s, 3H); 3.58 (s, 3H). |
| 36 | 6d | | N-(2-Amino-4,5-dichloro-phenyl)-4-[(3,4-dimethoxy-phenylamino)-methyl]-benzamide | $^1$H NMR (400 MHz, DMSO d$_6$): 9.53 (s, 1H); 7.88 (d, 2H, J = 8.0 Hz); 7.44 (d, 2H, J = 8.2 Hz); 7.27 (d, 1H, J = 8.0 Hz); 6.63 (d, 1H, J = 8.4 Hz); 6.30 (d, 1H, J = 2.0 Hz); 5.60-5.96 (m, 2H); 5.40 (s, 2H); 4.27 (d, 2H, J = 6.0 Hz), 3.65 (s, 3H); 3.57 (s, 3H). |

Example 7

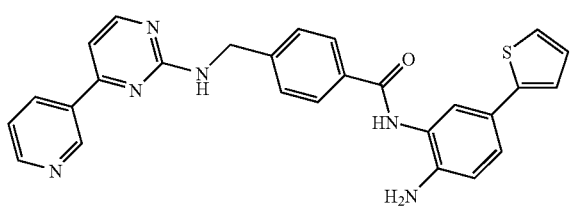

N-[2-amino-5-(2-thienyl)phenyl]-4-{[(4-pyridin-3-ylpyrimidin-2-yl)amino]methyl}benzamide (43)

diethyl ether were added to give a brown suspension. The solid was separated by filtration, rinsed with Et$_2$O and dried to afford the title compound 38 (36.97 g, 85% yield) as an orange crystalline solid. $^1$H NMR (400 MHz, CDCl$_3$) δ(ppm): 9.08 (d, J=2.2 Hz, 1H), 8.66 (dd, J=4.9, 1.4 Hz, 1H), 8.26-8.23 (m, 1H), 7.85 (d, J=12.1 Hz, 1H), 7.40 (dd, J=7.8, 4.9 Hz, 1H), 5.68 (d, J=12.1 Hz, 1H), 3.20 (s, 3H), 2.97 (s, 3H).

Step 2: Methyl (4-guanidinomethyl)benzoate (40)

To a stirred suspension of methyl 4-aminomethyl-benzoate hydrochloride (39, 15.7 g, 77.8 mmol) and diisopropylethylamine (29.5 ml, 171.2 mmol) in DMF (85.6 ml) at room temperature under nitrogen was added pyrazole-1-carboxa- Scheme 6

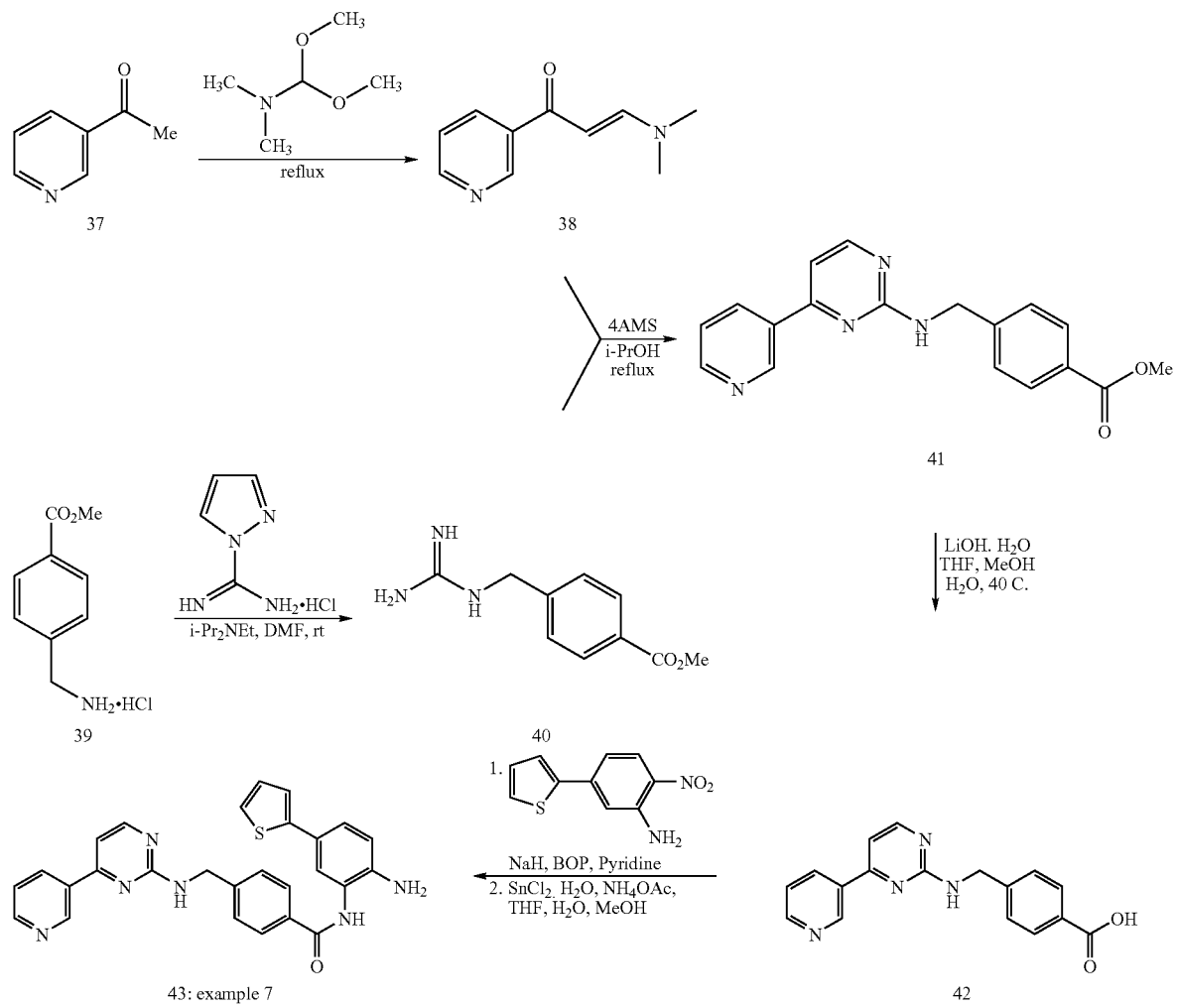

Step 1: 3-Dimethylamino-1-pyridin-3-yl-propenone (38)

A stirred solution of 3-acetylpyridine (37, 30.0 g, 247.6 mmol) and N,N-dimethylformamide dimethylacetal (65.8 ml, 495.2 mmol) was refluxed under nitrogen for 4 h. The reaction mixture was concentrated to dryness and 50 ml of midine hydrochloride (12.55 g, 85.6 mmol). After 4 h the reaction mixture as a clear solution was concentrated to dryness under vacuum and saturated aqueous solution of NaHCO$_3$ (35 ml) was added to give a suspension. The solid was separated by filtration and washed with cold water. The mother liquor was concentrated to produce additional amount of a solid material which was also collected by filtration. Both solids were combined, triturated with H₂O (50 ml), filtered off, washed with cold H₂O and diethyl ether, and dried to afford the title compound 40 (12.32 g, 77% yield) as a white crystalline solid. ¹H NMR: (400 MHz, DMSO-d₆) δ (ppm): 9.20-8.00 (m, 4H), AB system (δ$_A$=7.91, δ$_B$=7.39, J$_{AB}$=8.2 Hz, 4H), 4.39 (bs, 2H), 3.83 (s, 3H).

Step 3: Methyl 4-[(4-pyridin-3-yl-pyrimidin-2-ylamino)-methyl]-benzoate (41)

To a stirred suspension of compounds 38 (0.394 g, 1.9 mmol) and 40 (0.402 g, 2.3 mmol) in isopropyl alcohol (3.8 ml) at room temperature under nitrogen were added molecular sieves (0.2 g, 4, powder). The reaction mixture was refluxed for 5 h. MeOH (50 ml) was added, and the reaction mixture was brought to reflux again. A cloudy solution formed which was filtered through a celite pad, filtrate was concentrated to dryness and the residue was triturated with ethyl acetate (3 ml), filtered off and dried to afford the title compound 41 (0.317 g, 52%) as a white crystalline solid. ¹H NMR (400 MHz, DMSO-d₆) δ (ppm): 9.17 (bs, 1H), 8.64 (m, 1H), 8.38 (m, 2H), 7.98 (t, J=6.3 Hz, 1H), 7.88 (m, 2H), 7.48 (m, 3H), 7.24 (d, J=5.1 Hz, 1H), 4.64 (d, J=6.1 Hz, 2H), 3.81 (s, 3H).

Step 4: 4-[(4-Pyridin-3-yl-pyrimidin-2-ylamino)-methyl]-benzoic acid (42)

To a stirred solution of 41 (3.68 g, 11.5 mmol) in a mixture of THF (23 ml) and MeOH (23 ml) was added a solution of LiOH—H₂O (1.06 g, 25.3 mmol) in water (11.5 ml) at room temperature. The reaction mixture was stirred at 40° C. overnight, cooled to the room temperature, and an aqueous solution of HCl (12.8 ml, 2N) was added (pH~4-5). The mixture was concentrated to dryness; the formed solid was triturated with water, filtered off, washed with minimum H₂O and dried to afford the title compound 42 (3.44 g, 95%) as a white solid. ¹H NMR (400 MHz, DMSO-d₆) δ(ppm): 12.83 (bs, 1H), 9.23 (bs, 1H), 8.73-8.66 (m, 1H) 8.46-8.36 [m, included at 8.42 (d, J=5.1 Hz), 2H], 8.02 (t, J=6.3 Hz, 1H), 7.91 (d, J=8.2 Hz, 2H), 7.60-7.40 (m, 3H), 7.28 (d, J=5.1 Hz, 1H), 4.67 (d, J=6.3 Hz, 2H).

Step 5: N-(2-Amino-5-(thiophen-2-yl-phenyl)-4-[(4-pyridin-3-yl-pyrimidin-2-ylamino)-methyl]-benzamide (43)

Following the same procedure as described in Example 1, Steps 34, but substituting compound 4 for compound 42, the title compound was obtained in 62% yield.

¹H NMR (400 MHz, DMSO-d₆), δ (ppm): 9.65 (s, 1H), 9.22 (s, 1H), 8.66 (d, J=3.7 Hz, 1H), 8.39 (d, J=5.3 Hz, 2H), 8.01 (t, J=6.5 Hz, 1H), 7.93 (d, J=8.4 Hz, 2H), 7.53-7.44 (m, 4H), 7.32 (dd, J=5.1, 1.2 Hz, 1H), 7.28-7.24 (m, 2H), 7.21 (dd, J=3.7, 1.2 Hz, 1H), 6.02 (dd, J=5.1, 3.5 Hz, 1H), 6.78 (d, J=8.4 Hz, 1H), 5.13 (s, 2H), 4.65 (d, J=5.7, 2H). MS: (calc.) 478.2; (obt.) 479.5 (MH)⁺.

Example 8

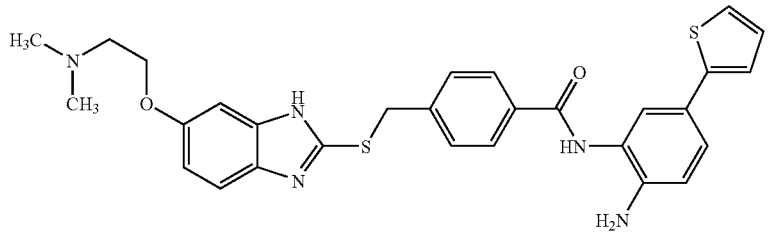

4-[({6-[2-(dimethylamino)ethoxy]-1H-benzimidazol-2-yl}thio)methyl]-N-[2-nitro-5-(2-thienyl)phenyl]benzamide (50)

Scheme 7

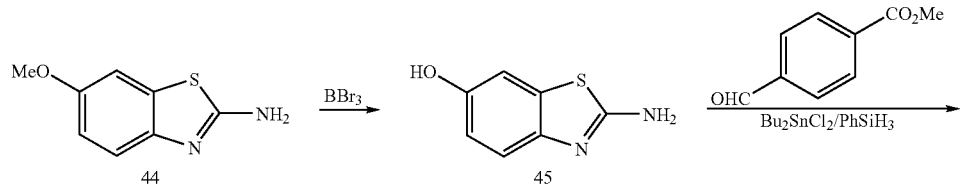

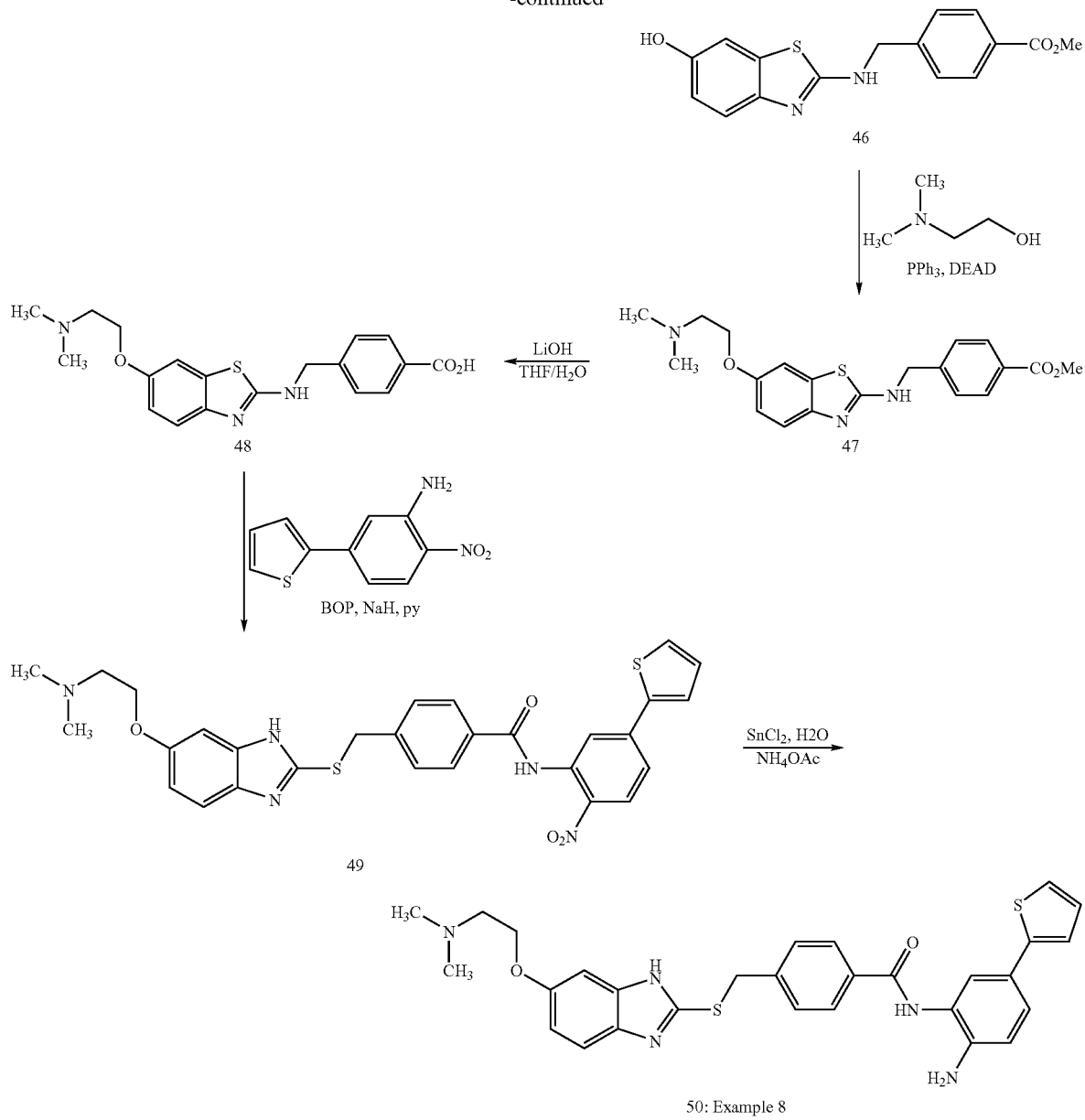

Step 1: 2-Amino-benzothiazol-6-ol (45)

The title compound 45 was obtained following the same procedure described in U.S. patent application Ser. No. 10/242,304, which is incorporated by reference in its entirety. The yield of the title compound was 49% yield. $^1$H NMR: (CD$_3$OD) δ(ppm): 7.93 (d, J=8.5 Hz, 2H), 7.50 (d, J=8.5 Hz, 2H), 7.31 (bs, 1H), 6.86 (bs, 1H), 6.76 (dd, J=8.8, 2.47 Hz, 1H), 4.49 (s, 2H), 3.94 (s, 3H).

Step 2: 4-[(6-Hydroxy-benzothiazol-2-ylamino)-methyl]-benzoic acid methyl ester (46)

The title compound 46 was obtained following the same procedure as for the reductive amination described in U.S. patent application Ser. No. 10/242,304, which is incorporated by reference in its entirety. The yield of the title compound was 92% yield. $^1$H NMR: (Acetone-d$_6$) δ(ppm): 8.06 (t, J=7.9 Hz, 2H), 7.65 (d, J=8.4 Hz, 2H), 7.36 (d, J=8.8 Hz, 1H), 7.21 (d, J=2.2 Hz, 1H), 6.88 (dd, J=8.8, 2.6 Hz, 1H), 4.87 (s, 2H), 3.95 (s, 3H). m/z: 315.2 (MH$^+$).

Step 3: 4-{[6-(2-Dimethylamino-ethoxy)-benzothiazol-2-ylamino]-methyl}-benzoic acid methyl ester (47)

The title compound 47 was obtained following the same procedure as for the Mitsunobu reaction described in U.S. patent application Ser. No. 10/242,304, which is incorporated by reference in its entirety. The yield of the title compound was 61% yield). $^1$H NMR: (CD$_3$OD) δ(ppm): 7.98 (d, J=8.4 Hz, 2H), 7.48 (d, J=8.0 Hz, 2H), 7.31 (d, J=8.8 Hz, 1H), 7.22 (d, J=2.5 Hz, 1H), 6.89 (dd, J=8.8, 2.7 Hz, 1H), 4.68 (s, 2H), 4.09 (t, J=5.5 Hz, 2H), 3.88 (s, 3H), 2.77 (t, J=5.5 Hz, 2H), 2.35 (s, 6H). m/z: 386.4 (MH+).

Step 4: 4-{[6-(2-Dimethylamino-ethoxy)-benzothiazol-2-ylamino]-methyl}-benzoic acid (48)

The title compound 48 was obtained following the same procedure as for the ester hydrolysis described in U.S. patent application Ser. No. 10/242,304, which is incorporated by reference in its entirety. The yield of the title compound was 63% yield. ¹H NMR: (CD₃OD) δ(ppm): 8.43 (bs, 1H), 7.92 (d, J=8.0 Hz, 2H), 7.48 (d, J=8.2 Hz, 2H), 7.38 (s, 1H), 7.30 (d, J=8.4 Hz, 1H), 6.87 (d, J=9.2 Hz, 1H), 4.66 (d, J=5.1 Hz, 2H), 4.17 (t, J=4.7 Hz, 2H), 3.06 (bs, 2H), 2.54 (s, 6H). m/z: 372.4 (MH+).

Step 5: 4-[6-(2-Dimethylamino-ethoxy)-1H-benzoimidazol-2-ylsulfanylmethyl]-N-(2-nitro-5-thiophen-2-yl-phenyl)-benzamide (49)

The title compound 49 was obtained following the same procedure as Example 1, step 3, but substituting compound 4 for compound 48 in 83% yield. ¹H NMR: (DMSO-d₆) δ(ppm): 10.92 (bs, 1H), 8.26 (bs, 1H), 8.16 (s, 1H), 8.05 (d, J=9.0 Hz, 1H), 7.82 (d, J=7.4 Hz, 2H), 7.74-7.67 (m, 2H), 7.31-7.21 (m, 5H), 6.79 (d, J=8.4 Hz, 1H), 4.54 (d, J=4.7 Hz, 2H), 3.99 (bs, 2H), 2.59 (t, J=5.9 Hz, 2H), 2.20 (s, 6H).

Step 6: N-[2-amino-5-(2-thienyl)phenyl]-4-[({6-[2-(dimethylamino)ethoxy]-1H-benzimidazol-2-yl}thio)methyl]benzamide N-(2-Amino-5-(thiophen-2-yl-phenyl)-4-{[6-{2-dimethylamino-ethoxy)-benzothiazol-2-ylamino]-methyl}-benzamide (50)

The title compound 50 was obtained following the same procedures as Example 1, step 4, but substituting compound 5 for compound 49 in 7% yield. ¹H NMR: (DMSCkl₆) d (ppm): 9.68 (s, 1H), 8.39 (bs, 1H), 7.95 (d, J=7.4 Hz, 2H), 7.47 (d, J=8.4 Hz, 2H), 7.44 (s, 1H), 7.32 (s, 1H), 7.27-7.21 (m, 3H), 7.02 (s, 1H), 6.80 (t, J=9.8 Hz, 2H), 5.14 (s, 2H), 5.63 (d, J=4.5 Hz, 2H), 4.05 (bs, 2H), 2.76 (bs, 2H), 2.32 (s, 6H). m/z: 544.5 (MH+).

Example 9

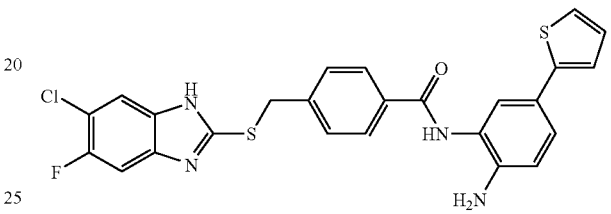

N-[2-amino-5-(2-thienyl)phenyl]-4-{[(6-chloro-5-fluoro-1H-benzimidazol-2-yl)thio]methyl}benzamide (55)

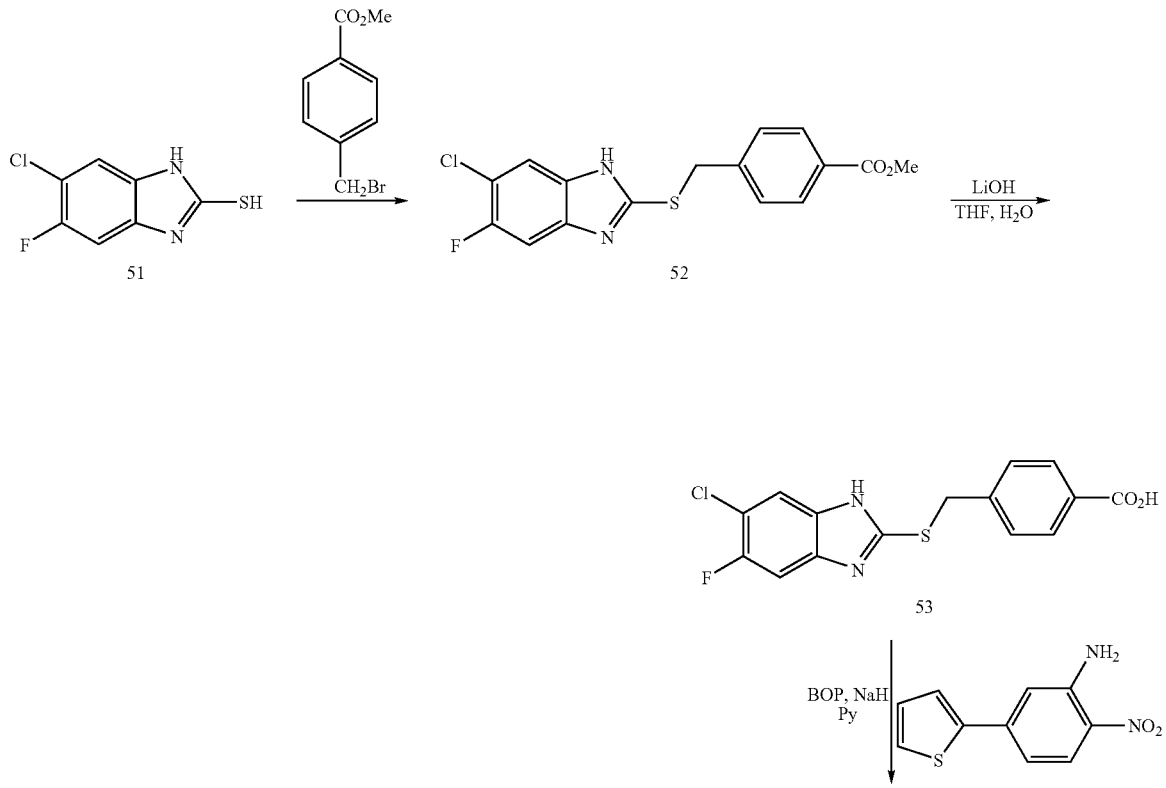

Scheme 8

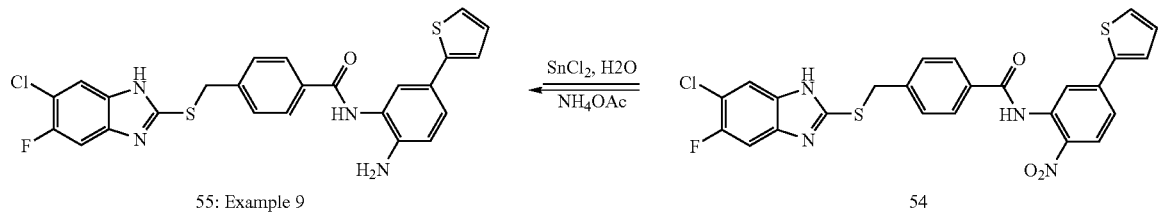

55: Example 9    54

Step 1: 4-(6-Chloro-5-fluoro-1H-benzoimidazol-2-ylsulfanylmethyl)-benzoic acid methyl ester (52)

The title compound 52 was obtained following the same procedure as for the S-alkylation described in U.S. patent application Ser. No. 10/242,304, which is incorporated by reference in its entirety. The yield of the title compound was 55% yield.

$^1$H NMR: (DMSO-d$_6$) δ(ppm): 7.85 (d, J=8.4 Hz, 2H), 7.55 (d, J=8.4 Hz, 2H), 3.80 (s, 2H), 3.34 (s, 3H). m/z: 351.2 (MH$^+$).

Step 2: 4-(6-[(Pyridin-3-ylmethyl)-amino]-benzothiazol-2-ylsulfanylmethyl)-benzoic acid methyl ester (53)

The title compound 53 was obtained following the same procedure as for the ester hydrolysis described in U.S. patent application Ser. No. 10/242,304, which is incorporated by reference in its entirety. The yield of the title compound was 83% yield.

$^1$H NMR: (DMSO-d$_6$) δ(ppm): 7.88 (d, J=8.2 Hz, 2H), 7.67 (d, J=6.8 Hz, 1H), 7.55 (d, J=8.2 Hz, 2H), 7.53 (d, J=6.8 Hz, 1H), 4.65 (s, 2H).

Step 3: N-(2-Amino-phenyl)-4-{6-[(pyridin-3-ylmethyl)-amino]-benzothiazol-2-yl sulfanylmethyl}-benzamide (54)

The title compound 54 was obtained following the same procedure as Example 1, step 3, but substituting compound 4 for compound 53 in 66% yield.

$^1$H NMR: (DMSO-d$_6$) δ(ppm): 12.89 (bs, 1H), 10.79 (s, 1H), 8.12 (d, J=2.0 Hz, 1H), 8.05 (d, J=8.8 Hz, 2H), 7.90-7.68 (m, 3H), 7.62 (d, J=8.4 Hz, 2H), 7.48 (bs, 1H), 7.21 (dd, J=4.9, 3.7 Hz, 1H), 4.65 (s, 2H). m/z: 539.5

Step 4: N-(2-Amino-5-(thiophen-2-yl-phenyl)-4-(6-chloro-5-fluoro-1H-benzoimidazol-2-ylsulfanylmethyl)-benzamide (55)

The title compound 55 was obtained following the same procedure as Example 1, step 4, but substituting compound 5 for compound 54 in 14% yield. $^1$H NMR: (DMSO-d$_6$) d (ppm): 12.96 (s, 0.5H), 12.92 (s, 0.5H), 9.71 (s, 1H), 7.96 (d, J=8.0 Hz, 2H), 8.35 (s, 0.5H), 7.79 (d, J=7.0 Hz, 0.5H), 7.64 (d, J=7.0 Hz, 0.5H), 7.62 (d, J=7.8 Hz, 2H), 7.50 (s, 0.5H), 7.48 (s, 1H), 7.38 (d, J=4.9 Hz, 1H), 7.32 (d, J=8.4 Hz, 1H), 7.27 (d, J=3.1 Hz, 1H), 7.08 (t, J=3.7 Hz, 1H), 6.83 (d, J=8.4 Hz, 1H), 5.19 (s, 2H), 4.69 (d, J=3.5 Hz, 2H). m/z: 509.5

Example 10

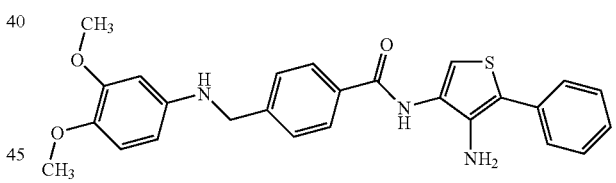

N-(4-amino-5-phenyl-3-thienyl)-4-{[(3,4-dimethoxyphenyl)amino]methyl}benzamide (61)

Scheme 9

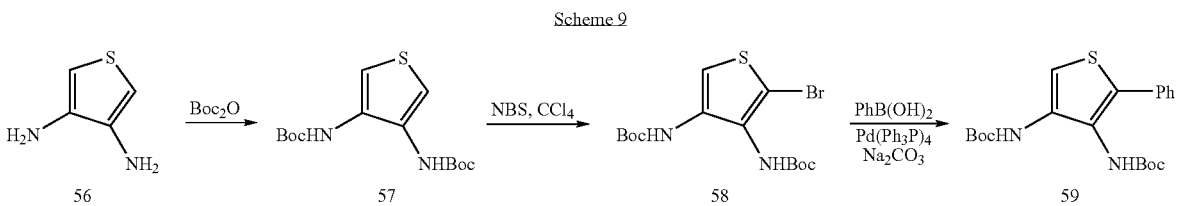

HBr, AcOH

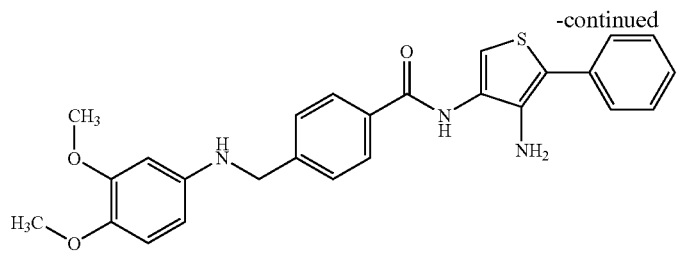

61: Example 10

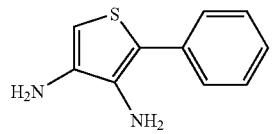

60

Step 1: (4-tert-Butoxycarbonylamino-thiophen-3-yl)-carbamic acid tert-butyl ester (57)

To a vigorously stirred THF (40 mL) solution of 3,4-diaminothiophene light petroleum ether (300 mL) was added (1.00 g, 8.77 mmol). To this mixture a solution of di-t-butyldicarbonate (3.82 g, 17.5 mmol) in petroleum ether (100 mL) was added over a period of 30 min. Stirring was continued for 16 h and the solvents were distilled off. The residue was dissolved in DCM and washed twice with 1N HCl, dried over MgSO$_4$ and concentrated in vacuum to a ~20 mL volume. Hexane was slowly added with stirring and brown crystalline material precipitated out. The product was collected by filtration, washed with hexane and the mother liquor was allowed to crystallize again to yield a second crop of the product. The two crops were combined thus affording the title compound 57 (2.19 g, 80% yield). This procedure is essentially as described in Brugier et al., Tetrahedron (1997) 30: 10331-10344, which is incorporated by reference in its entirety. $^1$H NMR: (CDCl$_3$) δ(ppm): 7.14 (s, 2H), 6.66 (bs, 1H), 1.54 (s, 18H).

Neutral 3,4-diaminothiophene is obtained by dissolving 3,4-diaminothiophene dihydrochloride (Toronto Research) (2.0 g, 10.7 mmol) in a minimum volume of 1N aqueous HCl and make the solution basic by addition of 2N aqueous NaOH. The precipitate is extracted twice with EtOAc and the combined organic layers dried with MgSO$_4$ and concentrated (1.00 g, 82% recovery).

Step 2: (2-Bromo-4-tert-butoxycarbonylamino-thiophen-3-yl)-carbamic acid tert-butyl ester (58)

NBS (1.22 g, 6.87 mmol) was added to a solution of compound 57 (2.16 g, 6.87 mmol) in CCl$_4$ (137 mL) at r.t. The mixture was stirred for 16 h. The solid material was filtered off and the filtrate was collected and washed with water. The organic layer was dried over MgSO$_4$ and concentrated in vacuum. The residue was purified by flash chromatography with DCM as an eluent affording the title compound 58 (1.92 g, 71% yield). $^1$H NMR: (CDCl$_3$) δ(ppm): 7.30 (bs, 1H), 6.00 (s, 1H), 1.45 (s, 9H), 1.43 (s, 9H). m/z: 415.4/417.4 (M+Na/M+2+Na). This procedure is essentially as described in Brugier et al., Tetrahedron, 56: 2985-2993 (2000), which is incorporated by reference in its entirety.

Step 3: (4-tert-Butoxycarbonylamino-5-phenyl-thiophen-3-yl)-carbamic acid tert-butyl ester (59)

In a flame-dried round-bottom flask, tetrakis(triphenylphosphine) palladium (59 mg, 0.051 mmol) was added to a degassed solution of compound 58 (400 mg, 1.02 mmol) in DME (5 mL). Phenylboronic acid (186 mg, 1.53 mmol), water (2.5 mL), and Na$_2$CO$_3$ (324 mg, 3.06 mmol) were successively added, degassing and purging with nitrogen between each addition. The mixture was refluxed under nitrogen atmosphere for 3 h and partitioned between Et$_2$O and water. The organic layer was dried over MgSO$_4$ and concentrated in vacuum. The title compound 59 (398 mg, 100% yield) was obtained as a brown oil. $^1$H NMR: (CDCl$_3$) δ(ppm): 7.51-7.31 (m, 6H), 1.54 (s, 18H). m/z: 413.5 (M+Na$^+$). This procedure is essentially as described in Brugier et al., Tetrahedron, 56: 2985-2993 (2000), which is incorporated by reference in its entirety.

Step 4: 2-Phenyl-thiophene-3,4-diamine (60)

To a solution of compound 59 in glacial acetic acid (102 µL) was added a 30% solution of HBr in acetic acid (102 µL). The mixture was stirred for 16 h at r.t. and Et$_2$O (10 mL) was added. The precipitate was collected by filtration and immediately dissolved in water, neutralized by addition of 2N aqueous NaOH and the precipitate was extracted with Et$_2$O. The organic layer was dried over MgSO$_4$ and concentrated in vacuum affording the title compound 60 (34 mg, 69% yield). This procedure is essentially as described in Brugier et al., Tetrahedron, 30: 10331-10344 (1997), which is incorporated by reference in its entirety. $^1$H NMR: (CDCl$_3$) δ(ppm): 7.49 (dd, J=8.4, 1.4 Hz, 2H), 7.41 (t, J=7.6 Hz, 2H), 7.26 (dd, J=10.2, 7.2 Hz, 1H), 6.22 (s, 1H), 3.51 (bs, 4H). m/z: 191.3 (MH$^+$).

Step 5: N-(4-Amino-5-phenyl-thiophen-3-yl)-4-[(3,4-dimethoxy-phenylamino)-methyl]-benzamide (61)

The title compound 61 was obtained following the same procedure as described in Example 6, step 2, but substituting compound 31 for compound 60 in 73% yield).

$^1$H NMR: (CD$_3$OD) δ(ppm): 7.91 (d, J=8.2 Hz, 2H), 7.52 (d, J=8.0 Hz, 2H), 7.51 (dd, J=7.0, 1.2 Hz, 2H), 7.42 (t, J=7.4 Hz, 2H), 7.38 (s, 1H), 7.28 (tt, J=7.4, 1.8 Hz, 1H), 6.71 (d, J=8.6 Hz, 1H), 6.37 (d, J=2.7 Hz, 1H), 6.13 (dd, J=8.6, 2.5 Hz, 1H), 4.38 (s, 2H), 3.74 (s, 3H), 3.71 (s, 3H). m/z: 460.5 (MH$^+$).

Example 11

62: Example 11

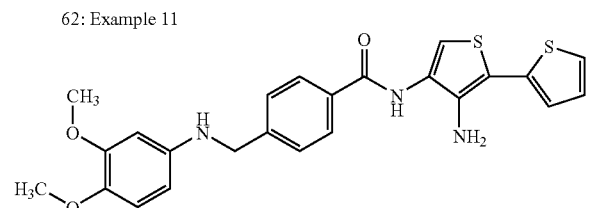

347

N-(3-amino-2,2'-bithien-4-yl)-4-{[(3,4-dimethoxyphenyl)amino]methyl}benzamide (62)

The title compound 62 was obtained following the same procedures as Example 10, substituting phenylboronic acid in the step 3 for 2-thiopheneboronic acid in 29% yield. $^1$H NMR: (DMSO-d$_6$) δ(ppm): 7.90 (d, J=8.4 Hz, 2H), 7.52 (d, J=8.4 Hz, 2H), 7.37 (dd, J=5.1, 1.2 Hz, 1H), 7.36 (s, 1H), 7.14 (dd, J=3.7, 1.2 Hz, 1H), 7.10 (dd, J=5.1, 3.5 Hz, 1H), 6.71 (d, J=7.4 Hz, 1H), 6.36 (d, J=2.5 Hz, 1H), 4.38 (s, 2H), 3.74 (s, 3H), 3.71 (s, 3H), m/z: 466.5 (MH$^+$).

348

Example 12

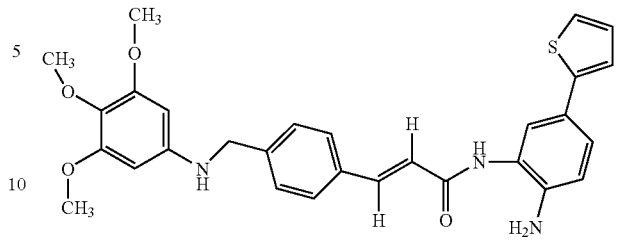

trans-N-[2-amino-5-(2-thienyl)phenyl]-3-(4-{[(3,4,5-trimethoxyphenyl)amino]methyl}phenyl)acrylamide (67)

Scheme 10

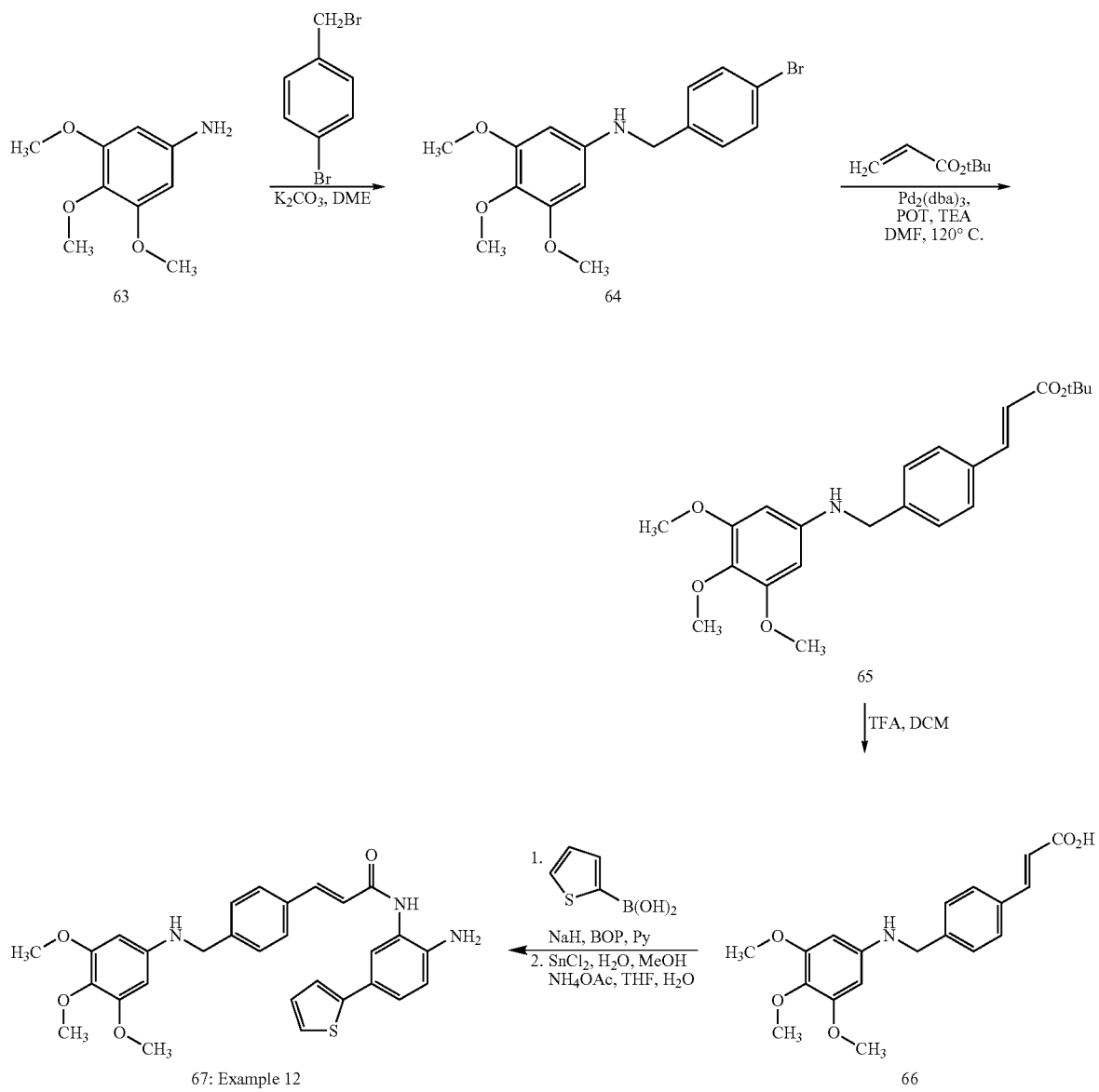

Steps 1-3: 3-{4-[(3,4,5-Trimethoxy-phenylamino)-methyl]-phenyl}-acrylic acid (66)

The title compound 66 and the synthetic pathway depicted in scheme 10 were described in U.S. patent application Ser. No. 10/242,304, which is incorporated by reference in its entirety.

Steps 4-5. N-(2-Amino-5-thiophen-2-yl-phenyl)-3-{4-[(3,4,5-trimethoxy-phenylamino)-methyl]-phenyl}-acrylamide (67)

The title compound 67 was obtained following the same procedures described in Example 1, steps 3 and 4, but substituting compound 4 for compound 66 in 32% yield.

$^1$H NMR (400 MHz, DMSO d$_6$): 9.40 (s, 1H); 7.67 (s, 1H); 7.56 (d, 2H, J=7.6 Hz); 7.51 (s, 1H); 7.42 (d, 2H, J=8.0 Hz); 7.33 (d, 1H, J=5.1 Hz); 7.23-7.19 (m, 2H); 7.03 (dd, 1H, J=3.7, 4.9 Hz); 6.85 (d, 1H, J=15.7 Hz); 6.76 (d, 1H, J=8.2 Hz); 6.08 (dd, 1H; J=5.7, 6.0 Hz); 5.87 (s, 2H); 5.19 (s, 2H); 4.25 (d, 2H, J=5.9 Hz), 3.63 (s, 6H); 3.49 (s, 3H).

Example 13

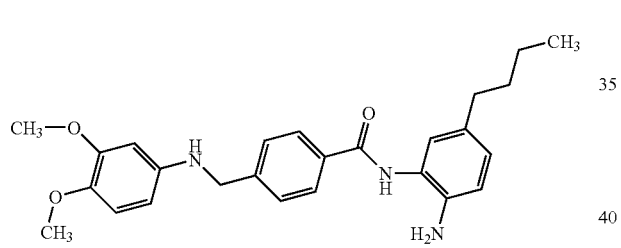

N-(2-amino-5-butylphenyl)-4-{[(3,4-dimethoxyphenyl)amino]methyl}benzamide (68) and Example 13a

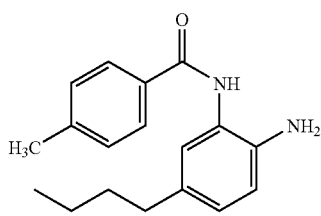

N-(2-amino-5-butylphenyl)-4-methylbenzamide

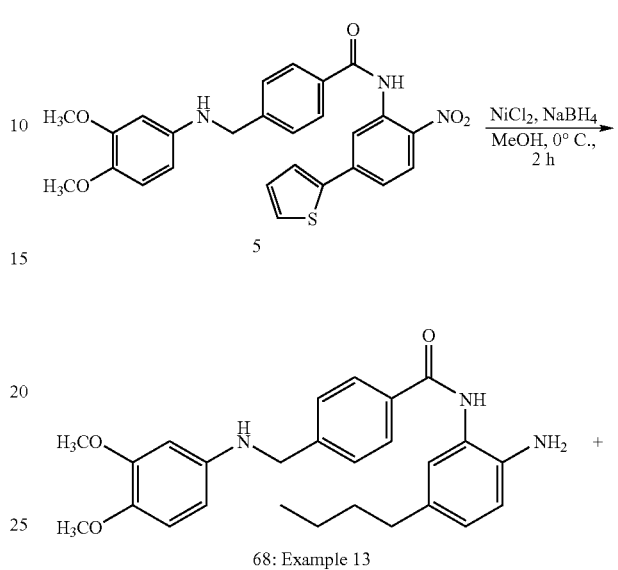

A stirred solution of nitrocompound 5 (207 mg; 0.42 mmol) and nickel(II)chloride hexahydrate (595 mg; 2.5 mmol) in methanol (6 mL) at 0° C. was treated with the solid sodium borohydride (430 mg; 11.4 mmol) and the mixture stirred at the same temperature for 2 h, quenched with acetone, poured into 5% NH$_4$OH in brine and extracted with dichloromethane. The organic layer was dried (Na$_2$SO$_4$), filtered and concentrated. After flash chromatography on a silica gel column (eluent 20% AcOEt in dichloromethane), compound 68 (62 mg; 0.143 mmol, 34%) and 69 (22 mg, 0.078 mmol, 19%) were obtained.

Compound 68: $^1$H NMR: (400.2 MHz, DMSO) δ (ppm): 9.58 (s, 1H); 7.89 (d, J=8.2, 2H); 7.45 (d, J=8.2, 2H); 6.97 (s, 1H); 6.78 (dd, J=2.0; 8.2, 1H); 6.67 (d, J=8.0, 1H); 6.64 (d, J=8.6, 1H); 6.31 (d, J=2.5, 1H); 5.99-5.96 (m, 2H); 4.68 (bs, 2H); 4.29 (d, J=6.3, 2H); 3.65 (s, 3H); 3.58 (s, 3H); 2.43 (t, J=7.4, 2H); 1.49 (m, J=7.4, 2H); 1.30 (m, J=7.4, 2H); 0.89 (t, J=7.4, 3H).

Compound 69: $^1$H NMR: (400.2 MHz, DMSO) δ (ppm): 9.57 (s, 1H); 7.86 (d, J=8.1, 2H); 7.30 (d, J=8.1, 2H); 6.78 (dd, J=2.0; 8.0, 1H); 6.68 (d, J=8.0, 1H); 4.67 (bs, 2H); 2.44 (t, J=7.4, 2H); 2.38 (s, 3H); 1.49 (m, J=7.4, 2H); 1.31 (m, J=7.4, 2H); 0.89 (t, J=7.4, 3H).

Example 14

N-(2-amino-4-butylphenyl)-4-{[(3,4-dimethoxyphenyl)amino]methyl}benzamide (70) and

Example 14a

N-(2-amino-4-butylphenyl)-4-methylbenzamide (71)

Following the same procedure as described in Example 13, but substituting the compound 5 for compound 15 in 53 and 9% yields, respectively.

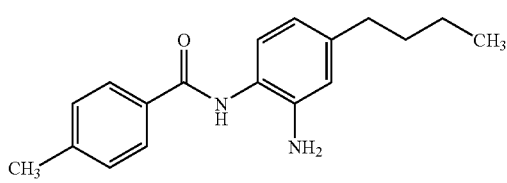

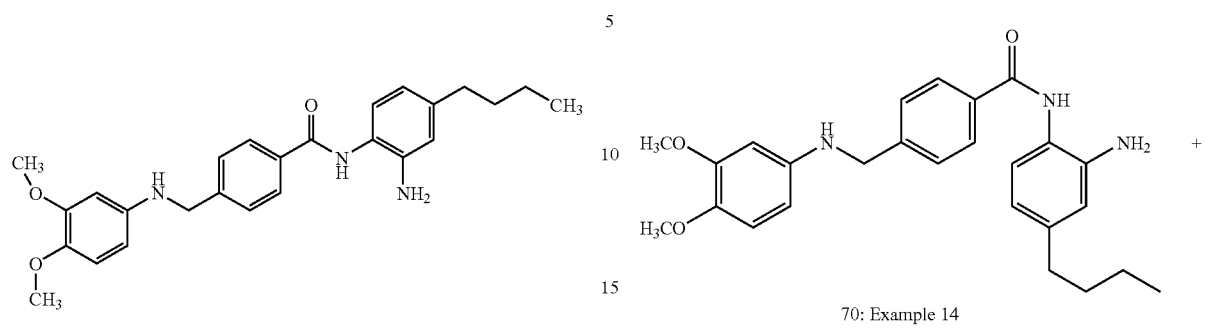

70: Example 14

71: Example 14a

Compound 70: $^1$H NMR: (400.2 MHz, DMSO) δ(ppm): 9.51 (s, 1H); 7.88 (d, J=8.4, 2H); 7.44 (d, J=8.4, 2H); 7.00 (d, J=8.3, 1H); 6.63 (d, J=8.3, 1H); 6.58 (d, J=2.0, 1H); 6.30 (d, J=2.5, 1H); 5.99-5.96 (m, 2H); 4.79 (bs, 2H); 4.29 (d, J=6.1, 2H); 3.65 (s, 3H); 3.59 (s, 3H); 2.45 (t, J=7.4, 2H); 1.52 (m, J=7.4, 2H); 1.30 (m, J=7.4, 2H); 0.90 (t, J=7.4, 3H).

Compound 71: $^1$H NMR: (400.2 MHz, DMSO) δ(ppm): 9.51 (s, 1H); 7.85 (d, J=8.0, 2H); 7.28 (d, J=8.0, 2H); 7.01 (d, J=8.5, 1H); 6.58 (d, J=2.0, 1H); 6.40 (d, J=2.0, 8.5, 1H); 4.78 (bs, 2H); 2.45 (t, J=7.4, 2H); 2.38 (s, 3H); 1.53 (m, J=7.4, 2H); 1.31 (m, J=7.4, 2H); 0.90 (t, J=7.4, 3H).

Example 15

Scheme 12

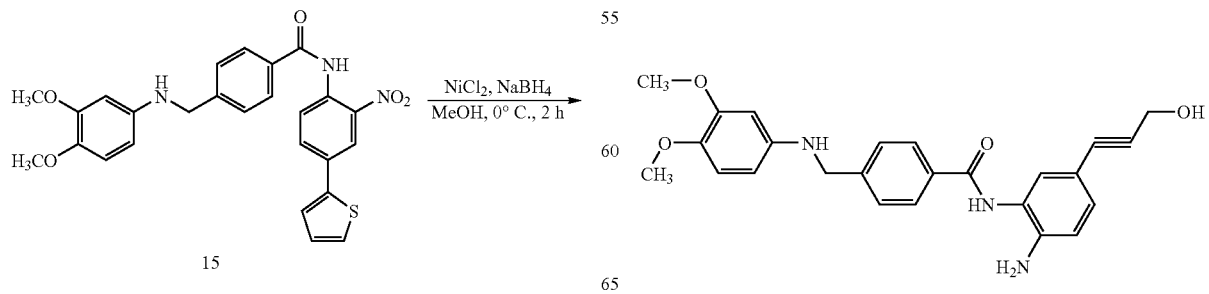

N-[2-amino-5-(3-hydroxyprop-1-yn-1-yl)phenyl]-4-
{[(3,4-dimethoxyphenyl)amino]methyl}benzamide
(76)
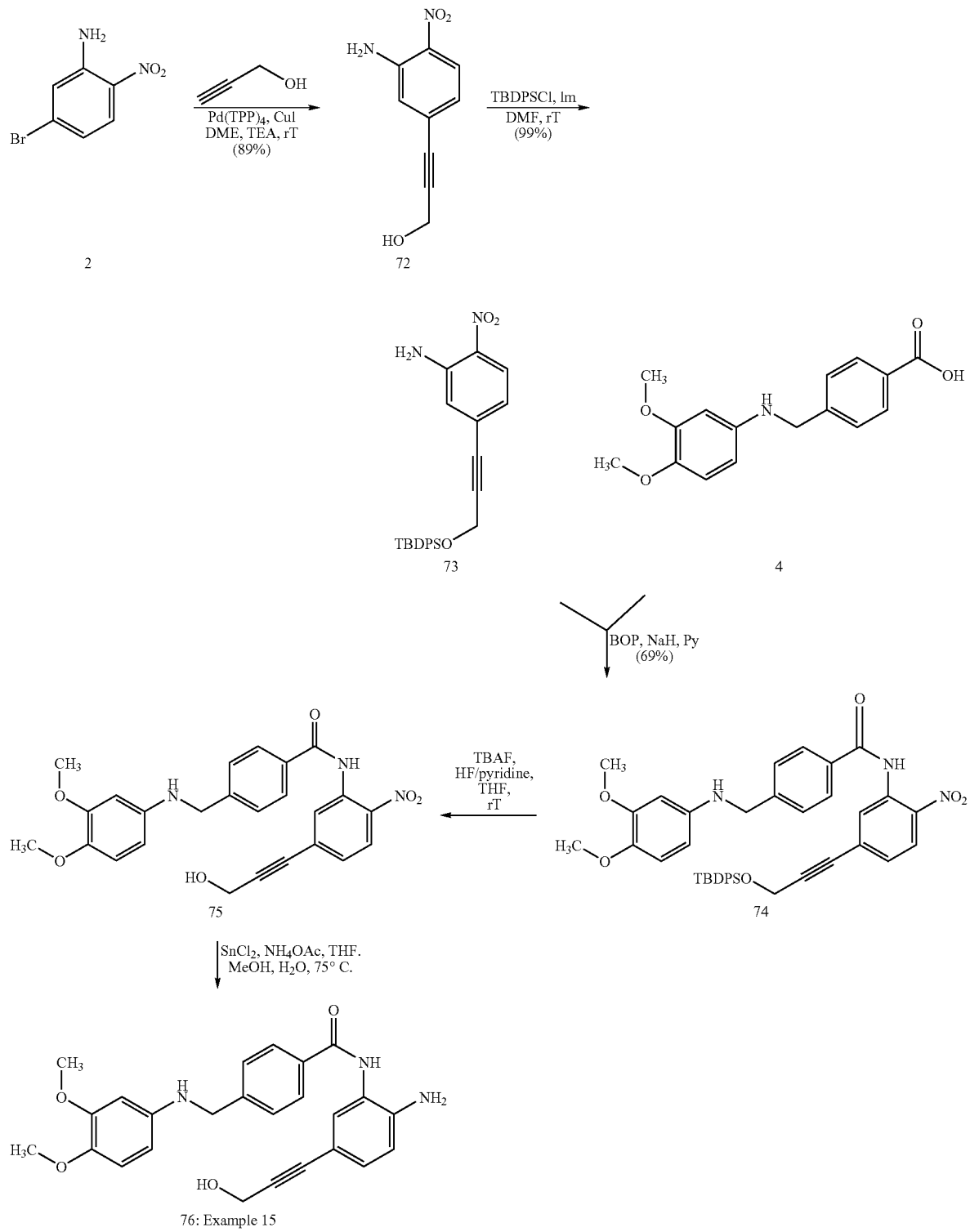

Step 1: 3-(3-Amino-4-nitro-phenyl)-prop-2-yn-1-ol (72)

A suspension of bromoarene 2 (447 mg g; 2.06 mmol); tetrakis(triphenylphosphine) palladium(0) (145 mg, 0.12 mmol) and copper(I)iodide (143 mg, 0.75 mmol) in degassed ethyleneglycol dimethylether (2.5 mL) and triethylamine (1.5 mL), was stirred at room temperature under nitrogen in the dark for 10 min and then treated with neat prop-2-yn-1-ol (0.7 mL, 12 mmol) (or any other alkyne of choice, 5 eq.), and the mixture stirred under the same conditions for 48 h, diluted with dichloromethane (50 mL), filtered through a celite pad and concentrated. Purification by flash chromatography (eluent 50 to 75% AcOEt in hexane) afforded compound 72 (328 mg, 83% yield).

$^1$H NMR: (400.2 MHz, DMSO) δ(ppm): 7.92 (d, J=8.8, 1H); 7.46 (bs, 2H); 7.04 (d, J=1.7, 1H); 6.57 (dd, J=1.7, 8.8, 1H); 5.41 (t, J=6.1, 1H); 4.30 (d, J=6.1, 2H).

Step 2: 5-[3-tert-Butyl-diphenyl-silanyloxy)-prop-1-ynyl]-2-nitro-phenylamine (73)

A solution of alcohol 72 (328 mg, 1.71 mmol) and imidazole (308 mg, 4.5 mmol) in N,N-dimethylformamide (3 mL) was treated with neat tert-butyl-chloro-diphenyl-silane (0.5 mL, 1.9 mmol) and the solution stirred under nitrogen for 18 h, diluted with ethyl acetate (300 mL), washed with 5% aqueous KHSO$_4$, then with saturated NaHCO$_3$ and finally with water, dried (MgSO$_4$), filtered and concentrated in vacuum. The crude mixture was purified by flash chromatography (eluent 50% ether in hexane, then 50% EtOAc in dichloromethane) to give compound 73 (691 mg, 94% yield).

$^1$H NMR: (400.2 MHz, DMSO) δ (ppm): 7.91 (d, J=8.8, 1H); 7.68-7.66 (m, 4H) 7.46-7.44 (m, 6H); 7.01 (d, J=1.7, 1H); 6.46 (dd, J=1.7, 8.8, 1H); 4.61 (d, 2H); 1.03 (d, 9H).

Step 3: N-{5-[3-(tert-Butyl-diphenyl-silanyloxy)-prop-1-ynyl]-2-nitro-phenyl}-4-[(3,4-dimethoxy-phenylamino)-methyl]-benzamide (74)

Following the same procedure as described in Example 1, step 3, but substituting compound 3 for compound 73 title compound was obtained in 77% yield.

$^1$H NMR: (400.2 MHz, DMSO) δ (ppm): 10.7 (s, 1H); 7.97 (d, J=8.6, 1H); 7.88 (d, J=8.4, 2H); 7.76 (d, J=1.8, 1H); 7.70-7.67 (m, 4H); 7.52 (d, J=8.4, 2H); 7.47-7.44 (m, 6H); 7.25 (d, J=7.4, 1H); 6.64 (d, J=8.6, 1H); 6.31 (d, J=2.8, 1H); 6.01-5.96 (m, 2H); 4.65 (s, 2H); 4.31 (d, J=6.1, 2H); 3.65 (s, 3H); 3.55 (s, 3H); 1.03 (d, 9H).

Step 4: 4-[(3,4-Dimethoxy-phenylamino)-methyl]-N-[5-(3-hydroxy-prop-1-ynyl)-2-nitro-phenyl]-benzamide (75)

A solution of compound 74 (871 mg, 1.24 mmol) in THF (3 mL) was treated with 1.0 M solution of tetrabutylammonium fluoride in THF (2.0 mL, 2.0 mmol) followed by 70% hydrogen fluoride in pyridine (0.1 mL), and the solution stirred under nitrogen for 12 h, diluted with ethyl acetate (200 mL) and washed with saturated NaHCO$_3$ (50 mL) and then with water (6×100 mL), dried (Na$_2$SO$_4$), filtered and concentrated in vacuum. The crude material (647 mg) was pure enough for the next step without further purification.

Step 5: N-[2-Amino-5-(3-hydroxy-prop-1-ynyl)-phenyl]-4-[(3,4-dimethoxy-phenylamino)-methyl]-benzamide (76)

Following the same procedure as described in Example 1, Step 4, but substituting compound 5 for compound 75 in 52% yield.

$^1$H NMR: (400.2 MHz, DMSO) δ (ppm): 9.51 (s, 1H); 7.88 (d, J=8.2, 2H); 7.45 (d, J=8.2, 2H); 7.22 (d, J=1.8, 1H); 6.99 (dd, J=1.8, 8.2, 1H); 6.69 (d, J=8.4, 1H); 6.63 (d, J=8.4, 1H); 6.31 (d, J=2.3, 1H); 5.99-5.96 (m, 2H); 5.30 (s, 2H); 5.19 (d, J=5.9, 1H); 4.29 (d, J=5.9, 2H); 4.23 (d, J=5.3, 2H); 3.65 (s, 3H); 3.55 (s, 3H).

Example 16

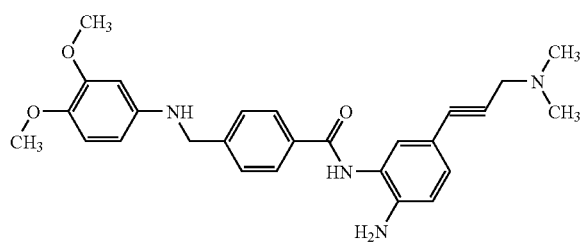

N-{2-amino-5-[3-(dimethylamino)prop-1-yn-1-yl]phenyl}-4-{[(3,4-dimethoxyphenyl)amino]methyl}benzamide (79)

Scheme 14

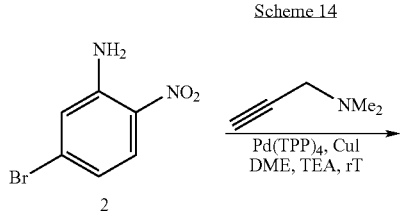

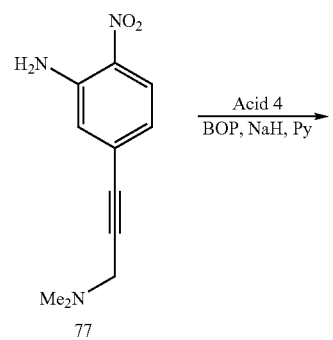

-continued

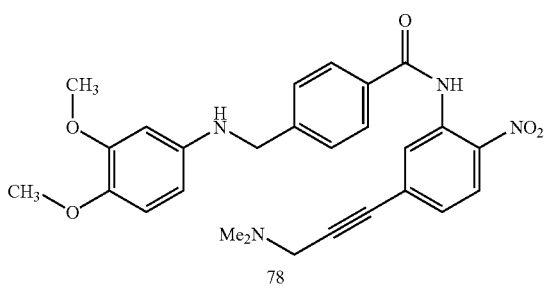

78

SnCl₂, NH₄OAc, THF, MeOH, H₂O, 75° C.

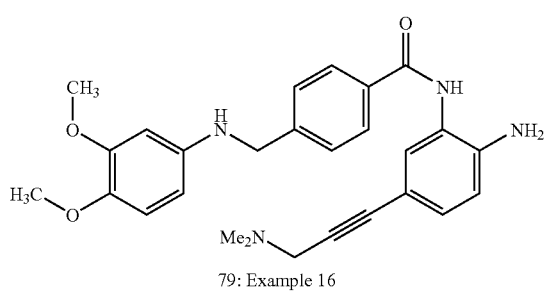

79: Example 16

Step 1:
5-(3-Dimethylamino-prop-1-ynyl)-2-nitro-phenylamine (77)

Following the same procedure described in Example 15, step 1 but substituting propargyl alcohol for N,N-dimethyl-propargyl amine, the title compound was obtained in 80% yield.

¹H NMR: (400.2 MHz, DMSO) δ (ppm): 8.02 (d, J=8.8, 1H); 6.87 (d, J=1.6, 1H); 6.69 (dd, J=1.6, 8.8, 1H); 6.18 (bs, 2H); 3.48 (s, 2H); 2.38 (s, 6H).

Step 2: 4-[(3,4-Dimethoxy-phenylamino)-methyl]-N-[5-(3-dimethylamino-prop-1-ynyl)-2-nitro-phenyl]-benzamide (78)

Following the same procedure described in Example 15, step 3 but substituting compound 73 for compound 77, the title compound was obtained in 86% yield.

¹H NMR: (400.2 MHz, DMSO) δ (ppm): 10.74 (s, 1H); 8.0 (d, J=8.4, 2H); 7.88 (d, J=8.4, 2H); 7.83 (d, J=1.8, 1H); 7.52 (d, J=8.4, 2H); 7.41 (dd, J=1.8, 8.4, 1H); 6.64 (d, J=8.6, 1H); 6.31 (d, J=2.6, 1H); 6.30 (d, J=6.6, 1H); 5.97 (dd, J=2.6, 8.6, 1H); 4.30 (d, J=6.6, 2H); 3.65 (s, 3H); 3.64 (s, 3H); 3.58 (s, 2H); 2.25 (s, 6H).

Step 3: N-[2-Amino-5-(3-dimethylamino-prop-1-ynyl)-phenyl]-4-[(3,4-dimethoxyphenylamino)-methyl]-benzamide (79)

Following the same procedure described in Example 15, step 5 but substituting compound 75 for compound 78, the title compound 79 was obtained in 63% yield.

¹H NMR: (400.2 MHz, DMSO) δ (ppm): 9.53 (s, 1H); 7.89 (d, J=8.2, 2H); 7.45 (d, J=8.2, 2H); 7.22 (d, J=1.8, 1H); 7.01 (dd, J=1.8, 8.2, 1H); 6.69 (d, J=8.2, 1H); 6.63 (d, J=8.2, 1H); 6.30 (d, J=2.5, 1H); 5.99-5.96 (m, 2H); 5.28 (s, 2H); 4.29 (d, J=6.1, 2H); 3.65 (s, 3H); 3.58 (s, 3H); 3.37 (s, 2H); 2.21 (s, 6H).

Example 17

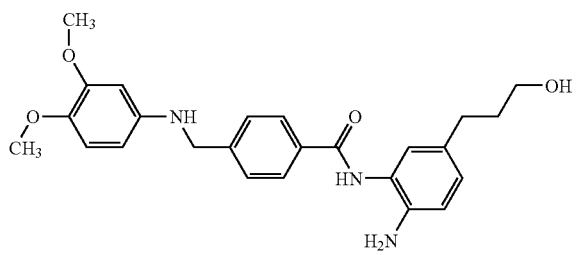

N-[2-amino-5-(3-hydroxypropyl)phenyl]-4-{[(3,4-dimethoxyphenyl)amino]methyl}benzamide (85)

Scheme 15

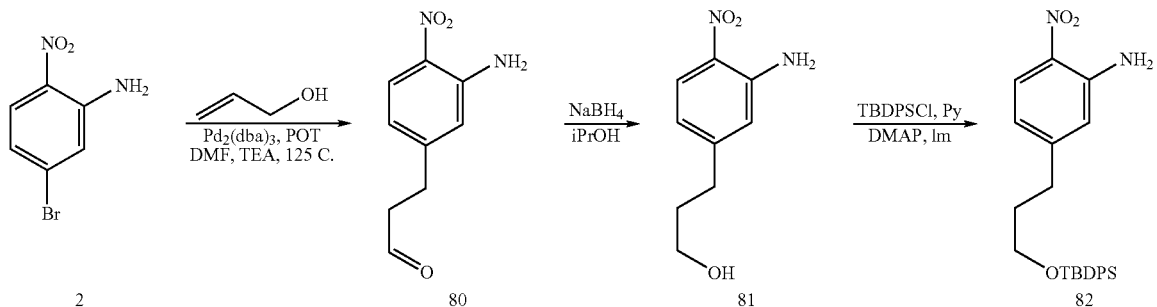

Acid 4
BOP, NaH, Py

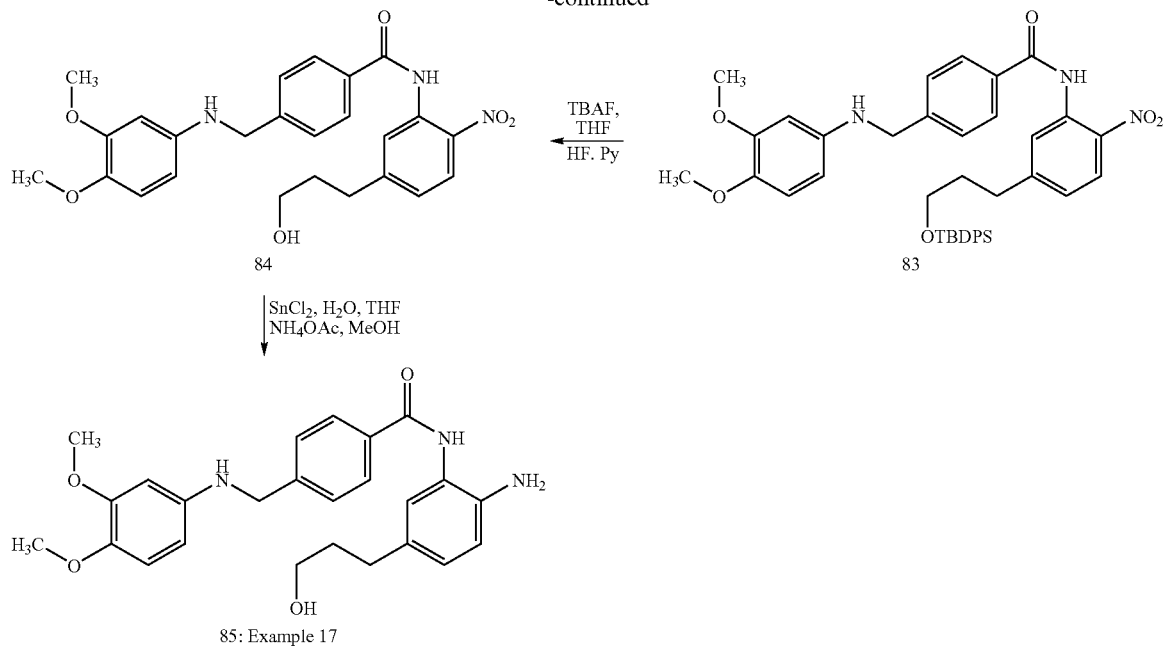

Step 1: 3-(3-Amino-4-nitro-phenyl)-propionaldehyde (80)

A solution of bromoarene 2 (1.544 g, 7.11 mmol) (or any haloarene of choice); tri-o-tolyl-phosphine (280 mg; 0.9 mmol) and trkdibenzylidene acetone)dipalladium(0) (280 mg; 0.3 mmol) in N,N-dimethylformamide (6 mL) and ethyl diisopropyl amine (3 mL) was treated with prop-2-en-1-ol (3 mL, 40 mmol) (or any alken-1-ol of choice, 6 eq.) and the solution was stirred at 120° C. for 3 h under nitrogen. The reaction mixture was concentrated under high vacuum and the residue was purified by flash chromatography (eluent 5% MeOH in dichloromethane) to afford the aldehyde 80 (253 mg, 18% yield).

$^1$H NMR: (400.2 MHz, CDCl3) δ (ppm): 9.68 (t, J=0.8, 1H); 7.89 (d, J=8.7, 1H); 6.51 (d, J=1.6, 1H); 6.39 (dd, J=2.0, 8.7, 1H); 6.02 (bs, 2H); 2.78 (t, J=6.7, 2H); 2.69 (m, J=0.8, 6.7, 2H).

Step 2: 3-(3-Amino-4-nitro-phenyl)-propan-1-ol (81)

A solution of aldehyde 80 (253 mg, 1.3 mmol) in tetrahydrofurane (1 mL) and propan-2-ol (2 mL) was treated with solid sodium borohydride (175 mg, 4.6 mmol) and stirred at −5° C. for 15 min. Acetone (5 mL) was added, stirred at the same temperature for 10 min and then diluted with ethyl acetate (100 mL), washed with 5% KHSO$_4$ in water, then saturated NaHCO$_3$ and finally with water, dried (MgSO$_4$), and used for the next step without further purification.

$^1$H NMR: (400.2 MHz, CDCl3) δ (ppm): 8.01 (d, J=8.8, 1H); 6.64 (d, J=1.8, 1H); 6.54 (dd, J=1.8, 8.8, 1H); 6.18 (bs, 2H); 3.69 (t, S=1.2, 2H); 2.68 (t, J=7.2, 2H); 1.91 (m, J=7.2, 2H).

Step 3: 5-[3-(tert-Butyl-diphenyl-silanyloxy)-propyl]-2-nitro-phenylamine (82)

Following the same procedure described in Example 15, step 2 but substituting compound 72 for compound 81, the title compound was obtained in 78% yield.

$^1$H NMR: (400.2 MHz, CDCl3) δ (ppm): 7.99 (d, J=8.8, 1H); 7.73 (d, J=1.6, 1H); 7.65-7.63 (m, 4H); 7.46-7.37 (m, 6H); 6.49 (dd, J=1.6, 8.8, 1H); 4.02 (bs, 2H); 3.71 (t, J=7.4, 2H); 2.69 (t, J=7.2, 2H); 1.87 (m, J=7.2, 2H); 1.10 (s, 9H).

Step 4: N-{5-[3-(tert-Butyl-diphenyl-silanyloxy)-propyl]-2-nitro-phenyl}-4-[(3,4-dimethoxyphenylamino)-methyl]-benzamide (83)

Following the same procedure described in Example 15, step 3 but substituting compound 73 for compound 82, the title compound was obtained in 71% yield.

$^1$H NMR: (400.2 MHz, CDCl3) δ (ppm): 11.3 (s, 1H); 8.75 (d, J=2.0, 1H); 8.61 (d, J=8.6, 1H); 7.86 (d, J=8.4, 2H); 7.57-7.54 (m, 4H); 7.44 (d, J=8.4, 2H); 7.34-7.27 (m, 6H); 6.88 (dd, J=2.0, 8.4, 1H); 6.62 (d, J=8.6, 1H); 6.21 (d, J=2.5, 1H); 6.08 (dd, J=2.5, 8.6, 1H); 4.32 (s, 2H); 3.72 (s, 3H); 3.71 (s, 3H); 3.62 (t, J=7.4, 2H); 2.76 (t, J=7.2, 2H); 1.84 (m, J=7.2, 2H); 0.99 (s, 9H).

Step 5: 4-[(3,4-Dimethoxy-phenylamino)-methyl]-N-[5-(3-hydroxy-propyl)-2-nitro-phenyl]-benzamide (84)

Following the same procedure described in Example 15, step 4 but substituting compound 74 for compound 83, the title compound was obtained in 99% yield.

$^1$H NMR: (400.2 MHz, CDCl3) δ (ppm): 11.4 (s, 1H); 8.86 (d, J=2.0, 1H); 8.21 (d, J=8.6, 1H); 7.95 (d, J=8.4, 2H); 7.57 (d, J=8.4, 2H); 7.07 (dd, J=2.0, 8.6, 1H); 6.74 (d, J=8.6, 1H); 6.42 (d, J=2.3, 1H); 6.31 (d, J=8.6, 1H); 4.43 (s, 2H); 3.83 (s, 3H); 3.82 (s, 3H); 3.74 (t, J=7.4, 2H); 2.87 (t, J=7.2, 2H); 2.01 (m, J=7.2, 2H); 1.62 (bs, 1H).

361

Step 6: N-[2-Amino-5-(3-hydroxy-propyl)-phenyl]-
4-[(3,4-dimethoxy-phenylamino)-methyl]-benzamide
(85)

Following the same procedure described in Example 15, step 5 but substituting compound 75 for compound 84, the title compound was obtained in 62% yield.

$^1$H NMR: (400.2 MHz, CDCl3) δ (ppm): 9.58 (s, 1H); 7.89 (d, J=8.1, 2H); 7.45 (d, J=8.1, 2H); 6.98 (s, 1H); 6.78 (dd, J=1.8, 8.0, 1H); 6.67 (d, J=8.0, 1H); 6.64 (d, J=8.6, 1H); 6.31 (d, J=2.5, 1H); 5.98 (m, 1H); 4.68 (bs, 2H); 4.40 (t, J=5.1, 1H); 4.29 (d, J=6.4, 2H); 3.65 (s, 3H); 3.58 (s, 3H); 3.37 (dt, J=5.1, 7.6, 2H); 2.46 (t, J=7.6, 2H); 1.65 (m, J=7.2, 2H).

362

Example 18

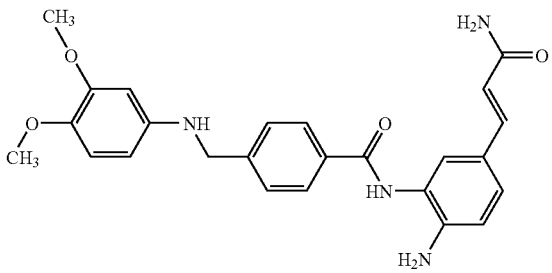

N-{2-amino-5-[(1E)-3-amino-3-oxoprop-1-en-1-yl]
phenyl}-4-{[(3,4-dimethoxyphenyl)amino]
methyl}benzamide (88)

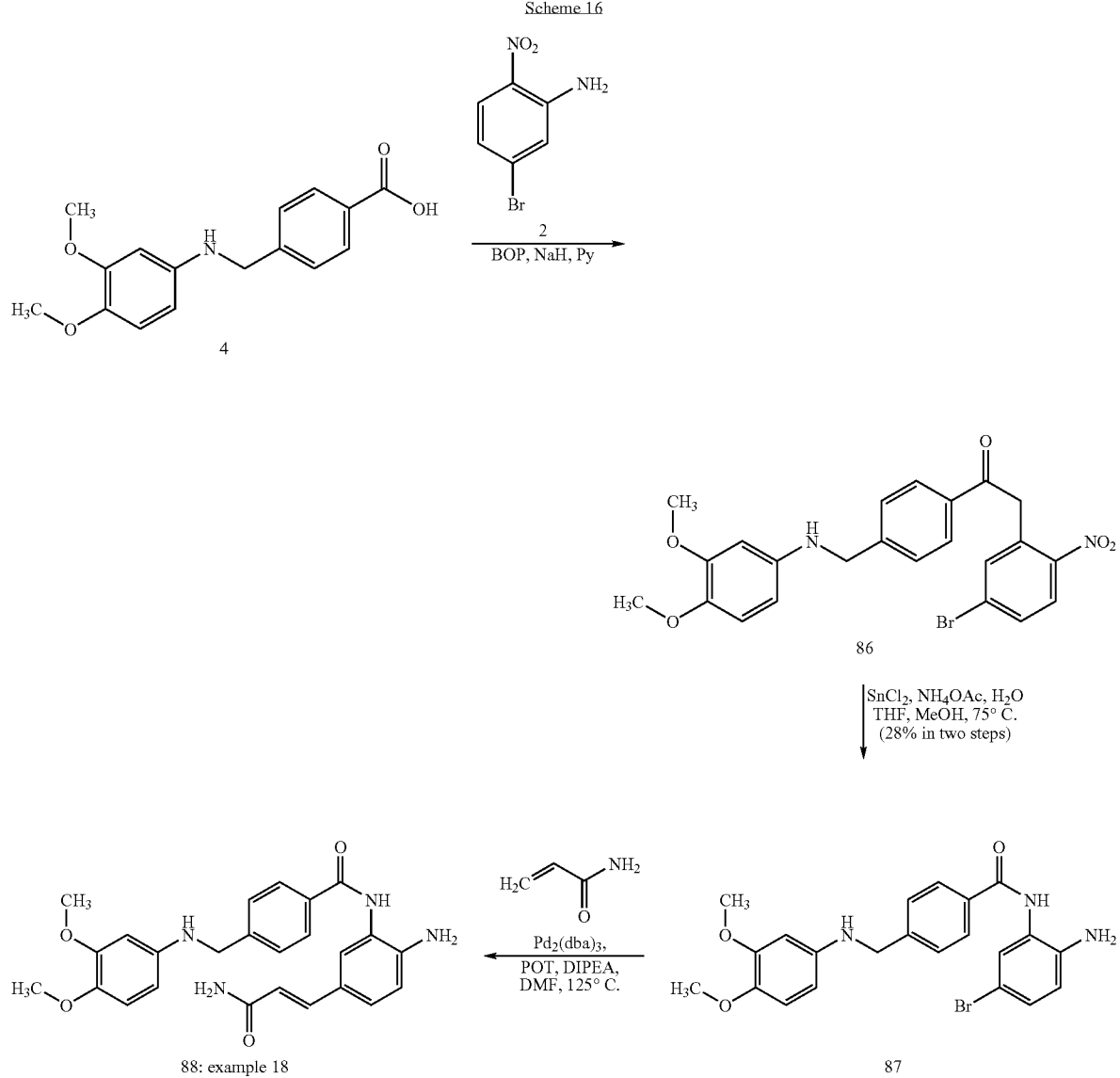

88: example 18

87

Step 1: N-(5-Bromo-2-nitro-phenyl)-4-[(3,4-dimethoxy-phenylamino)-methyl]-benzamide (86)

Following the same procedure as described in Example 1 step 3 but substituting compound 3 for compound 2, the title compound was obtained, which was used without further purification.

$^1$H NMR: (400.2 MHz, DMSO) δ (ppm): 10.4 (s, 1H); 8.08 (d, J=2.2, 1H); 7.96 (d, J=8.6, 1H); 7.87 (d, J=8.4, 2H); 7.60 (dd, J=2.2, 8.6, 1H); 7.52 (d, J=8.4, 2H); 6.64 (d, J=8.4, 1H); 6.30 (d, J=2.5, 1H); 5.97 (m, 2H); 4.31 (d, J=6.1, 2H); 3.65 (s, 3H); 3.58 (s, 3H).

Step 2: N-(2-Amino-5-bromo-phenyl)-4-[(3,4-dimethoxy-phenylamino)-methyl]-benzamide (87)

Following the same procedure described in Example 1, step 4 but substituting compound 5 for compound 86, the title compound was obtained in 28% yield (over two steps).

$^1$H NMR: (400.2 MHz, DMSO) δ (ppm): 9.58 (s, 1H), 7.89 (d, J=8.2 Hz, 2H), 7.46 (d, J=8.4 Hz, 2H), 7.35 (d, J=2.3 Hz, 1H), 7.08 (dd, J=8.4, 2.3 Hz, 1H), 6.70 (d, J=8.6 Hz, 1H), 6.64 (d, J=8.6 Hz, 1H), 6.31 (d, J=2.5 Hz, 1H), 5.99-5.96 (m, 2H), 5.12 (s, 2H), 4.29 (d, J=6.1 Hz, 2H), 3.65 (s, 3H), 3.58 (s, 3H).

Step 3: N-[2-Amino-5-(2-carbamoyl-vinyl)-phenyl]-4-[(3,4-dimethoxy-phenylamino)-methyl]-benzamide (88)

Following the same procedure described in Example 17, step 1 but substituting compound 2 for compound 87, the title compound was obtained in 18% yield.

$^1$H NMR: (400.2 MHz, DMSO) δ (ppm): 9.57 (s, 1H), 7.91 (d, J=8.2 Hz, 2H), 7.46 (d, J=8.2 Hz, 2H), 7.38 (d, J=2.0 Hz, 1H), 7.32 (bs, 1H); 7.23 (d, J=16 Hz, 1H), 7.15 (dd, J=2.0, 8.4 Hz, 1H); 6.82 (bs, 1H); 6.74 (d, J=8.4 Hz, 1H), 6.64 (d, J=8.6 Hz, 1H), 6.32 (m, 1H), 6.29 (d, J=16 Hz, 1H), 5.98 (m, 2H), 5.39 (bs, 2H), 4.30 (d, J=6.1 Hz, 2H), 3.66 (s, 3H), 3.59 (s, 3H).

Examples 19

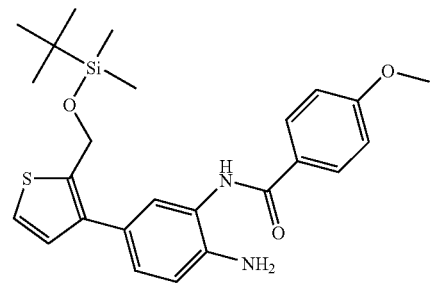

N-(2-Amino-5-(2-((tert-butyldimethylsilyloxy)methyl)thiophen-3-yl)phenyl)-4-methoxybenzamide (93) and Example 20

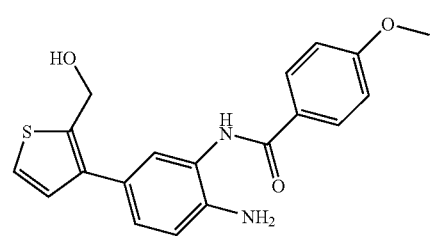

N-(2-amino-5-(2-hydroxymethyl)thiophen-3-yl)phenyl)-4-methoxybenzamide (94)

Scheme 17

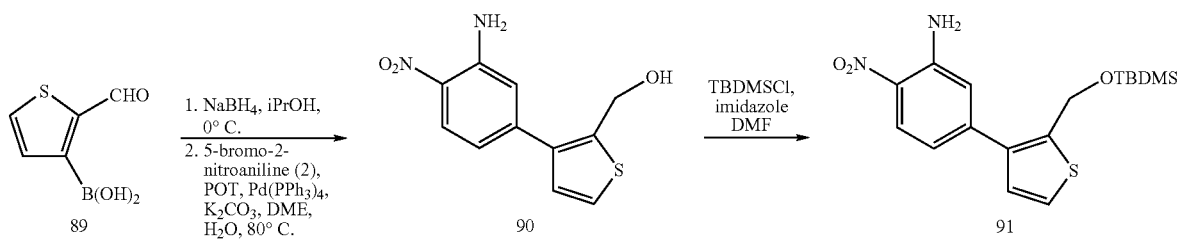

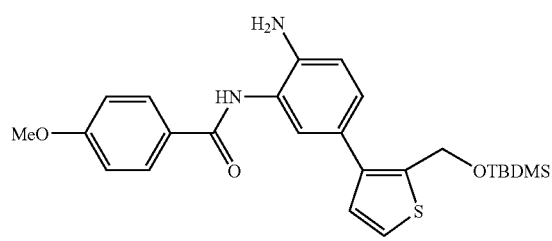

93: Example 19

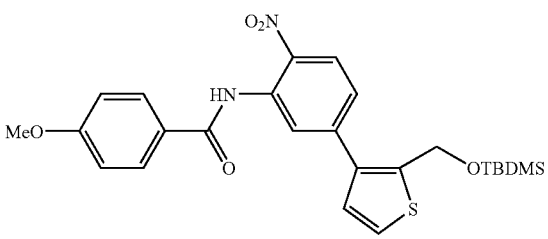

2-methoxybenzoyl chloride
Pyridine

92

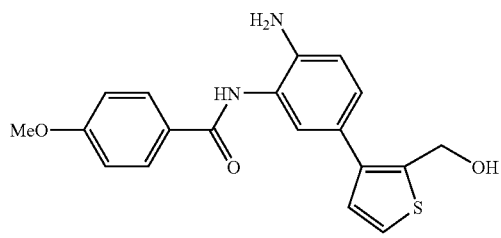

94: Example 20

Step 1. (3-(3-amino-4-nitrophenyl)thiophen-2-yl)methanol (90)

A suspension of the aldehyde 89 (500 mg, 3.21 mmol) and sodium borohydride (121 mg, 3.21 mmol) in isopropanol (5 ml) was stirred at 0° C. during 3 h. The excess of hydride was quenched with acetone, and the solvent was evaporated. A suspension of the resulting boronic acid (or any other boronic acid), 5-bromo-2-nitroaniline (2) (697 mg, 3.21 mmol) (scheme 1, Example 1) POT (305 mg, 1.00 mmol), Pd(PPh$_3$)$_4$ (241 mg, 0.209 mmol) and K$_2$CO$_3$ (1.33 g, 9.63 mmol) in DME (12 ml) and water (4 ml) was stirred during 16 h at 80° C. The solvent was evaporated; ethyl acetate was added and washed with saturated solution of NaCl. The organic layer was dried over MgSO$_4$, filtered and concentrated. After purification by flash chromatography on silica gel (eluent 40% EtOAc in Hexanes), 605 mg (75%) of compound 90 was obtained as a orange oil. $^1$H NMR: (400 MHz, DMSO) δ (ppm): 7.98 (d, J=9.0 Hz, 1H), 7.52 (d, J=5.3 Hz, 1H), 7.44 (s, 2H), 7.15 (d, J=5.3 Hz, 1H), 7.02 (d, J=1.8 Hz, 1H), 6.73 (dd, J=9.0, 2.0 Hz, 1H), 5.72 (t, J=5.4 Hz, 1H), 4.70 (d, J=5.5 Hz, 2H).

Step 2. 5-(2-((tert-butyldimethylsilyloxy)methyl)thiophen-3-yl)-2-nitrobenzenamine (91)

A solution of 90 (600 mg, 2.39 mmol), imidazole (245 mg, 3.60 mmol) and TBDMSCI (543 mg, 3.60 mmol) in DMF (20 ml) was stirred at room temperature during 16 h. The solvent was evaporated, ethyl acetate was added and washed with saturated solution of NaCl. The organic layer was dried over MgSO$_4$, filtered and concentrated. The residue was purified by flash chromatography (eluent 5-10% EtOAc in hexanes) to afford 674 mg (77%) of compound 91 as a yellow oil. $^1$H NMR: (400 MHz, DMSO) δ (ppm): 7.97 (d, J=8.8 Hz, 1H), 7.53 (d, J=5.1 Hz, 1H), 7.45 (s, 2H), 7.15 (d, J=5.3 Hz, 1H), 6.98 (d, J=1.8 Hz, 1H), 6.70 (dd, J=8.8, 2.0 Hz, 1H), 4.91 (s, 2H), 0.89 (s, 9H), 0.07 (s, 6H).

Step 3. 5 N-(5-(2-(((tert-Butyldimethylsilyloxy)methyl)thiophen-3-yl)-2-nitrophenyl)-4-methoxybenzamide (92)

A solution of 91 (636 mg, 1.74 mmol) and 4-methoxybenzoyl chloride (446 mg, 2.62 mmol) in pyridine (10 ml) was stirred at room temperature during 16 h. The solvent was evaporated, ethyl acetate was added and washed with a saturated solution of NH$_4$Cl and then with a saturated solution NaCl. The organic layer was dried over MgSO$_4$, filtered and concentrated. After purification by flash chromatography on silica gel (eluent 5-10% EtOAc in Hexanes), 804 mg (93%) of compound 92 was obtained as a yellow oil. $^1$H NMR: (400 MHz, DMSO) δ (ppm): 10.64 (s, 1H), 8.05 (d, J=8.6 Hz, 1H), 7.95-7.93 (m, 3H), 7.59 (d, J=5.3 Hz, 1H), 7.46 (dd, J=8.6, 2.0 Hz, 1H), 7.28 (d, J=5.3 Hz, 1H), 7.10 (dt, J=9.0, 2.2 Hz, 2H), 4.95 (s, 2H), 3.85 (s, 3H), 0.88 (s, 9H), 0.09 (s, 6H).

Step 4. N-(2-Amino-5-(2-((tert-butyldimethylsilyloxy)methyl)thiophen-3-yl)phenyl)-4-methoxybenzamide (93) and N-(2-amino-5-(2-(hydroxymethyl)thiophen-3-yl)phenyl)-4-methoxybenzamide (94)

A suspension of 92 (800 mg, 1.60 mmol), SnCl$_2$.2H$_2$O (2.17 g, 9.63 mmol) and NH$_4$OAc (1.23 g, 16.0 mmol) in a 1:1:1 mixture of MeOH/THF/water was stirred at room temperature during 16 h. Tin salts were filtered out and rinsed with EtOAc. The solvent was evaporated, ethyl acetate was added and washed with a saturated solution of NaHCO₃ and then with a saturated solution NaCl. The organic layer was dried OVER MgSO₄, filtered and concentrated. After purification by flash chromatography on silica gel (eluent 0.5-5% MeOH in DCM), 200 mg (27%) of compound 93 was obtained as a beige powder and 92 mg (16%) of compound 94 was obtained as a beige powder.

Compound 93: ¹H NMR: (DMSO) δ (ppm): 9.54 (s, 1H), 7.96 (d, J=8.8 Hz, 2H), 7.43 (d, J=5.1 Hz, 1H), 7.28 (d, J=1.8 Hz, 1H), 7.09-7.02 (m, 4H), 6.81 (d, J=8.2 Hz, 1H), 5.05 (s, 2H), 4.82 (s, 2H), 3.83 (s, 3H), 0.87 (s, 9H), 0.06 (s, 6H). MS: (calc.) 468.2; (obt.) 491.2 (M+Na)⁺.

Compound 94: ¹H NMR: (DMSO) δ (ppm): 9.57 (s, 1H), 7.96 (d, J=8.8 Hz, 2H), 7.40 (d, J=5.1 Hz, 1H), 7.23 (d, J=1.8 Hz, 1H), 7.09-7.02 (m, 4H), 6.81 (d, J=8.0 Hz, 1H), 5.51 (t, J=5.4 Hz, 1H), 5.01 (s, 2H), 4.64 (d, J=5.3 Hz, 2H), 3.83 (s, 3H). MS: (calc.) 354.1; (obt.) 354.1 (M+Na)⁺.

Examples 21

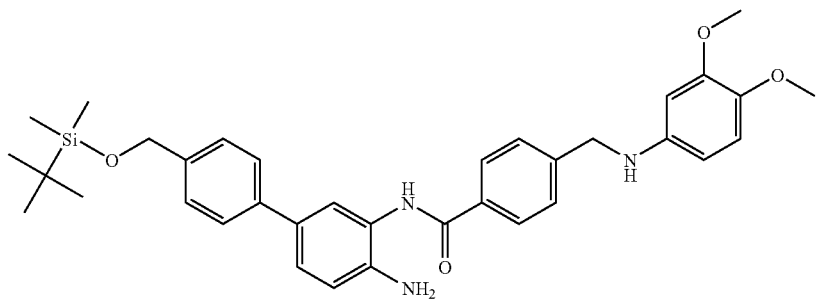

N-(2-Amino-5-(4-((tert-butyldimethylsilyloxy)methyl)phenyl)phenyl)-4-((3,4-dimethoxyphenylamino)methyl)benzamide (99) and Example 21-1

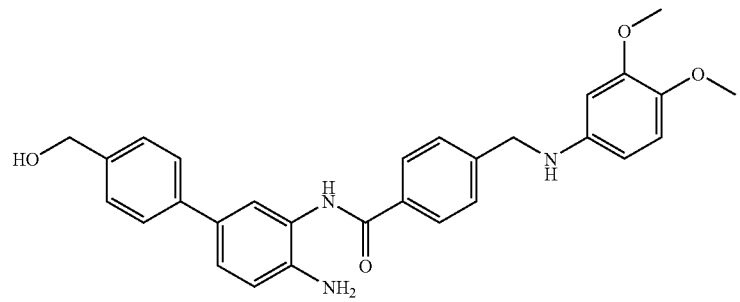

N-(2-amino-5-(4-(hydroxymethyl)phenyl)phenyl)-4-({3,4-dimethoxyphenylamino)methyl)benzamide (100)

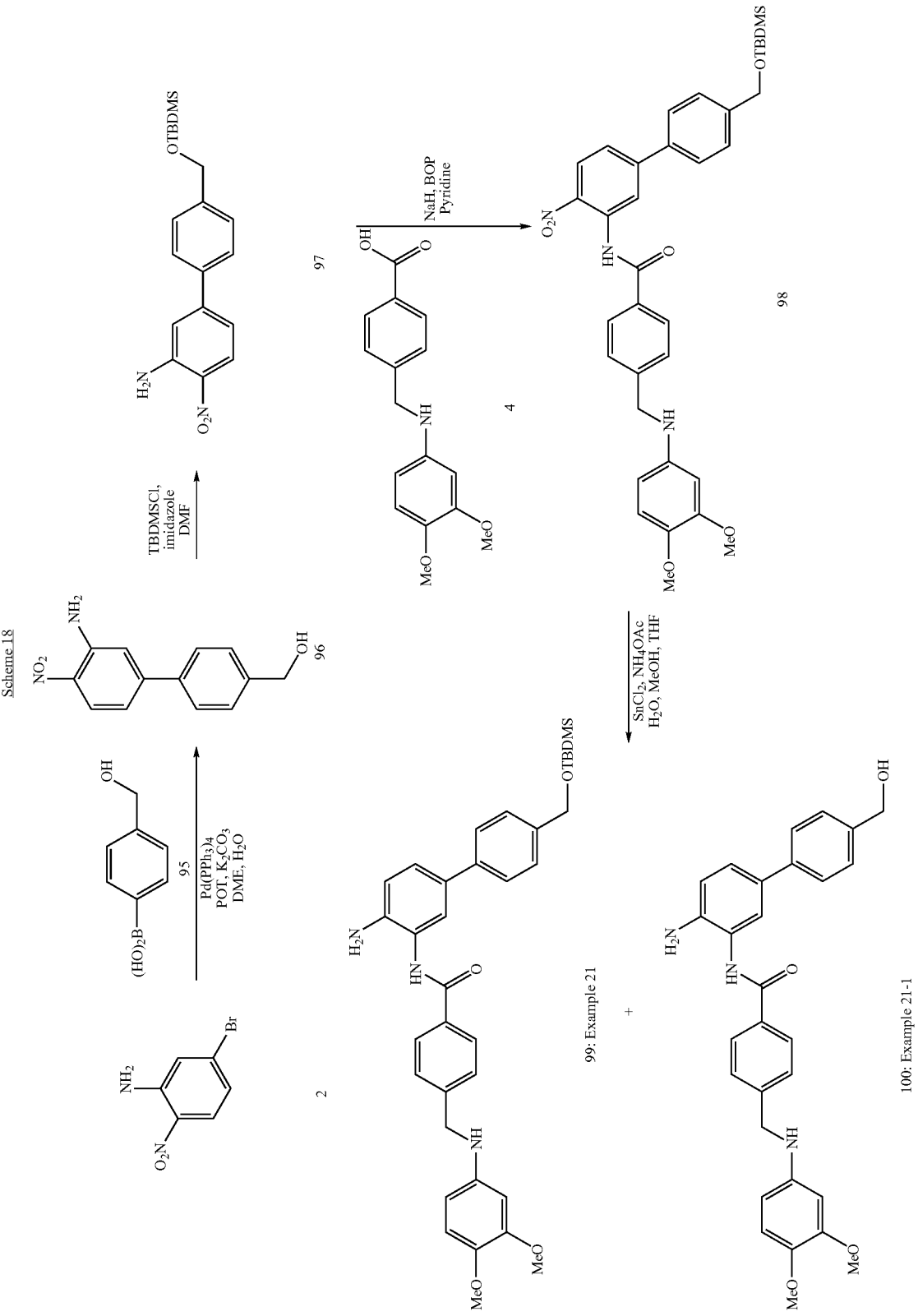

Steps 1 and 2. 2-Nitro-5-((4-(tert-butyldimethylsily-loxy)methyl)phenyl)aniline (97)

The compound 97 was obtained following the same procedure as for the Examples 19 and 20, steps 1 and 2 (scheme 17) in 78% yield. $^1$H NMR: (400 MHz, DMSO) δ (ppm): 8.01 (d, J=9.0 Hz, 1H), 7.61 (d, J=8.2 Hz, 2H), 7.46 (s, 2H), 7.41 (d, J=8.0 Hz, 2H), 7.27 (d, J=2.0 Hz, 1H), 6.91 (dd, J=9.0, 2.0 Hz, 1H), 0.92 (s, 9H), 0.11 (s, 6H).

Step 3. N-(2-nitro-5-(4-((tert-butyldimethylsilyloxy)methyl)phenyl)phenyl)-4-((3,4-dimethoxyphenylamino)methyl)benzamide (98)

The compound 98 was obtained following the same procedure as in the Example 1, step 3 (scheme 1) in 28% yield. $^1$H NMR: (DMSO) δ (ppm): 10.77 (s, 1H), 8.14 (d, J=2.0 Hz, 1H), 8.09 (d, J=8.6 Hz, 2H), 7.91 (d, J=8.4 Hz, 2H), 7.72 (d, J=8.2 Hz, 2H), 7.68 (dd, J=8.6, 2.2 Hz, 1H), 7.53 (d, J=8.4 Hz, 2H), 7.45 (d, J=8.4 Hz, 2H), 6.65 (d, J=8.6 Hz, 2H), 5.99-5.97 (m, 2H), 4.78 (s, 2H), 4.32 (d, J=6.3 Hz, 2H), 3.66 (s, 3H), 3.59 (s, 3H), 0.93 (s, 9H), 0.11 (s, 6H).

Step 4. N-(2-amino-5-(4-(tert-butyldimethylsilyloxy)methyl)phenyl)phenyl)-4-((3,4-dimethoxyphenylamino)methyl)benzamide (99) and N-(2-amino-5-(4-(hydroxymethyl)phenyl)phenyl)-4-((3,4-dimethoxyphenylamino)methyl)benzamide (100)

The compounds 99 and 100 were obtained following the same procedure as in Examples 19 and 20, step 4 (scheme 17).

Compound 99: $^1$H NMR: (DMSO) δ (ppm): 9.66 (s, 1H), 7.93 (d, J=8.0 Hz, 2H), 7.52-7.46 (m, 5H), 7.31-7.29 (m, 3H), 6.84 (d, J=7.6 Hz, 1H), 6.64 (d, J=8.6 Hz, 1H), 6.32 (s, 1H), 6.00-5.98 (m, 2H), 5.06 (s, 2H), 4.70 (s, 2H), 4.30 (d, J=5.9 Hz, 2H), 3.66 (s, 3H), 3.59 (s, 3H), 0.91 (s, 9H), 0.10 (s, 6H). MS: (calc.) 597.2 (obt.) 598.5 (MH)$^+$.

Compound 100: $^1$H NMR: (DMSO) δ (ppm): 9.67 (s, 1H), 7.93 (d, J=7.8 Hz, 2H), 7.50-7.46 (m, 5H), 7.31-7.29 (m, 3H), 6.84 (d, J=8.0 Hz, 1H), 6.64 (d, J=8.4 Hz, 1H), 6.32 (d, J=2.0 Hz, 1H), 6.00-5.98 (m, 2H), 5.15 (t, J=5.5 Hz, 1H), 5.06 (s, 2H), 4.49 (d, J=5.7 Hz, 2H), 4.31 (d, J=5.9 Hz, 2H), 3.66 (s, 3H), 3.59 (s, 3H). MS: (calc.) 483.2; (obt.) 484.4 (MH)$^+$.

Examples 22

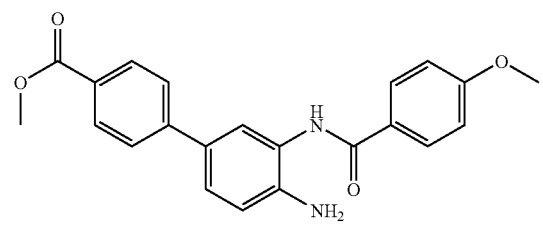

N-(2-Amino-5-(4-methoxycarbonylphenyl)phenyl)-4-methoxybenzamide (104) and

Example 23

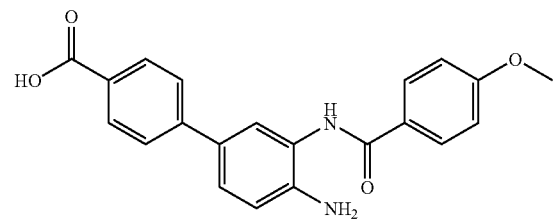

N-(2-Amino-5-(4-carboxyphenyl)phenyl)-4-methoxybenzamide (105)

Scheme 19

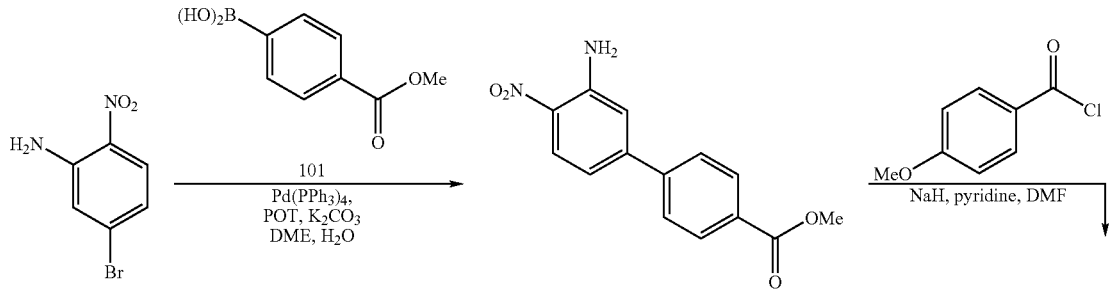

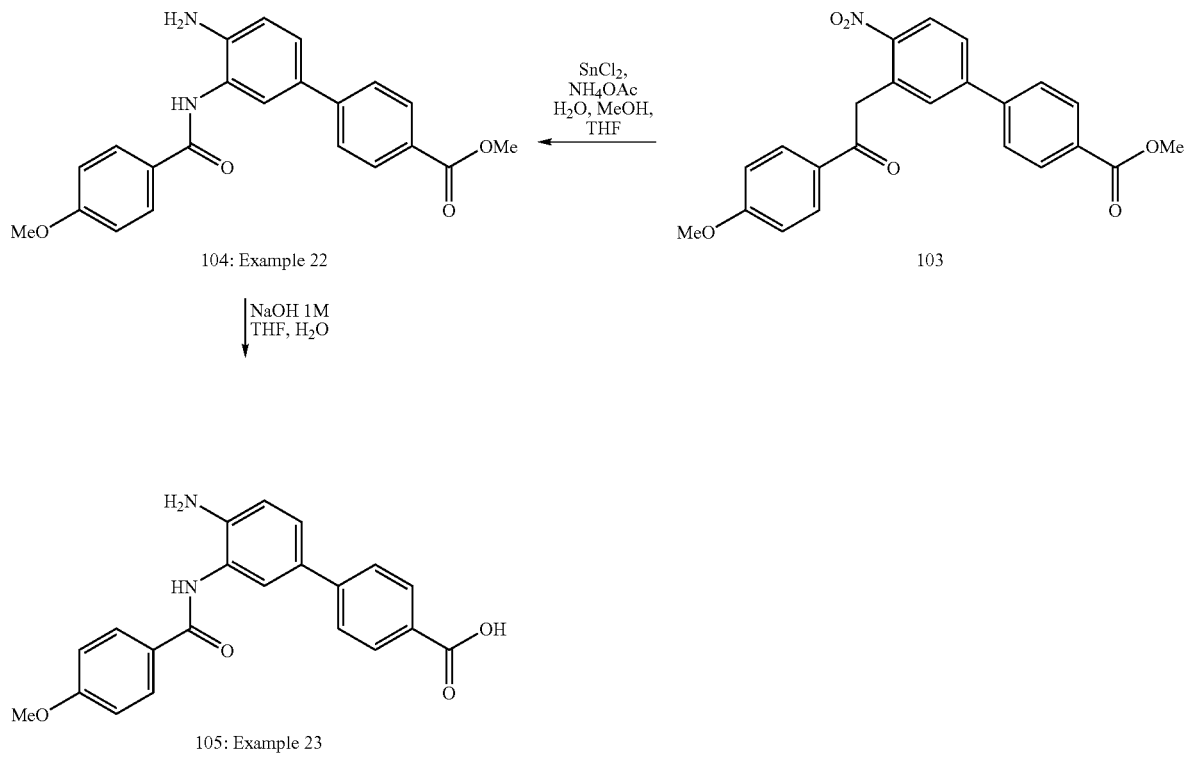

Step 1. 2-Nitro-5-(4-methoxycarbonylphenyl)aniline (102)

The compound 102 was obtained following the same procedure as in Example 19 and 20, step 1 (scheme 17) but substituting the boronic acid 89 for the boronic acid 101 in 70% yield. $^1$H NMR: (400 MHz, DMSO) δ (ppm): 8.07-8.04 (m, 3H), 7.78 (d, J=8.2 Hz, 2H), 7.50 (s, 2H), 7.34 (d, J=2.0 Hz, 1H), 6.96 (dd, J=9.0, 2.2 Hz, 1H), 3.88 (s, 3H).

Step 2. N-(2-Nitro-5-(4-methoxycarbonylphenyl)phenyl)-4-methoxybenzamide (103)

A suspension of 102 (599 mg, 2.20 mmol), NaH 60% (141 mg, 3.52 mmol) and 4-methoxybenzoyl chloride (450 mg, 2.64 mmol) in pyridine (5 ml) and DMF (12 ml) was stirred at room temperature during 48 h. The solid was filtered out and rinsed with MeOH to give 584 mg (82%) of the title compound 103 as a yellow solid. $^1$H NMR: (400 MHz, DMSO) δ (ppm): 10.72 (s, 1H), 8.13-8.08 (m, 3H), 7.96 (d, J=8.8 Hz, 2H), 7.90 (d, J=8.6 Hz, 2H), 7.74 (dd, J=8.6, 2.2 Hz, 1H), 7.11 (d, J=8.8 Hz, 1H), 3.89 (s, 3H), 3.86 (s, 3H).

Step 3. N-(2-Amino-5-(4-methoxycarbonylphenyl)phenyl)-4-methoxybenzamide (104)

The compound 104 was obtained following the same procedure as in Example 19 and 20, step 4 (scheme 17) in 10% yield. $^1$H NMR: (DMSO) δ (ppm): 9.61 (s, 1H), 7.98 (d, J=8.8, Hz, 2H), 7.95 (d, J=8.4 Hz, 2H), 7.71 (d, J=8.4 Hz, 2H), 7.60 (d, J=2.2 Hz, 1H), 7.43 (dd, J=8.4, 2.2 Hz, 1H), 7.04 (d, J=8.8 Hz, 2H), 6.86 (d, J=8.4 Hz, 1H), 5.27 (sb, 2H), 3.85 (s, 3H), 3.84 (s, 3H). MS: (calc.) 376.1; (obt.) 377.1 (MH)$^+$.

Step 4. N-(2-Amino-5-(4-carboxyphenyl)phenyl)-4-methoxybenzamide (105)

A solution of 104 (44 mg, 0.117) and NaOH 1M (0.24 ml, 0.24 mmol) in THF (1 ml) and water (1 ml) was stirred 48 h at 40° C. HCl 1M was added and the precipitate was filtered out. The solid was further purified by flash chromatography (eluent 3-5% MeOH in DCM), to give the compound 105 (34 mg, 80% yield). $^1$H NMR: (DMSO) δ (ppm): 9.61 (s, 1H), 7.98 (d, J=8.6 Hz, 2H), 7.93 (d, J=8.2 Hz, 2H), 7.66 (d, J=8.2 Hz, 2H), 7.58 (d, J=2.0 Hz, 1H), 7.40 (dd, J=8.2, 2.0 Hz, 1H), 7.04 (d, J=8.8 Hz, 2H), 6.86 (d, J=8.4 Hz, 1H), 5.23 (s, 2H), 3.84 (s, 3H). MS: (calc.) 362.1; (obt.) 363.1 (MH)$^+$.

Example 24

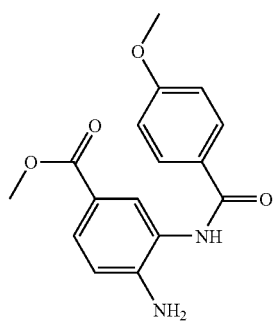

Methyl 4-amino-3-(4-methoxybenzamido)benzoate
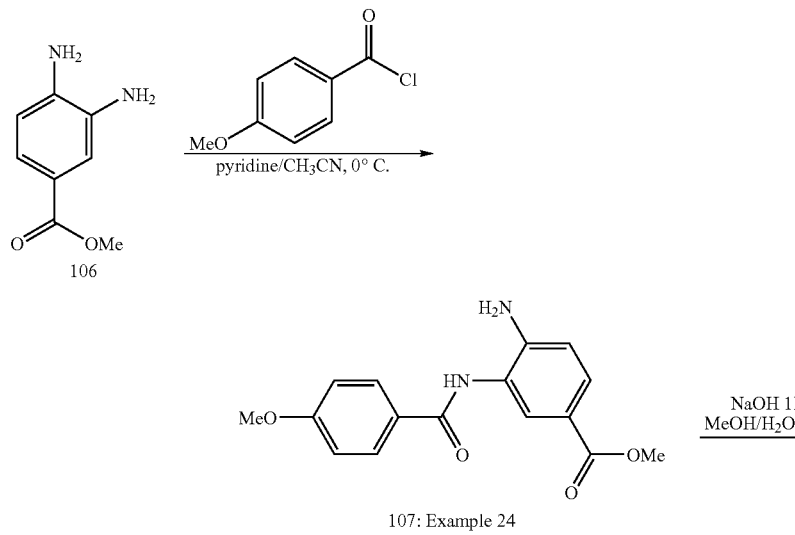
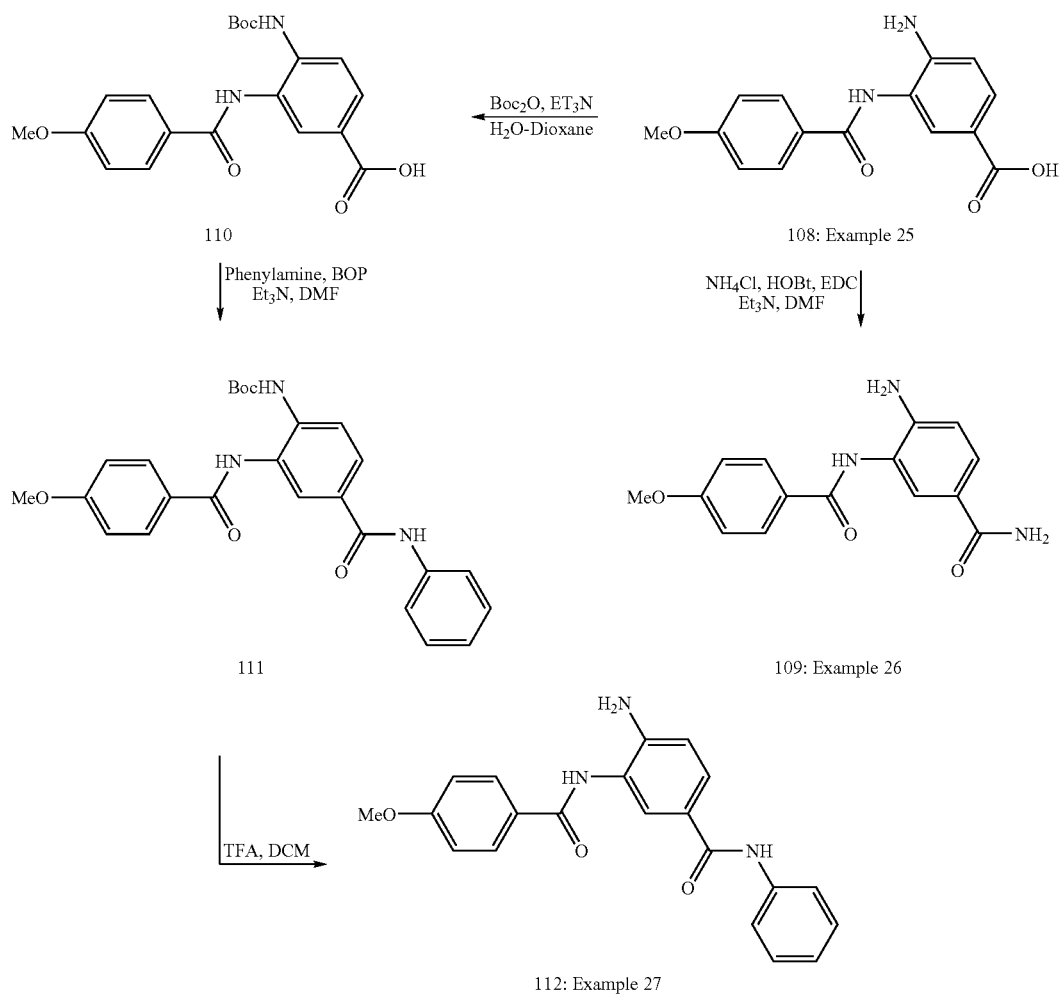

Step 1. Methyl 4-amino-3-(4-methoxybenzamido)benzoate (107)

A solution of 4-methoxybenzoyl chloride (1.03 g, 6.02 mmol) in CH₃CN (6 ml) was added drop wise to a solution of methyl 3,4-diaminobenzoate (106) (1.00 g, 6.02 mmol) and pyridine (0.49 ml, 6.02 mmol) in CH₃CN (25 ml) at 0° C. The reaction mixture was stirred for 3 h at 0° C. and the solvent was evaporated. Ethyl acetate was added and the organic layer was washed successively with saturated solutions of NH₄Cl, NaHCO₃ and NaCl, dried over MgSO₄, filtered and concentrated. After purification by flash chromatography on silica gel (eluent 1-3% MeOH in DCM), 1.03 g (56%) of compound 107 was obtained as a off white solid. ¹H NMR: (DMSO) δ(ppm): 9.51 (s, 1H), 7.96 (d, J=8.8 Hz, 2H), 7.75 (d, J=2.0 Hz, 1H), 7.56 (dd, J=8.4, 2.0 Hz, 1H), 7.03 (d, J=9.0 Hz, 2H), 6.75 (d, J=8.4 Hz, 1H), 5.80 (s, 2H), 3.83 (s, 3H), 3.75 (s, 3H). MS: (calc.) 300.1; (obt.) 301.1 (MH)⁺.

Example 25

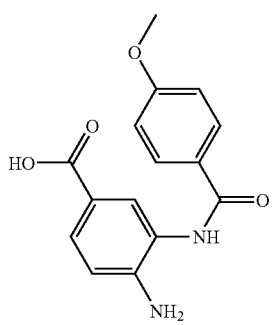

4-Amino-3-(4-methoxybenzamido)benzoic acid (108)

Step 1. 4-Amino-3-(4-methoxybenzamido)benzoic acid (108)

A suspension of 107 (400 mg, 1.33 mmol) and 1M NaOH (2.7 ml, 2.66 mmol) in 1:1 THF:MeOH (6 ml) was heated at 50° C. for 16 h. HCl 1M was added to reach pH=4 and the solid was filtered to give 370 mg (97%) of compound 108 as a white solid. ¹H NMR: (DMSO) δ (ppm): 9.52 (s, 1H), 7.96 (d, J=8.8 Hz, 2H), 7.71 (d, J=2.0 Hz, 1H), 7.54 (dd, J=8.4, 2.0 Hz, 1H), 7.02 (d, J=9.0 Hz, 2H), 6.74 (d, J=8.4 Hz, 1H), 5.69 (s, 2H), 3.83 (s, 3H). MS: (calc.) 361.1; (obt.) 362.3 (MH)⁺.

Example 26

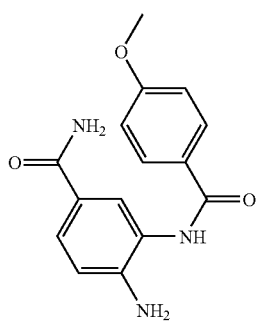

N-(2-amino-5-carbamoylphenyl)-4-methoxybenzamide (109)

Step 1. N-(2-amino-5-carbamoylphenyl)-4-methoxybenzamide (109)

A solution of 108 (200 mg, 0.70 mmol), NH₄Cl (74 mg, 1.40 mmol), HOBT-hydrate (104 mg, 0.77 mmol), EDC (119 mg, 0.77 mmol) and Et₃N (0.29 ml, 2.1 mmol) in DMF (3 ml) was stirred for 16 h at room temperature. The solvent was evaporated, ethyl acetate was added and the organic layer was washed successively with saturated solutions of NH₄Cl, NaHCO₃ and NaCl, dried over MgSO₄, filtered and concentrated. The crude product was triturated in ethyl acetate and filtered to give the title compound 109 (60 mg, 30%). ¹H NMR: (DMSO) δ (ppm): 9.57 (s, 1H), 7.96 (d, J=8.8 Hz, 2H), 7.67 (d, J=2.2 Hz, 1H), 7.59 (sb, 1H), 7.52 (dd, J=8.2, 2.0 Hz, 1H), 7.02 (d, J=8.8 Hz, 2H), 6.90 (sb, 1H), 6.72 (d, J=8.4 Hz, 1H), 5.41 (s, 2H), 3.83 (s, 3H). MS: (calc.) 285.1; (obt.) 286.1 (MH)⁺.

Example 27

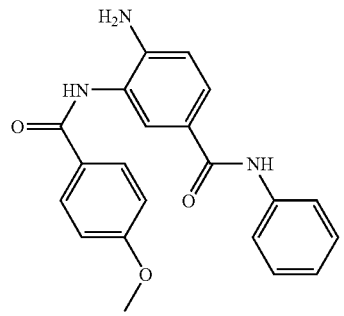

N-(2-amino-5-phenylcarbamoylphenyl)-4-methoxybenzamide (112)

Step 1. 4-(tert-Butoxycarbonyl)-3-(4-methoxybenzamido)benzoic acid (110)

A solution of 108 (700 mg, 2.45 mmol), BoC₂O (801 mg, 3.67 mmol) and Et₃N (0.51 ml, 3.67 mmol) in 2:1 dioxane: water (15 ml) was stirred for 16 h at room temperature. The solvent was concentrated and HCl 1 M was added to reach a pH=5. The precipitate was filtered to give 736 mg (78%) of the title compound 110 as a beige solid. ¹H NMR: (DMSO) δ (ppm): 9.81 (s, 1H), 8.87 (s, 1H), 8.02 (d, J=1.6 Hz, 1H), 7.95 (dt, J=9.0, 2.2 Hz, 2H), 7.75-7.74 (m, 2H), 7.07 (dt, J=9.0, 2.2 Hz, 2H), 3.84 (s, 3H), 1.46 (s, 9H).

Step 2. tert-Butyl 24-(methoxybenzamido)-(phenyl-carbamoyl)phenylcarbamate (111)

A solution of 110 (373 mg, 0.965 mmol), aniline (0.11 ml, 1.16 mmol), BOP (640 mg, 1.45 mmol) and Et$_3$N (0.40 ml, 1.45 mmol) in DMF (3 ml) was stirred during 16 h at room temperature. The solvent was evaporated, ethyl acetate was added and the organic layer was washed with saturated solutions of NH$_4$Cl, NaHCO$_3$ and NaCl, dried over MgSO$_4$, filtered and concentrated. After purification by flash chromatography on silica gel (eluent 30-40% AcOEt in hexane), 352 mg (79%) of compound III was obtained as a white solid. $^1$H NMR: (DMSO) δ (ppm): 10.17 (s, 1H), 9.86 (s, 1H), 8.83 (s, 1H), 7.97 (dt, J=9.0, 2.2 Hz, 2H), 7.84-7.73 (m, 4H), 7.35-7.31 (m, 2H), 7.10-7.05 (m, 3H), 3.85 (s, 3H), 1.47 (s, 9H).

Step 3. N-(2-amino-5-phenylcarbamoylphenyl)-4-methoxybenzamide (112)

A solution of 111 (343 mg, 0.743 mmol) and TFA (0.5 ml) in DCM (3 ml) was stirred for 16 h at room temperature. The solvent was evaporated and the solid was purified by flash chromatography (eluent 2-3% MeOH/DCM) to afford the title compound 112 as an off-white solid (230 mg, 86% yield). $^1$H NMR: (DMSO) δ (ppm): 9.83 (s, 1H), 9.62 (s, 1H), 7.99 (d, J=8.8 Hz, 2H), 7.82 (d, J=2.0 Hz, 1H), 7.73 (dd, J=8.8, 1.2 Hz, 2H), 7.67 (dd, J=8.4, 2.2 Hz, 1H), 7.31-7.27 (m, 2H), 7.05-7.01 (m, 3H), 6.80 (d, J=8.4 Hz, 1H), 3.84 (s, 3H). MS: (calc.) 361.1; (obt.) 362.1 (MH)$^+$.

Example 28

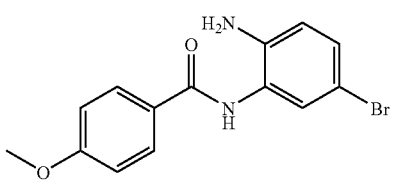

N-(2-amino-5-bromo-phenyl)-4-methoxy-benzamide (114)

Scheme 21

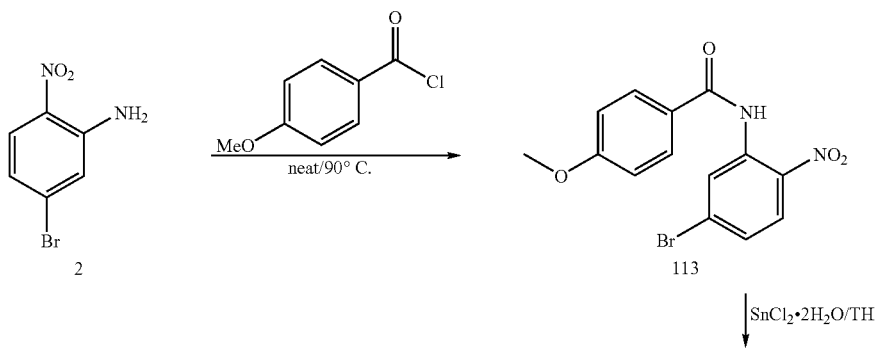

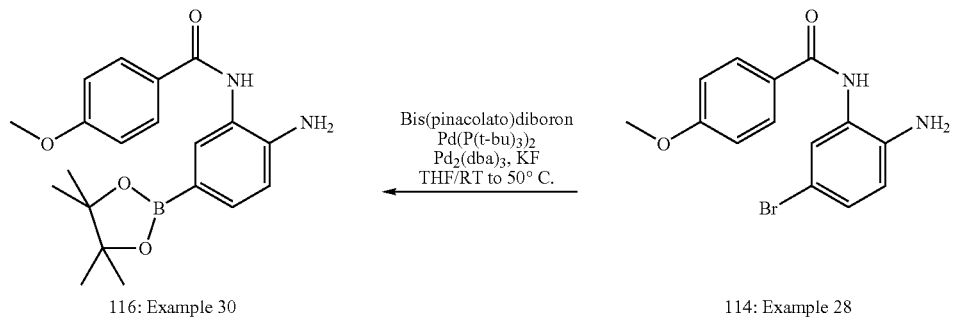

116: Example 30      114: Example 28

-continued

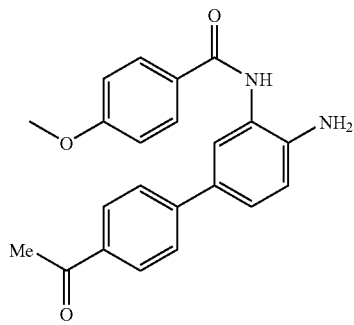

117: Example 31

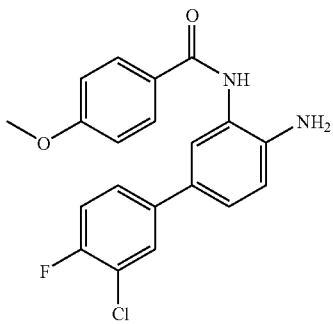

115: Example 29

Steps 1 and 2. N-(2-Amino-5-bromo-phenyl)-4-methoxy-benzamide (114)

In aflame dried, round bottom flask, 5-bromo-2-nitroaniline (2) (10.66 g, 49.09 mmol), (scheme 1, Example 1), and 4-methoxybenzoyl chloride (8.37 g, 49.09 mmol) were added. The mixture was heated to 90° C. The melted solids were stirred overnight to give a yellow-brown solid. THF (250 mL) was then added and the solution was treated with SnCl$_2$.2H$_2$O (55.38 g, 245.45 mmol, 5.0 eq) and stirred at room temperature for 2 hrs. Approx. half of the THF was evaporated then 200 mL of EtOAc and 100 mL sat. NaHCO$_3$ were added. The precipitated tin salt was taken out by filtration and a work-up was done on the filtrate with EtOAc. The combined organic layers were washed with water and brine and dried over MgSO$_4$. Most of the EtOAc was evaporated then hexane was added and the precipitate was collected by filtration to give the title compound 114 as a beige powder (13.40 g, 85% yield). $^1$H NMR (DMSO-d$_6$) δ(ppm): 9.52 (s, 1H), 7.93 (d, J=9.0 Hz, 2H), 7.34 (d, J=2.3 Hz, 1H), 7.08 (dd. J=8.6, 2.3 Hz, 1H), 7.02 (d, J=9.0 Hz, 2H), 6.71 (d, J=8.6 Hz, 1H) 5.10 (s, 2H), 3.82 (s, 3H).

Example 29

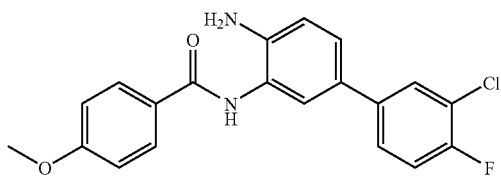

N-(2-amino-5-(3-chloro-4-fluorophenyl)phenyl)-4-methoxybenzamide (115)

Step 1. N-(2-Amino-5-(3-chloro-4-fluorophenyl) phenyl)-4-methoxybenzamide (115)

The compound 115 was obtained following the same Suzuki coupling procedure as in Examples 19 and 20 step 1 (scheme 17) in 84% yield. $^1$H NMR (DMSO) δ (ppm): 9.59 (s, 1H), 7.97 (d, J=8.8 Hz, 2H), 7.71 (dd, J=7.2, 2.3 Hz, 1H), 7.56-7.52 (m, 1H), 7.51 (d, J=2.2 Hz, 1H), 7.40 (t, J=9.0 1H), 7.33 (dd, J=8.2, 2.3, 1H), 7.04 (d, J=9.0 Hz, 2H), 6.84 (d, J=8.4 Hz, 1H), 5.16 (sb, 2H), 3.84 (s, 3H). MS: (calc.) 370.1; (obt.) 371.1 (MH)$^+$.

Example 30

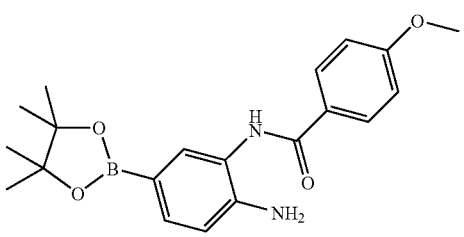

N-[2-Amino-5-(4,4,5,5-tetramethyl-[1,3,2]dioxaborolan-2-yl)-phenyl]-4-methoxy-benzamide (116)

Step 1. N-[2-Amino-5-(4,4,5,5-tetramethyl-[1,3,2] dioxaborolan-2-yl)-phenyl]-4-methoxy-benzamide (116)

In a 75 mL pressure vessel, N-(2-amino-5-bromo-phenyl)-4-methoxy-benzamide (114) (2.95 g, 9.19 mmol.), bis(pinacolato)diboron (2.80 g, 11.03 mmol) and THF (25 mL) were added. Air was then removed by vacuum and then the vessel was purged with nitrogen. Pd(P(t-Bu)$_3$)$_2$ (0.070 g, 0.14 mmol), Pd$_2$(dba)$_3$ (0.063 g, 0.07 mmol) and KF (1.76 g, 30.34 mmol, 3.3 eq.) were then added and the air was removed after each addition. The pressure vessel was sealed and the mixture was stirred at 50° C. for a week. The two palladium catalysts were added again after 2 and 4 days. After completion of the reaction, the mixture was extracted with EtOAc. The combined organic layers were rinsed with water and brine and concentrated. The obtained oil was then purified by column chromatography on silica gel with EtOAc/hexane (50:50) to give the title compound 116 as a pale yellow solid (1.53 g, 45%). $^1$H NMR (DMSO-d$_6$) δ(ppm): 9.47 (s, 1H), 7.95 (d, J=8.8 Hz, 2H), 7.41 (d, J=1.4 Hz, 1H), 7.24 (dd, J=7.8, 1.4 Hz, 1H), 7.01 (d, J=8.8 Hz, 2H), 6.70 (d, J=7.8 Hz, 1H), 5.31 (s, 2H), 3.82 (s, 3H), 1-25 (s, 12H).

Example 31

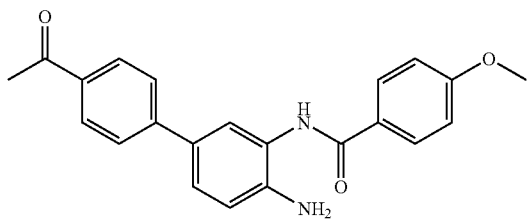

N-(4'-Acetyl-4-amino-biphenyl-3-yl)methoxy-benzamide (117)

Step 1. N-(4'-Acetyl-4-amino-biphenyl-3-yl)-4-methoxy-benzamide (117)

In a pressure vessel, N-[2-Amino-5-(4,4,5,5-tetramethyl-[1,3,2]dioxaborolan-2-yl)-phenyl]-4-methoxybenzamide (116) (170 mg, 0.462 mmol), 1-(4-bromophenyl)ethanone (184 mg, 0.923 mmol), (or any aryl bromide from the tables below), DME (4.6 mL per mmol of 116) and H$_2$O (2.15 mL per mmol of 116) were added. Air was then removed by vacuum and then the vessel was purged with nitrogen. Pd(PPh$_3$)$_4$ (27 mg, 0.023 mmol, 0.05 eq.) and Na$_2$CO$_3$ (147 mg, 1.38 mmol, 3.0 eq.) were then added and oxygen was removed after each addition. The pressure vessel was sealed and the mixture was stirred at 75° C. overnight. The mixture was cooled at room temp., water was added and the mixture was extracted with EtOAc. The combined organic layers were rinsed with brine, dried over MgSO$_4$ and concentrated to give 42 mg (25%) of the title compound 117. $^1$H NMR (DMSO-d$_6$) (ppm): 9.61 (s, 1H), 7.96 (dd, J=12.8, 8.8 Hz, 4H), 7.70 (d, J=8.8 Hz, 2H), 7.60 (d, J=2.1 Hz, 1H), 7.42 (dd, J=8.4, 2.3 Hz, 1H), 7.04 (d, J=8.8 Hz, 2H), 6.86 (d, J=8.2 Hz, 1H), 5.26 (s, 2H), 3.84 (s, 3H), 2.58 (s, 3H). MS (m/z): 360.41 (calc) 361.1 (MH+) (found).

TABLE 3a

| Commercially available aryl bromide | Example | Cmpd |
|---|---|---|
| Br—C₆H₄—C(O)Me | 31 | 117 |
| Br—C₆H₅ | 31aa | 117aa |
| Br—C₆H₄—CN | 31bb | 117bb |

TABLE 3a-continued

| Commercially available aryl bromide | Example | Cmpd |
|---|---|---|
| Br-thiophene-C(O)Me | 31cc | 117cc |
| Br—C₆H₄—CH₂CH₂OH | 31dd | 117dd |
| Br-pyridin-3-yl | 31ee | 117ee |
| Br—C₆H₄—S(O)₂Me | 31ff | 117ff |
| Br—C₆H₄—CH₂C(O)OH | 31gg | 117gg |
| Br—C₆H₄—NHC(O)Me | 31hh | 117hh |
| Br-pyridin-4-yl | 31ii | 117ii |
| Br—C₆H₄—OH | 31jj | 117ii |
| Br—C₆H₄—OMe | 31kk | 117jj |
| Br-2-methylbenzothiazole | 31ll | 117ll |
| Br—C₆H₄—CH₂CH₂OH (meta) | 31mm | 117mm |
| Br-pyrimidin-5-yl | 31nn | 117nn |

TABLE 3a-continued
| Commercially available aryl bromide | Example | Cmpd |
|---|---|---|
| 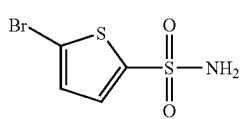 | 31oo | 117oo |
| 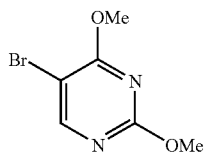 | 31pp | 117pp |
| 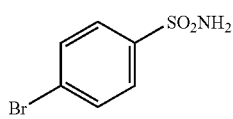 | 31qq | 117qq |
| 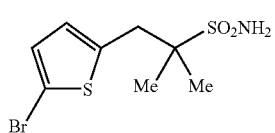 | 31rr | 117rr |
| 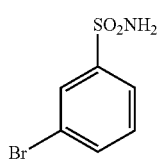 | 31ss | 117ss |
TABLE 3a-continued
| Commercially available aryl bromide | Example | Cmpd |
|---|---|---|
| 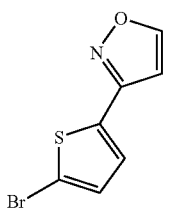 | 31tt | 117tt |
| 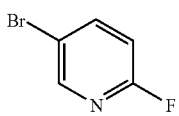 | 31uu | 117uu |
| 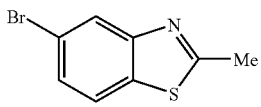 | 31ll | 117ll |
| 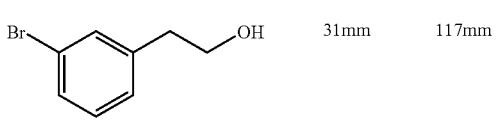 | 31mm | 117mm |

| Non-commercial aryl bromide | Example | Cmpd | Synthetic procedure |
|---|---|---|---|
| 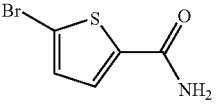 | 31vv | 117vv | J. Med. Chem. 1997, 40, p. 2936-2947, |
| 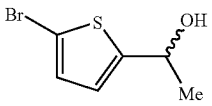 | 31ww | 117ww | <br>1-(5-Bromothiophen-2-yl)ethanol<br>A suspension of lithium aluminum hydride (364 mg, 9.76 (mmol) in diethyl ether (40 mL) was cooled down to −78° C. under $N_2$ and a solution of 2-acetyl-5-bromothiophene (1.00 g, 4.88 mmol) was slowly transferred via canula into the stirring suspension. The mixture was stirred for 2 h at −78° C. and quenched with caution with a 5% HCl solution. The grey mixture was allowed to warm to rt and stirred for additional 16 h. The supernatant was decanted and concentrated in vacuo. The remaining white aluminum aqueous layer was extracted twice with EtOAc. The extracts were combined with the residue produced after evaporation of the supernatant and were washed with $H_2O$, brine, dried over $MgSO_4$, filtered and concentrated again in vacuo affording the title 1-(5-bromothiophen-2-yl)ethanol (870 mg, 87% yield).<br>$^1$H NMR: (400 MHz, DMSO-$d_6$) δ (ppm): 7.00 (d, J = 3.7 Hz, 1H), 6.72 (dd, J = 3.7, 1.0 Hz, 1H), 5.66 (d, J = 4.9 Hz, 1H), 4.85 (quintd, J = 6.1, 1.2 Hz, 1H).<br>LRMS (m/z): 188.9 (M-$H_2O$). |
| 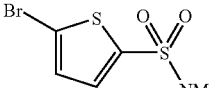 | 31xx | 117xx | 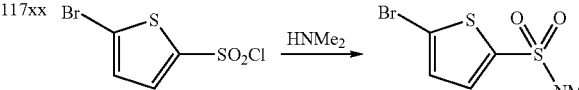<br>5-Bromothiophene-2-(N,N-dimethyl)sulfonamide<br>A round-bottom flask was charged with 5-bromothiophene-2-sulfonylchloride (1.00 g, 3.82 mmol) and a 2 M solution of N,N-dimethylamine (6 mL, 11.46 mmol) in THF was added. The mixture was stirred for 1 h and the solvent was removed in vacuo. The residue was partitioned between EtOAc and $H_2O$. The organic layer was washed with $H_2O$, brine, dried over $MgSO_4$, filtered and concentrated. The resulting colorless liquid was purified by flash chromatography on silica gel using EtOAc/hexanes as an eluent with increasing polarity (10:90 to 20:80) affording the title 5-bromothiophene-2-(N,N-dimethyl)sulfonamide (340 mg, 33% yield).<br>$^1$H NMR: (400 MHz, CDCl$_3$) δ (ppm): 7.30 (d, J = 4.0 Hz, 1H), 7.13 (d, J = 4.0 Hz, 1H), 2.78 (s, 6H).<br>LRMS: (m/z): 270.0/272.0 (M/M + 2)$^+$. |

Example 32

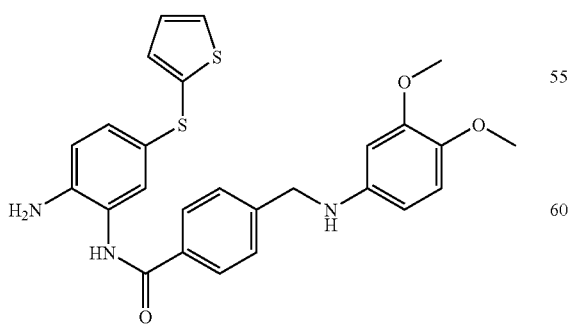

4-((3,4-Dimethoxyphenylamino)methyl)N-(2-amino-5-(thiophen-2-ylthio)phenyl)benzamide (122)

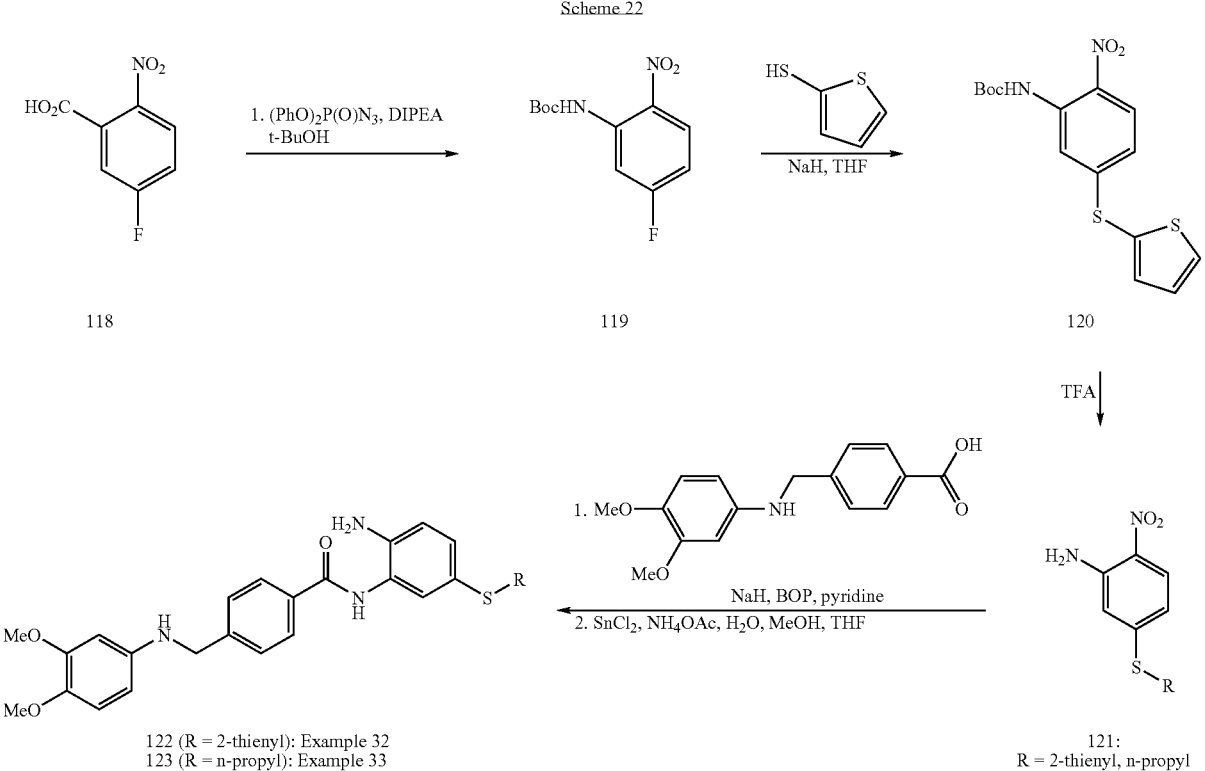

122 (R = 2-thienyl): Example 32
123 (R = n-propyl): Example 33

121:
R = 2-thienyl, n-propyl

Step 1. tert-Butyl 5-fluoro-2-nitrophenylcarbamate (119)

A flame-dried pressure vessel was charged with 5-fluoro-2-nitrobenzoic acid 118 (5.00 g, 27.0 mmol) and dry t-butyl alcohol (50 mL). To this solution were successively added N,N-di-isopropyl-N-ethylamine (5 mL) and diphenylphosphorylazide (6.42 mL, 29.7 mmol). The vessel was closed with teflon cap and the mixture was heated at 90° C. for 2 h. It was then allowed to cool to r.t. over 16 h. The solvent was removed in vacuo and the residue was partitioned between EtOAc and H$_2$O. The aqueous layer was extracted with fresh EtOAc and the combined organic layers were washed with HCl 1N, sat. NaHCO$_3$, brine, dried over MgSO$_4$, filtered and concentrated. The resulting yellow oil was purified by flash chromatography on silica gel using EtOAc/hexanes (10:90) as an eluent, affording the title compound 119 (6.03 g, 87% yield) as light yellow crystals. LRMS: (m/z): 279.3 (M+Na$^+$).

Step 2. tert-Butyl 2-nitro-5-(thiophen-2-ylthio) phenylcarbamate (120)

A pressure vessel was charged with thiophene-2-thiol (236 mg, 2.03 mmol) and THF (4 mL). To this solution were successively added sodium hydride (60% suspension in mineral oil) (86 mg, 2.15 mmol) and compound 119 (500 mg, 1.95 mmol). The vessel was closed with teflon cap and the mixture heated to 90° C. for 2 h. Ht was allowed to cool to r.t.; and the reaction was quenched with H$_2$O, followed by THF removal in vacuo. The residue was partitioned between EtOAc and H$_2$O. The aqueous layer was extracted with fresh EtOAc and the combined organic layers were washed with HCl 1N, sat. NaHCO$_3$, brine, dried over MgSO$_4$, filtered and concentrated. The residue was allowed to crystallize from a mixture of EtOAc/hexane over 72 hours, affording the title compound 120 (610 mg, 88% yield). $^1$H NMR: (400 MHz, Acetone-d$_6$) δ (ppm): 9.67 (s, 1H), 8.32 (d, J=2.2 Hz, 1H), 8.13 (d, J=8.8 Hz, 1H), 7.90 (dd, J=5.3, 1.2 Hz, 1H), 7.50 (dd, J=3.5, 1.2 Hz, 1H), 7.28 (dd, J=5.3, 3.5 Hz, 1H), 6.81 (dd, J=8.8, 2.0 Hz, 1H), 1.53 (s, 9H). LRMS: (m/z): 275.2 (M+Na$^+$).

Step 3. 2-Nitro-5-(thiophen-2-ylthio) aniline (121, R=2-thienyl)

Following the same procedure as in Example 27, step 3 (scheme 20) substituting compound 111 for compound 120 (550 mg, 1.56 mmol), the title compound 121 was obtained (271 mg, 69% yield). $^1$H NMR: (400 MHz, acetone-d$_6$) δ (ppm): 7.97 (d, J=9.0 Hz, 1H), 7.87 (dd, J=5.3, 1.2 Hz, 1H), 7.44 (dd, J=3.5, 1.2 Hz, 1H), 7.25 (dd, J=5.5, 3.7 Hz, 1H), 7.11 (bs, 2H), 6.66 (d, J=2.0 Hz, 1H), 6.42 (dd, J=9.0, 2.0 Hz, 1H). LRMS: (m/z): 253.1 (MH$^+$).

Steps 4 and 5. 4-((3,4-Dimethoxyphenylamino)methyl)-N-(2-amino-5-(thiophen-2-ylthio)phenyl)benzamide (122)

Following the same procedures as in Example 21, steps 3 and 4 (scheme 18) but substituting compound 97 for compound 121 the title compound 122 was obtained in 6% yield (over 2 steps). ¹H NMR: (400 MHz, DMSO-d₆) δ (ppm): 9.57 (s, 1H), 7.87 (d, J=8.4 Hz, 2H), 7.57 (dd, J=5.3, 1.2 Hz, 1H), 7.44 (d, J=8.4 Hz, 2H), 7.27 (d, J=2.0 Hz, 1H), 7.19 (dd, J=3.5, 1.2 Hz, 1H), 7.05 (dd, J=8.2, 2.2 Hz, 1H), 7.01 (dd, J=5.3, 3.5 Hz, 1H), 6.72 (d, J=8.2 Hz, 1H), 6.63 (d, J=8.6 Hz, 1H), 6.30 (d, J=2.5 Hz, 1H), 5.97 (dd, J=8.4, 2.5 Hz, 1H), 5.96 (d, J=6.5 Hz, 1H), 5.20 (s, 2H), 4.28 (d, J=6.3 Hz, 2H), 3.65 (s, 3H), 3.58 (s, 3H). LRMS: (m/z): 492.5 (MH⁺).

Example 33

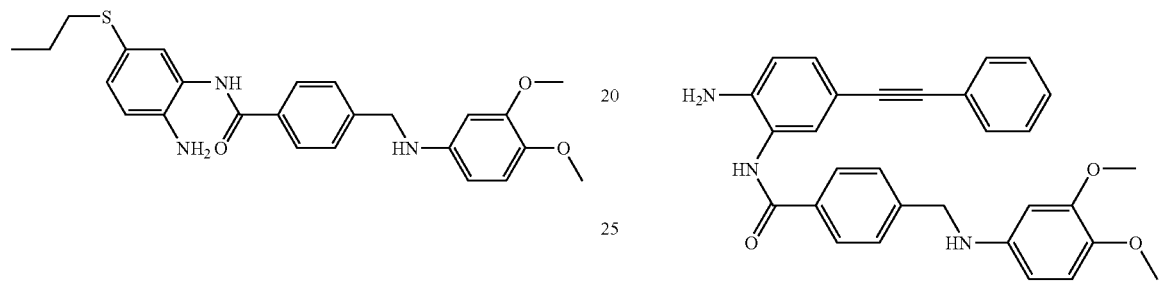

4-((3,4-Dimethoxyphenylamino)methyl)-N-(2-amino-5-propylthio)phenyl)benzamide (123)

Following the same procedures as in Example 21, steps 3 and 4 (scheme 18) but substituting compound 97 for the commercially available 2-nitro-5-(propylthio)aniline (121, R=n-propyl) (222 mg, 1.04 mmol), afforded the title compound (123) as a light yellow oil (102 mg, 22% yield for 2 steps). ¹H NMR: (400 MHz, DMSO-d₆) δ (ppm): 9.57 (s, 1H), 7.89 (d, J=8.2 Hz, 2H), 7.45 (d, J=8.0 Hz, 2H), 7.23 (d, J=0.4 Hz, 1H), 7.01 (dd, J=8.4, 2.2 Hz, 1H), 6.71 (d, J=8.4 Hz, 1H), 6.63 (d, J=8.6 Hz, 1H), 6.31 (d, J=2.3 Hz, 1H), 5.98 (dd, J=8.2, 2.5 Hz, 1H), 5.97 (d, J=5.9 Hz, 1H), 5.04 (s, 2H), 4.29 (d, J=5.9 Hz, 2H), 3.65 (s, 3H), 3.58 (s, 3H), 2.71 (t, J=7.0 Hz, 2H), 1.50 (sext, J=7.0 Hz, 2H), 0.93 (t, J=7.2 Hz, 3H). LRMS: (m/z): 452.5 (MH⁺).

Example 34

4-((3,4-dimethoxyphenylamino)methyl)-N-(2-amino-5-(2-phenylethynyl)phenyl)benzamide (125)

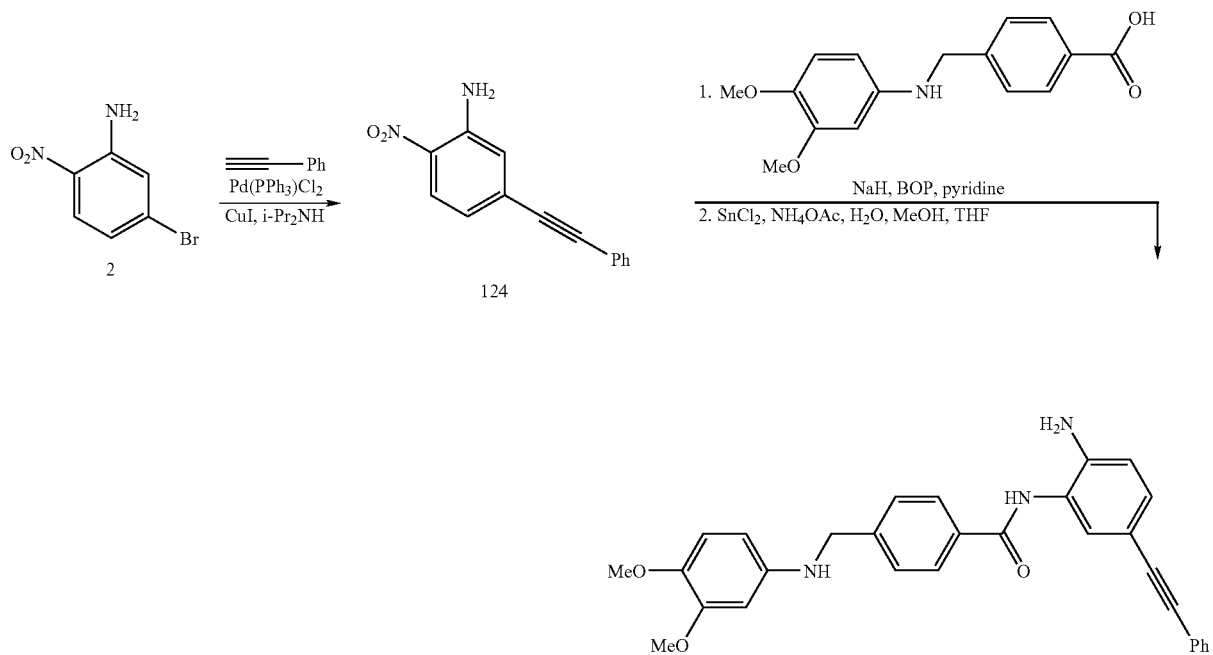

125: Example 34

Step 1. 2-Nitro-5-(2-phenylethynyl)benzenamine (124)

A flame-dried flask was charged with the 5-bromo-2-nitroaniline (2, 300 mg, 1.38 mmol) (scheme 1, Example 1), phenylacetylene (155 mg, 1.52 mmol) and ethyl acetate (13.8 mL). The solution was degassed under vacuum and put under $N_2$ atmosphere. Then, dichlorobis(triphenylphosphine)palladium (48 mg, 0.069 mmol) and copper iodide (26 mg, 0.138 mmol) were added. The yellow solution was degassed again (3 cycles) N,N-diisopropylamine (231 µl, 1.68 mmol) was added and the solution rapidly turned dark. It was degassed twice again and allowed to stir under $N_2$ atmosphere at r.t. over 16 h. Then it was passed through celite and the filtrate was successively washed with dilute aqueous ammonia ($NH_4OH$), saturated $NaHCO_3$, saturated $NH_4Cl$, brine, dried over $MgSO_4$, filtered and concentrated. The resulting dark solid was purified by flash chromatography on silica gel using EtOAc/hexanes as the eluent with increasing polarity (10:90 to 15:85) affording the title compound 124 (242 mg, 74% yield) as a deep yellow solid. $^1$H NMR: (400 MHz, $CD_3OD$) δ(ppm): 8.04 (dd, J=8.8, 0.4 Hz, 1H), 7.54-7.51 (m, 2H), 7.40-7.37 (m, 3H), 7.11 (dd, J=1.8, 0.4 Hz, 1H), 6.73 (dd, J=8.8, 1.8 Hz, 1H). LRMS: (m/z): 239.3 ($MH^+$).

Steps 2 and 3. 4-((3,4-Dimethoxyphenylamino)methyl)-N-(2-amino-5-(2-phenylethynyl)phenyl)benzamide (125)

Following the same procedures as in Example 21, steps 3 and 4 (scheme 18) but substituting compound 97 for compound 124 (240 mg, 1.01 mmol), compound 125 was synthesized (136 mg, 31% yield for 2 steps). $^1$H NMR: (400 MHz, $CD_3OD$) δ (ppm): 7.93 (d, J=8.4 Hz, 2H), 7.52 (d, J=8.2 Hz, 2H), 7.44 (dd, J=8.2, 1.8 Hz, 2H), 7.35-7.29 (m, 4H), 7.21 (dd, J=8.2, 2.0 Hz, 1H), 6.85 (d, J=8.4 Hz, 1H), 6.71 (d, J=8.4 Hz, 1H), 6.36 (d, J=2.7 Hz, 1H), 6.13 (dd, J=8.4, 2.5 Hz, 1H), 4.39 (s, 2H), 3.75 (s, 3H), 3.71 (s, 3H). LRMS: (m/z): 478.5 ($MH^+$).

Examples 34-1

4-((3,4-dimethoxyphenylamino)methyl)-N-(2-amino-5-styrylphenyl)benzamide (127)

Examples 35

4-((3,4-Dimethoxyphenylamino)methyl)-N-(2-amino-5-phenethylphenyl)benzamide (128) and

Example 36

N-(2-amino-5-phenethyl-phenyl)-4-methyl-benzamide (129)

Scheme 24

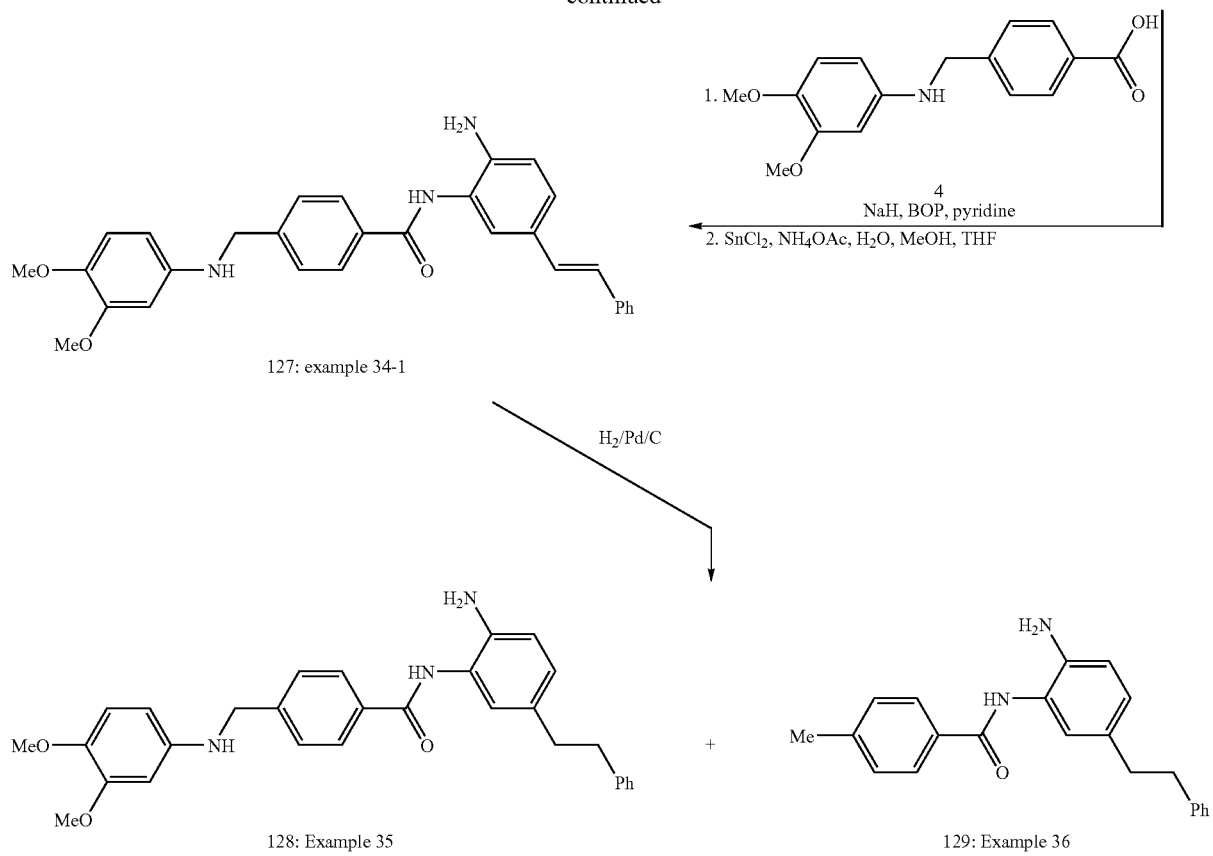

Step 1. 2-Nitro-5-styrylbenzenamine (126)

Following the same procedure as in Example 1, step 2 (scheme 1) but substituting 2-thiopheneboronic acid for trans-2-phenylvinylboronic acid (245 mg, 1.66 mmol), the title compound 126 was prepared (230 mg, 69% yield). $^1$H NMR: (400 MHz, acetone-$d_6$) δ (ppm): 7.89 (d, J=8.8 Hz, 1H), 7.49 (d, J=7.0 Hz, 2H), 7.27-7.18 (m, 3H), 7.19 (d, J=16.2 Hz, 1H), 7.05 (d, J=15.3 Hz, 1H), 7.02 (s, 1H), 6.93 (bs, 2H), 6.87 (dd, J=9.0, 1.6 Hz, 1H). LRMS: (m/z): 241.3 (MH$^+$).

Steps 2 and 3. 4-((3,4-dimethoxyphenylamino)methyl)-N-(2-amino-5-styrylphenyl)benzamide (127)

Following the same procedures as in Example 21, steps 3 and 4 (scheme 18) but substituting compound 97 for compound 126 (230 mg, 0.957 mmol), the title compound 127 was prepared (159 mg, 35% yield for 2 steps). $^1$H NMR: (400 MHz, Acetone-$d_6$) δ (ppm): 9.07 (s, 1H), 8.01 (d, J=8.2 Hz, 2H), 7.55 (d, J=8.2 Hz, 2H), 7.55-7.52 (m, 3H), 7.32 (t, J=7.4 Hz, 2H), 7.28 (dd, J=8.2, 2.2 Hz, 1H), 7.19 (t, J=7.2 Hz, 1H), 7.13 (d, J=16.4 Hz, 1H), 7.0 (d, J=16.2 Hz, 1H), 6.89 (d, J=8.2 Hz, 1H), 6.70 (d, J=8.4 Hz, 1H), 6.41 (d, J=2.7 Hz, 1H), 6.12 (dd, J=8.6, 2.7 Hz, 1H), 5.33 (bs, 1H), 4.85 (bs, 2H), 4.43 (s, 2H), 3.72 (s, 3H), 3.67 (s, 3H). LRMS: (m/z): 480.5 (MH$^+$).

Step 4. 4-((3,4-Dimethoxyphenylamino)methyl)-N-(2-amino-5-phenethylphenyl)benzamide (128) and N-(2-amino-5-phenethylphenyl)-4-methylbenzamide (129)

To a degassed solution of compound 127 (100 mg, 0.209 mmol) in a mixture of methanol and ethyl acetate (1:1) was added was added a catalytic amount of 10% palladium on charcoal and the mixture was put under $H_2$ atmosphere (1atm) and stirred for 1 h and filtered through celite and the filtrate was concentrated in vacuo. The mixture was separated by flash chromatography on silica gel using EtOAc/Hexanes with increasing polarity (40:60 to 60:40) as the eluent. The least polar compound 129 was isolated as a white solid (31 mg, 31% yield) and the most polar compound was further purified by crystallization from a mixture of ethyl acetate and hexanes affording compound 128 as light beige crystals (18 mg, 18% yield).

Compound 128: $^1$H NMR: (400 MHz, acetone-$d_6$) δ (ppm): 9.07 (s, 1H), 7.99 (d, J=8.2 Hz, 2H), 7.53 (d, J=8.6 Hz, 2H), 7.27-7.22 (m, 5H), 7.19-7.14 (m, 1H), 6.87 (dd, J=8.0, 2.0 Hz, 1H), 6.79 (d, J=8.0 Hz, 1H), 6.70 (d, J=8.4 Hz, 1H), 6.40 (d, J=2.8 Hz, 1H), 6.11 (dd, J=8.4, 2.5 Hz, 1H), 5.33 (bs, 1H), 4.51 (bs, 2H), 4.42 (s, 2H), 3.72 (s, 3H), 3.67 (s, 3H). LRMS: (m/z): 482.2 (MH$^+$).

Compound 129: $^1$H NMR: (400 MHz, acetone-$d_6$) δ (ppm): 9.03 (bs, 1H), 7.94 (d, J=8.0 Hz, 2H), 7.33 (d, J=7.8 Hz, 2H), 7.28-7.23 (m, 5H), 7.18-7.13 (m, 1H), 6.87 (dd, J=8.0, 2.0 Hz, 1H), 6.79 (d, J=8.2 Hz, 1H), 4.48 (bs, 2H), 2.90-2.86 (m, 2H), 2.83-2.78 (m, 2H), 2.42 (s, 3H). LRMS: (m/z): 331.1 (MH$^+$).

Example 37

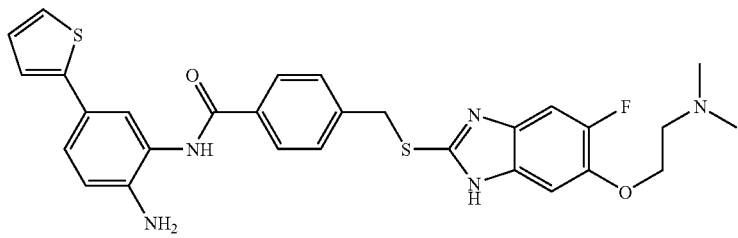

4-((6-(2-Dimethylamino)ethoxy)-5-fluoro-1H-benzo[d]imidazol-2-ylthio)methyl)-N-(2-amino-5-(thiophen-2-yl)phenyl)benzamide (131)

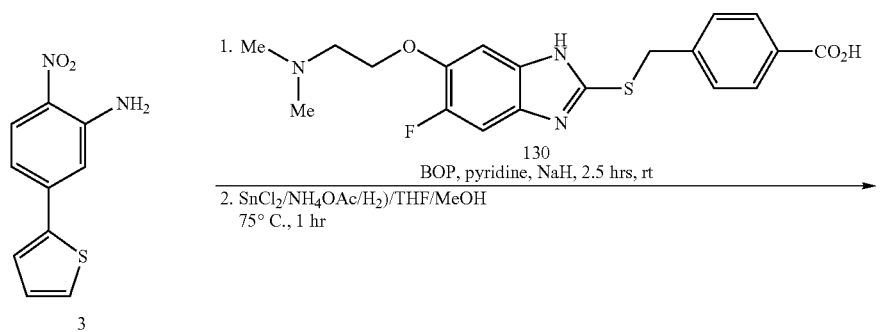

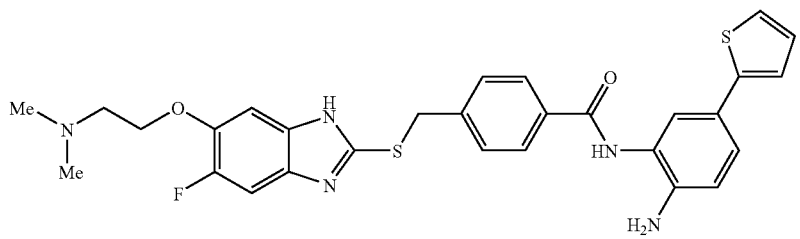

131: Example 37

Following the same procedures as in Example 1, steps 3 and 4 (scheme 1) but substituting compound 4 for compound 130 (300 mg, 0.559 mmol, described in the Patent Application WO 03/024448) the title compound 131 was prepared (7 mg, 3.7% yield over 2 steps). $^1$H NMR: (400 MHz, acetone-$d_6$) δ (ppm): 9.16 (bs, 1H), 7.97 (d, J=8.4 Hz, 2H), 7.62 (d, J=2.9 Hz, 1H), 7.61 (d, J=8.4 Hz, 2H), 7.32 (dd, J=8.2, 2.2 Hz, 1H), 7.28 (bs, 0.5H), 7.27 (dd, J=5.1, 1.0 Hz, 1H), 7.26 (bs, 0.5H), 7.22 (dd, J=3.5, 1.0 Hz, 1H), 7.21 (bs, 1H), 7.03 (dd, J=5.1, 3.5 Hz, 1H), 6.89 (d, J=8.2 Hz, 1H), 4.87 (bs, 2H), 4.65 (s, 2H), 4.16 (t, J=5.7 Hz, 2H), 2.73 (t, J=5.9 Hz, 2H), 2.30 (s, 6H). LRMS: (m/z): 562.3 (MH$^+$).

Example 38

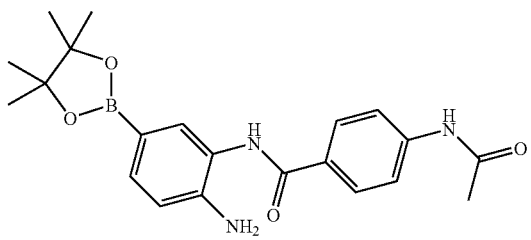

399

4-Acetamido-N-(2-amino-5-(4,4,5,5-tetramethyl-1,3,2-dioxaborolan-2-yl)phenyl)benzamide (134)

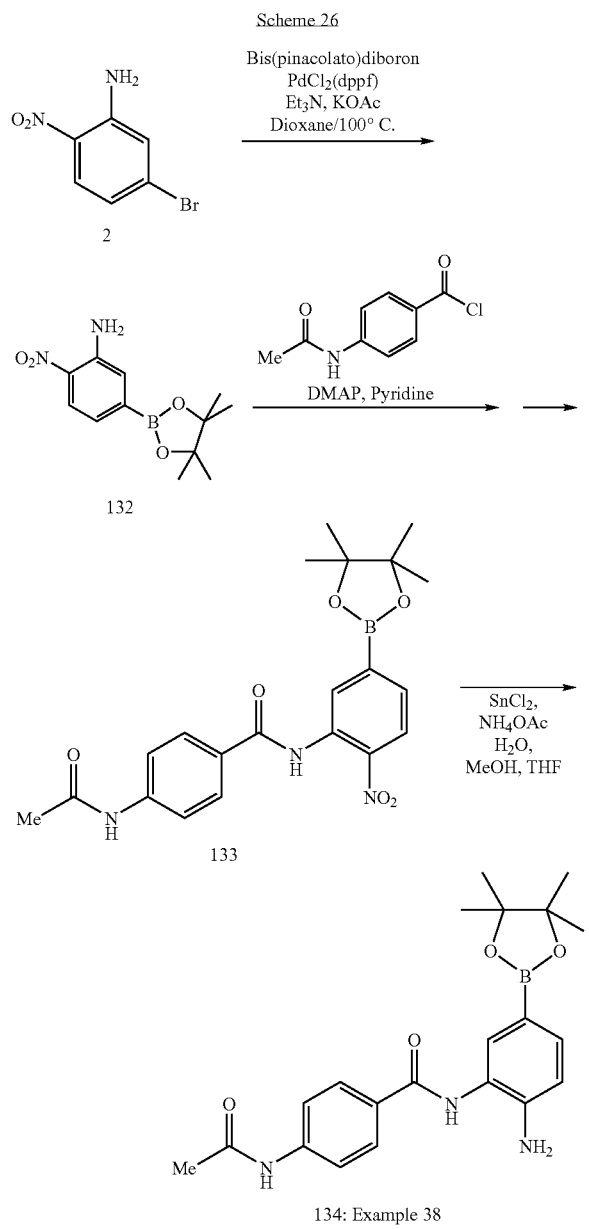

400

Step 2. 4-Acetylamino-N-[2-nitro-5-(4,4,5,5-tetramethyl-[1,3,2]dioxaborolan-2-yl)-phenyl]-benzamide (133)

To a solution of compound 132 (18 mg, 0.689 mmol) in pyridine (2.8 mL) was added 4-acetamidobenzoyl chloride (150 mg, 0.758 mmol) and 4-(dimethylamino)pyridine (8 mg, 0.07 mmol) and the mixture was stirred for 16 h. at r.t. Then, it was partitioned between EtOAc and $H_2O$, The aqueous layer was extracted with fresh EtOAc and the combined organic layers were washed with brine, dried over $MgSO_4$, filtered and concentrated in vacuo. The resulting crude oil was purified by flash chromatography on silica gel using methanol/EtOAc (5:95) as the eluent affording the title compound 133 (47 mg, 16% yield) as a 1:1 mixture with 4-acetamidobenzoic acid (hydrolyzed starting material). $^1$H NMR: (Acetone-$d_6$) δ(ppm): 10.76 (bs, 1H), 9.52 (bs, 1H), 9.00 (d, J=1.0 Hz, 1H), 8.20 (d, J=7.2 Hz, 1H), 7.99 (d, J=8.6 Hz, 2H), 7.85 (d, J=8.6 Hz, 2H), 7.64 (dd, J=8.2, 1.2 Hz, 1H), 2.15 (s, 3H), 1.40 (s, 12H).

Step 3. 4-Acetamido-N-(2-amino-5-(4,4,5,5-tetramethyl-1,3,2-dioxaborolan-2-yl)phenyl)benzamide (134)

Following the same procedures as in Example 19, step 4 (scheme 17) but substituting compound 92 for compound 133 (75 mg, 0.176 mmol), the title compound 134 was obtained (11 mg, 31% yield). $^1$H NMR: (acetone-$d_6$) δ(ppm): 9.42 (bs, 1H), 9.03 (bs, 1H), 8.03 (d, J=8.8 Hz, 2H), 7.77 (d, J=8.8 Hz, 2H), 7.60 (d, J=1.6 Hz, 1H), 7.39 (dd, J=8.0, 1.6 Hz, 1H), 6.84 (d, J=7.8 Hz, 1H), 5.01 (bs, 2H), 2.13 (s, 3H), 1.31 (s, 12H). LRMS: (m/z): 396.1 (MH$^+$).

Example 39

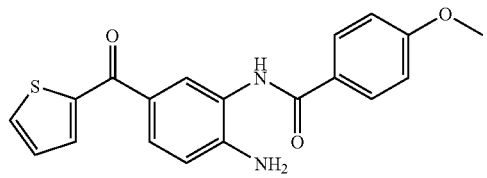

N-(2-amino-5-{thiophen-2-carbonyl)-phenyl)-4-methoxybenzamide (136)

Step 1. 5-(4,4,5,5-Tetramethyl-1,3,2-dioxaborolan-2-yl)-2-nitrobenzenamine (132)

Title compound 132 was prepared according to the procedure described in *J. Org. Chem.* 1995, 60, 7508-7510. The synthesis was performed starting from 2-nitro-5-bromoaniline (2, 300 mg, 1.38 mmol) (scheme 1, Example 1) and using dioxane as a solvent. Amount of the prepared compound 132 was 191 mg (52% yield). $^1$H NMR: (400 MHz, acetone-$d_6$) δ(ppm): 8.02 (d, J=8.6 Hz, 1H), 7.46 (d, J=1.0 Hz, 1H), 6.99 (s, 2H), 6.97 (dd, J=8.4, 1.2 Hz, 1H), 1.37 (s, 12H).

Scheme 27

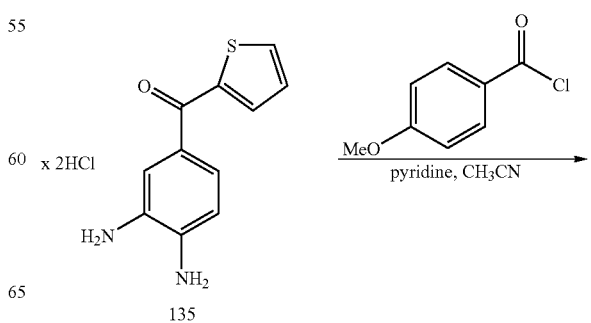

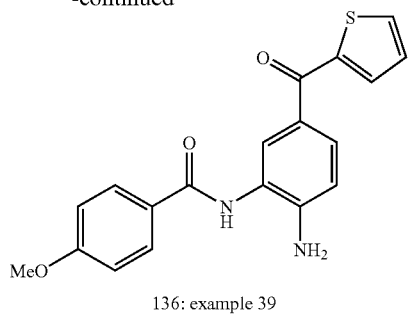

136: example 39

Step 1. N-(2-amino-5-(thiophen-2-carbonyl)-phenyl)-4-methoxybenzamide (136)

Following the same procedure as in Example 24, step 1 (scheme 20) but substituting compound 106 for 3,4-diaminobenzothiophenone dihydrochloride (135, 200 mg, 0.687 mmol) the title compound 136 was prepared as an orange foam (102 mg, 42% yield). 1H NMR: (400 MHz, DMSO-d$\delta$) $\delta$(ppm): 9.61 (s, 1H), 8.02 (d, J=6.3 Hz, 1H), 8.01 (d, J=8.6 Hz, 2H), 7.83 (d, J=2.0 Hz, 1H), 7.75 (d, J=3.2 Hz, 1H), 7.63 (dd, J=8.4, 2.0 Hz, 1H), 7.29 (dd, J=4.9, 3.2 Hz, 1H), 7.08 (d, J=8.8 Hz, 2H), 6.87 (d, J=8.6 Hz, 1H), 6.01 (s, 2H), 3.88 (s, 3H). LRMS: (m/z): 353.1 (MH$^+$).

Example 40

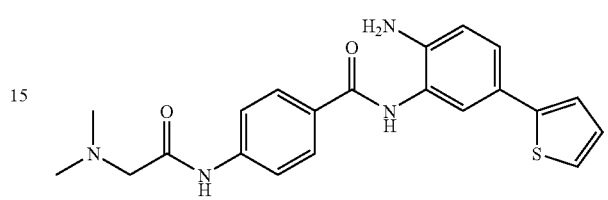

N-(2-Amino-5-(thiophen-2-ylphenyl)-4-(2-(N,N-dimethylamino)acetamido)benzamide (140)

Scheme 28

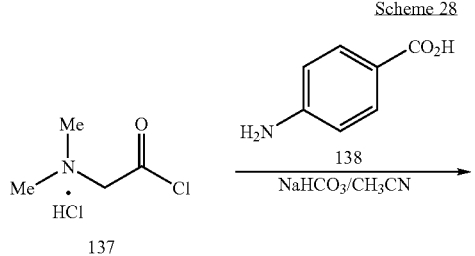

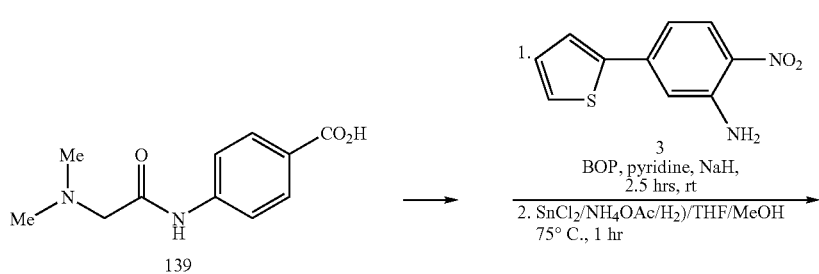

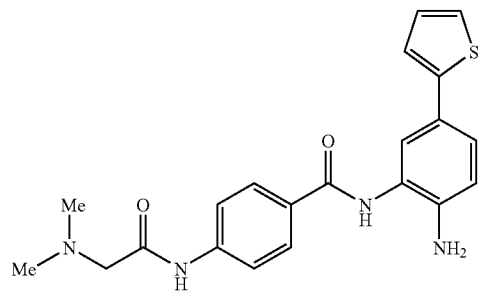

140: Example 40

Step 1. 4-(N,N-Dimethylamino)acetamidobenzoic acid (139)

To a solution of N,N-dimethylaminoacetyl chloride hydrochloride (137, 10.1 g, 64.2 mmol) in acetonitrile (300 ml.) was added powdered sodium bicarbonate (11.9 g, 141 mmol) followed by 4-aminobenzoic acid (138, 9.68 g, 70.6 mmol). The mixture was vigorously stirred over 16 h at r.t. and acetonitrile was decanted. The remaining gum was triturated with methanol and filtration afforded the title compound 139 (10.9 g, 76% yield). $^1$H NMR: (400 MHz, DMSO-d$_6$) δ(ppm): 10.21 (s, 1H), 7.84 (d, J=8.4 Hz, 2H), 7.76 (d, J=8.6 Hz, 2H), 4.17 (bs, 2H), 2.27 (s, 6H). LRMS: (m/z): 223.3 (MH$^+$).

Steps 2 and 3. N-(2-Amino-5-(thiophen-2-ylphenyl)-4-(2-(N,N-dimethylamino) acetamido)benzamide (140)

Following the same procedures as in Example 1, steps 3 and 4 (scheme 1) but substituting compound 4 for compound 139 [798 mg (37% pure), 1.24 mmol], the title compound 140 was prepared (7.4 mg, 1.5% yield over 2 steps). I H NMR: (400 MHz, CD3OD) δ (ppm): 7.99 (d, J=8.8 Hz, 2H), 7.77 (d, J=8.8 Hz, 2H), 7.48 (d, J=2.2 Hz, 1H), 7.35 (dd, J=8.2, 2.2 Hz, 1H), 7.22 (dd, J=5.1, 1.2 Hz, 1H), 7.20 (td, J=3.5, 1.2 Hz, 1H), 7.01 (dd, J=5.1, 3.7 Hz, 1H), 6.90 (d, J=8.6 Hz, 1H), 3.24 (s, 2H), 2.43 (s, 6H). LRMS: (m/z): 395.1 (MH$^+$).

Example 41a

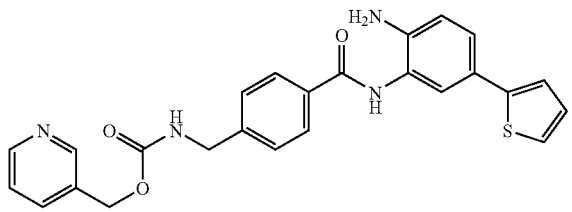

(Pyridin-3-yl)methyl 4-(2-amino-5-(thiophen-2-yl)phenylcarbamoyl)benzylcarbamate Scheme 29

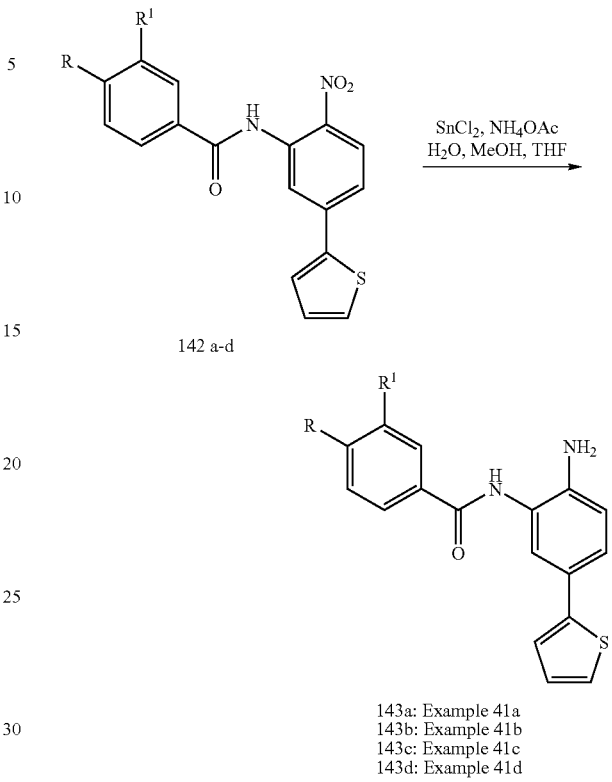

a: R$^1$ = H, R =
b: R$^1$ = H, R = F;
c: R$^1$ = H, R = SCF$_3$;
d: R$^1$ = Cl, R = F;

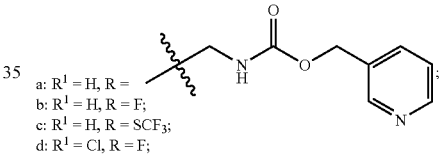

Steps 1 and 2. (Pyridin-3-yl)methyl 4-(2-amino-5-(thiophen-2-yl)phenylcarbamoyl)benzylcarbamate (143a)

To a suspension of compound 141a (U.S. Pat. No. 6,174,905 B$^1$) (533 mg, 1.75 mmol), in pyridine (5 mL, was added compound 3 (424 mg, 1.93 mmol), Example 1 (scheme 1). The resultant solution was stirred at r.t. for 4 h and concentrated in vacuo. The crude compound 142a (855 mg, 1.75 mmol) was dissolved in a 1:1 mixture of THF and methanol (14 mL) and tin chloride (II) dihydrate (1.97 g, 8.75 mmol) was added. The mixture was stirred for 3 h and solvents were removed in vacuo. The residue was suspended in methanol, adsorbed on silica gel and purified by flash chromatography on silica gel using methanol/dichloromethane (10:90) as an eluent. The resultant gum was dissolved in methanol and allowed to crystallize. Ethyl acetate was added and the remainder of the compound crashed out of solution by swirling in an ultra-sound bath. Filtration afforded the title compound 143a (63 mg, 8% yield over 2 steps) as a white solid. I H NMR: (400 MHz, DMSO-dβ) δ(ppm): 9.69 (bs, 1H), 8.58 (s, 1H), 8.53-8.51 (m, 1H), 7.98-7.96 (m, 1H), 7.94 (d, J=7.8 Hz, 2H), 7.78-7.76 (m, 1H), 7.46 (s, 1H), 7.40-7.38 (m, 1H), 7.37 (d, J=8.4 Hz, 2H), 7.29 (d, J=8.8 Hz, 1H), 7.24-7.23 (m, 1H), 7.05-7.03 (m, 1H), 6.80 (d, J=8.4 Hz, 1H), 5.15 (bs, 2H), 5.10 (s, 2H), 4.29 (d, J=6.1 Hz, 2H). LRMS: (m/z): 459.2 (MH+).

Example 41b

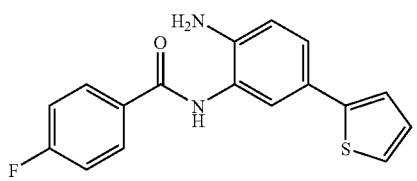

N-(2-Amino-5-(thiophen-2-yl-phenyl)-4-fluoro-benzamide (143b)

Compound 143b (Example 41b) was obtained similarly to the compound 143a (Example 41a) according to the scheme 29 starting from 4-fluorobenzoyl chloride (141b) via the nitro intermediate 142b. Yield 44% (over two steps).

Example 41c

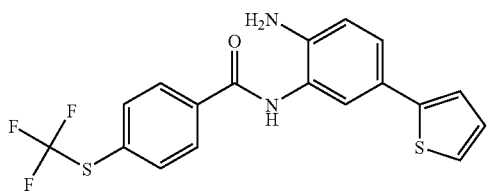

N-(2-Amino-5-(thiophen-2-yl-phenyl)-4-trifluoromethylsulfanyl-benzamide (143c)

Compound 143c (Example 41c) was obtained similarly to the compound 143a (Example 41a) according to the scheme 29 starting from 4-(trifluoromethylthio)benzoyl chloride (141c) via the nitro intermediate 142c. Yield 1.4% (over two steps).

Example 41d

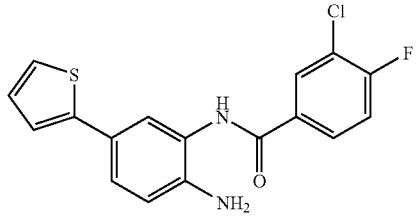

N-(2-Amino-5-(thiophen-2-yl-phenyl)-3-chloro-4-fluoro-benzamide (143d)

Compound 143d (Example 41d) was obtained similarly to the compound 143a (Example 41a) according to the scheme 29 starting from 3-chloro-4-fluorobenzoyl chloride (141d) via the nitro intermediate 142d. Yield 30% (over two steps).

Example 42

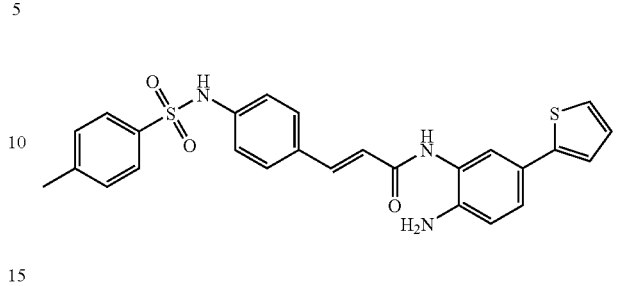

(E)-N-(2-Amino-5-(thiophen-2-yl)phenyl)-3-(4-(tosylamino)phenyl)acrylamide (146)

Scheme 30

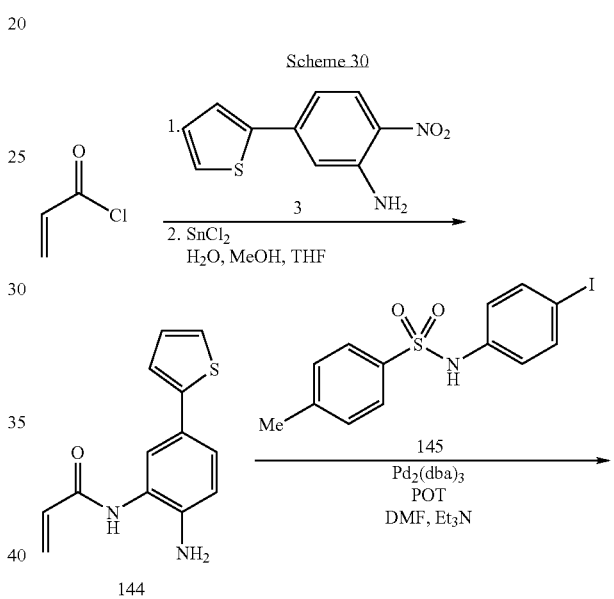

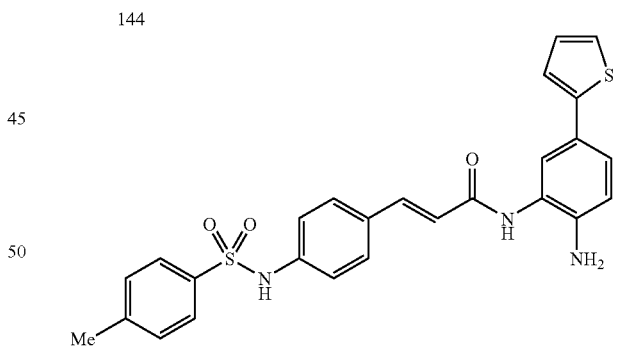

146: Example 42

Steps 1 and 2. W-(2-Amino-5-(thiophen-2-yl)phenyl) acrylamide (144)

A flame-dried r.t. flask was charged with compound 3 (100 mg, 0.453 mmol) and put under $N_2$ atmosphere. A trace amount of p-methoxyphenol (to prevent polymerization) was added followed by acryloyl chloride (74 μL, 0.906 mmol). The mixture was stirred for 1 h and put under high vacuum for 1 h. Then, THF (500 μL) was added followed by tin chloride (II) dihydrate (510 mg, 2.27 mmol). The solution was stirred for 1 h and purified by flash chromatography on silica gel using EtOAc/Hex with increasing polarity (50:50 to 90:10) as the eluent (traced of p-methoxyphenol was added before concentrating to avoid polymerization) affording the title compound 144 (70 mg, 63% yield for 2 steps). $^1$H NMR: (400 MHz, acetone-$d_6$) δ(ppm): 8.37 (d, J=1.8 Hz, 1H), 7.59 (dd, J=8.2, 1.9 Hz, 1H), 7.51 (d, J=1.6 Hz, 1H), 7.50 (dd, J=2.5, 1.2 Hz, 1H), 7.23 (d, J=8.2 Hz, 1H), 7.15 (dd, J=4.9, 3.7 Hz, 1H), 6.75 (d, J=0.8 Hz, 1H), 6.52 (dd, J=16.8, 10.0 Hz, 1H), 6.38 (d, J=16.8, 1.8 Hz, 1H), 5.80 (dd, J=10.2, 2.0 Hz, 1H). LRMS: (m/z): 245.1 (MH$^+$).

Step 3. (E)-N-(2-amino-5-(thiophen-2-yl)phenyl)-3-(4-(tosylamino)phenyl)acrylamide (146)

A pressure vessel was charged with compound 144 (70 mg, 0.287 mmol), DMF (800 µL), and compound 145 (WO 02/069947) (89 mg, 0.239 mmol). The solution was degassed under vacuum and put under N$_2$ atmosphere (3 cycles). Then, tris(dibenzylideneacetone)dipalladium (7 mg, 0.007 mmol) was added and the red solution was degassed again (3 cycles). Tri-o-tolylphosphine (4 mg, 0.014 mmol) was added and the solution rapidly turned dark. Triethylamine (100 µL, 0.717 mmol) was added and it was degassed twice again and allowed to stir under N$_2$ atmosphere at 90° C. for 3 h. Then it was passed through celite and the filtrate was concentrated in vacuo. It was purified by flash chromatography on silica gel using EtOAc as the eluent and then purified again but using methanol/chloroform (5:95) as the eluent. The combined fractions were allowed to crystallize from this mixture of solvent (methanol/chloroform 5:95) affording the title compound 146 (3.8 mg, 3% yield). $^1$H NMR: (400 MHz, Acetone-$d_6$) δ (ppm): 9.20 (bs, 1H), 8.84 (bs, 1H), 7.72 (d, J=8.0 Hz, 3H), 7.58 (d, J=15.7 Hz, 1H), 7.54 (d, J=8.4 Hz, 2H), 7.34 (d, J=8.6 Hz, 2H), 7.29-7.27 (m, 4H), 7.22 (d, J=3.5 Hz, 1H), 7.04 (t, J=4.9 Hz, 1H), 6.88 (d, J=8.4 Hz, 1H), 6.86 (d, J=15.3 Hz, 1H), 4.84 (bs, 2H), 2.38 (s, 3H). LRMS: (m/z): 490.1 (MH$^+$).

Example 43

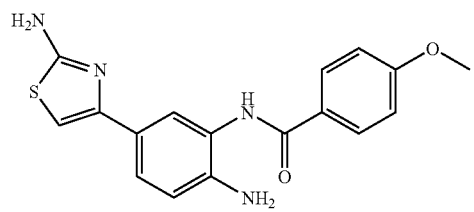

N-(2-Amino-5-(2-aminothiazol-4-yl)phenyl)-4-methoxybenzamide (153)

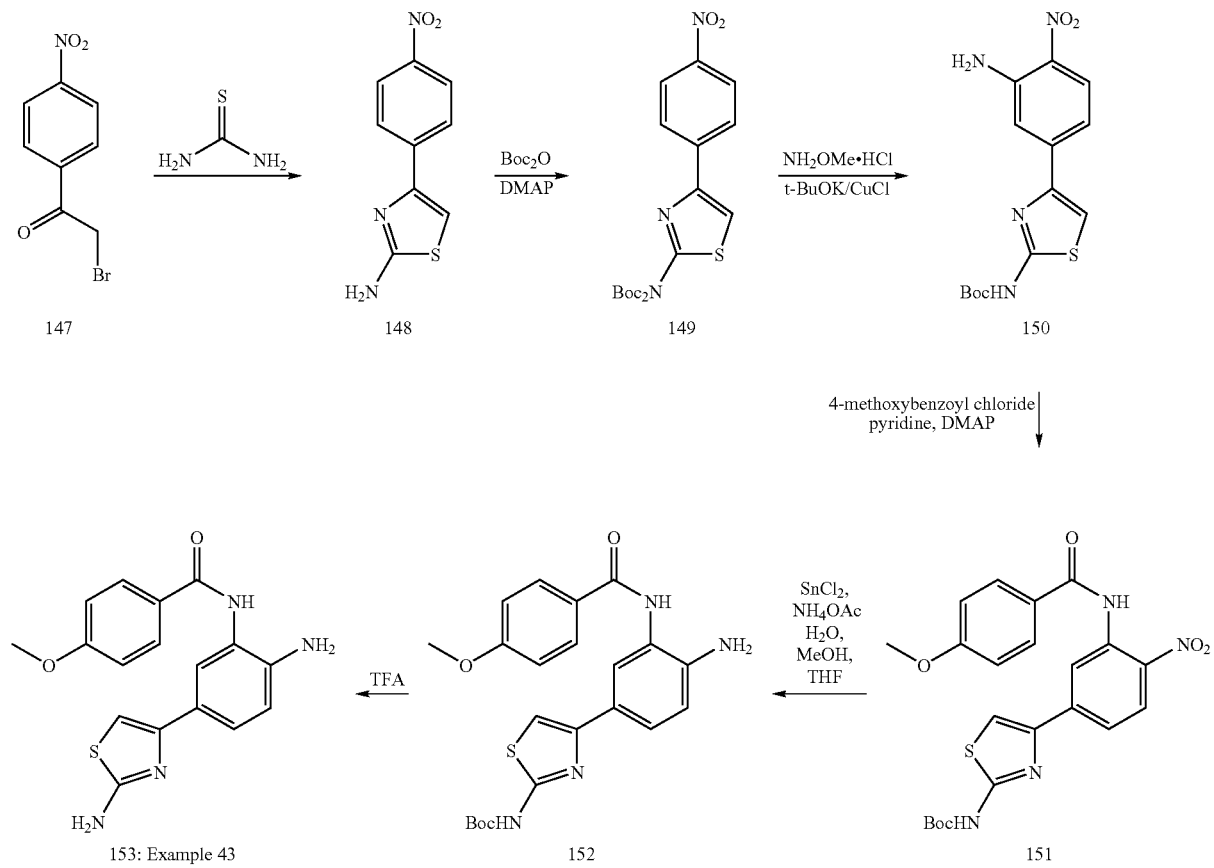

Scheme 31

Step 1. 4-(4-Nitrophenyl)thiazol-2-amine (148)

Title compound 148 was prepared in 96% yield according to the procedure described in *J. Heterocyclic Chem.* 1970, 7, 1137-1141, starting from 2-bromo-4'-nitroacetophenone 147. $^1$H NMR: (400 MHz, DMSO-$d_6$) δ(ppm): 8.21 (d, J=8.8 Hz, 2H), 8.02 (d, J=8.8 Hz, 2H), 7.40 (s, 1H), 7.22 (s, 2H). LRMS (m/z): 222.1 (MH$^+$).

Step 2. 2-(N,N-di-tert-Butylcarbamoyl)-4-(4-nitrophenyl)thiazole (149)

To a solution of compound 148 (1.00 g, 4.52 mmol) in THF (20 mL), was added di-tert-butyl dicarbonate (1.16 g, 9.94 mmol) and 4-(dimethylamino)pyridine (55 mg, 0.45 mmol) and the mixture was stirred at r.t. for 4 days. The remaining yellow solid was filtered off and the filtrate was concentrated in vacuo. The residue was partitioned between EtOAc and H$_2$O. The organic layer was washed with brine, dried over MgSO$_4$, filtered and concentrated. Crystallization from EtOAc/Hex (twice) afforded the title compound 149 (1.23 g, 65% yield) as beige crystals. $^1$H NMR: (400 MHz, DMSO-$d_6$) δ(ppm): 8.26 (d, J=9.0 Hz, 1H), 8.21 (s, 1H), 8.09 (d, J=9.0 Hz, 1H), 1.53 (s, 18H). LRMS: (m/z): 422.2 (MH$^+$).

Step 3. tert-Butyl 4-(3-amino-4-nitrophenyl)thiazol-2-ylcarbamate (150)

Title compound 150 was prepared in 62% yield according to the procedure described in *J. Chem. Soc. Perkin Trans.* 1999, 1437-1444; starting from the compound 149. $^1$H NMR: (400 MHz, DMSO-$d_6$) δ(ppm): 11.68 (s, 1H), 7.97 (d, J=9.0 Hz, 1H), 7.71 (s, 1H), 7.54 (s, 2H), 7.45 (d, J=2.0 Hz, 1H), 7.07 (dd, J=9.0, 2.0 Hz, 1H), 1.50 (s, 9H). LRMS: (m/z): 337.2 (MH$^+$).

Step 4. tert-Butyl 4-(3-(4-methoxybenzamido)-4-nitrophenyl)thiazol-2-ylcarbamate (151)

To a solution of compound 150 (390 mg, 1.28 mmol) in pyridine was added 4-methoxybenzoyl chloride (181 mg, 1.06 mmol) and 4-(N,N-dimethylamino)pyridine (13 mg, 0.11 mmol). The mixture was stirred for 16 h and partitioned between EtOAc and H$_2$O. The organic layer was washed with brine and some compound was collected by filtration. The filtrate was dried over MgSO$_4$, filtered and concentrated in vacuo and then crystallized from a mixture of EtOAc/Hexanes. The two crops were combined affording the title compound 151 (358 mg, 72% yield). $^1$H NMR: (400 MHz, CD$_3$OD) δ(ppm): 11.73 (s, 1H), 10.71 (s, 1H), 8.36 (d, J=2.0 Hz, 1H), 8.08 (d, J=8.6 Hz, 1H), 7.95 (d, J=9.0 Hz, 2H), 7.86 (d, J=0.8 Hz, 1H), 7.83 (dd, J=8.6, 2.0 Hz, 1H), 7.10 (d, J=9.0 Hz, 2H), 3.85 (s, 3H), 1.50 (s, 9H).

Step 5. tert-Butyl 4-(3-(4-methoxybenzamido)-4-aminophenyl)thiazol-2-ylcarbamate (152)

Following the same procedure as in Example 19, step 4 (scheme 17) but substituting compound 92 for compound 151 the title compound 152 was prepared in 62% yield. $^1$H NMR: (400 MHz, DMSO-$d_6$) δ (ppm): 8.06 (d, J=8.6 Hz, 2H), 7.83 (d, J=2.2 Hz, 1H), 7.55 (d, J=8.2, 2.0 Hz, 1H), 7.12 (s, 1H), 7.05 (d, J=9.0 Hz, 2H), 6.88 (d, J=8.2 Hz, 1H), 3.90 (s, 3H), 1.55 (s, 9H). LRMS: (m/z): 441.4 (MH$^+$).

Step 6. *N*-(2-Amino-5-(2-aminothiazol-4-yl)phenyl)-4-methoxybenzamide (153)

Following the same procedure as in Example 27, step 3 (scheme 20) but substituting compound III for compound 152 (201 mg, 0.457 mmol), the title compound 153 was obtained (63 mg, 100% yield). $^1$H NMR: (400 MHz, DMSO-$d_6$) δ (ppm): 9.55 (s, 1H), 7.96 (d, J=9.0 Hz, 2H), 7.60 (d, J=2.2 Hz, 1H), 7.39 (dd, J=8.2, 2.0 Hz, 1H), 7.02 (d, J=9.0 Hz, 2H), 6.90 (s, 2H), 6.73 (d, J=8.4 Hz, 1H), 6.63 (s, 1H), 4.98 (s, 2H), 3.83 (s, 3H). LRMS: (m/z): 341.2 (MH$^+$).

Example 44

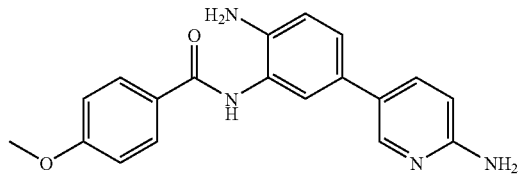

N-(2-Amino-5-(4-amino-3-pyridyl)phenyl)-4-methoxybenzamide (157)

Scheme 32

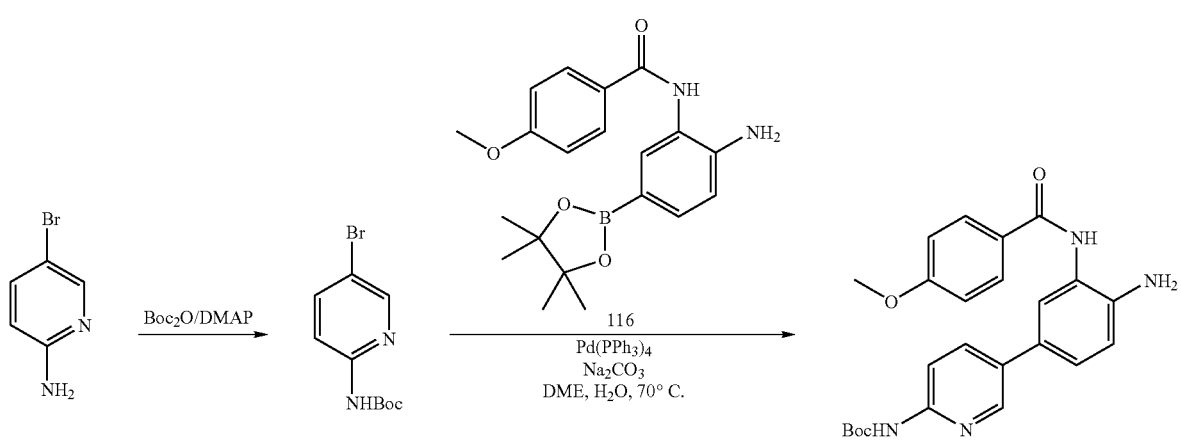

-continued

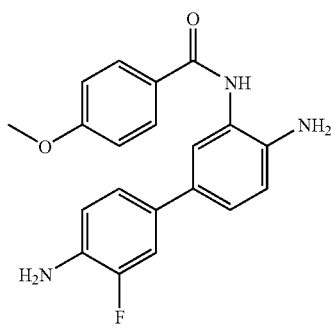

157a: Example 44a

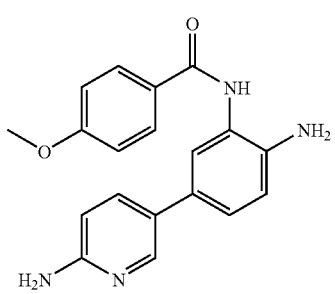

157: Example 44

Step 1. tert-Butyl 5-bromopyridin-2-ylcarbamate (155)

Following the same procedure as in Example 43, step 2 (scheme 31) but substituting compound 148 for 5-bromo-pyridine-2-yl-amine (154, 972 mg, 5.62 mmol) the title compound 155 was prepared (313 mg, 20% yield) $^1$H NMR: (400 MHz, CD$_3$OD) δ (ppm): 8.55 (dd, J=2.5, 0.8 Hz, 1H), 8.06 (dd, J=8.6, 2.5 Hz, 1H), 7.45 (dd, J=8.4, 0.6 Hz, 1H), 1.43 (s, 9H). LRMS: (m/z): 273.1/275.1 (M7M+2).

Step 2. N-(2-Amino-5-(4-tert-butylcarbamoyl-3-pyridyl)phenyl)-4-methoxybenzamide (156)

Following the same procedure as in Example 31, step 2 (scheme 21) but substituting compound 148 for compound 155 (135 mg, 0.494 mmol), the title compound 156 was obtained (36 mg, 25% yield). $^1$H NMR: (400 MHz, CD$_3$OD) δ (ppm): 8.41 (d, J=2.2 Hz, 1H), 7.98 (d, J=9.0 Hz, 2H), 7.92 (dd, J=8.8, 2.3 Hz, 1H), 7.85 (d, J=8.4 Hz, 1H), 7.45 (s, 1H), 7.34 (dd, J=8.4, 2.0 Hz, 1H), 7.04 (d, J=8.8 Hz, 2H), 6.98 (d, J=8.4 Hz, 1H), 3.88 (s, 3H), 1.55 (s, 9H). LRMS: (m/z): 435.2 (MH$^+$).

Step 3. N-(2-Amino-5-(4-amino-3-pyridyl)phenyl)methoxybenzamide (157)

Following the same procedure as in Example 27, step 3 (scheme 20) but substituting compound 111 for compound 156 (36 mg, 0.083 mmol), the title compound 157 was obtained (7 mg, 25% yield). $^1$H NMR: (400 MHz, acetone-d$_6$) δ (ppm): 8.94 (bs, 1H), 8.03 (d, J=1.8 Hz, 1H), 7.88 (d, J=8.8 Hz, 1H), 7.47 (dd, J=8.9, 2.5 Hz, 1H), 7.36 (d, J=2.3 Hz, 1H), 7.07 (dd, J=8.2, 2.3 Hz, 1H), 6.89 (d, J=8.8 Hz, 2H), 6.77 (d, J=8.2 Hz, 1H), 6.45 (dd, J=8.4, 0.6 Hz, 1H), 5.29 (bs, 2H), 3.74 (s, 3H). LRMS: (m/z): 335.1 (MH$^+$).

Example 44a

N-(4,4'-Diamino-3'-fluoro-biphenyl-3-yl)-4-methoxy-benzamide (157a)

N-(4,4'-Diamino-3'-fluoro-biphenyl-3-yl)-4-methoxy-benzamide (157a) was prepared similarly to the compound 157 (Example 44) according to the scheme 32 using instead of 5-bromo-pyridine-2-yl-amine (154) 4-bromo-2-fluoroaniline as a starting material.

Example 45

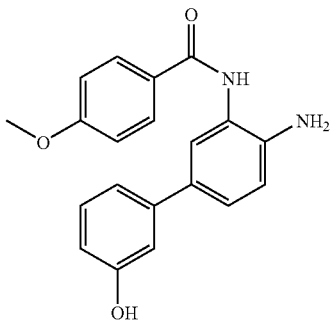

N-(4-amino-4'-hydroxybiphen-3-yl)-4-methoxybenzamide (160)

Scheme 33

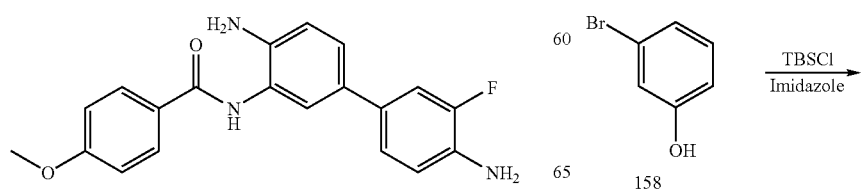

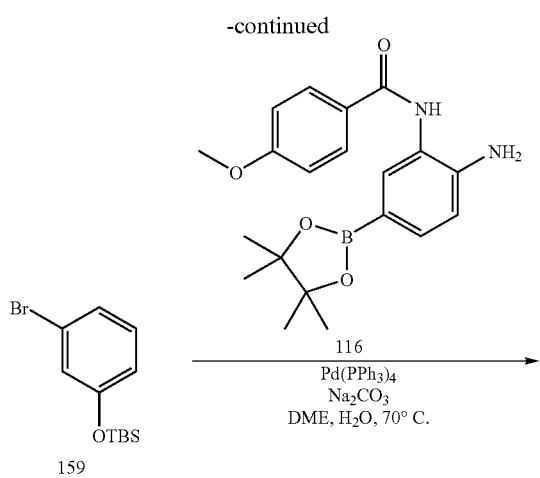

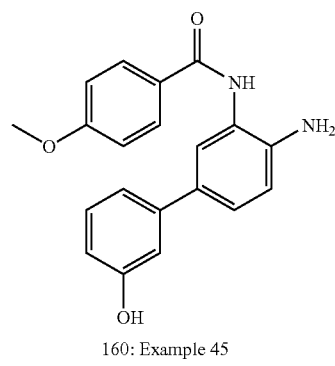

160: Example 45

Step 1. (3-Bromophenoxy)(tert-butyl)dimethylsilane (159)

Following the same procedure as in Example 19, step 2 (scheme 17) substituting compound 90 for 3-bromophenol 158 (200 mg, 0.501 mmol), the title compound 159 was obtained (14 mg, 5% yield). $^1$H NMR: (400 MHz, DMSO-$d_6$) δ (ppm): 7.21 (t, J=8.0 Hz, 1H), 7.14 (d, J=7.8 Hz, 1H), 7.01 (s, 1H), 6.86 (d, J=8.0 Hz, 1H), 0.95 (d, J=1.0 Hz, 9H), 0.20 (d, J=1.2 Hz, 6H).

Step 2. N-(4-amino-4'-hydroxybiphen-3-yl)-4-methoxybenzamide (160)

Following the same procedure as in Example 31, step 1 (scheme 21) but substituting 1-(4-bromophenyl)ethanone for compound 159 (312 mg, 1.09 mmol), the title compound 160 was obtained (79 mg, 44% yield). $^1$H NMR: (400 MHz, DMSO-$d_6$) δ (ppm): 9.58 (s, 1H), 9.35 (s, 1H), 7.97 (d, J=8.4 Hz, 2H), 7.43 (s, 1H), 7.23 (dd, J=8.2, 1.4 Hz, 1H), 7.16 (t, J=7.6 Hz, 1H), 7.04 (d, J=8.4 Hz, 2H), 6.95 (d, J=7.6 Hz, 1H), 6.91 (s, 1H), 6.82 (d, J=8.4 Hz, 1H), 6.62 (dt, J=8.0, 1.0 Hz, 1H), 5.05 (s, 2H), 3.84 (s, 3H). LRMS: (m/z): 335.2 (MH$^+$).

Example 46

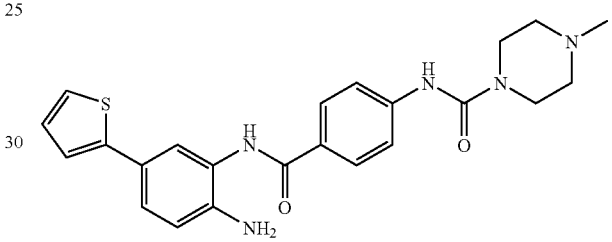

N-(4-((2-Amino-5-(thiophen-2-yl)phenyl)carbamoyl)phenyl)-4-methylpiperazine-1-carboxamide (164)

Scheme 34

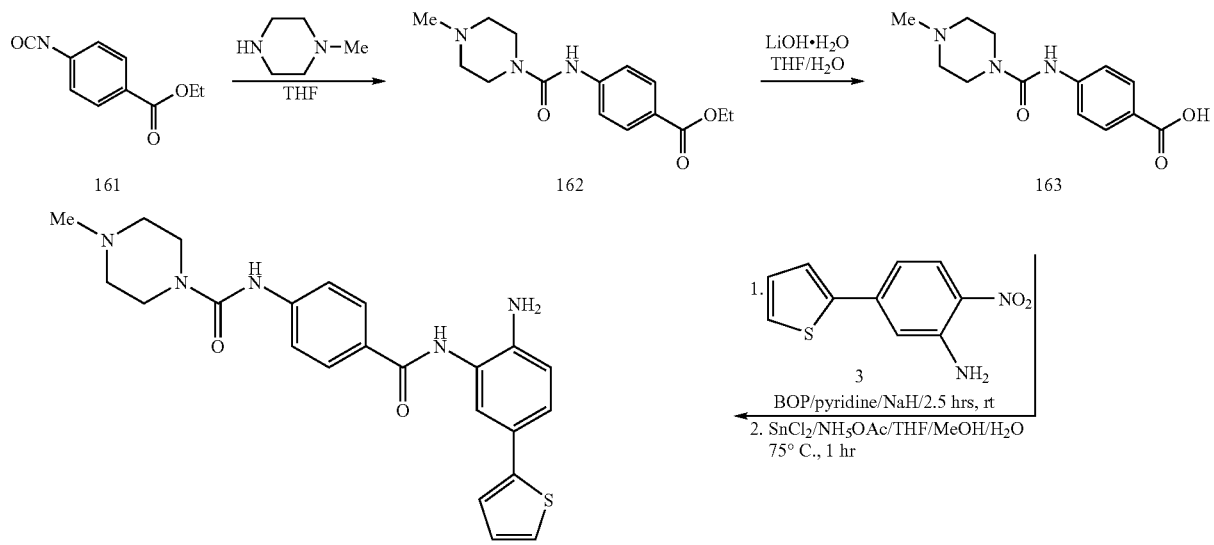

164: Example 46

Step 1. Ethyl 4-(1-methylpiperazine-4-carboxamido)benzoate (162)

A solution of N-methylpiperazine (0.61 ml, 5.49 mmol) and 4-ethylisocyanatobenzoate 161 (1.00 g, 5.23 mmol) in THF (10 mL) was stirred at room temperature for 16 h. The precipitate was filtered and rinsed with ether to give 1.40 g (92%) of the title compound 162 as a white powder. $^1$H NMR: (400 MHz, DMSO) δ (ppm): 8.87 (s, 1H), 7.81 (d, J=8.4 Hz, 2H), 7.59 (d, J=8.4 Hz, 2H), 7.25 (q, J=6.8 Hz, 2H), 3.45 (d, J=4.9 Hz, 4H), 2.31 (t, J=4.9 Hz, 4H), 2.19 (s, 3H), 1.30 (t, J=6.8 Hz, 3H).

Step 2. 4-(1-Methylpiperazine-4-carboxamido)benzoic acid (163)

A solution of 162 (1.39 g, 4.77 mmol) and LiOH.H$_2$O (300 mg, 7.16 mmol) in 1:1 THF:water (8 ml) was stirred at room temperature for 24 h. 1 M HCl was added to reach pH=5 and the solvent was evaporated. The title compound was purified by preparative HPLC (Aquasil C18, reverse phase, eluent: MeOH/water) to give 979 mg (78%) of the title compound 163 as a white powder. $^1$H NMR: (400 MHz, DMSO) δ (ppm): 8.81 (s, 1H), 7.78 (dt, J=8.6, 1.8 Hz, 2H), 7.53 (dt, J=8.8, 2.0 Hz, 2H), 3.44 (t, J=4.9 Hz, 4H), 2.31 (t, J=5.0 Hz, 4H), 2.19 (s, 3H).

Steps 3 and 4. 4-Methyl-piperazine-1-carboxylic acid [4-(2-nitro-5-(thiophen-2-yl-phenylcarbamoyl)-phenyl]-amide (164)

Following the same procedures as in Example 1, steps 3 and 4 (scheme 1) but substituting compound 4 for compound 163 title compound 164 was obtained in 8.4% yield (over two steps). $^1$H NMR: (DMSO) δ (ppm): 400 MHz, (DMSO) d (ppm): 9.57 (s, 1H), 8.80 (s, 1H), 7.89 (d, J=8.8 Hz, 2H), 7.59 (d, J=8.8 Hz, 2H), 7.44 (d, J=2.2 Hz, 1H), 7.34 (dd, J=5.1, 1.0 Hz, 1H), 7.27 (dd, J=8.2, 2.2 Hz, 1H), 7.23 (dd, J=3.5, 1.2 Hz, 1H), 7.03 (dd, J=5.1, 3.5 Hz, 1H), 6.79 (d, J=8.4 Hz, 1H), 5.12 (sb, 2H), 3.46 (t, J=4.8 Hz, 4H), 2.33 (t, J=4.9 Hz, 4H). MS: (calc.) 435.2; (obt.) 436.4 (MH)$^+$.

Example 47

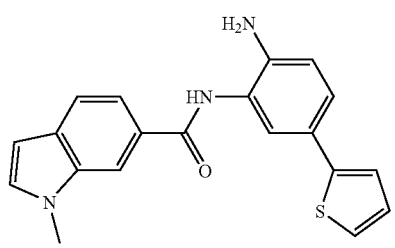

N-(2-amino-5-(thiophen-2-yl)phenyl)-1-methyl-1H-indole-6-carboxamide (41)

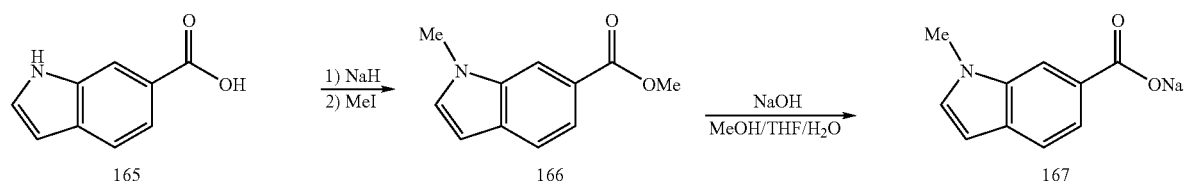

Scheme 35

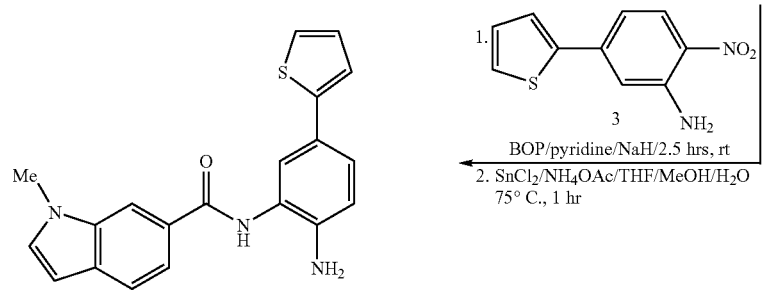

168: Example 47

417

Step 1: Methyl 1-methyl-1H-indole-6-carboxylate (166)

1H-Indole-6-carboxylic acid 37 (0.20 g, 1.24 mmol) was dissolved in dimethylformamide (10 mL) and cooled to 0° C. for the portion-wise addition of sodium hydride (0.20 g, 4.96 mmol). After complete addition, the reaction mixture was allowed to warm to rt and stirred for 1 hr then methyl iodide (0.15 mL, 2.48 mmol) was added to the reaction mixture. Quenching with water followed by rotary evaporation led to the crude residue, which was taken up with water and extracted with ethyl acetate. The organic phase was dried over magnesium sulfate, filtered and evaporated to provide crude 166 (it was used crude in the next step). MS: 189.08 (calc), 190.1 (obs).

Step 2: 1-Methyl-1H-indole-6-carboxylic acid (167)

Methyl 1-methyl-1H-indole-6-carboxylate 166 (1.24 mmol) was stirred with sodium hydroxide (0.59 g, 14.88 mmol) in a 2:2:1 mixture of methanol/THF/water (7.5 mL) for 36 hrs at rt to form a precipitate which was collected by filtration and lyophilized overnight to give the title compound 167 (0.54 g, 99% yield). MS: 175.06 (calc), 176.1 (obs).

418

Steps 3 and 4: N-(2-Amino-5-(thiophen-2-yl)phenyl)-1-methyl-1H-indole-6-carboxamide (168)

Following the same procedures as in Example 1, steps 3 and 4 (scheme 1) but substituting compound 4 for compound 167 title compound 168 was obtained in 0.5% yield (over two steps). $^1$H NMR: (DMSO) δ (ppm): 400 MHz, (DMSO) d (ppm): 9.72 (s, 1H), 8.19 (s, 1H), 7.67 (abq, J=29.4, 7.6 Hz, 2H), 7.52 (d, J=7.6 Hz, 2H), 7.36 (s, 1H), 7.31 (d, J=6.5 Hz, 1H), 7.26 (s, 1H), 7.06 (s, 1H), 6.83 (d, J=8.0 Hz, 1H), 6.52 (s, 1H), 5.16 (s, 2H), 3.90 (s, 3H). MS: 347.11 (calc), 348.1 (obs).

Example 48

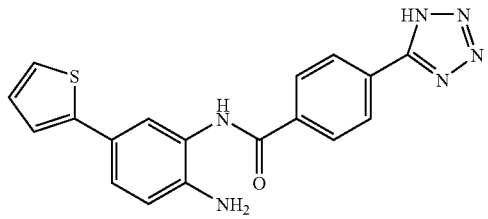

N-(2-amino-5-(thiophen-2-yl)phenyl)-4-(1H-tetrazol-5-yl)benzamide (172)

Scheme 36

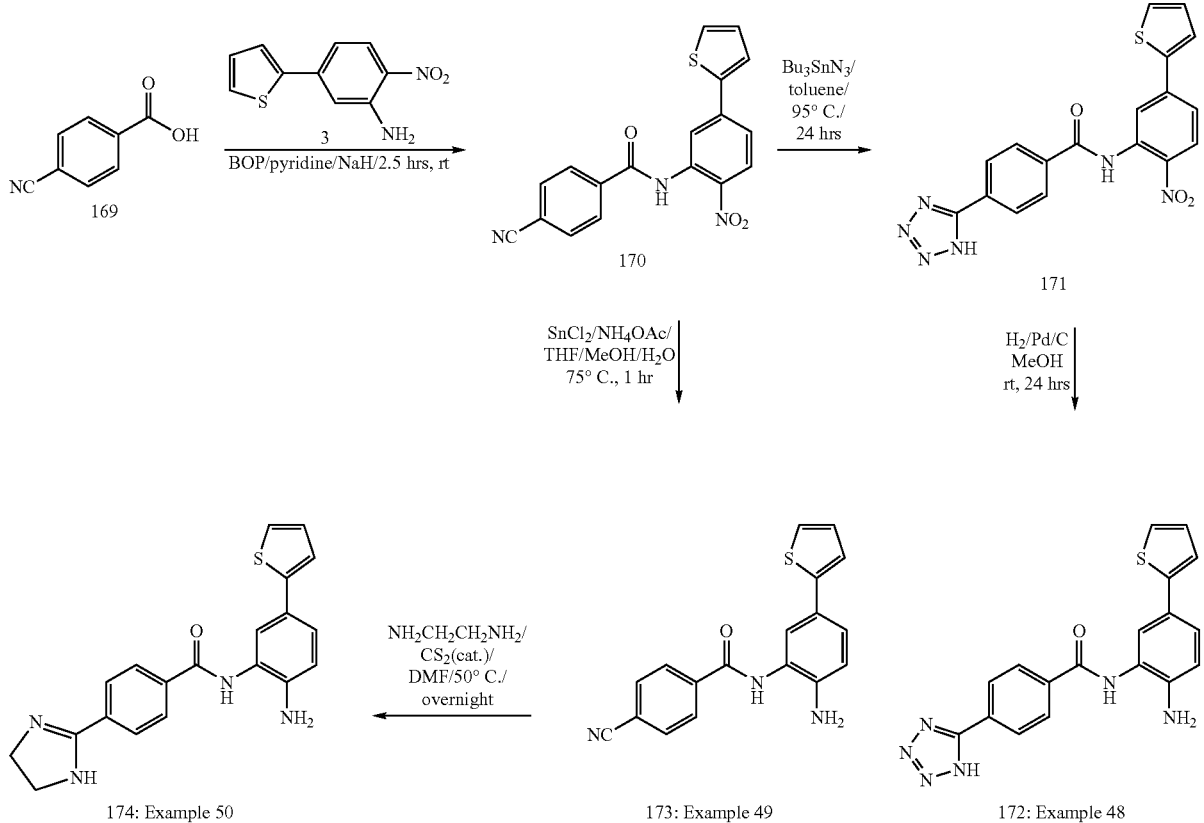

174: Example 50    173: Example 49    172: Example 48

Step 1. 4-Cyano-N-(2-nitro-5-(thiophen-2-yl-phenyl)-benzamide (170)

Following the same procedures as in Example 1, step 3 (scheme 1) but substituting compound 4 for compound 169 the title compound 170 was obtained in 51% yield. $^1$H NMR: (DMSO) δ (ppm): 400 MHz, (DMSO) δ (ppm): 8.15 (d, J=8.0 Hz, 2H), 8.10 (d, J=2.0 Hz, 1H), 7.93 (d, J=8.0 Hz, 2H), 7.85 (d, J=8.6 Hz, 1H), 7.67 (dd, J=4.9, 1.0 Hz, 1H), 7.64 (dd, J=3.7, 1.7 Hz, 1H), 7.45 (dd, J=8.4, 1.4 Hz, 1H), 7.20 to 7.17 (m, 1H). MS: 349.05 (calc), 348.0 (obs).

Step 2: N-(2-Nitro-5-(thiophen-2-yl)phenyl)-4-(1H-tetrazol-5-yl)benzamide (171)

The nitro-cyano compound 170 (60.5 mg, 0.17 mmol) was heated to 95° C. in the presence of tributyltin azide (0.06 mL, 0.21 mmol) in toluene (2 mL) for 24 hrs then solvent was evaporated and the residues was purified by flash chromatography (1:1 ethyl acetate:hexane) to provide tetrazole 171 (51.4 mg, 76% yield). $^1$H NMR: (DMSO) δ (ppm): 10.85 (s, 1H), 8.17 (d, J=14.9 Hz, 2H), 8.13 (s, 1H), 8.08 (d, J=8.4 Hz, 1H), 7.99 (d, J=7.4 Hz, 2H), 7.74 (m, 3H), 7.23 (d, J=3.7 Hz, 1H). MS: 392.07 (calc), 393.1 (obs).

Step 3: N-(2-Amino-5-(thiophen-2-yl)phenyl)-4-(1H-tetrazol-5-yl)benzamide (172)

The nitro compound 171 (20 mg, 0.05 mmol) was hydrogenated (1 atm) in the presence of 10% palladium on charcoal (catalytic amount) in methanol (1 mL) at room temperature for 2-3 hrs. The reaction mixture was filtered through a pad of Celite®, the filtrate was evaporated to give the crude product which was suspended in dichloromethane and stirred overnight at room temperature, then filtered to provide the title compound 172 (6.3 mg, 27% yield). $^1$H NMR: (DMSO) δ (ppm): 400 MHz, (DMSO) d (ppm): 9.71 (s, 1H), 8.07 (d, J=8.2 Hz, 2H), 8.00 (d, J=8.2 Hz, 2H), 7.48 (s, 1H), 7.34 (d, J=5.1 Hz, 1H), 7.28 (dd, J=8.2, 2.0 Hz, 1H), 7.24 (d, J=3.5 Hz, 1H), 7.03 (t, J=3.7 Hz, 1H), 6.79 (d, J=8.4 Hz, 1H), 5.17 (s, 2H). MS: 362.09 (calc), 363.1 (obs).

Example 49

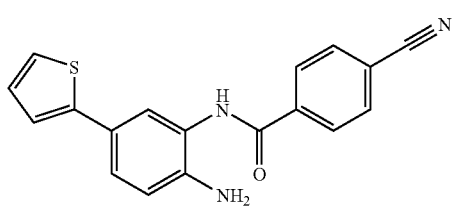

N-(2-Amino-5-(thiophen-2-yl)phenyl)-4-cyanobenzamide (173)

Step 1: N-(2-Amino-5-(thiophen-2-yl)phenyl)-4-cyanobenzamide (173)

Following the same procedures as in Example 1, step 4 (scheme 1) but substituting compound 4 for compound 170 the title compound 173 was obtained in 56% yield. $^1$H NMR: (DMSO) δ (ppm): 400 MHz, (DMSO) d (ppm): 9.92 (s, 1H), 8.14 (d, J=8.4 Hz, 2H), 8.00 (d, J=8.4 Hz, 2H), 7.44 (d, J=2.0 Hz, 1H), 7.34 (dd, J=5.1, 0.98 Hz, 1H), 7.30 (dd, J=8.2, 2.2 Hz, 1H), 7.23 (d, J=3.5 Hz, 1H), 7.03 (dd, J=5.1, 3.5 Hz, 1H), 6.79 (d, J=8.4 Hz, 1H), 5.24 (s, 2H). MS: 319.08 (calc), 320.1 (obs).

Example 50

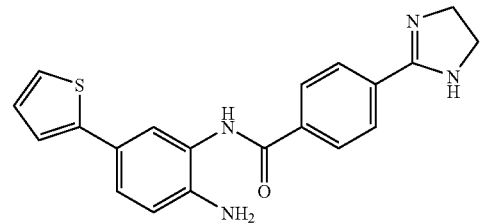

N-(2-Amino-5-(thiophen-2-yl)phenyl)-4-(4,5-dihydro-1H-imidazol-2-yl)benzamide (174)

Step 1: N-(2-Amino-5-(thiophen-2-yl)phenyl)-4-(4,5-dihydro-1H-imidazol-2-yl)benzamide (174)

N-(2-Amino-5-(thiophen-2-yl)phenyl)-4-cyanobenzamide 173 (30 mg, 0.1 mmol), ethylenediamine (0.126 mL, 1.9 mmol.) and carbon disulfide (catalyst) were stirred at 50° C. in DMF overnight. The reaction mixture was then evaporated to dryness, taken up in methanol and filtered to give the title compound 174 as a yellow solid (16.3 mg, 48%). $^1$H NMR: (DMSO) δ (ppm): 400 MHz, (DMSO) d (ppm): 9.78 (s, 1H), 8.02 (d, J=8.0 Hz, 2H), 7.92 (d, J=8.0 Hz, 2H), 7.45 (s, 1H), 7.33 (d, J=5.1 Hz, 1H), 7.28 (d, J=8.2 Hz, 1H), 7.22 (d, J=3.3 Hz, 1H), 7.03 (t, J=3.9 Hz, 1H), 6.79 (d, J=8.2 Hz, 1H), 5.18 (s, 2H), 3.63 (s, 4H). MS: 362.12 (calc), 363.1 (obs).

Example 51

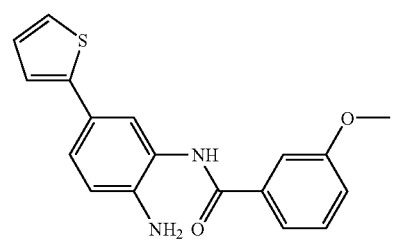

N-(2-amino-5-(thiophen-2-yl)phenyl)-3-methoxy-benzamide (181)

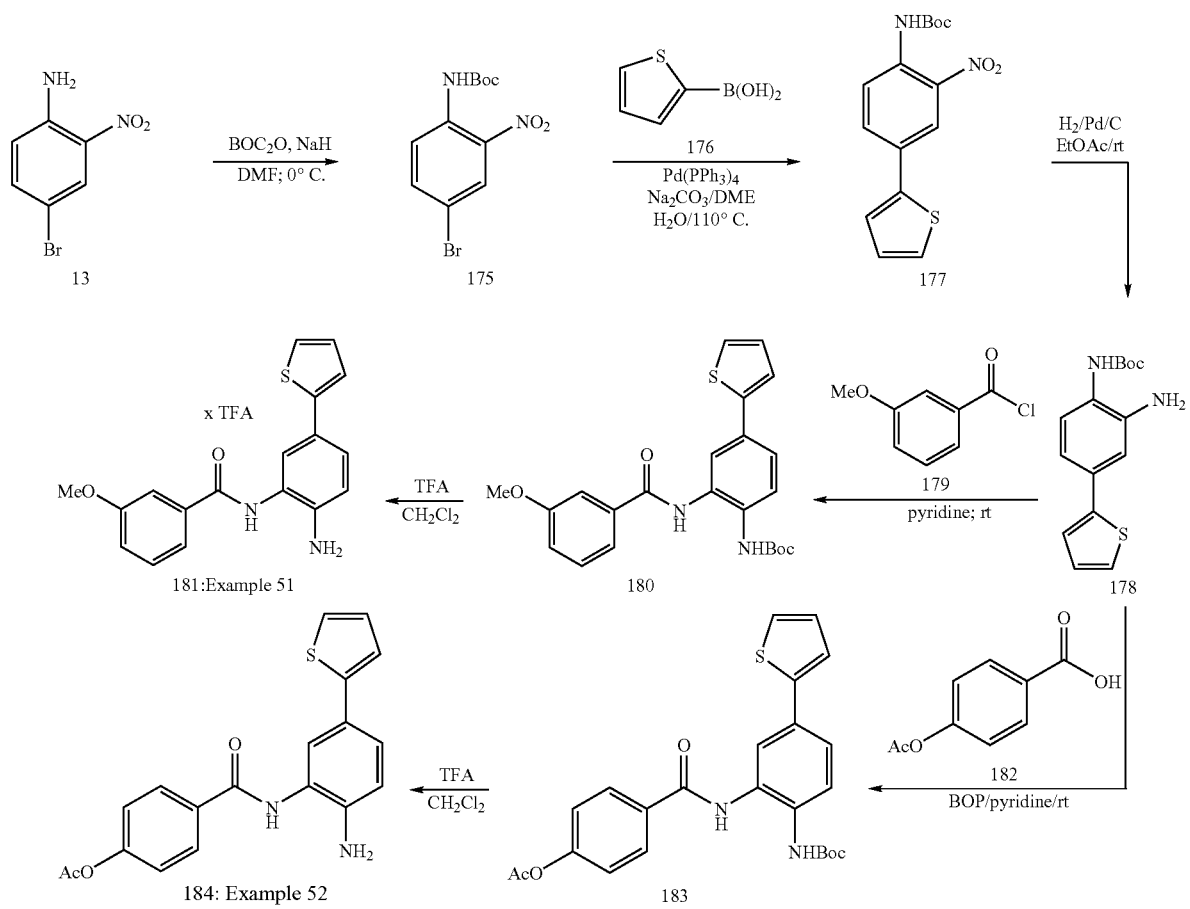

Step 1: tert-Butyl 4-bromo-2-nitrophenylcarbamate (175)

To a solution of 4-bromo-2-nitroaniline 13 (5.00 g, 23.07 mmol) in dimethylformamide (55 mL) at 0° C. was added sodium hydride (1.02 g, 25.38 mmol, 1.1 equ.) portion-wise. After complete $H_2$ evolution, a solution of Boc anhydride (5.04 g, 23.07 mmol, 1 equ.) in dimethylformamide (20 mL) was cannulated slowly into the reaction mixture over 30 minutes. The reaction was allowed to warm to rt then stirred overnight. It was then quenched with water and the DMF was removed in vacuo. The residue was taken up in water and extracted with ethyl acetate. The organic phase was dried over sodium sulfate, filtered and evaporated to provide 175 (3.72 g, 51%). $^1$H NMR: (DMSO) δ (ppm): 400 MHz, (DMSO) d (ppm): 9.67 (s, 1H), 8.10 (d, J=2.3 Hz, 1H), 7.84 (dd, J=8.6, 2.3 Hz, 1H), 7.56 (d, J=8.8 Hz, 1H), 1.44 (s, 9H). MS: (calc.) 316.01; (obt.) 217.1 (M−BoC)$^+$.

Step 2: tert-Butyl 2-nitro-4-(thiophen-2-yl)phenylcarbamate (177)

A solution of tert-butyl 4-bromo-2-nitrophenylcarbamate 175 (3.97 g, 12.5 mmol), 2-thiophene boronic acid 176 (1.68 g, 13.4 mmol), sodium carbonate (3.98 g, 37.56 mmol) and Pd(PPh$_3$)$_4$ (0.94 g, 0.814 mmol) were stirred at 110° C. in a mixture of DME and water (2:1, 70 mL) overnight. The solution was evaporated to dryness, diluted with water and extracted with ethyl acetate. The organic phase was washed with brine, dried over sodium sulfate, filtered and evaporated to provide the crude product which was purified by flash chromatography (10% ethyl acetate in hexane) to provide the title compound 177 (2.14 g, 53% yield). $^1$H NMR: (DMSO) δ (ppm): 400 MHz, (DMSO) d (ppm): 9.63 (s, 1H), 8.12 (d, J=2.3 Hz, 1H), 7.92 (dd, J=8.4, 2.2 Hz, 1H), 7.66 (d, J=8.4 Hz, 1H), 7.61 (q, J=2.2 Hz, 2H), 7.15 (dd, J=5.1, 3.7 Hz, 1H), 1.46 (s, 9H). MS: (calc.) 320.08; (obt.) 343.1 (M+Na).

Step 3: tert-Butyl 2-amino-4-(thiophen-2-yl)phenylcarbamate (178)

Following the same procedures as in Example 48, step 3 (scheme 36) but substituting compound 171 for compound 177 the title compound 178 was obtained (68% yield). $^1$H NMR: (DMSO) δ (ppm): 400 MHz, (DMSO) d (ppm): 8.34 (s, 1H), 7.43 (dd, J=5.1, 1.2 Hz, 1H), 7.27 (dd, J=3.5, 1.2 Hz, 1H), 7.24 (d, J=8.0 Hz, 1H), 7.06 (dd, J=5.1, 3.7 Hz, 1H), 6.95

(d, J=2.2 Hz, 1H), 6.82 (dd, J=8.2, 2.2 Hz, 1H), 5.00 (s, 2H), 1.47 (s, 9H). MS: (calc.) 290.11; (obt.) 291.1 (MH)⁺.

Step 4: tert-butyl 2-(3-methoxybenzamido)-4-(thiophen-2-yl)phenylcarbamate (180)

3-Methoxybenzoyl chloride 179 (0.20 g, 1.17 mmol) and 178 (0.34 g, 1.17 mmol) were stirred in pyridine (15 mL) at rt for 4 hrs then the pyridine was removed by rotary evaporation and the crude material was purified by column chromatography (25% ethyl acetate in hexanes) to provide the title compound 180 (0.44 g, 89% yield). ¹H NMR: (DMSO) δ (ppm): 400 MHz, (DMSO) d (ppm): 9.88 (s, 1H), 8.72 (s, 1H), 7.80 (s, 1H), 7.60 (d, J=8.4 Hz, 1H), 7.43 to 7.55 (m, 6H), 7.17 (dd, J=7.6, 1.8 Hz, 1H), 7.11 (dd, J=4.9, 3.5 Hz, 1H), 3.84 (s, 3H), 1.46 (s, 9H). MS: (calc.) 424.15; (obt.) 425.1 (MH)⁺.

Step 5: N-(2-Amino-5-(thiophen-2-yl)phenyl)-3-methoxybenzamide trifluoroacetate (181)

tert-Butyl 2-(3-methoxybenzamido)-4-(thiophen-2-yl)phenylcarbamate 180 (0.214 g, 0.504 mmol) was stirred in trifluoroacetic acid: dichloromethane solution (1:3, 4 mL) at rt for 5 hrs then solvent was evaporated. The crude residue was washed with dichloromethane and evaporated several times to get rid of excess trifluoroacetic acid to provide the title compound 181 (0.22 g, 100%). ¹H NMR: (DMSO) δ (ppm): 400 MHz, (DMSO) d (ppm): 9.96 (1H, s), 7.59-7.52 (3H, m), 7.46-7.41 (3H, m), 7.39 (1H, d, 2.2 Hz), 7.33 (1H, dd, 2.5 and 1.0 Hz), 7.16 (1H, dd, 5.7 and 1.8 Hz), 6.98 (1H, d, 8.4 Hz), 3.84 (3H, s). MS: 324.09 (calc), 325.1 (obs).

Example 52

4-(2-Amino-5-(thiophen-2-yl)phenylcarbamoyl)phenyl acetate (184)

Step 1: Acetic acid 4-(2-tert-butoxycarbonylamino-5-(thiophen-2-yl-phenylcarbamoyl)-phenyl ester (183)

tert-Butyl 2-amino-4-(thiophen-2-yl)phenylcarbamate 178 (0.198 g, 0.68 mmol), benzotriazol-1-yloxy-tris(dimethylamino)phosphonium hexafluorophosphate (BOP) (0.302 g, 0.68 mmol) and 4-acetoxybenzoic acid (182) (0.123 g, 0.68 mmol) were stirred in pyridine at rt overnight then solvent evaporated and purified by flash chromatography (35% ethyl acetate in hexanes) to provide 183 (0.11 g, 36%). ¹H NMR: (DMSO) δ (ppm): 400 MHz, (DMSO) d (ppm): 9.91 (s, 1H), 8.72 (s, 1H), 8.01 (d, J=8.8 Hz, 2H), 7.78 (d, J=1.8 Hz, 1H), 7.63 (d, J=8.4 Hz, 1H), 7.51 (dd, J=4.9, 0.98 Hz, 2H), 7.44 (dd, J=3.7, 0.98 Hz, 1H), 7.30 (d, J=8.6 Hz, 1H), 7.11 (dd, J=5.1 Hz, 1H), 2.32 (s, 3H), 1.46 (s, 9H). MS: (calc.) 452.14; (obt.) 475 (M+Na).

Step 2: Acetic acid 4-(2-amino-5-(thiophen-2-yl-phenylcarbamoyl)-phenyl ester trifluoroacetate (184)

Following the same procedure as for the Example 51, step 5 (the same scheme 37) but substituting compound 180 for the compound 183, the title compound 184 was obtained (16% yield). ¹H NMR: (DMSO) δ (ppm): 400 MHz, (DMSO) d (ppm): 9.73 (1H, s), 8.03 (2H, d, 8.4), 7.45 (1H, s), 7.34 (1H, d, 9.0 Hz), 7.30-7.22 (4H, m), 7.04 (1H, dd, 3.5 and 1.6 Hz), 6.79 (1H, d, 8.4 Hz), 5.18 (2H, s), 2.31 (3H, s). MS: 352.1 (calc), 353.1 (obs).

Example 53

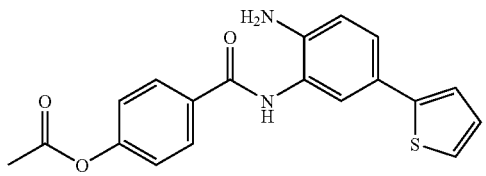

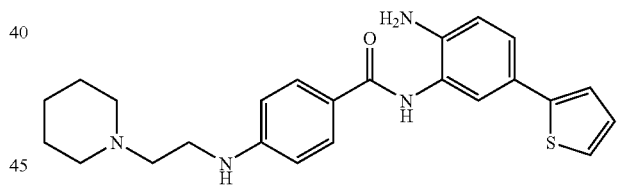

4-(2-Piperidin-1-yl)ethylamino)-N-(2-amino-5-(thiophen-2-yl)phenyl)benzamide (190)

Scheme 38

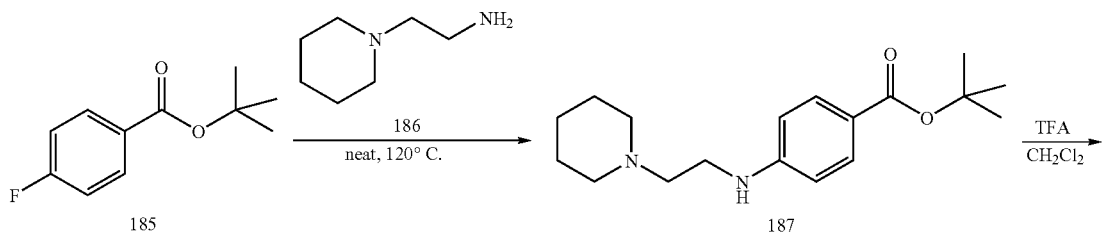

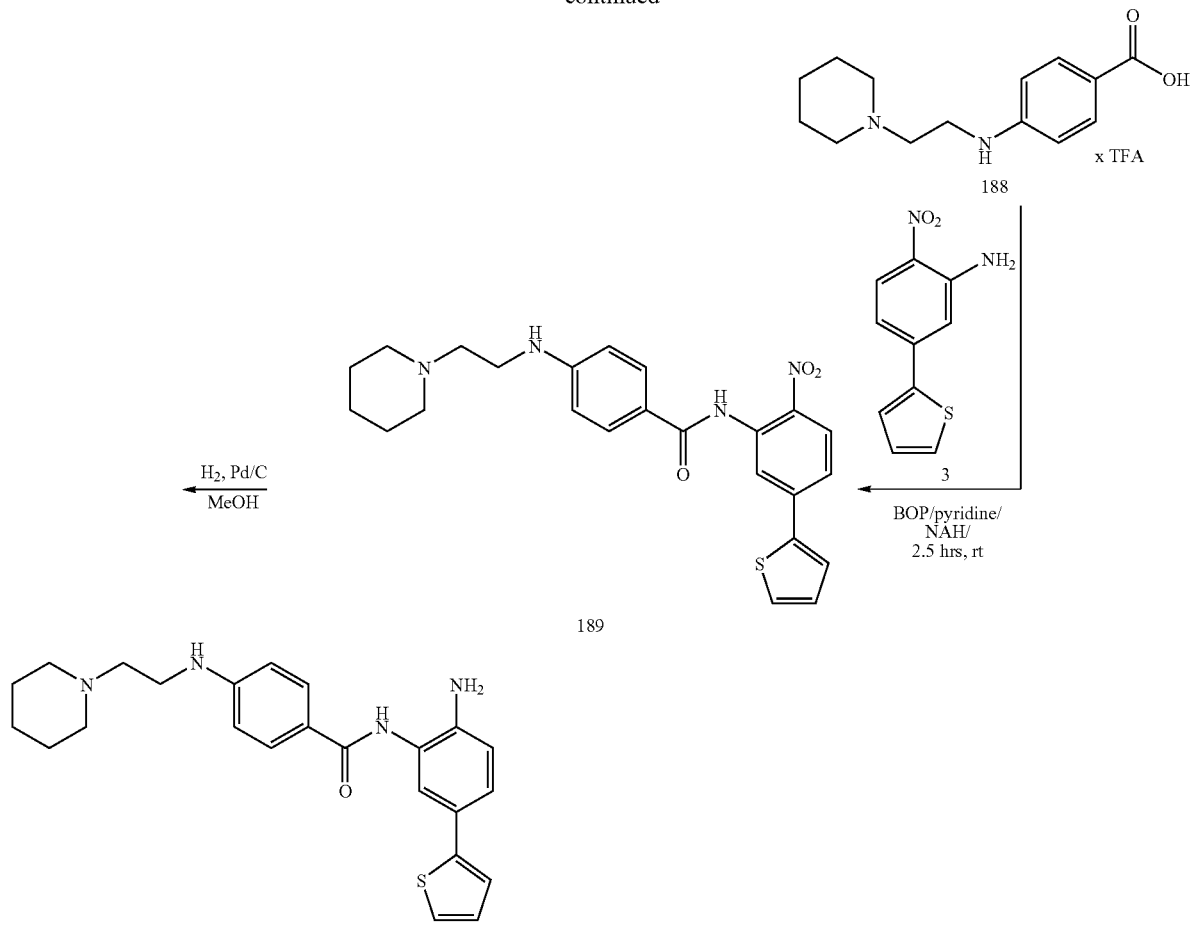

Step 1: tert-Butyl 4-(2-(piperidin-1-yl)ethylamino)benzoate (187)

tert-Butyl 4-fluorobenzoate 185 (0.502 g, 2.55 mmol) and 2-(piperidin-1-yl)ethanamine 186 (1.46 mL, 10.21 mmol) were stirred neat at 120° C. overnight then diluted with ethyl acetate, washed with saturated aqueous sodium bicarbonate (1×), brine (1×), dried over magnesium sulfate and evaporated to give 187 (0.501 g, 64%). $^1$H NMR: (DMSO) δ (ppm): 400 MHz, (DMSO) d (ppm): 7.59 (d, J=8.8 Hz, 2H), 6.55 (d, J=8.8 Hz, 2H), 6.24 (t, J=5.1 Hz, 1H), 4.11 (m, 2H), 3.21 to 3.13 (m, 6H), 2.44 (t, J=7.1 Hz, 2H), 2.37 (m, 2H), 1.49 (s, 9H), 1.47 to 1.38 (m, 2H). MS: 304.22 (calc), 249.1 (M-tBu).

Step 2: 4-(2-(Piperidin-1-yl)ethylamino)benzoic acid trifluoroacetate (188)

Following the same procedure as for the Example 51, step 5 (scheme 37) but substituting compound 187 for the compound 183, the title compound 188 was obtained (0.37 g, 90.5%). $^1$H NMR: (DMSO) δ (ppm): 400 MHz, (DMSO) d (ppm): 7.69 (d, J=8.6 Hz, 2H), 6.62 (d, J=8.8 Hz, 2H), 6.51 (t, J=6.8 Hz, 1H), 3.46 (d, J=5.7 Hz, 2H), 3.33 (s, 2H), 3.14 (d, J=11.5 Hz, 4H), 1.72 (m, 6H). MS: 248.15 (calc), 249.2 (obs).

Step 3: 4-(2-(Piperidin-1-yl)ethylamino)-N-(2-nitro-5-(thiophen-2-yl)phenyl)benzamide (189)

Following the same procedure as for the Example 1, step 3 (scheme 1), but substituting acid 4 for the acid 188, the title compound 189 was obtained (19% yield). MS: 450.17 (calc), 451.2 (obs).

Step 4: 4-(2-(Piperidin-1-yl)ethylamino)-N-(2-amino-5-(thiophen-2-yl)phenyl)benzamide (190)

Following the same procedure as for the Example 51, step 3 (scheme 37), but substituting nitro compound 177 for the nitro compound 189, the title compound 190 was obtained (8% Yield). $^1$H NMR: (DMSO) δ (ppm): 400 MHz, (DMSO) d (ppm): 9.34 (1H, s), [8.25 (2H, s) comes from formic salt], 7.77 (2H, d, 8.8), 7.44 (1H, d, 2.2 Hz), 7.34 (1H, dd, 4.0 and 1.2 Hz), 7.26-7.21 (2H, m), 7.03 (1H, dd, 3.5 and 1.4), 6.78 (1H, d, 8.2), 6.62 (1H, d, 8.8 Hz), 6.09 (1H, m), 3.25-3.15 (8H, m), 1.53 to 1.49 (4H, m), 1.39 (2H, m). MS: 420.2 (calc), 421.3 (obs).

Example 54

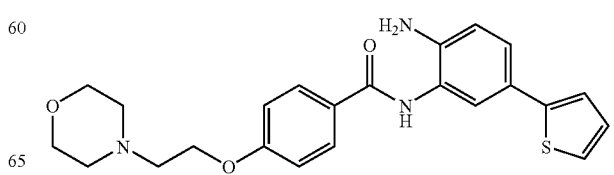

4-(2-Morpholinoethoxy)-N-(2-amino-5-(thiophen-2-yl)phenyl)benzamide 197

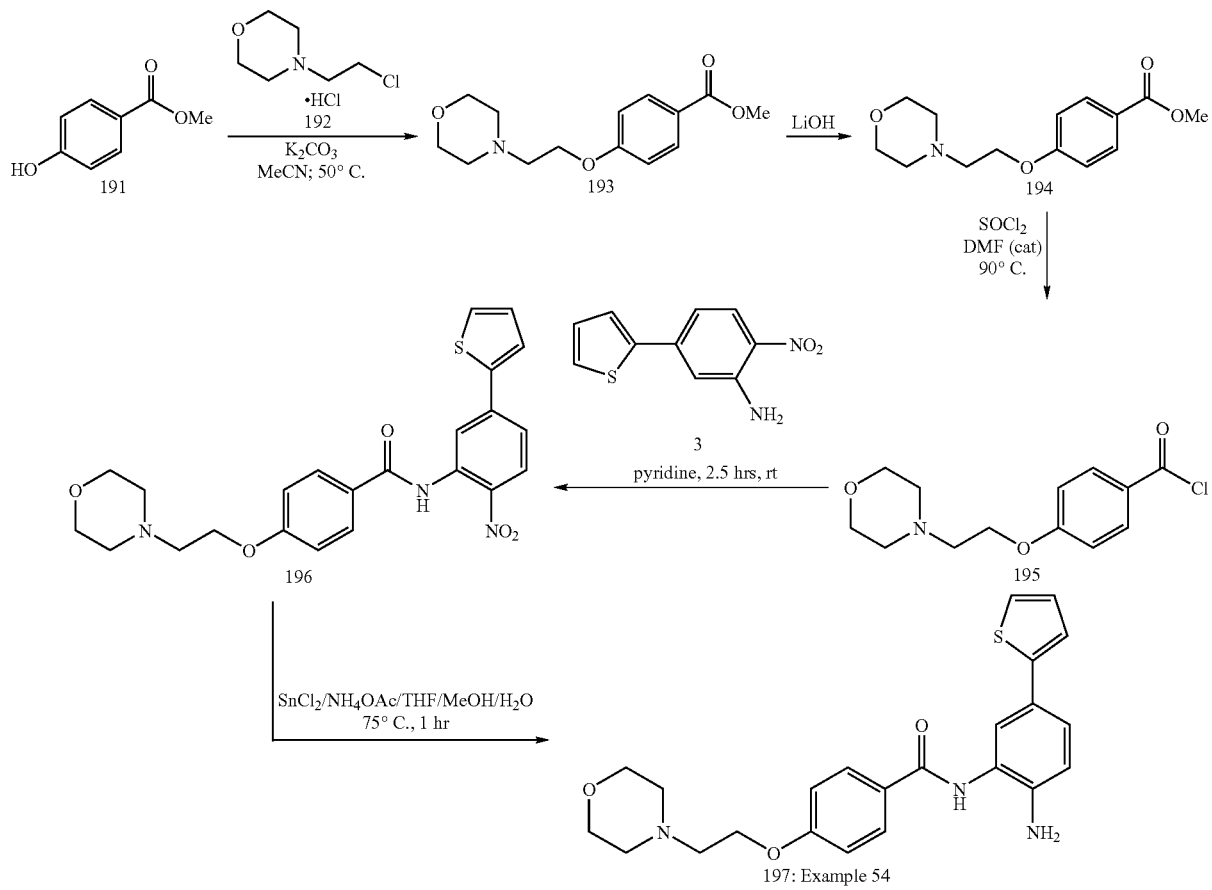

197: Example 54

Step 1: Methyl 4-(2-morpholinoethoxy)benzoate (193)

To a stirring solution of methyl 4-hydroxybenzoate 191 (1.08 g, 7.10 mmol) and 4-(2-chloroethyl)morpholine hydrochloride 192 (1.45 g, 7.82 mmol) in acetonitrile was added potassium carbonate (2.95 g, 21.3 mmol). The reaction mixture was heated to 50° C. overnight then cooled to rt and the resulting precipitate was filtered and washed with methanol to provide methyl 4-(2-morpholinoethoxy)benzoate 193 (2.67 g, 142%). $^1$H NMR: (DMSO) δ (ppm): 400 MHz, (DMSO) d (ppm): 7.87 (s, J=9.0 Hz, 2 h), 7.03 (d, J=9.0 Hz, 2H), 4.15 (t, J=5.7 Hz, 2H), 3.80 (s, 3H), 3.56 (t, J=4.5 Hz, 4H), 2.69 (t, J=5.7 Hz, 4H), 2.47 (m, 4H). MS: 265.13 (calc), 266.1 (obs).

Step 2: 4-(2-Morpholinoethoxy)benzoic acid (194)

Lithium hydroxide (hydrated) (0.59 g, 14.1 mmol) was added to a solution of methyl 4-(2-morpholinoethoxy)benzoate 193 (1.25 g, 4.7 mmol) in a 1:1 mixture of THF-water (20 mL). The reaction mixture was stirred at rt overnight then acidified with 1N HCl to pH 2, solvent was evaporated and the residue was lyophilized to provide crude 194 (1.66 g, >>100% Yield). $^1$H NMR: (DMSO) δ (ppm): 400 MHz, (DMSO) d (ppm): 7.88 (d, J=8.8 Hz, 2H), 7.05 (d, J=8.8 Hz, 2H), 4.53 (m, 2H), 3.89 (m, 4H), 3.53 (m, 2H), 3.26 to 3.14 (m, 4H). MS: 251.12 (calc), 252.1 (obs).

Step 3: 4-(2-Morpholinoethoxy)benzoyl chloride (195)

4-(2-Morpholinoethoxy)benzoic acid 194 (330 mg, 1.31 mmol) was dissolved in thionyl chloride (4 mL) and a few drops of dimethylformamide were added. The reaction mixture was allowed to stir at 80° C. in a sealed tube for 1.5 hrs then opened to leave evaporate overnight. The residue was placed on a vacuum pump overnight and used as is in the next reaction (0.30 g, 100%). MS: 269.08 (calc, COCl), 265.13 (calc, Me ester), 266.2 (obs, Me ester)

Step 4: 4-(2-Morpholinoethoxy)-N-(2-nitro-5-(thiophen-2-yl)phenyl)benzamide (196)

Following the same procedure as for the Example 51, step 4 (scheme 37) but substituting compound 178 for the compound 3, and compound 179 for compound 195, the title compound 196 was obtained (3% yield). MS: 453.14 (calc), 454.2 (obs).

Step 5: 4-(2-Morpholinoethoxy)-N-(2-amino-5-(thiophen-2-yl)phenyl)benzamide (197)

Following the same procedure as for the Example 1, step 4 (scheme 1) but substituting the nitro compound 5 for the nitro compound 196, title compound 197 was obtained (3 mg, 19%). ¹H NMR: (DMSO) δ (ppm): 400 MHz, (DMSO) d (ppm): 9.67 (1H, s), 8.01 (2H, d, 8.8), 7.44 (1H, d, 2.0 Hz), 7.36 (1H, dd, 4.1 and 1.0 Hz), 7.30 (1H, dd, 6.1 and 2.2 Hz), 7.24 (1H, dd, 2.5 and 1.2), 7.12 (2H, d, 8.8), 7.04 (1H, dd, 3.5 and 1.6 Hz), 6.82 (1H, d, 8.4 Hz), 4.44 (2H, t, 4.1), 3.65 to 3.15 (10H, m). MS: 423.16 (calc), 424.2 (obs).

Example 55

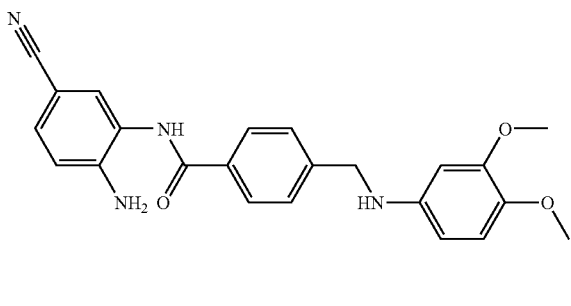

4-((3,4-Dimethoxyphenylamino)methyl)-N-(2-amino-5-cyanophenyl)benzamide (199)

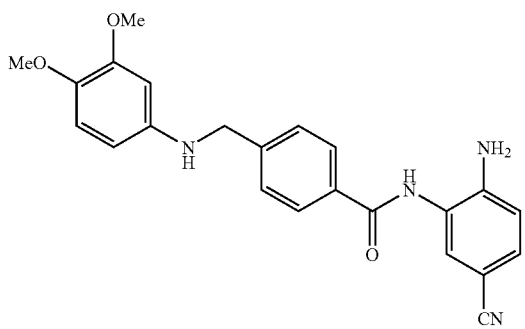

199: Example 55

Step 1: 4-((3,4-Dimethoxyphenylamino)methyl)-N-(2-amino-5-cyanophenyl)benzamide (199)

Following the same procedure as described in Example 27, step 2 (scheme 20), the title compound 199 was obtained in 16% yield. ¹H NMR: (DMSO) δ (ppm): 9.56 (bs, 1H), 7.89 (d, J=8.0 Hz, 2H), 7.52 (bs, 1H), 7.45 (d, J=8.4 Hz, 2H), 6.77 (d, J=8.4 Hz, 1H), 6.63 (d, J=8.4 Hz, 1H), 6.30 (d, J=2.4 Hz, 1H), 5.99-5.95 (m, 2H), 5.74 (bs, 1H), 4.92 (bs, 2H), 3.64 (s, 3H), 3.32 (s, 3H). MS: (calc); 402.5 (obt.) 403.4 (MH)⁺.

Example 56

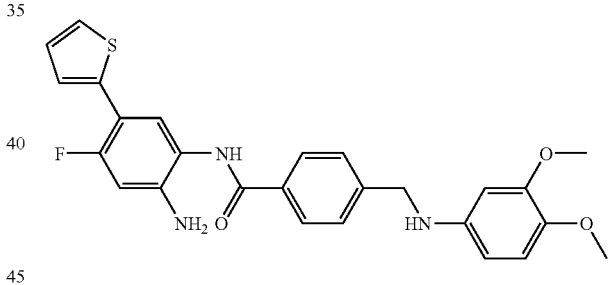

4-((3,4-Dimethoxyphenylamino)methyl-N-(2-amino-4-fluoro-5-(thiophen-2-yl)phenyl)benzamide (205)

Scheme 40

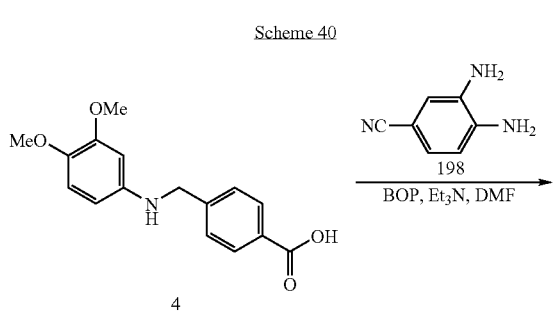

Scheme 41

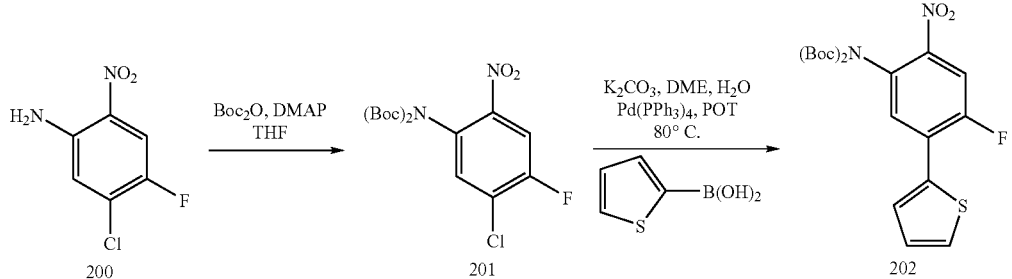

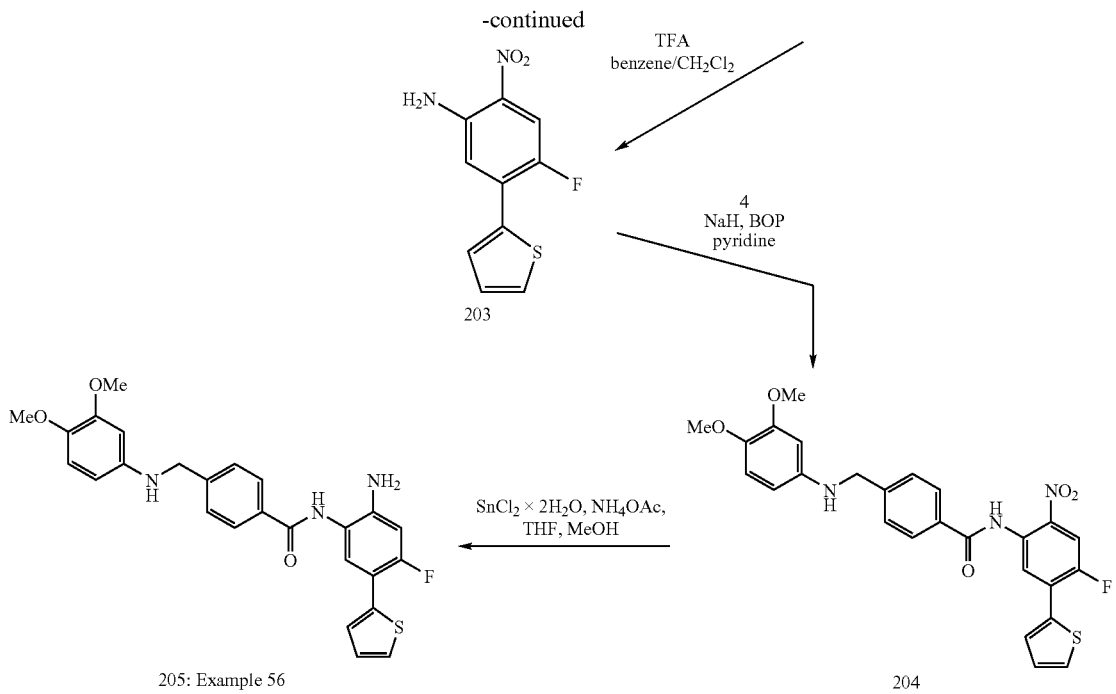

205: Example 56

Step 1: Di-tert-Butyl 5-chloro-4-fluoro-2-nitrophenylcarbamate (201)

Following the procedure described in Example 43, step 2 (scheme 31) using THF as a solvent but substituting compound 108 for compound 200, the title compound 201 was obtained in 55% yield. MS: (calc.) 390.8; (obt.) 413 (M+Na)+.

Step 2: Di-tert-butyl 4-fluoro-2-nitro-5-(thiophen-2-yl)phenylcarbamate (202)

Following the same procedure described in Example 1, step 2 (scheme 1), but substituting bromoarene 2 for compound 201, the title compound 202 was obtained (36% yield). $^1$H NMR: (CDCl3) δ (ppm): 7.85 (d, J=10.4 Hz, 1H), 7.56-7.54 (m, 1H), 7.49 (d, J=6.8 Hz, 1H), 7.44 (dd, J=1.2, 5.2 Hz, 1H), 7.10 (dd, J=0.8, 5.2 Hz, 1H), 1.36 (bs, 18H). MS: (calc.) 438.4; (obt.) 239.1 (MH−2 tert-Boc)+.

Step 3: 4-Fluoro-2-nitro-5-(thiophen-2-yl)benzenamine (203)

Following the procedure described in Example 27, step 3 (scheme 20) but substituting compound 111 for compound 202, the title compound 203 was obtained (32% yield). $^1$H NMR: (CD$_3$OD) δ (ppm): 7.86 (d, J=12.0 Hz, 1H), 7.63-7.60 (m, 2H), 7.31 (d, J=6.8 Hz, 1H), 7.17 (t, J=4.4 Hz, 1H). MS: (calc.) 238.3; (obt.) 239.1 (MH)+.

Step 4: 4-((3,4-dimethoxyphenylamino)methyl)-N-(4-fluoro-2-nitro-5-(thiophen-2-yl)phenyl)benzamide (204)

Following the procedure described in Example 1, step 3 (scheme 1) but substituting compound 3 for compound 203, the title compound 204 was obtained (89% yield). $^1$H NMR: (DMSO) δ (ppm): 10.70 (bs, 1H), 8.17 (d, J=7.2z, 1H), 8.10 (d, J=10.8 Hz, 1H), 7.90 (d, J=8.8 Hz, 2H), 7.85 (dd, J=5.2; 1.2 Hz, 1H), 7.73 (d, J=4.0 Hz, 1H), 7.52 (d, J=8.8 Hz, 2H), 7.62 (dt, J=5.2; 1.2 Hz, 1H), 6.40 (d, J=8.8 Hz, 1H), 6.31 (d, J=2.4 Hz, 1H), 6.01-5.96 (m, 2H), 4.31 (d, J=6.6 Hz, 2H), 3.65 (s$_1$ 3H), 3.58 (s, 3H). MS: (calc.) 507.5; (obt.) 508.3 (MH)+.

Step 5: 4-((3,4-Dimethoxyphenylamino)methyl)-N-(2-amino-4-fluoro-5-(thiophen-2-yl)phenyl)benzamide (205)

Following the procedure described in Example 1, step 4 (scheme 1) but substituting compound 5 for compound 204 and running the reaction at room temperature, the title compound 205 was obtained (41% yield). $^1$H NMR: (DMSO) δ (ppm): 9.65 (s, 1H), 7.96 (d, J=8.0 Hz, 2H), 7.48-7.51 (m, 4H), 7.31 (d, J=4.0 Hz, 1H), 7.11 (d, J=4.0 Hz, 1H), 6.80 (d, J=8.8 Hz, 1H), 6.50 (d, J=13.6 Hz, 1H), 6.35 (d, J=2.8 Hz, 1H), 6.03-6.01 (m, 2H), 5.50 (bs, 2H), 4.34 (d, J=6.0 Hz, 2H), 3.70 (s, 3H), 3.62 (s, 3H). MS: (calc.) 477.6; (obt.) 478.4 (MH)+.

Example 57a

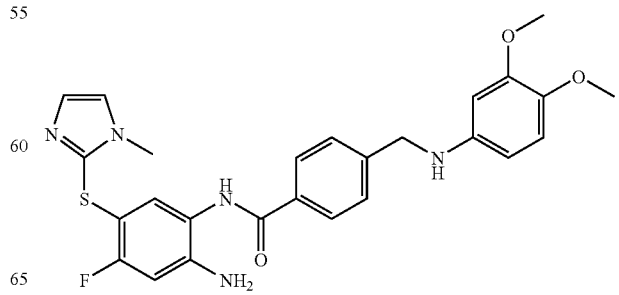

N-(5-(1-Methyl-1H-imidazol-2-ylthio)-2-amino-4-fluorophenyl)-4-((3,4-dimethoxyphenylamino)methyl)benzamide (209a)
Scheme 42
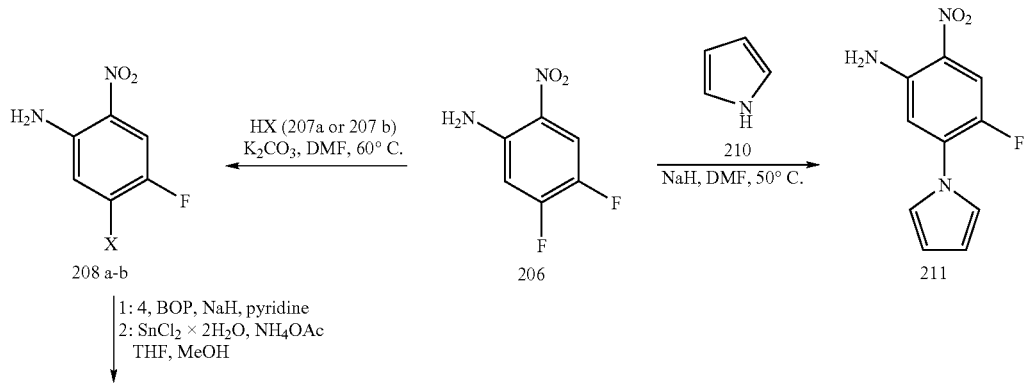
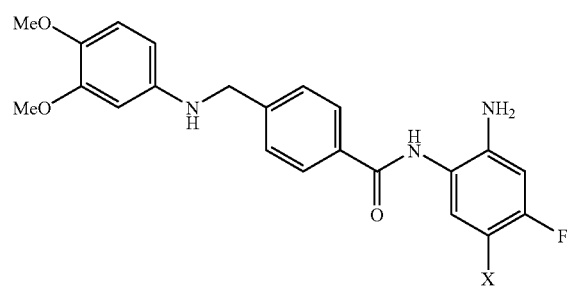
209a: Example 57a
209b: Example 57b
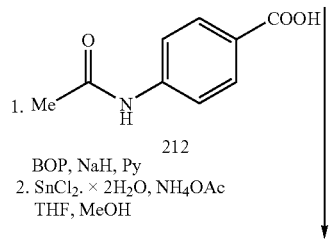
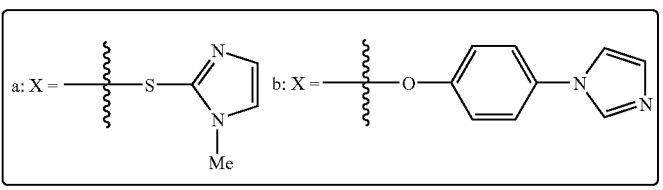
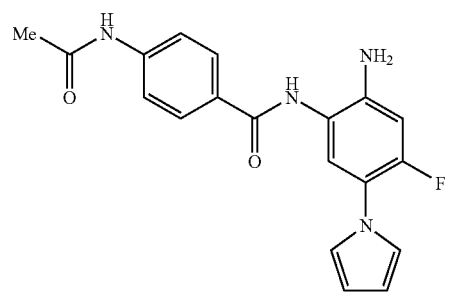
213: Example 58

Step 1: 5-(1-Methyl-1H-imidazol-2-ylthio)-4-fluoro-2-nitrobenzenamine (208a)

To a stirred solution of 206 (500 mg, 2.8 mmol) in DMF (20 mL), was added 1-methyl-1H-imidazole-2-thiol (207a, 2.8 mmol, 328 mg) and potassium carbonate (1.58 g, 11.49 mmol). The reaction mixture was stirred at 60° for 5 hours. Ethyl acetate was added and $K_2CO_3$ was removed by filtration. The filtrate was concentrated, evaporated under reduced pressure and the residue was purified by flash chromatography on silica gel, eluents hexane-EtOAc (1:2), then EtOAc (100%) to afford 208a (751 mg, 98% yield). MS: (calc.) 268.3; (obt.) 269.1 (MH)+.

Steps 2-3: N-(5-(1-Methyl-1H-imidazol-2-ylthio)-2-amino-4-fluorophenyl)-4-((3,4-dimethoxyphenylamino)methyl)benzamide (209a)

Following the procedures described in Example 1, steps 3 and 4 (scheme 1) but substituting compound 3 for compound 208a the title compound 209a was obtained in 28% yield. $^1$H NMR: (DMSO) δ (ppm): 9.5 (s, 1H), 7.86 (d, J=8.4 Hz, 2H), 7.43 (d, J=8.4 Hz, 2H), 7.2 (s, 1H), 7.10 (d, J=8.4 Hz, 1H), 6.90 (s, 1H), 6.6 (d, J=8.8 Hz, 1H), 6.56 (d, J=11.6 Hz, 1H), 6.29 (d, J=2.4 Hz, 1H), 5.95 (dd, J=2.4, 8.8 Hz, 2H), 5.52 (bs, 2H), 4.28 (bs, 2H), 3.64 (s, 6H), 3.57 (s, 3H). MS: (calc.) 507.6; (obt.) 508.4 (MH)+.

Example 57b

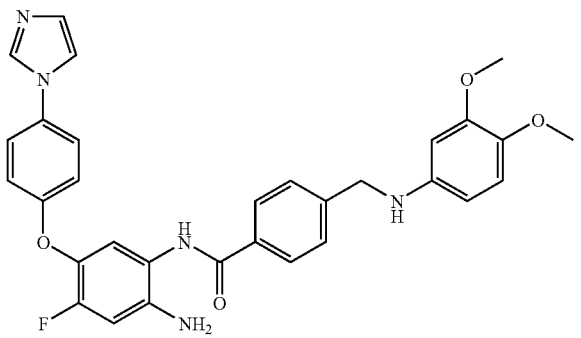

4-((3,4-Dimethoxyphenylamino)methyl)-N-(5-(4-(1H-imidazol-1-yl)phenoxy)-2-amino-4-fluorophenyl)benzamide (209b)

Step 1: 5-(4-1H-Imidazol-1-yl)phenoxy)-4-fluoro-2-nitrobenzenamine (208b)

Following the same procedure as described in Example 57a, step 1 (scheme 42) but substituting imidazole 207a for 4-(1H-imidazol-1-yl)phenol (207b), the compound 208b was obtained in 23% yield. MS: (calc.) 314.6; (obt.) 315.1 (MH)+.

Step 2-3: 4-((3,4-Dimethoxyphenylamino)methyl)-N-(5-(4-(H-imidazol-1-yl)phenoxy)-2-amino-4-fluorophenyl)benzamide (209b)

Following the procedures described in Example 1, steps 3 and 4 (scheme 1) but substituting compound 3 for compound 208b the title compound 209b was obtained in 65% yield. $^1$H NMR: (DMSO) δ (ppm): 7.87 (d, J=8.4 Hz, 2H), 7.75 (bs, 1H), 7.60 (d, J=8.0 Hz, 2H), 7.44 (d, J=8.4 Hz, 2H), 7.26 (bs, 1H), 7.14 (d, J=8.0 Hz, 1H), 7.03 (d, J=8.0 Hz, 2H), 6.723 (d, J=13.2 Hz, 1H), 6.62 (d, J=8.4 Hz, 1H), 6.29 (d, J=2.4 Hz, 1H), 5.96 (dd, J=2.4, 8.8 Hz, 2H), 4.28 (bs, 2H) 3.64 (s, 3H), 3.57 (s, 3H). MS: (calc.) 553.6; (obt.) 554.5 (MH)+.

Example 58

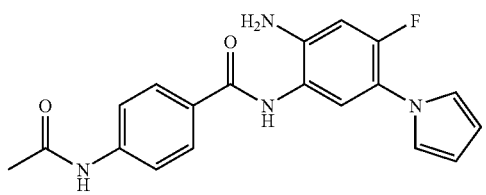

4-Acetamido-N-(2-amino-4-fluoro-5-(1H-pyrrol-1-yl)phenyl)benzamide (213)

Step 1: 4-Fluoro-2-nitro-5-1H-pyrrol-1-yl)benzenamine (211)

To a stirred solution of 206 (500 mg, 2.87 mmol) and pyrrole (210, 239 uL, 3.44 mmol) in DMF (10 mL), was added NaH (207 mg, 5.17 mmol). The reaction mixture was stirred for 18 hours at 50°, quenched with water (100 mL) and extracted with DCM (2×50 mL). The organic phase was dried with magnesium sulfate and concentrated under reduced pressure. The residue was purified by flash chromatography on silica gel, eluents hexanes-EtOAc 4:1, then hexanes-EtOAc 1:1, to afford the title compound 211 (145 mg, 25% yield). $^1$H NMR: (DMSO) δ: 7.94 (d, J=12.0 Hz, 1H), 7.12 (q, J=2.4, 4.4 Hz, 2H), 7.02 (d, J=6.8 Hz, 1H), 6.32 (t, J=2.4, 4.8 Hz, 2H). MS: (calc.) 221.8; (obt.) 222.1 (MH)+.

Step 2-3: 4-Acetamido-N-(2-amino-4-fluoro-5-(1H-pyrrol-1-yl)phenyl)benzamide (213)

Following the procedures described in Example 1, steps 3 and 4 (scheme 1) but substituting amine 3 for compound 211, and the acid 4 for 4-acetamidobenzoic acid (212) the title compound 213 was obtained in 40% yield. $^1$H NMR: (DMSO) δ (ppm): 10.11 (s, 1H), 9.48 (s, 1H), 7.83 (d, J=8.4 Hz, 2H), 7.56 (d, J=8.8 Hz, 2H), 7.20 (d, J=8.4 Hz, 1H), 6.86 (dd, J=2.0, 4.0 Hz, 2H), 6.62 (d, J=12.8 Hz, 1H), 6.10 (2H, dd, J=2.0, 4.0 Hz, 2H), 5.28 (bs, 2H), 2.09 (s, 3H). MS: (calc.) 352.36; (obt.) 353.2 (MH)+.

Example 59

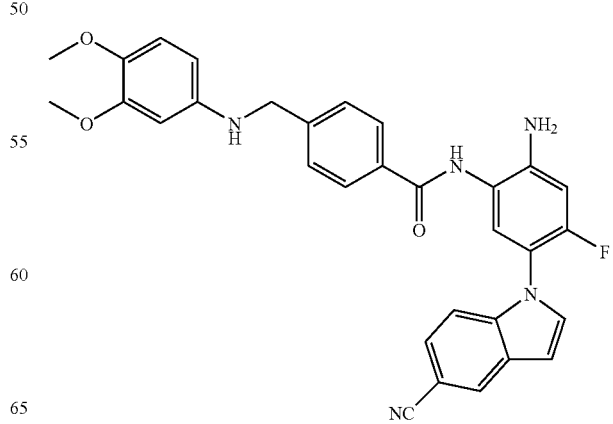

4-((3,4-dimethoxyphenylamino)methyl)-N-(2-amino-4-fluoro-5-indole-5-carbonitrile)benzamide (218)

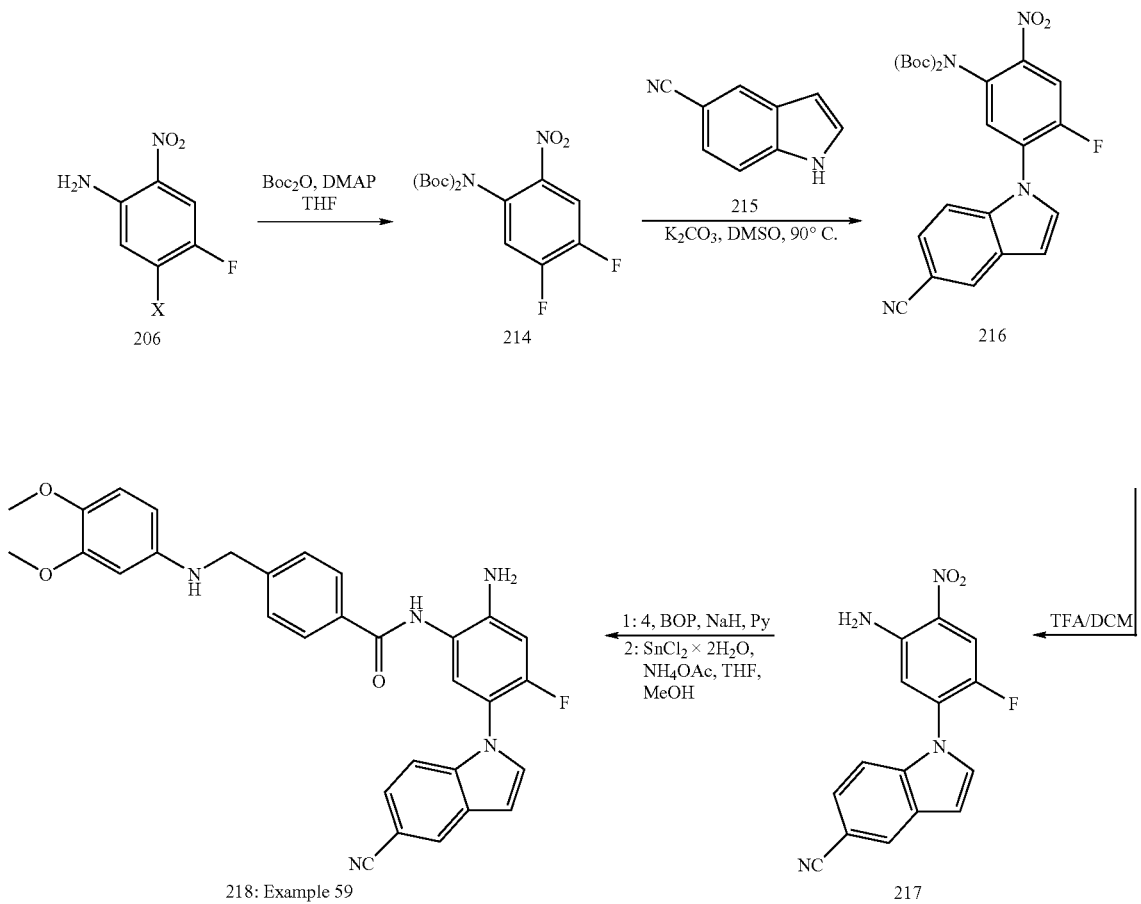

Scheme 43

Step 1: Di-tert-butyl 4,5-difluoro-2-nitrophenylcarbamate (214)

Following the procedure described in Example 43, step 2 (scheme 31) but substituting compound 148 for compound 206, the title compound 214 was obtained in 89% yield. $^1$H NMR: (CDCl3) δ (ppm): 7.99 (dd, J=7.6, 9.6 Hz, 1H), 7.18 (dd, $_F$J=7.2, 9.6 Hz, 1H), 1.42 (bs, 18H). MS: (calc.) 374.3; (obt.) 397.2 (MNa)$^+$.

Step 2: Di-tert-butyl 5-(5-cyano-1H-indol-1-yl)-4-fluoro-2-nitrophenylcarbamate (216)

Following the same procedure as described in Example 57a, step 1, but substituting DMF for DMSO and 1-methyl-1H-imidazole-2-thiol (207a) for 1H-indole-5-carbonitrile (215) the title compound 216 was obtained in 28% yield. $^1$H NMR: (CDCl$_3$) δ (ppm): 9.71 (bs, 1H), 8.88 (d, J=3.2 Hz, 1H), 8.21 (d, J=10.8 Hz, 1H), 8.02 (s, 1H), 7.55 (bs, 1H), 7.43 (dd, J=2.4, 6.0 Hz, 1H), 6.83 (d, J=3.6 Hz, 1H), 1.55 (s, 18H). MS: (calc.) 496.5; (obt.) 436.3 (M+K)$^+$.

Step 3: 1-(5-Amino-2-fluoro-4-nitrophenyl)-1H-indole-5-carbonitrile (217)

Following the procedure described in Example 27, step 3 (scheme 20) but substituting 111 for compound 216, the title compound 217 was obtained in 99% yield. MS: (calc.) 296.3; (obt.) 297.2 (MH)$^+$.

Steps 4-5: 4-((3,4-Dimethoxyphenylamino)methyl)-N-(2-amino-4-fluoro-5-indole-5-carbonitrile)benzamide (218)

Following the procedures described in Example 1, steps 3 and 4 but substituting compound 3 for compound 217 the title 218 was obtained in 41% yield. $^1$H NMR: (DMSO) δ (ppm): 8.08 (bs, 1H), 7.96 (d, J=8.0 Hz, 2H), 7.54 (d, J=8.0 Hz, 2H), 7.41-7.50 (m, 2H), 7.40 (d, J=8.0 Hz, 1H), 7.35 (d, J=7.6 Hz, 1H), 6.83 (d, J=8.0 Hz, 1H), 6.80 (d, J=2.4 Hz, 1H), 6.72 (d, J=8.8 Hz, 1H), 6.38 (d, J=2.4 Hz, 1H), 6.15 (dd, J=2.4, 8.8 Hz, 1H), 4.41 (bs, 2H), 3.76 (s, 3H), 3.73 (s, 3H). MS: (calc.) 535.5; (obt.) 536.3 (MH)$^+$.

Example 60
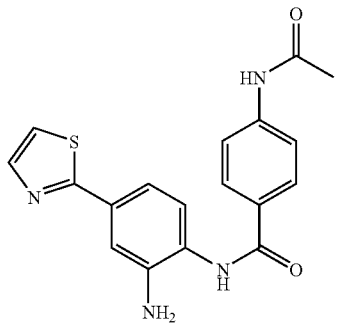
Example 61a
4-Acetamido-N-(2-amino-(5-(thiazol-2-yl)phenyl)benzamide (223) and
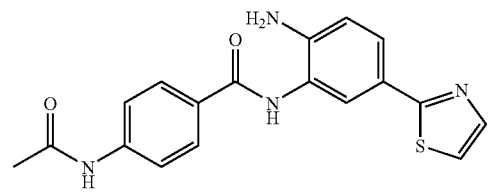
4-Acetamido-N-(2-amino-5-(thiazol-2-yl)phenyl)benzamide (224a)
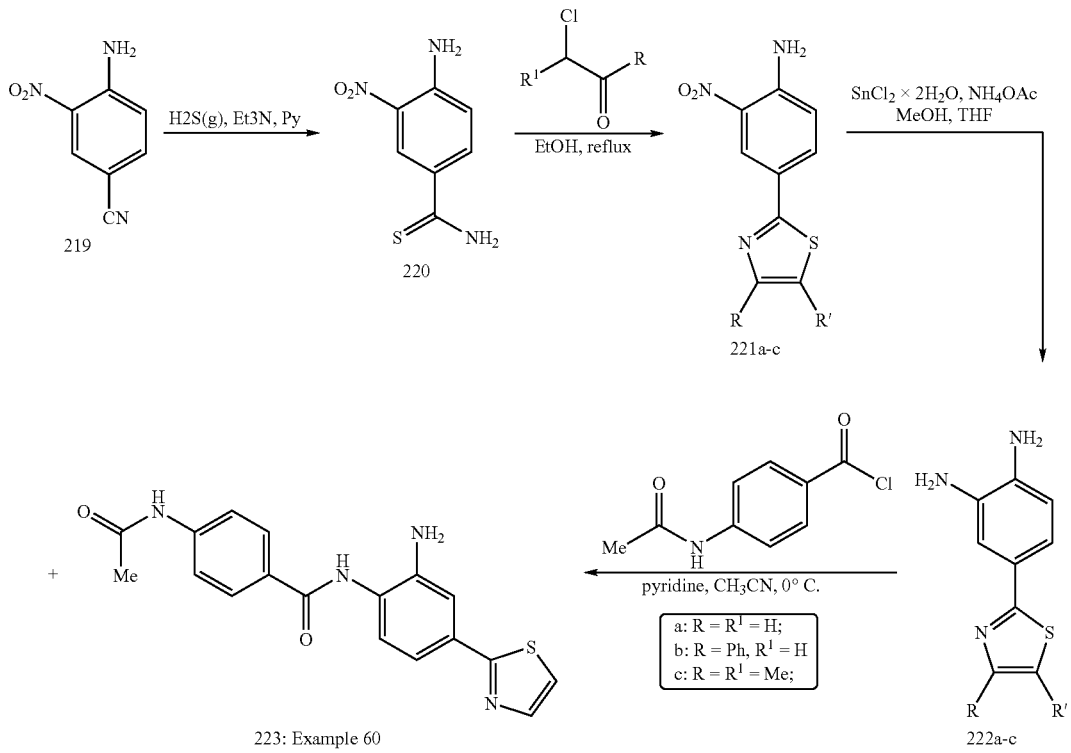
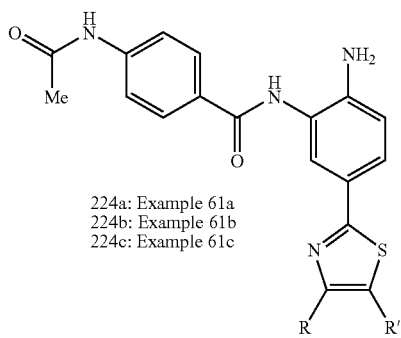

Step 1: 4-Amino-3-nitrobenzothioamide (220)

To a stirred solution of 219 (1.96 g, 12.02 mmol) in pyridine (15 mL) and $Et_3N$ (6 ml) was bubbled hydrogen sulfide for 40 minutes. When the reaction was completed nitrogen was bubbled for another 40 min. The residue was diluted in DCM and washed with water, HCl 10% and brine. Organic phases were collected, dried with sodium sulfate and concentrated under reduced pressure to afford the title compound 220 (2.11 g, 89% yield). $^1$H NMR: (DMSO) δ (ppm): 9.04 (bs, 1H), 8.31 (d, J=9.2 Hz, 1H), 7.28 (d, J=8.8 Hz, 1H). MS: (calc.) 197.2; (obt.) 198.1 $(MH)^+$.

Step 2: 2-Nitro-4-(thiazol-2-yl)benzenamine (221a)

To a stirred suspension of 220 (500 mg, 2.53 mmol) in ethanol (15 mL) was added chloroacetaldehyde (50% solution in water, 0.796 ml, 5.0 mmol). The mixture was heated at 80° C. for 18 hours, evaporated under reduced pressure and the residue was dissolved in DCM, washed with brine, dried with sodium sulfate and concentrated. The crude material was purified by flash chromatography on silica gel, eluents hexane-EtOAc (4:1), then EtOAC (100%), to afford the title compound 221a (104 mg, 19% yield). $^1$H NMR: $(CD_3OD)$ δ (ppm): 8.62 (d, J=2.0 Hz, 1H), 7.91 (dd, J=2.4, 8.8 Hz, 1H), 7.78 (d, J=3.2 Hz, 1H), 7.51 (d, J=3.2 Hz, 1H), 7.07 (d, J=8.8 Hz, 1H). MS: (calc.) 221.2; (obt.) 222.1 $(MH)^+$.

Step 3: 4-(Thiazol-2-yl)benzene-1,2-diamine (222a)

Following the procedure described in Example 1, step 4 (scheme 1) but substituting 5 for compound 221a, the title compound 222a was obtained (53% yield). $^1$H NMR: $(CD_3OD)$ δ (ppm): 7.68 (d, J=3.2 Hz, 1H), 7.38 (d, J=3.6 Hz, 1H), 7.26 (d, J=2.0 Hz, 1H), 7.19 (dd, J=2.0, 8.0 Hz, 1H), 6.70 (d, J=8.0 Hz, 1H). MS: (calc.) 191.2; (obt.) 192.3 $(MH)^+$.

Step 4. 4-Acetamido-N-(2-amino-4-(thiazol-2-yl)phenyl)benzamide (223) and 4-Acetamido-N-(2-amino-5-(thiazol-2-yl)phenyl)benzamide (224a)

To a stirred suspension of 222a (47 mg, 0.25 mmol) in acetonitrile (10 mL) and pyridine (20 uL) was added 4-acetamidobenzoyl chloride (49 mg, 0.25 mmol) in acetonitrile (1 mL) at 0° C. for 15 min. The reaction mixture was warmed up to room temperature and stirred for 4 hours, concentrated under reduced pressure. The crude was diluted in DCM and washed with $NaHCO_3$ and brine. The organic layer was dried with $Na_2SO_4$ and evaporated. The residue was purified by flash chromatography on silica gel, eluents hexane-EtOAc (1:3), then EtOAc (100%) to afford the title compounds 223 (3 mg, 4% yield) and 224a (5 mg, 5% yield).

223: $^1$H NMR: $(CD_3OD)$ δ (ppm): 7.95 (d, J=8.8 Hz, 2H), 7.60 (d, J=3.2 Hz, 1H), 7.73-7.71 (m, 2H), 7.56 (d, J=3.2 Hz, 1H), 7.48 (bs, 1H), 7.32 (bs, 2H), 2.17 (s, 3H). MS: (calc.) 352.4; (obt.) 353.2 $(MH)^+$.

224a: $^1$H NMR: (DMSO) δ (ppm): 10.18 (s, 1H), 9.64 (s, 1H), 8.00-7.94 (m, 5H), 7.84 (d, J=2.0 Hz, 1H), 7.68 (dd, J=1.6, 7.2 Hz, 2H), 7.61 (dd, J=2.0, 8.4 Hz, 1H), 7.42 (dt, J=1.6, 7.2 Hz, 2H), 7.32 (d, J=1.6, 7.2 Hz, 1H), 6.84 (d, J=8.4 Hz, 1H), 5.52 (bs, 2H), 2.09 (s, 3H). MS: (calc.) 428.5; (obt.) 429.1 $(MH)^+$.

Example 61b

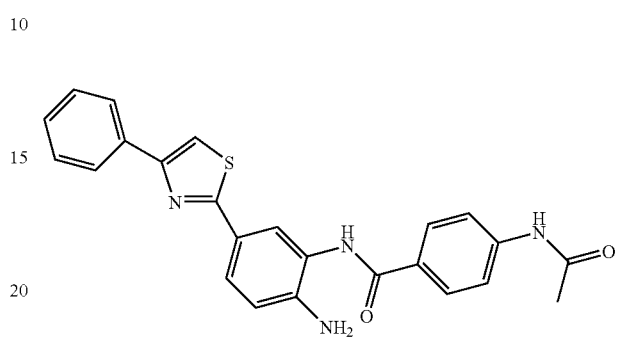

4-Acetamido-N-(2-amino-5-(4-phenylthiazol-2-yl)phenyl)benzamide (224b)

Following the same procedures as described in Example 61a, steps 1-4 (scheme 44) but substituting chloroacetaldehyde in the second step by 2-chloro-1-phenylethanone, the title 224b was obtained in 24% overall yield.

Example 61c

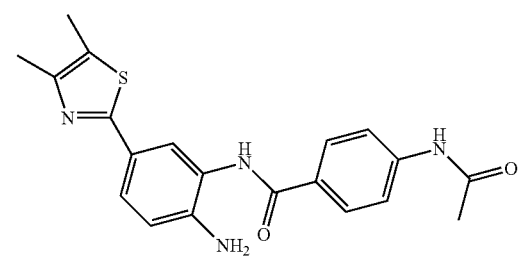

4-Acetamido-N-(2-amino-5-(4,5-dimethylthiazol-2-yl)phenyl)benzamide (224c)

Following the same procedures as described in Example 61a, steps 14 (scheme 44) but substituting chloroacetaldehyde in the second step by 3-chlorobutan-2-one, the title 224c was obtained in 3% overall yield.

Scheme 45

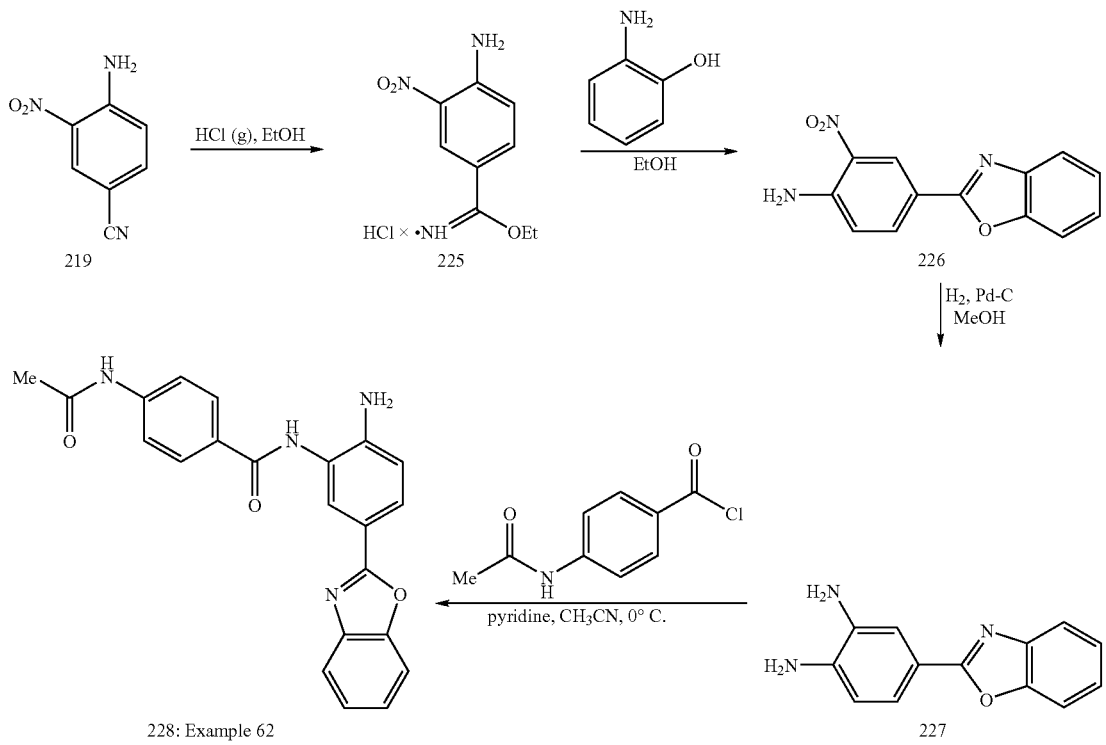

Example 62

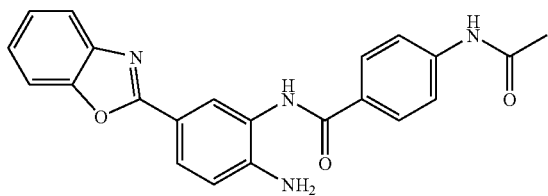

4-Acetamido-N-(2-amino-5-(benzo[d]oxazol-2-yl)phenyl)benzamide (228)

Step 1: 3-Nitro-4-benzenamine imidate (225)

Hydrogen chloride was bubbled into a reaction flask containing absolute ethanol (10 mL) during 5 min at 0° C. The compound 219 (2.00 g, 12.26 mmol) was added to the solution. The mixture was stirred at room temperature for 18 h, concentrated under reduced pressure and the solid residue was triturated with ethyl acetate to afford the title compound 225 as a yellow solid (2.72 g, 79% yield). $^1$H NMR: (DMSO) δ (ppm): 8.40 (d, J=2.0 Hz, 1H), 8.05 (bs, 2H), 7.65 (dd, J=2.0, 8.8 Hz, 1H), 7.06 (d, J=8.8 Hz, 1H). MS: (calc.) 209.2; (obt.) 210.1 (MH)$^+$.

Step 2: 4-(Benzo[d]oxazol-2-yl)-2-nitrobenzenamine (226)

The imidate 225 (500 mg, 1.77 mmol) in anhydrous ethanol (25 mL) was treated with o-aminophenol (232 mg, 2.1 mmol) and heated in a sealed flask at 95° C. for 5 h. The solvent was evaporated under reduced pressure and the residue was triturated with ethyl acetate to afford the title compound 226 (517 mg, quant. yield.). $^1$H NMR: (DMSO) δ (ppm): 8.45 (d, J=2.0 Hz, 1H), 8.14 (dd, J=2.0, 8.8 Hz, 1H), 8.06 (bs, 2 h), 7.79-7.75 (M, 2H), 7.41-7.39 (m, 2 h), 7.20 (d, J=1.6 Hz, 1H). MS: (calc.) 255.2; (obt.) 256.0 (MH)$^+$.

Step 3: 4-(Benzo[d]oxazol-2-yl)benzene-1,2-diamine (227)

To a stirred solution of 226 (517 mg, 1.77 mmol) in methanol (20 mL) was added palladium on charcoal (10%, 188 mg). The reaction was stirred under hydrogen atmosphere for 18 hours, filtered through a celite pad; the filtrate was evaporated under reduced pressure to afford title compound 227 (350 mg, 87% yield). $^1$H NMR: (DMSO) δ 7.673-7.641 (m, 2H), 7.39 (d, J=2.0 Hz, 1H), 7.32-7.30 (m, 3H), 6.64 (d, J=8.0 Hz, 1H). MS: (calc.) 225.2; (obt.) 226.1 (MH)$^+$.

Step 4. 4-Acetamido-N-(2-amino-5-(benzo[d]oxazol-2-yl)phenyl)benzamide (228)

To a stirred suspension of 227 (350 mg, 1.55 mmol) in acetonitrile (20 mL) and pyridine (2 ml) was added 4-acetamidobenzoyl chloride (307 mg, 1.55 mmol) in acetonitrile (5 ml) at 0° C. The solution was warmed up to room temperature and stirred for 4 hours. The reaction mixture was concentrated under reduced pressure and the residue was purified by flash chromatography on silica gel, eluents hexane-EtOAc (1:3), then EtOAc (100%), to afford 228 as a beige solid (5 mg, 1% yield). $^1$H NMR: (DMSO) δ (ppm): 10.22 (s, 1H), 9.62 (s, 1H), 8.05 (d, J=2.4 Hz, 1H), 7.89 (d, J=8.4 Hz, 2H), 7.80 (1H, dd, J=2.0, 8.4 Hz, 1H), 7.68-7.73 (m, 4H), 7.33-7.35 (m, 2H), 6.91 (d, J=8.4 Hz, 1H), 5.86 (bs, 2H), 2.12 (s, 3H). MS: (calc.) 386.41; (obt.) 387.1 (MH)$^+$.

Example 63

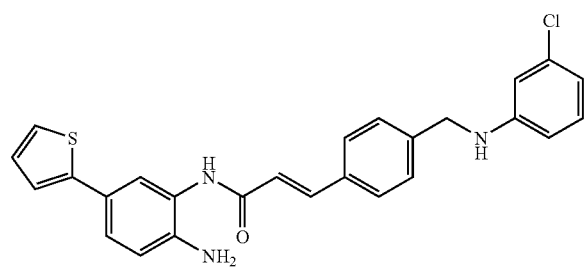

(E)-3-(4-(3-Chlorophenylamino)methyl)phenyl)-N-(2-amino-5-(thiophen-2-yl)phenyl)acrylamide (232)

Step 1. (E)-3-(4-((3-Chlorophenylamino)methyl) phenyl)acrylic acid (231)

To a solution of (E)-3-(4-formylphenyl)acrylic acid 229 (1 g, 5.67 mmol) and 3-chlorobenzenamine 230 (596 L, 5.67 mmol) in THF (8 ml), dibutyltin dichloride (173 mg, 0.57 mmol) was added followed by dropwise addition of phenylsilane (697 uL, 5.67 mmol). The resulting mixture was stirred at room temperature in the nitrogen atmosphere overnight, diluted with MeOH and concentrated under reduced pressure. The solid residue was triturated with DCM to yield the title compound 231 (1.24 g, 76% yield). $^1$H NMR: (DMSO) δ (ppm): 7.61 (d, J=8.0 Hz, 2H), 7.53 (d, J=16.0 Hz, 1H), 7.34 (d, J=8.4 Hz, 2H), 7.00 (t, J=8.0 Hz, 1H), 6.53 (t, J=2.0 Hz, 1H), 6.49-6.48 (m, 2H), 6.46 (d, J=16.0 Hz, 1H), 4.28 (bs, 2H). MS: (calc.) 287.7; (obt.) 288.1 (MH)$^+$.

Steps 2-3. (E)-3-(4-((3-Chlorophenylamino)methylphenyl)-N-(2-amino-5-(thiophen-2-yl)phenyl)acrylamide (232)

Following the procedure described in Example 1, steps 34 (scheme 1) but substituting acid 4 for the acid 231 title compound 232 was obtained in 60% yield. $^1$H NMR: (DMSO) δ (ppm): 9.42 (bs, 1H), 7.66-7.32 (m, 7H), 7.22-7.14 (m, 2H), 7.10-7.00 (m, 2H), 6.87-6.74 (m, 1H), 6.62-6.50 (m, 4H), 5.19 (bs, 1H), 4.29 (d, J=5.6 Hz, 2H). MS: (calc.) 459.2; (obt.) 460.3 (MH)$^+$.

Scheme 46

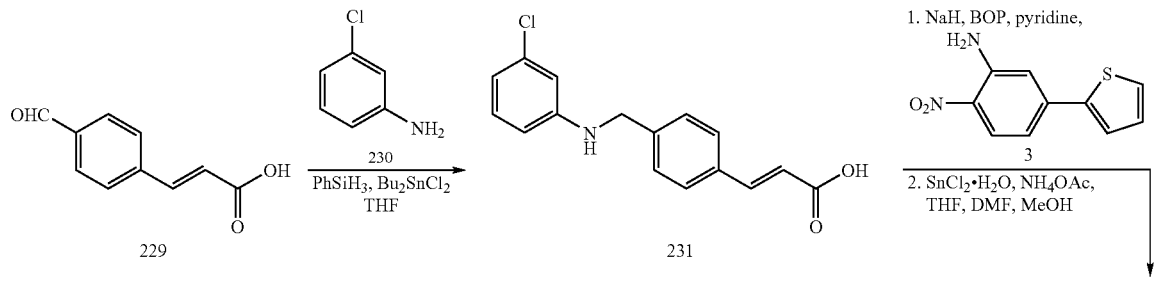

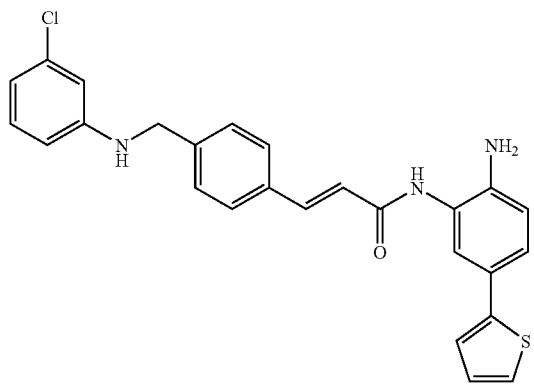

232: Example 63

Example 64

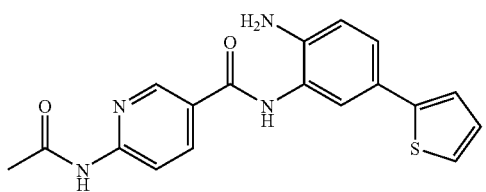

6-Acetamido-N-(2-amino-5-(thiophen-2-yl)phenyl)pyridine-3-carboxamide (235)

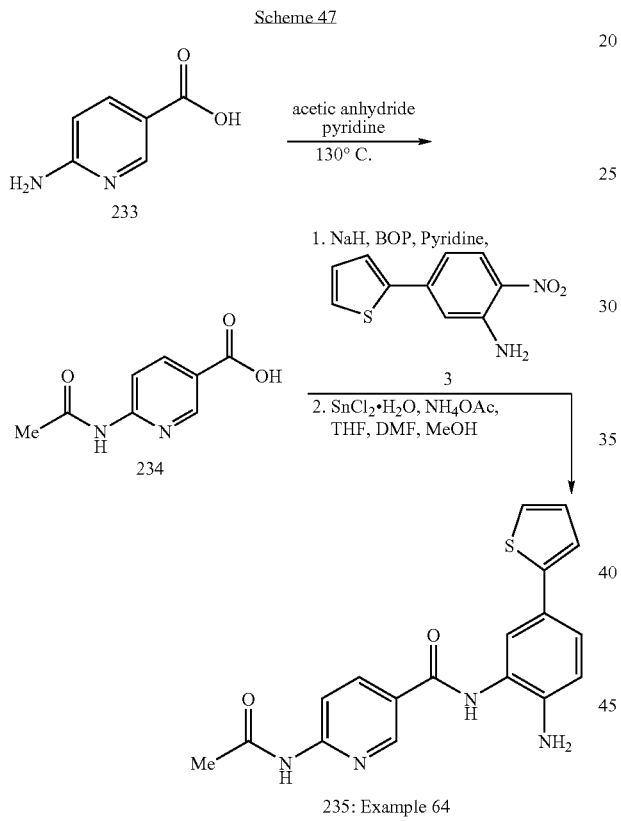

Scheme 47

235: Example 64

Step 1: β-Acetamidopyridine-5-carboxylic acid (234)

To a stirred solution of 233 (2 g, 14.48 mmol) in pyridine (60 mL) was added acetic anhydride (1.62 mL, 15.93 mmol). The reaction mixture was heated to 130° C. in a sealed vessel, stirred for 16 hours, concentrated under reduced pressure to 30 mL and cooled to 0° C. The resulting precipitate was filtered, washed with cold pyridine and water, and dried. This afforded 234 as a white solid (1.85 g, 71% yield). $^1$H-NMR (DMSO) δ: 10.82 (s, 1H), 8.77 (dd, J=2.2, 0.8 Hz, 1H), 8.20 (dd, J=8.7, 2.2 Hz, 1H), 8.14 (d, J=8.7 Hz, 1H), 2.12 (s, 3H).

Steps 2-3: 6-Acetamido-N-(2-amino-5-(thiophen-2-yl)phenyl)pyridine-3-carboxamide (235)

Following the procedures described in Example 1, steps 3 and 4 (with DMF as a co-solvent), but substituting acid 4 for the acid 234, the title compound 235 was obtained as a yellow solid (20 mg, 9% yield). $^1$H NMR: (DMSO) δ 10.79 (br s, 1H), 9.75 (br s, 1H), 8.90 (s, 1H), 8.31 (d, J=9.4 Hz, 1H), 8.15 (d, J=8.5 Hz, 1H), 7.42 (s, 1H), 7.33 (m, 1H), 7.28 (d, J=8.5 Hz, 1H), 7.22 (s, 1H), 7.02 (m, 1H), 6.78 (d, J=8.0 Hz, 1H), 5.20 (br s, 2H), 2.13 (s, 3H)

Example 65a

N-(2-amino-5-(thiophen-2-yl)phenyl)quinoxaline-6-carboxamide (238a)

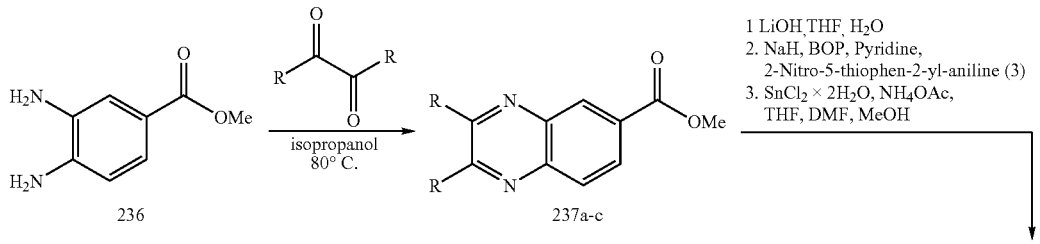

Scheme 48

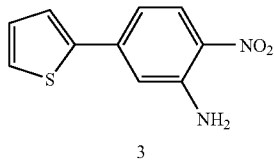
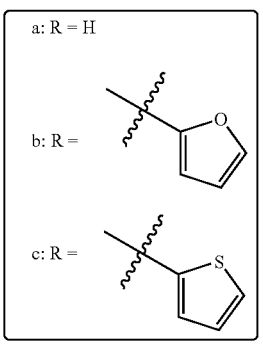
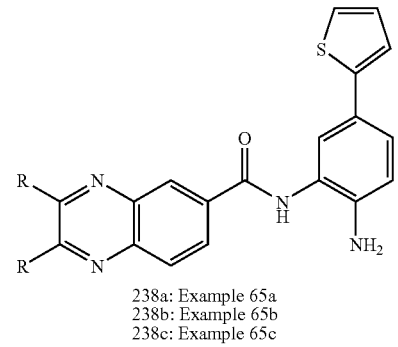

238a: Example 65a
238b: Example 65b
238c: Example 65c

Step 1: Methyl quinoxaline-6-carboxylate (237a)

To a stirred solution of 3,4-diamino-benzoic acid methyl ester (236, 2 g, 12.03 mmol) in isopropanol (50 mL) was added oxaldehyde as a 40% solution in water (13.23 mmol, 1.52 mL). The reaction mixture was heated at 80° C. for 2 hours, the solvent was removed under reduced pressure and the residue was dried under vacuum to yield 237a as a yellow solid (2.09 g, 93% yield). $^1$H NMR: (DMSO) δ 9.01 (s, 2H), 8.54 (d, J=1.6 Hz, 1H), 8.23 (dd, J=8.6, 2.0 Hz, 1H), 8.14 (dd, J=8.6, 0.6 Hz, 1H), 3.35 (s, 3H).

Steps 2-4: N-(2-Amino-5-(thiophen-2-yl)phenyl)quinoxaline-6-carboxamide (238a)

Following the same procedure as described in Example 4 step 3 and then the procedures described in Example 1, steps 3 and 4, (with DMF as a co-solvent), the title compound 238a was obtained as an orange solid in 26% yield (over the 3 steps). $^1$H NMR: (DMSO) δ 10.09 (br s, 1H), 9.04 (dd, J=6.7, 1.8 Hz, 2H), 8.79 (d, J=1.8 Hz, 1H), 8.37 (dd, J=8.9, 2.0 Hz, 1H), 8.20 (d, J=8.6 Hz, 1H), 7.51 (d, J=2.2 Hz, 1H), 7.34 (dd, J=4.9, 1.0 Hz, 1H), 7.30 (dd, J=2.1, 8.1 Hz, 1H), 7.24 (dd, J=3.5, 1.2 Hz, 1H), 7.04 (dd, J=4.9, 3.5 Hz, 1H), 6.81 (d, J=8.2 Hz, 1H), 5.28 (br s, 2H).

Example 5b

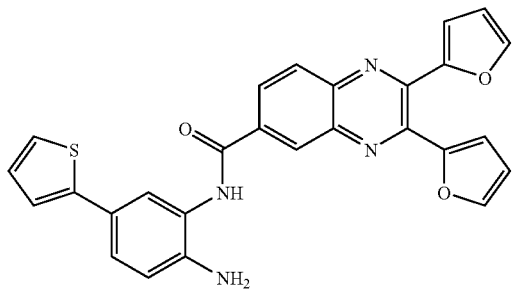

N-(2-Amino-5-(thiophen-2-yl)phenyl)-2,3-di(furan-2-yl)quinoxaline-6-carboxamide (238b)

Steps 1-4: N-(2-Amino-5-(thiophen-2-yl)phenyl)-2,3-di(furan-2-yl)quinoxaline-6-carboxamide (238b)

Following the same procedures as described in Example 65a but substituting in the step 1 oxaldehyde with 1,2-di(furan-2-yl)ethane-1,2-dione, the title compound 238b was obtained as an yellow solid in 28% yield (over the four steps). $^1$H NMR: (CD$_3$OD) δ 8.56 (s, 1H), 8.21 (d, J=8.6 Hz, 1H), 8.03 (d, J=8.8 Hz, 1H), 7.63 (s, 2H), 7.45 (d, J=1.7 Hz, 1H), 7.27 (d, J=8.4 Hz, 1H), 7.13-7.12 (m, 2H), 6.90 (t, J=4.1 Hz, 1H), 6.83 (d, J=8.4 Hz, 1H), 6.69 (t, J=3.9 Hz, 2H), 6.55-6.56 (m, 2H).

Example 65c

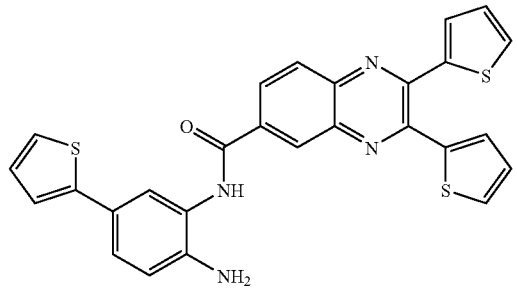

N-(2-Amino-5-(thiophen-2-yl)phenyl)-2,3-di(thiophen-2-yl)quinoxaline-6-carboxamide (238c)

Steps 1-4: N-(2-Amino-5-(thiophen-2-yl)phenyl)-2,3-di(thiophen-2-yl)quinoxaline-6-carboxamide (238c)

Following the same procedure as described in Example 65a but substituting in the step 1 oxaldehyde with 1,2-di(thiophen-2-yl)ethane-1,2-dione, the title compound 65c was obtained as an yellow solid in 25% yield (over the four steps). $^1$H NMR: (DMSO) δ 10.09 (s, 1H), 8.75 (d, J=1.8 Hz, 1H), 8.32 (dd, J=8.6, 2.0 Hz, 1H), 8.12 (d, J=8.6 Hz, 1H), 7.84-7.82 (m, 2H), 7.52 (d, J=2.0 Hz, 1H), 7.35-7.24 (m, 5H), 7.14-7.11 (m, 2H), 7.03 (dd, J=5.0, 3.5 Hz, 1H), 6.81 (d, J=8.4 Hz, 1H), 5.29 (s, 2H).

Example 66

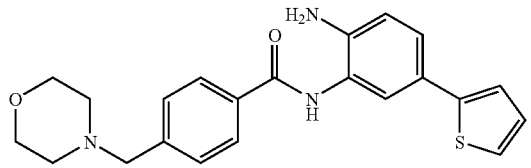

N-(2-Amino-5-(thiophen-2-yl)phenyl)-4-(morpholinomethyl)benzamide (242)

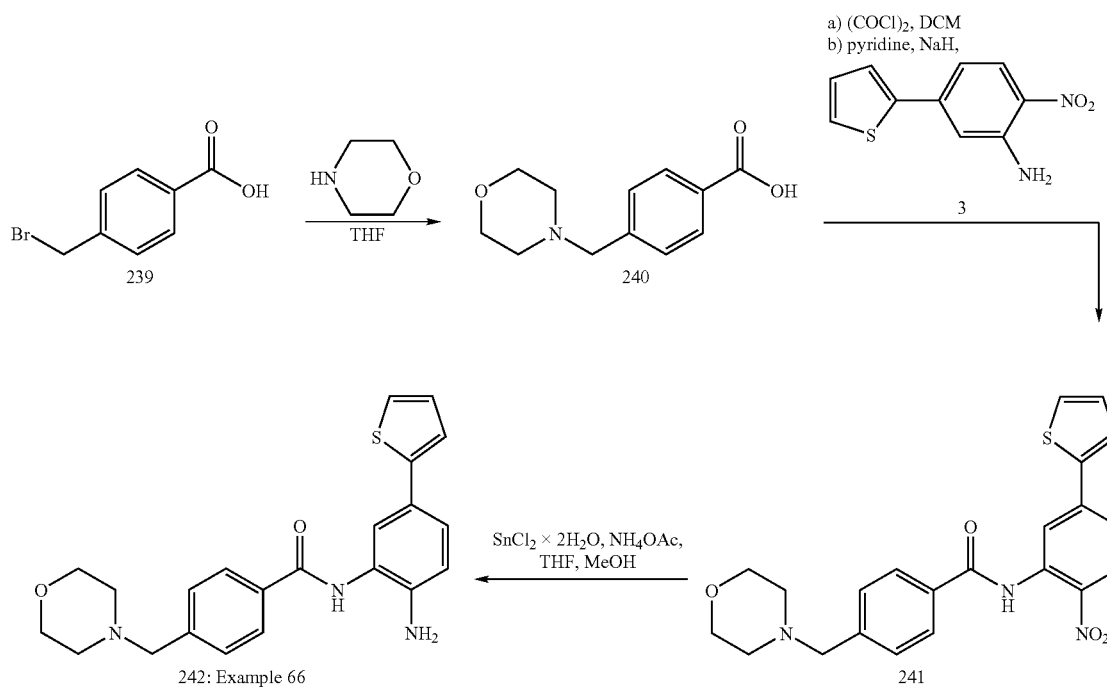

Scheme 49

Step 1: 4-(Morpholinomethyl)benzoic acid (240)

To a stirred solution of 4-bromomethyl-benzoic acid (239, 1.5 g, 6.78 mmol) in THF (15 mL) was added morpholine (0.61 mL, 6.78 mmol). The reaction mixture was allowed to stir for 10 minutes before the resulting white precipitate was filtered off and discarded. The filtrate was evaporated under reduced pressure and the remaining solid was dried under vacuum to afford the title compound 240 as a white solid (1.15 g, 75% yield). $^1$H NMR: (DMSO) δ 7.89-7.86 (m, 2H), 7.52 (d. J=8.4 Hz, 1H), 7.41 (d, J=8.0 Hz, 1H), 4.12 (s, 2H), 3.75-3.72 (m, 1H), 3.56-3.58 (m, 4H), 3.10-3.07 (m, 1H), 2.45-2.35 (m, 2H).

Step 2: 4-(Morpholinomethyl)-N-(2-nitro-5-(thiophen-2-yl)phenyl)benzamide (241)

To a stirred solution of 240 (221 mg, 1.0 mmol) in DCM (10 mL) was added oxalyl chloride (2M, 0.5 mL, 1.0 mmol) and DMF (1 drop). The resulting solution was stirred for 20 minutes. The DCM was removed under reduced pressure and pyridine was added (10 mL), followed by 2-nitro-5-(thiophen-2-yl-aniline (3, 220 mg, 1.0 mmol), and NaH (160 mg, 4.0 mmol). The reaction mixture was stirred for 1 hour before being quenched with acetic acid (2.0 mL). The pyridine was removed under reduced pressure and the residue was purified by flash chromatography on silica gel, eluent EtOAc-hexanes (4:1), to afford the title compound 241 as an orange solid (75 mg, 18% yield).

Step 3: N-(2-amino-5-(thiophen-2-yl)phenyl)-4-(morpholinomethyl)benzamide (242)

Following the same procedure as described in Example 1, step 4, and the title compound 242 was obtained as beige solid in 59% yield. $^1$H NMR: (CDCl$_3$) δ 8.61-8.59 (m, 1H), 8.02 (br s, 1H), 7.86 (d, J=8.0 Hz, 2H), 7.53 (br s, 1H), 7.44 (d, J=8.0 Hz, 2H), 7.33 (dd, J=8.2, 2.2 Hz, 1H), 7.30-7.26 (m, 1H), 7.17 (dd, J=5.1, 1.2 Hz, 1H), 7.15-7.14 (m, 1H), 7.01 (dd, J=5.1, 3.5 Hz, 1H), 6.82 (d, J=8.2 Hz, 1H), 3.73 (t, J=4.7 Hz, 4H), 3.57 (s, 2H), 2.47 (t, J=4.3 Hz, 4H).

Example 67a

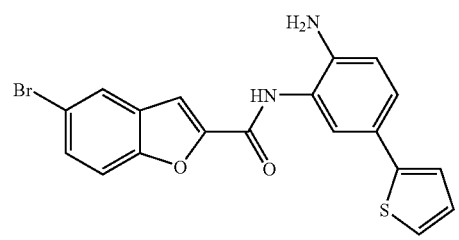

N-(2-amino-5-(thiophen-2-yl)phenyl)-5-bromoben-
zofuran-2-carboxamide (245a)

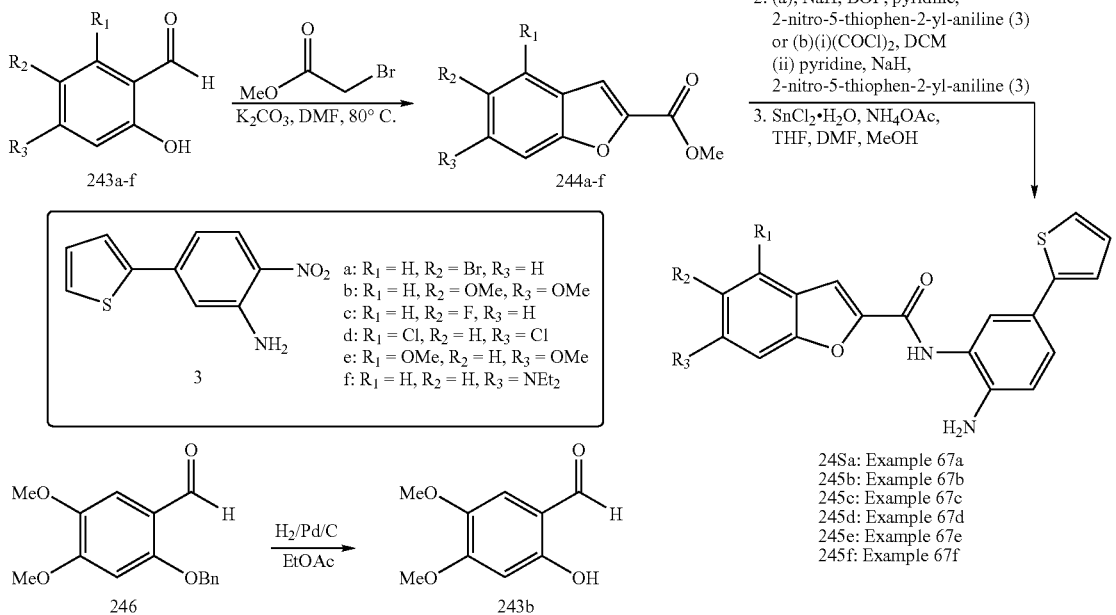

Scheme 50

245a: Example 67a
245b: Example 67b
245c: Example 67c
245d: Example 67d
245e: Example 67e
245f: Example 67f

Step 1: Methyl 5-bromobenzofuran-2-carboxylate (244a)

To a stirred solution of 5-bromo-2-hydroxybenzaldehyde (14a, 1.5 g, 7.46 mmol) in DMF (20 mL), was added methyl bromoacetate (8.21 mmol, 0.78 mL) and potassium carbonate (4.12 g, 29.84 mmol). The reaction mixture was heated at 80° and stirred for 15 hours, quenched with water (100 mL) and extracted with ethyl acetate (2×50 mL). The organic phase was dried with sodium sulfate, concentrated and the residue was purified by flash chromatography on silica gel, eluent hexanes-EtOAc (9:1). This afforded 244a as a white solid (650 mg, 35% yield). $^1$H NMR: (DMSO) δ 8.01-8.00 (m, 1H), 7.73-7.70 (m, 2H), 7.66-7.63 (m, 1H), 3.89 (s, 3H).

Steps 2-4: N-(2-Amino-5-(thiophen-2-yl)phenyl)-5-bromobenzofuran-2-carboxamide (245a)

Following the same procedure as described in Example 4 step 3 and then the procedures described in Example 66 step 2, and Example 1 step 3 and 4 (with DMF as a co-solvent), the title compound 245a was obtained as an orange solid in 13% yield (over the three steps). $^1$H NMR: (DMSO) δ 10.01 (s, 1H), 8.05 (d, J=1.6 Hz, 1H), 7.69-7.67 (m, 2H), 7.61 (dd, J=8.8, 2.0 Hz, 1H), 7.44 (d, J=2.2 Hz, 1H), 7.34 (dd, J=5.1, 1.2 Hz, 1H), 7.30 (dd, J=8.4, 2.2 Hz, 1H), 7.23 (dd, J=3.6, 1.2 Hz, 1H), 7.02 (dd, J=4.9, 3.6 Hz, 1H), 6.79 (d, J=8.4 Hz, 1H), 5.24 (s, 2H).

Example 67b

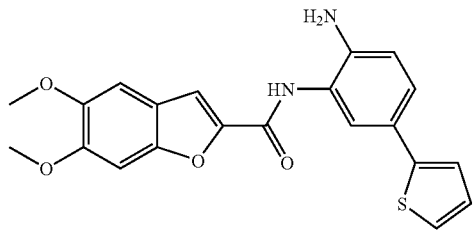

N-(2-Amino-5-(thiophen-2-yl)phenyl)-5,6-dimethoxybenzofuran-2-carboxamide (245b)

Step 1: 2-Hydroxy-4,5-dimethoxybenzaldehyde (243b)

To a stirred solution of 2-(benzyloxy)-4,5-dimethoxybenzaldehyde (246, 5.05 g, 18.6 mmol) in ethyl acetate (100 mL) was added 10% palladium on charcoal (250 mg). The flask was purged with hydrogen and then the reaction mixture was stirred under a hydrogen atmosphere (1 atm) for 15 hours, filtered through a celite pad, the filtrate was evaporated under reduced pressure, and the resulting solid dried under vacuum to afford 243b as a white solid (3.3 g, 98% yield). $^1$H NMR: (DMSO) δ 11.39 (s, 1H), 9.68 (s, 1H), 6.90 (d, J=2.5 Hz, 1H), 6.47 (s, 1H), 3.94 (s, 3H), 3.89 (s, 3H).

Steps 2-5: N-(2-Amino-5-(thiophen-2-yl)phenyl)-5,6-dimethoxybenzofuran-2-carboxamide (245b)

The title compound 245b was obtained as a light yellow solid in 9.1% yield (over four steps) following the same procedures as described in Example 67, but starting from 2-hydroxy-4,5-dimethoxybenzaldehyde (243b) instead of 243a, via the intermediate 244b. $^1$H NMR: (DMSO) δ 9.77 (s, 1H), 7.64 (s, 1H), 7.51 (d, J=2.1 Hz, 1H), 7.37 (dd, J=5.1, 1.2 Hz, 1H), 7.33 (d, J=2.2 Hz, 1H), 7.31-7.30 (m, 2H), 7.26 (dd, J=3.7, 1.2 Hz, 1H), 7.06 (dd, J=5.1, 3.5 Hz, 1H), 6.83 (d, J=8.5 Hz, 1H), 5.22 (s, 2H), 3.88 (s, 3H), 3.85 (s, 3H).

Example 67c

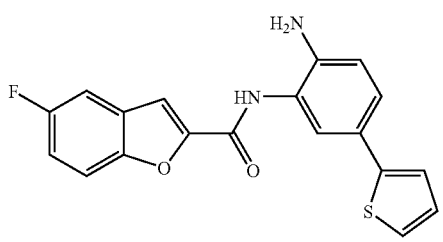

N-(2-Amino-5-(thiophen-2-yl)phenyl)-5-fluorobenzofuran-2-carboxamide (245c)

Steps 1-4: N-(2-Amino-5-(thiophen-2-yl)phenyl)-5-fluorobenzofuran-2-carboxamide (245c)

The title compound 245c was obtained as a light yellow solid in 5.6% yield (over four steps) following the same procedures as described in Example 67, but starting from 5-fluoro-2-hydroxybenzaldehyde (243c) instead of 243a, via the intermediate 244c. $^1$H NMR: (DMSO) δ 9.98 (s, 1H), 7.75-7.71 (m, 2H), 7.63 (dd, J=9.0, 2.8 Hz, 1H), 7.44 (d, J=2.0 Hz, 1H), 7.36-7.29 (m, 3H), 7.23 (dd, J=3.5, 1.1 Hz, 1H), 7.03 (dd, J=5.1, 3.7 Hz, 1H), 6.79 (d, J=8.4 Hz, 1H), 5.24 (s, 2H).

Example 67d

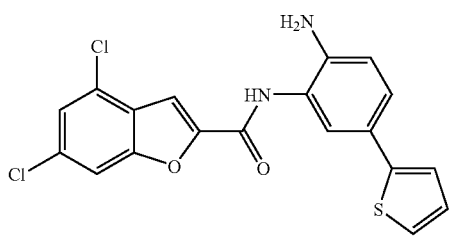

N-(2-amino-5-(thiophen-2-yl)phenyl)-4,6-dichlorobenzofuran-2-carboxamide (245d)

Steps 1-4: N-(2-amino-5-(thiophen-2-yl)phenyl)-4,6-dichlorobenzofuran-2-carboxamide (245d)

The title compound 245d was obtained as a light yellow solid in 5.9% yield (over four steps) following the same procedures as described in Example 67, but starting from 2,4-dichloro-6-hydroxybenzaldehyde (243d) instead of 243a, via the intermediate 244d. $^1$H NMR: (DMSO) δ 10.04 (s, 1H), 7.95 (dd, J=1.6, 1.0 Hz, 1H), 7.85 (s, 1H), 7.63 (d, J=1.6 Hz, 1H), 7.43 (d, J=2.2 Hz, 1H), 7.34 (dd, J=5.1, 1.2 Hz, 1H), 7.30 (dd, J=8.4, 2.3 Hz, 1H), 7.23 (dd, J=3.5, 1.2 Hz, 1H), 7.03 (dd, J=5.1, 3.5 Hz, 1H), 6.78 (d, J=8.3 Hz, 1H), 5.28 (s, 2H).

Example 67e

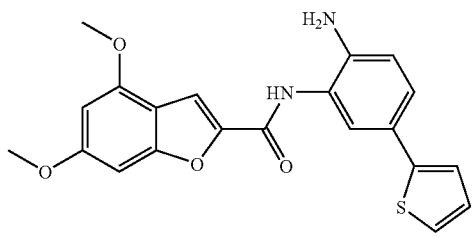

N-(2-amino-5-(thiophen-2-yl)phenyl)-4,6-dimethoxybenzofuran-2-carboxamide (245e)

Steps 1-4: N-(2-amino-5-(thiophen-2-yl)phenyl)-4,6-dimethoxybenzofuran-2-carboxamide (245e)

The title compound 245e was obtained as a light yellow solid in 4.8% yield (over four steps) following the same procedures as described in Example 67, but starting from 2-hydroxy-4,6-dimethoxybenzaldehyde (243e) instead of 243a, via the intermediate 244e. $^1$H NMR: (DMSO) δ 9.68 (s, 1H), 7.64 (s, 1H), 7.46 (d, J=2.0 Hz, 1H), 7.32 (d, J=1.0 Hz, 1H), 7.27 (dd, J=8.2, 2.1 Hz, 1H), 7.22 (dd, J=3.5, 1.0 Hz, 1H), 7.02 (dd, J=4.9, 3.5 Hz, 1H), 6.84 (s, 1H), 6.78 (d, J=8.4 Hz, 1H), 6.47 (d, J=1.7 Hz, 1H), 5.20 (s, 2H), 3.90 (s, 3H), 3.83 (s, 3H).

Example 67f

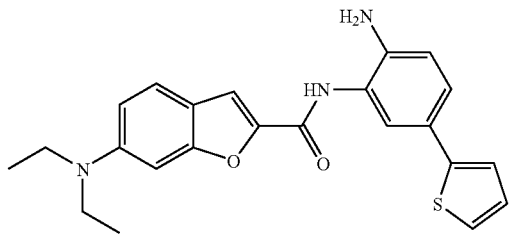

N-(2-amino-5-(thiophen-2-yl)phenyl)-6-(diethylamino)benzofuran-2-carboxamide (245f)

Steps 1-4: N-(2-amino-5-(thiophen-2-yl)phenyl)-6-(diethylamino)benzofuran-2-carboxamide (245f)

The title compound 245f was obtained as a light yellow solid in 18.1% yield (over four steps) following the same procedures as described in Example 67, but starting from 4-(diethylamino)-2-hydroxybenzaldehyde (243f), instead of 243a via the intermediate 244f. $^1$H NMR: (DMSO) δ 9.60 (s, 1H), 7.51-7.49 (m, 3H), 7.33 (dd, J=5.1, 1.2 Hz, 1H), 7.27

(dd, J=8.2, 2.1 Hz, 1H), 7.22 (dd, J=3.5, 1.2 Hz, 1H), 7.02 (dd, J=5.0, 3.5 Hz, 1H), 6.80-6.76 (m, 3H), 5.17 (s, 2H), 3.40 (q, J=6.8 Hz, 4H), 1.13 (t, J=7.0 Hz, 6H).

Example 68

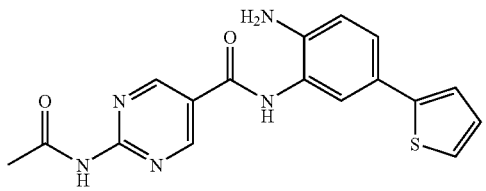

2-Acetamido-N-(2-amino-5-(thiophen-2-yl)phenyl)pyrimidine-5-carboxamide (250)

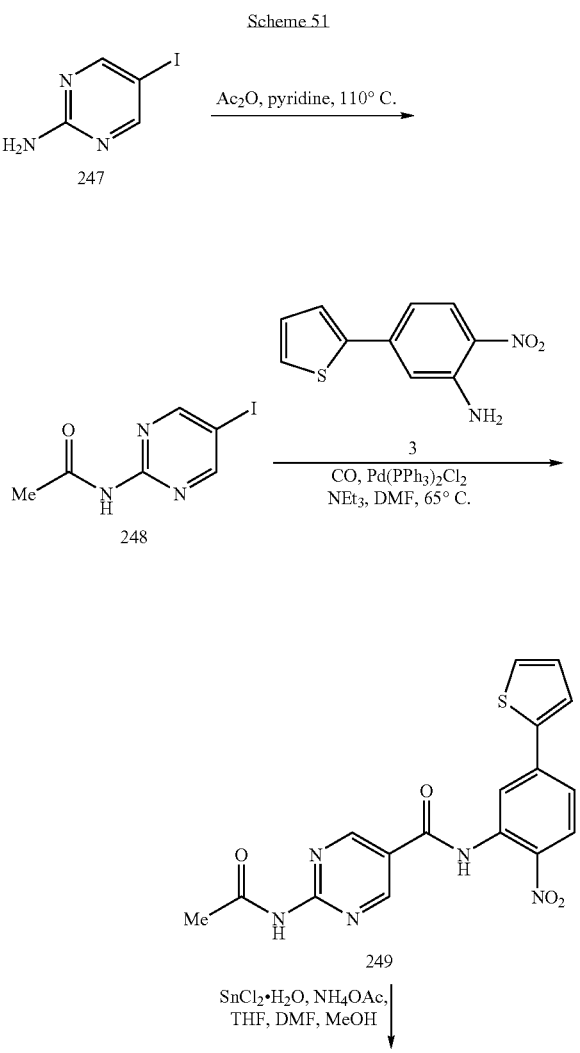

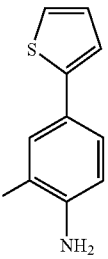

250: Example 68

Step 1: N-(5-Iodopyrimidin-2-yl)acetamide (248)

5-Iodo-pyrimidin-2-ylamine (17, 1.1 g, 4.98 mmol) and acetic anhydride (14.94 mmol, 1.41 mL) were dissolved in pyridine (20 mL) and stirred at H 0° C. for 48 hours. The reaction mixture was cooled and quenched with water (50 mL). Ethyl acetate (100 mL) was added and the resulting white precipitate was collected by filtration to afford title compound 248 as a white solid (300 mg, 23% yield). $^1$H NMR: (DMSO) δ 10.67 (s, 1H), 8.85 (s, 2H), 2.18 (s, 3H).

Step 2: 2-Acetamido-N-(2-nitro-5-(thiophen-2-yl)phenyl)pyrimidine-5-carboxamide (249)

To a stirred solution of 248 (265 mg, 1.01 mmol) and Pd(PPh$_3$)$_2$Cl$_2$ (35 mg, 0.05 mmol) in DMF (4 mL) was added 2-nitro-5-(thiophen-2-yl-aniline (3, 288 mg, 1.3 mmol) and triethylamine (1.5 mmol, 0.2 mL). The solution was purged with carbon monoxide and pressurized to 65 psi before being heated at 65° C. with stirring for 15 hours. The solution was cooled and diluted with ethyl acetate (20 mL). The resulting yellow precipitate was collected by filtration to afford 249 as a yellow solid (145 mg, 40% yield). $^1$H NMR: (DMSO) δ 11.02 (s, 1H), 10.97 (s, 1H), 9.15 (s, 2H), 8.10 (d, J=8.6 Hz, 1H), 8.03 (d, J=2.0 Hz, 1H), 7.80-7.76 (m, 3H), 7.26 (dd, J=4.9, 3.7 Hz, 1H), 2.28 (s, 3H).

Step 3: 2-Acetamido-N-(2-amino-5-(thiophen-2-yl)phenyl)pyrimidine-5-carboxamide (250)

Following the same procedure as described in Example 1, step 4, (with DMF as a co-solvent), the title compound 250 was obtained as a yellow solid in 32% yield. $^1$H NMR: (DMSO) δ 10.90 (s, 1H), 9.87 (s, 1H), 9.16 (s, 2H), 7.47 (d, J=2.2 Hz, 1H), 7.36 (dd, J=5.1, 1.2 Hz, 1H), 7.32 (dd, J=8.4, 2.2 Hz, 1H), 7.25 (dd, J=3.5, 1.1 Hz, 1H), 7.05 (dd, J=5.1, 3.7 Hz, 1H) 16.81 (d, J=8.4 Hz, 1H), 5.33 (br s, 2H), 2.26 (s, 3H).

Example 69a

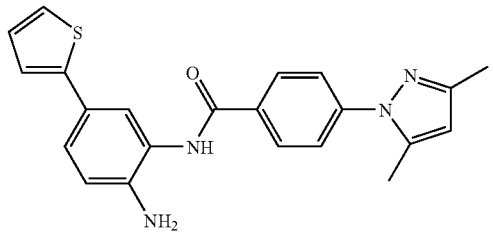

N-(2-Amino-5-(thiophen-2-yl)phenyl)-4-(3,5-dimethyl-1H-pyrazol-1-yl)benzamide (253a)

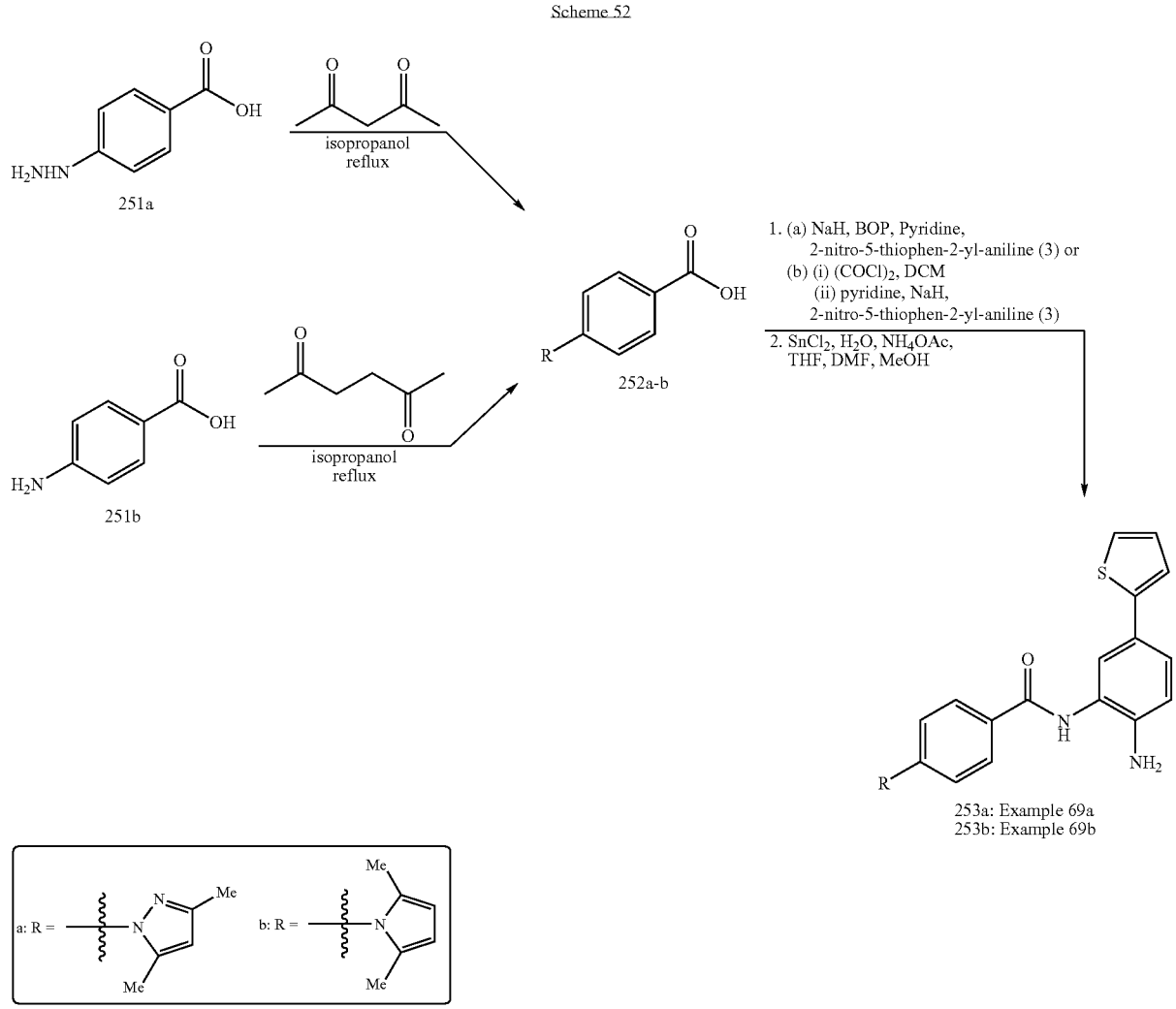

Step 1: 4-(3,5-Dimethyl-1H-pyrazol-1-yl)benzoic acid (252a)

4-Hydrazinylbenzoic acid (251a, 2 g, 13.2 mmol) and pentane-2,4-dione (1.35 mL, 13.2 mmol) were dissolved in isopropanol (40 mL) and refluxed for 15 hours. The solvent was removed under reduced pressure to afford 252a as a white solid (2.85 g, 99% yield). $^1$H NMR: (DMSO) δ 8.04 (d, J=8.6 Hz, 2H), 7.66 (d, J=8.8 Hz, 2H), 6.14 (s, 1H), 2.39 (s, 3H), 2.22 (s, 3H).

Steps 2-3: N-(2-Amino-5-(thiophen-2-yl)phenyl)-4-(3,5-dimethyl-1H-pyrazol-1-yl)benzamide (253a)

Starting from the acid 252a and following the same procedures as described in Example 66 step 2, and Example 1 step 4, (with DMF as a co-solvent), the title compound 253a was obtained as a white solid in 14% yield (over two steps). $^1$H NMR: (DMSO) δ 9.81 (s, 1H), 8.09 (d, J=8.4 Hz, 2H), 7.64 (d, J=8.6 Hz, 2H), 7.46 (d, J=2.0 Hz, 1H), 7.33 (dd, J=5.1, 1.2 Hz, 1H), 7.28 (dd, J=8.2, 2.2 Hz, 1H), 7.23 (dd, J=3.5, 1.0 Hz, 1H), 7.03 (dd, J=5.1, 3.5 Hz, 1H), 6.80 (d, J=8.3 Hz, 1H), 6.12 (s, 1H), 5.19 (s, 2H), 2.38 (s, 3H), 2.20 (s, 3H).

Example 69b

N-(2-Amino-5-(thiophen-2-yl)phenyl)-4-(2,5-dimethyl-1H-pyrrol-1-yl)benzamide (253b)

Step 1: 4-(3,5-Dimethyl-1H-pyrazol-1-yl)benzoic acid (252b)

4-Aminobenzoic acid (251b, 1.5 g, 10.9 mmol) and hexane-2,5-dione (1.28 mL, 10.9 mmol) were dissolved in isopropanol (40 mL) and refluxed for 15 hours. The solvent was removed under reduced pressure to afford 252b as a white solid (2.35 g, 99% yield). $^1$H NMR: (DMSO) δ 8.02 (d, J=8.6 Hz, 2H), 7.36 (d, J=8.6 Hz, 2H), 5.81 (s, 2H), 1.98 (s, 6H).

Steps 2-3: N-(2-Amino-5-(thiophen-2-yl)phenyl)-4-(2,5-dimethyl-3H-pyrrol-N-yl)benzamide (253b)

Starting from the acid 252b and following the same procedures as described in Example 66 step 2, and Example 1 step 4, (with DMF as a co-solvent), the title compound 253b was obtained as beige solid in 28% yield over two steps. $^1$H NMR: (DMSO) δ 9.85 (s, 1H), 8.14 (d, J=8.4 Hz, 2H), 7.49 (d, J=2.0 Hz, 1H), 7.44 (d, J=8.4 Hz, 2H), 7.37 (dd, J=5.1, 1.2 Hz, 1H), 7.32 (dd, J=8.5, 2.4 Hz, 1H), 7.26 (dd, J=3.6, 1.0 Hz, 1H), 7.07 (dd, J=5.1, 3.5 Hz, 1H), 6.83 (d, J=8.4 Hz, 1H) 15.86 (s, 2H), 5.24 (s, 2H), 2.05 (s, 6H).

Example 70a

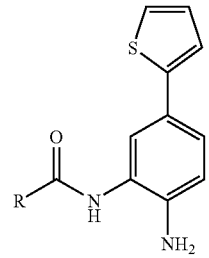

256a: Example 70a
256b: Example 70b
256c: Example 70c

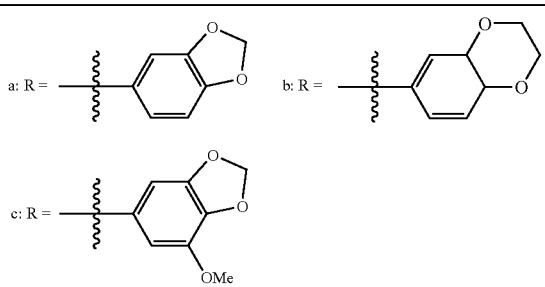

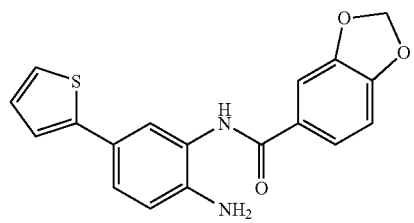

N-(2-amino-5-(thiophen-2-yl)phenyl)benzo[d][1,3]dioxole-5-carboxamide (256a)

Scheme 53

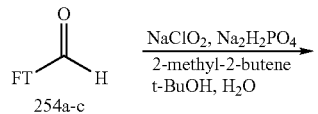

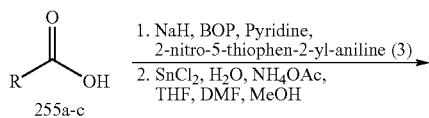

Step 1: Benzo[d][1,3]dioxole-5-carboxylic acid (255a)

To a stirred solution of benzo[d][1,3]dioxole-5-carbaldehyde (254a, 2 g, 13.3 mmol), Na$_2$H$_2$PO$_4$ (6.38 g, 53.2 mmol), and 2-methyl-2-butene (9.85 mL, 93.1 mmol) in t-BuOH (41 mL) and water (17 mL) was added sodium chlorite (7.19 g, 79.9 mmol). The resulting reaction mixture was stirred for 2 hours at room temperature. Water (100 mL) and 1M HCl (25 mL) were added and the mixture was extracted with EtOAc (2×50 mL). The organic phase was separated, dried with sodium sulfate and evaporated under reduced pressure. The resulting solid was triturated with EtOAc (20 mL) to yield the title compound 255a as a white solid (1.9 g, 86% yield). $^1$H NMR: (DMSO) δ 12.72 (br s, 1H), 7.53-7.50 (m, 1H), 7.34-7.32 (m, 1H), 6.99-6.95 (m, 1H), 6.10 (s, 2H).

Steps 2-3: N-(2-Amino-5-(thiophen-2-yl)phenyl)benzo[d][1,3]dioxole-5-carboxamide (256a)

Following the same procedures as described in Example 1, steps 3 and 4, (with DMF as a co-solvent), the title compound 256a was obtained as a light orange solid in 22% yield (over two steps). $^1$H NMR: (DMSO) δ 9.59 (s, 1H), 7.60 (dd, J=8.0, 1.6 Hz, 1H), 7.55 (d, J=1.6 Hz, 1H), 7.43 (d, J=2.2 Hz, 1H), 7.35 (dd, J=4.9, 0.6 Hz, 1H), 7.29 (dd, J=8.2, 2.2 Hz, 1H), 7.24 (dd, J=3.7, 1.0 Hz, 1H), 7.06-7.04 (m, 2H), 6.79 (d, J=8.2 Hz, 1H), 6.13 (s, 2H), 5.15 (br s, 2H).

Example 70b

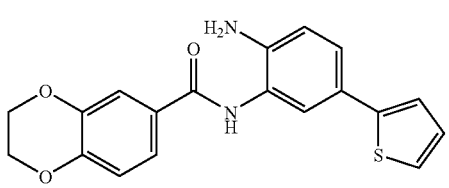

N-(2-Amino-5-(thiophen-2-yl)phenyl)-2,3-dihydrobenzo[b][1,4]dioxine-6-carboxamide (256b)

Steps 1-3: N-(2-Amino-5-(thiophen-2-yl)phenyl)-2,3-dihydrobenzo[b][1,4]dioxine-6-carboxamide (256b)

Following the same procedures as described in Example 70a step 1 and Example 1, steps 3 and 4, (with DMF as a co-solvent), the title compound 256b was obtained as an orange solid in 38% yield (over three steps). $^1$H NMR: (DMSO) δ 9.57 (s, 1H), 7.54 (d, J=2.1 Hz, 1H), 7.51 (dd, J=8.4, 2.1 Hz, 1H), 7.42 (d, J=2.1 Hz, 1H), 7.33 (dd, J=5.1, 1.2 Hz, 1H), 7.26 (dd, J=8.4, 2.3 Hz, 1H), 7.22 (dd, J=3.5, 1.2 Hz, 1H), 7.02 (dd, J=5.1, 3.5 Hz, 1H), 6.95 (d, J=8.2 Hz, 1H), 6.79 (d, J=8.4 Hz, 1H), 5.11 (s, 2H), 4.31-4.28 (m, 4H).

Example 70c

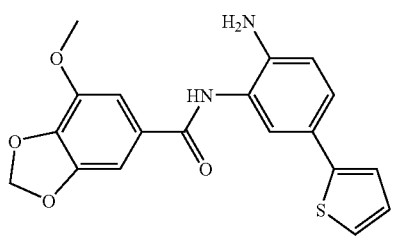

N-(2-Amino-5-(thiophen-2-yl)phenyl)-7-methoxybenzo[d][1,3]dioxole-5-carboxamide (256c)

Steps 1-3: N-(2-amino-5-(thiophen-2-yl)phenyl)-7-methoxybenzo[d][1,3]dioxole-5-carboxamide (256c)

Following the same procedures as described in Example 70a step 1 and Example 1, steps 3 and 4, (with DMF as a co-solvent), the title compound 256c was obtained as an orange solid in 20% yield (over three steps). $^1$H NMR: (DMSO) δ 9.60 (s, 1H), 7.41 (d, J=2.2 Hz, 1H), 7.36 (d, J=1.4 Hz, 1H), 7.34 (dd, J=5.2, 1.2 Hz, 1H), 7.30-7.26 (m, 2H), 7.23 (dd, J=3.6, 1.2 Hz, 1H), 7.04 (dd, J=4.9, 3.5 Hz, 1H), 6.79 (d, J=8.4 Hz, 1H), 6.10 (s, 2H), 5.14 (br s, 2H), 3.91 (s, 3H).

Example 71a

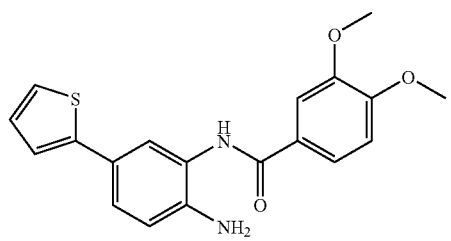

N-(2-Amino-5-(thiophen-2-yl)phenyl)-3,4-dimethoxybenzamide (258a)

Scheme 54

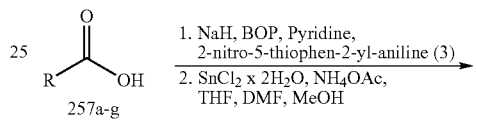

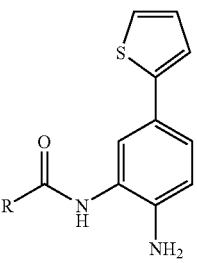

258a: Example 71a
258b: Example 71b
258c: Example 71c
258d: Example 71d
258e: Example 71e
258f: Example 71f
258g: Example 71g

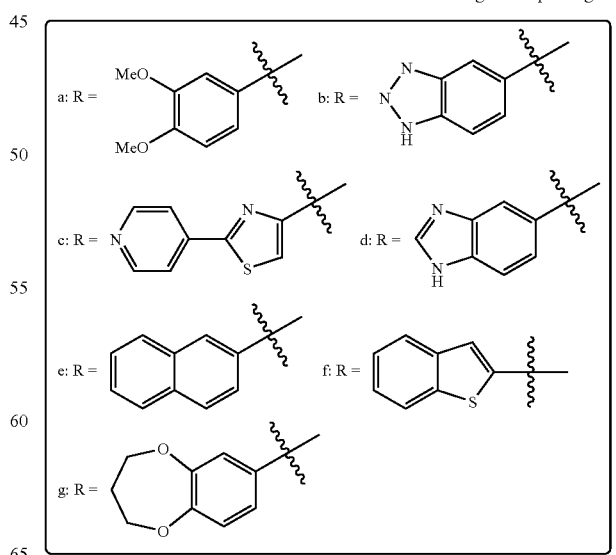

Steps 1-2: N-(2-Amino-5-(thiophen-2-yl)phenyl)-3,
4-dimethoxybenzamide (258a)

Following the same procedures as described in Example 1, steps 3 and 4, (with DMF as a co-solvent), but substituting compound 4 with compound 257a, the title compound 258a was obtained as a beige solid in 56% yield. $^1$H NMR: (DMSO) δ 9.64 (s, 1H), 7.63 (dd, J=8.2, 2.0 Hz, 1H), 7.57 (d, J=2.2 Hz, 1H), 7.42 (d, J=2.2 Hz, 1H), 7.33 (dd, J=5.1, 1.2 Hz, 1H), 7.28 (dd, J=8.3, 2.3 Hz, 1H), 7.23 (dd, J=3.5, 1.2 Hz, 1H), 7.05 (d, J=8.6 Hz, 1H), 7.02 (dd, J=5.1, 3.6 Hz, 1H), 6.79 (d, J=8.3 Hz, 1H), 5.12 (br s, 2H), 3.83 (s, 3H), 3.82 (s, 3H).

Example 71b

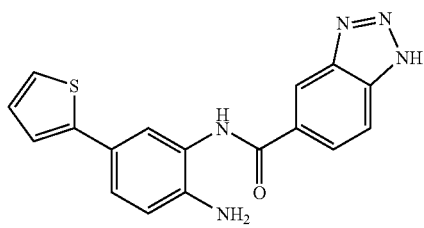

N-(2-Amino-5-(thiophen-2-yl)phenyl)-1H-benzo[d]
[1,2,3]triazole-5-carboxamide (258b)

Steps 1-2: N-(2-Amino-5-(thiophen-2-yl)phenyl)-
1H-benzo[d][1,2,3]triazole-5-carboxamide (28b)

Following the same procedures as described in Example 1, steps 3 and 4, (with DMF as a co-solvent), but substituting compound 4 with compound 257b, the title compound 258b was obtained as an orange solid in 16% yield (over two steps). $^1$H NMR: (DMSO) δ 9.90 (s, 1H), 8.66 (s, 1H), 8.05 (d, J=9.8 Hz, 1H), 7.96 (d, J=8.6 Hz, 1H), 7.49 (d, J=2.0 Hz, 1H), 7.33 (dd, J=5.1, 1.2 Hz, 1H), 7.30 (dd, J=8.2, 2.2 Hz, 1H), 7.23 (dd, J=3.5, 1.1 Hz, 1H), 7.03 (dd, J=5.0, 3.7 Hz, 1H) 6.81 (d, J=8.4 Hz, 1H), 5.23 (br s, 2H).

Example 71c

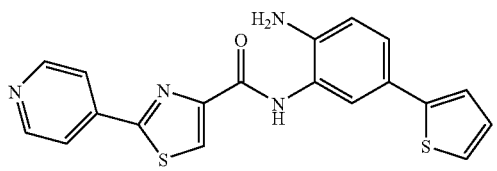

N-(2-Amino-5-(thiophen-2-yl)phenyl)-2-(pyridin-4-
yl)thiazole-4-carboxamide (258c)

Steps 1-2: N-(2-Amino-5-(thiophen-2-yl)phenyl)-2-
(pyridin-4-yl)thiazole-4-carboxamide (258c)

Following the same procedures as described in Example 1, steps 3 and 4, (with DMF as a co-solvent), but substituting compound 4 with compound 257c, the title compound 258c was obtained as an off white solid in 28% yield (over two steps). $^1$H NMR: (DMSO) δ 9.94 (s, 1H), 8.78 (m, 3H), 8.11 (dd, J=4.3, 1.6 Hz, 2H), 7.64 (d, J=2.2 Hz, 1H), 7.38 (dd, J=5.1, 1.0 Hz, 1H), 7.33 (dd, J=8.2, 2.1 Hz, 1H), 7.28 (dd, J=3.7, 1.2 Hz, 1H), 7.07 (dd, J=5.1, 3.7 Hz, 1H), 6.86 (d, J=8.4 Hz, 1H), 5.23 (s, 2H).

Example 71d

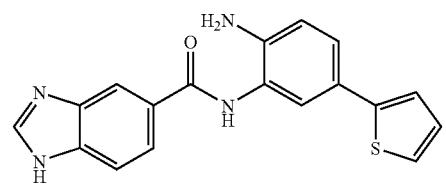

N-(2-Amino-5-(thiophen-2-yl)phenyl)-1H-benzo[d]
imidazole-5-carboxamide (28d)

Steps 1-2: N-(2-amino-5-(thiophen-2-yl)-phenyl)-
1H-benzo[d]imidazole-5-carboxamide (258d)

Following the same procedures as described in Example 1, steps 3 and 4, (with DMF as a co-solvent), but substituting compound 4 with compound 257d, the title compound 258d was obtained as a white solid in 29% yield (over two steps). $^1$H NMR: (DMSO) δ 9.72 (s, 1H), 8.34 (s, 2H), 7.87-7.85 (m, 2H), 7.48 (d, J=1.8 Hz, 1H), 7.34 (dd, J=5.1, 1.0 Hz, 1H), 7.28 (dd, J=8.1, 5.2 Hz, 1H), 7.23 (dd, J=3.5, 1.2 Hz, 1H), 7.03 (dd, J=5.1, 3.6 Hz, 1H), 6.80 (d, J=8.4 Hz, 1H), 5.15 (s, 2H).

Example 71e

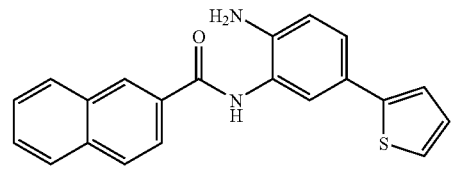

N-(2-amino-5-(thiophen-2-yl)phenyl)-2-naphtha-
mide (258e)

Steps 1-2: N-(2-Amino-5-(thiophen-2-yl)phenyl)-2-
naphthamide (258e)

Following the same procedures as described in Example 1, steps 3 and 4, (with DMF as a co-solvent), but substituting compound 4 with compound 257e, the title compound 258e was obtained as a yellow solid in 15% yield (over two steps). $^1$H NMR: (DMSO) δ 9.90 (s, 1H), 8.62 (s, 1H), 8.07-7.98 (m, 4H), 7.63-7.60 (m, 2H), 7.51 (d, J=2.1 Hz, 1H), 7.34 (dd, J=5.1, 1.2 Hz, 1H), 7.30 (dd, J=8.4, 2.2 Hz, 1H), 7.24 (dd, J=3.5, 1.2 Hz, 1H), 7.04 (dd, J=5.1, 3.7 Hz, 1H), 6.81 (d, J=8.4 Hz, 1H), 5.21 (s, 2H).

Example 71f

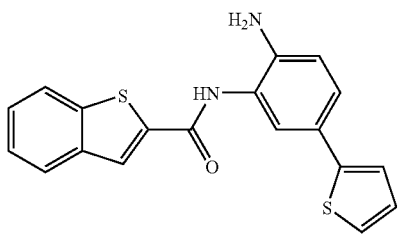

N-(2-amino-5-(thiophen-2-yl)phenyl)benzo[b]thiophene-2-carboxamide (258f)

Steps 1-2: N-(2-Amino-5-(thiophen-2-yl)phenyl)benzo[b]thiophene-2-carboxamide (258f)

Following the same procedures as described in Example 1, steps 3 and 4, (with DMF as a co-solvent), but substituting compound 4 with compound 257f, the title compound 258f was obtained as a brown solid in 12% yield (over two steps). $^1$H NMR: (DMSO) δ 9.99 (s, 1H), 8.32 (s, 1H), 8.03 (dd, J=8.4, 2.0 Hz, 1H), 7.97 (dd, J=6.6, 2.7 Hz, 1H), 7.49-7.43 (m, 3H), 7.33 (dd, J=5.0, 1.1 Hz, 1H), 7.30 (dd, J=8.2, 2.2 Hz, 1H), 7.24 (dd, J=3.6, 1.0 Hz, 1H), 7.03 (dd, J=5.2, 3.7 Hz, 1H), 6.80 (d, J=8.4 Hz, 1H), 5.24 (s, 2H).

Example 71g

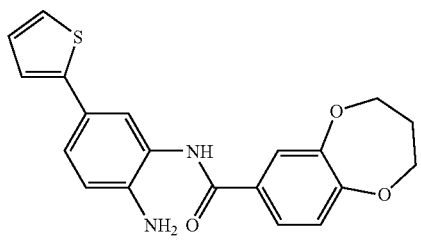

N-(2-amino-5-(thiophen-2-yl)phenyl)-3,4-dihydro-2H-benzo[b][1,4]dioxepine-7-carboxamide (258g)

Steps 1-2: N-(2-Amino-5-(thiophen-2-yl)phenyl)-3,4-dihydro-2H-benzo[b][1,4]dioxepine-7-carboxamide (258g)

Following the same procedures as described in Example 1, steps 3 and 4, (with DMF as a co-solvent), but substituting compound 4 with compound 257g, the title compound 258g was obtained as an orange solid in 15% yield (over two steps). $^1$H NMR: (DMSO) δ 9.61 (s, 1H), 7.63 (d, J=2.2 Hz, 1H), 7.59 (dd, J=8.4, 2.2 Hz, 1H), 7.41 (d, J=2.0 Hz, 1H), 7.33 (d, J=5.1 Hz, 1H), 7.27 (dd, J=8.2, 2.2 Hz, 1H), 7.22 (dd, J=3.5, 1.0 Hz, 1H), 7.06-7.01 (m, 2H), 6.78 (d, J=8.4 Hz, 1H), 5.12 (br s, 2H), 4.22-4.17 (m, 4H), 2.16 (quintet, J=5.5 Hz, 2H).

Example 72a

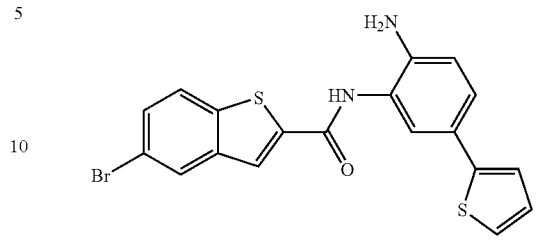

N-(2-Amino-5-(thiophen-2-yl)phenyl)-5-bromobenzo[b]thiophene-2-carboxamide (261a)

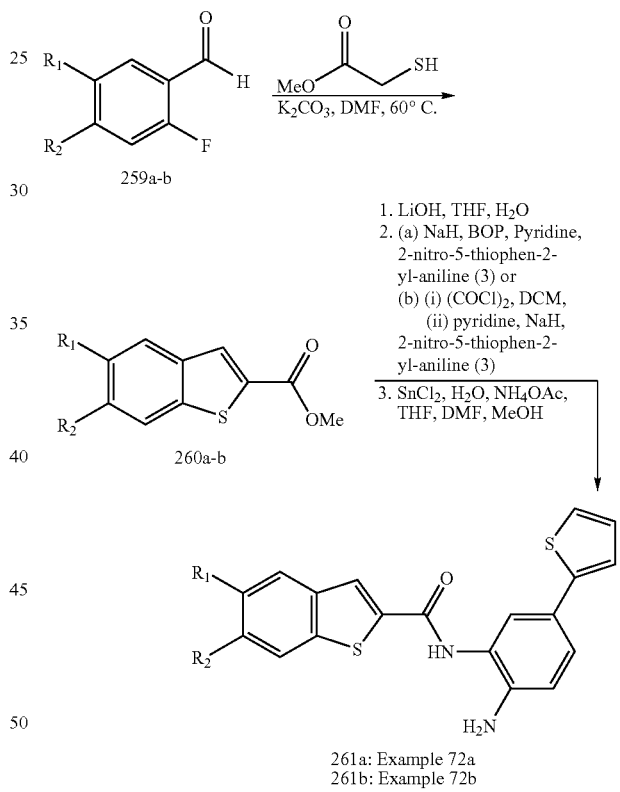

a: $R^1$ = Br, $R^2$ = H
b: $R^1$ = OMe, $R^2$ = OMe

261a: Example 72a
261b: Example 72b

Step 1: Methyl 5-bromobenzo[b]thiophene-2-carboxylate (260a)

To a stirred solution of 259a (2 g, 9.90 mmol) in DMF (20 mL) was added methyl thioglycolate (10.9 mmol, 0.97 mL) and potassium carbonate (5.47 g, 39.6 mmol). The resulting mixture was stirred at 60° C. for 15 hours. The DMF was removed under reduced pressure, water (50 mL) was added and the mixture was extracted with ethyl acetate (2×40 mL).

The organic phase was separated and dried with sodium sulfate, the solvent was removed under reduced pressure and the resulting solid was dried under vacuum. This afforded 260a as a white solid (1.3 g, 49% yield). $^1$H NMR: (DMSO) δ 8.22 (d, J=2.0 Hz, 1H), 8.11 (s, 1H), 8.00 (d, J=8.0 Hz, 1H), 7.62 (dd, J=8.6, 2.0 Hz, 1H), 3.88 (s, 3H).

Steps 2-4: N-(2-Amino-5-(thiophen-2-yl)phenyl)-5-bromobenzo[b]thiophene-2-carboxamide (261a)

Following the same procedure as described in Example 4 step 3 and then the procedures described in Example 66 step 2, and Example 1 step 4, (with DMF as a co-solvent), the title compound 261a was obtained as a beige solid in 32% yield (over three steps). $^1$H NMR: (DMSO) δ 10.08 (s, 1H), 8.27 (s, 1H), 8.23 (d, J=1.8 Hz, 1H), 8.02 (d, J=8.6 Hz, 1H), 7.60 (dd, J=8.6, 2.0 Hz, 1H), 7.43 (d, J=2.3 Hz, 1H), 7.34 (dd, J=5.0, 1.2 Hz, 1H), 7.30 (dd, J=8.2, 2.2 Hz, 1H), 7.24 (dd, J=3.5, 1.2 Hz, 1H), 7.03 (dd, J=5.1, 3.5 Hz, 1H), 6.79 (d, J=8.2 Hz, 1H), 5.25 (s, 2H).

Example 72b

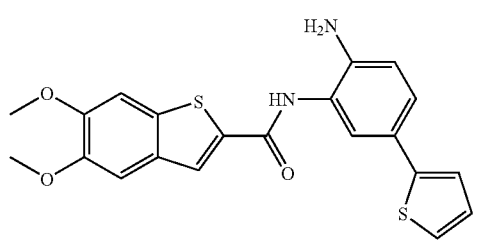

N-(2-Amino-5-(thiophen-2-yl)phenyl)-5,6-dimethoxybenzo[b]thiophene-2-carboxamide (261b)

Steps 1-4: N-(2-Amino-5-(thiophen-2-yl)phenyl)-5,6-dimethoxybenzo[b]thiophene-2-carboxamide (261b)

Following the same procedure as described in Example 72a step 1, but substituting compound 259a with compound 259b, then following the procedures described in Example 4 step 3 and Example 1, steps 3 and 4, (with DMF as a co-solvent), the title compound 261b was obtained as a yellow solid in 20% yield (over four steps). $^1$H NMR: (DMSO) δ 9.87 (s, 1H), 8.14 (s, 1H), 7.58 (s, 1H), 7.44 (d, J=2.2 Hz, 1H), 7.41 (s, 1H), 7.34 (dd, J=5.1, 1.1 Hz, 1H), 7.29 (dd, J=8.4, 2.3 Hz, 1H), 7.03 (dd, J=4.9, 3.5 Hz, 1H), 6.80 (d, J=8.4 Hz, 1H), 5.20 (s, 2H), 3.85 (s, 3H), 3.84 (s, 3H).

Example 73

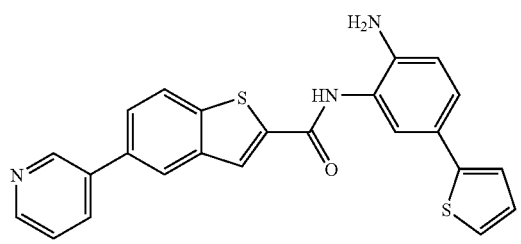

N-(2-amino-5-(thiophen-2-yl)phenyl)-5-(pyridin-3-yl)benzo[b]thiophene-2-carboxamide (262)

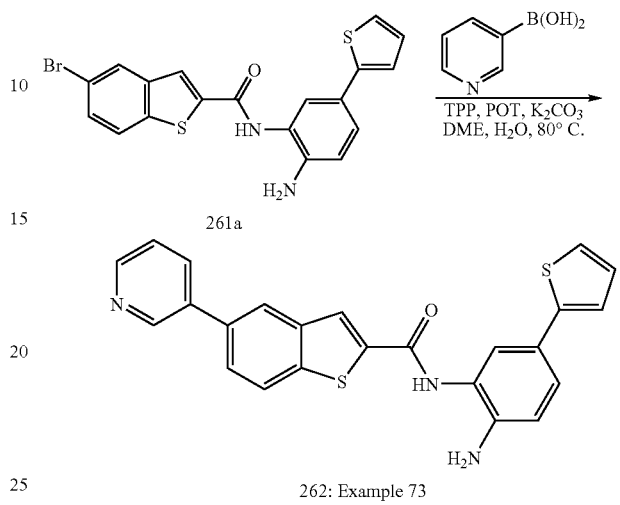

Step 1: N-(2-Amino-5-(thiophen-2-yl)phenyl)-5-(pyridin-3-yl)benzo[b]thiophene-2-carboxamide (262)

To a stirred solution of 261a (120 mg, 0.26 mmol) and pyridin-3-yl-3-boronic acid (123 mg, 0.34 mmol) in a 2:1 mixture of DME-water (9 mL), was added Pd(PPh$_3$)$_4$ (22 mg, 0.018 mmol), tri-o-toly phosphine (6 mg, 0.018 mmol) and potassium carbonate (109 mg, 0.79 mmol). The solution was degassed with N$_2$ for 5 minutes and then heated at 80° C. for 15 hours. Water (50 mL) was added and the mixture was extracted with ethyl acetate (2×40 mL). The organic layer was separated, dried with sodium sulfate and evaporated under reduced pressure. The residue was purified by flash chromatography on silica gel, eluent ethyl acetate. A subsequent trituration was performed with DCM for 15 minutes to yield 262 as a white solid (80 mg, 67% yield). $^1$H NMR: (DMSO) δ 10.09 (s, 1H), 8.99 (dd, J=2.3, 0.8 Hz, 1H), 8.58 (dd, J=4.7, 1.6 Hz, 1H), 8.38 (s, 1H), 8.33 (d, J=1.4 Hz, 1H), 8.17 (ddd, J=9.6, 3.9, 1.8 Hz, 1H), 7.83 (dd, J=8.5, 1.8 Hz, 1H), 7.53-7.50 (m, 2H), 7.46 (d, J=2.2 Hz, 1H), 7.34 (dd, J=5.1, 1.2 Hz, 1H), 7.31 (dd, J=8.2, 2.2 Hz, 1H), 7.25 (dd, J=3.5, 1.2 Hz, 1H), 7.03 (dd, J=5.1, 3.7 Hz, 1H), 6.81 (d, J=8.4 Hz, 1H), 5.74 (s, 2H).

Example 74

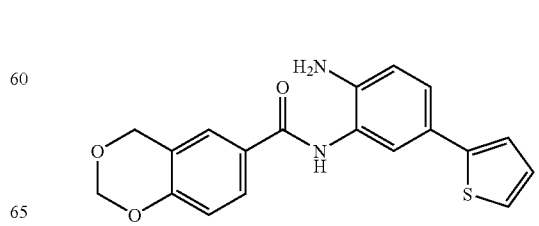

471

N-(2-Amino-5-(thiophen-2-yl)phenyl)-4H-benzo[d][1,3]dioxine-6-carboxamide (264)

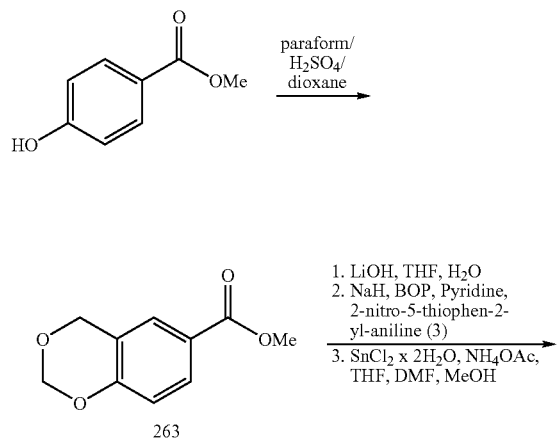

Scheme 57

264: Example 74

472

Step 1. 4H-Benzo[1,3]dioxine-5-carboxylic acid methyl ester (263)

Title compound 263 was prepared starting from methyl 4-hydroxybenzoate according to the procedure described in *Monatsh. Chem.*, 102; 1971; 946-950.

Steps 2-4: N-(2-Amino-5-(thiophen-2-yl)phenyl)-4H-benzo[d][1,3]dioxine-6-carboxamide (264)

Following the same procedure as described in Example 4 step 3, but substituting compound 21 with compound 263, then following the procedures described in Example 1, steps 3 and 4, (with DMF as a co-solvent), the title compound 264 was obtained as an off white solid in 37% yield (over three steps). $^{1}$H NMR: (DMSO) δ 9.60 (s, 1H), 7.82 (dd, J=8.6, 2.2 Hz, 1H), 7.74 (d, J=2.1 Hz, 1H), 7.41 (d, J=2.1 Hz, 1H), 7.33 (dd, J=5.1, 1.2 Hz, 1H), 7.26 (dd, J=8.4, 2.3 Hz, 1H), 7.21 (dd, J=3.5, 1.2 Hz, 1H), 7.02 (dd, J=5.1, 3.8 Hz, 1H), 6.94 (d, J=8.6 Hz, 1H), 6.77 (d, J=8.4 Hz, 1H), 5.32 (s, 2H), 5.11 (s, 2H), 4.94 (s, 2H).

Example 75

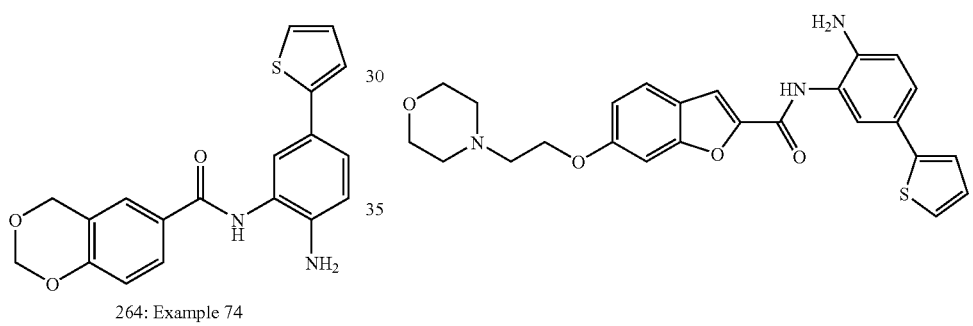

6-(2-Morpholinoethoxy)-N-(2-amino-5-(thiophen-2-yl)phenyl)benzofuran-2-carboxamide (269)

Scheme 58

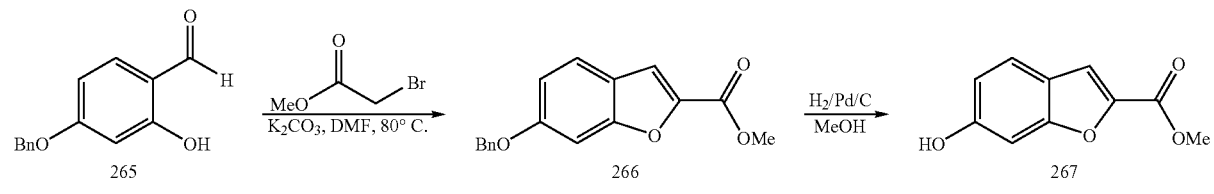

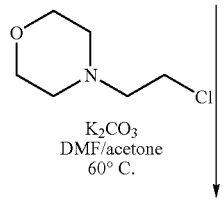

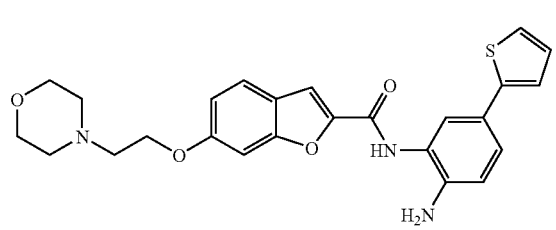 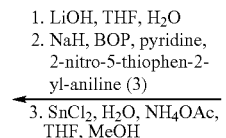 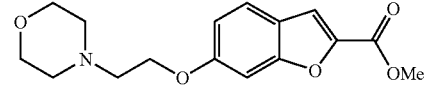

269: Example 75

1. LiOH, THF, H₂O
2. NaH, BOP, pyridine, 2-nitro-5-thiophen-2-yl-aniline (3)
3. SnCl₂, H₂O, NH₄OAc, THF, MeOH

268

Step 1: Methyl 6-(benzyloxy)benzofuran-2-carboxylate (266)

Following the same procedure as described in Example 67a step 1, but substituting compound 243a with compound 265, the title compound 266 was obtained as a white solid in 49% yield. $^1$H NMR: (DMSO) δ 7.68-7.64 (m, 2H), 7.49-7.45 (m, 2H), 7.42-7.31 (m, 4H), 7.07-7.04 (m, 1H), 5.18 (s, 2H), 3.85 (s, 2H).

Step 2: Methyl 6-hydroxybenzofuran-2-carboxylate (267)

To a stirred solution of 266 (1.2 g, 4.26 mmol) in methanol (20 mL) was added 10% palladium on charcoal (250 mg). The flask was purged with hydrogen gas for 1 minute and then the reaction was stirred under a hydrogen atmosphere for 15 hours. The palladium was filtered through a celite pad, the filtrate was evaporated under reduced pressure, and the resulting solid dried under vacuum to afford 267 as a white solid (700 mg, 86%). $^1$H NMR: (DMSO) δ 10.07 (s, 1H), 7.63 (s, 1H), 7.56 (d, J=8.0 Hz, 1H), 6.98 (s, 1H), 6.84 (d, J=9.0 Hz, 1H), 3.84 (s, 3H).

Step 3: Methyl 6-(2-morpholinoethoxy)benzofuran-2-carboxylate (268)

To a stirred solution of 267 (650 mg, 3.39 mmol) in a 1:1 mixture of DMF-acetone (20 mL) was added 4-(2-chloroethyl)morpholine (630 mg, 3.39 mmol) and potassium carbonate (937 mg, 6.78 mmol). The reaction mixture was stirred at 60° C. for 72 hours. The solvents were removed under reduced pressure and water (50 mL) was added to the residue. 2M Sodium carbonate solution (20 mL) was added and the resultant solution was extracted with ethyl acetate (2×40 mL).

The organic phase was separated, dried with sodium sulfate and the solvents removed under reduced pressure. The residue was purified by flash chromatography on silica gel, eluting with a gradient of 1:1 ethyl acetate-hexanes, then ethyl acetate, then 9:1 ethyl acetate-methanol. This afforded 268 as a clear oil (760 mg, 73% yield). $^1$H NMR: (DMSO) δ 7.67-7.63 (m, 2H), 7.32 (s, 1H), 6.98 (d, J=8.5 Hz, 1H), 4.14-4.16 (m, 2H), 3.85 (s, 3H), 3.57-3.55 (m, 4H), 2.88-2.86 (m, 2H), 2.72-2.70 (m, 4H).

Steps 4-6: 6-(2-Morpholinoethoxy)-N-(2-amino-5-(thiophen-2-yl)phenyl)benzofuran-2-carboxamide (269)

Following the same procedure as described in Example 4 step 3, but substituting compound 21 with compound 268, then following the procedures described in Example 1, steps 3 and 4, the title compound 269 was obtained as an off white solid in 1.3% yield (over three steps). $^1$H NMR: (DMSO) δ 7.21 (d, 1H), 7.14 (d, 2H), 6.95 (d, 1H), 6.84-6.79 (m, 3H), 6.62-6.57 (m, 2H), 6.49 (d, 1H), 3.80 (m, 2H), 3.30 (m, 4H), 2.46 (m, 2H), 2.21 (m, 4H).

Example 76

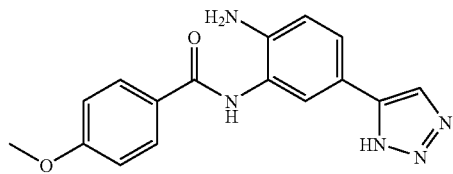

N-(2-Amino-5-(3H-1,2,3-triazol-4-yl)phenyl)-4-methoxybenzamide (273)

Scheme 59

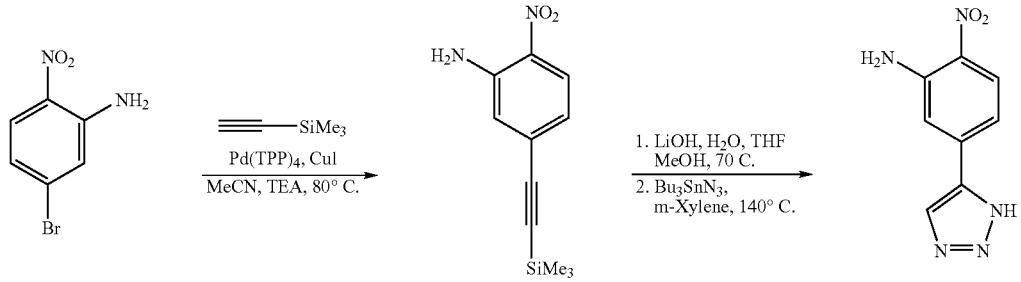

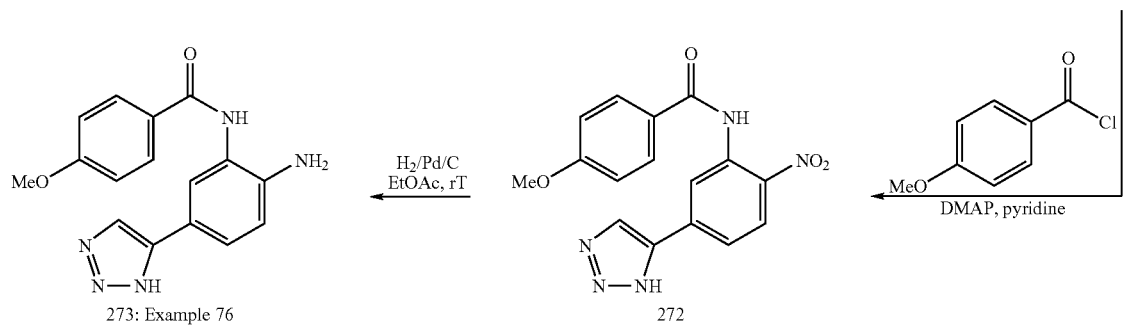

Step 1: 5-(2-(Trimethylsilyl)ethynyl)-2-nitrobenzenamine (270)

Following a procedure described in Example 15, step 1 (scheme 13) but running the reaction at 80° C. instead of the room temperature the title compound 270 was obtained in 68% yield. $^1$H NMR: (400.2 MHz, CDCl$_3$) δ (ppm): 8.06 (d, J=8.8 Hz; 1H); 6.92 (d, J=1.6 Hz; 1H); 6.76 (dd, J=1.6, 8.8 Hz; 1H); 5.70 (bs; 2H); 0.29 (s; 9H). MS: calc: 234.3; found: 235.1 (M+H).

Step 2: 2-Nitro-5-(3H-1,2,3-triazol-4-yl)benzenamine (271)

The cleavage of the trimethylsilyl group was achieved employing the same procedure as described in Example 4, step 3 (scheme 3) but substituting compound 21 for the compound 270. The crude product was used in the next cycloaddition step following the procedure described in Example 48, step 2 (scheme 26) but using m-xylene instead of toluene as a solvent, to afford the title compound 271 (9% yield in two steps). MS: calc: 205.2; found: 206.1 (M+H)

Step 3: 4-Methoxy-N-(2-nitro-5-(3H-1,2,3-triazol-4-yl)phenyl)benzamide (272)

Following the same procedure described in Example 43, step 4 (scheme 31) but substituting compound 150 for compound 271, the title compound 272 was obtained as an oil and used in the next step without further purification.

Step 4: N-(2-Amino-5-(3H-1,2,3-triazol-4-yl)phenyl)-4-methoxybenzamide (273)

Following the same procedure as described in Example 48, step 3 (scheme 36) but substituting compound 171 for the compound 272 and using ethyl acetate as a solvent instead of methanol, the title compound 273 was obtained in 25% yield (over two steps). $^1$H NMR: (400.2 MHz, DMSO) δ (ppm): 9.62 (s, 1H); 8.08 (bs, 2H); 7.97 (d, J=8.5 Hz; 2H); 7.62 (s, 1H); 7.45 (d, J=8.2 Hz; 1H); 7.03 (d, J=8.5 Hz; 2H); 6.82 (d, J=8.2 Hz; 1H); 5.11 (bs, 2H); 3.83 (s, 3H). MS: calc: 309.3; found: 310.1 (M+H)

Example 77

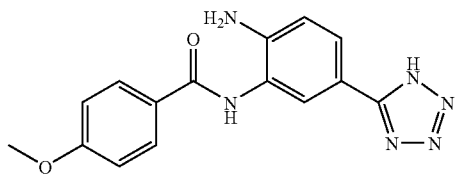

N-(2-amino-5-(1H-tetrazol-5-yl)phenyl)-4-methoxybenzamide 277

Scheme 60

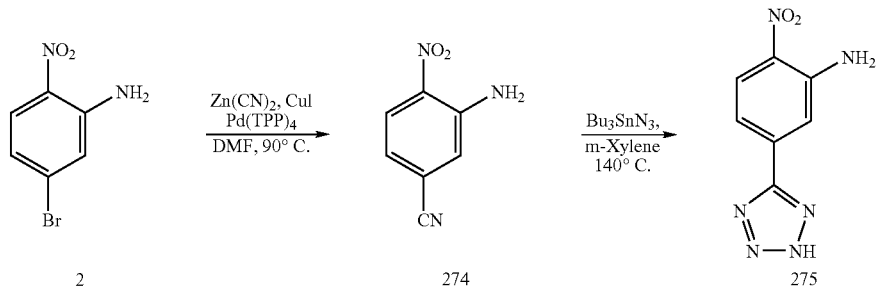

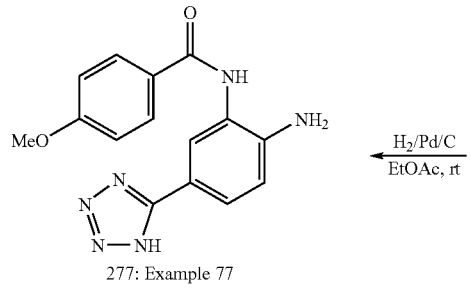

277: Example 77

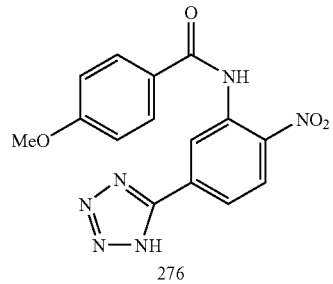

276

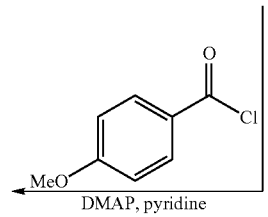

Step 1: 3-Amino-4-nitrobenzonitrile (274)

A suspension of bromoarene 2 (801 mg; 3.7 mmol) and zinc cyanide (570 mg; 4.85 mmol; 1.3 eq.) in degassed dimethylformamide (15 mL) was stirred at room temperature under nitrogen in the dark for 45 min and then treated with tetrakis(triphenylphosphine) palladium(O) (310 mg, 1.6 mmol). The mixture was stirred at 90° C. for 18 h; filtered through a celite pad, concentrated under reduced pressure and purified by flash chromatography on silica gel, eluent EtOAc-hexane (1:1) to afford the title compound 274 (380 mg, 63% yield). $^1$H NMR: (400.2 MHz, CDCl$_3$) δ (ppm): 8.22 (d, J=8.6 Hz; 1H); 7.19 (d, J=1.8 Hz; 1H); 6.95 (dd, J=1.8, 8.6 Hz; 1H); 6.27 (bs; 2H). MS: calc: 163.1; found: 164.1 (M+H)

Step 2: 2-Nitro-5-(1H-tetrazol-5-yl)benzenamine (275)

Following the procedure as described in Example 48, step 2 (scheme 36), but using m-xylene instead of toluene as a solvent, the title compound 275 was obtained in 79% yield. $^1$H NMR: (400.2 MHz, CDCl$_3$) δ (ppm): 8.21 (d, J=9.0 Hz; 1H); 7.74 (d, J=1.6 Hz; 1H); 7.50 (dd, J=1.6, 9.0 Hz; 1H); 6.29 (bs; 2H). MS: calc: 206.2; found: 207.1 (M+H)

Step 3: 4-Methoxy-N-(2-nitro-5-(1H-tetrazol-5-yl)phenyl)benzamide (276)

Following the same procedure as described in Example 43, step 4 (scheme 31) but substituting compound 150 for compound 275, the title compound 276 was obtained as an oil and was taken to the next step without further purification.

Step 4: N-(2-amino-5-(1H-tetrazol-5-yl)phenyl)-4-methoxybenzamide (277)

Following the same procedure as described in Example 48, step 3 (scheme 36) but substituting compound 171 for the compound 276 the title compound 277 was obtained in 14% yield (over two steps). $^1$H NMR: (400.2 MHz, DMSO) δ (ppm): 9.63 (s, 1H); 7.98 (d, J=8.8 Hz; 2H); 7.81 (d, J=2.0 Hz; 1H); 7.61 (dd; J=2.0, 8.4 Hz; 1H); 7.04 (d, J=8.8 Hz; 2H); 6.85 (d, J=8.4 Hz; 1H); 3.85 (s, 3H). MS: calc: 310.3; found: 311.1 (M+H)

Example 78

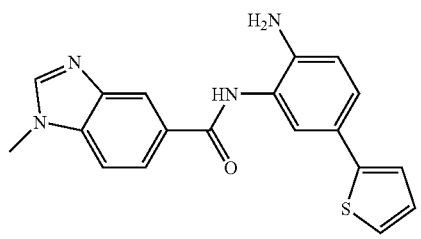

N-(2-amino-5-(thiophen-2-yl)phenyl)-1-methyl-1H-benzo[d]imidazole-5-carboxamide (283)

Scheme 61

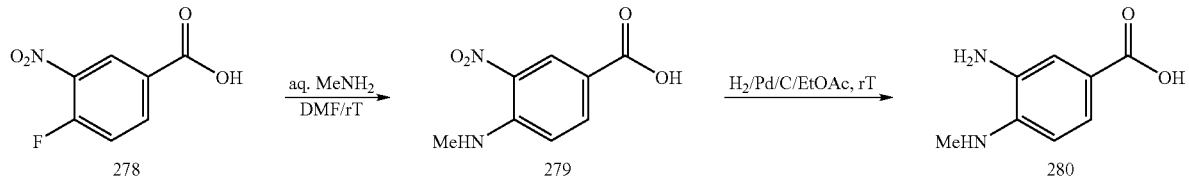

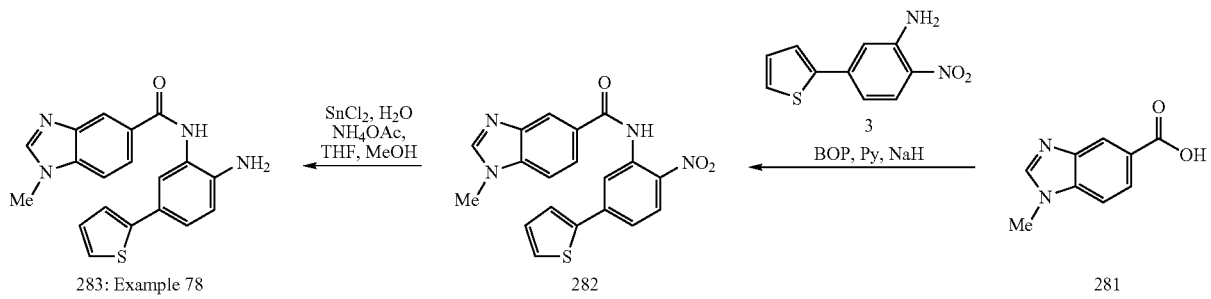

283: Example 78      282      281

Step 1: 4-(Methylamino)-3-nitrobenzoic acid (279)

A 40% solution of methylamine in water (11 mL; 128 mmol) (or any other primary amine) was slowly added to a stirring suspension of 4-fluoro-3-nitrobenzoic acid (278, 6.1 g; 32.9 mmol) in DMF (20 mL) at room temperature. After the addition was completed the mixture was stirred at the same temperature for 60 min; concentrated in vacuo, and suspended in 5% $KHSO_4$ (final pH=2). The suspension was stirred overnight; the precipitate was collected by filtration, washed with water, then with ether and dried to afford the title compound 279 (6.5 g; 100% yield). $^1$H NMR: (400.2 MHz, DMSO) δ (ppm): 12.8 (bs; 1H); 8.59 (d, J=2.0 Hz; 1H); 8.55 (q, J=5.0 Hz; 1H); 7.96 (dd, J=2.0, 9.1 Hz; 1H); 7.04 (d, J=9.1 Hz; 1H); 3.00 (d, J=5.0 Hz; 3H). MS: calc: 196.2; found: 197.1 (M+H)

Step 2: 3-Amino-4-(methylamino)benzoic acid (280)

Following the same procedure as described in Example 48, step 3 (scheme 36) but substituting compound 171 for compound 279, to give the title compound in 81% yield. $^1$H NMR: (400.2 MHz, DMSO) δ (ppm): 7.48 (d, J=8.6 Hz; 1H); 7.42 (s; 1H); 7.54 (d, J=8.6 Hz; 1H); 3.57 (bs; >4H); 2.80 (s; 3H). MS: calc: 166.1; found: 167.1 (M+H)

Step 3: I-Methyl-1H-benzo[d]imidazole-5-carboxylic acid (281)

A solution of the di-amino compound 280 (678 mg; 4.1 mmol) (or an o-aminophenol) in 50% $HCO_2H$ (or any other carboxylic acid or an ortho-ester) in water (or anhydrous solvent if an ortho-ester is used) was stirred at 85° C. for 13 h, concentrated, the residue was re-dissolved in water and lyophillized to afford the title compound 281 (712 mg, 99% yield). $^1$H NMR: (400.2 MHz, DMSO) δ (ppm): 12.9 (bs; 1H); 8.80 (s; 1H); 8.26 (d, J=1.6 Hz; 1H); 7.96 (dd, J=1.6, 8.6 Hz; 1H); 7.79 (d, J=8.6 Hz; 1H); 3.95 (s, 3H). MS: calc: 176.2; found: 177.1 (M+H).

Step 4: 1-Methyl-N-(2-nitro-5-(thiophen-2-yl)phenyl)-1H-benzo[d]imidazole-5-carboxamide (282)

Following the same procedure as described in Example 1, step 3 (scheme 1) but substituting compound 4 for compound 281 the title compound 282 was obtained in 56% yield. $^1$H NMR: (400.2 MHz, DMSO) δ (ppm): 10.9 (bs, 1H); 8.35 (bs, 2H), 8.24 (d, J=2.1 Hz, 1H), 8.01 (d, J=8.6 Hz, 1H), 7.91 (dd; J=1.6, 8.4 Hz; 1H); 7.75 (m, 3H); 7.70 (dd; J=2.1, 8.6 Hz; 1H); 7.23 (dd; J=3.7, 4.9 Hz; 1H); 3.91 (s, 3H). MS: calc: 378.4; found: 379.1 (M+H)

Step 5: N-(2-Amino-5-(thiophen-2-yl)phenyl)-1-methyl-1H-benzo[d]imidazole-5-carboxamide (283)

Following the same procedure as described in Example 1, step 4 (scheme 1) but substituting compound 5 for compound 282, the title compound 283 was obtained in 99% yield. $^1$H NMR: (400.2 MHz, DMSO) δ (ppm): 9.75 (s, 1H), 8.38 (d, J=1.0 Hz, 1H), 8.34 (s, 1H), 7.95 (dd; J=1.4, 8.4 Hz; 1H); 7.68 (d, J=8.4 Hz, 1H), 7.50 (d; J=2.2 Hz; 1H); 7.34 (dd; J=1.0, 5.0 Hz; 1H); 7.28 (dd; J=2.2, 8.4 Hz; 1H); 7.24 (dd; J=1.4, 3.6 Hz; 1H); 7.04 (dd; J=3.6, 5.0 Hz; 1H); 6.81 (d; J=8.4 Hz; 1H); 3.90 (s, 3H). MS: calc: 348.4; found: 349.1 (M+H)

Example 79

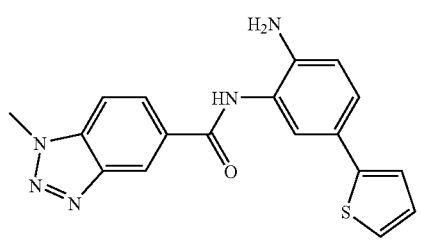

N-(2-amino-5-(thiophen-2-yl)phenyl)-1-methyl-1H-benzo[d][1,2,3]triazole-5-carboxamide (286)

Scheme 62

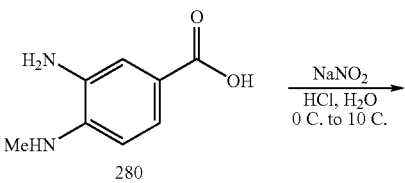

280

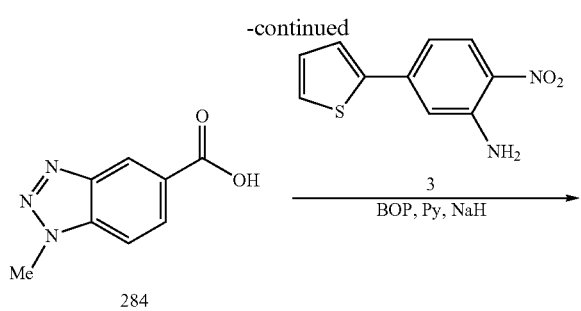

284

(final pH=6); concentrated and purified by preparative HPLC in reverse phase mode (column aquasil C-18, elution 5% to 95% MeOH in water), to afford the title compound 284 (211 mg; 18% yield). $^1$H NMR: (400.2 MHz, DMSO) δ (ppm): 8.35 (s; 1H); 8.08 (dd, J=1.4, 8.6 Hz; 1H); 7.75 (d, J=1.4 Hz; 1H); 4.03 (s, 3H). MS: calc: 177.1; found: 178.1 (M+H).

Step 2: 1-Methyl-N-(2-nitro-5-(thiophen-2-yl)phenyl)-1H-benzo[d][1,2,3]triazole-5-carboxamide (285)

Following the same procedure as described in Example 1, step 3 (scheme 1) but substituting compound 4 for compound 284, the title compound 285 was obtained in 56% yield. $^1$H NMR: (400.2 MHz, DMSO) δ (ppm): 11.0 (bs, 1H); 8.72 (bs, 1H), 8.12 (m, 2H), 8.07 (d, J=8.7 Hz, 1H), 8.01 (d, J=8.7 Hz, 1H), 7.73 (m, 3H), 7.23 (t; J=4.7 Hz; 1H); 4.38 (s, 3H). MS: calc: 379.4; found: 380.0 (M+H)

Step 3: N-(2-Amino-5-(thiophen-2-yl)phenyl)-1-methyl-1H-benzo[d][1,2,3]triazole-5-carboxamide (286)

Following the same procedure described in Example 1, step 4 (scheme 1) but substituting compound 5 for compound 285, the title compound 286 was obtained in 99% yield. $^1$H NMR: (400.2 MHz, DMSO) δ (ppm): 9.88 (s, 1H); 8.75 (s, 1H), 8.15 (dd; J=1.0, 8.6 Hz; 1H); 7.95 (dd, J=1.0, 8.6 Hz, 1H), 7.49 (d, J=2.0 Hz, 1H), 7.34 (dd; J=1.2, 5.1 Hz; 1H); 7.30 (dd; J=2.0, 8.3 Hz; 1H); 7.24 (dd; J=1.2, 3.5 Hz; 1H); 7.04 (dd; J=3.5, 5.1 Hz; 1H); 6.81 (d; J=8.3 Hz; 1H); 5.24 (bs, 2H); 4.37 (s, 3H). MS: calc: 349.4; found: 350.1 (M+H)

Example 80

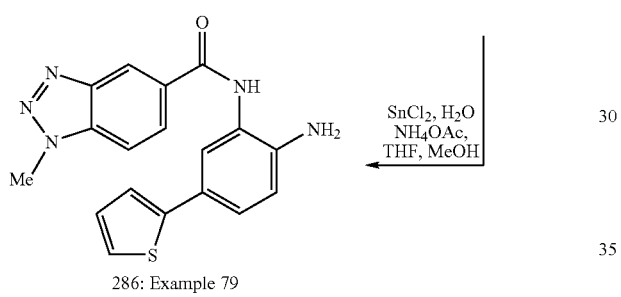

285

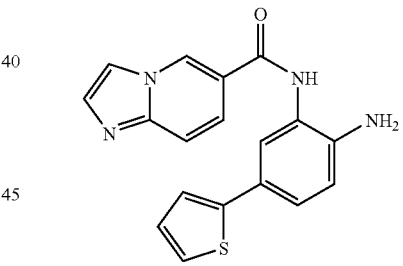

N-(2-amino-5-(thiophen-2-yl)phenyl)H-imidazo[1,2-a]pyridine-6-carboxamide (291)

286: Example 79

Step 1:
1-Methyl-1H-benzo[d][1,2,3]triazole-5-carboxylic acid (284)

To a stirred suspension of the diamine 280 (1.08 g; 6.48 mmol) (or any other o-arylenediamine) in water (25 mL) at 0° C., concentrated HCl (5.4 mL) was added drop wise followed by slow addition of a solution of NaNO$_2$ (643 mg; 9.3 mmol) in water (10 mL). The reaction mixture was stirred at 0° C. for 2 h and then was allowed to warm up to 10° C. over 4 h; neutralized with a solution of KOH (5.6 g) in water (30 mL)

Scheme 63

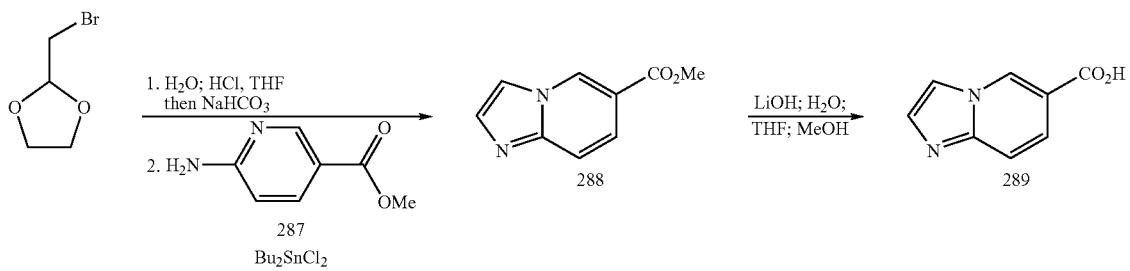

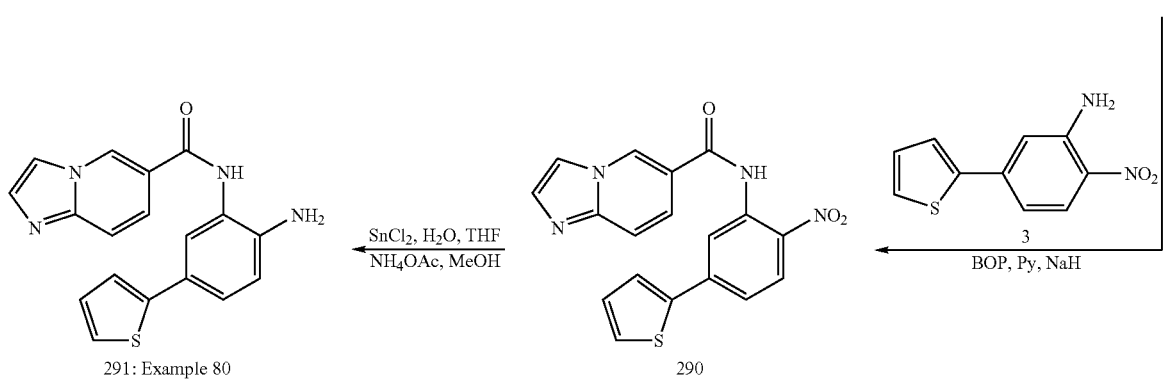

Step 1: Methyl H-imidazo[1,2-a]pyridine-6-carboxylate (288)

A solution of 2-(bromomethylyl)-1,3-dioxolane (0.18 mL; 1.67 mmol) in THF (3 mL) and water (0.2 mL) was treated with concentrated HCl (3 drops) and stirred at 88° C. for 50 min. The solution was cooled down to 0° C. and transferred into a vial containing 2-amino-5-methoxycarbonylpyridine (287, 204 mg; 1.34 mmol), Bu$_2$SnCl$_2$ (134 mg; 0.40 mmol) and NaHCO$_3$ (410 mg) and stirred at room temperature for 2 days. The reaction mixture was diluted with ethyl acetate (60 mL) and washed with saturated aqueous sodium chloride. The organic layer was dried (MgSO$_4$), filtered and concentrated. After chromatographic purification of the residue using preparative TLC on silica gel (eluent 50% ethyl acetate in dichloromethane), the title compound 288 was obtained (74 mg, 31% yield). $^1$H NMR: (500.7 MHz, CDCl$_3$) δ (ppm): 9.00 (s, 1H); 7.80 (m, 4H); 4.00 (s, 3H). MS: calc: 176.1; found: 177.1 (M+H)

Step 2: H-Imidazo[1,2-a]pyridine-6-carboxylic acid (289)

Following the same procedure described for Example 46, step 2 (scheme 34) but substituting compound 162 for compound 288, the title compound 289 was obtained in 99% yield. MS: calc: 162.1; found: 163.1 (M+H)

Step 3: N-(2-Nitro-5-(thiophen-2-yl)phenyl)H-imidazo[1,2-a]pyridine-6-carboxamide (290)

Following the same procedure as described in Example 1, step 3 (scheme 1) but substituting compound 4 for compound 289, the title compound 290 was obtained in 22% yield. MS: calc: 364.2; found: 365.2 (M+H)

Step 4: N-(2-amino-5-(thiophen-2-yl)phenyl) H-imidazo[1,2-a]pyridine-6-carboxamide (291)

Following the same procedure described in Example 1, step 4 (scheme 1) but substituting compound 5 for compound 290, the title compound 291 was obtained in 45% yield. $^1$H NMR (400.2 MHz, DMSO) δ (ppm): 9.19 (s, 1H); 7.99 (s, 1H); 7.86 (d; J=8.5 Hz; 1H); 7.67 (s, 1H); 7.64 (d; J=8.5 Hz; 1H); 7.50 (s, 1H); 7.37 (d; J=8.5 Hz; 1H); 7.22 (d; J=4.9 Hz; 1H); 7.21 (m, 1H); 7.01 (t; J=4.9 Hz; 1H); 6.91 (d; J=8.5 Hz; 1H). MS: calc: 334.4; found: 335.1 (M+H)

Example 81

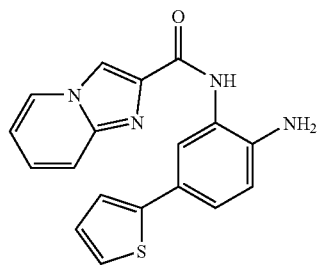

N-(2-amino-5-(thiophen-2-yl)phenyl)H-imidazo[1,2-a]pyridine-2-carboxamide (296)

Scheme 64

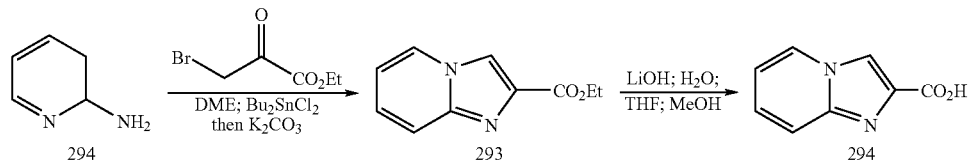

-continued

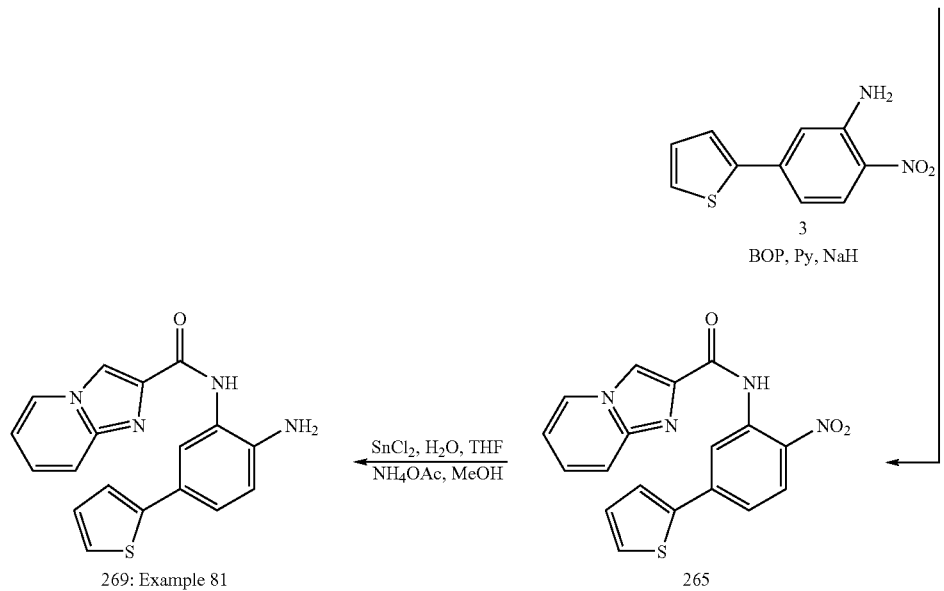

269: Example 81

265

Step 1: Ethyl H-imidazo[1,2-a]pyridine-2-carboxylate (293)

To a solution of 2-aminopyridine (292, 1.1022 g; 11.71 mmol) and Bu$_2$SnCl$_2$ (431 mg; 1.3 mmol) in DME (20 mL), ethyl 3-bromopyruvate (1.56 mL; 11.16 mmol) was added to give an instant yellow precipitate. The suspension was stirred at room temperature for 2 h, then solid K$_2$CO$_3$ (2.6 g; 18.8 mmol) was added and the mixture stirred for additional 20 h at the same temperature. The reaction mixture was then diluted with ethyl acetate (200 mL) and washed with saturated aqueous sodium chloride. The organic layer was dried (MgSO$_4$), filtered and concentrated. The residue was purified by flash chromatography on silica gel (eluent 50% ethyl acetate in dichloromethane), to afford the title compound 293 (1.31 g, 59% yield) as a white crystalline material. $^1$H NMR (400.2 MHz, DMSO) δ (ppm): 8.54 (m, 1H); 8.53 (d; J=0.9 Hz; 1H); 7.59 (ddd; J=1.3, 2.0, 9.2 Hz; 1H); 7.33 (ddd; J=1.3, 6.7, 9.2 Hz; 1H); 6.98 (dt; J=0.9, 7.8 Hz; 1H); 4.30 (q; J=7.0 Hz; 2H); 1.32 (t; J=7.0 Hz; 3H). MS: calc: 190.0; found: 191.1 (M+H).

Step 2: H-Imidazo[1,2-a]pyridine-2-carboxylic acid (294)

Following the same procedure described in Example 46, step 2 (scheme 34) but substituting compound 162 for compound 293, the title compound 294 was obtained in 99% yield. $^1$H NMR (400.2 MHz, DMSO) δ (ppm): 8.63 (dt, J=1.2, 6.7 Hz; 1H); 8.55 (d; J=0.8 Hz; 1H); 7.63 (m; 1H); 7.42 (ddd; J=1.2, 6.7, 7.8 Hz; 1H); 7.06 (dt; J=1.2, 7.8 Hz; 1H); MS: calc: 162.1; found: 163.1 (M+H)

Step 3: N-(2-Nitro-5-(thiophen-2-yl)phenyl)H-imidazo[1,2-a]pyridine-2-carboxamide (295)

Following the same procedure as described in Example 1, step 3 (scheme 1) but substituting compound 4 for compound 294 the title compound 295 was obtained in 95% yield. $^1$H NMR (400.2 MHz, DMSO) δ (ppm): 11.9 (s, 1H); 9.07 (d, J=1.8 Hz; 1H); 8.63 (m; 2H); 8.25 (d, J=8.8 Hz; 1H); 7.77 (ddd; J=1.0, 5.0, 12.3 Hz; 1H); 7.71 (dd; J=1.0, 9.2 Hz; 1H); 7.66 (dd; J=1.8, 8.8 Hz; 1H); 7.41 (ddd; J=1.2, 6.7, 9.2 Hz; 1H); 7.25 (dd; J=3.7, 5.0 Hz; 1H); 7.05 (dt; J=1.2, 12.3 Hz; 1H). MS: calc: 364.2; found: 365.1 (M+H).

Step 4: N-(2-Amino-5-(thiophen-2-yl)phenyl)H-imidazo[1,2-a]pyridine-2-carboxamide (296)

Following the same procedure described in Example 1, step 4 (scheme 1) but substituting compound 5 for compound 223, the title compound 296 was obtained in 85% yield. $^1$H NMR (400.2 MHz, DMSO) δ (ppm): 9.73 (s, 1H), 8.62 (dt, J=1.2; 6.8 Hz, 1H), 8.50 (d, J=0.7 Hz; 1H); 7.76 (d; J=2.2 Hz; 1H); 7.66 (d, J=0.7 Hz, 1H), 7.39 (dd; J=1.6, 6.8 Hz; 1H); 7.36 (dt; J=1.6, 4.9 Hz; 1H); 7.26 (dd; J=2.2, 8.2 Hz; 1H); 7.24 (dd; J=1.2, 3.6 Hz; 1H); 7.05 (m; 1H); 7.01 (dd; J=1.2, 6.8 Hz; 1H); 6.84 (d; J=8.2 Hz; 1H); 5.13 (bs, 2H). MS: calc: 334.4; found: 335.1 (M+H).

Example 82

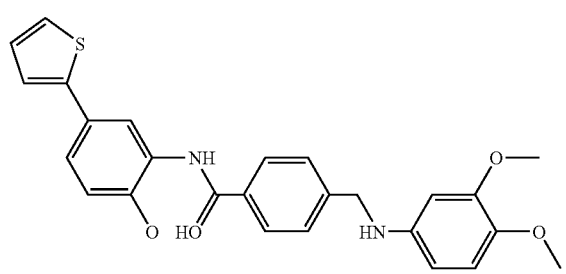

4-((3,4-Dimethoxyphenylamino)methyl)-N-(2-hydroxy-5-(thiophen-2-yl)phenyl)benzamide (301)

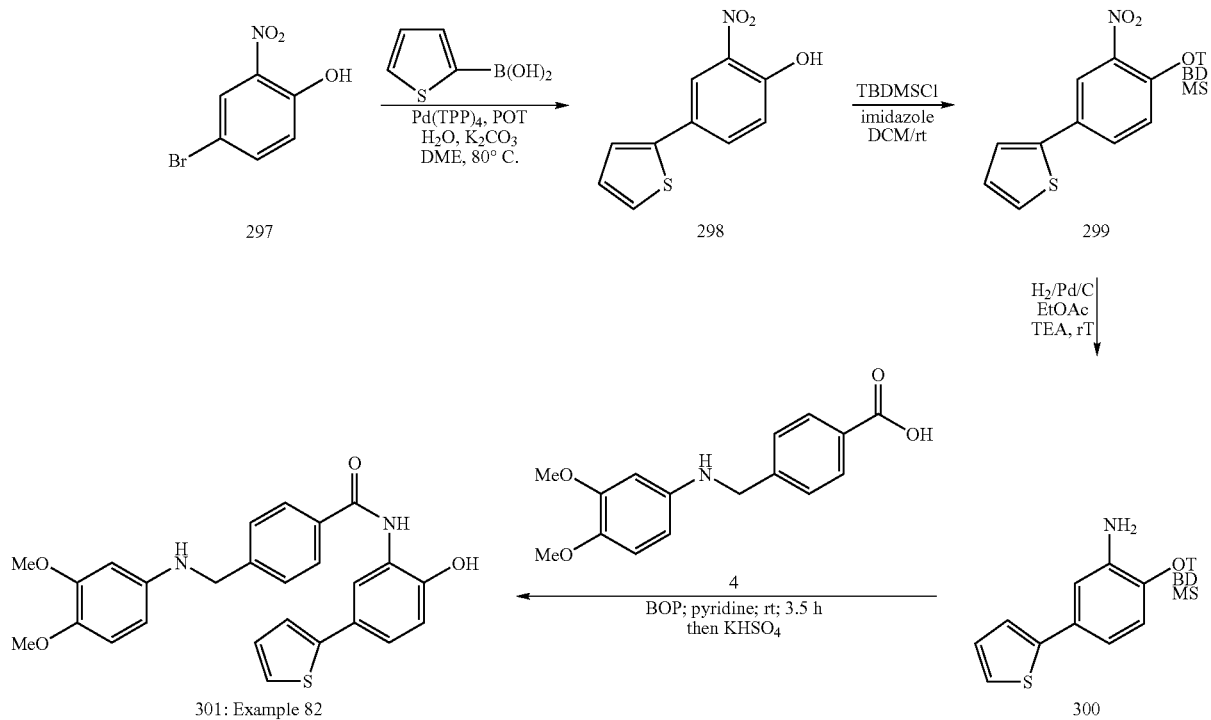

Scheme 65

Step 1: 2-Nitro-4-(thiophen-2-yl)phenol (298)

Following the same procedure as described in Example 1, step 2 (scheme 1) but substituting compound 2 for compound 297, the title compound 298 was obtained in 18% yield. $^1$H NMR: (499.7 MHz, DMSO) δ (ppm): 8.09 (s, 1H); 7.82 (d, J=9.0 Hz; 1H); 7.54 (d, J=3.5 Hz; 1H); 7.50 (s, 1H); 7.18 (d, J=9.0 Hz; 1H); 7.13 (m, 1H). MS: calc: 221.0; found: 219.9 (M−H).

Step 2: (2-Nitro-4-(thiophen-2-yl)phenoxy)(tert-butyl)dimethylsilane (299)

Following the same procedure as described in Example 19, step 2 (scheme 17) but substituting compound 90 for the compound 298 and using dichloromethane as a solvent instead of DMF, the title compound 299 was obtained which was used in the next step without further purification.

Step 3: (2-Amino-4-(thiophen-2-yl)phenoxy)(tert-butyl)dimethylsilane (300)

Following the same procedure described for Example 48, step 3 (scheme 36) but substituting compound 171 for compound 299 and using ethyl acetate and triethylamine as a solvent instead methanol, the title compound 300 was obtained in 41% yield over two steps. MS: calc: 305.5; found: 306.1 (M+H).

Step 4: 4-((3,4-Dimethoxyphenylamino)methyl)-N-(2-hydroxy-5-(thiophen-2-yl)phenyl)benzamide (301)

Following the same procedure as described in Example 1, step 3 (Example 1) but substituting compound 3 for compound 300 and not using NaH as a base, the title compound 301 was obtained in 17% yield (with 10% recovery of the starting material 228). $^1$H NMR: (400.2 MHz, DMSO) δ (ppm): 10.1 (s, 1H); 9.52 (s, 1H); 8.00 (s, 1H); 7.92 (d, J=7.0, 2H); 7.49 (d, J=7.0, 2H); 7.42 (m, 1H); 7.33 (d, J=8.0, 1H); 7.29 (s, 1H); 7.07 (s, 1H); 6.93 (d, J=8.0, 1H); 6.65 (d, J=8.5, 1H); 6.32 (s, 1H); 5.98 (m, 2H); 4.30 (s, 2H); 3.65 (s, 3H); 3.58 (s, 3H). MS: calc: 460.5; found: 461.1 (M+H)

Example 83

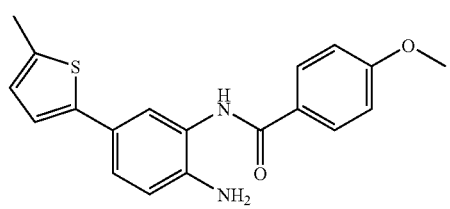

N-(2-amino-5-(5-methylthiophen-2-yl)phenyl)-4-methoxybenzamide (302)

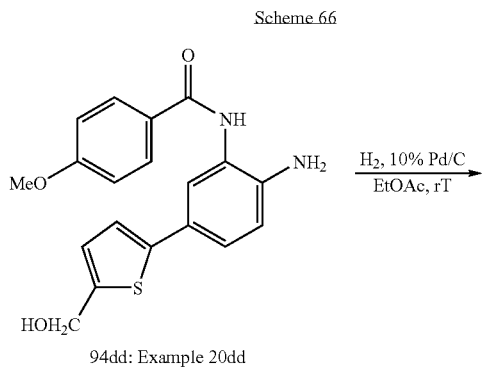

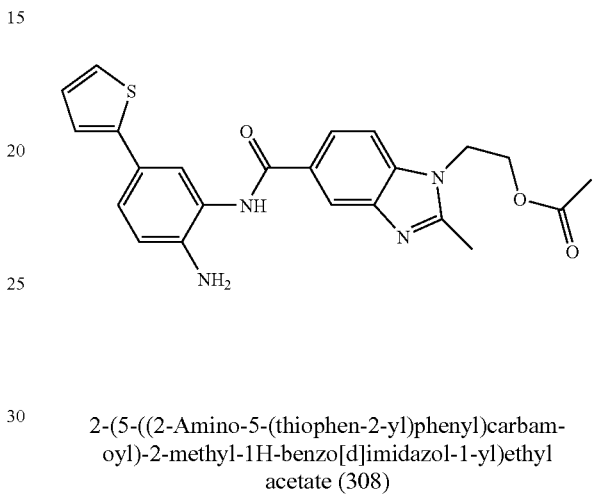

Following the same procedure as described in Example 48, step 3 (scheme 36) but substituting compound 171 for compound 94dd and using ethyl acetate as a solvent instead of methanol, the title compound 302 was obtained in 26% yield.

$^1$H NMR: (400.2 MHz, DMSO) δ (ppm): 9.60 (s, 1H), 7.96 (d, J=8.0, Hz, 2H); 7.36 (d, J=2.1 Hz, 1H); 7.20 (dd, J=2.1, 8.3 Hz, 1H); 7.03 (d, J=8.0, Hz, 2H); 7.00 (d, J=3.5 Hz, 1H); 6.78 (d, J=8.3 Hz, 1H), 6.70 (dd, J=1.1, 3.5 Hz, 1H); 3.83 (s, 3H); 2.42 (d, J=1.1 Hz, 3H). MS: calc: 338.4; found: 338.4 (M+H).

Example 84

2-(5-((2-Amino-5-(thiophen-2-yl)phenyl)carbamoyl)-2-methyl-1H-benzo[d]imidazol-1-yl)ethyl acetate (308)

Scheme 67
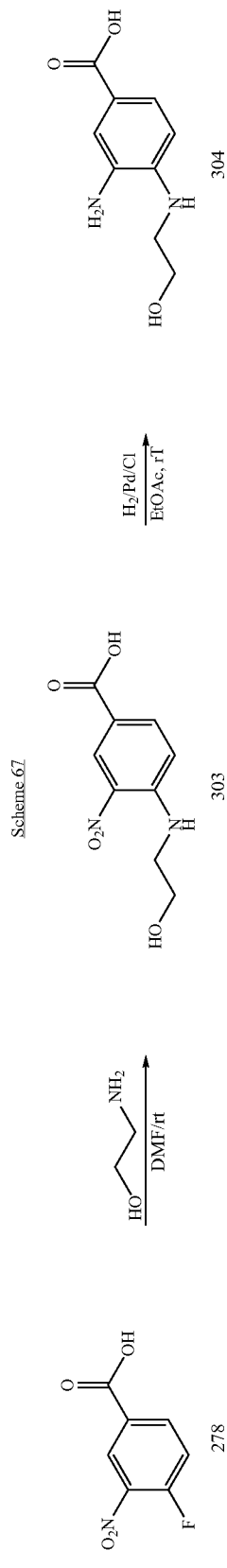
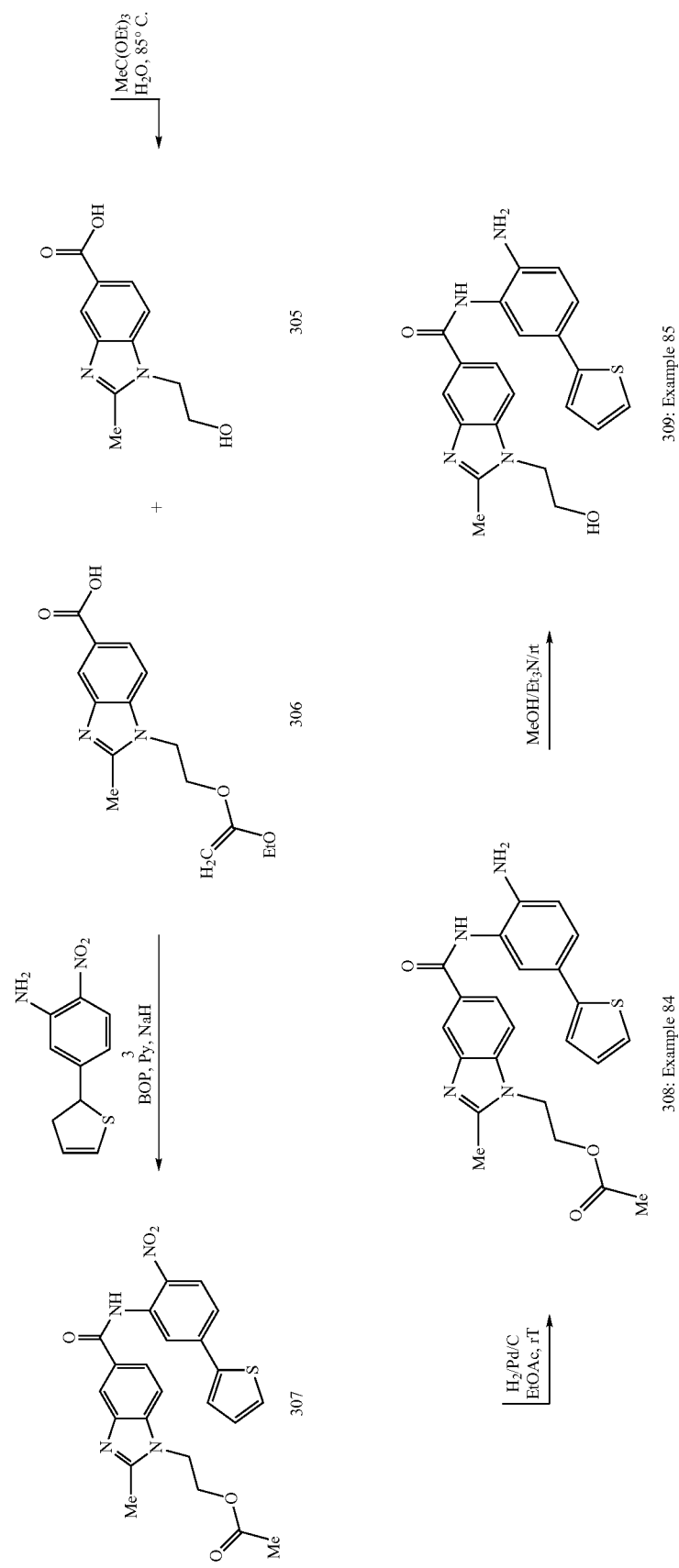

Step 1: 4-(2-Hydroxyethylamino)-3-nitrobenzoic acid (303)

Following the same procedure as described for Example 78, step 1 (scheme 61) but using ethanolamine instead of methylamine and isopropanol as a solvent instead of DMF, the title compound 303 was obtained in 99% yield. MS: calc: 226.2; found: 225.1 (M−H).

Step 2: 4-(2-Hydroxyethylamino)-3-aminobenzoic acid (304)

Following the same procedure described for Example 78, step 2 (scheme 61), the title compound 304 was obtained in 100% yield. MS: calc: 196.2; found: 197.1 (M+H).

Step 3: 1-(2-Hydroxyethyl)-2-methyl-1H-benzo[d]imidazole-5-carboxylic acid (305) and 1-(2-(1-ethoxyvinyloxy)ethyl)-2-methyl-1H-benzo[d]imidazole-5-carboxylic acid (306)

A stirred suspension of diamine 304 (1.18 g; 6.01 mmol) in triethylortoacetate (20 mL; 109 mmol; 18 eq.) was treated with trifluoroacetic acid (1.10 mL) at room temperature. In 5 min the mixture turned into an amber solution which was stirred at the same temperature for 4 h; concentrated and purified by preparative HPLC (C-18 aquasil column, elution with 5% to 95% MeOH in water) to afford hydroxyacid 305 (701 mg; 53% yield) and, as a side product, ketene acetal 306 (373 mg; 21% yield).

Compound 305: $^1$H NMR: (499.7 MHz, DMSO) δ (ppm): 13.1 (bs; 1H), 8.21 (s; 1H); 7.9 (d, J=8.0 Hz; 1H); 7.84 (d, J=8.0 Hz; 1H); 5.1 (bs; 1H); 4.42 (s; 2H); 3.75 (s; 2H); 2.75 (s; 3H);. MS: calc: 220.2; found: 221.1 (M+H)

Compound 306: $^1$H NMR: (400.2 MHz, DMSO) δ (ppm): 8.17 (m; 2H); 8.08 (d, J=9.2 Hz; 1H); 5.03 (d, J=3.9 Hz; 1H); 4.84 (d, J=3.9 Hz; 1H); 4.63 (t, J=4.5 Hz; 2H); 4.22 (q, J=7.0 Hz; 2H); 3.84 (t, J=4.5 Hz; 2H); 2.92 (s; 3H); 1.39 (t; J=7.0 Hz; 3H). MS: calc: 290.3; found: 291.1 (M+H)

Step 4: 2-(5-(2-Nitro-5-(thiophen-2-yl)phenylcarbamoyl)-2-methyl-1H-benzo[d]imidazol-1-yl)ethyl acetate (307)

Following the same procedure as described in Example 1, step 3 (scheme 1) but substituting compound 4 for compound 306 the title compound 307 was obtained in 6% yield. MS: calc: 464.49; found: 465.2 (M+H)

Step 5: 2-(5-((2-Amino-5-(thiophen-2-yl)phenyl)carbamoyl)-2-methyl-1H-benzo[d]imidazol-1-yl)ethyl acetate (308)

Following the same procedure as described in Example 48, step 3 (scheme 36) but substituting compound 171 for the compound 307 and using ethyl acetate as a solvent instead of methanol, the title compound 308 was obtained in 96% yield. $^1$H NMR: (DMSO) δ (ppm): 9.70 (s, 1H), 8.23 (s, 1H); 7.87 (dd; J=1.0, 8.4 Hz; 1H); 7.62 (d, J=8.4 Hz; 1H); 7.48 (d; J=2.0 Hz; 1H); 7.34 (dd; J=0.8, 4.8 Hz; 1H); 7.28 (dd; J=2.0, 8.0 Hz; 1H); 7.23 (dd; J=0.8, 3.6 Hz; 1H); 7.03 (dd; J=1.2, 4.8 Hz; 1H); 6.81 (d; J=8.0 Hz; 1H); 5.15 (bs, 2H); 4.52 (t; J=4.8 Hz; 2H); 4.35 (t; J=4.8 Hz; 2H); 2.60 (s, 3H); 1.91 (s, 3H). MS: calc: 434.5; found: 435.2 (M+H)

Example 85

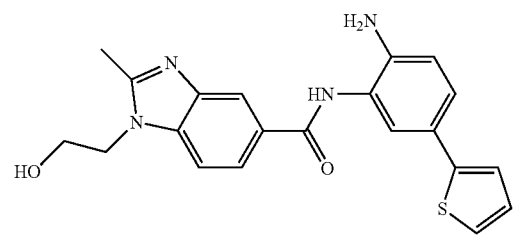

N-(2-Amino-5-(thiophen-2-yl)phenyl)-1-(2-hydroxyethyl)-2-methyl-1H-benzo[d]imidazole-5-carboxamide (309)

A solution of acetate 308 (18 mg; 41 μmol) and triethylamine (0.5 mL) in dry methanol (2.0 mL) was stirred at room temperature for 16 h and then concentrated in vacuo to give the title compound 309 in quantitative yield. $^1$H NMR: (400.2 MHz, DMSO) δ (ppm): 9.70 (s, 1H), 8.22 (s, 1H), 7.84 (dd; J=1.4, 8.2 Hz; 1H); 7.57 (d, J=8.4 Hz, 1H), 7.49 (d; J=2.2 Hz; 1H); 7.34 (dd; J=1.4, 5.1 Hz; 1H); 7.28 (dd; J=2.2, 8.2 Hz; 1H); 7.23 (dd; J=1.1, 3.5 Hz; 1H); 7.04 (dd; J=3.5, 5.1 Hz; 1H); 6.80 (d; J=8.4 Hz; 1H); 5.14 (bs, 2H); 5.00 (bs, 1H); 4.28 (t; J=5.4 Hz; 2H); 3.72 (t; J=5.4 Hz; 2H); 2.59 (s, 3H). MS: calc: 392.5; found: 393.2 (M+H).

Example 86

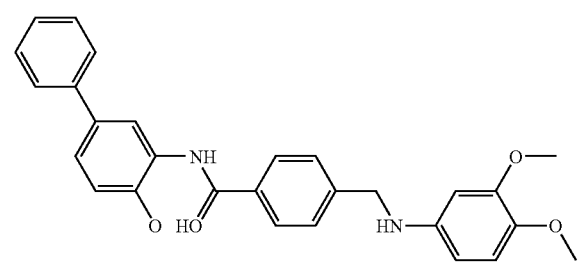

4-((3,4-Dimethoxyphenylamino)methyl)-N-(2-hydroxy-5-(phenyl)phenyl)benzamide (312)

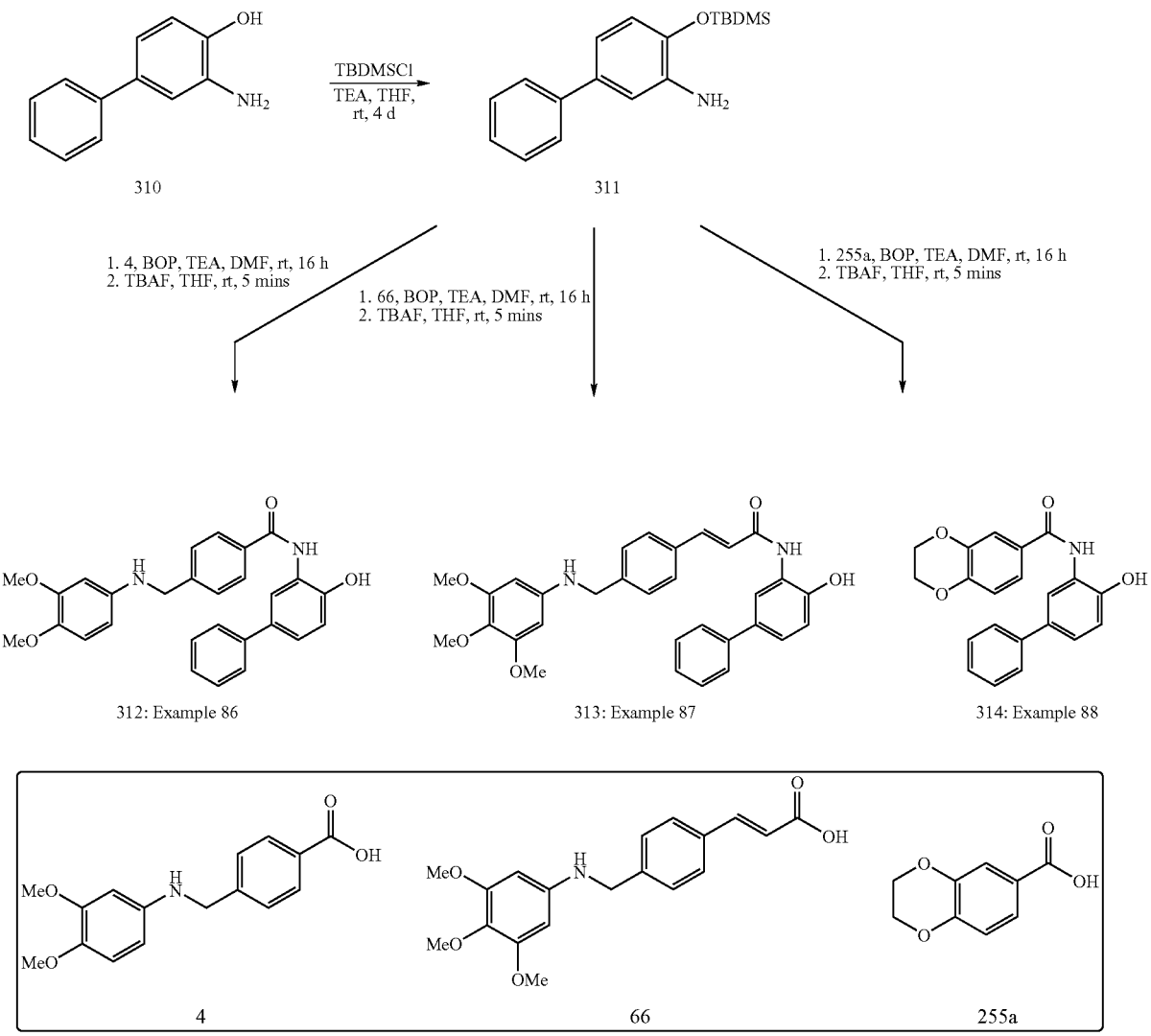

Step 1. 4-(tert-Butyl-dimethyl-silanyloxy)-biphenyl-3-ylamine (311)

To a solution of the 2-amino-4-phenylphenol (310, 2.05 g, 11.06 mmol) and triethylamine (3.08 mL, 22.12 mmol) in THF (20 mL) was added TBDMSCl (2.00 g, 13.28 mmol). The resulting solution was stirred at room temperature for 4 days prior to being diluted with saturated NaCl solution (25 mL), and extracted with ethyl acetate. The organic layer was dried over $Na_2SO_4$, filtered and concentrated. After purification by flash chromatography (eluent 0-50% EtOAc in hexanes), of the title compound 311 was obtained as a reddish-brown solid (2.51 g, 77% yield). $^1$H NMR: (DMSO) δ (ppm): 0.05 (s, 6H), 1.05 (s, 9H), 6.49-6.57 (m, 2H), 6.72 (d, J=8.1 Hz, 1H), 7.25 (m, 1H), 7.29-7.38 (m, 2H), 7.50 (d, J=7.9 Hz, 2H). MS: (calc.) 299.5; (obt.) 300.2 $(MH)^+$.

Step 2. 4-((3,4-Dimethoxyphenylamino)methyl)-N-(2-hydroxy-5-(phenyl)phenyl)-benzamide (312)

To a solution of acid 4 (scheme 1) (125 mg, 0.439 mmol) in DMF (3 mL) was added BOP (293 mg, 0.662 mmol). After stirring this solution for 10 minutes, aniline 311 (197 mg, 0.659 mmol) was added, along with triethylamine (0.31 mL, 2.22 mmol). The resulting solution was stirred at room temperature for 16 h prior to removal of the solvent, and dissolution of the residue in THF (5 mL). A solution of TBAF in THF (1.0 M, 0.66 mL, 0.659 mmol) was then added, and the reaction mixture was stirred at room temperature for 5 minutes, diluted with a saturated solution of NaCl (10 mL), and extracted with ethyl acetate. The organic layer was dried over $Na_2SO_4$, filtered and concentrated. After purification by flash chromatography (eluent 0-80% EtOAc in hexanes), the title compound 312 was obtained as a light yellow solid (82 mg, 41% yield). $^1$H NMR: (DMSO) δ (ppm): 3.62 (s, 3H), 3.69 (s, 3H), 4.34 (d, J=5.7 Hz, 2H), 6.03 (m, 2H), 6.35 (d, J=2.2 Hz, 1H), 6.68 (d, J=8.4 Hz, 1H), 7.03 (d, J=8.4 Hz, 1H), 7.32 (t, J=7.2 Hz, 1H), 7.37 (dd, J=10.4, 1.6 Hz, 1H), 7.45 (t, J=7.6 Hz, 2H), 7.52 (d, J=8.0 Hz, 2H), 7.59 (d, J=7.6 Hz, 2H), 7.95 (d, J=8.0 Hz, 2H), 8.03 (br s. 1H), 9.58 (br s, 1H), 10.00 (br s, 1H). MS: (calc.) 454.5; (obt.) 455.4 (MH)$^+$.

Example 87

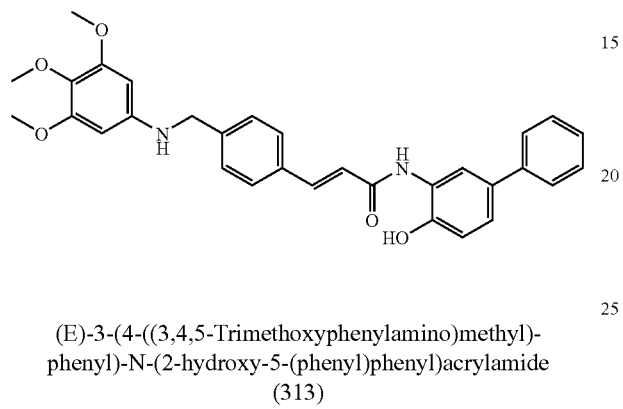

(E)-3-(4-((3,4,5-Trimethoxyphenylamino)methyl)-phenyl)-N-(2-hydroxy-5-(phenyl)phenyl)acrylamide (313)

Following the same procedure as described in Example 86 but substituting acid 4 for the acid 66 (scheme 10) the compound 313 was obtained as a light yellow solid in 22% yield. $^1$H NMR: (DMSO) δ (ppm): 3.54 (s, 3H), 3.68 (s, 3H), 4.30 (d, J=5.9 Hz, 2H), 5.92 (s, 2H), 6.13 (t, J=6.3 Hz, 1H), 7.01 (d, J=8.2 Hz, 1H), 7.21 (d, J=15.7 Hz, 1H), 7.29 (dd, J=8.4, 2.3 Hz, 1H), 7.33 (d, J=7.2 Hz, 1H), 7.42-7.50 (m, 4H), 7.54-7.64 (m, 4H), 8.34 (s, 1H), 9.55 (br s, 1H), 10.21 (br s, 1H). MS: (calc.) 510.6; (obt.) 511.2 (MH)$^+$.

Example 88

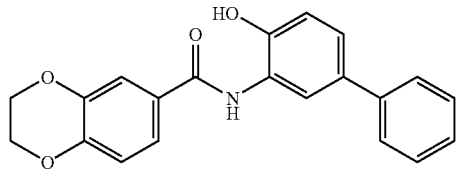

2,3-Dihydro-N-(2-hydroxy-5-phenyl)phenyl)benzo[b][1,4]dioxine-carboxamide (314)

Following the same procedure as described in Example 86 but substituting acid 4 for the acid 255a (scheme 53) the compound 314 was obtained as a light yellow solid in 22% yield. $^1$H NMR: (DMSO) δ (ppm): 4.30 (d, J=5.9 Hz, 2H), 6.98 (d, J=8.3 Hz, 1H), 7.26-7.36 (m, 2H), 7.42 (t, J=7.3 Hz, 2H), 7.50-7.60 (m, 2H), 7.97 (br s. 1H), 9.47 (br s, 1H), 9.93 (br s, 1H). MS: (calc.) 347.4; (obt.) 348.1 (MH)$^+$.

Example 89

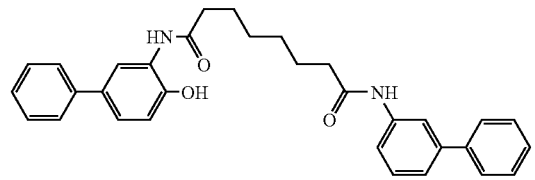

$N^1$-(2-hydroxy-5-(phenyl)phenyl)-$N^8$-(3-(phenyl)phenyl)octanediamide (317)

Scheme 69

[Structure of compound 315]

[Structure of compound 316]

[Structure of compound 317: Example 89]

Step 1. 7-(3-(Phenyl)phenylcarbamoyl)heptanoic acid (316)

To a solution of 3-amino-biphenyl (315, 536 mg, 3.17 mmol) in THF/pyridine (2:1, 6 mL) was added methyl 7-(chlorocarbonyl)heptanoate (0.49 mL, 3.48 mmol), and the resulting solution was stirred at room temperature for 16 h. After dilution with saturated NaCl solution (15 mL) and extraction with ethyl acetate, the organic layer was dried over $Na_2SO_4$, filtered and concentrated. The residue was then dissolved in THF/methanol/$H_2O$ (1:1:2, 8 mL), followed by the treatment of LiOH—$H_2O$ (665 mg, 15.85 mmol). The reaction mixture was stirred at room temperature for 1 h prior to acidification (pH=1), and extraction with ethyl acetate. The organic layer was dried over $Na_2SO_4$, filtered and concentrated. After purification by flash chromatography (eluent 0-100% EtOAc in hexanes), the title compound 316 was obtained as a white solid (889 mg, 86% yield). $^1$H NMR: (DMSO) δ (ppm): 1.30-1.40 (m, 4H), 1.50-1.59 (m, 2H), 1.60-1.68 (m, 2H), 2.24 (t, J=7.4 Hz, 2H), 2.37 (t, J=7.4 Hz, 2H), 7.32 (dt, J=7.8, 1.6 Hz, 1H), 7.36-7.42 (m, 2H), 7.46-7.52 (m, 2H), 7.58-7.64 (m, 3H), 7.96 (s, 1H), 10.07 (br s, 1H). MS: (calc.) 325.4; (obt.) 326.1 (MH)$^+$.

Step 2. $N^1$-(2-Hydroxy-5-(phenyl)phenyl)-$N^8$-(3-(phenyl)phenyl)octanediamide (317)

Following the same procedure as described in Example 86, step 2 (scheme 68) but substituting acid 4 for the acid 316 the compound 317 was obtained as a light brown solid in 31% yield. $^1$H NMR: (DMSO) δ (ppm): 1.34-1.46 (m, 4H), 1.60-1.74 (m, 4H), 2.38 (t, J=6.8 Hz, 2H), 2.47 (t, J=7.0 Hz, 2H), 6.98 (d, J=8.2 Hz, 1H), 7.20-7.70 (m, 15H), 7.96 (s, 1H), 8.10 (s, 1H), 9.34 (br s, 1H), 10.00 (br s, 1H). MS: (calc.) 492.6; (obt.) 493.5 (MH)$^+$.

Example 90

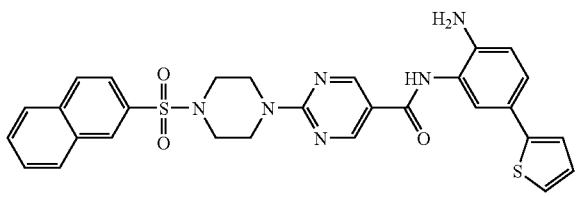

2-[4-(Naphthalene-2-sulfonyl)-piperazin-1-yl]-pyrimidine-5-carboxylic acid (2-amino-5-thiophen-2-yl-phenyl)-amide (320)

Scheme 70

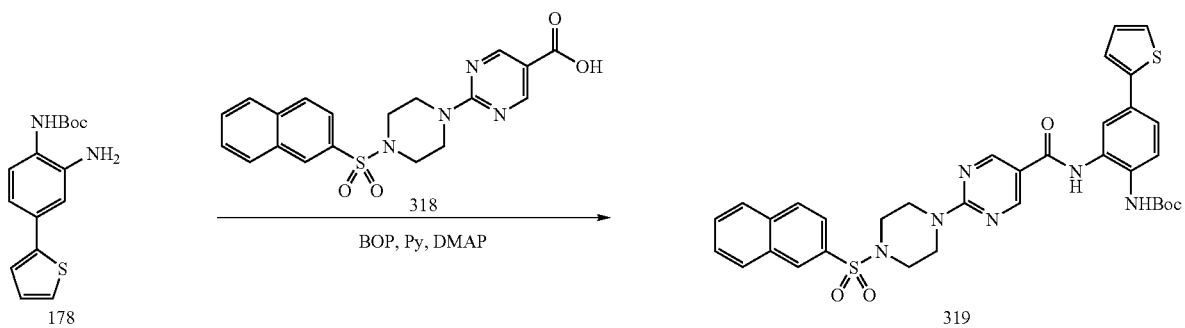

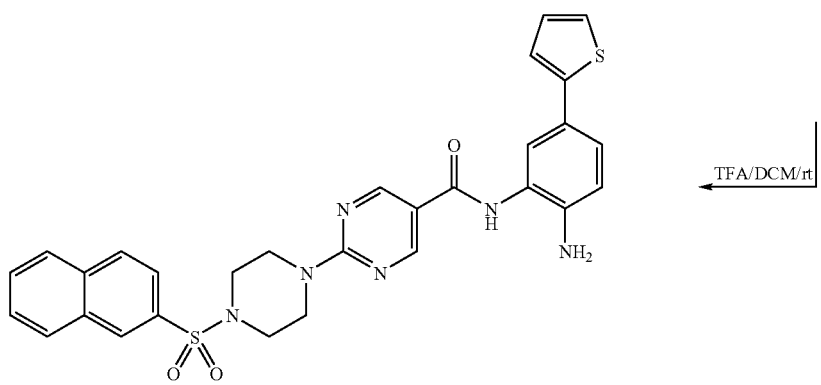

320: Example 90

Step 1: [2-({2-[4-(Naphthalene-2-sulfonyl)-piper-azin-1-yl]-pyrimidine-5-carbonyl}-amino)-4-thiophen-2-yl-phenyl]-carbamic acid tert-butyl ester (319)

Following the same procedure as described in Example 52, step 1 (scheme 37) but substituting compound 182 for 2-[4-(naphthalene-2-sulfonyl)-piperazin-1-yl]-pyrimidine-5-carboxylic acid (318, WO 03/076422) title compound 319 was obtained in 75% yield. $^1$H NMR: (400.2 MHz, DMSO) δ (ppm): 9.7 (bs, 1H); 8.81 (s, 2H); 8.60 (bs, 1H); 8.44 (s, 1H); 8.20 (d, J=7.6 Hz, 1H); 8.15 (d, J=8.6 Hz, 1H); 8.05 (d, J=6.9 Hz, 1H); 7.75 (dd; J=1.8, 8.6 Hz; 1H); 7.71 (dd; J=1.3, 6.9 Hz; 1H); 7.68 (m, 2H); 7.63 (d, J=8.6 Hz, 1H); 7.47 (m, 2H); 7.40 (dd; J=1.3, 3.5 Hz; 1H); 7.09 (dd; J=3.5, 5.1 Hz; 1H); 3.97 (t, J=4.1 Hz, 4H); 3.07 (t, J=4.1 Hz, 4H); 1.41 (s, 9H). MS: calc: 670.8; found: 671.3 (M+H)

Step 2: 2-[4-(Naphthalene-2-sulfonyl)-piperazin-1-yl]-pyrimidine-5-carboxylic acid (2-amino-5-(thiophen-2-yl-phenyl)-amide (320)

Following the same procedure described in Example 52, step 2 (scheme 37) but substituting compound 183 for compound 319 the title compound 320 was obtained in 99% yield. $^1$H NMR: (400.2 MHz, DMSO) δ (ppm): 9.52 (bs, 1H); 8.83 (s, 2H); 8.44 (s, 1H); 8.20 (d, J=7.6 Hz, 1H); 8.15 (d, J=8.6 Hz, 1H); 8.05 (d, J=8.0 Hz, 1H); 7.75 (dd; J=1.8, 8.6 Hz; 1H); 7.69 (m, 2H); 7.37 (d, J=1.8 Hz, 1H); 7.31 (dd; J=1.2, 5.1 Hz; 1H); 7.25 (dd; J=2.2, 8.4 Hz; 1H); 7.19 (dd; J=1.2, 3.5 Hz; 1H); 7.01 (dd; J=3.5, 5.1 Hz; 1H); 6.74 (d, J=8.2 Hz, 1H); 5.16 (bs, 2H); 3.96 (t, J=4.3 Hz, 4H); 3.07 (t, J=4.3 Hz, 4H); MS: calc: 570.7; found: 571.3 (M+H)

Example 91

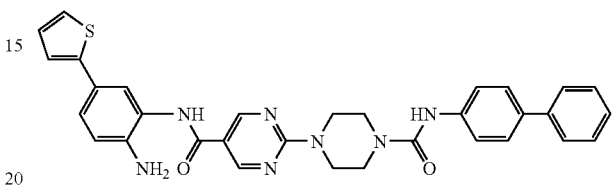

2-[4-(Biphenyl-4-ylcarbamoyl)-piperazin-1-yl]-pyrimidine-5-carboxylic acid (2-amino-5-thiophen-2-yl-phenyl)-amide (323)

Scheme 71

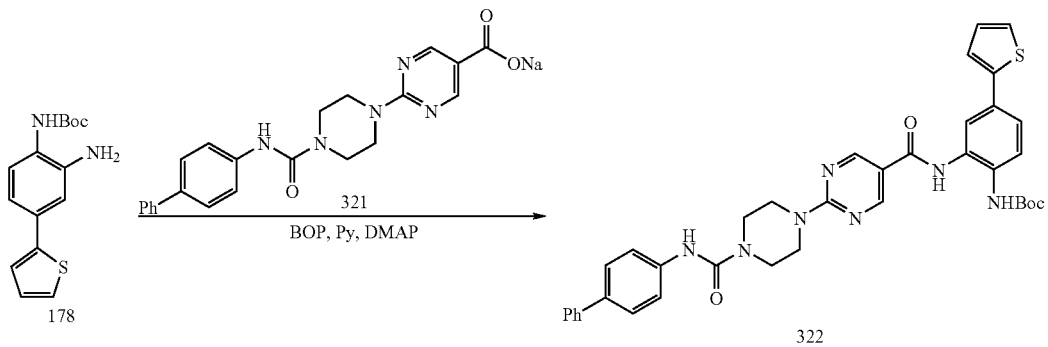

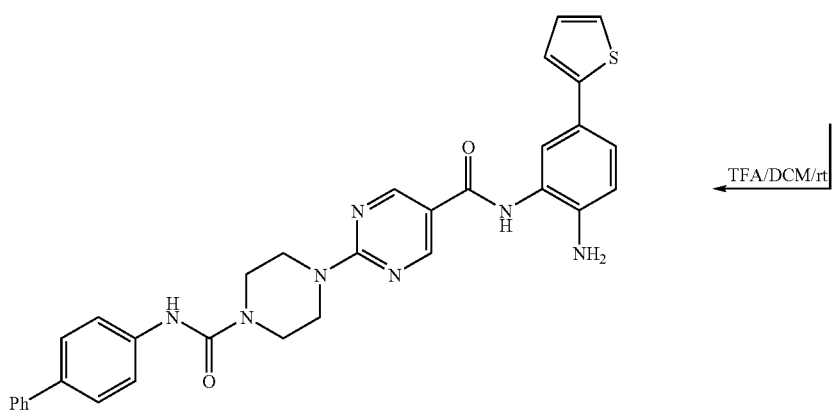

323: Example 91

Step 1: [2-({2-[4-(Biphenyl-4-ylcarbamoyl)-piperazin-1-yl]-pyrimidine-5-carbonyl}-amino)-4-thiophen-2-yl-phenyl]-carbamic acid tert-butyl ester (322)

Following the same procedure as described in Example 52, step 1 (scheme 37) but substituting compound 182 for 2-[4-(biphenyl-4-ylcarbamoyl)piperazin-1-yl]-pyrimidine-5-carboxylic acid sodium salt (321, WO 03/076421) the title compound 322 was obtained in 29% yield. $^1$H NMR: (400.2 MHz, DMSO) δ (ppm): 9.78 (bs, 1H); 8.93 (s, 2H); 8.75 (bs, 1H); 8.67 (bs, 1H); 7.76 (d, J=2.0 Hz, 1H); 7.67 (d, J=8.4 Hz, 1H); 7.63 (d, J=1.2 Hz, 1H); 7.61 (m, 1H); 7.57 (m, 4H); 7.50 (m, 2H); 7.42 (m, 3H); 7.29 (m, 1H); 7.11 (dd; J=3.5, 5.1 Hz; 1H); 3.94 (t, J=4.5 Hz, 4H); 3.60 (t, J=4.5 Hz, 4H); 1.47 (s, 9H). MS: calc: 675.8; found: 698.5 (M+Na)

Step 2: [4-(Biphenyl-4-ylcarbamoyl)-piperazin-1-yl]-pyrimidine-5-carboxylic acid (2-amino-5-(thiophen-2-yl-phenyl)-amide (323)

Following the same procedure as described in Example 52, step 2 (scheme 37) but substituting compound 183 for compound 322 the title compound 323 was obtained in 99% yield. $^1$H NMR: (400.2 MHz, DMSO) δ (ppm): 9.59 (bs, 1H); 8.93 (s, 2H); 8.75 (bs, 1H); 7.63 (d, J=1.2 Hz, 1H); 7.61 (m, 1H); 7.57 (m, 4H); 7.41 (m, 3H); 7.33 (dd; J=1.2, 5.1 Hz; 1H); 7.29 (m, 2H); 7.23 (dd; J=1.2, 2.5 Hz; 1H); 7.03 (dd; J=3.7, 5.1 Hz; 1H); 6.78 (d, J=8.2 Hz, 1H); 5.22 (bs, 2H); 3.93 (t, J=3.9 Hz, 4H); 3.60 (t, J=3.9 Hz, 4H). MS: calc: 575.7; found: 576.3 (M+H

Example 92

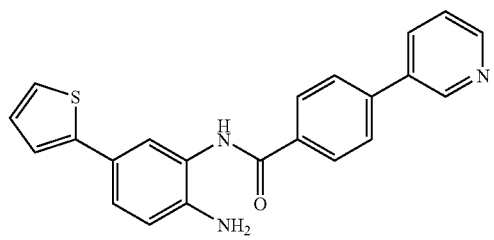

N-(2-Amino-5-(thiophen-2-yl)phenyl)-4-(pyridin-3-yl)benzamide (327)

Scheme 72

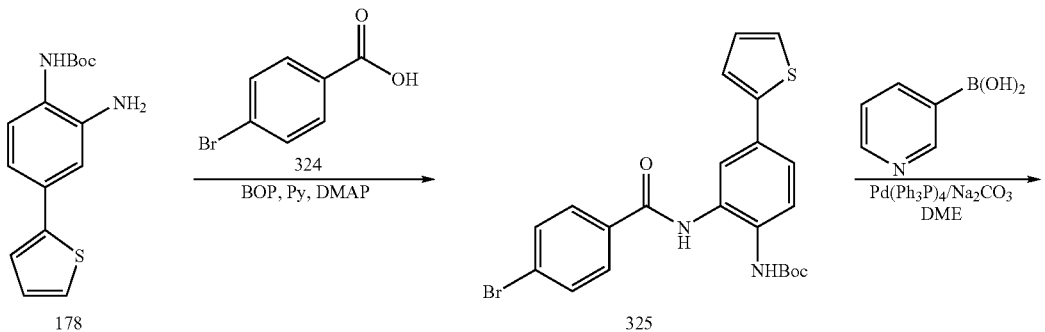

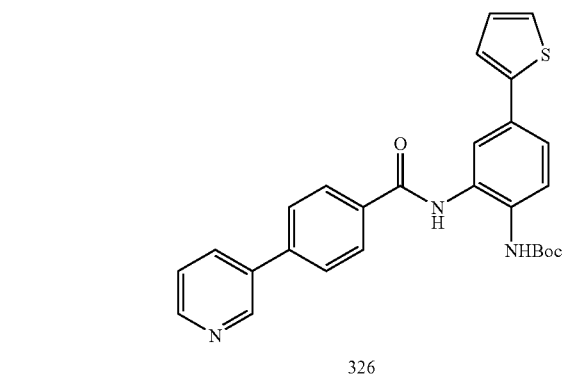

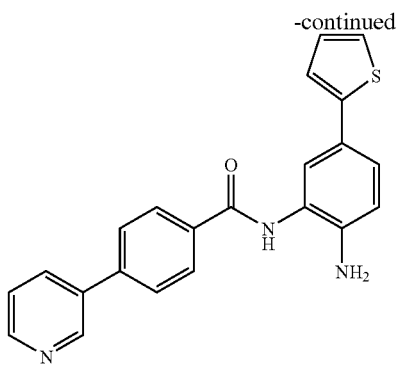

327: Example 92

Step 1. tert-Butyl 2-(4-bromobenzamido)-4-(thiophen-2-yl)phenylcarbamate (325)

Following the same procedure as in Example 52, step 1 (scheme 37) but substituting compound 182 for compound 324 title compound 325 was obtained in 47% yield. $^1$H NMR: (400 MHz, DMSO-$d_6$) δ (ppm): 9.94 (s, 1H), 8.72 (s, 1H), 7.91 (d, J=8.6 Hz, 2H), 7.76 (d, J=8.2, 2H), 7.75 (d, J=2.2 Hz, 1H), 7.62 (d, J=8.9 Hz, 1H), 7.51 (dd, J=4.9, 1.2 Hz, 1H), 7.50 (dd, J=8.6, 2.2 Hz, 7.44 (d, J=3.7, 1.2 Hz, 1H), 7.11 (dd, J=5.1, 3.5 Hz, 1H), 1.45 (s, 9H). LRMS: (m/z): 495.1/497.1 ((M/M+2)+23).

Steps 2 and 3. N-(2-Amino-5-(thiophen-2-yl)phenyl)-4-(pyridin-3-yl)benzamide (327)

Following the same procedure as in Example 29, step 1 (scheme 21) but substituting bromide 114 for the bromide 325 and using 3-pyridine boronic acid as a coupling partner, (Suzuki coupling) the compound 326 was obtained and used without purification for the next step.

Following the same procedure as in Example 52, step 2 (scheme 37) but replacing compound 183 by compound 326 the title compound 327 was obtained (14% yield over the two steps). $^1$H NMR: (400 MHz, DMSO-$d_6$) δ (ppm): 9.80 (s, 1H), 8.98 (d, J=2.2 Hz, 1H), 8.60 (dd, J=4.7, 1.6 Hz, 1H), 8.17 (d, J=8.6 Hz, 1H), 8.12 (d, J=8.0 Hz, 2H), 7.90 (d, J=8.6 Hz, 2H), 7.52 (dd, J=7.2, 4.1 Hz, 1H), 7.48 (s, 1H), 7.35 (d, J=4.1 Hz, 1H), 7.29 (dd, J=8.4, 2.3 Hz, 1H), 7.24 (d, J=3.3 Hz, 1H), 7.04 (dd, J=5.1, 1.4, 1H), 6.80 (d, J=8.2 Hz, 1H), 5.19 (s, 2H). LRMS: (m/z): 372.3 (MH$^+$).

Example 93

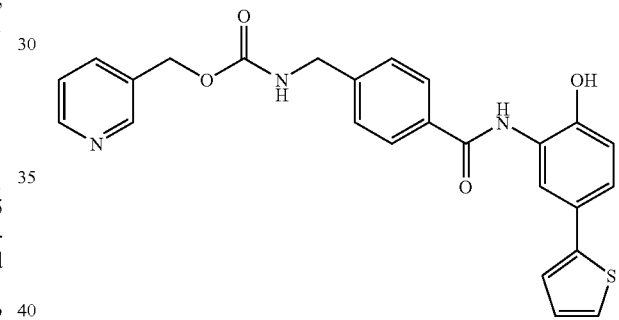

(Pyridin-3-yl)methyl 4-(2-hydroxy-5-(thiophen-2-yl)phenylcarbamoyl)benzyl carbamate (333)

Scheme 73

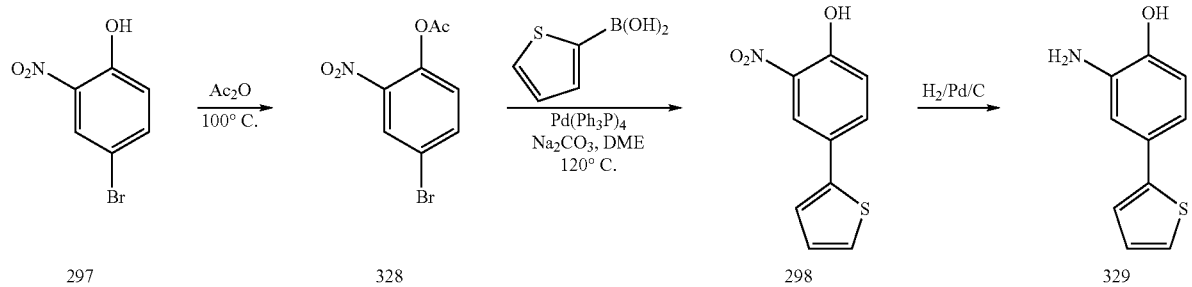

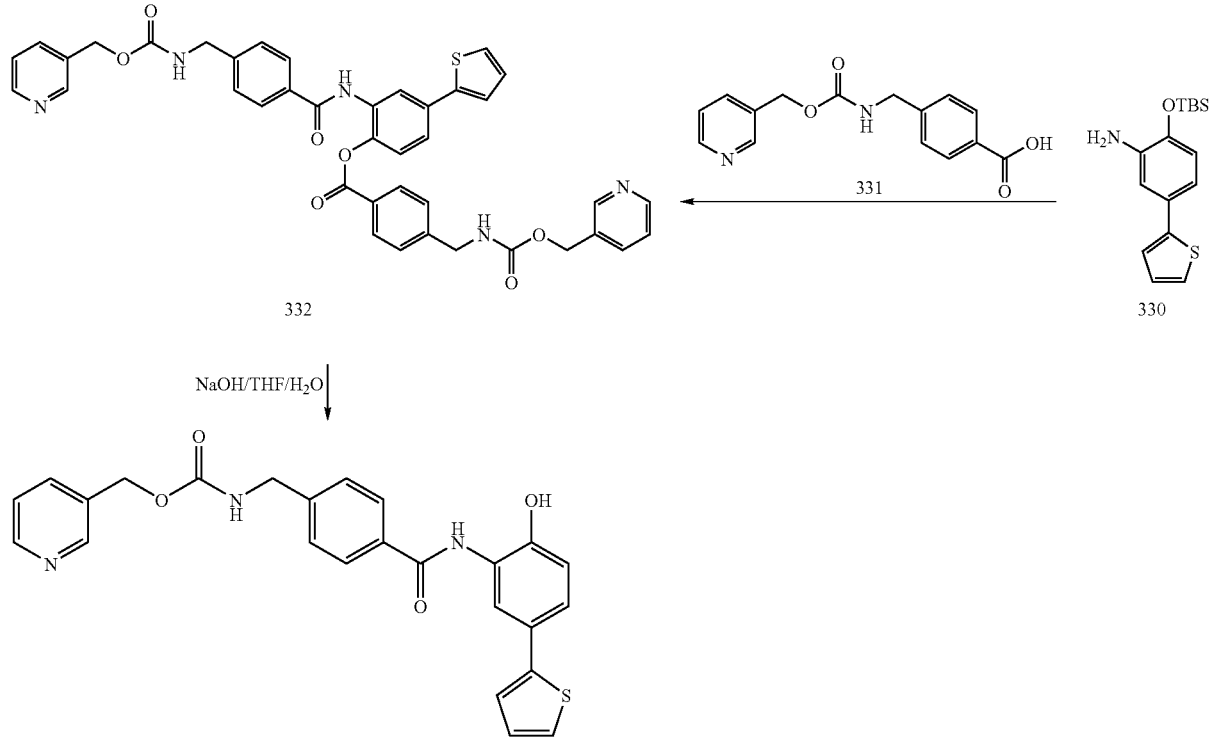

333: Example 93

Step 1. 4-Bromo-2-nitrophenyl acetate (328)

A solution of 4-bromo-2-nitrophenol (297, 1.00 g, 4.59 mmol) (scheme 65) in acetic anhydride (10 mL) was heated in a pressure vessel at 130-140° C. for 16 h. Most of the solvent was evaporated in vacuo and the resulting oil was kept in the freezer for 3 days. Crystallization occurred while thawing. The white crystals were suspended in a mixture of EtOAc/hexanes (9:1) and collected by filtration affording the title compound 328 (1.03 g, 87% yield). $^1$H NMR: (400 MHz, DMSO-$d_6$) δ (ppm): 8.33 (d, J=2.3 Hz, 1H), 8.02 (dd, J=8.6, 2.3 Hz, 1H), 7.45 (d, J=8.6 Hz, 1H), 2.33 (s, 3H). LRMS: (m/z): 282.0/284.0 ((M$^+$/M+2)+23).

Step 2. 2-Nitro (thiophen-2-yl)phenol (298)

Following the same procedure as in Example 44, step 2 (scheme 32) but substituting bromide 155 for bromide 328 (1.00 g, 3.85 mmol) and boronate 116 for 2-thiophene boronic acid (517 mg, 4.04 mmol) and heating at 120° C., the title compound 298 was obtained (270 mg, 32% yield). $^1$H NMR: (DMSO-$d_6$) δ (ppm): 11.21 (bs, 1H), 8.07 (d, J=2.3 Hz, 1H), 7.80 (dd, J=8.6, 2.3 Hz, 1H), 7.49 (dd, J=3.5, 1.2 Hz, 1H), 7.16 (d, J=8.6 Hz, 1H), 7.11 (dd, J=5.1, 3.5 Hz, 1H), 7.07 (d, J=8.8 Hz, 1H).

Step 3. 2-Amino-4-(thiophen-2-yl)phenol (329)

Following the same procedure as in Example 51, step 3 (scheme 37) but substituting compound 177 for compound 298 (270 mg, 1.22 mmol), the title compound 329 was obtained (233 mg, 100% yield). $^1$H NMR: (DMSO-$d_6$) δ (ppm): 9.21 (bs, 1H), 7.33 (dd, J=5.1, 1.0 Hz, 1H), 7.14 (dd, J=3.5, 1.2 Hz, 1H), 7.01 (dd, J=5.1, 3.5 Hz, 1H), 6.85 (d, J=2.2 Hz, 1H), 6.63 (d, J=8.0 Hz, 1H), 6.53 (d, J=8.2 Hz, 1H), 4.65 (bs, 2H). LRMS: (m/z): 192.1 (MH$^+$).

Step 4. O-tert-Butyldimethylsilyl-2-amino-4-(thiophen-2-yl)phenol (330)

Following the same procedure as in Example 19, step 2 (scheme 17) but substituting compound 90 for compound 329 (233 mg, 1.22 mmol), the title compound 330 was obtained (211 mg, 57% yield). $^1$H NMR: (DMSO-$d_6$) δ (ppm): 7.75 (dd, J=5.1, 1.2 Hz, 1H), 7.66 (dd, J=3.5, 1.2 Hz, 1H), 7.50 (d, J=2.2 Hz, 1H), 7.47 (dd, J=5.3, 3.7 Hz, 1H), 7.28 (dd, J=8.2, 2.2 Hz, 1H), 7.21 (d, J=8.2 Hz, 1H), 4.88 (bs, 2H), 1.50 (s, 9H), 0.73 (s, 6H). LRMS: (m/z): 306.3 (MH$^+$).

Steps 5 and 6: (Pyridin-3-yl)methyl 4-(2-hydroxy-5-(thiophen-2-yl)phenylcarbamoyl)benzylcarbamate (333)

To a solution of acid 331 (383 mg, 0.691 mmol) (U.S. Pat. No. 6,174,905 B1) in DMF (6 mL) was added Et$_3$N (194 μL, 1.39 mmol) and BOP (954 mg, 2.08 mmol). The mixture was stirred for 15 min. and a solution of compound 330 (211 mg, 0.691 mmol) in DMF (4 mL) was added followed by Et$_3$N (510 μL, 3.66 mmol). The mixture was stirred for 16 hours at rt and then concentrated in vacuo at 80° C. The residue was partitioned between EtOAc and H$_2$O, the organic phase was extracted twice with HCl 1N and the combined acidic extracts were neutralized with saturated NaHCO$_3$. A precipitate formed which was extracted with EtOAc; the extract was washed with brine, dried over MgSO$_4$, filtered and concentrated. The resulting material was purified by flash chromatography using as an eluent a mixture MeOH/DCM with increasing polarity (7:93 to 10:90) affording the intermediate compound 332 (99 mg, 20% yield). $^1$H NMR: (DMSO-$d_6$) δ (ppm): 10.11 (s, 1H), 8.56 (bs, 2H), 8.51 (bs, 2H), 8.02 (d, J=7.8 Hz, 2H), 7.92-7.90 (m, 2H), 7.79 (d, J=8.2 Hz, 2H), 7.76-7.74 (m, 2H), 7.61 (d, J=7.4 Hz, 1H), 7.57 (d, J=5.1 Hz, 1H), 7.53 (d, J=3.5 Hz, 1H), 7.41 (d, J=8.2 Hz, 2H), 7.38 (d, J=7.8 Hz, 2H), 7.29 (d, J=8.2 Hz, 1H), 7.27 (d, J=5.9 Hz, 1H), 7.16 (dd, J=5.1, 3.7 Hz, 1H), 5.08 (s, 2H), 5.07 (s, 2H), 4.28 (d, J=7.2 Hz, 2H), 7.23 (d, J=5.5 Hz, 2H). LRMS: (m/z): 728.3 (MH$^+$).

To a solution of compound 332 (10 mg, 0.0137 mmol) in THF (500 μL) was added excess NaOH (500 μL of a solution prepared by dissolving one pellet in 1 mL of H$_2$O). The mixture was stirred at 60° C. for 1 h, partitioned between EtOAc and H$_2$O. The aqueous layer was extracted with EtOAc and the organic phase was extracted with HCl 1N. The acidic extract was neutralized with saturated NaHCO$_3$ to form a precipitate which was extracted with EtOAc; the extract was washed with brine, dried over MgSO$_4$, filtered and concentrated. The resulting material was purified by preparative TLC using MeOH/DCM (7:93) affording the title compound 333 (2.9 mg, 46% yield). $^1$H NMR: (Acetone-$d_6$) δ (ppm): 9.37 (bs, 1H), 9.35 (bs, 1H), 8.47 (d, J=1.2 Hz, 8.38 (d, J=3.9 Hz, 1H), 7.97 (s, 1H), 7.87 (d, J=8.4 Hz, 2H), 7.64 (d, J=7.4 Hz, 1H), 7.35 (d, J=8.2 Hz, 2H), 7.25 (dd, J=8.4, 2.3 Hz, 1H), 7.22 (dd, J=5.1, 1.2 Hz, 1H), 7.16 (dd, J=3.7, 1.2 Hz, 1H), 6.93 (d, J=8.1 Hz, 1H), 6.93 (d, J=1.6 Hz, 1H), 6.86 (d, J=8.4 Hz, 1H), 5.01 (s, 2H), 4.31 (d, J=6.3 Hz, 2H). LRMS: (m/z): 460.2 (MH$^+$).

Example 94

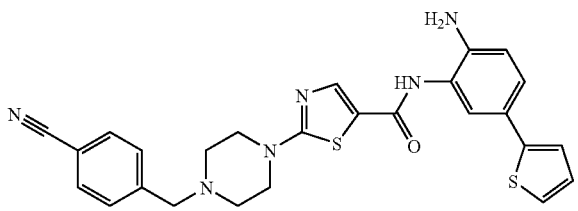

2-(4-(4-Cyanobenzyl)piperazin-1-yl)-N-(2-amino-5-(thiophen-2-yl)phenyl)thiazole-5-carboxamide (341)

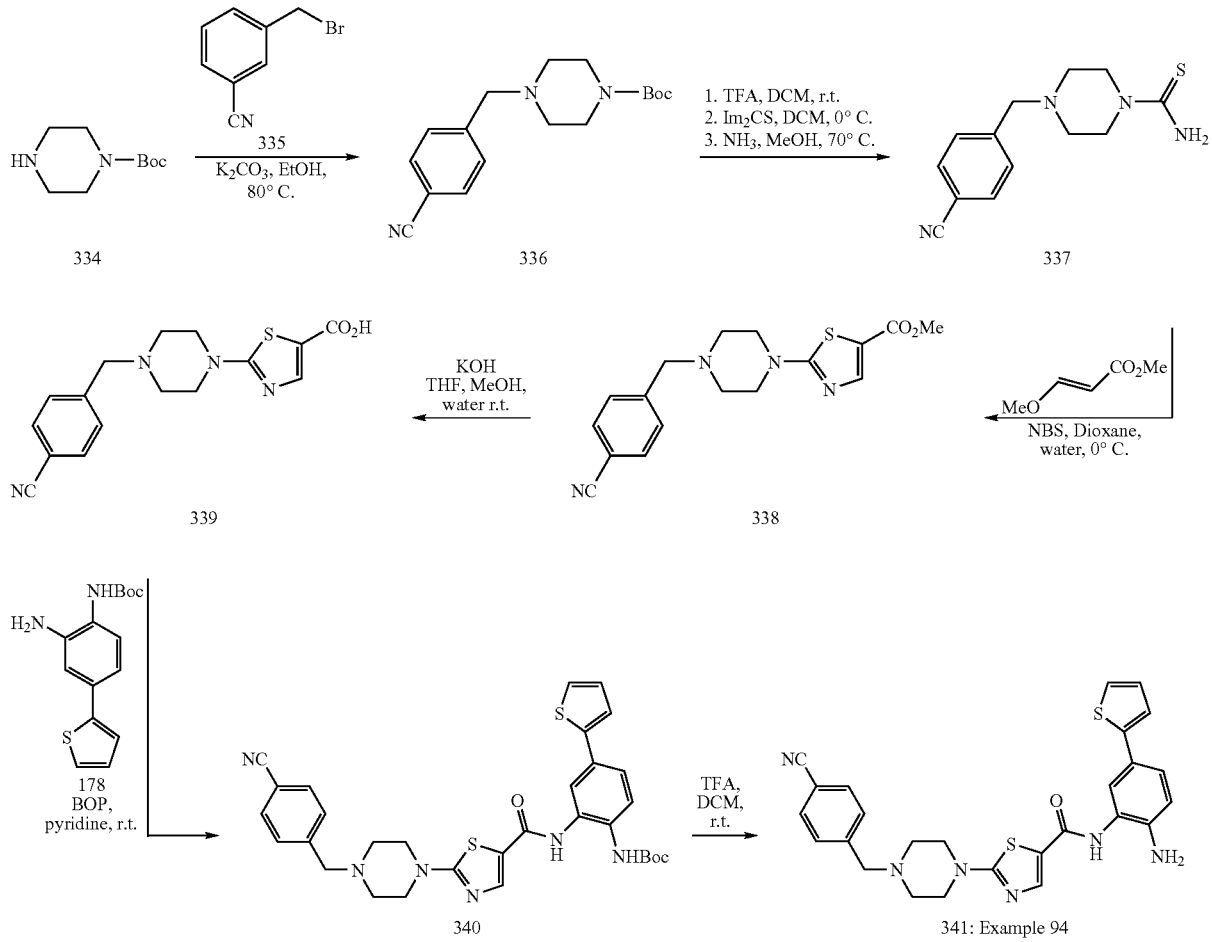

Step 1: tert-Butyl 4-(4-cyanobenzyl)piperazine-1-carboxylate (336)

A solution of tert-butyl piperazine-1-carboxylate (334, 1 g, 5.37 mmol), 3-(bromomethyl)benzonitrile (335, 1.26 g, 6.45 mmol) and $K_2CO_3$ (1.48 g, 10.74 mmol) in EtOH (20 mU was refluxed for four hours. The reaction mixture was then concentrated, diluted with EtOAc (20 ml.) and washed with water (20 mL). The organic phase was separated, dried with $Na_2SO_4$, filtered and concentrated. Crude product was purified by flash chromatography using the gradient 10%-25% EtOAc in hexanes as an eluent to afford the title compound 336 (1.374 g 85%). MS: calc: 301.3; found: 302.1 (M+H)

Step 2: 4-(4-Cyanobenzyl)piperazine-1-carbothioamide (337)

A solution of tert-butyl 4-(4-cyanobenzyl)piperazine-1-carboxylate (336, 1.374 g, 4.56 mmol) in DCM (5 mL) and TFA (5 mL) was stirred at room temperature for one hour. The reaction mixture was concentrated and the residue was added to a solution of thiocarbonyldiimidazole (1.21 g, 6.84 mmol, 1.5 equiv.) in dry DCM (20 mL) under $N_2$ at 0° C. Obtained solid was diluted with MeOH (20 mL) and transferred to a pressure vial. Ammonia gas was bubbled in for 10 min and the flask was capped and stirred at 80° C. for two days. The reaction mixture was concentrated and purified by flash chromatography using 60% EtOAc in hexane as an eluent, to afford the title compound 337 (593 mg, 50% yield). MS: calc: 260.1; found: 261.2 (M+H)

Step 3: Methyl 2-(4-(4-cyanobenzyl)piperazin-1-yl)thiazole-5-carboxylate (338)

A solution of (E)-methyl 3-methoxyacrylate (290 mg, 280 mL, 2.51 mmol) in 1:1 mixture of dioxane/water (4 mL) was treated with NBS (507 mg, 2.85 mmol) at 0° C. and stirred for 1 hour. The mixture was transferred to a flask containing the thioamide 337 (593 mg, 2.28 mmol) at room temperature and the resulting mixture was refluxed for 1.5 hours. It was cooled down, quenched by adding saturated $NH_4Cl$ solution (5 mL) and concentrated. Obtained material was partitioned between EtOAc and water. Organic phase was dried with $Na_2SO_4$, filtered and concentrated. The crude product was purified by flash chromatography using 60% EtOAc in hexanes as an eluent, to afford the title compound 338 (602 mg, 77% yield). MS: calc: 342.1; found: 343.1 (M+H)

Step 4: 2-(4-(4-Cyanobenzyl)piperazin-1-yl)thiazole-5-carboxylic acid (339)

1:1:1 solution of THF/water/MeOH (9 mL) of ester 338 (602 mg, 1.76 mmol) and KOH (600 mg, 10.71 mmol, 6 equiv.) was stirred at room temperature for 1 hour. The reaction mixture was then concentrated and partitioned between ether and water. Aqueous layer was collected and acidified with 1M HCl solution to pH=3 and extracted with EtOAc (3×5 mL). Organic phase was dried with $Na_2SO_4$, filtered and concentrated. Crude product 339 (WO 03/092686) was used directly in the next step. MS: calc: 328.1; found: 329.1 (M+H)

Step 5: tert-Butyl 2-(2-(4-(4-cyanobenzyl)piperazin-1-yl)thiazole-5-carboxamido)-4-(thiophen-2-yl)phenylcarbamate (340)

A solution of acid 339 (113 mg, 0.34 mmol) amine 178 (100 mg, 0.34 mmol) and BOP (152 mg, 0.34 mmol) in pyridine (2 mL) was stirred at room temperature overnight. The reaction mixture was concentrated and purified by flash chromatography using gradient eluent 50%-75% EtOAc in hexanes to afford the title compound 340 (96 mg, 47% yield). MS: calc: 600.1; found: 601.3 (M+H)

Step 6: 2-(4-(4-Cyanobenzyl)piperazin-1-yl)-N-(2-amino-5-(thiophen-2-yl)phenyl) thiazole-5-carboxamide (341)

A solution of compound 340 (96 mg, 0.16 mmol) in 1:1 DCM/TFA (6 mL) was stirred at room temperature for 1 hour. The mixture was concentrated and purified by flash chromatography using EtOAc as an eluent, to afford the title compound 341 (47 mg, 59% yield). $^1$H NMR: (400.2 MHz, $CD_3OD$) δ (ppm): 7.95 (br.s, 1H), 7.75 (m, 1H), 7.68 (m, 2H), 7.53 (t, 1H, J=7.6 Hz), 7.42 (s, 1H), 7.33 (d, 1H, J=8.2 Hz), 7.20 (m, 2H), 7.00 (m, 1H), 6.87 (d, 1H, J=8.3 Hz), 3.72 (s, 2H), 3.60 (m, 4H), 2.68 (m, 4H). MS: calc: 500.1; found: 501.2 (M+H)

Example 95

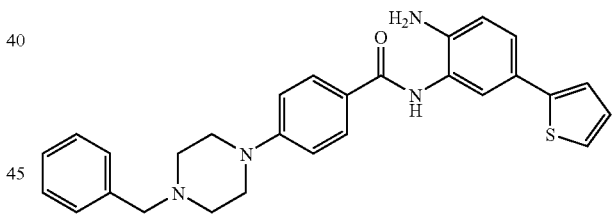

N-(2-Amino-5-(thiophen-2-yl)phenyl)-4-(4-benzylpiperazin-1-yl)benzamide (344)

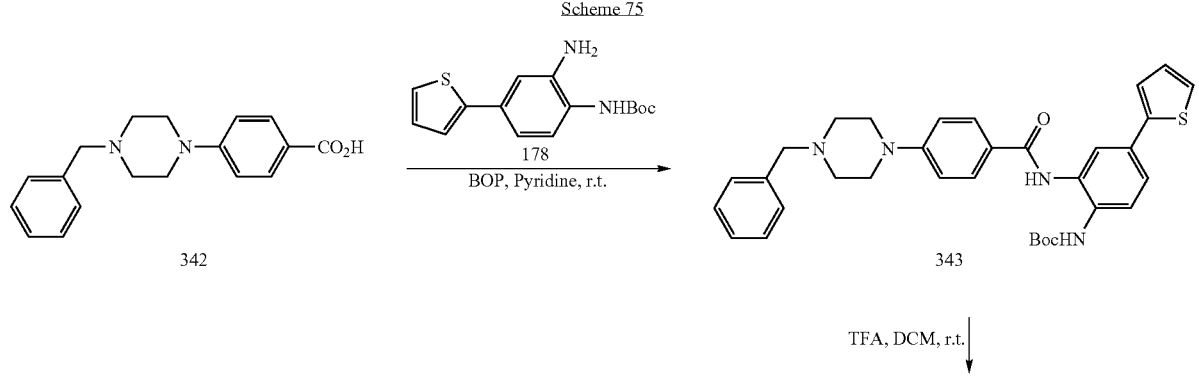

Scheme 75

-continued

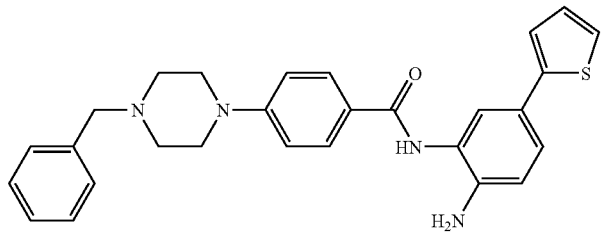

344: Example 95

Step 1: tert-Butyl 2-(4-(4-benzylpiperazin-1-yl)benzamido)-4-(thiophen-2-yl)phenylcarbamate (343)

Following the procedure as described in Example 94, step 5 (scheme 74) but substituting 2-(4-(4-cyanobenzyl)piperazin-1-yl)thiazone-5-carboxylic acid (339 WO 03/092686)) for 4-(4-benzylpiperazin-1-yl)benzoic acid (342, WO 03/087057) the title compound 343 was obtained in 18% yield. MS: calc: 568.2; found: 569.3 (M+H)

Step 2: N-(2-Amino-5-(thiophen-2-yl)phenyl)-4-(4-benzylpiperazin-1-yl)benzamide (344)

A solution of compound 343 (36 mg, 0.06 mmol) in 1:1 DCM/TFA (6 mL) was stirred at room temperature for 1 hour. The mixture was concentrated and partitioned between water and EtOAc. Organic phase was washed with NaHCO$_3$ solution, dried with Na$_2$SO$_4$, filtered and concentrated to afford the title compound 344 (5 mg, 17% yield). $^1$H NMR: (400.2 MHz, CDCl$_3$) δ (ppm): 2.625 (t, J=5 Hz, 4H), 3.35 (t, J=5 Hz, 4H), 3.59 (s, 2H), 4.00 (s, 2H), 6.84 (d, J=8 Hz, 1H), 6.90 (d, J=9 Hz, 2H), 7.01 (m, 1H), 7.16 (m, 2H), 7.25 (m, 6H), 7.50 (s, 1H), 7.75 (s, 1H), 7.81 (d, J=9 Hz, 2H). MS: calc: 468.0; found: 469.0 (M+H)

Example 96

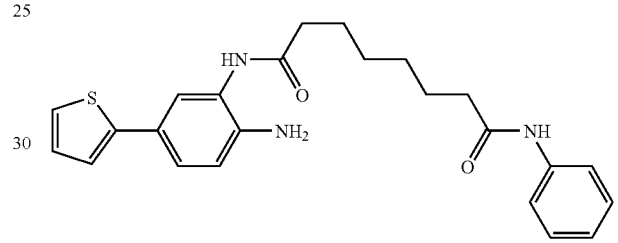

N1-(2-amino-5-(thiophen-2-yl)phenyl)-N8-phenyloctanediamide (347)

Scheme 76

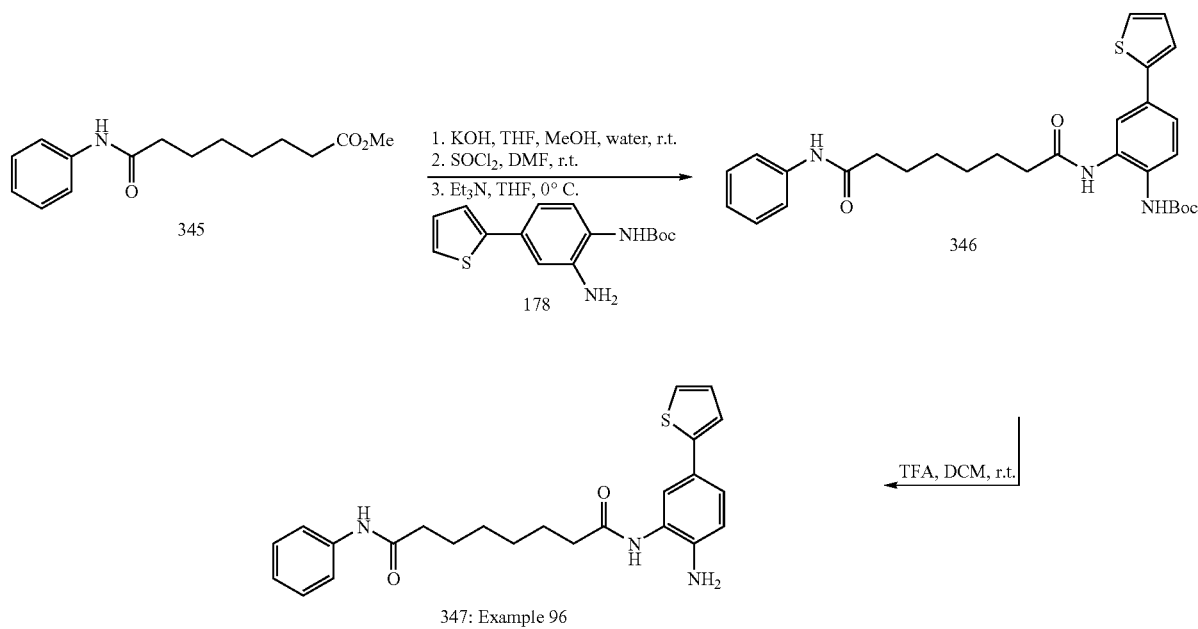

347: Example 96

Step 1: tert-Butyl 2-(N1-phenyloctanediamido) 4-(thiophen-2-yl)phenylcarbamate (346)

A solution of methyl 7-(phenylcarbamoyl)heptanoate (345, U.S. Pat. No. 5,369,108) (124 mg, 0.46 mmol) and KOH (100 mg, 1.77 mmol) in THF/water/MeOH (1:1:1, 9 mL) was stirred at room temperature for 1 hour. The reaction mixture was then concentrated and partitioned between ether and water. Aqueous layer was collected, acidified with 1M HCl solution to pH=3 and extracted with EtOAc (3×5 mL). Combined organic phase was dried with Na$_2$SO$_4$, filtered and concentrated. Crude acid was diluted in thionyl chloride (3 mL) and DMF (1 drop) and stirred at room temperature for 20 min. The reaction mixture was concentrated in vacuo, diluted with THF (3 mL) and cooled to 0° C. a was treated with Et$_3$N (62 mg, 86 L, 0.61 mmol) and amine 178 (120 mg, 0.41 mmol) and stirred at 0° C. for 30 min. The reaction mixture was quenched by the addition of saturated NH$_4$Cl solution and extracted with EtOAc (3×3 mL). Combined organic phase was dried with Na$_2$SO$_4$, filtered and concentrated. Crude product was purified by flash chromatography using 50% EtOAc in hexanes as an eluent, to afford the title compound 346 (111 mg, 52% yield). MS: calc: 521.2; found: 522.3 (M+H)

Step 2: N1-(2-Amino-5-(thiophen-2-yl)phenyl)-N8-phenyloctanediamide (347)

A solution of compound 346 (111 mg, 0.06 mmol) in 2:1 DCM/TFA (3 mL) was stirred at room temperature for 1 hour. The mixture was quenched by addition of saturated NaHCO$_3$ solution and extracted with DCM. Organic phase was dried with Na$_2$SO$_4$, filtered and concentrated. Crude product was purified by flash chromatography using EtOAc as an eluent to afford the title compound 347 (20 mg, 22% yield). $^1$H NMR: (400.2 MHz, CD$_3$OD) δ (ppm): 7.51 (br.s, 2H), 7.38 (s, 1H), 7.16-7.27 (m, 5H), 6.9-7.1 (m, 2H), 6.84 (m, 1H), 2.42 (m, 4H), 1.76 (m, 4H), 1.49 (m, 4H). MS: calc: 421.2; found: 422.2 (M+H)

Example 97

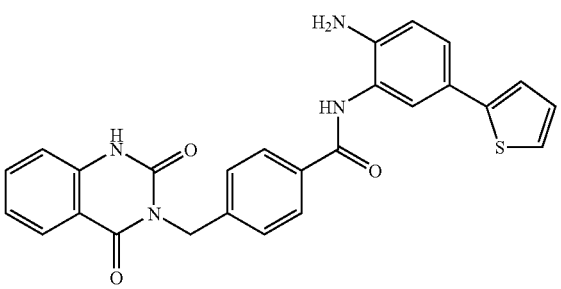

N-(2-Amino-5-(thiophen-2-yl)phenyl)-4-(1,2-dihydro-2,4-dioxoquinazolin-3(4H)-yl)methyl)benzamide (349)

Scheme 77

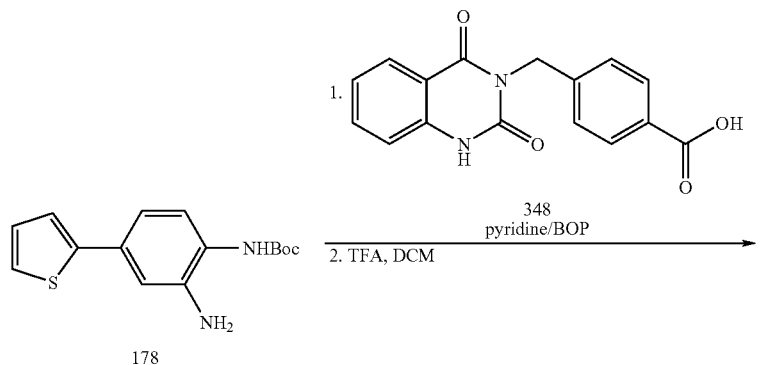

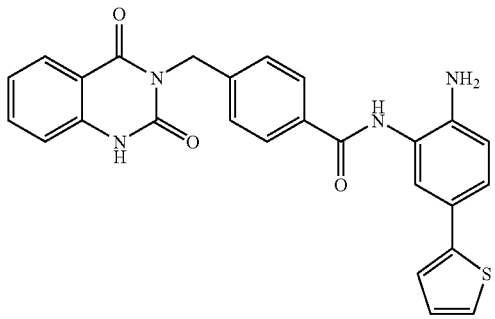

349: Example 97

517

Steps 1 and 2: N-(2-Amino-5-(thiophen-2-yl)phenyl)-4-(1,2-dihydro-2,4-dioxo quinazolin-3(4H)-yl)methyl)benzamide (349)

Following the same procedures as described in Example 52, steps 1 and 2 (scheme 37) but substituting acid 182 for 4-((1,2-dihydro-2,4-dioxoquinazolin-3(4H)-yl)methyl)benzoic acid 348 (WO 03/024448 or JP 2003137866A); the title compound 349 was obtained in 55% yield. $^1$H NMR (DMSO-$d_6$) (ppm): 11.57 (s, 1H), 9.81 (s, 1H), 7.95-7.92 (m, 3H), 7.68 (td, J=7.2, 1.4 Hz, 1H), 7.48 (d, J=1.8 Hz, 1H), 7.42 (d, J=8.2 Hz, 2H), 7.38 (d, J=5.1 Hz, 1H), 7.34 (dd, J=8.2, 2.0 Hz, 1H), 7.27 (d, J=3.3 Hz, 1H), 7.24-7.20 (m, 2H), 7.05 (dd, J=4.9, 3.5 Hz, 1H), 6.89 (d, J=8.4 Hz, 1H), 5.17 (s, 2H). (The NH$_2$ group is missing, overlapped by H$_2$O). MS (m/z): 468.53 (calc) 469.2 (MH+) (found).

518

Example 98

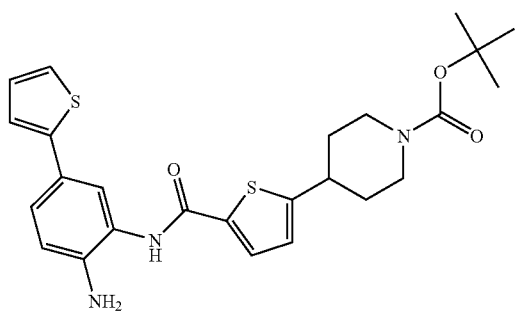

tert-Butyl 4-(5-(2-amino-5-(thiophen-2-yl)phenylcarbamoyl)thiophen-2-yl)piperidine-1-carboxylate (355)

Scheme 78

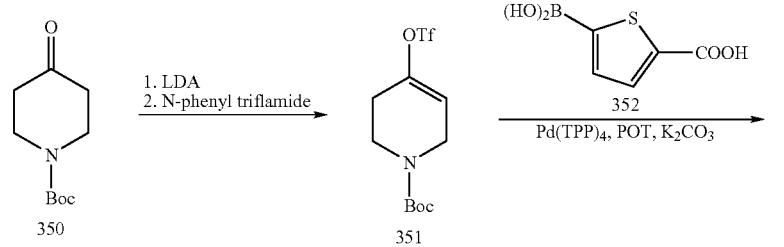

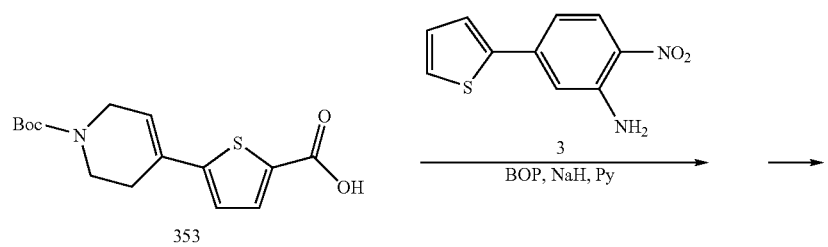

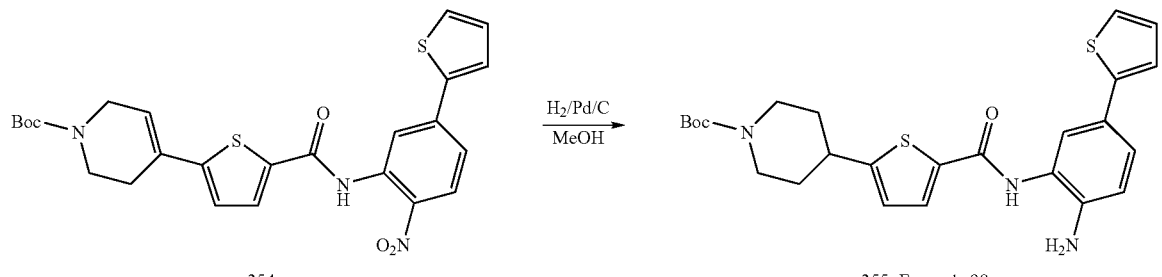

Step 1: 1-(tert-Butoxycarbonyl)-1,2,3,6-tetrahydropyridin-4-yl trifluoromethanesulfonate (351)

Butyl lithium (14.96 mmol, 1.4M, 2.09 mL) and diisopropyl amine (14.96 mmol, 10.68 ml) were added to dry THF at −78° C. to generate LDA in solution. Tert-butyl 4-oxopiperidine-1-carboxylate (350, 2.71 g, 13.6 mmol) in THF (10 mL) was added to the LDA solution. The resulting reaction mixture was warmed to room temperature and allowed to stir for additional 30 minutes, cooled to −78° C. once again, and N-phenyltrifluoromethanesulfonimide (5.1 g, 14.3 mmol) solution in THF was added via syringe. The combined reaction mixture was warmed to room temperature and allowed to stir for 3 additional hours, quenched with water (50 mL) and extracted with ethyl acetate (2×50 mL). The extract was dried over sodium sulfate, evaporated and the residue was purified by flash chromatography on silica gel, eluent 7:1 mixture hexanes-ethyl acetate, to afford the title compound 351 as light yellow oil (2.55 g, 57% yield). $^1$H-NMR (DMSO) δ: 6.00 (s, 1H), 3.97-3.96 (m, 2H), 3.53 (t, J=5.7 Hz, 2H), 2.41-2.40 (m, 2H), 1.41 (s, 9H).

Step 2: 5-(1-(tert-butoxycarbonyl)-1,2,3,6-tetrahydropyridin-4-yl)thiophene-2-carboxylic acid (353)

To a stirred solution of 351 (1.1 g, 3.32 mmol) and 352 (571 mg, 3.32 mmol) in a 2:1 mixture of DME-water (30 mL), was added Pd(PPh$_3$)$_4$ (268 mg, 0.232 mmol), tri-o-tolyl phosphine (71 mg, 0.232 mmol) and potassium carbonate (1.38 g, 9.96 mmol). The reaction mixture was degassed with nitrogen for 5 minutes and stirred at 80° C. for 15 hours, cooled, treated with water (50 mL) and extracted with ethyl acetate (2×40 mL). The organic layer was separated, dried with sodium sulfate and evaporated under reduced pressure to form a residue which was purified by flash chromatography, eluting with a gradient solvent system from 2:1 hexanes-ethyl acetate to 1:1 hexanes-ethyl acetate. A subsequent trituration was performed with 10% ethyl acetate in hexanes for 15 minutes to afford 353 as a beige solid (330 mg, 33% yield). $^1$H NMR: (DMSO) δ 7.60 (d, J=2.2 Hz, 1H), 7.14 (d, J=3.7 Hz, 1H), 6.28-6.29 (m, 1H), 4.00-3.99 (m, 2H), 3.52 (t, J=5.9 Hz, 2H), 2.45-2.46 (m, 2H), 1.42 (s, 9H).

Step 3: tert-Butyl 4-(5-(2-nitro-5-(thiophen-2-yl)phenylcarbamoyl)thiophen-2-yl)-5,6-dihydropyridine-1(2H)-carboxylate (354)

Compound 353 (270 mg, 0.87 mmol), 2-nitro-5-(thiophen-2-yl)benzenamine (3, 193 mg, 0.87 mmol), and BOP (386 mg, 0.87 mmol) were dissolved in dry pyridine (10 mL). Sodium hydride (140 mg, 3.50 mmol) was added and the resulting solution was stirred at room temperature for 2 hours, quenched with glacial acetic acid (1 mL), and the pyridine was removed under reduced pressure. Water (50 mL) was added and the mixture was extracted with ethyl acetate (2×50 mL). The extract was dried with sodium sulphate and evaporated to yield a residue which was triturated with ethyl acetate for 15 minutes, to afford the title compound 354 as a yellow solid (270 mg, 61% yield). $^1$H NMR: (DMSO) δ 10.79 (s, 1H), 8.06-8.04 (m, 2H), 7.86 (d, J=3.9 Hz, 1H), 7.75-7.68 (m, 3H), 7.25-7.20 (m, 2H), 6.32 (s, 1H), 4.04-4.01 (m, 2H), 3.54 (t, J=5.3 Hz, 2H), 1.43 (s, 9H).

Step 4: tert-Butyl 4-(5-(2-amino-5-(thiophen-2-yl)phenylcarbamoyl)thiophen-2-yl)piperidine-1-carboxylate (355)

To a stirred solution of 354 (270 mg, 0.53 mmol) in methanol (25 mL) was added 10% palladium on charcoal (150 mg). The resulting mixture was purged with H$_2$ gas and stirred under a hydrogen atmosphere for 3 days, filtered through a celite pad, evaporated and purified by flash chromatography, eluent 1:1 hexanes-ethyl acetate, to afford the title compound 355 as a white solid (24 mg, 10% yield). $^1$H NMR: (CD$_3$OD) δ 7.73 (d, J=3.3 Hz, 1H), 7.45 (d, J=2.1 Hz, 1H), 7.34 (dd, J=8.2, 2.2 Hz, 1H), 7.23-7.19 (m, 2H), 7.01 (dd, J=4.7, 3.7 Hz, 1H), 6.96 (d, J=3.9 Hz, 1H), 6.88 (d, J=8.1 Hz, 1H), 4.17 (d, J=13.1 Hz, 2H), 3.00-2.90 (m, 2H), 2.04 (d, J=12.1 Hz, 2H), 1.60-1.54 (m, 2H).

Example 99

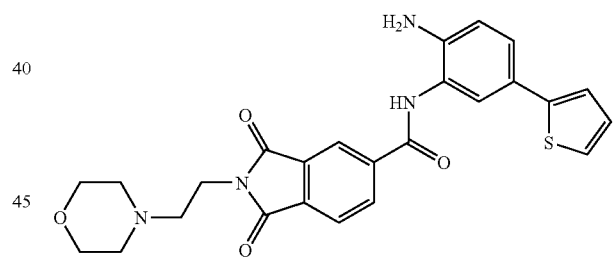

N-(2-amino-5-(thiophen-2-yl)phenyl)-2-(2-morpholinoethyl)-1,3-dioxoisoindoline-5-carboxamide (358)

Scheme 79

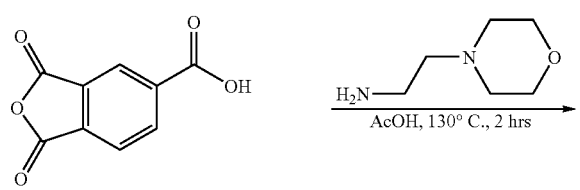

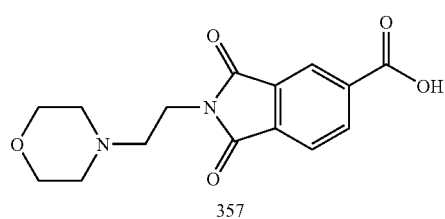

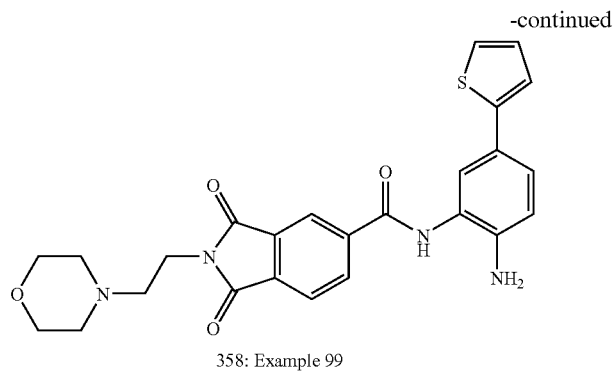

358: Example 99

Step 1: 2-(2-Morpholinoethyl)-1,3-dioxoisoindoline-5-carboxylic acid (357)

1,2,4-Benzenetricarboxylic anhydride (356, 0.487 g, 2.53 mmol) and 4-(2-aminoethyl)morpholine (0.33 g, 2.53 mmol) were allowed to stir 2 hours at 130° C. in acetic acid (10 mL). The reaction mixture was then cooled to room temperature and the precipitated solid was collected by filtration, washed with $H_2O$ and dried under vacuum, to afford title compound 357 as a white powder (0.63 g, 82% yield). $^1H$ NMR (DMSO) δ (ppm): 8.26 (dd, J=7.6, 1.4 Hz, 1H), 8.15 (dd, J=1.4, 0.6 Hz, 1H), 7.92 (dd, J=7.6, 0.6 Hz, 1H), 3.73 (t, J=6.5 Hz, 2H), 3.50 (t, J=4.5 Hz, 4H), 2.59 (t, J=6.5 Hz, 2H), 2.47 (overlapped with DMSO, 4H). MS: 304.3 (calc), 305.1 (obs).

Step 2 and 3: N-(2-Amino-5-(thiophen-2-yl)phenyl)-2-(2-morpholinoethyl)-1,3-dioxoisoindoline-5-carboxamide (358)

Following the same procedures outlined in Example 71a, steps 2 and 3 (scheme 54) but substituting 3,4-dimethoxybenzoic acid (257a) for compound 357, the title compound 358 was obtained in 18% yield (over the two steps). $^1H$ NMR: (DMSO) δ (ppm): 10.03 (s, 1H), 8.45 (s, 1H), 8.38 (d, J=7.6 Hz, 1H), 7.99 (d, J=7.6 Hz, 1H), 7.44 (d, J=2.0 Hz, 1H), 7.32 (dd, J=11.9, 5.1 Hz, 1H), 7.28 (d, J=2.0 Hz, 1H), 7.03 (d, J=4.9 Hz, 1H), 6.78 (d, J=8.2 Hz, 1H), 5.27 (s, 2H), 3.73 (t, J=6.3 Hz, 2H), 3.48 (m, 4H), 2.54 (t, J=6.5 Hz, 2H), 2.41 (m, 4H). MS: 476.15 (calc), 477.2 (obs).

Example 100

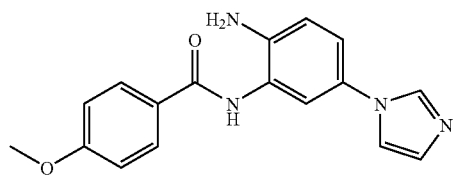

N-(2-amino-5-(1H-imidazol-1-yl)phenyl)-4-methoxybenzamide (361)

Scheme 80

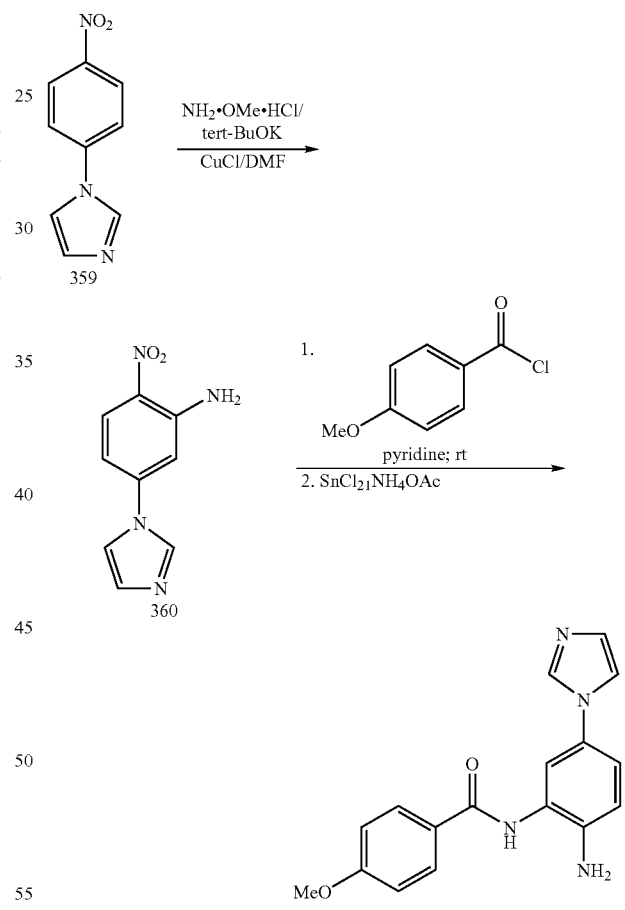

361: Example 100

Step 1: 5-(1H-imidazol-1-yl)-2-nitrobenzenamine (360)

Following the same procedure as described in Example 1, step 1 (scheme 1) but substituting 1-bromo-4-nitrobenzene (1) for 1-(4-nitrophenyl)-1H-imidazole (359), title compound 360 was obtained in 32% yield. MS: 204.06 (calc), 205.1 (found).

Steps 2 and 3: N-(2-amino-5-(1H-imidazol-1-yl) phenyl)-4-methoxybenzamide (361)

Following the same procedure as described in Example 19, steps 3 and 4 (scheme 17) but substituting compound 91 for compound 360, the title compound 361 was obtained in 10.5% yield (over 2 steps). $^1$H NMR: (DMSO) δ (ppm): 9.62 (s, 1H), 7.96 (d, J=9.0 Hz, 3H), 7.52 (m, 1H), 7.42 (d, J=2.5 Hz, 1H), 7.19 (dd, J=8.6, 2.5 Hz, 1H), 7.04 (d, J=8.8 Hz, 2H), 7.03 (s, 1H), 6.85 (d, J=8.4 Hz, 1H), 5.11 (s, 2H), 3.83 (s, 3H). MS: 308.13 (calc), 309.2 (obs).

Pharmaceutical Compositions

In a second aspect, the invention provides pharmaceutical compositions comprising an inhibitor of histone deacetylase according to the invention and a pharmaceutically acceptable carrier, excipient, or diluent. Compounds of the invention may be formulated by any method well known in the art and may be prepared for administration by any route, including, without limitation, parenteral, oral, sublingual, transdermal, topical, intranasal, intratracheal, or intrarectal. In certain preferred embodiments, compounds of the invention are administered intravenously in a hospital setting. In certain other preferred embodiments, administration may preferably be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term pharmaceutically acceptable salts refers to salts that retain the desired biological activity of the above-identified compounds and exhibit minimal or no undesired toxicological effects. Examples of such salts include, but are not limited to acid addition salts formed with inorganic acids (for Example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z−, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate). As used herein, the term "salt" is also meant to encompass complexes, such as with an alkaline metal or an alkaline earth metal.

The active compound is included in the pharmaceutically acceptable carrier or diluent in an amount sufficient to deliver to a patient a therapeutically effective amount without causing serious toxic effects in the patient treated. A preferred dose of the active compound for all of the above-mentioned conditions is in the range from about 0.01 to 300 mg/kg, preferably 0.1 to 100 mg/kg per day, more generally 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

Inhibition of Histone Deacetylase

In a third aspect, the invention provides a method of inhibiting histone deacetylase in a cell, comprising contacting a cell in which inhibition of histone deacetylase is desired with an inhibitor of histone deacetylase according to the invention. Because compounds of the invention inhibit histone deacetylase, they are useful research tools for in vitro study histone deacetylases and their role in biological processes. In addition, the compounds of the invention selectively inhibit certain isoforms of HDAC.

Measurement of the enzymatic activity of a histone deacetylase can be achieved using known methodologies. For Example, Yoshida et al., J. Biol. Chem., 265: 17174-17179 (1990), describes the assessment of histone deacetylase enzymatic activity by the detection of acetylated histones in trichostatin A treated cells. Taunton et al., Science, 272: 408-411 (1996), similarly describes methods to measure histone deacetylase enzymatic activity using endogenous and recombinant HDAC-1.

In some preferred embodiments, the histone deacetylase inhibitor interacts with and reduces the activity of all histone deacetylases in the cell. In some other preferred embodiments according to this aspect of the invention, the histone deacetylase inhibitor interacts with and reduces the activity of fewer than all histone deacetylases in the cell. In certain preferred embodiments, the inhibitor interacts with and reduces the activity of one histone deacetylase (e.g., HDAC-1), but does not interact with or reduce the activities of other histone deacetylases (e.g., HDAC-2, HDAC-3, HDAC-4, HDAC-5, HDAC-6, HDAC-7, and HDAC-8). As discussed below, certain particularly preferred histone deacetylase inhibitors are those that interact with, and reduce the enzymatic activity of, a histone deacetylase that is involved in tumorigenesis. Certain other preferred histone deacetylase inhibitors interact with and reduce the enzymatic activity of a fungal histone deacetylase.

Preferably, the method according to the third aspect of the invention causes an inhibition of cell proliferation of the contacted cells. The phrase "inhibiting cell proliferation" is used to denote an ability of an inhibitor of histone deacetylase to retard the growth of cells contacted with the inhibitor as compared to cells not contacted. An assessment of cell proliferation can be made by counting contacted and non-contacted cells using a Coulter Cell Counter (Coulter, Miami, Fla.) or a hemacytometer. Where the cells are in a solid growth (e.g., a solid tumor or organ), such an assessment of cell proliferation can be made by measuring the growth with calipers and comparing the size of the growth of contacted cells with non-contacted cells.

Preferably, growth of cells contacted with the inhibitor is retarded by at least 50% as compared to growth of non-contacted cells. More preferably, cell proliferation is inhibited by 100% (i.e., the contacted cells do not increase in number). Most preferably, the phrase "inhibiting cell proliferation" includes a reduction in the number or size of contacted cells, as compared to non-contacted cells. Thus, an inhibitor of histone deacetylase according to the invention that inhibits cell proliferation in a contacted cell may induce the contacted cell to undergo growth retardation, to undergo growth arrest, to undergo programmed cell death (i.e., to apoptose), or to undergo necrotic cell death.

The cell proliferation inhibiting ability of the histone deacetylase inhibitors according to the invention allows the synchronization of a population of asynchronously growing cells. For Example, the histone deacetylase inhibitors of the invention may be used to arrest a population of non-neoplastic cells grown in vitro in the G1 or G2 phase of the cell cycle. Such synchronization allows, for Example, the identification of gene and/or gene products expressed during the G1 or G2 phase of the cell cycle. Such synchronization of cultured cells may also be useful for testing the efficacy of a new transfection protocol, where transfection efficiency varies and is dependent upon the particular cell cycle phase of the cell to be transfected. Use of the histone deacetylase inhibitors of the invention allows the synchronization of a population of cells, thereby aiding detection of enhanced transfection efficiency.

In some preferred embodiments, the contacted cell is a neoplastic cell. The term "neoplastic cell" is used to denote a cell that shows aberrant cell growth. Preferably, the aberrant cell growth of a neoplastic cell is increased cell growth. A neoplastic cell may be a hyperplastic cell, a cell that shows a lack of contact inhibition of growth in vitro, a benign tumor cell that is incapable of metastasis in vivo, or a cancer cell that is capable of metastasis in vivo and that may recur after attempted removal. The term "tumorigenesis" is used to denote the induction of cell proliferation that leads to the development of a neoplastic growth. In some embodiments, the histone deacetylase inhibitor induces cell differentiation in the contacted cell. Thus, a neoplastic cell, when contacted with an inhibitor of histone deacetylase may be induced to differentiate, resulting in the production of a non-neoplastic daughter cell that is phylogenetically more advanced than the contacted cell.

In some preferred embodiments, in neoplastic cells, antitumor activity of an HDAC inhibitor can be assessed by analyzing expression of certain tumor suppressor genes, such as $p21^{WAF1/Cip1}$. HDAC inhibitors induce $p21^{WAF1/Cip1}$ expression in human cancer cells, which leads to retardation of cell proliferation.

In some preferred embodiments, the contacted cell is in an animal. Thus, the invention provides a method for treating a cell proliferative disease or condition in an animal, comprising administering to an animal in need of such treatment a therapeutically effective amount of a histone deacetylase inhibitor of the invention. Preferably, the animal is a mammal, more preferably a domesticated mammal. Most preferably, the animal is a human.

The term "cell proliferative disease or condition" is meant to refer to any condition characterized by aberrant cell growth, preferably abnormally increased cellular proliferation. Examples of such cell proliferative diseases or conditions include, but are not limited to, cancer, restenosis, and psoriasis. In particularly preferred embodiments, the invention provides a method for inhibiting neoplastic cell proliferation in an animal comprising administering to an animal having at least one neoplastic cell present in its body a therapeutically effective amount of a histone deacetylase inhibitor of the invention.

It is contemplated that some compounds of the invention have inhibitory activity against a histone deacetylase from a protozoal source. Thus, the invention also provides a method for treating or preventing a protozoal disease or infection, comprising administering to an animal in need of such treatment a therapeutically effective amount of a histone deacetylase inhibitor of the invention. Preferably the animal is a mammal, more preferably a human. Preferably, the histone deacetylase inhibitor used according to this embodiment of the invention inhibits a protozoal histone deacetylase to a greater extent than it inhibits mammalian histone deacetylases, particularly human histone deacetylases.

The present invention further provides a method for treating a fungal disease or infection comprising administering to an animal in need of such treatment a therapeutically effective amount of a histone deacetylase inhibitor of the invention. Preferably the animal is a mammal, more preferably a human. Preferably, the histone deacetylase inhibitor used according to this embodiment of the invention inhibits a fungal histone deacetylase to a greater extent than it inhibits mammalian histone deacetylases, particularly human histone deacetylases.

The term "therapeutically effective amount" is meant to denote a dosage sufficient to cause inhibition of histone deacetylase activity in the cells of the subject, or a dosage sufficient to inhibit cell proliferation or to induce cell differentiation in the subject. Administration may be by any route, including, without limitation, parenteral, oral, sublingual, transdermal, topical, intranasal, intratracheal, or intrarectal. In certain particularly preferred embodiments, compounds of the invention are administered intravenously in a hospital setting. In certain other preferred embodiments, administration may preferably be by the oral route.

When administered systemically, the histone deacetylase inhibitor is preferably administered at a sufficient dosage to attain a blood level of the inhibitor from about 0.01 μM to about 100 μM, more preferably from about 0.05 μM to about 50 μM, still more preferably from about 0.1 μM to about 25 μM, and still yet more preferably from about 0.5 μM to about 25 μM. For localized administration, much lower concentrations than this may be effective, and much higher concentrations may be tolerated. One of skill in the art will appreciate that the dosage of histone deacetylase inhibitor necessary to produce a therapeutic effect may vary considerably depending on the tissue, organ, or the particular animal or patient to be treated.

In certain preferred embodiments of the third aspect of the invention, the method further comprises contacting the cell with an antisense oligonucleotide that inhibits the expression of a histone deacetylase. The combined use of a nucleic acid level inhibitor (e.g., antisense oligonucleotide) and a protein level inhibitor (i.e., inhibitor of histone deacetylase enzyme activity) results in an improved inhibitory effect, thereby reducing the amounts of the inhibitors required to obtain a given inhibitory effect as compared to the amounts necessary when either is used individually. The antisense oligonucleotides according to this aspect of the invention are complementary to regions of RNA or double-stranded DNA that encode HDAC-1, HDAC-2, HDAC-3, HDAC-4, HDAC-5, HDAC-6, HDAC-7, and/or HDAC-8 (see e.g., GenBank Accession Number U50079 for HDAC-1, GenBank Accession Number U31814 for HDAC-2, and GenBank Accession Number U75697 for HDAC-3).

For purposes of the invention, the term "oligonucleotide" includes polymers of two or more deoxyribonucleosides, ribonucleosides, or 2-substituted ribonucleoside residues, or any combination thereof. Preferably, such oligonucleotides have from about 6 to about 100 nucleoside residues, more preferably from about 8 to about 50 nucleoside residues, and most preferably from about 12 to about 30 nucleoside residues. The nucleoside residues may be coupled to each other by any of the numerous known internucleoside linkages.

Such internucleoside linkages include without limitation phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate and sulfone internucleoside linkages. In certain preferred embodiments, these internucleoside linkages may be phosphodiester, phosphotriester, phosphorothioate, or phosphoramidate linkages, or combinations thereof. The term oligonucleotide also encompasses such polymers having chemically modified bases or sugars and/or having additional substituents, including without limitation lipophilic groups, intercalating agents, diamines and adamantane.

For purposes of the invention the term "2'-substituted ribonucleoside" includes ribonucleosides in which the hydroxyl group at the 2' position of the pentose moiety is substituted to produce a 2'-0-substituted ribonucleoside. Preferably, such substitution is with a lower alkyl group containing 1-6 saturated or unsaturated carbon atoms, or with an aryl or alkyl group having 2-6 carbon atoms, wherein such alkyl, aryl or alkyl group may be unsubstituted or may be substituted, e.g., with halo, hydroxy, trifluoromethyl, cyano, nitro, acyl, acyloxy, alkoxy, carboxyl, carbalkoxyl, or amino groups. The term "2'-substituted ribonucleoside" also includes ribonucleosides in which the 2'-hydroxyl group is replaced with an amino group or with a halo group, preferably fluoro.

Particularly preferred antisense oligonucleotides utilized in this aspect of the invention include chimeric oligonucleotides and hybrid oligonucleotides.

For purposes of the invention, a "chimeric oligonucleotide" refers to an oligonucleotide having more than one type of internucleoside linkage. One preferred Example of such a chimeric oligonucleotide is a chimeric oligonucleotide comprising a phosphorothioate, phosphodiester or phosphorodithioate region, preferably comprising from about 2 to about 12 nucleotides, and an alkylphosphonate or alkylphosphonothioate region (see e.g., Pederson et al. U.S. Pat. Nos. 5,635,377 and 5,366,878). Preferably, such chimeric oligonucleotides contain at least three consecutive internucleoside linkages selected from phosphodiester and phosphorothioate linkages, or combinations thereof.

For purposes of the invention, a "hybrid oligonucleotide" refers to an oligonucleotide having more than one type of nucleoside. One preferred Example of such a hybrid oligonucleotide comprises a ribonucleotide or 2'-substituted ribonucleotide region, preferably comprising from about 2 to about 12 2'-substituted nucleotides, and a deoxyribonucleotide region. Preferably, such a hybrid oligonucleotide contains at least three consecutive deoxyribonucleosides and also contains ribonucleosides, 2'-substituted ribonucleosides, preferably 2'-0-substituted ribonucleosides, or combinations thereof (see e.g., Metelev and Agrawal, U.S. Pat. No. 5,652, 355).

The exact nucleotide sequence and chemical structure of an antisense oligonucleotide utilized in the invention can be varied, so long as the oligonucleotide retains its ability to inhibit expression of the gene of interest. This is readily determined by testing whether the particular antisense oligonucleotide is active. Useful assays for this purpose include quantitating the mRNA encoding a product of the gene, a Western blotting analysis assay for the product of the gene, an activity assay for an enzymatically active gene product, or a soft agar growth assay, or a reporter gene construct assay, or an in vivo tumor growth assay, all of which are described in detail in this specification or in Ramchandani et al. (1997) Proc. Natl. Acad. Sci. USA 94: 684-689.

Antisense oligonucleotides utilized in the invention may conveniently be synthesized on a suitable solid support using well known chemical approaches, including H-phosphonate chemistry, phosphoramidite chemistry, or a combination of H-phosphonate chemistry and phosphoramidite chemistry (i.e., H-phosphonate chemistry for some cycles and phosphoramidite chemistry for other cycles). Suitable solid supports include any of the standard solid supports used for solid phase oligonucleotide synthesis, such as controlled-pore glass (CPG) (see, e.g., Pon, R. T. (1993) Methods in Molec. Biol. 20: 465-496).

Particularly preferred oligonucleotides have nucleotide sequences of from about 13 to about 35 nucleotides which include the nucleotide sequences shown in Table 4. Yet additional particularly preferred oligonucleotides have nucleotide sequences of from about 15 to about 26 nucleotides of the nucleotide sequences shown in Table 1.

TABLE 4

| Oligo | Target | Accession Number | Nucleotide Position | Sequence | position within Gene | Seq ID No. |
|---|---|---|---|---|---|---|
| HDAC1 AS1 | Human HDAC1 | U50079 | 1585-1604 | 5'-GAAACGTGAGGGACTCAGCA-3' | 3'-UTR | Seq ID No: 1 |
| HDAC1 AS2 | Human HDAC1 | U50079 | 1565-1584 | 5'-GGAAGCCAGAGCTGGAGAGG-3' | 3'-UTR | Seq ID No: 2 |
| HDAC1 MM | Human HDAC1 | U50079 | 1585-1604 | 5'-GTTAGGTGAGGCACTGAGGA-3' | 3'-UTR | Seq ID No: 3 |
| HDAC2 AS | Human HDAC2 | U31814 | 1643-1622 | 5'-GCTGAGCTGTTCTGATTTGG-3' | 3'-UTR | Seq ID No: 4 |
| HDAC2 MM | Human HDAC2 | U31814 | 1643-1622 | 5'-CGTGAGCACTTCTCATTTCC-3' | 3'-UTR | Seq ID No: 5 |
| HDAC3 AS | Human HDAC3 | AF039703 | 1276-1295 | 5'-CGCTTTCCTTGTCATTGACA-3' | 3'-UTR | Seq ID No: 6 |
| HDAC3 MM | Human HDAC3 | AF039703 | 1276-1295 | 5'-GCCTTTCCTACTCATTGTGT-3' | 3'-UTR | Seq ID No: 7 |
| HDAC4 AS1 | Human HDAC4 | AB006626 | 514-33 | 5'-GCTGCCTGCCGTGCCCACCC-3' | 5'-UTR | Seq ID No: 8 |
| HDAC4 MM1 | Human HDAC4 | AB006626 | 514-33 | 5'-CGTGCCTGCGCTGCCCACGG-3' | 5'-UTR | Seq ID No: 9 |
| HDAC4 AS2 | Human HDAC4 | AB006626 | 7710-29 | 5'-TACAGTCCATGCAACCTCCA-3' | 3'-UTR | Seq ID No: 10 |
| HDAC4 MM4 | Human HDAC4 | AB006626 | 7710-29 | 5'-ATCAGTCCAACCAACCTCGT-3' | 3'-UTR | Seq ID No: 11 |
| HDAC5 AS | Human HDAC5 | AF039691 | 2663-2682 | 5'-CTTCGGTCTCACCTGCTTGG-3' | 3'-UTR | Seq ID No: 12 |
| HDAC6 AS | Human HDAC6 | AJ011972 | 3791-3810 | 5'-CAGGCTGGAATGAGCTACAG-3' | 3'-UTR | Seq ID No: 13 |
| HDAC6 MM | Human HDAC6 | AJ011972 | 3791-3810 | 5'-GACGCTGCAATCAGGTAGAC-3' | 3'-UTR | Seq ID No: 14 |
| HDAC7 AS | Human HDAC7 | AF239243 | 2896-2915 | 5'-CTTCAGCCAGGATGCCCACA-3' | 3'-UTR | Seq ID No: 15 |

TABLE 4-continued

| Oligo | Target | Accession Number | Nucleotide Position | Sequence | position within Gene | Seq ID No. |
|---|---|---|---|---|---|---|
| HDAC8 AS1 | Human HDAC8 | AF230097 | 51-70 | 5'-CTCCGGCTCCTCCATCTTCC-3' | 5'-UTR | Seq ID No: 16 |
| HDAC8 AS2 | Human HDAC8 | AF230097 | 1328-1347 | 5'-AGCCAGCTGCCACTTGATGC-3' | 3'-UTR | Seq ID No: 17 |

The following Examples are intended to further illustrate certain preferred embodiments of the invention, and are not intended to limit the scope of the invention.

ASSAY EXAMPLES

Assay Example 1

Inhibition of Histone Deacetylase Enzymatic (HDAC-1) Activity

The following protocol was used to assay the compounds of the invention. In the assay, the buffer used was 25 mM HEPES, pH 8.0, 137 mM NaCl, 2.7 mM KCl, 1 mM $MgCl_2$ and the substrate was Boc-Lys(Ac)-AMC in a 50 mM stock solution in DMSO. The enzyme stock solution was 4.08 µg/mL in buffer.

The compounds were pre-incubated (2 µl in DMSO diluted to 13 µl in buffer for transfer to assay plate) with enzyme (20 µl of 4.08 µg/ml) for 10 minutes at room temperature (35 µl pre-incubation volume). The mixture was pre-incubated for 5 minutes at room temperature. The reaction was started by bringing the temperature to 37° C. and adding 16 µl substrate. Total reaction volume was 501. The reaction was stopped after 20 minutes by addition of 50 µl developer, prepared as directed by Biomol (Fluor-de-Lys developer, Cat. # KI-105). A plate was incubated in the dark for 10 minutes at room temperature before reading ($\lambda_{Ex}$=360 nm, $\lambda_{Em}$=470 nm, Cut-off filter at 435 nm).

TABLE 5

INHIBITION OF HISTONE DEACETYLASE*

| Cpd | Name | HDAC-1 (µM) |
|---|---|---|
| 6 | N-[2-amino-5-(2-thienyl)phenyl]-4-{[(3,4-dimethoxyphenyl)amino]methyl}benzamide | a |
| 12 | N-[2-amino-5-(2-thienyl)phenyl]-4-{[(3-fluoro-4-methoxyphenyl)amino]methyl}benzamide | a |
| 23 | N-[2-amino-5-(2-thienyl)phenyl]-1-(3,4,5-trimethoxybenzyl) indoline-6-carboxamide | a |
| 29 | N-[2-amino-5-(2-thienyl)phenyl]-5-{[(3,4,5-trimethoxyphenyl)amino]methyl}-1-benzofuran-2-carboxamide | a |
| 43 | N-[2-amino-5-(2-thienyl)phenyl]-4-{[(4-pyridin-3-ylpyrimidin-2-yl)amino]methyl}benzamide | a |
| 50 | N-[2-amino-5-(2-thienyl)phenyl]-4-[({6-[2-(dimethylamino)ethoxy]-1H-benzimidazol-2-yl}thio)methyl]benzamide | a |
| 67 | (2E)trans-N-[2-amino-5-(2-thienyl)phenyl]-3-(4-{[(3,4,5-trimethoxyphenyl)amino]methyl}phenyl)acrylamide | a |
| 90 | N-[2-amino-5-(3-thienyl)phenyl]-4-{[(3,4-dimethoxyphenyl)amino]methyl}benzamide | a |
| 91 | N-[2-amino-5-(3-furanyl)phenyl]-4-{[(3,4-dimethoxyphenyl)amino]methyl}benzamide | a |
| 92 | N-[2-amino-5-(phenyl)phenyl]-4-{[(3,4-dimethoxyphenyl)amino]methyl}benzamide | a |
| B | N-(2-amino-4,5-difluorophenyl)-4-{[(3,4-dimethoxyphenyl)amino]methyl}benzamide | b |
| 5 | 4-[(3,4-dimethoxy-phenylamino)-methyl]-N-(2-nitro-5-thiophen-2-yl-benzamide | c |
| 15 | 4-[(3,4-dimethoxy-phenylamino)-methyl]-N-(2-nitro-4-thiophen-2-yl-phenyl)-benzamide | c |
| 16 | N-[2-amino-4-(2-thienyl)phenyl]-4-{[(3,4-dimethoxyphenyl)amino]methyl}benzamide | b |
| 18 | N-(2-amino-4-bromophenyl)-4-{[(3,4-dimethoxyphenyl)amino]methyl}benzamide | b |
| 32 | 4-{[(3,4-dimethoxyphenyl)amino]methyl}-N-[3-(2-thienyl)phenyl]benzamide | c |
| 33 | 4-{[(3,4-dimethoxyphenyl)amino]methyl}-N-[3-flurophenyl]benzamide | a |
| 34 | N-(3-amin0-2-naphthyl)-4-{[(3,4-dimethoxyphenyl)amino]methyl}benzamide | c |
| 35 | N-(2-amino-5-chloro-4-fluorophenyl)-4-{[(3,4-dimethoxyphenyl)amino]methyl}benzamide | b |
| 36 | N-(2-amino-4,5-dichlorophenyl)-4-{[(3,4-dimethoxyphenyl)amino]methyl}benzamide | b |
| 61 | N-(4-amino-5-phenyl-3-thienyl)-4-{[(3,4-dimethoxyphenyl)amino]methyl}benzamide | c |
| 62 | N-(3-amino-2,2'-bithien-4-yl)-4-{[(3,4-dimethoxyphenyl)amino]methyl}benzamide | c |
| 68 | N-(2-amino-5-butylphenyl)-4-{[(3,4-dimethoxyphenyl)amino]methyl}benzamide | b |
| 69 | N-(2-amino-5-butylphenyl)-4-methylbenzamide | b |
| 71 | N-(2-amino-4-butylphenyl)-4-methylbenzamide | c |
| 76 | N-[2-amino-5-(3-hydroxyprop-1-yn-1-yl)phenyl]-4-{[(3,4-dimethoxyphenyl)amino]methyl}benzamide | a |
| 87 | N-(2-amino-5-bromophenyl)-4-{[(3,4-dimethoxyphenyl)amino]methyl}benzamide | b |
| 88 | N-{2-amino-5-[(1E)-3-amino-3-oxoprop-1-en-1-yl]phenyl}-4-{[(3,4-dimethoxyphenyl)amino]methyl}benzamide | b |
| 93 | N-[2-amino-5-(trifluoromethyl)phenyl]-4-{[(3,4-dimethoxyphenyl)amino]methyl}benzamide; | d |
| 94 | N-[2,6-diaminophenyl]-4-{[(3,4-dimethoxyphenyl)amino]methyl}benzamide | b |

*data above the bold line is for compounds having a planar ring structure para to the anilinyl amino (i.e., compounds of the invention); cells with two symbols are for results from two measurements.

Unless specified otherwise, in all the tables in this specification:

a<1; 1≦b≦20; c≧20; d=9999

Tables 6A and 6b below display comparative data for the compounds of the invention demonstrating the increased HDAC-1 inhibitory activity resulting from incorporating a planar substituent.

TABLE 6A

| Compound | STRUCTURE | HDAC-1 activity (μm) |
|---|---|---|
| AAA | MeO-, MeO- phenyl-NH-CH2-phenyl-C(O)NH-(2-aminophenyl) | a |
| A | MeO-, MeO- phenyl-NH-CH2-phenyl-C(O)NH-(2-amino-5-CF3-phenyl) | b |
| 87 | MeO-, MeO- phenyl-NH-CH2-phenyl-C(O)NH-(2-amino-5-Br-phenyl) | b |
| 6 | MeO-, MeO- phenyl-NH-CH2-phenyl-C(O)NH-(2-amino-5-(2-thienyl)-phenyl) | a |

TABLE 6A-continued

| Compound | STRUCTURE | HDAC-1 activity (μm) |
|---|---|---|
| 7 | 3,4-dimethoxyphenyl-NH-CH₂-(4-benzamido)-N-(2-amino-5-(thiophen-3-yl)phenyl) | a |
| 8 | 3,4-dimethoxyphenyl-NH-CH₂-(4-benzamido)-N-(2-amino-5-(furan-3-yl)phenyl) | a |
| 9 | 3,4-dimethoxyphenyl-NH-CH₂-(4-benzamido)-N-(2-amino-5-phenylphenyl) | a |

TABLE 6B

| Compound | STRUCTURE | HDAC-1 Activity (μM) |
|---|---|---|
| XX | 4-(pyridin-3-yl)pyrimidin-2-yl-NH-CH₂-(4-benzamido)-N-(2-aminophenyl) | a |

TABLE 6B-continued

| Compound | STRUCTURE | HDAC-1 Activity (μM) |
|---|---|---|
| 43 | 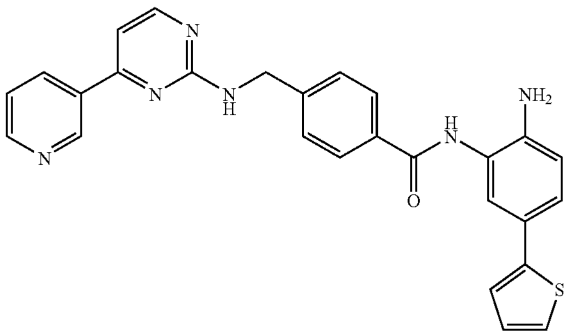 | a |
| AAA | 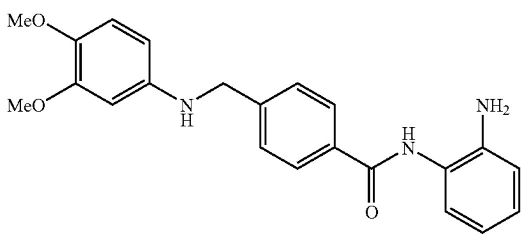 | a |
| 6 | 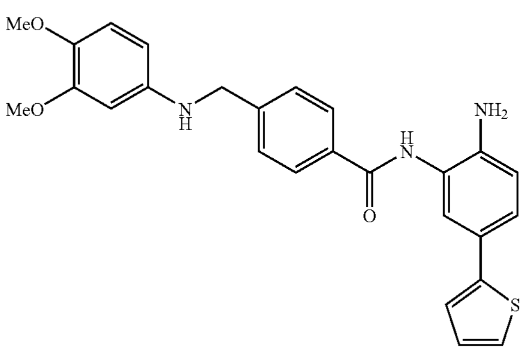 | a |
| QQ | 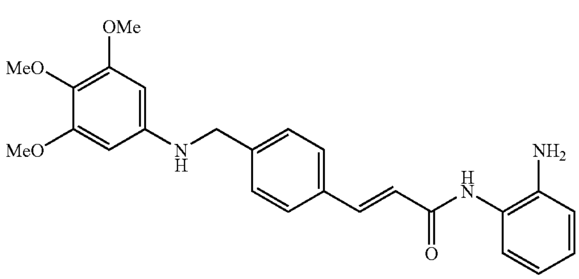 | b |

TABLE 6B-continued

| Compound | STRUCTURE | HDAC-1 Activity (μM) |
|---|---|---|
| 67 | (structure: 3,4,5-trimethoxyphenyl-NH-CH2-phenyl-CH=CH-C(=O)-NH-(2-amino-5-thiophen-2-yl-phenyl)) | a |

Assay Example 2

Figure 2:
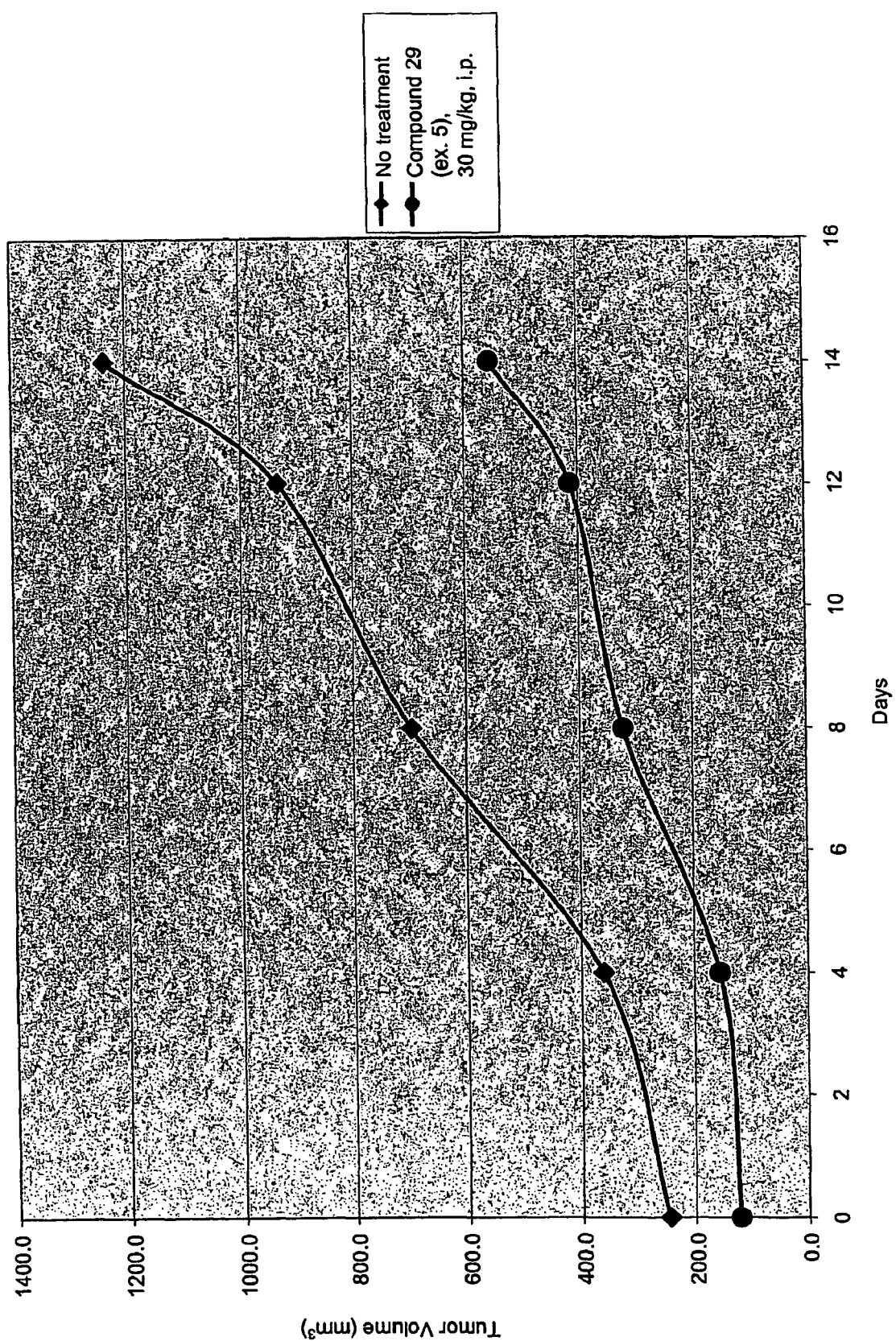
FIG. 2 displays antineoplastic effects of a histone deacetylase inhibitor in A549 human lung cancer using compound 29.
Figure 3:
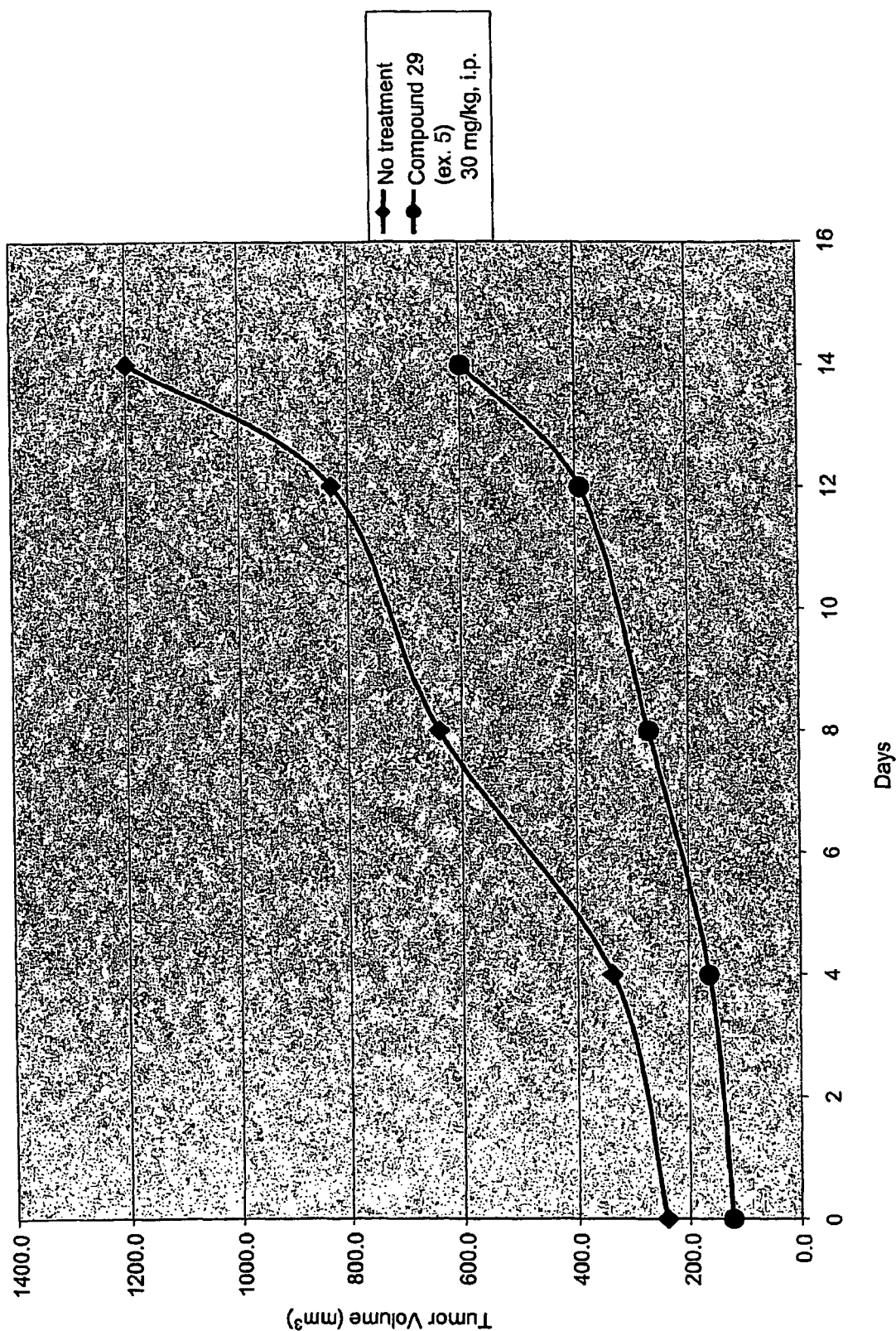
FIG. 3 displays antineoplastic effects of a histone deacetylase inhibitor in SW48 human colorectal cancer using compound 29.
Figure 4:
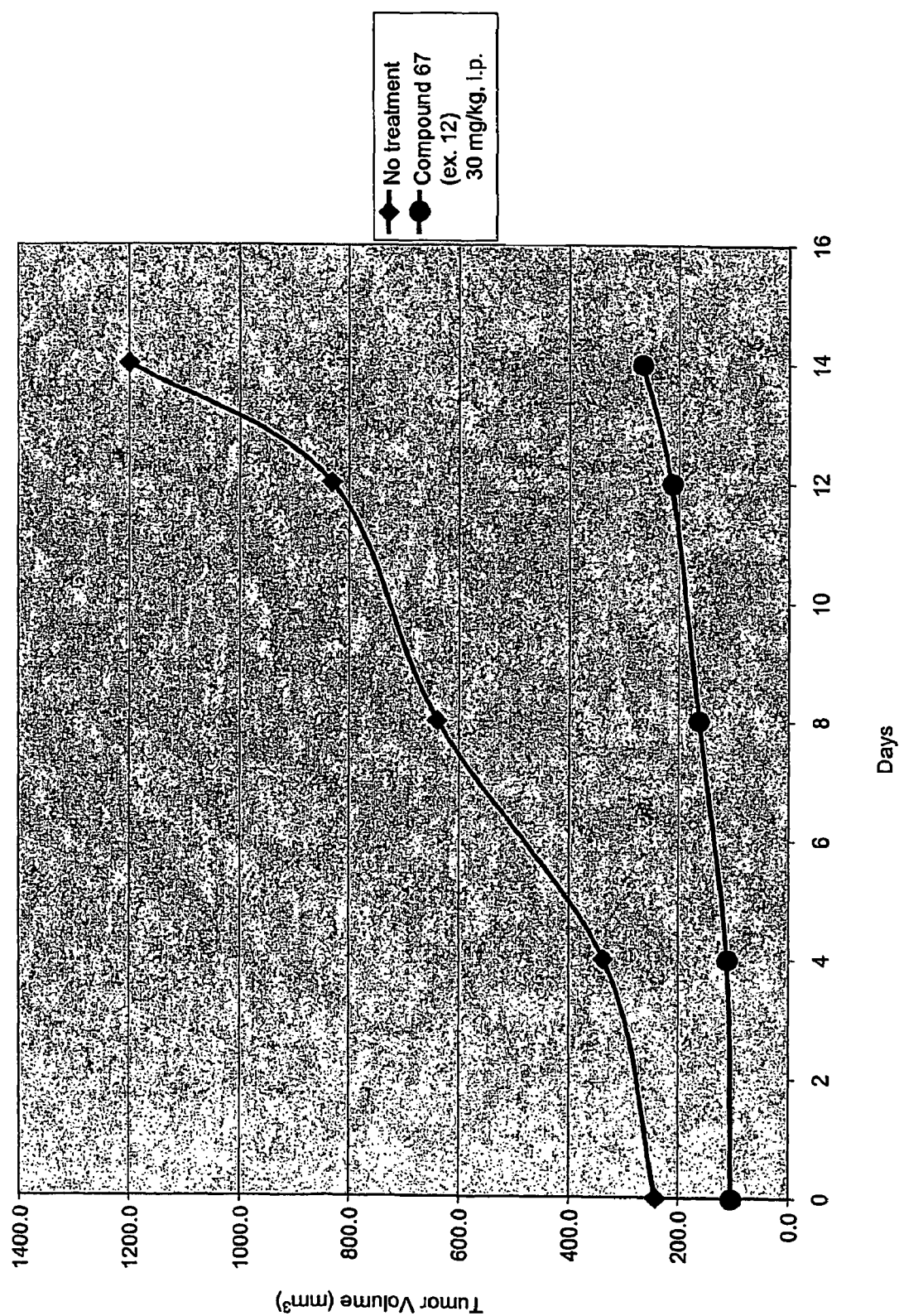
FIG. 4 displays antineoplastic effects of a histone deacetylase inhibitor in W48 human colorectal cancer using compound 67.
Figure 5:
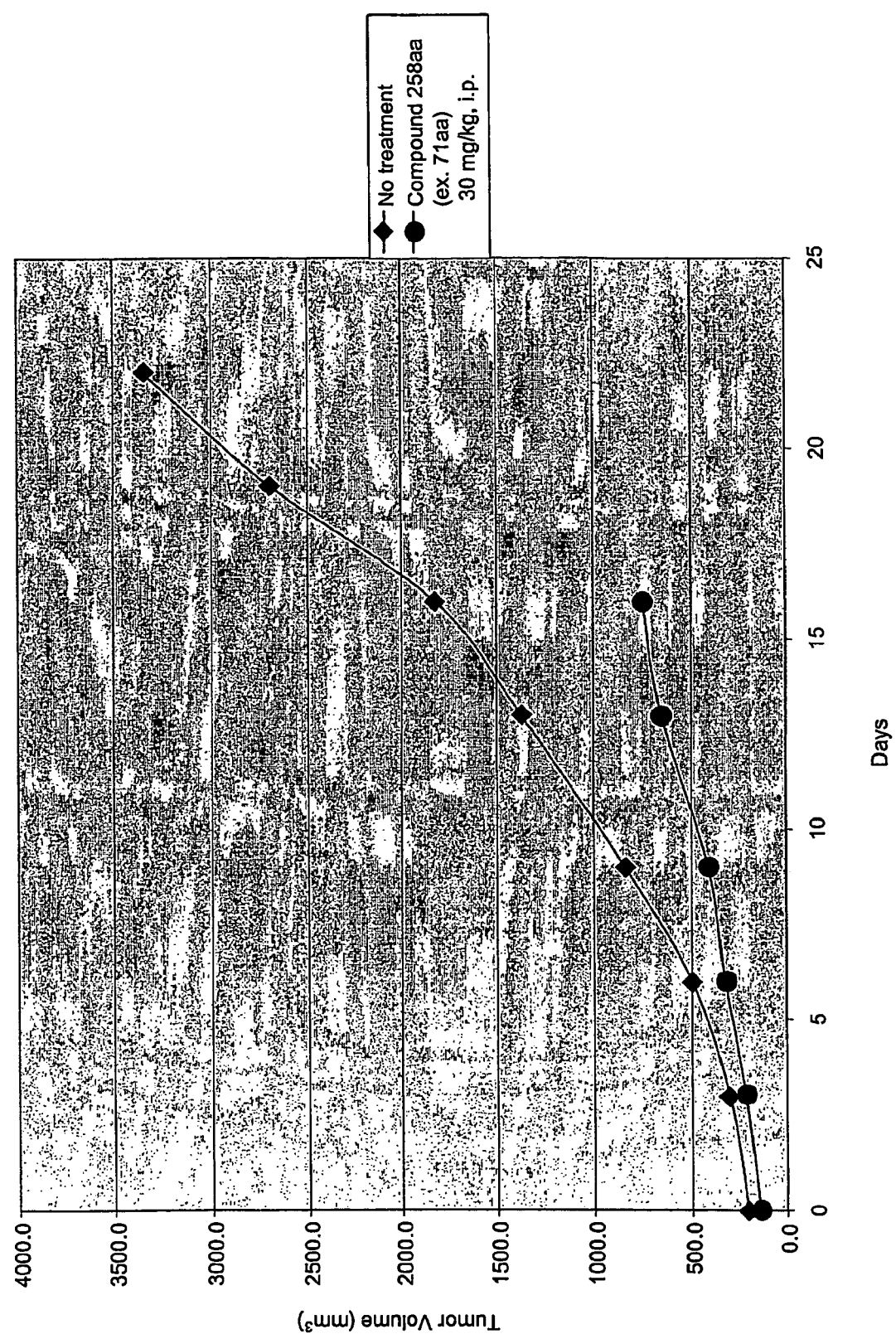
FIG. 5 displays antineoplastic effects of a histone deacetylase inhibitor in A549 human lung cancer using compound 258aa.
Figure 6:
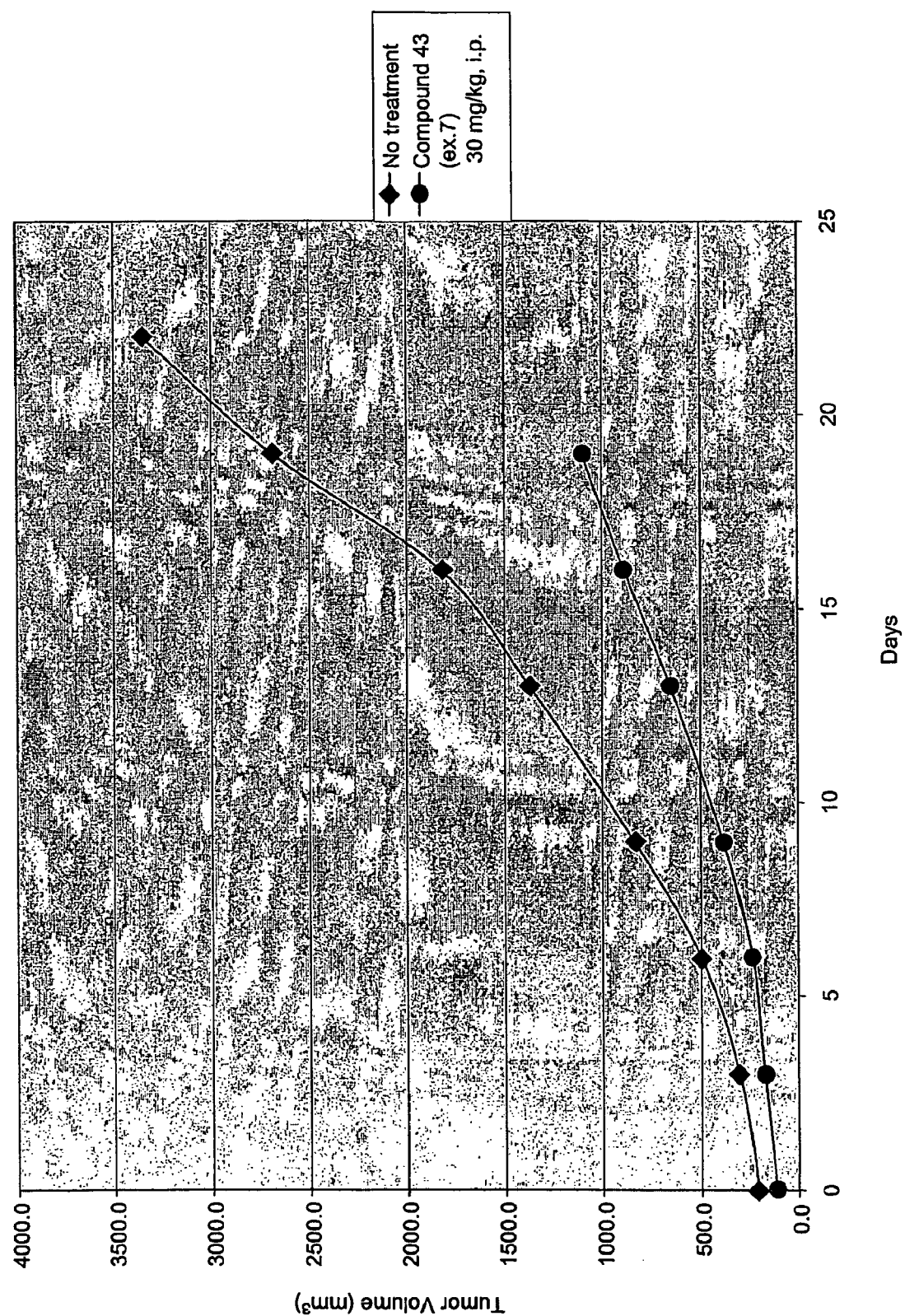
FIG. 6 displays antineoplastic effects of a histone deacetylase inhibitor in A549 human lung cancer using compound 43.
Figure 7:
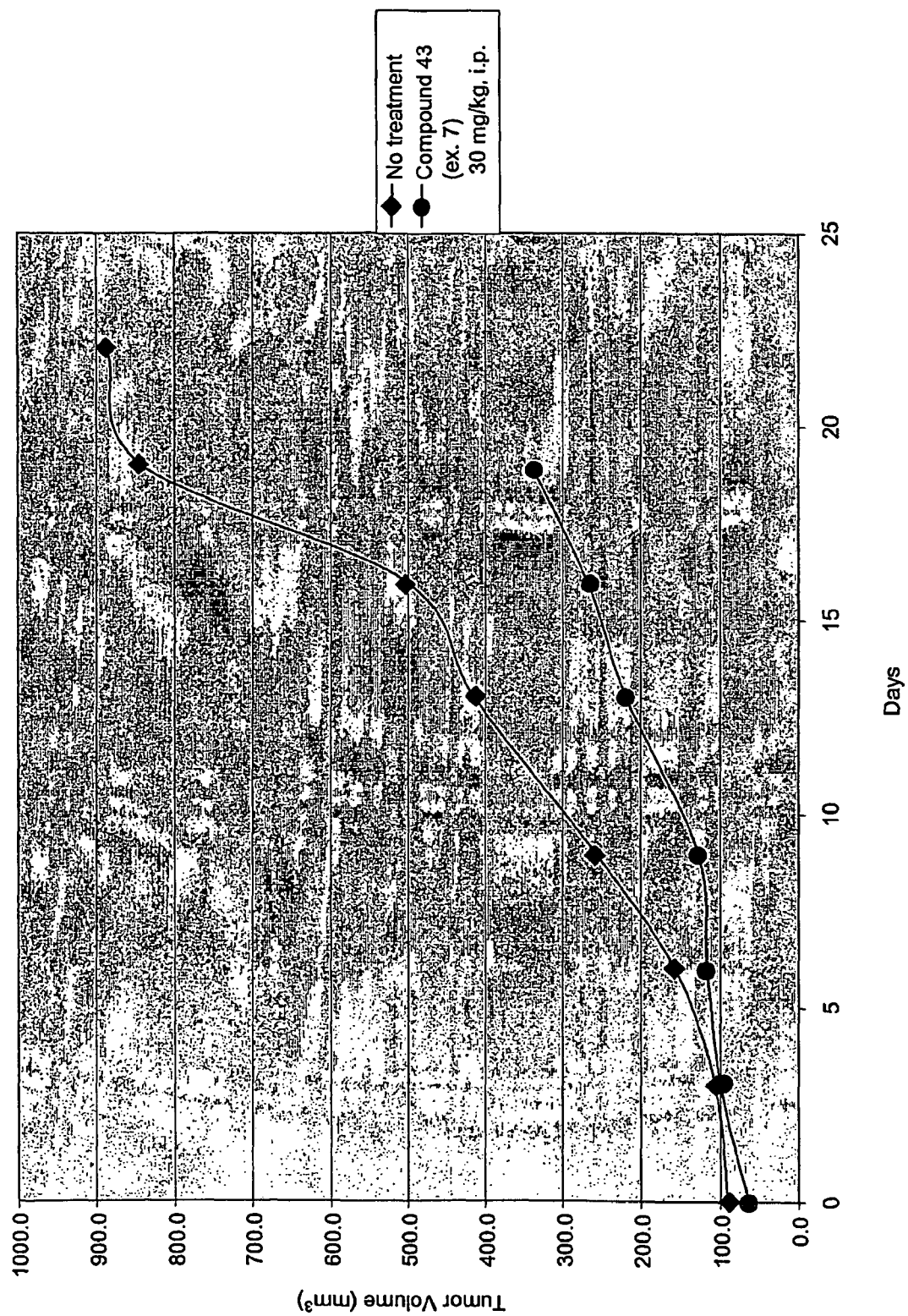
FIG. 7 displays antineoplastic effects of a histone deacetylase inhibitor in A431 vulval carcinoma using compound 43.
Figure 8:
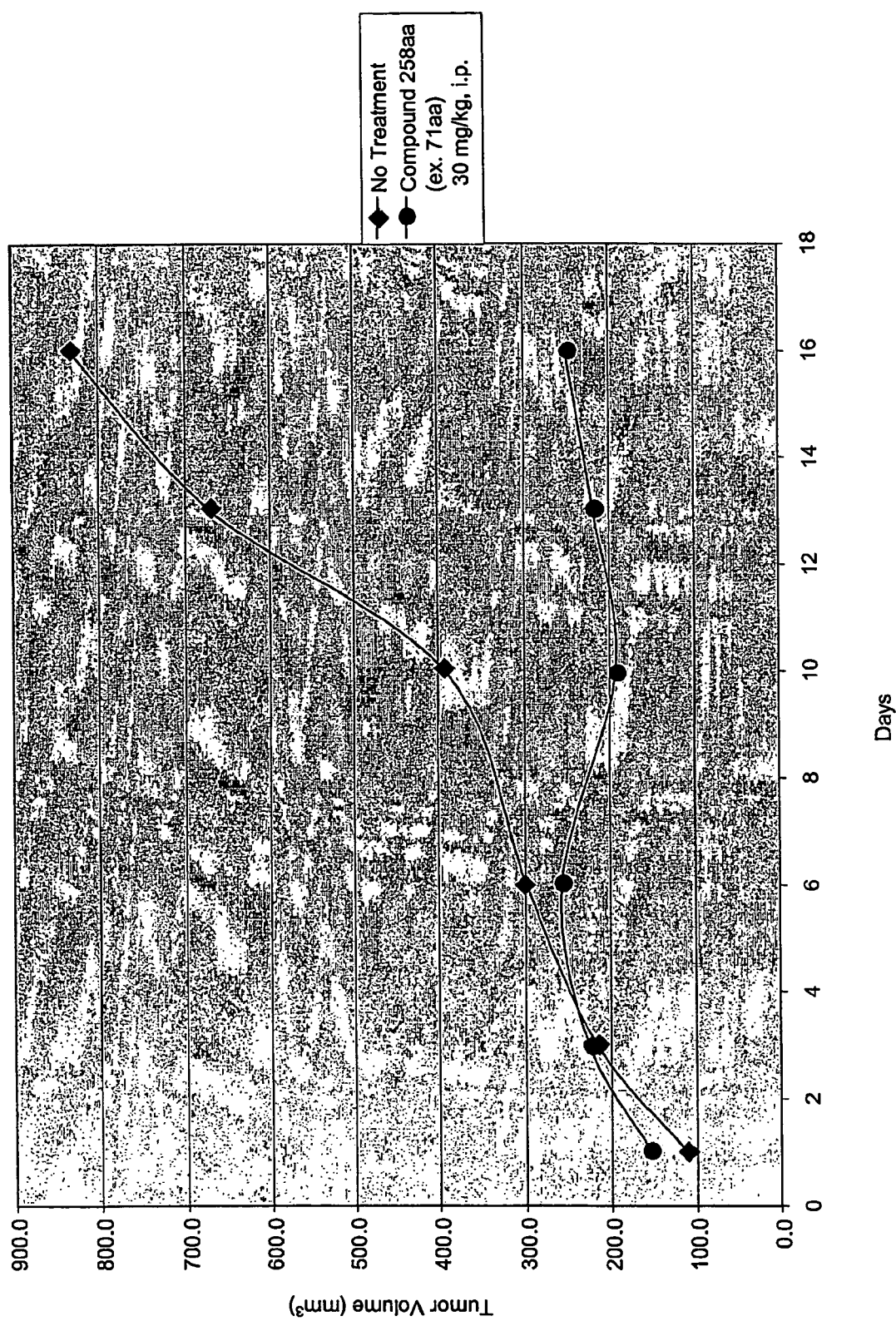
FIG. 8 displays antineoplastic effects of a histone deacetylase inhibitor in A431 vulval carcinoma using compound 258aa.
Figure 9:
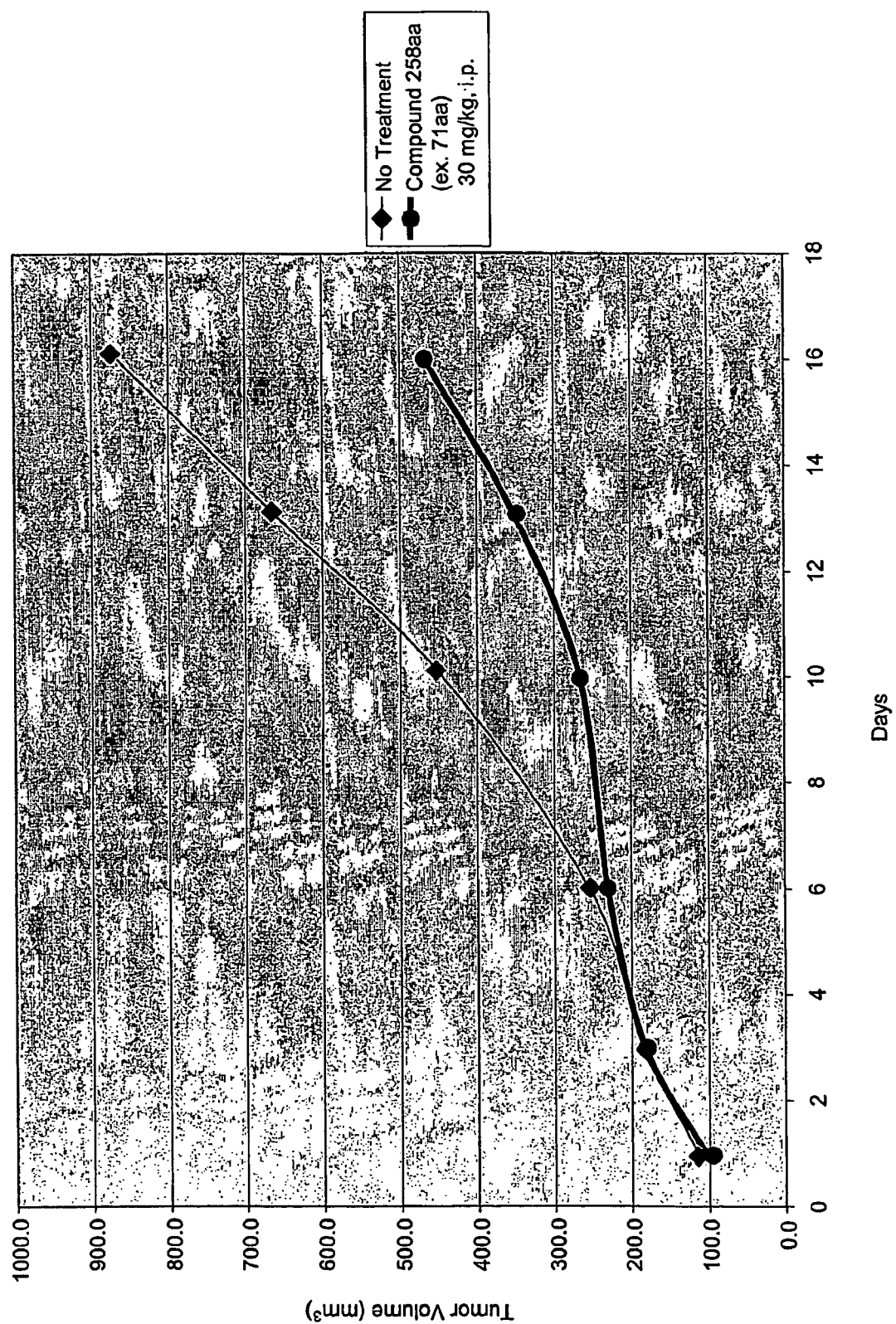
FIG. 9 displays antineoplastic effects of a histone deacetylase inhibitor in hct116 human colorectal cancer using compound 258aa.
Figure 10:
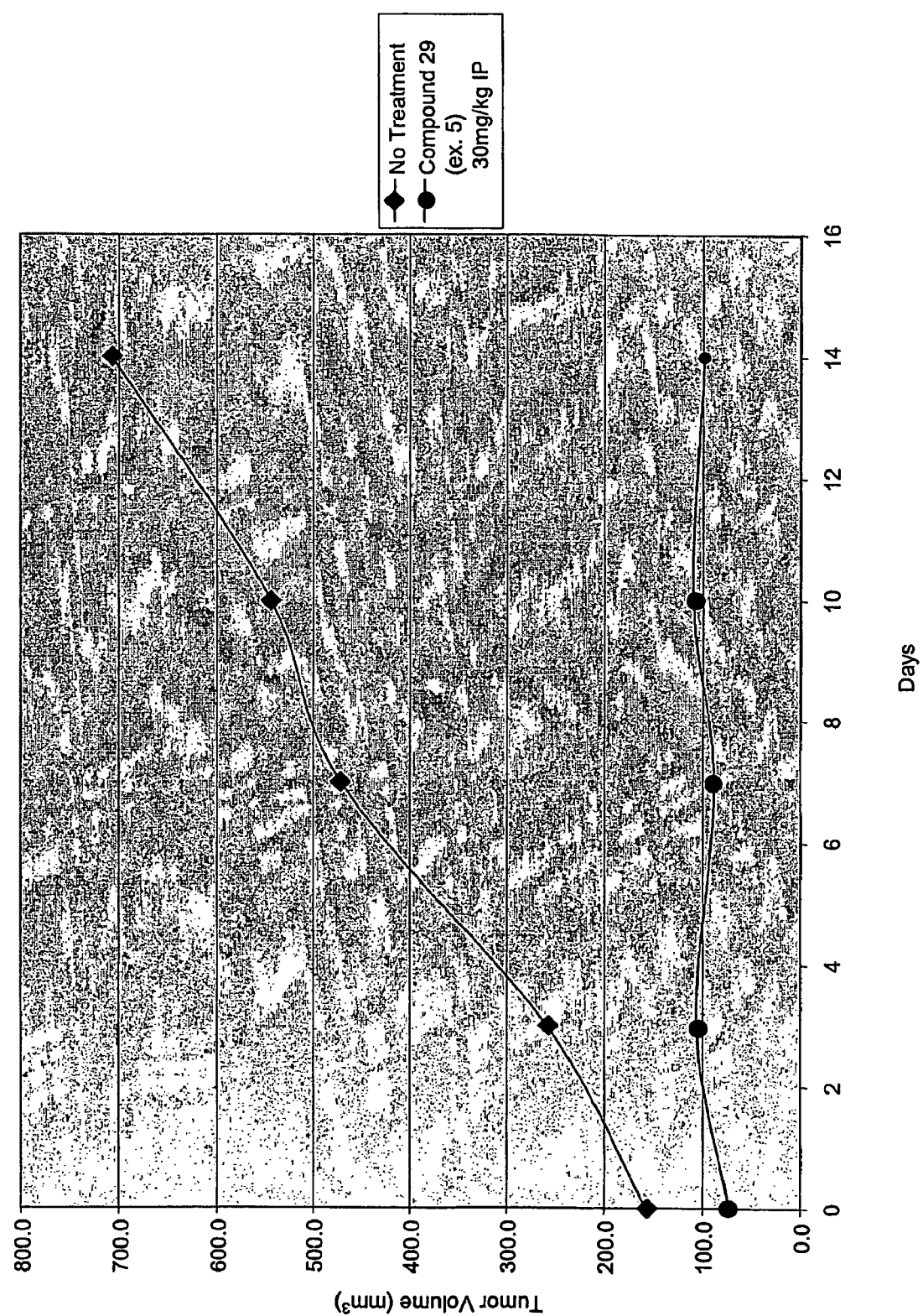
FIG. 10 displays antineoplastic effects of a histone deacetylase inhibitor in colo205 human colorectal cancer using compound 29.

Antineoplastic Effects of Histone Deacetylase Inhibitors on Human Tumor Xenografts In Vivo Eight to ten week old female BCDI mice (Taconic Labs, Great Barrington, N.Y.) were injected subcutaneously in the flank area with $2 \times 10^6$ preconditioned HCTI 16 human colorectal carcinoma cells, A549 human lung cancer, SW48 human colorectal cancer, A431 vulval caracinoma and colo205 human colorectal cancer. Preconditioning of these cells was done by a minimum of three consecutive tumor transplantations in the same strain of nude mice. Subsequently, tumor fragments of approximately 30 mgs were excised and implanted subcutaneously in mice, in the left flank area, under Forene anesthesia (Abbott Labs, Geneva, Switzerland). When the tumors reached a mean volume of 100 mm³, the mice were treated intravenously, subcutaneously, or intraperitoneally by daily injection, with a solution of the histone deacetylase inhibitor in an appropriate vehicle, such as PBS, DMSO/water, or Tween 80/water, at a starting dose of 10 mg/kg. The optimal dose of the HDAC inhibitor was established by dose response experiments according to standard protocols. Tumor volume was calculated every second day post infusion according to standard methods (e.g., Meyer et al., Int. J. Cancer 43: 851-856 (1989)). Treatment with the HDAC inhibitors according to the invention caused a significant reduction in tumor weight and volume relative to controls treated with vehicle only (i.e., no HDAC inhibitor). The results for histone deacetylase inhibitors compounds 6, 29, 67, 258aa, and 43 are displayed in FIGS. 1-10.

Assay Example 3

Combined Antineoplastic Effect of Histone Deacetylase Inhibitors and Histone Deacetylase Antisense Oligonucleotides on Tumor Cells In Vivo The purpose of this Example is to illustrate the ability of the combined use of a histone deacetylase inhibitor of the invention and a histone deacetylase antisense oligonucleotide to enhance inhibition of tumor growth in a mammal. Preferably, the antisense oligonucleotide and the HDAC inhibitor inhibit the expression and activity of the same histone deacetylase.

Mice bearing implanted HCT116 tumors (mean volume 100 mm³) are treated daily with saline preparations containing from about 0.1 mg to about 30 mg per kg body weight of histone deacetylase antisense oligonucleotide. A second group of mice is treated daily with pharmaceutically acceptable preparations containing from about 0.01 mg to about 5 mg per kg body weight of HDAC inhibitor.

Some mice receive both the antisense oligonucleotide and the HDAC inhibitor. Of these mice, one group may receive the antisense oligonucleotide and the HDAC inhibitor simultaneously intravenously via the tail vein. Another group may receive the antisense oligonucleotide via the tail vein, and the HDAC inhibitor subcutaneously. Yet another group may receive both the antisense oligonucleotide and the HDAC inhibitor subcutaneously. Control groups of mice are similarly established which receive no treatment (e.g., saline only), a mismatch antisense oligonucleotide only, a control compound that does not inhibit histone deacetylase activity, and a mismatch antisense oligonucleotide with a control compound.

Tumor volume is measured with calipers. Treatment with the antisense oligonucleotide plus the histone deacetylase protein inhibitors according to the invention causes a significant reduction in tumor weight and volume relative to controls.

Table 6C provides data on inhibition of HDAC1 enzyme, on antiproliferative activities (HCT116 human colon cancer cells) of the compounds using 3-[4,5-dimethylthiazol-2-yl-2, 5-diphenyltetrazolium]bromide (MTT) assay, as well as induction of $p21^{WAF1/Cip1}$ tumor suppressor gene.

TABLE 6C

| Example | Compound | HD-1 μM | MTT HCT116 μM | P21 (HCT116) μM |
|---|---|---|---|---|
| 41a | 143a | a | a | b |
| 41b | 143b | a | b | b |
| 41c | 143c | a | b | b |
| 42 | 146 | a | a | b |
| 46 | 164 | a | a | b |
| 46cc | 164cc | a | a | b |
| 49 | 173 | a | b | b |
| 51 | 181 | a | a | b |
| 52 | 184 | a | a | b |
| 66 | 242 | a | a | b |

TABLE 6C-continued

| Example | Compound | HD-1 μM | MTT HCT116 μM | P21 (HCT116) μM |
|---|---|---|---|---|
| 67e | 245e | a | a | b |
| 70a | 256a | a | a | b |
| 70b | 256b | a | a | b |
| 70c | 256c | a | a | b |
| 71d | 258d | a | a | b |
| 71aa | 258aa | a | a | b |
| 71cc | 258cc | a | a | b |
| 71hh | 258hh | a | a | b |
| 71mm | 258mm | a | a | b |
| 71nn | 258nn | a | b | b |
| 71pp | 258pp | a | a | b |
| 71qq | 258qq | a | a | b |
| 78 | 283 | a | a | b |
| 79 | 286 | a | b | b |
| 79aa | 286aa | a | a | b |
| 97 | 349 | a | a | b |

MTT Assay.

Compounds at various concentrations were added to human colon cancer HCT116 cells plated in 96-well plates. Cells were incubated for 72 hours at 37° C. in 5% $CO_2$ incubator. MTT (3-[4,5-dimethylthiazol-2-yl]-2,5 diphenyl tetrazolium bromide, Sigma) was added at a final concentration of 0.5 mg/ml and incubated with the cells for 4 hours before an equal volume of solubilization buffer (50% N,N-dimethylformamide, 20% SDS, pH 4.7) was added onto cultured cells. After overnight incubation, solubilized dye was quantified by colorimetric reading at 570 nM using a reference at 630 nM. OD values were converted to cell numbers according to a standard growth curve of the relevant cell line. The concentration which reduces cell numbers to 50% of those of DMSO-treated cells is determined as MTT $IC_{50}$.

$p21^{WAF1/Cip1}$ Assay.

HCT116 cells were stably transfected with reporter plasmids encoding the p21 promoter-driven luciferase. Cells were treated with indicated concentration of HDAC inhibitors for 16 hours before cells were harvested and luciferase activity analyzed. The effective concentration (EC) of MS-275 was designated as 1 uM. The ability of HDAC inhibitor was compared with that of MS-275 (T. Suzuki, et. al J. Med. Chem., 1999, 3001-3003). Lower EC of a given compound indicates that this compound is more potent than MS-275 to induce p21 expression.

We claim:

1. A histone deacetylase inhibitor of formula (1):

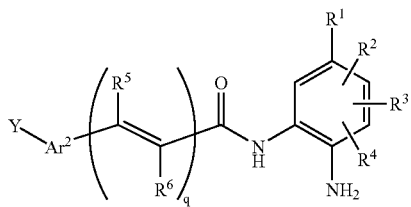

or a pharmaceutically acceptable salt thereof, wherein $Ar^2$ is a saturated or mono- or poly- unsaturated $C_5$-$C_{14}$- mono- or fused poly-cyclic hydrocarbyl, optionally containing one, two, three, or four annular heteroatoms per ring optionally substituted with one or more groups selected from $C_1$-$C_7$-alkyl, hydroxy, $C_1$-$C_7$-alkoxy, halo, and amino, provided that an annular O or S is not adjacent to another annular O or S;

$R^5$ and $R^6$ are independently selected from the group consisting of hydrogen, $C_1$-$C_7$-alkyl, aryl, and aralkyl;

$R^2$, $R^3$ and $R^4$ are independently selected from the group consisting of hydrogen, halogen, —$NH_2$, nitro, hydroxy, aryl, heterocyclyl, $C_3$-$C_8$-cycloalkyl, heteroaryl, $C_1$-$C_7$-alkyl, haloalkyl, $C_1$-$C_7$-alkenyl, $C_1$-$C_7$-alkynyl, $C_1$-$C_7$-acyl, $C_1$-$C_7$-alkyl-aryloxy, $C_1$-$C_7$-alkyl-arylsulfanyl, $C_1$-$C_7$-alkyl-arylsulfinyl, $C_1$-$C_7$-alkyl-arylsulfonyl, $C_1$-$C_7$-alkyl-arylaminosulfonyl, $C_1$-$C_7$-alkyl-arylamine, $C_1$-$C_7$-alkynyl-C(O)-amine, $C_1$-$C_7$-alkenyl-C(O)-amine, $C_1$-$C_7$-alkynyl-$R^9$, $C_1$-$C_7$-alkenyl-$R^9$ wherein $R^9$ is hydrogen, hydroxy, amino, $C_1$-$C_7$-alkyl or $C_1$-$C_7$-alkoxy;

q is 0 or 1;

$R^1$ is a mono-, bi-, or tri-cyclic aryl or heteroaryl, each of which is optionally substituted;

Y is $Cy^2$-$X^1$- and $Cy^2$ is hydrogen, cycloalkyl, aryl, heteroaryl, or heterocyclyl, each of which is optionally substituted and each of which is optionally fused to one or two aryl or heteroaryl rings, or to one or two saturated or partially unsaturated cycloalkyl or heterocyclic rings, and wherein any of the aforementioned rings are optionally substituted; and $X^1$ is selected from the group consisting of a covalent bond, $M^1$-$L^2$-$M^1$, and $L^2$-$M^2$-$L^2$ wherein $L^2$, at each occurrence, is independently selected from the group consisting of a chemical bond, $C_0$-$C_4$-hydrocarbyl, $C_0$-$C_4$-hydrocarbyl-(NH)—$C_0$-$C_4$-hydrocarbyl, $C_0$-$C_4$-hydrocarbyl-(S)—$C_0$-$C_4$-hydrocarbyl, and $C_0$-$C_4$-hydrocarbyl-(O)—$C_0$-$C_4$-hydrocarbyl, provided that $L^2$ is not a chemical bond when $X^1$ is $M^1$-$L^2$-$M^1$;

$M^1$, at each occurrence, is independently selected from the group consisting of —O—, —N($R^7$)—, —S—, —S(O)—, —S(O)$_2$—, —S(O)$_2$N($R^7$)—, —N($R^7$)—S(O)$_2$—, —C(O)—, —C(O)—NH—, —NH—C(O)—, —NH—C(O)—O— and —O—C(O)—NH—, —NH—C(O)—NH—, $R^7$ is selected from the group consisting of hydrogen, $C_1$-$C_6$-hydrocarbyl, aryl, aralkyl, acyl, $C_0$-$C_6$-hydrocarbyl-heterocyclyl, and $C_0$-$C_6$-hydrocarbyl-heteroaryl, wherein the hydrocarbyl moieties are optionally substituted with —OH, —$NH_2$, —N(H)$CH_3$, —N($CH_3$)$_2$, or halo; and $M^2$ is selected from the group consisting of $M^1$, heteroarylene, and heterocyclylene, either of which rings optionally is substituted; and provided that when $R^1$ is N-imidazolyl, $R^2$-$R^4$ are H, q is 0, and $Ar^2$ is pyridine, Y is not Cl; and when $R^1$ is p-aminophenyl, $R^2$-$R^4$ are H, q is 0, and $Ar^2$ is phenyl, Y is not H.

2. The compound according to claim 1 wherein $R^1$ is phenyl, naphthyl, anthracenyl, or fluorenyl.

3. The compound according to claim 1 wherein $R^1$ is furanyl or thienyl.

4. The compound according to claim 2 wherein $R^2$, $R^3$, and $R^4$ are all —H.

5. The compound according to claim 3 wherein $R^2$, $R^3$, and $R^4$ are all —H.

6. The compound according to claim 1, wherein $X^1$ is selected from the group consisting of a —N(Z)-$C_0$-$C_7$-alkyl-, —O—$C_0$-$C_7$-alkyl-, —C(H)=CH—$C_0$-$C_7$-alkyl-, —S—$C_0$-$C_7$-alkyl-, or —$C_1$-$C_7$-alkyl-, wherein Z is —H or —$C_1$-$C_7$-alkyl- optionally substituted with —OH, —$NH_2$, or halo.

7. The compound according to claim 1, wherein $X^1$ is selected from methylene, aminomethyl, and thiomethyl.

8. The compound according to claim 1, wherein $Cy^2$ is selected from

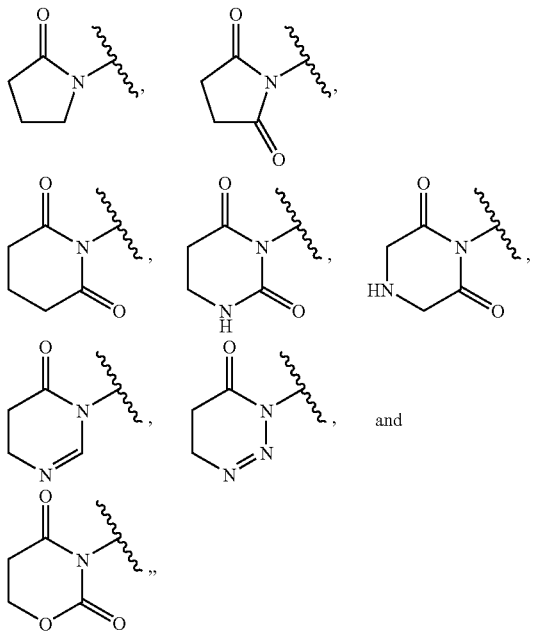

each of which optionally is substituted and optionally is fused to one or more aryl rings.

9. The compound according to claim 1 wherein $Cy^2$ is aryl or heteroaryl, each optionally substituted.

10. The compound according to claim 1 wherein $Cy^2$ is phenyl, pyrimidinyl, benzoimidazolyl or benzothiazolyl, each of which is optionally substituted.

11. The compound according to claim 10 wherein $Cy^2$ has from one and three substituents independently selected from the group consisting of $C_1$-$C_7$-alkoxy, halo, di-$C_1$-$C_7$-alkylamino-$C_1$-$C_7$-alkoxy and heteroaryl.

12. The compound according to claim 11 wherein the substituents are selected from methoxy, fluoro, chloro, pyridinyl and dimethylamino-ethoxy.

13. The compound according to claim 12 wherein $Cy^2$ is phenyl substituted with one to three $CH_3O$—.

14. The compound according to claim 1 wherein Y is $(V'-L^4)_t-V-L^3-$, and $L^3$ is a direct bond, —$C_1$-$C_6$-hydrocarbyl, —($C_1$-$C_3$-hydrocarbyl)$_{m1}$-X'—($C_1$-$C_3$-hydrocarbyl)$_{m2}$, —NH—($C_0$-$C_3$-hydrocarbyl), ($C_1$-$C_3$-hydrocarbyl)-NH—, or —NH—($C_1$-$C_3$-hydrocarbyl)-NH—;

m1 and m2 are independently 0 or 1;

X' is —N($R^{21}$)—, —C(O)N($R^{21}$)—, N($R^{21}$)C(O)—, —O—, or —S—;

$R^{21}$ is —H, V"-($C_1$-$C_6$-hydrocarbyl)$_a$;

$L^4$ is ($C_1$-$C_6$-hydrocarbyl)$_a$-M-($C_1$-$C_6$-hydrocarbyl)$_b$;

a and b are independently 0 or 1;

M is —NH—, —NHC(O)—, —C(O)NH—, —C(O)—, —SO$_2$—, —NHSO$_2$—, or —SO$_2$NH—

V, V', and V" are independently selected from cycloalkyl, heterocyclyl, aryl, and heteroaryl;

t is 0 or 1.

15. The compound according to claim 14 wherein Y is V-$L^3$ and $L^3$ is —NH—CH— or —CH—NH—;

V is phenyl optionally substituted with from 1 to 3 moieties independently selected from halo, hydroxy, $C_1$-$C_6$-hydrocarbyl, $C_1$-$C_6$-hydrocarbyl-oxy or -thio (particularly methoxy or methylthio), wherein each of the hydrocarbyl moieties are optionally substituted with one or more moieties independently selected from halo, nitroso, amino, sulfonamido, and cyano.

16. The compound according to claim 15 wherein V is an optionally substituted ring moiety selected from:

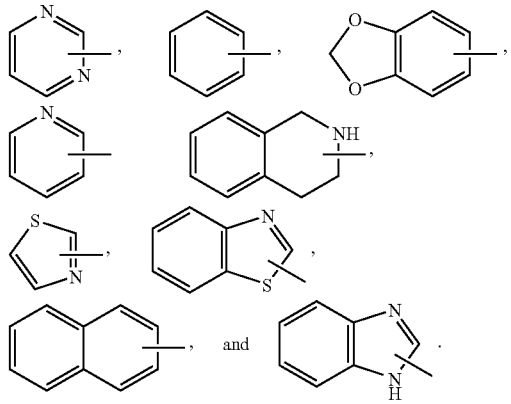

17. The compound according to claim 1 wherein $Cy^2$ is cycloalkyl, aryl, heteroaryl, or heterocyclyl, each of which optionally is substituted, and each of which optionally is fused to one or more aryl or heteroaryl rings, or to one or more saturated or partially unsaturated cycloalkyl or heterocyclic rings, each of which rings optionally is substituted, provided that when $Cy^2$ is a cyclic moiety having —C(O)—, —C(S)—, —S(O)—, or —S(O)$_2$— in the ring, then $Cy^2$ is not additionally substituted with a group comprising an aryl or heteroaryl ring; and $X^1$ is selected from the group consisting of a chemical bond, $L^3$, $W^1$-$L^3$, $L^3$-$W^1$, $W^1$-$L^3$-$W^1$, and $L^3$-$W^1$-$L^3$, wherein $W^1$, at each occurrence, is S, O, or N($R^9$), where $R^9$ is selected from the group consisting of hydrogen, alkyl, aryl, and aralkyl; and $L^3$ is $C_1$-$C_4$ alkylene, $C_2$-$C_4$ alkenylene, or $C_2$-$C_4$ alkynylene.

18. The compound according to claim 1 wherein Y is selected from:

a) $A_1$-$L_1$-$B_1$—, wherein $A_1$ is an optionally substituted aryl, optionally substituted heteroaryl or optionally substituted heterocyclyl; wherein $L_1$ is —(CH$_2$)$_{0-1}$NH(CH$_2$)$_{0-1}$—, —NHC(O)—, or —NHCH$_2$—; and wherein $B_1$ is phenyl or a covalent bond;

b) $A_2$-$L_2$-$B_2$—, wherein $A_2$ is CH$_3$(C=CH$_2$)—; optionally substituted cycloalkyl, optionally substituted alkyl, or optionally substituted aryl; wherein $L_2$ is —C≡C—; and wherein $B_2$ is a covalent bond;

c) $A_3$-$L_3$-$B_3$—, wherein $A_3$ is an optionally substituted aryl, optionally substituted heteroaryl or optionally substituted heterocyclyl; wherein $L_3$ is a covalent bond; and wherein $B_3$ is —CH$_2$NH—;

d) $A_4$-$L_4$-$B_4$—, wherein $A_4$ is an optionally substituted aryl; wherein $L_4$ is —NHCH$_2$—; and wherein $B_4$ is a thienyl group;

e) A$_5$-L$_5$-B$_5$—, wherein A$_5$ is an optionally substituted heteroaryl or optionally substituted heterocyclyl; wherein L$_5$ is a covalent bond; and wherein B$_5$ is —SCH$_2$—;
f) morpholinyl-CH$_2$—
g) optionally substituted aryl;
h) A$_6$-L$_6$-B$_6$—, wherein A$_6$ is an optionally substituted aryl, optionally substituted heteroaryl or optionally substituted heterocyclyl; wherein L$_6$ is a covalent bond; and wherein B$_6$ is —NHCH$_2$—;
i) A$_7$-L$_7$-B$_7$—, wherein A$_7$ is an optionally substituted heteroaryl or optionally substituted heterocyclyl; wherein L$_7$ is a covalent bond; and wherein B$_7$ is —CH$_2$—;
j) optionally substituted heteroaryl or optionally substituted heterocyclyl;
k) A$_8$-L$_8$-B$_8$—, wherein A$_8$ is optionally substituted phenyl; wherein L$_8$ is a covalent bond; and wherein B$_8$ is —O—;
l) A$_9$-L$_9$-B$_9$—; wherein A$_9$ is an optionally substituted aryl; wherein L$_9$ is a covalent bond; and wherein B$_9$ is a furan group;
m) A$_{10}$-L$_{10}$-B$_{10}$—, wherein A$_{10}$ is an optionally substituted heteroaryl or optionally substituted heterocyclyl; wherein L$_{10}$ is —CH(CH$_2$CH$_3$)—; and wherein B$_{10}$ is —NHCH$_2$—;
n) A$_{11}$-L$_{11}$-B$_{11}$—, wherein A$_{11}$ is an optionally substituted heteroaryl or optionally substituted heterocyclyl; wherein L$_{11}$ is a covalent bond; and wherein B$_{11}$ is —OCH$_2$—;
o) A$_{12}$-L$_{12}$-B$_{12}$—, wherein A$_{12}$ is an optionally substituted aryl, optionally substituted heteroaryl or optionally substituted heterocyclyl; wherein L$_{12}$ is —NHC(O)—; and wherein B$_{12}$ is —N(optionally substituted aryl)CH$_2$—;
P) A$_{13}$-L$_{13}$-B$_{13}$—, wherein A$_{13}$ is an optionally substituted aryl, optionally substituted heteroaryl or optionally substituted heterocyclyl; wherein L$_{13}$ is a covalent bond; and wherein B$_{13}$ is —NHC(O)—;
q) A$_{14}$-L$_{14}$-B$_{14}$—, wherein A$_{14}$ is an optionally substituted aryl, optionally substituted heteroaryl or optionally substituted heterocyclyl; wherein L$_{14}$ is —NHC(O) (optionally substituted heteroaryl); and wherein B$_{14}$ is —S—S—;
r) F$_3$CC(O)NH—;
s) A$_{15}$-L$_{15}$-B$_{15}$—, wherein A$_{15}$ is an optionally substituted aryl, optionally substituted heteroaryl or optionally substituted heterocyclyl; wherein L$_{15}$ is —(CH$_2$)$_{0-1}$NH (optionally substituted heteroaryl)-; and wherein B$_{15}$ is —NHCH$_2$—;
t) A$_{16}$-L$_{15}$-B$_{16}$—, wherein A$_{16}$ is an optionally substituted aryl, optionally substituted heteroaryl or optionally substituted heterocyclyl; wherein L$_{16}$ is a covalent bond; and wherein B$_{16}$ is —N(optionally substituted alkyl)CH$_2$—; and
u) A$_{17}$-L$_{17}$-B$_{17}$—, wherein A$_{17}$ is an optionally substituted aryl, optionally substituted heteroaryl or optionally substituted heterocyclyl; wherein L$_{17}$ is a covalent bond; and wherein B$_{17}$ is -(optionally substituted aryl-CH$_2$)$_2$—N—.

19. The compound according to claim 1 wherein Y is selected from:
a) D$_1$-E$_1$-F$_1$—, wherein D$_1$ is an optionally substituted aryl, optionally substituted heteroaryl or optionally substituted heterocyclyl; wherein E$_1$ is —CH$_2$— or a covalent bond; and wherein F$_1$ is a covalent bond;
b) D$_2$-E$_2$-F$_2$—, wherein D$_2$ is an optionally substituted aryl, optionally substituted heteroaryl or optionally substituted heterocyclyl; wherein E$_2$ is —NH(CH$_2$)$_{0-2}$-; and wherein F$_2$ is a covalent bond;
c) D$_3$-E$_3$-F$_3$—, wherein D$_3$ is an optionally substituted aryl, optionally substituted heteroaryl or optionally substituted heterocyclyl; wherein E$_3$ is —(CH$_2$)$_{0-2}$NH—; and wherein F$_3$ is a covalent bond;
d) D$_4$-E$_4$-F$_4$—, wherein D$_4$ is an optionally substituted aryl, optionally substituted heteroaryl or optionally substituted heterocyclyl; wherein E$_4$ is —S(CH$_2$)$_{0-2}$—; and wherein F$_4$ is a covalent bond;
e) D$_5$-E$_5$-F$_5$—, wherein D$_5$ is an optionally substituted aryl, optionally substituted heteroaryl or optionally substituted heterocyclyl; wherein E$_5$ is —(CH$_2$)$_{0-2}$S—; and wherein F$_5$ is a covalent bond; and
f) D$_6$-E$_6$-F$_6$—, wherein D$_6$ is an optionally substituted aryl, optionally substituted heteroaryl or optionally substituted heterocyclyl; wherein E$_6$ is —NH(CH$_2$)$_{0-2}$NH—; and wherein F$_6$ is a covalent bond.

20. The compound according to claim 2 wherein R$^2$ to R$^4$ are independently hydrogen, —NH$_2$, nitro, furanyl, chloro, fluoro, butyl, trifluoromethyl, bromo, thienyl, phenyl, —CHCHC(O)—NH$_2$, —C≡CCH$_2$—R$^9$ wherein R$^9$ is hydrogen, C$_1$-C$_7$-alkyl, hydroxy, amino, or C$_1$-C$_7$-alkoxy.

21. The compound according to claim 3 wherein R$^2$ to R$^4$ are independently hydrogen, —NH$_2$, nitro, furanyl, chloro, fluoro, butyl, trifluoromethyl, bromo, thienyl, phenyl, —CHCHC(O)—NH$_2$, —C≡CCH$_2$—R$^9$ wherein R$^9$ is hydrogen, C$_1$-C$_7$-alkyl, hydroxy, amino, or C$_1$-C$_7$-alkoxy.

22. The compound according to claim 1 wherein q is 0 and X$^1$ is independently selected from the group consisting of a —NH—CH$_2$—, —S—CH$_2$— and —CH$_2$—.

23. The compound according to claim 1 wherein Ar$^2$ has the formula

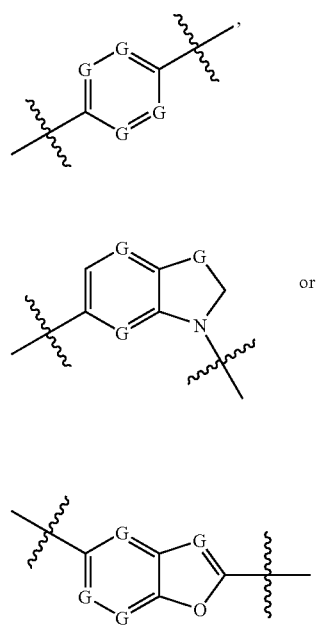

and wherein G, at each occurrence, is independently N or C, and C is optionally substituted.

24. The compound according to claim 23 wherein Ar² has the formula

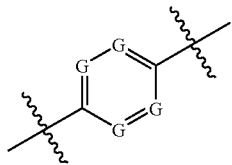

25. The compound according to claim 23 wherein Ar² is selected from the group consisting of phenylene, benzofuranylene and indolinylene.

26. The compound according to claim 1 wherein the moiety formed by Cy²-X¹ is selected from:

—CH₃, 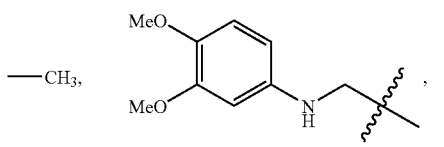

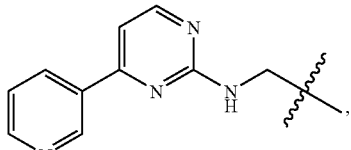

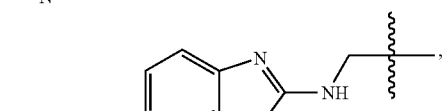

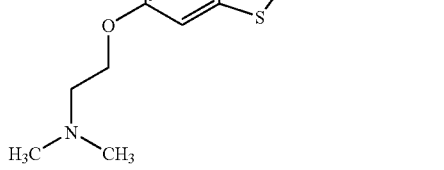

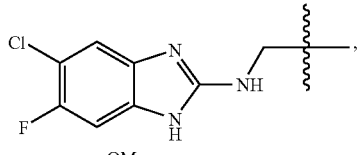

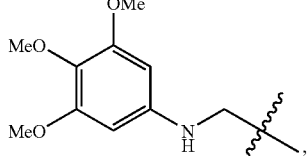

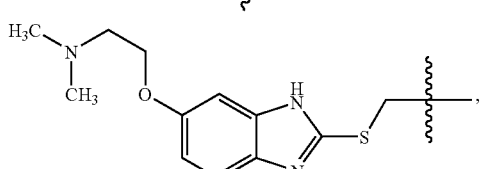

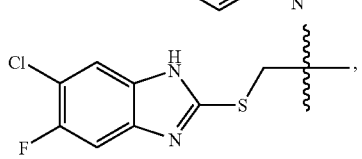

-continued

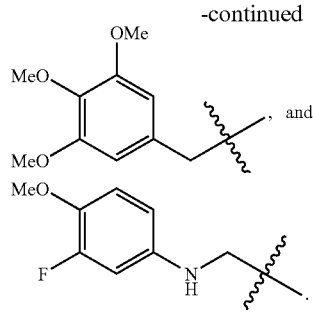

27. The compound of claim 1 of formula (2):

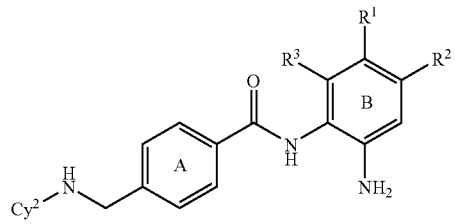

(2)

or a pharmaceutically acceptable salt thereof, wherein

R² and R³ are independently selected from the group consisting of hydrogen, trifluoromethyl, butyl, —(CH₂)₃—OH, chloro, fluoro, amino, phenyl, thienyl, furanyl, —CHCCHC(O)NH₂, —C≡CCH₂—OH, —C≡CCH₂—OCH₃; and the A ring is optionally further substituted with from 1 to 3 substituents independently selected from methyl, hydroxy, methoxy, halo, and amino.

28. The compound according to claim 27 wherein Cy² is selected from:

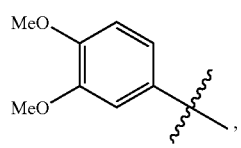

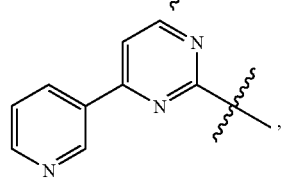

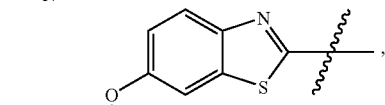

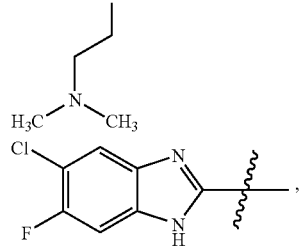

-continued

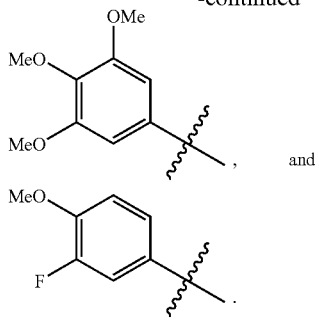

29. The compound according to claim 27 wherein the A ring is not further substituted.

30. The compound according to claim 27 wherein $R^2$ and $R^3$ are —H.

31. A compound according to claim 1 selected from:
N-[2-amino-5-(2-thienyl)phenyl]-4-{[(3,4-dimethoxyphenyl)amino]methyl}benzamide;
N-[2-amino-5-(2-thienyl)phenyl]-4-{[(4-pyridin-3-ylpyrimidin-2-yl)amino]methyl}benzamide;
N-[2-amino-5-(2-thienyl)phenyl]-4-[({6-[2-(dimethylamino)ethoxy]-1H-benzimidazol-2-yl}thio)methyl]benzamide;
N-[2-amino-5-(2-thienyl)phenyl]-4-{[(5-chloro-6-fluoro-1H-benzimidazol-2-yl)amino]methyl}benzamide;
N-[2-amino-5-(2-thienyl)phenyl]-5-{[(3,4,5-trimethoxyphenyl)amino]methyl}-1-benzofuran-2-carboxamide;
N-[2-amino-5-(2-thienyl)phenyl]-1-(3,4,5-trimethoxybenzyl)indoline-6-carboxamide;
trans-N-[2-amino-5-(2-thienyl)phenyl]-3-(4-{[(3,4,5-trimethoxyphenyl)amino]methyl}phenyl)acrylamide;
N-[2-amino-5-(2-thienyl)phenyl]-4-{[(3-fluoro-4-methoxyphenyl)amino]methyl}benzamide;
N-[2-amino-5-(2-thienyl)phenyl]-4-{[(6-chloro-5-fluoro-1H-benzimidazol-2-yl)thio]methyl}benzamide;
and a pharmaceutically acceptable salt of any one or more of the foregoing.

32. A pharmaceutical composition comprising a compound according to claims 1 and a pharmaceutically acceptable carrier, diluent, or excipient.

* * * * *

SEQUENCE LISTING

<160> NUMBER OF SEQ ID NOS: 17

<210> SEQ ID NO 1
<211> LENGTH: 20
<212> TYPE: DNA
<213> ORGANISM: Artificial
<220> FEATURE:
<223> OTHER INFORMATION: Synthetic oligonucleotides: accession number U50079

<400> SEQUENCE: 1
gaaacgtgag ggactcagca                                               20

<210> SEQ ID NO 2
<211> LENGTH: 20
<212> TYPE: DNA
<213> ORGANISM: Artificial
<220> FEATURE:
<223> OTHER INFORMATION: Synthetic oligonucleotides: accession number U50079

<400> SEQUENCE: 2
ggaagccaga gctggagagg                                               20

<210> SEQ ID NO 3
<211> LENGTH: 20
<212> TYPE: DNA
<213> ORGANISM: Artificial
<220> FEATURE:
<223> OTHER INFORMATION: Synthetic oligonucleotides: accession number U50079

<400> SEQUENCE: 3
gttaggtgag gcactgagga                                               20

<210> SEQ ID NO 4
<211> LENGTH: 20
<212> TYPE: DNA
<213> ORGANISM: Artificial

```
<220> FEATURE:
<223> OTHER INFORMATION: Synthetic oligonucleotides: accession number
      U31814

<400> SEQUENCE: 4
gctgagctgt tctgatttgg                                              20

<210> SEQ ID NO 5
<211> LENGTH: 20
<212> TYPE: DNA
<213> ORGANISM: Artificial
<220> FEATURE:
<223> OTHER INFORMATION: Synthetic oligonucleotides: accession number
      U31814

<400> SEQUENCE: 5
cgtgagcact tctcatttcc                                              20

<210> SEQ ID NO 6
<211> LENGTH: 20
<212> TYPE: DNA
<213> ORGANISM: Artificial
<220> FEATURE:
<223> OTHER INFORMATION: Synthetic oligonucleotides: accession number
      AF039703

<400> SEQUENCE: 6
cgctttcctt gtcattgaca                                              20

<210> SEQ ID NO 7
<211> LENGTH: 20
<212> TYPE: DNA
<213> ORGANISM: Artificial
<220> FEATURE:
<223> OTHER INFORMATION: Synthetic oligonucleotides: accession number
      AF039703

<400> SEQUENCE: 7
gcctttccta ctcattgtgt                                              20

<210> SEQ ID NO 8
<211> LENGTH: 20
<212> TYPE: DNA
<213> ORGANISM: Artificial
<220> FEATURE:
<223> OTHER INFORMATION: Synthetic oligonucleotides: accession number
      AB006626

<400> SEQUENCE: 8
gctgcctgcc gtgcccaccc                                              20

<210> SEQ ID NO 9
<211> LENGTH: 20
<212> TYPE: DNA
<213> ORGANISM: Artificial
<220> FEATURE:
<223> OTHER INFORMATION: Synthetic oligonucleotides: accession number
      AB006626

<400> SEQUENCE: 9
cgtgcctgcg ctgcccacgg                                              20

<210> SEQ ID NO 10
<211> LENGTH: 20
<212> TYPE: DNA
<213> ORGANISM: Artificial
<220> FEATURE:
```

```
<223> OTHER INFORMATION: Synthetic oligonucleotides: accession number
     AB006626

<400> SEQUENCE: 10
tacagtccat gcaacctcca                                                  20

<210> SEQ ID NO 11
<211> LENGTH: 20
<212> TYPE: DNA
<213> ORGANISM: Artificial
<220> FEATURE:
<223> OTHER INFORMATION: Synthetic oligonucleotides: accession number
     AB006626

<400> SEQUENCE: 11
atcagtccaa ccaacctcgt                                                  20

<210> SEQ ID NO 12
<211> LENGTH: 20
<212> TYPE: DNA
<213> ORGANISM: Artificial
<220> FEATURE:
<223> OTHER INFORMATION: Synthetic oligonucleotides: accession number
     AF039691

<400> SEQUENCE: 12
cttcggtctc acctgcttgg                                                  20

<210> SEQ ID NO 13
<211> LENGTH: 20
<212> TYPE: DNA
<213> ORGANISM: Artificial
<220> FEATURE:
<223> OTHER INFORMATION: Synthetic oligonucleotides: accession number
     AJ011972

<400> SEQUENCE: 13
caggctggaa tgagctacag                                                  20

<210> SEQ ID NO 14
<211> LENGTH: 20
<212> TYPE: DNA
<213> ORGANISM: Artificial
<220> FEATURE:
<223> OTHER INFORMATION: Synthetic oligonucleotides: accession number
     AJ011972

<400> SEQUENCE: 14
gacgctgcaa tcaggtagac                                                  20

<210> SEQ ID NO 15
<211> LENGTH: 20
<212> TYPE: DNA
<213> ORGANISM: Artificial
<220> FEATURE:
<223> OTHER INFORMATION: Synthetic oligonucleotides: accession number
     AF239243

<400> SEQUENCE: 15
cttcagccag gatgcccaca                                                  20

<210> SEQ ID NO 16
<211> LENGTH: 20
<212> TYPE: DNA
<213> ORGANISM: Artificial
<220> FEATURE:
<223> OTHER INFORMATION: Synthetic oligonucleotides: accession number
```

```
    AF230097

<400> SEQUENCE: 16
ctccggctcc tccatcttcc                                               20

<210> SEQ ID NO 17
<211> LENGTH: 20
<212> TYPE: DNA
<213> ORGANISM: Artificial
<220> FEATURE:
<223> OTHER INFORMATION: Synthetic oligonucleotides: accession number
      AF230097

<400> SEQUENCE: 17
agccagctgc cacttgatgc                                               20
```